US011541126B1

(12) United States Patent
Baum et al.

(10) Patent No.: US 11,541,126 B1
(45) Date of Patent: Jan. 3, 2023

(54) ANTI-ASGR1 ANTIBODY TLR8 AGONIST COMPRISING CONJUGATES AND USES THEREOF

(71) Applicant: Silverback Therapeutics, Inc., Seattle, WA (US)

(72) Inventors: Peter R. Baum, Seattle, WA (US); Robert Dubose, Seattle, WA (US); Valerie Odegard, Seattle, WA (US); Philip Tan, Seattle, WA (US); Peter A. Thompson, Seattle, WA (US); Sean W. Smith, Seattle, WA (US); Brenda Stevens, Seattle, WA (US)

(73) Assignee: SILVERBACK THERAPEUTICS, INC., Seattle, WA (US)

( * ) Notice: Subject to any disclaimer, the term of this patent is extended or adjusted under 35 U.S.C. 154(b) by 0 days.

(21) Appl. No.: 17/365,959

(22) Filed: Jul. 1, 2021

Related U.S. Application Data

(63) Continuation of application No. PCT/US2021/039974, filed on Jun. 30, 2021.

(60) Provisional application No. 63/213,155, filed on Jun. 21, 2021, provisional application No. 63/151,561, filed on Feb. 19, 2021, provisional application No. 63/090,158, filed on Oct. 9, 2020, provisional application No. 63/047,221, filed on Jul. 1, 2020.

(51) Int. Cl.
*A61K 47/68* (2017.01)
*C07K 16/28* (2006.01)
*A61K 31/55* (2006.01)
*A61K 45/06* (2006.01)
*A61K 47/65* (2017.01)
*A61K 39/00* (2006.01)
*A61P 31/20* (2006.01)

(52) U.S. Cl.
CPC .......... *A61K 47/6803* (2017.08); *A61K 31/55* (2013.01); *A61K 45/06* (2013.01); *A61K 47/65* (2017.08); *A61K 47/6849* (2017.08); *A61P 31/20* (2018.01); *C07K 16/2851* (2013.01); *A61K 2039/505* (2013.01); *C07K 2317/24* (2013.01); *C07K 2317/33* (2013.01)

(58) Field of Classification Search
None
See application file for complete search history.

(56) References Cited

U.S. PATENT DOCUMENTS

| | | | |
|---|---|---|---|
| 5,846,514 A | 12/1998 | Foster et al. | |
| 6,043,238 A | 3/2000 | Cooper et al. | |
| 6,334,997 B1 | 1/2002 | Foster et al. | |
| 6,942,972 B2 | 9/2005 | Farooqui et al. | |
| 7,387,271 B2 | 6/2008 | Noelle et al. | |
| 7,923,560 B2 | 4/2011 | Wightman et al. | |
| 8,236,318 B2 | 8/2012 | Keler et al. | |
| 8,357,374 B2 | 1/2013 | Carson et al. | |
| 8,729,088 B2 | 5/2014 | Carson et al. | |
| 8,951,528 B2 | 2/2015 | Stoermer et al. | |
| 9,556,167 B2 | 1/2017 | Spiegel et al. | |
| 9,655,964 B2 | 5/2017 | Perez et al. | |
| 9,670,272 B2 | 6/2017 | Nitsch et al. | |
| 9,670,276 B2 | 6/2017 | Lacy et al. | |
| 9,676,845 B2 | 6/2017 | Imhof-Jung et al. | |
| 9,695,233 B2 | 7/2017 | Duerr et al. | |
| 9,827,329 B2 | 11/2017 | Li | |
| 9,856,319 B2 | 1/2018 | Ghayur et al. | |
| 9,878,052 B2 | 1/2018 | Li | |
| 9,914,776 B2 | 3/2018 | Ast et al. | |
| 9,926,379 B2 | 3/2018 | Bruenker et al. | |
| 9,943,416 B2 | 4/2018 | Arramon et al. | |
| 9,944,573 B2 | 4/2018 | Radaelli et al. | |
| 9,956,091 B2 | 5/2018 | de Villiers et al. | |
| 10,233,184 B2 | 3/2019 | Gao et al. | |
| 10,239,862 B2 | 3/2019 | Coburn et al. | |
| 10,253,003 B2 | 4/2019 | Last et al. | |
| 10,428,045 B2 | 10/2019 | Coburn et al. | |
| 10,442,790 B2 | 10/2019 | Coburn et al. | |
| 10,472,420 B2 | 11/2019 | Stoermer et al. | |
| 10,519,131 B2 | 12/2019 | Coburn et al. | |
| 2004/0091491 A1 | 5/2004 | Kedl et al. | |
| 2004/0141950 A1 | 7/2004 | Noelle et al. | |
| 2004/0213797 A1 | 10/2004 | Bodmer et al. | |
| 2006/0135459 A1 | 6/2006 | Epstein et al. | |
| 2006/0142202 A1 | 6/2006 | Alkan et al. | |
| 2007/0092940 A1 | 4/2007 | Eigenbrot et al. | |
| 2008/0234251 A1 | 9/2008 | Doherty et al. | |
| 2008/0306050 A1 | 12/2008 | Doherty et al. | |
| 2009/0004194 A1 | 1/2009 | Kedl | |
| 2009/0035323 A1 | 2/2009 | Stoermer et al. | |
| 2009/0047249 A1 | 2/2009 | Graupe et al. | |

(Continued)

FOREIGN PATENT DOCUMENTS

CA 3085424 A1 6/2019
CN 102753542 A 10/2012

(Continued)

OTHER PUBLICATIONS

Alves, "Antibody conjugation and formulation," *Antibody Therapeutics* 2(1):33-39, 2019.

(Continued)

*Primary Examiner* — Elly-Gerald Stoica
(74) *Attorney, Agent, or Firm* — Seed Intellectual Property Law Group LLP

(57) ABSTRACT

The disclosure provides conjugates of anti-ASGR1 antibodies or antigen binding fragments thereof to a myeloid cell agonist, compositions comprising the conjugates, and methods of treating liver viral infections with the conjugates. The disclosure also provides for anti-ASGR1 antibodies or antigen binding fragments thereof and methods for using the antibodies or antigen binding fragments thereof in treating liver viral infections.

30 Claims, 30 Drawing Sheets

Specification includes a Sequence Listing.

(56) References Cited

U.S. PATENT DOCUMENTS

| | | |
|---|---|---|
| 2009/0074711 A1 | 3/2009 | Glennie |
| 2009/0087440 A1 | 4/2009 | Vicari et al. |
| 2009/0123467 A1 | 5/2009 | Bedi et al. |
| 2010/0029585 A1 | 2/2010 | Howbert et al. |
| 2010/0143301 A1 | 6/2010 | Desai et al. |
| 2010/0291109 A1 | 11/2010 | Kedl |
| 2011/0033383 A1 | 2/2011 | Spencer et al. |
| 2011/0092485 A1 | 4/2011 | Howbert et al. |
| 2011/0098248 A1 | 4/2011 | Halcomb et al. |
| 2011/0117013 A1 | 5/2011 | Mack et al. |
| 2011/0118235 A1 | 5/2011 | Howbert et al. |
| 2011/0274653 A1 | 11/2011 | Banchereau et al. |
| 2011/0287038 A1 | 11/2011 | Slawin et al. |
| 2012/0039916 A1 | 2/2012 | Zurawski et al. |
| 2012/0082658 A1 | 4/2012 | Hershberg |
| 2012/0151504 A1 | 6/2012 | Schwalbe et al. |
| 2012/0219615 A1 | 8/2012 | Hershberg et al. |
| 2012/0231023 A1 | 9/2012 | Zurawski et al. |
| 2012/0263732 A1 | 10/2012 | Gladue et al. |
| 2013/0129729 A1 | 5/2013 | Kischel et al. |
| 2013/0171152 A1 | 7/2013 | Spriggs et al. |
| 2013/0251673 A1 | 9/2013 | Hartman et al. |
| 2013/0295091 A1 | 11/2013 | Esslinger et al. |
| 2013/0295110 A1 | 11/2013 | Binder et al. |
| 2013/0309256 A1 | 11/2013 | Lyon et al. |
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0154252 A1 | 6/2014 | Thompson et al. |
| 2014/0205653 A1 | 7/2014 | Dubensky, Jr. et al. |
| 2014/0275167 A1 | 9/2014 | Hartman |
| 2014/0341976 A1 | 11/2014 | Dubensky, Jr. et al. |
| 2014/0350031 A1 | 11/2014 | Mc Gowan et al. |
| 2015/0044279 A1 | 2/2015 | Miller et al. |
| 2015/0141625 A1 | 5/2015 | Stoermer et al. |
| 2015/0174268 A1 | 6/2015 | Li |
| 2015/0299194 A1 | 10/2015 | Hoves et al. |
| 2016/0015803 A1 | 1/2016 | Kedl |
| 2016/0015821 A1 * | 1/2016 | Hubbell ............ A61K 39/35 424/194.1 |
| 2016/0108045 A1 | 4/2016 | Andres et al. |
| 2016/0129095 A1 | 5/2016 | Noelle et al. |
| 2016/0130358 A1 | 5/2016 | Bhakta et al. |
| 2016/0168164 A1 | 6/2016 | Mc Gowan et al. |
| 2016/0199510 A1 | 7/2016 | McDonald et al. |
| 2016/0250223 A1 | 9/2016 | Smith et al. |
| 2016/0257653 A1 | 9/2016 | Hoves et al. |
| 2016/0289341 A1 | 10/2016 | Wu |
| 2016/0289343 A1 | 10/2016 | Wu |
| 2016/0375148 A1 | 12/2016 | Li |
| 2017/0014423 A1 | 1/2017 | Hoves et al. |
| 2017/0028079 A1 | 2/2017 | Li |
| 2017/0071944 A1 | 3/2017 | Geleziunas et al. |
| 2017/0088620 A1 | 3/2017 | Nioi et al. |
| 2017/0121421 A1 | 5/2017 | Cortez et al. |
| 2017/0145087 A1 | 5/2017 | Krause et al. |
| 2017/0145116 A1 | 5/2017 | Regula et al. |
| 2017/0151329 A1 | 6/2017 | Krause et al. |
| 2017/0158758 A1 | 6/2017 | Ramasubramanyan et al. |
| 2017/0158759 A1 | 6/2017 | Krause et al. |
| 2017/0158772 A1 | 6/2017 | Thompson et al. |
| 2017/0174786 A1 | 6/2017 | Bacac et al. |
| 2017/0190783 A1 | 7/2017 | Bacac et al. |
| 2017/0253670 A1 | 9/2017 | Klein et al. |
| 2017/0298139 A1 | 10/2017 | Thompson et al. |
| 2017/0349669 A1 | 12/2017 | Imhof-Jung et al. |
| 2018/0065938 A1 | 3/2018 | Chin et al. |
| 2018/0079805 A1 | 3/2018 | Imhof-Jung et al. |
| 2018/0086755 A1 | 3/2018 | Chin et al. |
| 2018/0117171 A1 | 5/2018 | Mooney et al. |
| 2018/0258048 A1 | 9/2018 | Coburn et al. |
| 2018/0263985 A1 | 9/2018 | Geleziunas et al. |
| 2019/0015516 A1 | 1/2019 | Jackson et al. |
| 2019/0016808 A1 | 1/2019 | Li |
| 2019/0038765 A1 | 2/2019 | Van Berkel et al. |
| 2019/0055247 A1 | 2/2019 | He et al. |
| 2019/0076547 A1 | 3/2019 | Alonso et al. |
| 2019/0336615 A1 | 11/2019 | Thompson et al. |
| 2020/0031798 A1 | 1/2020 | Coburn et al. |
| 2020/0113912 A1 | 4/2020 | Odegard et al. |
| 2020/0147234 A1 | 5/2020 | Thomas-Karyat |
| 2020/0199242 A1 | 6/2020 | Thompson |
| 2021/0077632 A1 | 3/2021 | Smith et al. |
| 2021/0115109 A1 | 4/2021 | Thompson et al. |
| 2021/0130473 A1 | 5/2021 | Baum et al. |
| 2021/0139477 A1 | 5/2021 | Smith et al. |
| 2021/0139604 A1 | 5/2021 | Thompson et al. |
| 2021/0154317 A1 | 5/2021 | Thompson et al. |

FOREIGN PATENT DOCUMENTS

| | | |
|---|---|---|
| CN | 102781933 A | 11/2012 |
| CN | 103562186 A | 2/2014 |
| EP | 2436696 A1 | 4/2012 |
| EP | 2604625 A1 | 6/2013 |
| EP | 2787005 A1 | 10/2014 |
| EP | 2663580 B1 | 12/2016 |
| EP | 2817338 B1 | 7/2017 |
| EP | 2747781 B1 | 11/2017 |
| WO | 00/76505 A1 | 12/2000 |
| WO | 03/094836 A2 | 11/2003 |
| WO | 2004/091658 A1 | 10/2004 |
| WO | 2005/065678 A1 | 7/2005 |
| WO | 2006/028029 A1 | 3/2006 |
| WO | 2006/052900 A2 | 5/2006 |
| WO | 2007/005874 A2 | 1/2007 |
| WO | 2007/024612 A2 | 3/2007 |
| WO | 2009/018500 A1 | 2/2009 |
| WO | 2009/084659 A1 | 7/2009 |
| WO | 2011/012637 A2 | 2/2011 |
| WO | 2011/017070 A1 | 2/2011 |
| WO | 2011/022508 A2 | 2/2011 |
| WO | 2011/022509 A2 | 2/2011 |
| WO | 2011/090088 A1 | 7/2011 |
| WO | 2011/104381 A2 | 9/2011 |
| WO | 2011/147921 A1 | 12/2011 |
| WO | 2012/021834 A1 | 2/2012 |
| WO | 2012/078688 A2 | 6/2012 |
| WO | 2012/097173 A2 | 7/2012 |
| WO | 2012/097177 A2 | 7/2012 |
| WO | 2012/122396 A1 | 9/2012 |
| WO | 2012/151199 A1 | 11/2012 |
| WO | 2013/093465 A2 | 6/2013 |
| WO | 2013/096835 A1 | 6/2013 |
| WO | 2013/173687 A1 | 11/2013 |
| WO | 2014/012479 A1 | 1/2014 |
| WO | 2014/023709 A1 | 2/2014 |
| WO | 2014/023813 A1 | 2/2014 |
| WO | 2014/052828 A1 | 4/2014 |
| WO | 2014/056953 A1 | 4/2014 |
| WO | 2014/076221 A1 | 5/2014 |
| WO | 2014/122144 A1 | 8/2014 |
| WO | 2014/128189 A1 | 8/2014 |
| WO | 2014/172532 A2 | 10/2014 |
| WO | 2015/103987 A1 | 7/2015 |
| WO | 2015/103989 A1 | 7/2015 |
| WO | 2015/103990 A1 | 7/2015 |
| WO | 2015/108595 A1 | 7/2015 |
| WO | 2015/112749 A2 | 7/2015 |
| WO | 2015/162293 A1 | 10/2015 |
| WO | 2016/004875 A1 | 1/2016 |
| WO | 2016/004876 A1 | 1/2016 |
| WO | 2016/016299 A1 | 2/2016 |
| WO | 2016/036678 A1 | 3/2016 |
| WO | 2016/040856 A2 | 3/2016 |
| WO | 2016/064899 A1 | 4/2016 |
| WO | 2016/075670 A1 | 5/2016 |
| WO | 2016/096174 A1 | 6/2016 |
| WO | 2016/096778 A1 | 6/2016 |
| WO | 2016/100302 A2 | 6/2016 |
| WO | 2016/120305 A1 | 8/2016 |
| WO | 2016/142250 A1 | 9/2016 |
| WO | 2017/023779 A1 | 2/2017 |

(56) References Cited

FOREIGN PATENT DOCUMENTS

| | | |
|---|---|---|
| WO | 2017/024296 A1 | 2/2017 |
| WO | 2017/027645 A1 | 2/2017 |
| WO | 2017/027646 A1 | 2/2017 |
| WO | 2017/046112 A1 | 3/2017 |
| WO | 2017/058944 A1 | 4/2017 |
| WO | 2017/072662 A1 | 5/2017 |
| WO | 2017/091745 A1 | 6/2017 |
| WO | 2017/093404 A1 | 6/2017 |
| WO | 2017/093406 A1 | 6/2017 |
| WO | 2017/100305 A2 | 6/2017 |
| WO | 2017/117269 A1 | 7/2017 |
| WO | 2017/118405 A1 | 7/2017 |
| WO | 2017/123657 A1 | 7/2017 |
| WO | 2017/123669 A1 | 7/2017 |
| WO | 2017/139623 A1 | 8/2017 |
| WO | 2017/147368 A1 | 8/2017 |
| WO | 2017/161349 A1 | 9/2017 |
| WO | 2017/190669 A1 | 11/2017 |
| WO | 2017/202703 A1 | 11/2017 |
| WO | 2017/202704 A1 | 11/2017 |
| WO | 2017/216054 A1 | 12/2017 |
| WO | 2018/002358 A1 | 1/2018 |
| WO | 2018/009466 A1 | 1/2018 |
| WO | 2018/009916 A1 | 1/2018 |
| WO | 2018/045204 A1 | 3/2018 |
| WO | 2018/060323 A1 | 4/2018 |
| WO | 2018/065360 A1 | 4/2018 |
| WO | 2018/098203 A1 | 5/2018 |
| WO | 2018/100558 A2 | 6/2018 |
| WO | 2018/112108 A1 | 6/2018 |
| WO | 2018/136412 A2 | 7/2018 |
| WO | 2018/138685 A2 | 8/2018 |
| WO | 2018/140831 A2 | 8/2018 |
| WO | 2018/144955 A1 | 8/2018 |
| WO | 2018/152453 A1 | 8/2018 |
| WO | 2018/156625 A1 | 8/2018 |
| WO | 2018/170179 A1 | 9/2018 |
| WO | 2018/191746 A1 | 10/2018 |
| WO | 2018/198091 A1 | 11/2018 |
| WO | 2018/227018 A1 | 12/2018 |
| WO | 2018/227023 A1 | 12/2018 |
| WO | 2019/084060 A1 | 5/2019 |
| WO | 2019/099412 A1 | 5/2019 |
| WO | 2019/118884 A1 | 6/2019 |
| WO | 2019/195278 A1 | 10/2019 |
| WO | 2019/227059 A1 | 11/2019 |
| WO | 2020/013803 A1 | 1/2020 |
| WO | 2020/047187 A1 | 3/2020 |
| WO | 2020/056008 A1 | 3/2020 |
| WO | 2020/056192 A1 | 3/2020 |
| WO | 2020/056194 A1 | 3/2020 |
| WO | 2020/056198 A2 | 3/2020 |
| WO | WO 2020/056192 | 3/2020 |
| WO | 2020/092385 A1 | 5/2020 |
| WO | 2020/190725 A1 | 7/2020 |
| WO | 2020/181040 A1 | 9/2020 |
| WO | 2020/190731 A1 | 9/2020 |
| WO | 2020/190734 A1 | 9/2020 |
| WO | 2020/190760 A1 | 9/2020 |
| WO | 2020/190762 A1 | 9/2020 |
| WO | 2020/252254 A1 | 12/2020 |
| WO | 2020/252294 A1 | 12/2020 |
| WO | 2021/011834 A1 | 1/2021 |
| WO | 2021/030665 A1 | 2/2021 |
| WO | 2021/072203 A1 | 4/2021 |
| WO | 2022/006340 A1 | 1/2022 |
| WO | WO 2022/006340 | 1/2022 |

OTHER PUBLICATIONS

Berge et al., "Pharmaceutical Salts," *J. Pharm. Sci*, 66(1): 1-19, Jan. 1977.
Bolt Biotherapeutics: "A First-in-human Study Using BDC-1001 in Advanced HER2-Expressing Solid Tumors," URL: https://clinicaltrials.gov/ct2/show/record/NCT04278144?term=NCT04278144&draw=1&rank=1, download date Jan. 12, 2021. (4 pages).
Challita-Eid et al., "Enfortumab Vedotin Antibody-Drug Conjugate Targeting Nectin-4 is a Highly Potent Therapeutic Agent in Multiple Preclinical Cancer Models," *Cancer Research* 76(10):3003-3013, Mar. 2016, (12 pages).
Database Caplus Chemical Abstracts Service, Columbus, Ohio, US; Database Accession No. 2017:1888322, Abstract of WO 2017202704, F. Hoffmann-La Roche AG, 2017, (19 pages).
Derycke et al., "Nectin 4 Overexpression in Ovarian Cancer Tissues and Serum: Potential Role as a Serum Biomarker," *Am J Clin Pathol*. 734(5):835-845, 2010 (NIH Public Access Author Manuscript, available in PMC Feb. 20, 2011), (17 pages).
Extended European Search Report, dated Mar. 4, 2020, for European Application No. 18767012.0. (4 pages).
Extended European Search Report, dated Sep. 4, 2020, for European Application No. 18744145.6. (9 pages).
Fabre-Lafay et al., "Nectin-4 is a new histological and serological tumor associated marker for breast cancer," *BMC Cancer* 7:73, 2007. (16 pages).
Fedorak et al., "A novel colon-specific steroid prodrug enhances sodium chloride absorption in rat colitis," *Am. J. Physiol.* 269:G210-218, 1995.
Gadd et al., "Targeted Activation of Toll-Like Receptors: Conjugation of a Toll-Like Receptor 7 Agonist to a Monoclonal Antibody Maintains Antigen Binding and Specificity," *Bioconjugate Chemistry* 26:1743-1752, 2015.
Hochhaus et al., "A Selective HPLC/RIA for Dexamethasone and its Prodrug Dexamethasone-21-sulphobenzoate Sodium in Biological Fluids," *Biomed. Chrom.* 6:283-286, 1992.
International Search Report and Written Opinion, dated Feb. 18, 2020, for International Patent Application No. PCT/US2019/050621. (23 pages).
International Search Report and Written Opinion, dated Jul. 3, 2018, for International Patent Application No. PCT/US2018/022510. (18 pages).
International Search Report and Written Opinion, dated Jul. 30, 2018, for International Patent Application No. PCT/US2018/015607. (16 pages).
International Search Report, dated Aug. 3, 2017, for International Patent Application No. PCT/CN2017/083031. (7 pages).
International Search Report and Written Opinion, dated Apr. 16, 2019, for International Patent Application No. PCT/US2018/065768. (17 pages).
International Search Report and Written Opinion, dated Jan. 22, 2021, for International Patent Application No. PCT/US2020/055000. (12 pages).
Jain et al., "Current ADC Linker Chemistry," *Pharm Res* 52:3526-3540, 2015.
Larsen et al., "Prodrug forms for the sulfonamide group. I. Evaluation of N-acyl derivatives, N-sulfonylamidines, N-sulfonylsulfilimines and sulfonylureas as possible prodrug derivatives," *Int. J. Pharmaceutics* 37-95, 1987.
Larsen et al., "Prodrug forms for the sulfonamide group. II. Water-soluble amino acid derivatives of N-methylsulfonamides as possible prodrugs," *Int. J. Pharmaceutics* 47:103-110, 1988.
Lattanzio et al., "Membranous Nectin-4 expression is a risk factor for distant relapse of T1-T2, N0 luminal—A early breast cancer," *Oncogenesis* 3:e118; 2014, (7 pages).
Li et al., "Generation of tumor-targeted antibody-CpG conjugates," *Journal of Immunological Methods* 559:45-51, 2013.
Ma et al., "Expression and clinical significance of Nectin-4 in hepatocellular carcinoma," *OncoTargets and Therapy* 9:183-190, 2016.
McLeod et al., "A Glucocorticoid Prodrug Facilitates Normal Mucosal Function in Rat Colitis Without Adrenal Suppression," *Gastroenterol.* 106(2):405-413, Feb. 1994.
Mencin et al., "Toll-like receptors as targets in chronic liver diseases," *Gut* 58:104-120, 2008.
Moyes et al., "Abstract 3271: A systemically administered, conditionally active TLR8 agonist for the treatment of HER2-expressing tumors," Cancer Research, Proceedings of the American Association for Cancer Research Annual Meeting 2019, URL: https://

(56) References Cited

OTHER PUBLICATIONS cancerres.aacrjournals.org/content/79/13_Supplement/3271, download date May 11, 2019. (4 pages).
M-Rabet et al., "Nectin-4: a new prognostic biomarker for efficient therapeutic targeting of primary and metastatic triple-negative breast cancer," *Annals of Oncology* 28(4):169-116, 2017.
Mullins et al., "Intratumoral immunotherapy with TLR7/8 agonist MEDI9197 modulates the tumor microenvironment leading to enhanced activity when combined with other immunotherapies," *Journal of ImmunoTherapy of Cancer* 7:244, 2019, (18 pages).
Nishii et al., "Systemic administration of a TLR7 agonist attenuates regulatory T cells by dendritic cell modification and overcomes resistance to PD-L1 blockade therapy" *Oncotarget* 9(17):13301-13312, 2018.
Nishiwada et al., "Nectin-4 expression contributes to tumor proliferation, angiogenesis and patient prognosis in human pancreatic cancer," *Journal of Experimental & Clinical Cancer Research* 34:30, 2015. (9 pages).
Notice of Allowance, dated Dec. 19, 2018, for U.S. Appl. No. 15/774,262, Coburn, "Benzazepine Compounds, Conjugates, and Uses Thereof," 12 pages.
Notice of Allowance, dated Jun. 14, 2019, for U.S. Appl. No. 15/973,506, Coburn, "Benzazepine Compounds, Conjugates, and Uses Thereof", 7 pages.
Notice of Allowance, dated May 13, 2019, for U.S. Appl. No. 16/274,132, Coburn, "Benzazepine Compounds, Conjugates, and Uses Thereof," 9 pages.
Notice of Allowance, dated May 13, 2019, for U.S. Appl. No. 16/274,130, Coburn, "Benzazepine Compounds, Conjugates, and Uses Thereof," 9 pages.
Notice of Allowance, dated Sep. 5, 2019, for U.S. Appl. No. 15/973,506, Coburn, "Benzazepine Compounds, Conjugates, and Uses Thereof", 7 pages.
Office Action, dated Dec. 6, 2018, for U.S. Appl. No. 15/973,506, Coburn, "Benzazepine Compounds, Conjugates, and Uses Thereof," 12 pages.
Office Action, dated Mar. 11, 2019, for U.S. Appl. No. 16/274,130, Coburn, "Benzazepine Compounds, Conjugates, and Uses Thereof," 14 pages.
Office Action, dated Mar. 11, 2019, for U.S. Appl. No. 16/274,132, Coburn, "Benzazepine Compounds, Conjugates, and Uses Thereof," 15 pages.
Pockros et al., "Oral resiquimod in chronic HCV infection: Safety and efficacy in 2 placebo-controlled, double-blind phase IIa studies," *Journal of Hepatology* 47:174-182, 2007.
Sato-Kaneko et al., "Combination immunotherapy with TLR agonists and checkpoint inhibitors suppresses head and neck cancer," *JCT Insight* 2(18):e93397, 2017. (18 pages).
Savva et al., "Targeting Toll-like receptors: promising therapeutic strategies for the management of sepsis-associated pathology and infectious diseases," *Frontiers in Immunology* 4(387):1-16, Nov. 2013.
Schrama et al., "Antibody targeted drugs as cancer therapeutics," *Nature Reviews* 5:147-159, Feb. 2006.
Sharma et al., "Systemic Targeting of CpG—ODN to the Tumor Microenvironment with Anti-neu-CpG Hyrid Molecule and T Regulatory Cell Depletion Induces Memory Responses in BALB-neuT Tolerant Mice," *Cancer Res* 68(18):7530-7540, Sep. 15, 2008.
Shouval et al., "Conjugates between Monoclonal Antibodies to HBsAg and Cytosine Arabinoside", *Journal of Hepatology* 3(Suppl. 2):S87-S95, 1986.
Silverback Therapeutics, "A Study of SBT6050 Alone and in Combination with Pembrolizumab in Patients with Advanced HER2 Expressing Solid Tumors" URL: https://clinicaltrials.gov/ct2/show/record/NCT04460456, download date Jan. 13, 2021. (4 pages).
Sinkula et al., "Rationale for Design of Biologically Reversible Drug Derivatives: Prodrugs," *J. Pharm. Sci.* 64(2):181-210, Feb. 1975.
Terashima et al., "R-268712, an orally active transforming growth factor-β type I receptor inhibitor, prevents glomerular sclerosis in a Thy1 nephritis model," *European Journal of Pharmacology* 734(2014): 60-66, Mar. 24, 2014.
Van Beuge et al., "Enhanced Effectivity of an ALK5-Inhibitor after Cell-Specific Delivery to Hepatic Stellate Cells in Mice with Liver Injury," *PLOS ONE* 8(2):e56442, Feb. 2013. (9 pages).
Wu, "Strategies for designing synthetic immune agonists," *Immunology* 148:315-325, 2016.
Zeindler et al., "Nectin-4 Expression is an Independent Prognostic Biomarker and Associated With Better Survival in Triple-Negative Breast Cancer," *Front. Med.* 6(200):1-7, Sep. 2019.
Zhang et al., "High expression of Nectin-4 is associated with unfavorable prognosis in gastric cancer," *Oncology Letters* 15:8789-8795, 2018.
Zhang et al., "Synthesis and in vitro anti-hepatitis B and C virus activities of ring-expanded ('fat') nucleobase analogues containing the imidazo[4,5-*e*][1,3]diazepine-4,8-dione ring system," *Bioorganic & Medicinal Chemistry Letters* 15:5397-5401, 2005.
U.S. Appl. No. 16/620,437, filed Dec. 6, 2019.
U.S. Appl. No. 17/275,528, filed Mar. 11, 2021.
U.S. Appl. No. 17/275,542, filed Mar. 11, 2021.
International Search Report and Written Opinion, dated Oct. 18, 2021, for International Application No. PCT/US2021/039974, 14 pages.
Altschul et al., "Gapped BLAST and PSI-BLAST: a new generation of protein database search programs," *Nucleic Acids Res.* 25(17): 3389-3402, 1997.
Capon et al., "Designing CD4 immunoadhesins for AIDS therapy," *Nature* 337:525-531, 1989.
Co et al., "Chimeric and Humanized Antibodies with Specificity for the CD33 Antigen," *J Immunol* 148:1149-1154, 1992.
Co et al., "Humanized antibodies for antiviral therapy," *Proc Natl Acad Sci USA* 88:2869-2873, 1991.
Evans, "Synthesis of Radiolabeled Compounds," *J. Radioanal. Chem.* 64(1-2): 9-32, 1981.
Guiducci et al., "RNA recognition by human TLR8 can lead to autoimmune inflammation," *J. Exp. Med.* 210(13): 2903-2919, 2013.
Jones et al., "Replacing the complementarity-determining regions in a human antibody with those from a mouse," *Letters to Nature* 321:522-525, 1986.
Kabalka et al., "The Synthesis of Radiolabeled Compounds via Organometallic Intermediates," *Tetrahedron* 45(21): 6601-6621, 1989.
Kim et al., "High Cleavage Efficiency of a 2A Peptide Derived from Procine Teschovirus-1 in Human Cell Lines, Zebrafish and Mice," *PLOS One* 6(4):e18556, 2011.
Metcalf et al., (Eds.). *Cellular Adhesion: Molecular Definition To Therapeutic Potential*, Plenum Press, New York; 1994, 16, Mark III et al., "Derivation of Therapeutically Active Humanized and Veneered Anti-CD18 Antibodies," pp. 291-312.
Queen et al., "A humanized antibody that binds to the interleukin 2 receptor," *Proc Natl Acad Sci USA* 86:10029-10033, 1989.
Riechmann et al., "Reshaping human antibodies for therapy," *Nature* 332:323-321, 1988.
Scholten et al., "Codon modification of T cell receptors allows enhanced functional expression in transgenic human T cells," *Clin. Immunol.* 119: 135-145, 2006.
Tan et al., "'Superhumanized' Antibodies: Reduction of Immunogenic Potential by Complementarity-Determining Region Grafting with Human Germline Sequences: Application to an Anti-CD28," *J Immunol* 169: 1119-1125, 2002.
Tempest et al., "Reshaping a Human Monoclonal Antibody to Inhibit Human Respiratory Syncytial Virus Infection In Vivo," *Bio/Technol* 9:266-271, 1991.
Verhoeyen et al., "Reshaping Human Antibodies: Grafting an Antilysozyme Activity," *Science* 239:1534-1536, 1988.
Wang et al., "The Functional Effects of Physical Interactions among Toll-like Receptors 7, 8, and 9," *Biol. Chem.* 281(49):31421-31434, 2006.
U.S. Appl. No. 17/103,644.
U.S. Appl. No. 17/275,542.

(56) References Cited

OTHER PUBLICATIONS

U.S. Appl. No. 17/735,841.
Chow et al., "Phase Ib Trial of the Toll-like Receptor 8 Agonist, Motolimod (VTX-2337), Combined with Cetuximab in Patients with Recurrent or Metastatic SCCHN," *Clin. Cancer Res.* 23(10):2442-2450, May 2017.
Dowling et al., "The Ultra-Potent and Selective TLR8 Agonist VTX-294 Activates Human Newborn and Adult Leukocytes," *PLOS One* 8(3):Mar. 2013, (11 pages).

\* cited by examiner

| Conjugate Dose (mg/kg) | Mean Liver Payload $C_{max}$ (ng/g) | % Dose in Liver[1] |
|---|---|---|
| 5 (0.125 mg) | 60.8 | ~8% |
| 10 (0.25 mg) | 62.1 | ~4% |
| 20 (0.5 mg) | 122 | ~4% |

[1] Estimated total amount of payload in liver vs. amount dosed on conjugate

FIG. 13

| DAR | Conjugate Dose (mg/kg) | Payload C$_{max}$ (ng/g) | % Dose in Liver[1] |
|---|---|---|---|
| 2 | 0.5 | 13.9 (5.2, 23) | 10 |
| | 2 | 191 (120, 260) | 34 |
| | 6 | 834 (550, 1100) | 50 |
| | 0.1 | 63.8 | ~100 |
| | 0.5 | 192 | 74 |
| 4 | 0.5 | 64.1 (37, 91) | 25 |
| | 2 | 372[2] | 36 |
| | 6 | 838[3] | 27 |

[1] Assuming 3 kg animal and payload ~1.2% and 0.64% of conjugate dose for DAR4 and DAR2, respectively
[2] 2 and [3] 7 days post-dose - likely underestimate C$_{max}$

*FIG. 16*

| | | | |
|---|---|---|---|
| NHP Dose Level | 0.5 mg/kg (MPAD) | <2 mg/kg (BED) | 6 mg/kg (Supra-Efficacious Dose) | Projected NOAEL ≥12 mg/kg |
| Mouse Equivalent Dose[1] (ASGR1-TLR8 Surrogate) | 10 mg/kg (0.25 mg) | 20 mg/kg (0.5 mg) | — | — |
| Human Equivalent Dose[2] | 0.16 mg/kg | <0.65 mg/kg | 1.9 mg/kg | ≥3.9 mg/kg |
| Margin/Index[3] | ≥24 Safety Margin | ≥12 Therapeutic Index[4] | | |

MPAD = Minimum Pharmacologically Active Dose; BED = Biologically Effective Dose; NOAEL = No Observed Adverse Effect Level

[1] Based on similar liver payload level to NHP dose;  [2] By standard allometric approach per FDA Guidance;
[3] Relative to projected NOAEL of ≥12 mg/kg;  [4] Assuming BED of 1 mg/kg

*FIG. 19*

ANTI-ASGR1 ANTIBODY TLR8 AGONIST COMPRISING CONJUGATES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860234_406C1_SEQUENCE_LISTING.txt. The text file is 422 KB, was created on Jul. 1, 2021, and is being submitted electronically via EFS-Web.

BACKGROUND

Millions of people worldwide are affected by viral infections of the liver, such as Hepatitis B (HBV) or Hepatitis C (HCV). These infections can be chronic, leading to cirrhosis and significant liver damage. In 2015, 1.3 million individuals died from HBV and HCV infections. Although antiviral medications can be used to treat these infections, treatment is not always effective. This is due, in part, because viruses such as HBV can achieve immunological ignorance or tolerance and avoid detection by the innate immune system. Therefore, there is a need for alternative strategies to treat viral infections of the liver.

BRIEF SUMMARY

The disclosure provides a myeloid cell agonist conjugate comprising: (a) an anti-asialoglycoprotein receptor 1 (ASGR1) antibody, or an antigen-binding fragment thereof, comprising a heavy chain variable region (VH) and a light chain variable region (VL), wherein: (i) the VH comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; (ii) the VH comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; (iii) the VH comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; (iv) the VH comprises a CDR1 (VH-CDR1) comprising the amino acid sequence of SEQ ID NO:1, a VH-CDR2 comprising the amino acid sequence selected from any one of SEQ ID NOS:6-8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence selected from any one of SEQ ID NOS:23-25, and a VL-CDR3 comprising the amino acid sequence of SEQ ID NO:33; (v) the VH comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26 or SEQ ID NO:27, and a VL-CDR3 comprising the amino acid sequence of SEQ ID NO:34; (vi) the VH comprises a CDR1 (VH-CDR1) comprising the amino acid sequence of SEQ ID NO:5, a VH-CDR2 comprising the amino acid sequence of SEQ ID NO:12, a VH-CDR3 comprising the amino acid sequence of SEQ ID NO:17; and the VL comprises a CDR1 (VL-CDR1) comprising the amino acid sequence of SEQ ID NO:22, a VL-CDR2 comprising the amino acid sequence of SEQ ID NO:32, and a VL-CDR3 comprising the amino acid sequence of SEQ ID NO:37; (vii) the VH comprises a CDR1 (VH-CDR1) comprising the amino acid sequence of SEQ ID NO:3, a VH-CDR2 comprising the amino acid sequence of SEQ ID NO:10, a VH-CDR3 comprising the amino acid sequence of SEQ ID NO:15; and the VL comprises a CDR1 (VL-CDR1) comprising the amino acid sequence of SEQ ID NO:20, a VL-CDR2 comprising the amino acid sequence selected from any one of SEQ ID NOS:28-30, and a VL-CDR3 comprising the amino acid sequence of SEQ ID NO:35; or (viii) the VH comprises a CDR1 (VH-CDR1) comprising the amino acid sequence of SEQ ID NO:4, a VH-CDR2 comprising the amino acid sequence of SEQ ID NO:11, a VH-CDR3 comprising the amino acid sequence of SEQ ID NO:16; and the VL comprises a CDR1 (VL-CDR1) comprising the amino acid sequence of SEQ ID NO:21, a VL-CDR2 comprising the amino acid sequence of SEQ ID NO:31, and a VL-CDR3 comprising the amino acid sequence of SEQ ID NO:36; (b) a myeloid cell agonist; and (c) a linker covalently attached to the myeloid cell agonist and the antibody.

In some embodiments, the conjugate is represented by Formula (I):

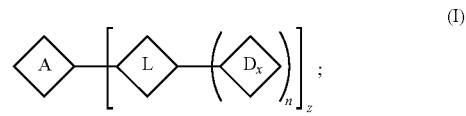

wherein: A is the anti-ASGR1 antibody or antigen-binding fragment thereof, L is the linker; $D_x$ is the myeloid cell agonist, wherein the myeloid cell agonist is a TLR8 agonist; n is selected from 1 to 20; and z is selected from 1 to 20. In some embodiments, n is an integer from 1 to about 10, or from 1 to about 5, or is 1 or 2, or is 1. In some embodiments, n is an integer from 1 to 10, or from 1 to 5, or is 1 or 2, or is 1. In some embodiments, n is 1, 2, 3, 4, 5, 6, 7, 8, 9 or 10. In some embodiments, z is from 1 to about 10, or from 1 to about 9, or from 1 to about 8, or 2 to about 6, or about 3 to about 5, or about 4. In some embodiments, z is from 1 to 10, or from 1 to 9, or from 1 to 8, or 2 to 6, or about 3 to 5, or 4. In some embodiments, z is 1, 2, 3, 4, 5, 6, 7, 8, 9, 10, 11, 12, 13, 14, 15, 16, 17, 18, 19, or 20.

The disclosure provides a myeloid cell agonist conjugate or salt thereof represented by the formula:

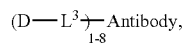

wherein Antibody is an anti-ASGR1 antibody, antibody construct, or targeting moiety comprising light chain CDR1, CDR2 and CDR3 set forth in the light chain variable region amino acid sequence selected from any one of SEQ ID NOS:131-133 and 244-249, and heavy chain CDR1, CDR2 and CDR3 set forth in the heavy chain variable region amino acid sequence selected from any one of SEQ ID NOS:43-88 and 238-243; light chain CDR1, CDR2 and CDR3 set forth in the light chain variable region amino acid sequence selected from any one of SEQ ID NOS:134-137, and heavy chain CDR1, CDR2 and CDR3 set forth in the heavy chain variable region amino acid sequence selected from any one of SEQ ID NOS:89-93; light chain CDR1, CDR2 and CDR3 set forth in the light chain variable region amino acid sequence selected from any one of SEQ ID NOS:143-149, and heavy chain CDR1, CDR2 and CDR3 set forth in the heavy chain variable region amino acid sequence selected from any one of SEQ ID NOS:113-125; light chain CDR1, CDR2 and CDR3 set forth in the light chain variable region amino acid sequence selected from any one of SEQ ID NOS:138-141, and heavy chain CDR1, CDR2 and CDR3 set forth in the heavy chain variable region amino acid sequence selected from any one of SEQ ID NOS:94-102; or light chain CDR1, CDR2 and CDR3 set forth in the light chain variable region amino acid sequence of SEQ ID NO:142, and heavy chain CDR1, CDR2 and CDR3 set forth in the heavy chain variable region amino acid sequence selected from any one of SEQ ID NOS:103-112; as determined by the Kabat index, and $L^3$-D is a linker-TLR8 agonist and has the structure:

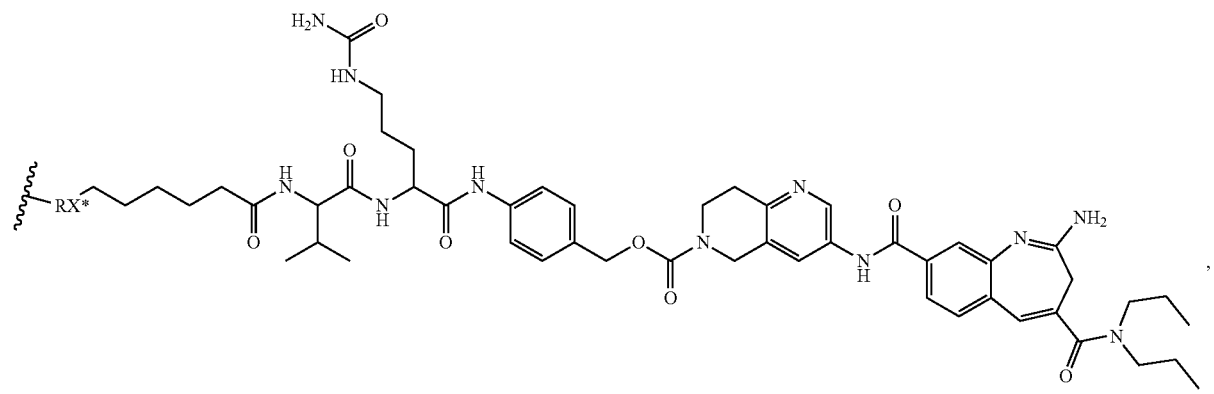

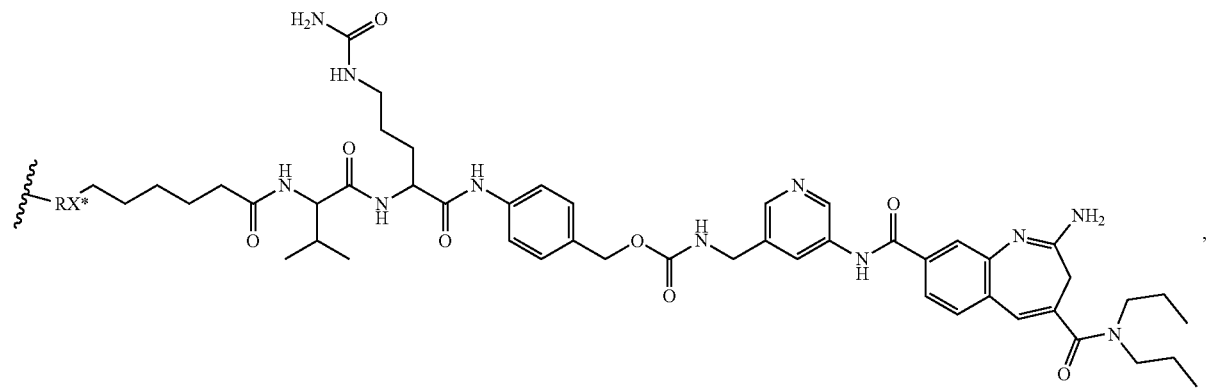

or

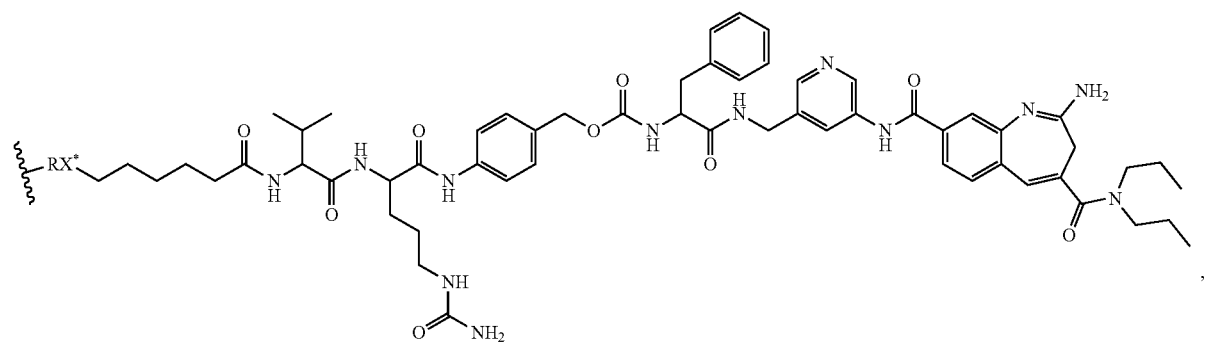

wherein RX* is a bond, a succinimide moiety, or a hydrolyzed succinimide moiety bound to a residue of the antibody, antibody construct, or targeting moiety, wherein

on RX* represents the point of attachment to a cysteine residue of the antibody, antibody construct, or targetin moiety.

The disclosure provides a pharmaceutical composition comprising a myeloid cell agonist conjugate of the disclosure and a pharmaceutically acceptable excipient.

The disclosure provides a method of treating a liver viral infection (e.g., Hepatitis B, Hepatitis C), comprising administering to a subject in need thereof an effective amount of a myeloid cell agonist conjugate or a pharmaceutical composition of the disclosure.

The disclosure provides an isolated monoclonal antibody, or an antigen-binding fragment thereof, that specifically binds to ASGR1, wherein the antibody or antigen-binding fragment thereof comprises a heavy chain variable region (VH) and a light chain variable region (VL), wherein: (i) the VH comprises a CDR1 (VH-CDR1) comprising the amino acid sequence of SEQ ID NO:1, a VH-CDR2 comprising the amino acid sequence selected from any one of SEQ ID NOS:6-8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence selected from any one of SEQ ID NOS:23-25, and a VL-CDR3 comprising the amino acid sequence of SEQ ID NO:33; (ii) the VH comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26 or SEQ ID NO:27, and a VL-CDR3 comprising the amino acid sequence of SEQ ID NO:34; (iii) the VH comprises a CDR1 (VH-CDR1) comprising the amino acid sequence of SEQ ID NO:5, a VH-CDR2 comprising the amino acid sequence of SEQ ID NO:12, a VH-CDR3 comprising the amino acid sequence of SEQ ID NO:17; and the VL comprises a CDR1 (VL-CDR1) comprising the amino acid sequence of SEQ ID NO:22, a VL-CDR2 comprising the amino acid sequence of SEQ ID NO:32, and a VL-CDR3 comprising the amino acid sequence of SEQ ID NO:37; (iv) the VH comprises a CDR1 (VH-CDR1) comprising the amino acid sequence of SEQ ID NO:3, a VH-CDR2 comprising the amino acid sequence of SEQ ID NO:10, a VH-CDR3 comprising the amino acid sequence of SEQ ID NO:15; and the VL comprises a CDR1 (VL-CDR1) comprising the amino acid sequence of SEQ ID NO:20, a VL-CDR2 comprising the amino acid sequence selected from any one of SEQ ID NOS:28-30, and a VL-CDR3 comprising the amino acid sequence of SEQ ID NO:35; or (v) the VH comprises a CDR1 (VH-CDR1) comprising the amino acid sequence of SEQ ID NO:4, a VH-CDR2 comprising the amino acid sequence of SEQ ID NO:11, a VH-CDR3 comprising the amino acid sequence of SEQ ID NO:16; and the VL comprises a CDR1 (VL-CDR1) comprising the amino acid sequence of SEQ ID NO:21, a VL-CDR2 comprising the amino acid sequence of SEQ ID NO:31, and a VL-CDR3 comprising the amino acid sequence of SEQ ID NO:36. The disclosure provides a conjugate comprising an anti-ASGR1 antibody of the disclosure and a small molecule drug, such as a TLR8 agonist, TLR7 agonist, or both.

The disclosure provides a pharmaceutical composition comprising an anti-ASGR1 antibody of the disclosure or a conjugate comprising such an antibody and a small molecule drug and a pharmaceutically acceptable carrier. In some embodiments, the average myeloid cell agonist-to-antibody ratio of the conjugate ranges from about 2 to about 8, about 3 to about 8, about 3 to about 7, or about 3 to about 5. In some embodiments, the average myeloid cell agonist-to-antibody ratio of the conjugate ranges from 2 to 8, 3 to 8, 3 to 7, or 3 to 5. In some embodiments, the average myeloid cell agonist-to-antibody ratio of the conjugate is at least 2, at least 3, at least 4, at least 5, at least 6, at least 7, or at least 8. As used throughout the disclosure, the term "myeloid cell agonist-to-antibody ratio" may also be referred to as a "drug-to-antibody ratio (DAR)". In some embodiments, the DAR of the conjugate is at least 2. In some embodiments, the DAR of the conjugate is between 2 and 2.5. In some embodiments, the DAR of the conjugate is 2. In some embodiments, the DAR of the conjugate is at least 4. In some embodiments, the DAR of the conjugate is between 4 and 4.5. In some embodiments, the DAR of the conjugate is 4.

The disclosure provides an isolated nucleic acid that encodes an anti-ASGR1 antibody or the heavy chain, the light chain, the heavy chain variable region, or the light chain variable region of the anti-ASGR1 antibody. The disclosure also provides a vector comprising the isolated nucleic acid, an isolated host cell comprising the isolated nucleic acid or the vector, and an isolated host cell that expresses an anti-ASGR1 antibody of the disclosure.

The disclosure provides a method of treating a liver viral infection (e.g., Hepatitis B, Hepatitis C) comprising administering to the subject having an effective amount of an anti-ASGR1 antibody, a conjugate comprising an anti-ASGR1 antibody and a small molecule drug, or a pharmaceutical composition of comprising the antibody or the conjugate of the disclosure.

In some embodiments of the methods of the disclosure, the subject is a rodent (e.g., a mouse, a rat, a gerbil, or a guinea pig). In some embodiments, the subject is non-human primate (NHP). In some embodiments, the subject is human. In some embodiments, the subject is male. In some embodiments, the subject is female. In some embodiments, the subject is a child, an adult, or a senior. In some embodiments, the subject is at risk of developing a condition of the disclosure. In some embodiments, the subject is at risk of developing cancer, including liver cancer. In some embodiments, the subject is at risk of developing an infection, including a liver infection.

BRIEF DESCRIPTION OF THE DRAWINGS

In FIG. 8A, dotted line is LLOQ for HBsAg ELISA. In FIG. 8B, average plasma anti-HBsAg IgG was determined by ELISA. p-values determined by T-test by comparison to vehicle group.

FIG. 13 is a table demonstrating that liver PK following ASGR1-S treatment in the AAV-HBV mouse model can be used to define target exposures in non-human primates (NHPs). Subcutaneous (SC) doses assessed are similar to those in FIGS. 6A and 6B. Liver payload PK was used as measure of conjugate uptake. Results provided in this table defined a target payload liver concentration of approximately 100 ng/g. Seroconversion in the AAV-HBV model was observed in some animals at 5 mg/kg and 10 mg/kg.

FIG. 16 is a table providing liver payload exposure data from the NHP studies in FIG. 14 after subcutaneous (SC) doses of DAR2 and DAR4 ASGR1-TLR8 conjugates. Efficiency of liver update is similar for DAR2 versus DAR4 ASGR1-TLR8 conjugates. For both DAR2 and DAR4, liver exposures increased with dose and the estimated % dose in liver were generally between about 30% and about 70%. For example, 2 mg/kg DAR2 results in similar or approximately 2-fold greater payload levels compared to target exposure. This ASGR1-TLR8 conjugate contains a humanized anti-ASGR1 antibody.

FIG. 19 is a chart demonstrating that the safety and PD profiles of an ASGR1-TLR8 conjugate in NHP indicated favorable safety margin and therapeutic index for DAR2 in humans. This ASGR1-TLR8 conjugate contains a humanized anti-ASGR1 antibody. Mouse liver PK data (see FIG. 13) provided a bridge from efficacious doses in AAV-HBV model to NHP.

DETAILED DESCRIPTION

Figure 1A:
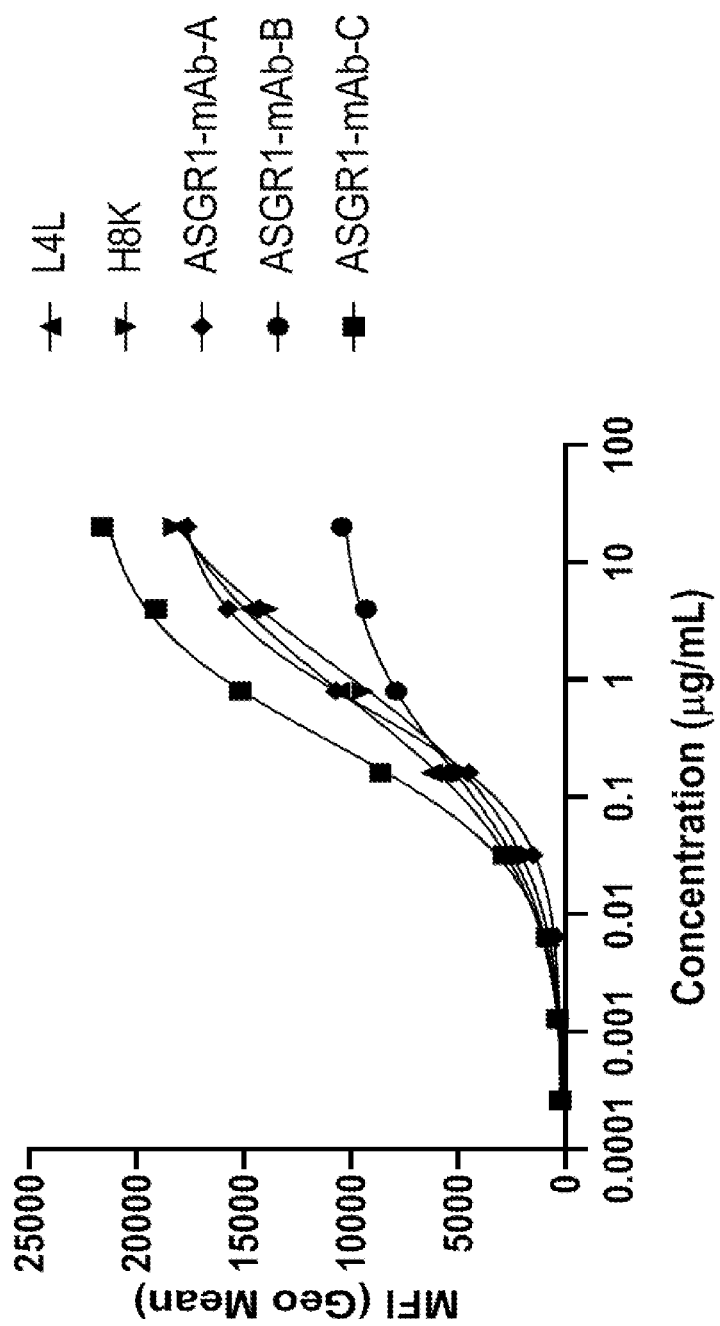
FIGS. 1A-1D are a series of graphs showing the binding of various mouse and humanized anti-ASGR1 antibodies to ASGR1-expressing cell line HepG2.

The disclosure provides anti-ASGR1 antibodies, myeloid cell agonist conjugates comprising anti-ASGR1 antibodies, and pharmaceutical compositions that comprise such antibodies and conjugates. The antibodies, conjugates and pharmaceutical compositions of the disclosure are useful in treating a liver viral infection alone or in combination with other anti-viral therapeutic agents.

Anti-ASGR1 antibodies and myeloid cell agonist conjugates comprising such antibodies as provided in the disclosure are capable of specifically binding to ASGR1 expressing cells. The myeloid cell agonist conjugates are also capable of inducing TNF-α production from human peripheral blood mononuclear cells (PBMCs) in the presence of ASGR1 expressing tumor cells, which indicates that the myeloid cells are being activated by the conjugates of this disclosure.

Unexpectedly, addition of a G27Y mutation in the VH region of certain exemplary humanized anti-ASGR1 antibodies stabilizes the antibody structure, resulting in more homogenous recovery.

Surprisingly, certain exemplary anti-ASGR1 antibodies (e.g., H8K and L4L) of the disclosure were determined to belong to a unique epitope bin compared to reference anti-ASGR1 antibodies and block with ASGR1 ligand (GalNAc) binding to ASGR1. While certain exemplary anti-ASGR1 antibodies (e.g., G2D, J4F, and K2E) belonged to the same epitope bin as a reference anti-ASGR1 antibody, G2D and K2E antibodies unexpectedly differ from the reference anti-ASGR1 antibody in that: they do not exhibit off-target binding to rat CLEC10A whereas the reference antibody does; and the G2D antibody does not compete with ASGR1 ligand (GalNAc) binding and K2E antibody only minimally blocks GalNAc binding, whereas the reference antibody competes with GalNAc binding. In addition, certain exemplary anti-ASGR1 antibodies exhibited calcium sensitivity in binding with ASGR1 (e.g., during association and/or disassociation with ASGR1).

Furthermore, as shown in the Examples, treatment of a mouse model for chronic HBV infection with anti-ASGR1-myeloid cell agonist surrogate induced anti-viral T cell and B cell response, significantly lowered both viral DNA and HBsAg antigen, and led to anti-HBsAg seroconversion in infected mice, without deleterious effects on body weight or signs of liver damage. Co-culture experiments also demonstrated that activation of myeloid cells by anti-ASGR1-TLR8 agonist elicited robust anti-viral cytokine response and activated B-cells. These results demonstrate the therapeutic utility for targeting ASGR1 expressing cells with a myeloid cell agonist for treating liver viral infections.

Prior to setting forth this disclosure in more detail, it may be helpful to an understanding thereof to provide definitions of certain terms to be used throughout the disclosure. Additional definitions are set forth throughout the disclosure.

As used throughout the disclosure, the singular form "a," "an," and "the" includes plural references unless the context clearly dictates otherwise. It should be understood that the terms "a" and "an" as used throughout the disclosure refer to "one or more" of the enumerated components.

The use of the alternative (e.g., "or") should be understood to mean either one, both, or any combination thereof of the alternatives. As used throughout the disclosure, the terms "include" and "comprise" are used synonymously.

The phrase "at least one of" when followed by a list of items or elements refers to an open ended set of one or more of the elements in the list, which may, but does not necessarily, include more than one of the elements.

The term "about" as used throughout the disclosure in the context of a number refers to a range centered on that number and spanning 15% less than that number and 15% more than that number. The term "about" used in the context of a range refers to an extended range spanning 15% less than that the lowest number listed in the range and 15% more than the greatest number listed in the range.

Throughout the disclosure, any concentration range, percentage range, ratio range, or integer range is to be understood to include any value (including integers or fractions) or subrange within the recited range unless otherwise indicated.

As used throughout the disclosure, the term "antibody" refers to an immunoglobulin molecule that specifically binds to, or is immunologically reactive toward, a specific antigen. An antibody can include, for example, polyclonal, monoclonal, and genetically engineered antibodies, and antigen binding fragments thereof. An antibody can be, for example, murine, chimeric, humanized, heteroconjugate, bispecific, diabody, triabody, or tetrabody.

As used throughout the disclosure, an "antigen-binding domain" or "antigen-binding fragment refers to a region of a molecule that specifically binds to an antigen. An antigen binding domain can be an antigen-binding portion of an antibody or an antibody fragment. An antigen-binding fragment can include, for example, a Fab', F(ab')2, Fab, Fv, rIgG, scFv, hcAbs (heavy chain antibodies), a single domain antibody, VHH, VNAR, sdAbs, or nanobody.

As used throughout the disclosure, an "Fc domain" refers to a domain from an Fc portion of an antibody that can specifically bind to an Fc receptor, such as an Fcγ receptor or an FcRn receptor.

As used throughout the disclosure, an "antibody construct" refers to a molecule, e.g., a protein, peptide, antibody or portion thereof, that contains an antigen binding domain and an Fc region (e.g., an Fc domain from within the Fc region).

As used throughout the disclosure, "targeting moiety" refers to a structure that has a selective affinity for or selectively binds to a target molecule relative to other non-target molecules. A targeting moiety may include, for example, an antibody, an antibody construct, a peptide, a polypeptide, a ligand, carbohydrate, a polynucleotide, an oligonucleotide, or a receptor or a binding portion thereof. The target biological molecule may be a biological receptor or other structure of a cell, such as a tumor antigen.

As used throughout the disclosure, "identical" or "identity" refer to the similarity between a DNA, RNA, nucleotide, amino acid, or protein sequence to another DNA, RNA, nucleotide, amino acid, or protein sequence. Identity can be expressed in terms of a percentage of sequence identity of a first sequence to a second sequence. Percent (%) sequence identity with respect to a reference DNA sequence can be the percentage of DNA nucleotides in a candidate sequence that are identical with the DNA nucleotides in the reference DNA sequence after aligning the sequences. Percent (%) sequence identity with respect to a reference amino acid sequence can be the percentage of amino acid residues in a candidate sequence that are identical with the amino acid residues in the reference amino acid sequence after aligning the sequences and introducing gaps, if necessary, to achieve the maximum percent sequence identity, and not considering any conservative substitutions as part of the sequence identity. As used throughout the disclosure, the percent sequence identity values is generated using the NCBI BLAST 2.0 software as defined by Altschul et al., "Gapped BLAST and PSI-BLAST: a new generation of protein database search programs," Nucleic Acids Res. 2007, 25, 3389-3402, with the parameters set to default values.

A "small molecule" is an organic compound with a molecular weight of less than 1500, or 100, or 900, or 750, or 600, or 500 Daltons. A "small molecule drug" is a small molecule that has a therapeutic effect such as treating a disease or disorder. In some embodiments, a small molecule drug is a small molecule agonist that has an octanol-water partition coefficient (log P) in the range of from 3 to 6, or from 4 to 5, or from 2 to 4. In some embodiments, a small molecule agonist has a polar surface area of less than 200, or less than 150 A2. In some embodiments, the small molecule agonist has not more than five, or not more than three, hydrogen bond donors, and not more than 10, or not more than three hydrogen bond acceptors. A small molecule is not a protein, a polysaccharide, or a nucleic acid.

As used throughout the disclosure, "specifically binds" and the like refers to the specific association or specific binding between the antigen binding domain and the antigen, as compared with the interaction of the antigen binding domain with a different antigen (i.e., non-specific binding). In some embodiments, an antigen binding domain that recognizes or specifically binds to an antigen has a dissociation constant ($K_D$) of <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Specific binding does not require that the antigen binding domain does not associate with or bind to any other antigen, but rather that it preferentially associates with or binds to the antigen, as compared to association with or binding to an unrelated antigen.

As used throughout the disclosure, "ASGR1," also known as asialoglycoprotein receptor 1, is a major subunit of asialoglycoprotein receptor. Asialoglycoprotein receptor is a hetero-oligomeric protein composed of major and minor subunits and is highly expressed on the surface of hepatocytes, several human carcinoma cell lines, and liver cancers. Asialoglycoprotein receptor mediates the endocytosis of plasma glycoproteins to which the terminal sialic acid residue on their complex carbohydrate moieties has been removed. The receptor recognizes terminal galactose and N-acetylgalactosamine units. After ligand binding to the receptor, the resulting complex is internalized and transported to a sorting organelle, where receptor and ligand are disassociated. The receptor then returns to the cell membrane surface. The asialoglycoprotein receptor may facilitate hepatic infection by multiple viruses including hepatitis B. ASGR1 includes mammalian ASGR1 proteins, e.g., mouse, rat, rabbit, guinea pig, pig, sheep, dog, non-human primate, and human. In some embodiments, ASGR1 refers to an alternatively spliced variant. In some embodiments, ASGR1 is a human ASGR1 having the amino acid sequence set forth in accession NP_001184145.1 or NP_001662.1.

As used throughout the disclosure, an "immune cell" refers to a T cell, B cell, NK cell, NKT cell, or an antigen presenting cell. In some embodiments, an immune cell is a T cell, B cell, NK cell, or NKT cell. In some embodiments, an immune cell is an antigen presenting cell. In some embodiments, an immune cell is not an antigen presenting cell.

As used throughout the disclosure, an "immune stimulatory compound" is a compound that activates or stimulates an immune cell, such as a myeloid cell or an APC.

As used throughout the disclosure, a "myeloid cell" refers to a dendritic cell, a macrophage, a monocyte, a myeloid derived suppressor cell (MDSC).

As used throughout the disclosure, a "myeloid cell agonist" refers to a compound that activates or stimulates an immune response by a myeloid cell.

As used throughout the disclosure, a "benzazepine compound" refers to small molecule chemical compound comprising a benzazepine moiety, where the benzazepine moiety is a benzene ring fused to a 7-membered ring that comprises one or two nitrogen ring members. In addition to the bond where the ring is fused to the benzene ring, the 7-membered ring includes two double bonds (e.g., an azepine or diazepine ring), one double bond (e.g., a dihydroazepine or dihydro-diazepine ring), or no double bonds (e.g., a tetrahydroazepine, azepane, tetrahydrodiazepine, or diazepane ring). The benzazepine moiety is optionally substituted. In some embodiments, the benzazepine moiety is an optionally substituted 4,5-dihydro-3H-benzo[b]azepine. In some embodiments, the benzazepine moiety has the structure:

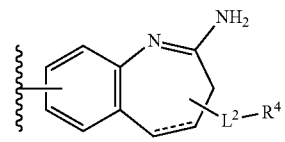

wherein --- is a double bond or a single bond;
$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)—, —C(O)N($R^{10}$)N($R^{10}$)—, —N($R^{10}$)C(O)O—, —OC(O)N ($R^{10}$)—, —C(N$R^{10}$)—, —N($R^{10}$)C(N$R^{10}$)—, —C(N$R^{10}$)N ($R^{10}$)—, —N($R^{10}$)C(N$R^{10}$)N($R^{10}$)—, —S(O)$_2$—, —OS (O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S (O)N($R^{10}$)—;

$R^{12}$ is independently selected at each occurrence from halogen, —O$R^{10}$, —S$R^{10}$, —N($R^{10}$)$_2$, —C(O)$R^{10}$, —C(O) N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O) $R^{10}$, —S(O)$R^{10}$, —S(O)$_2R^{10}$, —P(O)(O$R^{10}$)$_2$, —OP(O) (O$R^{10}$)$_2$, —NO$_2$, =O, =S, =N($R^{10}$), —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), —CN, $C_{1-6}$ alkyl, $C_{2-6}$ alkenyl, $C_{2-6}$ alkynyl;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O) N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl; and $R^{10}$ is independently selected at each occurrence from hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H5, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl; and the moiety is optionally substituted at any position.

The terms "salt" or "pharmaceutically acceptable salt" refer to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, trifluoroacetic acid and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "$C_{x-y}$" when used in conjunction with a chemical moiety, such as alkyl, alkenyl, or alkynyl is meant to include groups that contain from x to y carbons in the chain. For example, the term "$C_{1-6}$ alkyl" refers to substituted or unsubstituted saturated hydrocarbon groups, including straight-chain alkyl and branched-chain alkyl groups that contain from 1 to 6 carbons. The term —$C_{x-y}$ alkylene- refers to a substituted or unsubstituted alkylene chain with from x to y carbons in the alkylene chain. For example —$C_{1-6}$ alkylene- may be selected from methylene, ethylene, propylene, butylene, pentylene, and hexylene, any one of which is optionally substituted.

The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond, respectively. The term —$C_{x-y}$ alkenylene- refers to a substituted or unsubstituted alkenylene chain with from x to y carbons in the alkenylene chain. For example, —$C_{2-6}$ alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$ alkynylene- refers to a substituted or unsubstituted alkynylene chain with from x to y carbons in the alkenylene chain. For example, —$C_{2-6}$ alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. In some embodiments, an alkylene comprises one to five carbon atoms (i.e., $C_1$-$C_5$ alkylene). In some embodiments, an alkylene comprises one to four carbon atoms (i.e., $C_1$-$C_4$ alkylene). In some embodiments, an alkylene comprises one to three carbon atoms (i.e., $C_1$-$C_3$ alkylene). In some embodiments, an alkylene comprises one to two carbon atoms (i.e., $C_1$-$C_2$ alkylene). In some embodiments, an alkylene comprises one carbon atom (i.e., $C_1$ alkylene). In some embodiments, an alkylene comprises five to eight carbon atoms (i.e., $C_5$-$C_8$alkylene). In some embodiments, an alkylene comprises two to five carbon atoms (i.e., $C_2$-$C_5$ alkylene). In some embodiments, an alkylene comprises three to five carbon atoms (i.e., $C_3$-$C_5$ alkylene). Unless stated otherwise specifically in the specification, an alkylene chain is optionally substituted by one or more substituents such as those substituents of the disclosure.

"Alkenylene" refers to a divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. In some embodiments, an alkenylene comprises two to five carbon atoms (i.e., $C_2$-$C_5$ alkenylene). In some embodiments, an alkenylene comprises two to four carbon atoms (i.e., $C_2$-$C_4$ alkenylene). In some embodiments, an alkenylene comprises two to three carbon atoms (i.e., $C_2$-$C_3$ alkenylene). In some embodiments, an alkenylene comprises two carbon atoms (i.e., $C_2$ alkenylene). In some embodiments, an alkenylene comprises five to eight carbon atoms (i.e., $C_5$-$C_8$alkenylene). In some embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents throughout the disclosure.

"Alkynylene" refers to a divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. In some embodiments, an alkynylene comprises two to five carbon atoms (i.e., $C_2$-$C_5$ alkynylene). In some embodiments, an alkynylene comprises two to four carbon atoms (i.e., $C_2$-$C_4$ alkynylene). In some embodiments, an alkynylene comprises two to three carbon atoms (i.e., $C_2$-$C_3$ alkynylene). In some embodiments, an alkynylene comprises two carbon atoms (i.e., $C_2$ alkynylene). In some embodiments, an alkynylene comprises five to eight carbon atoms (i.e., $C_5$-$C_8$ alkynylene). In some embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described throughout the disclosure.

"Heteroalkylene" refers to a divalent hydrocarbon chain including at least one heteroatom in the chain, containing no unsaturation, and preferably having from one to twelve carbon atoms and from one to 6 heteroatoms, e.g., —O—, —NH—, —S—. The heteroalkylene chain is attached to the rest of the molecule through a single bond and to the radical group through a single bond. The points of attachment of the heteroalkylene chain to the rest of the molecule and to the radical group are through the terminal atoms of the chain. In some embodiments, a heteroalkylene comprises one to five carbon atoms and from one to three heteroatoms. In some embodiments, a heteroalkylene comprises one to four carbon atoms and from one to three heteroatoms. In some embodiments, a heteroalkylene comprises one to three carbon atoms and from one to two heteroatoms. In some embodiments, a heteroalkylene comprises one to two carbon atoms and from one to two heteroatoms. In some embodiments, a heteroalkylene comprises one carbon atom and from one to two heteroatoms. In some embodiments, a heteroalkylene comprises five to eight carbon atoms and from one to four heteroatoms. In some embodiments, a heteroalkylene comprises two to five carbon atoms and from one to three heteroatoms. In some embodiments, a heteroalkylene comprises three to five carbon atoms and from one to three heteroatoms. Unless stated otherwise specifically in the specification, a heteroalkylene chain is optionally substituted by one or more substituents such as those substituents described throughout the disclosure.

The term "carbocycle" as used throughout the disclosure refers to a saturated, unsaturated or aromatic ring in which each atom of the ring is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. The term "unsaturated carbocycle" refers to carbocycles with at least one degree of unsaturation and excluding aromatic carbocycles. Examples of unsaturated carbocycles include cyclohexadiene, cyclohexene, and cyclopentene.

The term "heterocycle" as used throughout the disclosure refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more carbons are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or substitutable heteroatoms, e.g., —NH—, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In some embodiments, substituted refers to moieties having substituents replacing two hydrogen atoms on the same carbon atom, such as substituting the two hydrogen atoms on a single carbon with an oxo, imino or thioxo group. As used throughout the disclosure, the term "substituted" is contemplated to include all permissible substituents of organic compounds. In some embodiments, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds of the disclosure which satisfy the valences of the heteroatoms.

In some embodiments, substituents may include any substituents of the disclosure, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$, (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties of the disclosure are understood to include substituted variants. For example, reference to a "heteroaryl" group or moiety implicitly includes both substituted and unsubstituted variants.

In addition, it should be understood that the individual compounds (e.g., proteins), or groups of compounds, derived from the various combinations of the structures and substituents (e.g., domains, regions or peptide components) of the disclosure, are disclosed by the disclosure to the same extent as if each compound or group of compounds was set forth individually. Thus, selection of particular structures or particular substituents is within the scope of the disclosure.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities of the disclosure are intended to include all Z-, E- and tautomeric forms as well.

A "tautomer" refers to a molecule wherein a proton shift from one atom of a molecule to another atom of the same molecule is possible. The compounds provided in the disclosure, in some embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

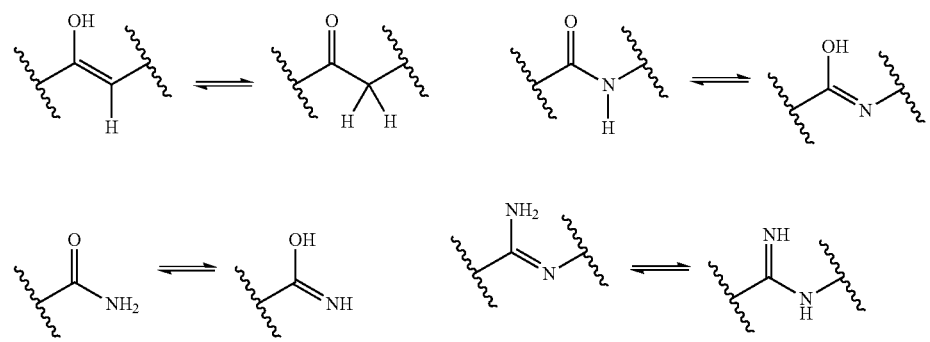

-continued

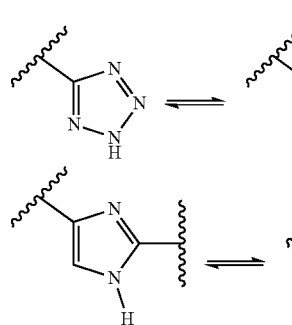 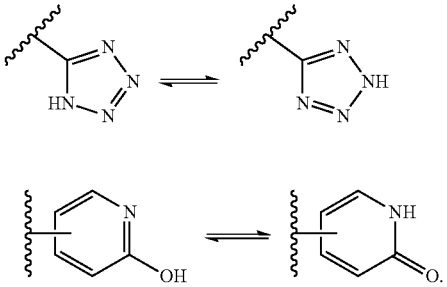

As used throughout the disclosure, a "conjugate" refers to an antibody or antigen binding fragment thereof attached to at least one immune stimulatory compound, optionally via a linker.

The phrases "intravenous administration" and "administered intravenously" as used throughout the disclosure refer to injection or infusion of a conjugate into a vein of a subject.

The phrases "intravenous slow infusion" and "IV slow infusion" as used throughout the disclosure refer to an intravenous infusion that results in a Tmax of about 4 hours or more.

The phrases "subcutaneous administration", "subcutaneously administering" and the like refer to administration of a conjugate into the subcutis of a subject. For clarity, a subcutaneous administration is distinct from an intratumoral injection into a tumor or cancerous lesion located in the subcuta.

The phrase "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Anti-ASGR1 Antibodies

The disclosure provides antibodies (e.g., isolated monoclonal antibodies) that specifically bind to ASGR1, also referred to as anti-ASGR1 antibodies, or antigen-binding fragments thereof.

In some embodiments of the disclosure, an antibody or antigen binding fragment thereof comprises two light chain polypeptides (light chains) and two heavy chain polypeptides (heavy chains), held together covalently by disulfide linkages.

In some embodiments, the heavy chain typically comprises a heavy chain variable region (VH) and a heavy chain constant region. In some embodiments, the heavy chain constant region typically comprises three domains, CH1, CH2, and CH3. Nonlimiting exemplary heavy chain constant regions include human IgG1, human IgG2, human IgG3, and human IgG4 constant regions. In some embodiments, an antibody of the disclosure comprises an IgG1 constant region. Exemplary heavy chain constant regions include human IgG1 heavy chain constant region (SEQ ID NO:230), human IgG1null heavy chain constant region (SEQ ID NO:231), mouse IgG2a heavy chain constant region (SEQ ID NO:233), and rat IgG2b heavy chain constant region (SEQ ID NO:235).

In some embodiments the light chain comprises a light chain variable region (VL) and a light chain constant region. Nonlimiting exemplary light chain constant regions include kappa and lambda constant regions. A nonlimiting exemplary human kappa constant region is shown in SEQ ID NO:232. Another exemplary light chain constant region is mouse kappa constant region shown in SEQ ID NO:234. Another exemplary light chain constant region is rat kappa constant region shown in SEQ ID NO:236.

The constant domains provide the general framework of the antibody and may not be involved directly in binding the antibody to an antigen, but can be involved in various effector functions, such as participation of the antibody in antibody-dependent cellular cytotoxicity (ADCC), ADCP (antibody-dependent cellular phagocytosis), CDC (complement-dependent cytotoxicity) and complement fixation, binding to Fc receptors (e.g., CD16, CD32, FcRn), greater in vivo half-life relative to a polypeptide lacking an Fc region, protein A binding, and perhaps even placental transfer (see Capon et al., Nature 337:525, 1989). As used throughout the disclosure, "an Fc region constant domain portion" or "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In some embodiments, an Fc region portion includes the CH2 and CH3 domains of an IgG, IgA, or IgD antibody and any combination thereof, or the CH3 and CH4 domains of an IgM or IgE antibody and any combination thereof.

An Fc region or domain may interact with different types of FcRs. The different types of FcRs may include, for example, FcγRI, FcγRIIA, FcγRIIB, FcγRIIIA, FcγRIIIB, FcαRI, FcµR, FcεRI, FcεRII, and FcRn. FcRs may be located on the membrane of certain immune cells including, for example, B lymphocytes, natural killer cells, macrophages, neutrophils, follicular dendritic cells, eosinophils, basophils, platelets, and mast cells. Once the FcR is engaged by the Fc domain, the FcR may initiate functions including, for example, clearance of an antigen-antibody complex via receptor-mediated endocytosis, antibody-dependent cell-mediated cytotoxicity (ADCC), antibody dependent cell-mediated phagocytosis (ADCP), trogocytosis, trogoptosis, and ligand-triggered transmission of signals across the plasma membrane that can result in alterations in secretion, exocytosis, and cellular metabolism. FcRs may deliver signals when FcRs are aggregated by antibodies and multivalent antigens at the cell surface. The aggregation of FcRs with immunoreceptor tyrosine-based activation motifs (ITAMs) may sequentially activate SRC family tyrosine kinases and SYK family tyrosine kinases. ITAM comprises a twice-repeated YxxL sequence flanking seven variable residues. The SRC and SYK kinases may connect the transduced signals with common activation pathways.

In some embodiments, an Fc region or domain can exhibit reduced binding affinity to one or more Fc receptors. In some embodiments, an Fc region or domain can exhibit reduced binding affinity to one or more Fcγ receptors. In some embodiments, an Fc region or domain can exhibit reduced binding affinity to FcRn receptors. In some embodiments, an Fc region or domain can exhibit reduced binding affinity to Fcγ and FcRn receptors. In some embodiments, an Fc domain is an Fc null domain or region. As used throughout the disclosure, an "Fc null" refers to a domain that exhibits weak to no binding to any of the Fcgamma receptors. In some embodiments, an Fc null domain or region exhibits a reduction in binding affinity (e.g., increase in Kd) to Fcγ receptors of at least about 1000-fold.

The Fc region or domain may have one or more, two or more, three or more, or four or more, or up to five amino acid substitutions that decrease binding of the Fc region or domain to an Fc receptor. In some embodiments, an Fc region or domain exhibits decreased binding to FcγRI (CD64), FcγRIIA (CD32), FcγRIIIA (CD16a), FcγRIIIB (CD16b), or any combination thereof. In order to decrease binding affinity of an Fc region or domain to an Fc receptor, an Fc region or domain may comprise one or more amino acid substitutions that has the effect of reducing the affinity of the Fc domain or region to an Fc receptor. In some embodiments, the Fc region or domain is an IgG1 and the one or more substitutions in the Fc region or domain comprise any one or more of IgG1 heavy chain mutations corresponding to E233P, L234V, L234A, L235A, L235E, ΔG236, G237A, E318A, K320A, K322A, A327G, A330S, or P331S according to the EU index of Kabat numbering.

In some embodiments, the Fc region or domain can comprise a sequence of the IgG1 isoform that has been modified from the wild-type IgG1 sequence. A modification can comprise a substitution at more than one amino acid residue, such as at 5 different amino acid residues including L235V/F243L/R292P/Y300L/P396L (IgG1VLPLL) according to the EU index of Kabat numbering. A modification can comprise a substitution at more than one amino acid residues, such as at two different amino acid residues including S239D/I332E (IgG1DE) according to the EU index of Kabat numbering. A modification can comprise a substitution at more than one amino acid residue, such as at three different amino acid residues including S298A/E333A/K334A (IgG1AAA) according to the EU index of Kabat numbering. Non-limiting exemplary human IgG1 heavy chain constant regions are shown in SEQ ID NOS:230 and 231. In some embodiments, an antibody of the disclosure comprises a mouse IgG2a heavy chain constant region shown in SEQ ID NO:233. In some embodiments, an antibody of the disclosure comprises a rat IgG2b heavy chain constant region shown in SEQ ID NO:235.

An antibody or Fc domain may be modified to acquire or improve at least one constant region-mediated biological effector function relative to an unmodified antibody or Fc domain, e.g., to enhance FcγR interactions. In some embodiments, a modification can increase CD32b binding (and support transdelivery in a PBMC assay) comprises a substitution at S267L and E329F (IgG1LF, also known as SELF double mutant) according to the EU index of Kabat numbering. For example, an antibody with a constant region that binds to FcγRIIA, FcγRIIB and/or FcγRIIIA with greater affinity than the corresponding wild type constant region may be produced according to the methods described of the disclosure. An Fc domain that binds to FcγRIIA, FcγRIIB and/or FcγRIIIA with greater affinity than the corresponding wild type Fc domain may be produced according to the methods of the disclosure.

In some embodiments, an Fc region or domain found in an anti-ASGR1 antibody of the disclosure is capable of mediating one or more of these effector functions, or lacks one or more or all of these activities or have one or more of the effector activities increased by way of, for example, one or more mutations as compared to the unmodified Fc region or domain.

In some embodiments, the antigen-recognition regions of the antibody variable domains comprise six complementarity determining regions (CDRs), or hypervariable regions, that lie within the framework of the heavy chain variable region and light chain variable region at the N-terminal ends of the two heavy and two light chains.

In some embodiments, an antigen binding domain comprises a light chain complementary determining region 1 (LCDR1), a light chain complementary determining region 2 (LCDR2), a light chain complementary determining region 3 (LCDR3), a heavy chain complementary determining region 1 (HCDR1), a heavy chain complementary determining region 2 (HCDR2), and a heavy chain complementary determining region 3 (HCDR3). In some embodiments, an antibody may be a heavy-chain only antibody, in which case the antigen binding domain comprises HCDR1, HCDR2, and HCDR3, and the antibody lacks a light chain.

In some embodiments, an anti-ASGR1 antibody or antigen binding fragment thereof comprises:

a heavy chain CDR1 (VH-CDR1) comprising the amino acid sequence of SEQ ID NO:1, a VH-CDR2 comprising the amino acid sequence selected from any one of SEQ ID NOS:6-8, a VH-CDR3 comprising the amino acid sequence of SEQ ID NO:13; and a light chain CDR1 (VL-CDR1) comprising the amino acid sequence of SEQ ID NO:18, a VL-CDR2 comprising the amino acid sequence selected from any one of SEQ ID NOS:23-25, and a VL-CDR3 comprising the amino acid sequence of SEQ ID NO:33;

a VH-CDR1 comprising the amino acid sequence of SEQ ID NO:2, a VH-CDR2 comprising the amino acid sequence of SEQ ID NO:9, a VH-CDR3 comprising the amino acid sequence of SEQ ID NO:14; and a VL-CDR1 comprising the amino acid sequence of SEQ ID NO:19, a VL-CDR2 comprising the amino acid sequence of SEQ ID NO:26 or SEQ ID NO:27, and a VL-CDR3 comprising the amino acid sequence of SEQ ID NO:34;

a VH-CDR1 comprising the amino acid sequence of SEQ ID NO:5, a VH-CDR2 comprising the amino acid sequence of SEQ ID NO:12, a VH-CDR3 comprising the amino acid sequence of SEQ ID NO:17; and a VL-CDR1 comprising the amino acid sequence of SEQ ID NO:22, a VL-CDR2 comprising the amino acid sequence of SEQ ID NO:32, and a VL-CDR3 comprising the amino acid sequence of SEQ ID NO:37;

a VH-CDR1 comprising the amino acid sequence of SEQ ID NO:3, a VH-CDR2 comprising the amino acid sequence of SEQ ID NO:10, a VH-CDR3 comprising the amino acid sequence of SEQ ID NO:15; and a VL-CDR1 comprising the amino acid sequence of SEQ ID NO:20, a VL-CDR2 comprising the amino acid sequence selected from any one of SEQ ID NOS:28-30, and a VL-CDR3 comprising the amino acid sequence of SEQ ID NO:35; or a VH-CDR1 comprising the amino acid sequence of SEQ ID NO:4, a VH-CDR2 comprising the amino acid sequence of SEQ ID NO:11, a VH-CDR3 comprising the amino acid sequence of SEQ ID NO:16; and a VL-CDR1 comprising the amino acid sequence of SEQ ID NO:21, a VL-CDR2 comprising the amino acid sequence of SEQ ID NO:31, and a VL-CDR3 comprising the amino acid sequence of SEQ ID NO:36.

In some embodiments, the antibody or antigen binding fragment thereof comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33.

In some embodiments, the antibody or antigen binding fragment thereof comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33.

In some embodiments, the antibody or antigen binding fragment thereof comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34.

In some embodiments, the antibody or antigen binding fragment thereof comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:24, and a VL-CDR3 comprising the amino acid sequence of SEQ ID NO:33.

In some embodiments, the antibody or antigen binding fragment thereof comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:24, and a VL-CDR3 comprising the amino acid sequence of SEQ ID NO:33.

In some embodiments, the antibody or antigen binding fragment thereof comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:27, and a VL-CDR3 comprising the amino acid sequence of SEQ ID NO:34.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:38, and a light chain variable region (VL) comprising an amino acid sequence that is at least 90%, 91%, 92%, 93%, 94%, 95%, 96%, 97%, 98%, or 99% identical to the amino acid sequence of SEQ ID NO:126, provided that the amino acid sequences of the VH-CDRs (i.e., SEQ ID NOS:1, 6, and 13) and VL-CDRs (i.e., SEQ ID NOS:18, 23, and 33) are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence selected from any one of SEQ ID NOS:43-88 and 238-243, and a light chain variable region (VL) comprising an amino acid sequence that is at least 90%, 91%, 92%, 93%, 94%, 95%, 96%, 97%, 98%, or 99% identical to the amino acid sequence selected from any one of SEQ ID NOS:131-133 and 244-249, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:240, and a light chain variable region (VL) comprising an amino acid sequence that is at least 90%, 91%, 92%, 93%, 94%, 95%, 96%, 97%, 98%, or 99% identical to the amino acid sequence of SEQ ID NO:247, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:239, and a light chain variable region (VL) comprising an amino acid sequence that is at least 90%, 91%, 92%, 93%, 94%, 95%, 96%, 97%, 98%, or 99% identical to the amino acid sequence of SEQ ID NO:247, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:39, and a light chain comprising an amino acid sequence that is at least 90%, 91%, 92%, 93%, 94%, 95%, 96%, 97%, 98%, or 99% identical to the amino acid sequence of SEQ ID NO:127, provided that the amino acid sequences of the VH-CDRs (i.e., SEQ ID NOS:2, 9, and 14) and VL-CDRs (i.e., SEQ ID NOS:19, 26, and 34) are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence selected from any one of SEQ ID NOS:89-93, and a light chain variable region (VL) comprising an amino acid sequence that is at least 90%, 91%, 92%, 93%, 94%, 95%, 96%, 97%, 98%, or 99% identical to the amino acid sequence selected from any one of SEQ ID NOS:134-137, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:89, and a light chain variable region (VL) comprising an amino acid sequence that is at least 90%, 91%, 92%, 93%, 94%, 95%, 96%, 97%, 98%, or 99% identical to the amino acid sequence of SEQ ID NO:134, provided that the amino acid sequences of the VH-CDRs and VL-CDRs are unchanged. In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:89, and a light chain variable region (VL) comprising an amino acid sequence that is at least 90%, 91%, 92%, 93%, 94%, 95%, 96%, 97%, 98%, or 99% identical to the amino acid sequence of SEQ ID NO:136, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:42, and a light chain variable region (VL) comprising an amino acid sequence that is at least 90%, 91%, 92%, 93%, 94%, 95%, 96%, 97%, 98%, or 99% identical to the amino acid sequence of SEQ ID NO:130, provided that the amino acid sequences of the VH-CDRs (i.e., SEQ ID NOS:5, 12, and 17) and VL-CDRs (i.e., SEQ ID NOS:22, 32, and 37) are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence selected from any one of SEQ ID NOS:113-125, and a light chain variable region (VL) comprising an amino acid sequence that is at least 90%, 91%, 92%, 93%, 94%, 95%, 96%, 97%, 98%, or 99% identical to the amino acid sequence selected from any one of SEQ ID NOS:143-149, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:40, and a light chain variable region (VL) comprising an amino acid sequence that is at least 90%, 91%, 92%, 93%, 94%, 95%, 96%, 97%, 98%, or 99% identical to the amino acid sequence of SEQ ID NO:128, provided that the amino acid sequences of the VH-CDRs (i.e., SEQ ID NOS:3, 10, and 15) and VL-CDRs (i.e., SEQ ID NOS:20, 28, and 35) are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence selected from any one of SEQ ID NOS:94-102, and a light chain variable region (VL) comprising an amino acid sequence that is at least 90%, 91%, 92%, 93%, 94%, 95%, 96%, 97%, 98%, or 99% identical to the amino acid sequence selected from any one of SEQ ID NOS:138-141, provided that the amino acid sequences of the VH-CDRs and VL-CDRs are unchanged.

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:41, and a light chain variable region (VL) comprising an amino acid sequence that is at least 90%, 91%, 92%, 93%, 94%, 95%, 96%, 97%, 98%, or 99% identical to the amino acid sequence of SEQ ID NO:129, provided that the amino acid sequences of the VH-CDRs (i.e., SEQ ID NOS:4, 11, and 16) and VL-CDRs (i.e., SEQ ID NOS:21, 31, and 36) are unchanged.

In some embodiments, an antibody or antigen binding fragment thereof may be identified by its heavy and/or light chain CDRs using any one of the following methods: Kabat, Chothia, AbM, Contact, IMGT, and/or Aho. In some embodiments, an antibody or antigen binding fragment thereof may be identified by CDRs provided in Tables B1 through B5. In some embodiments, an anti-ASGR1 antibody or antigen binding fragment thereof may be identified by CDRs provided in Tables B1 through B5. In some embodiments, an anti-ASGR1 antibody or antigen binding fragment thereof may be identified by CDRs provided in Table B1. In some embodiments, an anti-ASGR1 antibody or antigen binding fragment thereof may be identified by CDRs provided in Table B2. In some embodiments, an anti-ASGR1 antibody or antigen binding fragment thereof may be identified by CDRs provided in Table B3. In some embodiments, an anti-ASGR1 antibody or antigen binding fragment thereof may be identified by CDRs provided in Table B4. In some embodiments, an anti-ASGR1 antibody or antigen binding fragment thereof may be identified by CDRs provided in Table B5.

TABLE B1

| | hzG2D Anti-ASGR1 CDRs | | | | |
|---|---|---|---|---|---|
| Antibody CDR Identity | Kabat | Chothia | AbM | Contact | IMGT |
| VH CDR1 | GYYMH (SEQ ID NO:1) | GYSFTGY (SEQ ID NO:252) | GYSFTGYYMH (SEQ ID NO:253) | TGYYMH (SEQ ID NO:254) | GYSFTGYY (SEQ ID NO: 255) |
| VH CDR2 | RINPNNGATNYNQNFKD (SEQ ID NO:6; G2D) RINPNQGATNYNQNFKD (SEQ ID NO:7; G2.1D) RINPNNAATNYNQNFKD (SEQ ID NO:8; G2.2D) | NPNNAA (SEQ ID NO:256) | RINPNNAATN (SEQ ID NO:257) | WMGRINPNNAATN (SEQ ID NO:258) | INPNNAAT (SEQ ID NO :259) |
| VH CDR3 | VNFYY (SEQ ID NO:13) | VNFYY (SEQ ID NO:13) | VNFYY (SEQ ID NO:13) | TSVNFY (SEQ ID NO:260) | TSVNFYY (SEQ ID NO:261) |
| VL CDR1 | KASQVINSYLS (SEQ ID NO:18) | KASQVINSYLS (SEQ ID NO:18) | KASQVINSYLS (SEQ ID NO:18) | NSYLSWF (SEQ ID NO:262) | QVINSY (SEQ ID NO:263) |

TABLE B1-continued hzG2D Anti-ASGR1 CDRs

| Antibody CDR Identity | Kabat | Chothia | AbM | Contact | IMGT |
|---|---|---|---|---|---|
| VL CDR2 | RANTLVD (SEQ ID NO:23; G2D) RANTLVS (SEQ ID NO:24; G2.1D) RANTLVE (SEQ ID NO:25; G2.2D) | RANTLVD (SEQ ID NO:23) | RANTLVD (SEQ ID NO:23) | SLIYRANTLV (SEQ ID NO:264) | RA |
| VL CDR3 | LQYAEFPYT (SEQ ID NO:33) | LQYAEFPYT (SEQ ID NO:33) | LQYAEFPYT (SEQ ID NO:33) | LQYAEFPY (SEQ ID NO:265) | LQYAEFPYT (SEQ ID NO:33) |

TABLE B2 hzK2E Anti-ASGR1 CDRs

| Antibody CDR Identity | Kabat | Chothia | AbM | Contact | IMGT |
|---|---|---|---|---|---|
| VH CDR1 | SYTMH (SEQ ID NO:2) | GYTFTSY (SEQ ID NO:266) | GYTFTSYTMH (SEQ ID NO:267) | TSYTMH (SEQ ID NO:268) | GYTFTSYT (SEQ ID NO:269) |
| VH CDR2 | YISPSSGYTEYNQKFKD (SEQ ID NO:9) | SPSSGY (SEQ ID NO:270) | YISPSSGYTE (SEQ ID NO:271) | WMGYISPSSGYTE (SEQ ID NO:272) | ISPSSGYT (SEQ ID NO:273) |
| VH CDR3 | KFDY (SEQ ID NO:14) | KFDY (SEQ ID NO:14) | KFDY (SEQ ID NO:14) | ARKFD (SEQ ID NO:274) | ARKFDY (SEQ ID NO:275) |
| VL CDR1 | KASQDINSYLS (SEQ ID NO:19) | KASQDINSYLS (SEQ ID NO:19) | KASQDINSYLS (SEQ ID NO:19) | NSYLSWF (SEQ ID NO:262) | QDINSY (SEQ ID NO:276) |
| VL CDR2 | RANRLVD (SEQ ID NO:26) | RANRLVD (SEQ ID NO:26) | RANRLVD (SEQ ID NO:26) | SLIYRANRLV (SEQ ID NO:277) | RA |
| VL CDR3 | LQYDEFPFT (SEQ ID NO:34) | LQYDEFPFT (SEQ ID NO:34) | FGQGTKLEIKRTV (SEQ ID NO:278) | LQYDEFPF (SEQ ID NO:279) | LQYDEFPFT (SEQ ID NO:34) |

TABLE B3 hzL4L Anti-ASGR1 CDRs

| Antibody CDR Identity | Kabat | Chothia | AbM | Contact | IMGT |
|---|---|---|---|---|---|
| VH CDR1 | SDYAWN (SEQ ID NO:3) | GGSISSDY (SEQ ID NO:280) | GGSISSDYAWN (SEQ ID NO:281) | SSDYAWN (SEQ ID NO:282) | GGSISSDYA (SEQ ID NO:283) |
| VH CDR2 | YISYSGSTRYNPSLKS (SEQ ID NO:10) | SYSGS (SEQ ID NO:284) | YISYSGSTR (SEQ ID NO:285) | WIGYISYSGSTR (SEQ ID NO:286) | ISYSGST (SEQ ID NO:287) |
| VH CDR3 | RYRYDEGYGMDY (SEQ ID NO:15) | RYRYDEGYGMDY (SEQ ID NO:15) | RYRYDEGYGMDY (SEQ ID NO:15) | ARRYRYDEGYGMD (SEQ ID NO:288) | ARRYRYDEGYGMDY (SEQ ID NO:289) |
| VL CDR1 | RASENIYSNLA (SEQ ID NO:20) | RASENIYSNLA (SEQ ID NO:20) | RASENIYSNLA (SEQ ID NO:20) | YSNLAWY (SEQ ID NO:290) | ENIYSN (SEQ ID NO:291) |
| VL CDR2 | AATNLAD (SEQ ID NO:28) | AATNLAD (SEQ ID NO:28) | AATNLAD (SEQ ID NO:28) | LLIYAATNLA (SEQ ID NO:292) | AA |
| VL CDR3 | QHFWGTPPWT (SEQ ID NO:35) | QHFWGTPPWT (SEQ ID NO:35) | QHFWGTPPWT (SEQ ID NO:35) | QHFWGTPPW (SEQ ID NO:293) | QHFWGTPPWT (SEQ ID NO:35) |

TABLE B4 hzJ4F Anti-ASGR1 CDRs

| Antibody CDR Identity | Kabat | Chothia | AbM | Contact | IMGT |
|---|---|---|---|---|---|
| VH CDR1 | SYWIN (SEQ ID NO:5) | GYTFTSY (SEQ ID NO:266) | GYTFTSYWIN (SEQ ID NO:294) | TSYWIN (SEQ ID NO:295) | GYTFTSYW (SEQ ID NO:296) |
| VH CDR2 | RIVPGSGSTYYNEMFKD (SEQ ID NO:12) | VPGSGS (SEQ ID NO:297) | RIVPGSGSTY (SEQ ID NO:298) | WMGRIVPGSGSTY (SEQ ID NO:299) | IVPGSGST (SEQ ID NO:300) |
| VH CDR3 | KPNFDV (SEQ ID NO:17) | KPNFDV (SEQ ID NO:17) | KPNFDV (SEQ ID NO:17) | ARKPNFD (SEQ ID NO:301) | ARKPNFDV (SEQ ID NO:302) |
| VL CDR1 | KASQNVGTNVA (SEQ ID NO:22) | KASQNVGTNVA (SEQ ID NO:22) | KASQNVGTNVA (SEQ ID NO:22) | GTN VAWY (SEQ ID NO:303) | QNVGTN (SEQ ID NO:304) |
| VL CDR2 | SASYRFS (SEQ ID NO:32) | SASYRFS (SEQ ID NO:32) | SASYRFS (SEQ ID NO:32) | AVIYSASYRF (SEQ ID NO:305) | SA |
| VL CDR3 | QQYNSYPLT (SEQ ID NO:37) | QQYNSYPLT (SEQ ID NO:37) | QQYNSYPLT (SEQ ID NO:37) | QQYNSYPL (SEQ ID NO:306) | QQYNSYPLT (SEQ ID NO:37) |

TABLE B5 hzH8K Anti-ASGR1 CDRs

| Antibody CDR Identity | Kabat | Chothia | AbM | Contact | IMGT |
|---|---|---|---|---|---|
| VH CDR1 | SDYAWN (SEQ ID NO:4) | GGSISSDY (SEQ ID NO:280) | GGSISSDYAWN (SEQ ID NO:281) | SSDYAWN (SEQ ID NO:282) | GGSISSDYA (SEQ ID NO:283) |
| VH CDR2 | YRSYRGSTSYNPSLKS (SEQ ID NO:11) | SYRGS (SEQ ID NO:307) | YRSYRGSTS (SEQ ID NO:308) | WIGYRSYRGSTS (SEQ ID NO:309) | RSYRGST (SEQ ID NO:310) |
| VH CDR3 | RGYYGSSSHWYFDV (SEQ ID NO:16) | RGYYGSSSHWYFDV (SEQ ID NO:16) | RGYYGSSSHWYFDV (SEQ ID NO:16) | ARRGYYGSSSHWYFD (SEQ ID NO:311) | ARRGYYGSSSHWYFDV (SEQ ID NO:312) |
| VL CDR1 | RASENIYSYLA (SEQ ID NO:21) | RASENIYSYLA (SEQ ID NO:21) | RASENIYSYLA (SEQ ID NO:21) | YSYLAWY (SEQ ID NO:313) | ENIYSY (SEQ ID NO:314) |
| VL CDR2 | NAKTLAE (SEQ ID NO:31) | NAKTLAE (SEQ ID NO:31) | NAKTLAE (SEQ ID NO:31) | LLIYNAKTLA (SEQ ID NO:315) | NA |
| VL CDR3 | QHHYGTPLT (SEQ ID NO:36) | QHHYGTPLT (SEQ ID NO:36) | QHHYGTPLT (SEQ ID NO:36) | QHHYGTPL (SEQ ID NO:316) | QHHYGTPLT (SEQ ID NO:36) |

In some embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence selected from any one of SEQ ID NOS:103-112, and a light chain variable region (VL) comprising an amino acid sequence that is at least 90%, 91%, 92%, 93%, 94%, 95%, 96%, 97%, 98%, or 99% identical to the amino acid sequence of SEQ ID NO:142, provided that the amino acid sequences of the VH-CDRs and VL-CDRs are unchanged.

In some embodiments, the antibody or antigen binding fragment thereof comprises a heavy chain variable region (VH) comprising an amino acid sequence of SEQ ID NO:38, and a light chain variable region (VL) comprising an amino acid sequence of SEQ ID NO:126.

In some embodiments, the antibody or antigen binding fragment thereof comprises a VH comprising an amino acid sequence selected from any one of SEQ ID NOS:43-88 and 238-243, and a VL comprising an amino acid sequence selected from any one of SEQ ID NOS:131-133 and 244-249.

In some embodiments, the antibody or antigen binding fragment thereof comprises a VH comprising the amino acid sequence of SEQ ID NO:43 and a VL comprising the amino acid sequence of SEQ ID NO:131.

In some embodiments, the antibody or antigen binding fragment thereof comprises a VH comprising the amino acid sequence of SEQ ID NO:44 and a VL comprising the amino acid sequence of SEQ ID NO:131.

In some embodiments, the antibody or antigen binding fragment thereof comprises a VH comprising the amino acid sequence of SEQ ID NO:45 and a VL comprising the amino acid sequence of SEQ ID NO:131.

In some embodiments, the antibody or antigen binding fragment thereof comprises a VH comprising the amino acid sequence of SEQ ID NO:46 and a VL comprising the amino acid sequence of SEQ ID NO:131.

In some embodiments, the antibody or antigen binding fragment thereof comprises a VH comprising the amino acid sequence of SEQ ID NO:47 and a VL comprising the amino acid sequence of SEQ ID NO:131.

In some embodiments, the antibody or antigen binding fragment thereof comprises a VH comprising the amino acid sequence of SEQ ID NO:48 and a VL comprising the amino acid sequence of SEQ ID NO:131.

In some embodiments, the antibody or antigen binding fragment thereof comprises a VH comprising the amino acid sequence of SEQ ID NO:49 and a VL comprising the amino acid sequence of SEQ ID NO:131.

In some embodiments, the antibody or antigen binding fragment thereof comprises a VH comprising the amino acid sequence of SEQ ID NO:50 and a VL comprising the amino acid sequence of SEQ ID NO:131.

In some embodiments, the antibody or antigen binding fragment thereof comprises a VH comprising the amino acid sequence of SEQ ID NO:51 and a VL comprising the amino acid sequence of SEQ ID NO:131.

In some embodiments, the antibody or antigen binding fragment thereof comprises a VH comprising the amino acid sequence of SEQ ID NO:52 and a VL comprising the amino acid sequence of SEQ ID NO:131.

In some embodiments, the antibody or antigen binding fragment thereof comprises a VH comprising the amino acid sequence of SEQ ID NO:53 and a VL comprising the amino acid sequence of SEQ ID NO:131.

In some embodiments, the antibody or antigen binding fragment thereof comprises a VH comprising the amino acid sequence of SEQ ID NO:54 and a VL comprising the amino acid sequence of SEQ ID NO:131.

In some embodiments, the antibody or antigen binding fragment thereof comprises a VH comprising the amino acid sequence of SEQ ID NO:55 and a VL comprising the amino acid sequence of SEQ ID NO:131.

In some embodiments, the antibody or antigen binding fragment thereof comprises a VH comprising the amino acid sequence of SEQ ID NO:56 and a VL comprising the amino acid sequence of SEQ ID NO:131.

In some embodiments, the antibody or antigen binding fragment thereof comprises a VH comprising the amino acid sequence of SEQ ID NO:57 and a VL comprising the amino acid sequence of SEQ ID NO:131.

In some embodiments, the antibody or antigen binding fragment thereof comprises a VH comprising the amino acid sequence of SEQ ID NO:58 and a VL comprising the amino acid sequence of SEQ ID NO:131.

In some embodiments, the antibody or antigen binding fragment thereof comprises a VH comprising the amino acid sequence of SEQ ID NO:59 and a VL comprising the amino acid sequence of SEQ ID NO:131.

In some embodiments, the antibody or antigen binding fragment thereof comprises a VH comprising the amino acid sequence of SEQ ID NO:60 and a VL comprising the amino acid sequence of SEQ ID NO:131.

In some embodiments, the antibody or antigen binding fragment thereof comprises a VH comprising the amino acid sequence of SEQ ID NO:61 and a VL comprising the amino acid sequence of SEQ ID NO:131.

In some embodiments, the antibody or antigen binding fragment thereof comprises a VH comprising the amino acid sequence of SEQ ID NO:62 and a VL comprising the amino acid sequence of SEQ ID NO:131.

In some embodiments, the antibody or antigen binding fragment thereof comprises a VH comprising the amino acid sequence of SEQ ID NO:63 and a VL comprising the amino acid sequence of SEQ ID NO:131.

In some embodiments, the antibody or antigen binding fragment thereof comprises a VH comprising the amino acid sequence of SEQ ID NO:64 and a VL comprising the amino acid sequence of SEQ ID NO:131.

In some embodiments, the antibody or antigen binding fragment thereof comprises a VH comprising the amino acid sequence of SEQ ID NO:65 and a VL comprising the amino acid sequence of SEQ ID NO:131.

In some embodiments, the antibody or antigen binding fragment thereof comprises a VH comprising the amino acid sequence of SEQ ID NO:66 and a VL comprising the amino acid sequence of SEQ ID NO:131.

In some embodiments, the antibody or antigen binding fragment thereof comprises a VH comprising the amino acid sequence of SEQ ID NO:67 and a VL comprising the amino acid sequence of SEQ ID NO:131.

In some embodiments, the antibody or antigen binding fragment thereof comprises a VH comprising the amino acid sequence of SEQ ID NO:68 and a VL comprising the amino acid sequence of SEQ ID NO:131.

In some embodiments, the antibody or antigen binding fragment thereof comprises a VH comprising the amino acid sequence of SEQ ID NO:69 and a VL comprising the amino acid sequence of SEQ ID NO:131.

In some embodiments, the antibody or antigen binding fragment thereof comprises a VH comprising the amino acid sequence of SEQ ID NO:70 and a VL comprising the amino acid sequence of SEQ ID NO:131.

In some embodiments, the antibody or antigen binding fragment thereof comprises a VH comprising the amino acid sequence of SEQ ID NO:71 and a VL comprising the amino acid sequence of SEQ ID NO:131.

In some embodiments, the antibody or antigen binding fragment thereof comprises a VH comprising the amino acid sequence of SEQ ID NO:72 and a VL comprising the amino acid sequence of SEQ ID NO:131.

In some embodiments, the antibody or antigen binding fragment thereof comprises a VH comprising the amino acid sequence of SEQ ID NO:73 and a VL comprising the amino acid sequence of SEQ ID NO:131.

In some embodiments, the antibody or antigen binding fragment thereof comprises a VH comprising the amino acid sequence of SEQ ID NO:74 and a VL comprising the amino acid sequence of SEQ ID NO:131.

In some embodiments, the antibody or antigen binding fragment thereof comprises a VH comprising the amino acid sequence of SEQ ID NO:75 and a VL comprising the amino acid sequence of SEQ ID NO:131.

In some embodiments, the antibody or antigen binding fragment thereof comprises a VH comprising the amino acid sequence of SEQ ID NO:76 and a VL comprising the amino acid sequence of SEQ ID NO:131.

In some embodiments, the antibody or antigen binding fragment thereof comprises a VH comprising the amino acid sequence of SEQ ID NO:77 and a VL comprising the amino acid sequence of SEQ ID NO:131.

In some embodiments, the antibody or antigen binding fragment thereof comprises a VH comprising the amino acid sequence of SEQ ID NO:78 and a VL comprising the amino acid sequence of SEQ ID NO:131.

In some embodiments, the antibody or antigen binding fragment thereof comprises a VH comprising the amino acid sequence of SEQ ID NO:79 and a VL comprising the amino acid sequence of SEQ ID NO:131.

In some embodiments, the antibody or antigen binding fragment thereof comprises a VH comprising the amino acid sequence of SEQ ID NO:80 and a VL comprising the amino acid sequence of SEQ ID NO:131.

In some embodiments, the antibody or antigen binding fragment thereof comprises a VH comprising the amino acid sequence of SEQ ID NO:81 and a VL comprising the amino acid sequence of SEQ ID NO:131.

In some embodiments, the antibody or antigen binding fragment thereof comprises a VH comprising the amino acid sequence of SEQ ID NO:82 and a VL comprising the amino acid sequence of SEQ ID NO:131.

In some embodiments, the antibody or antigen binding fragment thereof comprises a VH comprising the amino acid sequence of SEQ ID NO:83 and a VL comprising the amino acid sequence of SEQ ID NO:131.

In some embodiments, the antibody or antigen binding fragment thereof comprises a VH comprising the amino acid sequence of SEQ ID NO:84 and a VL comprising the amino acid sequence of SEQ ID NO:131.

In some embodiments, the antibody or antigen binding fragment thereof comprises a VH comprising the amino acid sequence of SEQ ID NO:85 and a VL comprising the amino acid sequence of SEQ ID NO:131.

In some embodiments, the antibody or antigen binding fragment thereof comprises a VH comprising the amino acid sequence of SEQ ID NO:86 and a VL comprising the amino acid sequence of SEQ ID NO:131.

In some embodiments, the antibody or antigen binding fragment thereof comprises a VH comprising the amino acid sequence of SEQ ID NO:87 and a VL comprising the amino acid sequence of SEQ ID NO:131.

In some embodiments, the antibody or antigen binding fragment thereof comprises a VH comprising the amino acid sequence of SEQ ID NO:88 and a VL comprising the amino acid sequence of SEQ ID NO:131.

In some embodiments, the antibody or antigen binding fragment thereof comprises a VH comprising the amino acid sequence of SEQ ID NO:238 and a VL comprising the amino acid sequence of SEQ ID NO:131.

In some embodiments, the antibody or antigen binding fragment thereof comprises a VH comprising the amino acid sequence of SEQ ID NO:239 and a VL comprising the amino acid sequence of SEQ ID NO:131.

In some embodiments, the antibody or antigen binding fragment thereof comprises a VH comprising the amino acid sequence of SEQ ID NO:240 and a VL comprising the amino acid sequence of SEQ ID NO:131.

In some embodiments, the antibody or antigen binding fragment thereof comprises a VH comprising the amino acid sequence of SEQ ID NO:241 and a VL comprising the amino acid sequence of SEQ ID NO:131.

In some embodiments, the antibody or antigen binding fragment thereof comprises a VH comprising the amino acid sequence of SEQ ID NO:242 and a VL comprising the amino acid sequence of SEQ ID NO:131.

In some embodiments, the antibody or antigen binding fragment thereof comprises a VH comprising the amino acid sequence of SEQ ID NO:243 and a VL comprising the amino acid sequence of SEQ ID NO:131.

In some embodiments, the antibody or antigen binding fragment thereof comprises a VH comprising the amino acid sequence of SEQ ID NO:43 and a VL comprising the amino acid sequence of SEQ ID NO:132.

In some embodiments, the antibody or antigen binding fragment thereof comprises a VH comprising the amino acid sequence of SEQ ID NO:44 and a VL comprising the amino acid sequence of SEQ ID NO:132.

In some embodiments, the antibody or antigen binding fragment thereof comprises a VH comprising the amino acid sequence of SEQ ID NO:45 and a VL comprising the amino acid sequence of SEQ ID NO:132.

In some embodiments, the antibody or antigen binding fragment thereof comprises a VH comprising the amino acid sequence of SEQ ID NO:46 and a VL comprising the amino acid sequence of SEQ ID NO:132.

In some embodiments, the antibody or antigen binding fragment thereof comprises a VH comprising the amino acid sequence of SEQ ID NO:47 and a VL comprising the amino acid sequence of SEQ ID NO:132.

In some embodiments, the antibody or antigen binding fragment thereof comprises a VH comprising the amino acid sequence of SEQ ID NO:48 and a VL comprising the amino acid sequence of SEQ ID NO:132.

In some embodiments, the antibody or antigen binding fragment thereof comprises a VH comprising the amino acid sequence of SEQ ID NO:49 and a VL comprising the amino acid sequence of SEQ ID NO:132.

In some embodiments, the antibody or antigen binding fragment thereof comprises a VH comprising the amino acid sequence of SEQ ID NO:50 and a VL comprising the amino acid sequence of SEQ ID NO:132.

In some embodiments, the antibody or antigen binding fragment thereof comprises a VH comprising the amino acid sequence of SEQ ID NO:51 and a VL comprising the amino acid sequence of SEQ ID NO:132.

In some embodiments, the antibody or antigen binding fragment thereof comprises a VH comprising the amino acid sequence of SEQ ID NO:52 and a VL comprising the amino acid sequence of SEQ ID NO:132.

In some embodiments, the antibody or antigen binding fragment thereof comprises a VH comprising the amino acid sequence of SEQ ID NO:53 and a VL comprising the amino acid sequence of SEQ ID NO:132.

In some embodiments, the antibody or antigen binding fragment thereof comprises a VH comprising the amino acid sequence of SEQ ID NO:54 and a VL comprising the amino acid sequence of SEQ ID NO:132.

In some embodiments, the antibody or antigen binding fragment thereof comprises a VH comprising the amino acid sequence of SEQ ID NO:55 and a VL comprising the amino acid sequence of SEQ ID NO:132.

In some embodiments, the antibody or antigen binding fragment thereof comprises a VH comprising the amino acid sequence of SEQ ID NO:56 and a VL comprising the amino acid sequence of SEQ ID NO:132.

In some embodiments, the antibody or antigen binding fragment thereof comprises a VH comprising the amino acid sequence of SEQ ID NO:57 and a VL comprising the amino acid sequence of SEQ ID NO:132.

In some embodiments, the antibody or antigen binding fragment thereof comprises a VH comprising the amino acid sequence of SEQ ID NO:58 and a VL comprising the amino acid sequence of SEQ ID NO:132.

In some embodiments, the antibody or antigen binding fragment thereof comprises a VH comprising the amino acid sequence of SEQ ID NO:59 and a VL comprising the amino acid sequence of SEQ ID NO:132.

In some embodiments, the antibody or antigen binding fragment thereof comprises a VH comprising the amino acid sequence of SEQ ID NO:60 and a VL comprising the amino acid sequence of SEQ ID NO:132.

In some embodiments, the antibody or antigen binding fragment thereof comprises a VH comprising the amino acid sequence of SEQ ID NO:61 and a VL comprising the amino acid sequence of SEQ ID NO:132.

In some embodiments, the antibody or antigen binding fragment thereof comprises a VH comprising the amino acid sequence of SEQ ID NO:62 and a VL comprising the amino acid sequence of SEQ ID NO:132.

In some embodiments, the antibody or antigen binding fragment thereof comprises a VH comprising the amino acid sequence of SEQ ID NO:63 and a VL comprising the amino acid sequence of SEQ ID NO:132.

In some embodiments, the antibody or antigen binding fragment thereof comprises a VH comprising the amino acid sequence of SEQ ID NO:64 and a VL comprising the amino acid sequence of SEQ ID NO:132.

In some embodiments, the antibody or antigen binding fragment thereof comprises a VH comprising the amino acid sequence of SEQ ID NO:65 and a VL comprising the amino acid sequence of SEQ ID NO:132.

In some embodiments, the antibody or antigen binding fragment thereof comprises a VH comprising the amino acid sequence of SEQ ID NO:66 and a VL comprising the amino acid sequence of SEQ ID NO:132.

In some embodiments, the antibody or antigen binding fragment thereof comprises a VH comprising the amino acid sequence of SEQ ID NO:67 and a VL comprising the amino acid sequence of SEQ ID NO:132.

In some embodiments, the antibody or antigen binding fragment thereof comprises a VH comprising the amino acid sequence of SEQ ID NO:68 and a VL comprising the amino acid sequence of SEQ ID NO:132.

In some embodiments, the antibody or antigen binding fragment thereof comprises a VH comprising the amino acid sequence of SEQ ID NO:69 and a VL comprising the amino acid sequence of SEQ ID NO:132.

In some embodiments, the antibody or antigen binding fragment thereof comprises a VH comprising the amino acid sequence of SEQ ID NO:70 and a VL comprising the amino acid sequence of SEQ ID NO:132.

In some embodiments, the antibody or antigen binding fragment thereof comprises a VH comprising the amino acid sequence of SEQ ID NO:71 and a VL comprising the amino acid sequence of SEQ ID NO:132.

In some embodiments, the antibody or antigen binding fragment thereof comprises a VH comprising the amino acid sequence of SEQ ID NO:72 and a VL comprising the amino acid sequence of SEQ ID NO:132.

In some embodiments, the antibody or antigen binding fragment thereof comprises a VH comprising the amino acid sequence of SEQ ID NO:73 and a VL comprising the amino acid sequence of SEQ ID NO:132.

In some embodiments, the antibody or antigen binding fragment thereof comprises a VH comprising the amino acid sequence of SEQ ID NO:74 and a VL comprising the amino acid sequence of SEQ ID NO:132.

In some embodiments, the antibody or antigen binding fragment thereof comprises a VH comprising the amino acid sequence of SEQ ID NO:75 and a VL comprising the amino acid sequence of SEQ ID NO:132.

In some embodiments, the antibody or antigen binding fragment thereof comprises a VH comprising the amino acid sequence of SEQ ID NO:76 and a VL comprising the amino acid sequence of SEQ ID NO:132.

In some embodiments, the antibody or antigen binding fragment thereof comprises a VH comprising the amino acid sequence of SEQ ID NO:77 and a VL comprising the amino acid sequence of SEQ ID NO:132.

In some embodiments, the antibody or antigen binding fragment thereof comprises a VH comprising the amino acid sequence of SEQ ID NO:78 and a VL comprising the amino acid sequence of SEQ ID NO:132.

In some embodiments, the antibody or antigen binding fragment thereof comprises a VH comprising the amino acid sequence of SEQ ID NO:79 and a VL comprising the amino acid sequence of SEQ ID NO:132.

In some embodiments, the antibody or antigen binding fragment thereof comprises a VH comprising the amino acid sequence of SEQ ID NO:80 and a VL comprising the amino acid sequence of SEQ ID NO:132.

In some embodiments, the antibody or antigen binding fragment thereof comprises a VH comprising the amino acid sequence of SEQ ID NO:81 and a VL comprising the amino acid sequence of SEQ ID NO:132.

In some embodiments, the antibody or antigen binding fragment thereof comprises a VH comprising the amino acid sequence of SEQ ID NO:82 and a VL comprising the amino acid sequence of SEQ ID NO:132.

In some embodiments, the antibody or antigen binding fragment thereof comprises a VH comprising the amino acid sequence of SEQ ID NO:83 and a VL comprising the amino acid sequence of SEQ ID NO:132.

In some embodiments, the antibody or antigen binding fragment thereof comprises a VH comprising the amino acid sequence of SEQ ID NO:84 and a VL comprising the amino acid sequence of SEQ ID NO:132.

In some embodiments, the antibody or antigen binding fragment thereof comprises a VH comprising the amino acid sequence of SEQ ID NO:85 and a VL comprising the amino acid sequence of SEQ ID NO:132.

In some embodiments, the antibody or antigen binding fragment thereof comprises a VH comprising the amino acid sequence of SEQ ID NO:86 and a VL comprising the amino acid sequence of SEQ ID NO:132.

In some embodiments, the antibody or antigen binding fragment thereof comprises a VH comprising the amino acid sequence of SEQ ID NO:87 and a VL comprising the amino acid sequence of SEQ ID NO:132.

In some embodiments, the antibody or antigen binding fragment thereof comprises a VH comprising the amino acid sequence of SEQ ID NO:88 and a VL comprising the amino acid sequence of SEQ ID NO:132.

In some embodiments, the antibody or antigen binding fragment thereof comprises a VH comprising the amino acid sequence of SEQ ID NO:238 and a VL comprising the amino acid sequence of SEQ ID NO:132.

In some embodiments, the antibody or antigen binding fragment thereof comprises a VH comprising the amino acid sequence of SEQ ID NO:239 and a VL comprising the amino acid sequence of SEQ ID NO:132.

In some embodiments, the antibody or antigen binding fragment thereof comprises a VH comprising the amino acid sequence of SEQ ID NO:240 and a VL comprising the amino acid sequence of SEQ ID NO:132.

In some embodiments, the antibody or antigen binding fragment thereof comprises a VH comprising the amino acid sequence of SEQ ID NO:241 and a VL comprising the amino acid sequence of SEQ ID NO:132.

In some embodiments, the antibody or antigen binding fragment thereof comprises a VH comprising the amino acid sequence of SEQ ID NO:242 and a VL comprising the amino acid sequence of SEQ ID NO:132.

In some embodiments, the antibody or antigen binding fragment thereof comprises a VH comprising the amino acid sequence of SEQ ID NO:243 and a VL comprising the amino acid sequence of SEQ ID NO:132.

In some embodiments, the antibody or antigen binding fragment thereof comprises a VH comprising the amino acid sequence of SEQ ID NO:43 and a VL comprising the amino acid sequence of SEQ ID NO:133.

In some embodiments, the antibody or antigen binding fragment thereof comprises a VH comprising the amino acid sequence of SEQ ID NO:44 and a VL comprising the amino acid sequence of SEQ ID NO:133.

In some embodiments, the antibody or antigen binding fragment thereof comprises a VH comprising the amino acid sequence of SEQ ID NO:45 and a VL comprising the amino acid sequence of SEQ ID NO:133.

In some embodiments, the antibody or antigen binding fragment thereof comprises a VH comprising the amino acid sequence of SEQ ID NO:46 and a VL comprising the amino acid sequence of SEQ ID NO:133.

In some embodiments, the antibody or antigen binding fragment thereof comprises a VH comprising the amino acid sequence of SEQ ID NO:47 and a VL comprising the amino acid sequence of SEQ ID NO:133.

In some embodiments, the antibody or antigen binding fragment thereof comprises a VH comprising the amino acid sequence of SEQ ID NO:48 and a VL comprising the amino acid sequence of SEQ ID NO:133.

In some embodiments, the antibody or antigen binding fragment thereof comprises a VH comprising the amino acid sequence of SEQ ID NO:49 and a VL comprising the amino acid sequence of SEQ ID NO:133.

In some embodiments, the antibody or antigen binding fragment thereof comprises a VH comprising the amino acid sequence of SEQ ID NO:50 and a VL comprising the amino acid sequence of SEQ ID NO:133.

In some embodiments, the antibody or antigen binding fragment thereof comprises a VH comprising the amino acid sequence of SEQ ID NO:51 and a VL comprising the amino acid sequence of SEQ ID NO:133.

In some embodiments, the antibody or antigen binding fragment thereof comprises a VH comprising the amino acid sequence of SEQ ID NO:52 and a VL comprising the amino acid sequence of SEQ ID NO:133.

In some embodiments, the antibody or antigen binding fragment thereof comprises a VH comprising the amino acid sequence of SEQ ID NO:53 and a VL comprising the amino acid sequence of SEQ ID NO:133.

In some embodiments, the antibody or antigen binding fragment thereof comprises a VH comprising the amino acid sequence of SEQ ID NO:54 and a VL comprising the amino acid sequence of SEQ ID NO:133.

In some embodiments, the antibody or antigen binding fragment thereof comprises a VH comprising the amino acid sequence of SEQ ID NO:55 and a VL comprising the amino acid sequence of SEQ ID NO:133.

In some embodiments, the antibody or antigen binding fragment thereof comprises a VH comprising the amino acid sequence of SEQ ID NO:56 and a VL comprising the amino acid sequence of SEQ ID NO:133.

In some embodiments, the antibody or antigen binding fragment thereof comprises a VH comprising the amino acid sequence of SEQ ID NO:57 and a VL comprising the amino acid sequence of SEQ ID NO:133.

In some embodiments, the antibody or antigen binding fragment thereof comprises a VH comprising the amino acid sequence of SEQ ID NO:58 and a VL comprising the amino acid sequence of SEQ ID NO:133.

In some embodiments, the antibody or antigen binding fragment thereof comprises a VH comprising the amino acid sequence of SEQ ID NO:59 and a VL comprising the amino acid sequence of SEQ ID NO:133.

In some embodiments, the antibody or antigen binding fragment thereof comprises a VH comprising the amino acid sequence of SEQ ID NO:60 and a VL comprising the amino acid sequence of SEQ ID NO:133.

In some embodiments, the antibody or antigen binding fragment thereof comprises a VH comprising the amino acid sequence of SEQ ID NO:61 and a VL comprising the amino acid sequence of SEQ ID NO:133.

In some embodiments, the antibody or antigen binding fragment thereof comprises a VH comprising the amino acid sequence of SEQ ID NO:62 and a VL comprising the amino acid sequence of SEQ ID NO:133.

In some embodiments, the antibody or antigen binding fragment thereof comprises a VH comprising the amino acid sequence of SEQ ID NO:63 and a VL comprising the amino acid sequence of SEQ ID NO:133.

In some embodiments, the antibody or antigen binding fragment thereof comprises a VH comprising the amino acid sequence of SEQ ID NO:64 and a VL comprising the amino acid sequence of SEQ ID NO:133.

In some embodiments, the antibody or antigen binding fragment thereof comprises a VH comprising the amino acid sequence of SEQ ID NO:65 and a VL comprising the amino acid sequence of SEQ ID NO:133.

In some embodiments, the antibody or antigen binding fragment thereof comprises a VH comprising the amino acid sequence of SEQ ID NO:66 and a VL comprising the amino acid sequence of SEQ ID NO:133.

In some embodiments, the antibody or antigen binding fragment thereof comprises a VH comprising the amino acid sequence of SEQ ID NO:67 and a VL comprising the amino acid sequence of SEQ ID NO:133.

In some embodiments, the antibody or antigen binding fragment thereof comprises a VH comprising the amino acid sequence of SEQ ID NO:68 and a VL comprising the amino acid sequence of SEQ ID NO:133.

In some embodiments, the antibody or antigen binding fragment thereof comprises a VH comprising the amino acid sequence of SEQ ID NO:69 and a VL comprising the amino acid sequence of SEQ ID NO:133.

In some embodiments, the antibody or antigen binding fragment thereof comprises a VH comprising the amino acid sequence of SEQ ID NO:70 and a VL comprising the amino acid sequence of SEQ ID NO:133.

In some embodiments, the antibody or antigen binding fragment thereof comprises a VH comprising the amino acid sequence of SEQ ID NO:71 and a VL comprising the amino acid sequence of SEQ ID NO:133.

In some embodiments, the antibody or antigen binding fragment thereof comprises a VH comprising the amino acid sequence of SEQ ID NO:72 and a VL comprising the amino acid sequence of SEQ ID NO:133.

In some embodiments, the antibody or antigen binding fragment thereof comprises a VH comprising the amino acid sequence of SEQ ID NO:73 and a VL comprising the amino acid sequence of SEQ ID NO:133.

In some embodiments, the antibody or antigen binding fragment thereof comprises a VH comprising the amino acid sequence of SEQ ID NO:74 and a VL comprising the amino acid sequence of SEQ ID NO:133.

In some embodiments, the antibody or antigen binding fragment thereof comprises a VH comprising the amino acid sequence of SEQ ID NO:75 and a VL comprising the amino acid sequence of SEQ ID NO:133.

In some embodiments, the antibody or antigen binding fragment thereof comprises a VH comprising the amino acid sequence of SEQ ID NO:76 and a VL comprising the amino acid sequence of SEQ ID NO:133.

In some embodiments, the antibody or antigen binding fragment thereof comprises a VH comprising the amino acid sequence of SEQ ID NO:77 and a VL comprising the amino acid sequence of SEQ ID NO:133.

In some embodiments, the antibody or antigen binding fragment thereof comprises a VH comprising the amino acid sequence of SEQ ID NO:78 and a VL comprising the amino acid sequence of SEQ ID NO:133.

In some embodiments, the antibody or antigen binding fragment thereof comprises a VH comprising the amino acid sequence of SEQ ID NO:79 and a VL comprising the amino acid sequence of SEQ ID NO:133.

In some embodiments, the antibody or antigen binding fragment thereof comprises a VH comprising the amino acid sequence of SEQ ID NO:80 and a VL comprising the amino acid sequence of SEQ ID NO:133.

In some embodiments, the antibody or antigen binding fragment thereof comprises a VH comprising the amino acid sequence of SEQ ID NO:81 and a VL comprising the amino acid sequence of SEQ ID NO:133.

In some embodiments, the antibody or antigen binding fragment thereof comprises a VH comprising the amino acid sequence of SEQ ID NO:82 and a VL comprising the amino acid sequence of SEQ ID NO:133.

In some embodiments, the antibody or antigen binding fragment thereof comprises a VH comprising the amino acid sequence of SEQ ID NO:83 and a VL comprising the amino acid sequence of SEQ ID NO:133.

In some embodiments, the antibody or antigen binding fragment thereof comprises a VH comprising the amino acid sequence of SEQ ID NO:84 and a VL comprising the amino acid sequence of SEQ ID NO:133.

In some embodiments, the antibody or antigen binding fragment thereof comprises a VH comprising the amino acid sequence of SEQ ID NO:85 and a VL comprising the amino acid sequence of SEQ ID NO:133.

In some embodiments, the antibody or antigen binding fragment thereof comprises a VH comprising the amino acid sequence of SEQ ID NO:86 and a VL comprising the amino acid sequence of SEQ ID NO:133.

In some embodiments, the antibody or antigen binding fragment thereof comprises a VH comprising the amino acid sequence of SEQ ID NO:87 and a VL comprising the amino acid sequence of SEQ ID NO:133.

In some embodiments, the antibody or antigen binding fragment thereof comprises a VH comprising the amino acid sequence of SEQ ID NO:88 and a VL comprising the amino acid sequence of SEQ ID NO:133.

In some embodiments, the antibody or antigen binding fragment thereof comprises a VH comprising the amino acid sequence of SEQ ID NO:238 and a VL comprising the amino acid sequence of SEQ ID NO:133.

In some embodiments, the antibody or antigen binding fragment thereof comprises a VH comprising the amino acid sequence of SEQ ID NO:239 and a VL comprising the amino acid sequence of SEQ ID NO:133.

In some embodiments, the antibody or antigen binding fragment thereof comprises a VH comprising the amino acid sequence of SEQ ID NO:240 and a VL comprising the amino acid sequence of SEQ ID NO:133.

In some embodiments, the antibody or antigen binding fragment thereof comprises a VH comprising the amino acid sequence of SEQ ID NO:241 and a VL comprising the amino acid sequence of SEQ ID NO:133.

In some embodiments, the antibody or antigen binding fragment thereof comprises a VH comprising the amino acid sequence of SEQ ID NO:242 and a VL comprising the amino acid sequence of SEQ ID NO:133.

In some embodiments, the antibody or antigen binding fragment thereof comprises a VH comprising the amino acid sequence of SEQ ID NO:243 and a VL comprising the amino acid sequence of SEQ ID NO:133.

In some embodiments, the antibody or antigen binding fragment thereof comprises a VH comprising the amino acid sequence of SEQ ID NO:43 and a VL comprising the amino acid sequence of SEQ ID NO:244.

In some embodiments, the antibody or antigen binding fragment thereof comprises a VH comprising the amino acid sequence of SEQ ID NO:44 and a VL comprising the amino acid sequence of SEQ ID NO:244.

In some embodiments, the antibody or antigen binding fragment thereof comprises a VH comprising the amino acid sequence of SEQ ID NO:45 and a VL comprising the amino acid sequence of SEQ ID NO:244.

In some embodiments, the antibody or antigen binding fragment thereof comprises a VH comprising the amino acid sequence of SEQ ID NO:46 and a VL comprising the amino acid sequence of SEQ ID NO:244.

In some embodiments, the antibody or antigen binding fragment thereof comprises a VH comprising the amino acid sequence of SEQ ID NO:47 and a VL comprising the amino acid sequence of SEQ ID NO:244.

In some embodiments, the antibody or antigen binding fragment thereof comprises a VH comprising the amino acid sequence of SEQ ID NO:48 and a VL comprising the amino acid sequence of SEQ ID NO:244.

In some embodiments, the antibody or antigen binding fragment thereof comprises a VH comprising the amino acid sequence of SEQ ID NO:49 and a VL comprising the amino acid sequence of SEQ ID NO:244.

In some embodiments, the antibody or antigen binding fragment thereof comprises a VH comprising the amino acid sequence of SEQ ID NO:50 and a VL comprising the amino acid sequence of SEQ ID NO:244.

In some embodiments, the antibody or antigen binding fragment thereof comprises a VH comprising the amino acid sequence of SEQ ID NO:51 and a VL comprising the amino acid sequence of SEQ ID NO:244.

In some embodiments, the antibody or antigen binding fragment thereof comprises a VH comprising the amino acid sequence of SEQ ID NO:52 and a VL comprising the amino acid sequence of SEQ ID NO:244.

In some embodiments, the antibody or antigen binding fragment thereof comprises a VH comprising the amino acid sequence of SEQ ID NO:53 and a VL comprising the amino acid sequence of SEQ ID NO:244.

In some embodiments, the antibody or antigen binding fragment thereof comprises a VH comprising the amino acid sequence of SEQ ID NO:54 and a VL comprising the amino acid sequence of SEQ ID NO:244.

In some embodiments, the antibody or antigen binding fragment thereof comprises a VH comprising the amino acid sequence of SEQ ID NO:55 and a VL comprising the amino acid sequence of SEQ ID NO:244.

In some embodiments, the antibody or antigen binding fragment thereof comprises a VH comprising the amino acid sequence of SEQ ID NO:56 and a VL comprising the amino acid sequence of SEQ ID NO:244.

In some embodiments, the antibody or antigen binding fragment thereof comprises a VH comprising the amino acid sequence of SEQ ID NO:57 and a VL comprising the amino acid sequence of SEQ ID NO:244.

In some embodiments, the antibody or antigen binding fragment thereof comprises a VH comprising the amino acid sequence of SEQ ID NO:58 and a VL comprising the amino acid sequence of SEQ ID NO:244.

In some embodiments, the antibody or antigen binding fragment thereof comprises a VH comprising the amino acid sequence of SEQ ID NO:59 and a VL comprising the amino acid sequence of SEQ ID NO:244.

In some embodiments, the antibody or antigen binding fragment thereof comprises a VH comprising the amino acid sequence of SEQ ID NO:60 and a VL comprising the amino acid sequence of SEQ ID NO:244.

In some embodiments, the antibody or antigen binding fragment thereof comprises a VH comprising the amino acid sequence of SEQ ID NO:61 and a VL comprising the amino acid sequence of SEQ ID NO:244.

In some embodiments, the antibody or antigen binding fragment thereof comprises a VH comprising the amino acid sequence of SEQ ID NO:62 and a VL comprising the amino acid sequence of SEQ ID NO:244.

In some embodiments, the antibody or antigen binding fragment thereof comprises a VH comprising the amino acid sequence of SEQ ID NO:63 and a VL comprising the amino acid sequence of SEQ ID NO:244.

In some embodiments, the antibody or antigen binding fragment thereof comprises a VH comprising the amino acid sequence of SEQ ID NO:64 and a VL comprising the amino acid sequence of SEQ ID NO:244.

In some embodiments, the antibody or antigen binding fragment thereof comprises a VH comprising the amino acid sequence of SEQ ID NO:65 and a VL comprising the amino acid sequence of SEQ ID NO:244.

In some embodiments, the antibody or antigen binding fragment thereof comprises a VH comprising the amino acid sequence of SEQ ID NO:66 and a VL comprising the amino acid sequence of SEQ ID NO:244.

In some embodiments, the antibody or antigen binding fragment thereof comprises a VH comprising the amino acid sequence of SEQ ID NO:67 and a VL comprising the amino acid sequence of SEQ ID NO:244.

In some embodiments, the antibody or antigen binding fragment thereof comprises a VH comprising the amino acid sequence of SEQ ID NO:68 and a VL comprising the amino acid sequence of SEQ ID NO:244.

In some embodiments, the antibody or antigen binding fragment thereof comprises a VH comprising the amino acid sequence of SEQ ID NO:69 and a VL comprising the amino acid sequence of SEQ ID NO:244.

In some embodiments, the antibody or antigen binding fragment thereof comprises a VH comprising the amino acid sequence of SEQ ID NO:70 and a VL comprising the amino acid sequence of SEQ ID NO:244.

In some embodiments, the antibody or antigen binding fragment thereof comprises a VH comprising the amino acid sequence of SEQ ID NO:71 and a VL comprising the amino acid sequence of SEQ ID NO:244.

In some embodiments, the antibody or antigen binding fragment thereof comprises a VH comprising the amino acid sequence of SEQ ID NO:72 and a VL comprising the amino acid sequence of SEQ ID NO:244.

In some embodiments, the antibody or antigen binding fragment thereof comprises a VH comprising the amino acid sequence of SEQ ID NO:73 and a VL comprising the amino acid sequence of SEQ ID NO:244.

In some embodiments, the antibody or antigen binding fragment thereof comprises a VH comprising the amino acid sequence of SEQ ID NO:74 and a VL comprising the amino acid sequence of SEQ ID NO:244.

In some embodiments, the antibody or antigen binding fragment thereof comprises a VH comprising the amino acid sequence of SEQ ID NO:75 and a VL comprising the amino acid sequence of SEQ ID NO:244.

In some embodiments, the antibody or antigen binding fragment thereof comprises a VH comprising the amino acid sequence of SEQ ID NO:76 and a VL comprising the amino acid sequence of SEQ ID NO:244.

In some embodiments, the antibody or antigen binding fragment thereof comprises a VH comprising the amino acid sequence of SEQ ID NO:77 and a VL comprising the amino acid sequence of SEQ ID NO:244.

In some embodiments, the antibody or antigen binding fragment thereof comprises a VH comprising the amino acid sequence of SEQ ID NO:78 and a VL comprising the amino acid sequence of SEQ ID NO:244.

In some embodiments, the antibody or antigen binding fragment thereof comprises a VH comprising the amino acid sequence of SEQ ID NO:79 and a VL comprising the amino acid sequence of SEQ ID NO:244.

In some embodiments, the antibody or antigen binding fragment thereof comprises a VH comprising the amino acid sequence of SEQ ID NO:80 and a VL comprising the amino acid sequence of SEQ ID NO:244.

In some embodiments, the antibody or antigen binding fragment thereof comprises a VH comprising the amino acid sequence of SEQ ID NO:81 and a VL comprising the amino acid sequence of SEQ ID NO:244.

In some embodiments, the antibody or antigen binding fragment thereof comprises a VH comprising the amino acid sequence of SEQ ID NO:82 and a VL comprising the amino acid sequence of SEQ ID NO:244.

In some embodiments, the antibody or antigen binding fragment thereof comprises a VH comprising the amino acid sequence of SEQ ID NO:83 and a VL comprising the amino acid sequence of SEQ ID NO:244.

In some embodiments, the antibody or antigen binding fragment thereof comprises a VH comprising the amino acid sequence of SEQ ID NO:84 and a VL comprising the amino acid sequence of SEQ ID NO:244.

In some embodiments, the antibody or antigen binding fragment thereof comprises a VH comprising the amino acid sequence of SEQ ID NO:85 and a VL comprising the amino acid sequence of SEQ ID NO:244.

In some embodiments, the antibody or antigen binding fragment thereof comprises a VH comprising the amino acid sequence of SEQ ID NO:86 and a VL comprising the amino acid sequence of SEQ ID NO:244.

In some embodiments, the antibody or antigen binding fragment thereof comprises a VH comprising the amino acid sequence of SEQ ID NO:87 and a VL comprising the amino acid sequence of SEQ ID NO:244.

In some embodiments, the antibody or antigen binding fragment thereof comprises a VH comprising the amino acid sequence of SEQ ID NO:88 and a VL comprising the amino acid sequence of SEQ ID NO:244.

In some embodiments, the antibody or antigen binding fragment thereof comprises a VH comprising the amino acid sequence of SEQ ID NO:238 and a VL comprising the amino acid sequence of SEQ ID NO:244.

In some embodiments, the antibody or antigen binding fragment thereof comprises a VH comprising the amino acid sequence of SEQ ID NO:239 and a VL comprising the amino acid sequence of SEQ ID NO:244.

In some embodiments, the antibody or antigen binding fragment thereof comprises a VH comprising the amino acid sequence of SEQ ID NO:240 and a VL comprising the amino acid sequence of SEQ ID NO:244.

In some embodiments, the antibody or antigen binding fragment thereof comprises a VH comprising the amino acid sequence of SEQ ID NO:241 and a VL comprising the amino acid sequence of SEQ ID NO:244.

In some embodiments, the antibody or antigen binding fragment thereof comprises a VH comprising the amino acid sequence of SEQ ID NO:242 and a VL comprising the amino acid sequence of SEQ ID NO:244.

In some embodiments, the antibody or antigen binding fragment thereof comprises a VH comprising the amino acid sequence of SEQ ID NO:243 and a VL comprising the amino acid sequence of SEQ ID NO:244.

In some embodiments, the antibody or antigen binding fragment thereof comprises a VH comprising the amino acid sequence of SEQ ID NO:43 and a VL comprising the amino acid sequence of SEQ ID NO:245.

In some embodiments, the antibody or antigen binding fragment thereof comprises a VH comprising the amino acid sequence of SEQ ID NO:44 and a VL comprising the amino acid sequence of SEQ ID NO:245.

In some embodiments, the antibody or antigen binding fragment thereof comprises a VH comprising the amino acid sequence of SEQ ID NO:45 and a VL comprising the amino acid sequence of SEQ ID NO:245.

In some embodiments, the antibody or antigen binding fragment thereof comprises a VH comprising the amino acid sequence of SEQ ID NO:46 and a VL comprising the amino acid sequence of SEQ ID NO:245.

In some embodiments, the antibody or antigen binding fragment thereof comprises a VH comprising the amino acid sequence of SEQ ID NO:47 and a VL comprising the amino acid sequence of SEQ ID NO:245.

In some embodiments, the antibody or antigen binding fragment thereof comprises a VH comprising the amino acid sequence of SEQ ID NO:48 and a VL comprising the amino acid sequence of SEQ ID NO:245.

In some embodiments, the antibody or antigen binding fragment thereof comprises a VH comprising the amino acid sequence of SEQ ID NO:49 and a VL comprising the amino acid sequence of SEQ ID NO:245.

In some embodiments, the antibody or antigen binding fragment thereof comprises a VH comprising the amino acid sequence of SEQ ID NO:50 and a VL comprising the amino acid sequence of SEQ ID NO:245.

In some embodiments, the antibody or antigen binding fragment thereof comprises a VH comprising the amino acid sequence of SEQ ID NO:51 and a VL comprising the amino acid sequence of SEQ ID NO:245.

In some embodiments, the antibody or antigen binding fragment thereof comprises a VH comprising the amino acid sequence of SEQ ID NO:52 and a VL comprising the amino acid sequence of SEQ ID NO:245.

In some embodiments, the antibody or antigen binding fragment thereof comprises a VH comprising the amino acid sequence of SEQ ID NO:53 and a VL comprising the amino acid sequence of SEQ ID NO:245.

In some embodiments, the antibody or antigen binding fragment thereof comprises a VH comprising the amino acid sequence of SEQ ID NO:54 and a VL comprising the amino acid sequence of SEQ ID NO:245.

In some embodiments, the antibody or antigen binding fragment thereof comprises a VH comprising the amino acid sequence of SEQ ID NO:55 and a VL comprising the amino acid sequence of SEQ ID NO:245.

In some embodiments, the antibody or antigen binding fragment thereof comprises a VH comprising the amino acid sequence of SEQ ID NO:56 and a VL comprising the amino acid sequence of SEQ ID NO:245.

In some embodiments, the antibody or antigen binding fragment thereof comprises a VH comprising the amino acid sequence of SEQ ID NO:57 and a VL comprising the amino acid sequence of SEQ ID NO:245.

In some embodiments, the antibody or antigen binding fragment thereof comprises a VH comprising the amino acid sequence of SEQ ID NO:58 and a VL comprising the amino acid sequence of SEQ ID NO:245.

In some embodiments, the antibody or antigen binding fragment thereof comprises a VH comprising the amino acid sequence of SEQ ID NO:59 and a VL comprising the amino acid sequence of SEQ ID NO:245.

In some embodiments, the antibody or antigen binding fragment thereof comprises a VH comprising the amino acid sequence of SEQ ID NO:60 and a VL comprising the amino acid sequence of SEQ ID NO:245.

In some embodiments, the antibody or antigen binding fragment thereof comprises a VH comprising the amino acid sequence of SEQ ID NO:61 and a VL comprising the amino acid sequence of SEQ ID NO:245.

In some embodiments, the antibody or antigen binding fragment thereof comprises a VH comprising the amino acid sequence of SEQ ID NO:62 and a VL comprising the amino acid sequence of SEQ ID NO:245.

In some embodiments, the antibody or antigen binding fragment thereof comprises a VH comprising the amino acid sequence of SEQ ID NO:63 and a VL comprising the amino acid sequence of SEQ ID NO:245.

In some embodiments, the antibody or antigen binding fragment thereof comprises a VH comprising the amino acid sequence of SEQ ID NO:64 and a VL comprising the amino acid sequence of SEQ ID NO:245.

In some embodiments, the antibody or antigen binding fragment thereof comprises a VH comprising the amino acid sequence of SEQ ID NO:65 and a VL comprising the amino acid sequence of SEQ ID NO:245.

In some embodiments, the antibody or antigen binding fragment thereof comprises a VH comprising the amino acid sequence of SEQ ID NO:66 and a VL comprising the amino acid sequence of SEQ ID NO:245.

In some embodiments, the antibody or antigen binding fragment thereof comprises a VH comprising the amino acid sequence of SEQ ID NO:67 and a VL comprising the amino acid sequence of SEQ ID NO:245.

In some embodiments, the antibody or antigen binding fragment thereof comprises a VH comprising the amino acid sequence of SEQ ID NO:68 and a VL comprising the amino acid sequence of SEQ ID NO:245.

In some embodiments, the antibody or antigen binding fragment thereof comprises a VH comprising the amino acid sequence of SEQ ID NO:69 and a VL comprising the amino acid sequence of SEQ ID NO:245.

In some embodiments, the antibody or antigen binding fragment thereof comprises a VH comprising the amino acid sequence of SEQ ID NO:70 and a VL comprising the amino acid sequence of SEQ ID NO:245.

In some embodiments, the antibody or antigen binding fragment thereof comprises a VH comprising the amino acid sequence of SEQ ID NO:71 and a VL comprising the amino acid sequence of SEQ ID NO:245.

In some embodiments, the antibody or antigen binding fragment thereof comprises a VH comprising the amino acid sequence of SEQ ID NO:72 and a VL comprising the amino acid sequence of SEQ ID NO:245.

In some embodiments, the antibody or antigen binding fragment thereof comprises a VH comprising the amino acid sequence of SEQ ID NO:73 and a VL comprising the amino acid sequence of SEQ ID NO:245.

In some embodiments, the antibody or antigen binding fragment thereof comprises a VH comprising the amino acid sequence of SEQ ID NO:74 and a VL comprising the amino acid sequence of SEQ ID NO:245.

In some embodiments, the antibody or antigen binding fragment thereof comprises a VH comprising the amino acid sequence of SEQ ID NO:75 and a VL comprising the amino acid sequence of SEQ ID NO:245.

In some embodiments, the antibody or antigen binding fragment thereof comprises a VH comprising the amino acid sequence of SEQ ID NO:76 and a VL comprising the amino acid sequence of SEQ ID NO:245.

In some embodiments, the antibody or antigen binding fragment thereof comprises a VH comprising the amino acid sequence of SEQ ID NO:77 and a VL comprising the amino acid sequence of SEQ ID NO:245.

In some embodiments, the antibody or antigen binding fragment thereof comprises a VH comprising the amino acid sequence of SEQ ID NO:78 and a VL comprising the amino acid sequence of SEQ ID NO:245.

In some embodiments, the antibody or antigen binding fragment thereof comprises a VH comprising the amino acid sequence of SEQ ID NO:79 and a VL comprising the amino acid sequence of SEQ ID NO:245.

In some embodiments, the antibody or antigen binding fragment thereof comprises a VH comprising the amino acid sequence of SEQ ID NO:80 and a VL comprising the amino acid sequence of SEQ ID NO:245.

In some embodiments, the antibody or antigen binding fragment thereof comprises a VH comprising the amino acid sequence of SEQ ID NO:81 and a VL comprising the amino acid sequence of SEQ ID NO:245.

In some embodiments, the antibody or antigen binding fragment thereof comprises a VH comprising the amino acid sequence of SEQ ID NO:82 and a VL comprising the amino acid sequence of SEQ ID NO:245.

In some embodiments, the antibody or antigen binding fragment thereof comprises a VH comprising the amino acid sequence of SEQ ID NO:83 and a VL comprising the amino acid sequence of SEQ ID NO:245.

In some embodiments, the antibody or antigen binding fragment thereof comprises a VH comprising the amino acid sequence of SEQ ID NO:84 and a VL comprising the amino acid sequence of SEQ ID NO:245.

In some embodiments, the antibody or antigen binding fragment thereof comprises a VH comprising the amino acid sequence of SEQ ID NO:85 and a VL comprising the amino acid sequence of SEQ ID NO:245.

In some embodiments, the antibody or antigen binding fragment thereof comprises a VH comprising the amino acid sequence of SEQ ID NO:86 and a VL comprising the amino acid sequence of SEQ ID NO:245.

In some embodiments, the antibody or antigen binding fragment thereof comprises a VH comprising the amino acid sequence of SEQ ID NO:87 and a VL comprising the amino acid sequence of SEQ ID NO:245.

In some embodiments, the antibody or antigen binding fragment thereof comprises a VH comprising the amino acid sequence of SEQ ID NO:88 and a VL comprising the amino acid sequence of SEQ ID NO:245.

In some embodiments, the antibody or antigen binding fragment thereof comprises a VH comprising the amino acid sequence of SEQ ID NO:238 and a VL comprising the amino acid sequence of SEQ ID NO:245.

In some embodiments, the antibody or antigen binding fragment thereof comprises a VH comprising the amino acid sequence of SEQ ID NO:239 and a VL comprising the amino acid sequence of SEQ ID NO:245.

In some embodiments, the antibody or antigen binding fragment thereof comprises a VH comprising the amino acid sequence of SEQ ID NO:240 and a VL comprising the amino acid sequence of SEQ ID NO:245.

In some embodiments, the antibody or antigen binding fragment thereof comprises a VH comprising the amino acid sequence of SEQ ID NO:241 and a VL comprising the amino acid sequence of SEQ ID NO:245.

In some embodiments, the antibody or antigen binding fragment thereof comprises a VH comprising the amino acid sequence of SEQ ID NO:242 and a VL comprising the amino acid sequence of SEQ ID NO:245.

In some embodiments, the antibody or antigen binding fragment thereof comprises a VH comprising the amino acid sequence of SEQ ID NO:243 and a VL comprising the amino acid sequence of SEQ ID NO:245.

In some embodiments, the antibody or antigen binding fragment thereof comprises a VH comprising the amino acid sequence of SEQ ID NO:43 and a VL comprising the amino acid sequence of SEQ ID NO:246.

In some embodiments, the antibody or antigen binding fragment thereof comprises a VH comprising the amino acid sequence of SEQ ID NO:44 and a VL comprising the amino acid sequence of SEQ ID NO:246.

In some embodiments, the antibody or antigen binding fragment thereof comprises a VH comprising the amino acid sequence of SEQ ID NO:45 and a VL comprising the amino acid sequence of SEQ ID NO:246.

In some embodiments, the antibody or antigen binding fragment thereof comprises a VH comprising the amino acid sequence of SEQ ID NO:46 and a VL comprising the amino acid sequence of SEQ ID NO:246.

In some embodiments, the antibody or antigen binding fragment thereof comprises a VH comprising the amino acid sequence of SEQ ID NO:47 and a VL comprising the amino acid sequence of SEQ ID NO:246.

In some embodiments, the antibody or antigen binding fragment thereof comprises a VH comprising the amino acid sequence of SEQ ID NO:48 and a VL comprising the amino acid sequence of SEQ ID NO:246.

In some embodiments, the antibody or antigen binding fragment thereof comprises a VH comprising the amino acid sequence of SEQ ID NO:49 and a VL comprising the amino acid sequence of SEQ ID NO:246.

In some embodiments, the antibody or antigen binding fragment thereof comprises a VH comprising the amino acid sequence of SEQ ID NO:50 and a VL comprising the amino acid sequence of SEQ ID NO:246.

In some embodiments, the antibody or antigen binding fragment thereof comprises a VH comprising the amino acid sequence of SEQ ID NO:51 and a VL comprising the amino acid sequence of SEQ ID NO:246.

In some embodiments, the antibody or antigen binding fragment thereof comprises a VH comprising the amino acid sequence of SEQ ID NO:52 and a VL comprising the amino acid sequence of SEQ ID NO:246.

In some embodiments, the antibody or antigen binding fragment thereof comprises a VH comprising the amino acid sequence of SEQ ID NO:53 and a VL comprising the amino acid sequence of SEQ ID NO:246.

In some embodiments, the antibody or antigen binding fragment thereof comprises a VH comprising the amino acid sequence of SEQ ID NO:54 and a VL comprising the amino acid sequence of SEQ ID NO:246.

In some embodiments, the antibody or antigen binding fragment thereof comprises a VH comprising the amino acid sequence of SEQ ID NO:55 and a VL comprising the amino acid sequence of SEQ ID NO:246.

In some embodiments, the antibody or antigen binding fragment thereof comprises a VH comprising the amino acid sequence of SEQ ID NO:56 and a VL comprising the amino acid sequence of SEQ ID NO:246.

In some embodiments, the antibody or antigen binding fragment thereof comprises a VH comprising the amino acid sequence of SEQ ID NO:57 and a VL comprising the amino acid sequence of SEQ ID NO:246.

In some embodiments, the antibody or antigen binding fragment thereof comprises a VH comprising the amino acid sequence of SEQ ID NO:58 and a VL comprising the amino acid sequence of SEQ ID NO:246.

In some embodiments, the antibody or antigen binding fragment thereof comprises a VH comprising the amino acid sequence of SEQ ID NO:59 and a VL comprising the amino acid sequence of SEQ ID NO:246.

In some embodiments, the antibody or antigen binding fragment thereof comprises a VH comprising the amino acid sequence of SEQ ID NO:60 and a VL comprising the amino acid sequence of SEQ ID NO:246.

In some embodiments, the antibody or antigen binding fragment thereof comprises a VH comprising the amino acid sequence of SEQ ID NO:61 and a VL comprising the amino acid sequence of SEQ ID NO:246.

In some embodiments, the antibody or antigen binding fragment thereof comprises a VH comprising the amino acid sequence of SEQ ID NO:62 and a VL comprising the amino acid sequence of SEQ ID NO:246.

In some embodiments, the antibody or antigen binding fragment thereof comprises a VH comprising the amino acid sequence of SEQ ID NO:63 and a VL comprising the amino acid sequence of SEQ ID NO:246.

In some embodiments, the antibody or antigen binding fragment thereof comprises a VH comprising the amino acid sequence of SEQ ID NO:64 and a VL comprising the amino acid sequence of SEQ ID NO:246.

In some embodiments, the antibody or antigen binding fragment thereof comprises a VH comprising the amino acid sequence of SEQ ID NO:65 and a VL comprising the amino acid sequence of SEQ ID NO:246.

In some embodiments, the antibody or antigen binding fragment thereof comprises a VH comprising the amino acid sequence of SEQ ID NO:66 and a VL comprising the amino acid sequence of SEQ ID NO:246.

In some embodiments, the antibody or antigen binding fragment thereof comprises a VH comprising the amino acid sequence of SEQ ID NO:67 and a VL comprising the amino acid sequence of SEQ ID NO:246.

In some embodiments, the antibody or antigen binding fragment thereof comprises a VH comprising the amino acid sequence of SEQ ID NO:68 and a VL comprising the amino acid sequence of SEQ ID NO:246.

In some embodiments, the antibody or antigen binding fragment thereof comprises a VH comprising the amino acid sequence of SEQ ID NO:69 and a VL comprising the amino acid sequence of SEQ ID NO:246.

In some embodiments, the antibody or antigen binding fragment thereof comprises a VH comprising the amino acid sequence of SEQ ID NO:70 and a VL comprising the amino acid sequence of SEQ ID NO:246.

In some embodiments, the antibody or antigen binding fragment thereof comprises a VH comprising the amino acid sequence of SEQ ID NO:71 and a VL comprising the amino acid sequence of SEQ ID NO:246.

In some embodiments, the antibody or antigen binding fragment thereof comprises a VH comprising the amino acid sequence of SEQ ID NO:72 and a VL comprising the amino acid sequence of SEQ ID NO:246.

In some embodiments, the antibody or antigen binding fragment thereof comprises a VH comprising the amino acid sequence of SEQ ID NO:73 and a VL comprising the amino acid sequence of SEQ ID NO:246.

In some embodiments, the antibody or antigen binding fragment thereof comprises a VH comprising the amino acid sequence of SEQ ID NO:74 and a VL comprising the amino acid sequence of SEQ ID NO:246.

In some embodiments, the antibody or antigen binding fragment thereof comprises a VH comprising the amino acid sequence of SEQ ID NO:75 and a VL comprising the amino acid sequence of SEQ ID NO:246.

In some embodiments, the antibody or antigen binding fragment thereof comprises a VH comprising the amino acid sequence of SEQ ID NO:76 and a VL comprising the amino acid sequence of SEQ ID NO:246.

In some embodiments, the antibody or antigen binding fragment thereof comprises a VH comprising the amino acid sequence of SEQ ID NO:77 and a VL comprising the amino acid sequence of SEQ ID NO:246.

In some embodiments, the antibody or antigen binding fragment thereof comprises a VH comprising the amino acid sequence of SEQ ID NO:78 and a VL comprising the amino acid sequence of SEQ ID NO:246.

In some embodiments, the antibody or antigen binding fragment thereof comprises a VH comprising the amino acid sequence of SEQ ID NO:79 and a VL comprising the amino acid sequence of SEQ ID NO:246.

In some embodiments, the antibody or antigen binding fragment thereof comprises a VH comprising the amino acid sequence of SEQ ID NO:80 and a VL comprising the amino acid sequence of SEQ ID NO:246.

In some embodiments, the antibody or antigen binding fragment thereof comprises a VH comprising the amino acid sequence of SEQ ID NO:81 and a VL comprising the amino acid sequence of SEQ ID NO:246.

In some embodiments, the antibody or antigen binding fragment thereof comprises a VH comprising the amino acid sequence of SEQ ID NO:82 and a VL comprising the amino acid sequence of SEQ ID NO:246.

In some embodiments, the antibody or antigen binding fragment thereof comprises a VH comprising the amino acid sequence of SEQ ID NO:83 and a VL comprising the amino acid sequence of SEQ ID NO:246.

In some embodiments, the antibody or antigen binding fragment thereof comprises a VH comprising the amino acid sequence of SEQ ID NO:84 and a VL comprising the amino acid sequence of SEQ ID NO:246.

In some embodiments, the antibody or antigen binding fragment thereof comprises a VH comprising the amino acid sequence of SEQ ID NO:85 and a VL comprising the amino acid sequence of SEQ ID NO:246.

In some embodiments, the antibody or antigen binding fragment thereof comprises a VH comprising the amino acid sequence of SEQ ID NO:86 and a VL comprising the amino acid sequence of SEQ ID NO:246.

In some embodiments, the antibody or antigen binding fragment thereof comprises a VH comprising the amino acid sequence of SEQ ID NO:87 and a VL comprising the amino acid sequence of SEQ ID NO:246.

In some embodiments, the antibody or antigen binding fragment thereof comprises a VH comprising the amino acid sequence of SEQ ID NO:88 and a VL comprising the amino acid sequence of SEQ ID NO:246.

In some embodiments, the antibody or antigen binding fragment thereof comprises a VH comprising the amino acid sequence of SEQ ID NO:238 and a VL comprising the amino acid sequence of SEQ ID NO:246.

In some embodiments, the antibody or antigen binding fragment thereof comprises a VH comprising the amino acid sequence of SEQ ID NO:239 and a VL comprising the amino acid sequence of SEQ ID NO:246.

In some embodiments, the antibody or antigen binding fragment thereof comprises a VH comprising the amino acid sequence of SEQ ID NO:240 and a VL comprising the amino acid sequence of SEQ ID NO:246.

In some embodiments, the antibody or antigen binding fragment thereof comprises a VH comprising the amino acid sequence of SEQ ID NO:241 and a VL comprising the amino acid sequence of SEQ ID NO:246.

In some embodiments, the antibody or antigen binding fragment thereof comprises a VH comprising the amino acid sequence of SEQ ID NO:242 and a VL comprising the amino acid sequence of SEQ ID NO:246.

In some embodiments, the antibody or antigen binding fragment thereof comprises a VH comprising the amino acid sequence of SEQ ID NO:243 and a VL comprising the amino acid sequence of SEQ ID NO:246.

In some embodiments, the antibody or antigen binding fragment thereof comprises a VH comprising the amino acid sequence of SEQ ID NO:43 and a VL comprising the amino acid sequence of SEQ ID NO:247.

In some embodiments, the antibody or antigen binding fragment thereof comprises a VH comprising the amino acid sequence of SEQ ID NO:44 and a VL comprising the amino acid sequence of SEQ ID NO:247.

In some embodiments, the antibody or antigen binding fragment thereof comprises a VH comprising the amino acid sequence of SEQ ID NO:45 and a VL comprising the amino acid sequence of SEQ ID NO:247.

In some embodiments, the antibody or antigen binding fragment thereof comprises a VH comprising the amino acid sequence of SEQ ID NO:46 and a VL comprising the amino acid sequence of SEQ ID NO:247.

In some embodiments, the antibody or antigen binding fragment thereof comprises a VH comprising the amino acid sequence of SEQ ID NO:47 and a VL comprising the amino acid sequence of SEQ ID NO:247.

In some embodiments, the antibody or antigen binding fragment thereof comprises a VH comprising the amino acid sequence of SEQ ID NO:48 and a VL comprising the amino acid sequence of SEQ ID NO:247.

In some embodiments, the antibody or antigen binding fragment thereof comprises a VH comprising the amino acid sequence of SEQ ID NO:49 and a VL comprising the amino acid sequence of SEQ ID NO:247.

In some embodiments, the antibody or antigen binding fragment thereof comprises a VH comprising the amino acid sequence of SEQ ID NO:50 and a VL comprising the amino acid sequence of SEQ ID NO:247.

In some embodiments, the antibody or antigen binding fragment thereof comprises a VH comprising the amino acid sequence of SEQ ID NO:51 and a VL comprising the amino acid sequence of SEQ ID NO:247.

In some embodiments, the antibody or antigen binding fragment thereof comprises a VH comprising the amino acid sequence of SEQ ID NO:52 and a VL comprising the amino acid sequence of SEQ ID NO:247.

In some embodiments, the antibody or antigen binding fragment thereof comprises a VH comprising the amino acid sequence of SEQ ID NO:53 and a VL comprising the amino acid sequence of SEQ ID NO:247.

In some embodiments, the antibody or antigen binding fragment thereof comprises a VH comprising the amino acid sequence of SEQ ID NO:54 and a VL comprising the amino acid sequence of SEQ ID NO:247.

In some embodiments, the antibody or antigen binding fragment thereof comprises a VH comprising the amino acid sequence of SEQ ID NO:55 and a VL comprising the amino acid sequence of SEQ ID NO:247.

In some embodiments, the antibody or antigen binding fragment thereof comprises a VH comprising the amino acid sequence of SEQ ID NO:56 and a VL comprising the amino acid sequence of SEQ ID NO:247.

In some embodiments, the antibody or antigen binding fragment thereof comprises a VH comprising the amino acid sequence of SEQ ID NO:57 and a VL comprising the amino acid sequence of SEQ ID NO:247.

In some embodiments, the antibody or antigen binding fragment thereof comprises a VH comprising the amino acid sequence of SEQ ID NO:58 and a VL comprising the amino acid sequence of SEQ ID NO:247.

In some embodiments, the antibody or antigen binding fragment thereof comprises a VH comprising the amino acid sequence of SEQ ID NO:59 and a VL comprising the amino acid sequence of SEQ ID NO:247.

In some embodiments, the antibody or antigen binding fragment thereof comprises a VH comprising the amino acid sequence of SEQ ID NO:60 and a VL comprising the amino acid sequence of SEQ ID NO:247.

In some embodiments, the antibody or antigen binding fragment thereof comprises a VH comprising the amino acid sequence of SEQ ID NO:61 and a VL comprising the amino acid sequence of SEQ ID NO:247.

In some embodiments, the antibody or antigen binding fragment thereof comprises a VH comprising the amino acid sequence of SEQ ID NO:62 and a VL comprising the amino acid sequence of SEQ ID NO:247.

In some embodiments, the antibody or antigen binding fragment thereof comprises a VH comprising the amino acid sequence of SEQ ID NO:63 and a VL comprising the amino acid sequence of SEQ ID NO:247.

In some embodiments, the antibody or antigen binding fragment thereof comprises a VH comprising the amino acid sequence of SEQ ID NO:64 and a VL comprising the amino acid sequence of SEQ ID NO:247.

In some embodiments, the antibody or antigen binding fragment thereof comprises a VH comprising the amino acid sequence of SEQ ID NO:65 and a VL comprising the amino acid sequence of SEQ ID NO:247.

In some embodiments, the antibody or antigen binding fragment thereof comprises a VH comprising the amino acid sequence of SEQ ID NO:66 and a VL comprising the amino acid sequence of SEQ ID NO:247.

In some embodiments, the antibody or antigen binding fragment thereof comprises a VH comprising the amino acid sequence of SEQ ID NO:67 and a VL comprising the amino acid sequence of SEQ ID NO:247.

In some embodiments, the antibody or antigen binding fragment thereof comprises a VH comprising the amino acid sequence of SEQ ID NO:68 and a VL comprising the amino acid sequence of SEQ ID NO:247.

In some embodiments, the antibody or antigen binding fragment thereof comprises a VH comprising the amino acid sequence of SEQ ID NO:69 and a VL comprising the amino acid sequence of SEQ ID NO:247.

In some embodiments, the antibody or antigen binding fragment thereof comprises a VH comprising the amino acid sequence of SEQ ID NO:70 and a VL comprising the amino acid sequence of SEQ ID NO:247.

In some embodiments, the antibody or antigen binding fragment thereof comprises a VH comprising the amino acid sequence of SEQ ID NO:71 and a VL comprising the amino acid sequence of SEQ ID NO:247.

In some embodiments, the antibody or antigen binding fragment thereof comprises a VH comprising the amino acid sequence of SEQ ID NO:72 and a VL comprising the amino acid sequence of SEQ ID NO:247.

In some embodiments, the antibody or antigen binding fragment thereof comprises a VH comprising the amino acid sequence of SEQ ID NO:73 and a VL comprising the amino acid sequence of SEQ ID NO:247.

In some embodiments, the antibody or antigen binding fragment thereof comprises a VH comprising the amino acid sequence of SEQ ID NO:74 and a VL comprising the amino acid sequence of SEQ ID NO:247.

In some embodiments, the antibody or antigen binding fragment thereof comprises a VH comprising the amino acid sequence of SEQ ID NO:75 and a VL comprising the amino acid sequence of SEQ ID NO:247.

In some embodiments, the antibody or antigen binding fragment thereof comprises a VH comprising the amino acid sequence of SEQ ID NO:76 and a VL comprising the amino acid sequence of SEQ ID NO:247.

In some embodiments, the antibody or antigen binding fragment thereof comprises a VH comprising the amino acid sequence of SEQ ID NO:77 and a VL comprising the amino acid sequence of SEQ ID NO:247.

In some embodiments, the antibody or antigen binding fragment thereof comprises a VH comprising the amino acid sequence of SEQ ID NO:78 and a VL comprising the amino acid sequence of SEQ ID NO:247.

In some embodiments, the antibody or antigen binding fragment thereof comprises a VH comprising the amino acid sequence of SEQ ID NO:79 and a VL comprising the amino acid sequence of SEQ ID NO:247.

In some embodiments, the antibody or antigen binding fragment thereof comprises a VH comprising the amino acid sequence of SEQ ID NO:80 and a VL comprising the amino acid sequence of SEQ ID NO:247.

In some embodiments, the antibody or antigen binding fragment thereof comprises a VH comprising the amino acid sequence of SEQ ID NO:81 and a VL comprising the amino acid sequence of SEQ ID NO:247.

In some embodiments, the antibody or antigen binding fragment thereof comprises a VH comprising the amino acid sequence of SEQ ID NO:82 and a VL comprising the amino acid sequence of SEQ ID NO:247.

In some embodiments, the antibody or antigen binding fragment thereof comprises a VH comprising the amino acid sequence of SEQ ID NO:83 and a VL comprising the amino acid sequence of SEQ ID NO:247.

In some embodiments, the antibody or antigen binding fragment thereof comprises a VH comprising the amino acid sequence of SEQ ID NO:84 and a VL comprising the amino acid sequence of SEQ ID NO:247.

In some embodiments, the antibody or antigen binding fragment thereof comprises a VH comprising the amino acid sequence of SEQ ID NO:85 and a VL comprising the amino acid sequence of SEQ ID NO:247.

In some embodiments, the antibody or antigen binding fragment thereof comprises a VH comprising the amino acid sequence of SEQ ID NO:86 and a VL comprising the amino acid sequence of SEQ ID NO:247.

In some embodiments, the antibody or antigen binding fragment thereof comprises a VH comprising the amino acid sequence of SEQ ID NO:87 and a VL comprising the amino acid sequence of SEQ ID NO:247.

In some embodiments, the antibody or antigen binding fragment thereof comprises a VH comprising the amino acid sequence of SEQ ID NO:88 and a VL comprising the amino acid sequence of SEQ ID NO:247.

In some embodiments, the antibody or antigen binding fragment thereof comprises a VH comprising the amino acid sequence of SEQ ID NO:238 and a VL comprising the amino acid sequence of SEQ ID NO:247.

In some embodiments, the antibody or antigen binding fragment thereof comprises a VH comprising the amino acid sequence of SEQ ID NO:239 and a VL comprising the amino acid sequence of SEQ ID NO:247.

In some embodiments, the antibody or antigen binding fragment thereof comprises a VH comprising the amino acid sequence of SEQ ID NO:240 and a VL comprising the amino acid sequence of SEQ ID NO:247.

In some embodiments, the antibody or antigen binding fragment thereof comprises a VH comprising the amino acid sequence of SEQ ID NO:241 and a VL comprising the amino acid sequence of SEQ ID NO:247.

In some embodiments, the antibody or antigen binding fragment thereof comprises a VH comprising the amino acid sequence of SEQ ID NO:242 and a VL comprising the amino acid sequence of SEQ ID NO:247.

In some embodiments, the antibody or antigen binding fragment thereof comprises a VH comprising the amino acid sequence of SEQ ID NO:243 and a VL comprising the amino acid sequence of SEQ ID NO:247.

In some embodiments, the antibody or antigen binding fragment thereof comprises a VH comprising the amino acid sequence of SEQ ID NO:43 and a VL comprising the amino acid sequence of SEQ ID NO:248.

In some embodiments, the antibody or antigen binding fragment thereof comprises a VH comprising the amino acid sequence of SEQ ID NO:44 and a VL comprising the amino acid sequence of SEQ ID NO:248.

In some embodiments, the antibody or antigen binding fragment thereof comprises a VH comprising the amino acid sequence of SEQ ID NO:45 and a VL comprising the amino acid sequence of SEQ ID NO:248.

In some embodiments, the antibody or antigen binding fragment thereof comprises a VH comprising the amino acid sequence of SEQ ID NO:46 and a VL comprising the amino acid sequence of SEQ ID NO:248.

In some embodiments, the antibody or antigen binding fragment thereof comprises a VH comprising the amino acid sequence of SEQ ID NO:47 and a VL comprising the amino acid sequence of SEQ ID NO:248.

In some embodiments, the antibody or antigen binding fragment thereof comprises a VH comprising the amino acid sequence of SEQ ID NO:48 and a VL comprising the amino acid sequence of SEQ ID NO:248.

In some embodiments, the antibody or antigen binding fragment thereof comprises a VH comprising the amino acid sequence of SEQ ID NO:49 and a VL comprising the amino acid sequence of SEQ ID NO:248.

In some embodiments, the antibody or antigen binding fragment thereof comprises a VH comprising the amino acid sequence of SEQ ID NO:50 and a VL comprising the amino acid sequence of SEQ ID NO:248.

In some embodiments, the antibody or antigen binding fragment thereof comprises a VH comprising the amino acid sequence of SEQ ID NO:51 and a VL comprising the amino acid sequence of SEQ ID NO:248.

In some embodiments, the antibody or antigen binding fragment thereof comprises a VH comprising the amino acid sequence of SEQ ID NO:52 and a VL comprising the amino acid sequence of SEQ ID NO:248.

In some embodiments, the antibody or antigen binding fragment thereof comprises a VH comprising the amino acid sequence of SEQ ID NO:53 and a VL comprising the amino acid sequence of SEQ ID NO:248.

In some embodiments, the antibody or antigen binding fragment thereof comprises a VH comprising the amino acid sequence of SEQ ID NO:54 and a VL comprising the amino acid sequence of SEQ ID NO:248.

In some embodiments, the antibody or antigen binding fragment thereof comprises a VH comprising the amino acid sequence of SEQ ID NO:55 and a VL comprising the amino acid sequence of SEQ ID NO:248.

In some embodiments, the antibody or antigen binding fragment thereof comprises a VH comprising the amino acid sequence of SEQ ID NO:56 and a VL comprising the amino acid sequence of SEQ ID NO:248.

In some embodiments, the antibody or antigen binding fragment thereof comprises a VH comprising the amino acid sequence of SEQ ID NO:57 and a VL comprising the amino acid sequence of SEQ ID NO:248.

In some embodiments, the antibody or antigen binding fragment thereof comprises a VH comprising the amino acid sequence of SEQ ID NO:58 and a VL comprising the amino acid sequence of SEQ ID NO:248.

In some embodiments, the antibody or antigen binding fragment thereof comprises a VH comprising the amino acid sequence of SEQ ID NO:59 and a VL comprising the amino acid sequence of SEQ ID NO:248.

In some embodiments, the antibody or antigen binding fragment thereof comprises a VH comprising the amino acid sequence of SEQ ID NO:60 and a VL comprising the amino acid sequence of SEQ ID NO:248.

In some embodiments, the antibody or antigen binding fragment thereof comprises a VH comprising the amino acid sequence of SEQ ID NO:61 and a VL comprising the amino acid sequence of SEQ ID NO:248.

In some embodiments, the antibody or antigen binding fragment thereof comprises a VH comprising the amino acid sequence of SEQ ID NO:62 and a VL comprising the amino acid sequence of SEQ ID NO:248.

In some embodiments, the antibody or antigen binding fragment thereof comprises a VH comprising the amino acid sequence of SEQ ID NO:63 and a VL comprising the amino acid sequence of SEQ ID NO:248.

In some embodiments, the antibody or antigen binding fragment thereof comprises a VH comprising the amino acid sequence of SEQ ID NO:64 and a VL comprising the amino acid sequence of SEQ ID NO:248.

In some embodiments, the antibody or antigen binding fragment thereof comprises a VH comprising the amino acid sequence of SEQ ID NO:65 and a VL comprising the amino acid sequence of SEQ ID NO:248.

In some embodiments, the antibody or antigen binding fragment thereof comprises a VH comprising the amino acid sequence of SEQ ID NO:66 and a VL comprising the amino acid sequence of SEQ ID NO:248.

In some embodiments, the antibody or antigen binding fragment thereof comprises a VH comprising the amino acid sequence of SEQ ID NO:67 and a VL comprising the amino acid sequence of SEQ ID NO:248.

In some embodiments, the antibody or antigen binding fragment thereof comprises a VH comprising the amino acid sequence of SEQ ID NO:68 and a VL comprising the amino acid sequence of SEQ ID NO:248.

In some embodiments, the antibody or antigen binding fragment thereof comprises a VH comprising the amino acid sequence of SEQ ID NO:69 and a VL comprising the amino acid sequence of SEQ ID NO:248.

In some embodiments, the antibody or antigen binding fragment thereof comprises a VH comprising the amino acid sequence of SEQ ID NO:70 and a VL comprising the amino acid sequence of SEQ ID NO:248.

In some embodiments, the antibody or antigen binding fragment thereof comprises a VH comprising the amino acid sequence of SEQ ID NO:71 and a VL comprising the amino acid sequence of SEQ ID NO:248.

In some embodiments, the antibody or antigen binding fragment thereof comprises a VH comprising the amino acid sequence of SEQ ID NO:72 and a VL comprising the amino acid sequence of SEQ ID NO:248.

In some embodiments, the antibody or antigen binding fragment thereof comprises a VH comprising the amino acid sequence of SEQ ID NO:73 and a VL comprising the amino acid sequence of SEQ ID NO:248.

In some embodiments, the antibody or antigen binding fragment thereof comprises a VH comprising the amino acid sequence of SEQ ID NO:74 and a VL comprising the amino acid sequence of SEQ ID NO:248.

In some embodiments, the antibody or antigen binding fragment thereof comprises a VH comprising the amino acid sequence of SEQ ID NO:75 and a VL comprising the amino acid sequence of SEQ ID NO:248.

In some embodiments, the antibody or antigen binding fragment thereof comprises a VH comprising the amino acid sequence of SEQ ID NO:76 and a VL comprising the amino acid sequence of SEQ ID NO:248.

In some embodiments, the antibody or antigen binding fragment thereof comprises a VH comprising the amino acid sequence of SEQ ID NO:77 and a VL comprising the amino acid sequence of SEQ ID NO:248.

In some embodiments, the antibody or antigen binding fragment thereof comprises a VH comprising the amino acid sequence of SEQ ID NO:78 and a VL comprising the amino acid sequence of SEQ ID NO:248.

In some embodiments, the antibody or antigen binding fragment thereof comprises a VH comprising the amino acid sequence of SEQ ID NO:79 and a VL comprising the amino acid sequence of SEQ ID NO:248.

In some embodiments, the antibody or antigen binding fragment thereof comprises a VH comprising the amino acid sequence of SEQ ID NO:80 and a VL comprising the amino acid sequence of SEQ ID NO:248.

In some embodiments, the antibody or antigen binding fragment thereof comprises a VH comprising the amino acid sequence of SEQ ID NO:81 and a VL comprising the amino acid sequence of SEQ ID NO:248.

In some embodiments, the antibody or antigen binding fragment thereof comprises a VH comprising the amino acid sequence of SEQ ID NO:82 and a VL comprising the amino acid sequence of SEQ ID NO:248.

In some embodiments, the antibody or antigen binding fragment thereof comprises a VH comprising the amino acid sequence of SEQ ID NO:83 and a VL comprising the amino acid sequence of SEQ ID NO:248.

In some embodiments, the antibody or antigen binding fragment thereof comprises a VH comprising the amino acid sequence of SEQ ID NO:84 and a VL comprising the amino acid sequence of SEQ ID NO:248.

In some embodiments, the antibody or antigen binding fragment thereof comprises a VH comprising the amino acid sequence of SEQ ID NO:85 and a VL comprising the amino acid sequence of SEQ ID NO:248.

In some embodiments, the antibody or antigen binding fragment thereof comprises a VH comprising the amino acid sequence of SEQ ID NO:86 and a VL comprising the amino acid sequence of SEQ ID NO:248.

In some embodiments, the antibody or antigen binding fragment thereof comprises a VH comprising the amino acid sequence of SEQ ID NO:87 and a VL comprising the amino acid sequence of SEQ ID NO:248.

In some embodiments, the antibody or antigen binding fragment thereof comprises a VH comprising the amino acid sequence of SEQ ID NO:88 and a VL comprising the amino acid sequence of SEQ ID NO:248.

In some embodiments, the antibody or antigen binding fragment thereof comprises a VH comprising the amino acid sequence of SEQ ID NO:238 and a VL comprising the amino acid sequence of SEQ ID NO:248.

In some embodiments, the antibody or antigen binding fragment thereof comprises a VH comprising the amino acid sequence of SEQ ID NO:239 and a VL comprising the amino acid sequence of SEQ ID NO:248.

In some embodiments, the antibody or antigen binding fragment thereof comprises a VH comprising the amino acid sequence of SEQ ID NO:240 and a VL comprising the amino acid sequence of SEQ ID NO:248.

In some embodiments, the antibody or antigen binding fragment thereof comprises a VH comprising the amino acid sequence of SEQ ID NO:241 and a VL comprising the amino acid sequence of SEQ ID NO:248.

In some embodiments, the antibody or antigen binding fragment thereof comprises a VH comprising the amino acid sequence of SEQ ID NO:242 and a VL comprising the amino acid sequence of SEQ ID NO:248.

In some embodiments, the antibody or antigen binding fragment thereof comprises a VH comprising the amino acid sequence of SEQ ID NO:243 and a VL comprising the amino acid sequence of SEQ ID NO:248.

In some embodiments, the antibody or antigen binding fragment thereof comprises a VH comprising the amino acid sequence of SEQ ID NO:43 and a VL comprising the amino acid sequence of SEQ ID NO:249.

In some embodiments, the antibody or antigen binding fragment thereof comprises a VH comprising the amino acid sequence of SEQ ID NO:44 and a VL comprising the amino acid sequence of SEQ ID NO:249.

In some embodiments, the antibody or antigen binding fragment thereof comprises a VH comprising the amino acid sequence of SEQ ID NO:45 and a VL comprising the amino acid sequence of SEQ ID NO:249.

In some embodiments, the antibody or antigen binding fragment thereof comprises a VH comprising the amino acid sequence of SEQ ID NO:46 and a VL comprising the amino acid sequence of SEQ ID NO:249.

In some embodiments, the antibody or antigen binding fragment thereof comprises a VH comprising the amino acid sequence of SEQ ID NO:47 and a VL comprising the amino acid sequence of SEQ ID NO:249.

In some embodiments, the antibody or antigen binding fragment thereof comprises a VH comprising the amino acid sequence of SEQ ID NO:48 and a VL comprising the amino acid sequence of SEQ ID NO:249.

In some embodiments, the antibody or antigen binding fragment thereof comprises a VH comprising the amino acid sequence of SEQ ID NO:49 and a VL comprising the amino acid sequence of SEQ ID NO:249.

In some embodiments, the antibody or antigen binding fragment thereof comprises a VH comprising the amino acid sequence of SEQ ID NO:50 and a VL comprising the amino acid sequence of SEQ ID NO:249.

In some embodiments, the antibody or antigen binding fragment thereof comprises a VH comprising the amino acid sequence of SEQ ID NO:51 and a VL comprising the amino acid sequence of SEQ ID NO:249.

In some embodiments, the antibody or antigen binding fragment thereof comprises a VH comprising the amino acid sequence of SEQ ID NO:52 and a VL comprising the amino acid sequence of SEQ ID NO:249.

In some embodiments, the antibody or antigen binding fragment thereof comprises a VH comprising the amino acid sequence of SEQ ID NO:53 and a VL comprising the amino acid sequence of SEQ ID NO:249.

In some embodiments, the antibody or antigen binding fragment thereof comprises a VH comprising the amino acid sequence of SEQ ID NO:54 and a VL comprising the amino acid sequence of SEQ ID NO:249.

In some embodiments, the antibody or antigen binding fragment thereof comprises a VH comprising the amino acid sequence of SEQ ID NO:55 and a VL comprising the amino acid sequence of SEQ ID NO:249.

In some embodiments, the antibody or antigen binding fragment thereof comprises a VH comprising the amino acid sequence of SEQ ID NO:56 and a VL comprising the amino acid sequence of SEQ ID NO:249.

In some embodiments, the antibody or antigen binding fragment thereof comprises a VH comprising the amino acid sequence of SEQ ID NO:57 and a VL comprising the amino acid sequence of SEQ ID NO:249.

In some embodiments, the antibody or antigen binding fragment thereof comprises a VH comprising the amino acid sequence of SEQ ID NO:58 and a VL comprising the amino acid sequence of SEQ ID NO:249.

In some embodiments, the antibody or antigen binding fragment thereof comprises a VH comprising the amino acid sequence of SEQ ID NO:59 and a VL comprising the amino acid sequence of SEQ ID NO:249.

In some embodiments, the antibody or antigen binding fragment thereof comprises a VH comprising the amino acid sequence of SEQ ID NO:60 and a VL comprising the amino acid sequence of SEQ ID NO:249.

In some embodiments, the antibody or antigen binding fragment thereof comprises a VH comprising the amino acid sequence of SEQ ID NO:61 and a VL comprising the amino acid sequence of SEQ ID NO:249.

In some embodiments, the antibody or antigen binding fragment thereof comprises a VH comprising the amino acid sequence of SEQ ID NO:62 and a VL comprising the amino acid sequence of SEQ ID NO:249.

In some embodiments, the antibody or antigen binding fragment thereof comprises a VH comprising the amino acid sequence of SEQ ID NO:63 and a VL comprising the amino acid sequence of SEQ ID NO:249.

In some embodiments, the antibody or antigen binding fragment thereof comprises a VH comprising the amino acid sequence of SEQ ID NO:64 and a VL comprising the amino acid sequence of SEQ ID NO:249.

In some embodiments, the antibody or antigen binding fragment thereof comprises a VH comprising the amino acid sequence of SEQ ID NO:65 and a VL comprising the amino acid sequence of SEQ ID NO:249.

In some embodiments, the antibody or antigen binding fragment thereof comprises a VH comprising the amino acid sequence of SEQ ID NO:66 and a VL comprising the amino acid sequence of SEQ ID NO:249.

In some embodiments, the antibody or antigen binding fragment thereof comprises a VH comprising the amino acid sequence of SEQ ID NO:67 and a VL comprising the amino acid sequence of SEQ ID NO:249.

In some embodiments, the antibody or antigen binding fragment thereof comprises a VH comprising the amino acid sequence of SEQ ID NO:68 and a VL comprising the amino acid sequence of SEQ ID NO:249.

In some embodiments, the antibody or antigen binding fragment thereof comprises a VH comprising the amino acid sequence of SEQ ID NO:69 and a VL comprising the amino acid sequence of SEQ ID NO:249.

In some embodiments, the antibody or antigen binding fragment thereof comprises a VH comprising the amino acid sequence of SEQ ID NO:70 and a VL comprising the amino acid sequence of SEQ ID NO:249.

In some embodiments, the antibody or antigen binding fragment thereof comprises a VH comprising the amino acid sequence of SEQ ID NO:71 and a VL comprising the amino acid sequence of SEQ ID NO:249.

In some embodiments, the antibody or antigen binding fragment thereof comprises a VH comprising the amino acid sequence of SEQ ID NO:72 and a VL comprising the amino acid sequence of SEQ ID NO:249.

In some embodiments, the antibody or antigen binding fragment thereof comprises a VH comprising the amino acid sequence of SEQ ID NO:73 and a VL comprising the amino acid sequence of SEQ ID NO:249.

In some embodiments, the antibody or antigen binding fragment thereof comprises a VH comprising the amino acid sequence of SEQ ID NO:74 and a VL comprising the amino acid sequence of SEQ ID NO:249.

In some embodiments, the antibody or antigen binding fragment thereof comprises a VH comprising the amino acid sequence of SEQ ID NO:75 and a VL comprising the amino acid sequence of SEQ ID NO:249.

In some embodiments, the antibody or antigen binding fragment thereof comprises a VH comprising the amino acid sequence of SEQ ID NO:76 and a VL comprising the amino acid sequence of SEQ ID NO:249.

In some embodiments, the antibody or antigen binding fragment thereof comprises a VH comprising the amino acid sequence of SEQ ID NO:77 and a VL comprising the amino acid sequence of SEQ ID NO:249.

In some embodiments, the antibody or antigen binding fragment thereof comprises a VH comprising the amino acid sequence of SEQ ID NO:78 and a VL comprising the amino acid sequence of SEQ ID NO:249.

In some embodiments, the antibody or antigen binding fragment thereof comprises a VH comprising the amino acid sequence of SEQ ID NO:79 and a VL comprising the amino acid sequence of SEQ ID NO:249.

In some embodiments, the antibody or antigen binding fragment thereof comprises a VH comprising the amino acid sequence of SEQ ID NO:80 and a VL comprising the amino acid sequence of SEQ ID NO:249.

In some embodiments, the antibody or antigen binding fragment thereof comprises a VH comprising the amino acid sequence of SEQ ID NO:81 and a VL comprising the amino acid sequence of SEQ ID NO:249.

In some embodiments, the antibody or antigen binding fragment thereof comprises a VH comprising the amino acid sequence of SEQ ID NO:82 and a VL comprising the amino acid sequence of SEQ ID NO:249.

In some embodiments, the antibody or antigen binding fragment thereof comprises a VH comprising the amino acid sequence of SEQ ID NO:83 and a VL comprising the amino acid sequence of SEQ ID NO:249.

In some embodiments, the antibody or antigen binding fragment thereof comprises a VH comprising the amino acid sequence of SEQ ID NO:84 and a VL comprising the amino acid sequence of SEQ ID NO:249.

In some embodiments, the antibody or antigen binding fragment thereof comprises a VH comprising the amino acid sequence of SEQ ID NO:85 and a VL comprising the amino acid sequence of SEQ ID NO:249.

In some embodiments, the antibody or antigen binding fragment thereof comprises a VH comprising the amino acid sequence of SEQ ID NO:86 and a VL comprising the amino acid sequence of SEQ ID NO:249.

In some embodiments, the antibody or antigen binding fragment thereof comprises a VH comprising the amino acid sequence of SEQ ID NO:87 and a VL comprising the amino acid sequence of SEQ ID NO:249.

In some embodiments, the antibody or antigen binding fragment thereof comprises a VH comprising the amino acid sequence of SEQ ID NO:88 and a VL comprising the amino acid sequence of SEQ ID NO:249.

In some embodiments, the antibody or antigen binding fragment thereof comprises a VH comprising the amino acid sequence of SEQ ID NO:238 and a VL comprising the amino acid sequence of SEQ ID NO:249.

In some embodiments, the antibody or antigen binding fragment thereof comprises a VH comprising the amino acid sequence of SEQ ID NO:239 and a VL comprising the amino acid sequence of SEQ ID NO:249.

In some embodiments, the antibody or antigen binding fragment thereof comprises a VH comprising the amino acid sequence of SEQ ID NO:240 and a VL comprising the amino acid sequence of SEQ ID NO:249.

In some embodiments, the antibody or antigen binding fragment thereof comprises a VH comprising the amino acid sequence of SEQ ID NO:241 and a VL comprising the amino acid sequence of SEQ ID NO:249.

In some embodiments, the antibody or antigen binding fragment thereof comprises a VH comprising the amino acid sequence of SEQ ID NO:242 and a VL comprising the amino acid sequence of SEQ ID NO:249.

In some embodiments, the antibody or antigen binding fragment thereof comprises a VH comprising the amino acid sequence of SEQ ID NO:243 and a VL comprising the amino acid sequence of SEQ ID NO:249.

In some embodiments, the antibody or antigen binding fragment thereof comprises a VH comprising the amino acid sequence of SEQ ID NO:39, and a VL comprising the amino acid sequence of SEQ ID NO:127.

In some embodiments, the antibody or antigen binding fragment thereof comprises a VH comprising the amino acid sequence selected from any one of SEQ ID NOS:89-93, and a VL comprising the amino acid sequence selected from any one of SEQ ID NOS:134-137.

In some embodiments, the antibody or antigen binding fragment thereof comprises a VH comprising the amino acid sequence of SEQ ID NO:89 and a VL comprising the amino acid sequence of SEQ ID NO:134.

In some embodiments, the antibody or antigen binding fragment thereof comprises a VH comprising the amino acid sequence of SEQ ID NO:90 and a VL comprising the amino acid sequence of SEQ ID NO:134.

In some embodiments, the antibody or antigen binding fragment thereof comprises a VH comprising the amino acid sequence of SEQ ID NO:91 and a VL comprising the amino acid sequence of SEQ ID NO:134.

In some embodiments, the antibody or antigen binding fragment thereof comprises a VH comprising the amino acid sequence of SEQ ID NO:92 and a VL comprising the amino acid sequence of SEQ ID NO:134.

In some embodiments, the antibody or antigen binding fragment thereof comprises a VH comprising the amino acid sequence of SEQ ID NO:93 and a VL comprising the amino acid sequence of SEQ ID NO:134.

In some embodiments, the antibody or antigen binding fragment thereof comprises a VH comprising the amino acid sequence of SEQ ID NO:89 and a VL comprising the amino acid sequence of SEQ ID NO:135.

In some embodiments, the antibody or antigen binding fragment thereof comprises a VH comprising the amino acid sequence of SEQ ID NO:90 and a VL comprising the amino acid sequence of SEQ ID NO:135.

In some embodiments, the antibody or antigen binding fragment thereof comprises a VH comprising the amino acid sequence of SEQ ID NO:91 and a VL comprising the amino acid sequence of SEQ ID NO:135.

In some embodiments, the antibody or antigen binding fragment thereof comprises a VH comprising the amino acid sequence of SEQ ID NO:92 and a VL comprising the amino acid sequence of SEQ ID NO:135.

In some embodiments, the antibody or antigen binding fragment thereof comprises a VH comprising the amino acid sequence of SEQ ID NO:93 and a VL comprising the amino acid sequence of SEQ ID NO:135.

In some embodiments, the antibody or antigen binding fragment thereof comprises a VH comprising the amino acid sequence of SEQ ID NO:89 and a VL comprising the amino acid sequence of SEQ ID NO:136.

In some embodiments, the antibody or antigen binding fragment thereof comprises a VH comprising the amino acid sequence of SEQ ID NO:90 and a VL comprising the amino acid sequence of SEQ ID NO:136.

In some embodiments, the antibody or antigen binding fragment thereof comprises a VH comprising the amino acid sequence of SEQ ID NO:91 and a VL comprising the amino acid sequence of SEQ ID NO:136.

In some embodiments, the antibody or antigen binding fragment thereof comprises a VH comprising the amino acid sequence of SEQ ID NO:92 and a VL comprising the amino acid sequence of SEQ ID NO:136.

In some embodiments, the antibody or antigen binding fragment thereof comprises a VH comprising the amino acid sequence of SEQ ID NO:93 and a VL comprising the amino acid sequence of SEQ ID NO:136.

In some embodiments, the antibody or antigen binding fragment thereof comprises a VH comprising the amino acid sequence of SEQ ID NO:89 and a VL comprising the amino acid sequence of SEQ ID NO:137.

In some embodiments, the antibody or antigen binding fragment thereof comprises a VH comprising the amino acid sequence of SEQ ID NO:90 and a VL comprising the amino acid sequence of SEQ ID NO:137.

In some embodiments, the antibody or antigen binding fragment thereof comprises a VH comprising the amino acid sequence of SEQ ID NO:91 and a VL comprising the amino acid sequence of SEQ ID NO:137.

In some embodiments, the antibody or antigen binding fragment thereof comprises a VH comprising the amino acid sequence of SEQ ID NO:92 and a VL comprising the amino acid sequence of SEQ ID NO:137.

In some embodiments, the antibody or antigen binding fragment thereof comprises a VH comprising the amino acid sequence of SEQ ID NO:93 and a VL comprising the amino acid sequence of SEQ ID NO:137.

In some embodiments, the antibody or antigen binding fragment thereof comprises a VH comprising the amino acid sequence of SEQ ID NO:42, and a VL comprising the amino acid sequence of SEQ ID NO:130.

In some embodiments, the antibody or antigen binding fragment thereof comprises a VH comprising the amino acid sequence selected from any one of SEQ ID NOS:113-125, and a VL comprising the amino acid sequence selected from any one of SEQ ID NOS:143-149.

In some embodiments, the antibody or antigen binding fragment thereof comprises a VH comprising the amino acid sequence of SEQ ID NO:113 and a VL comprising the amino acid sequence of SEQ ID NO:143.

In some embodiments, the antibody or antigen binding fragment thereof comprises a VH comprises the amino acid sequence of SEQ ID NO:121 and a VL comprising the amino acid sequence of SEQ ID NO:143.

In some embodiments, the antibody or antigen binding fragment thereof comprises a VH comprising the amino acid sequence of SEQ ID NO:118 and a VL comprising the amino acid sequence of SEQ ID NO:143.

In some embodiments, the antibody or antigen binding fragment thereof comprises a VH comprising the amino acid sequence of SEQ ID NO:122 and a VL comprising the amino acid sequence of SEQ ID NO:143.

In some embodiments, the antibody or antigen binding fragment thereof comprises a VH comprising the amino acid sequence of SEQ ID NO:123 and a VL comprising the amino acid sequence of SEQ ID NO:143.

In some embodiments, the antibody or antigen binding fragment thereof comprises a VH comprising the amino acid sequence of SEQ ID NO:113 and a VL comprising the amino acid sequence of SEQ ID NO:144.

In some embodiments, the antibody or antigen binding fragment thereof comprises a VH comprising the amino acid sequence of SEQ ID NO:121 and a VL comprising the amino acid sequence of SEQ ID NO:144.

In some embodiments, the antibody or antigen binding fragment thereof comprises a VH comprising the amino acid sequence of SEQ ID NO:118 and a VL comprising the amino acid sequence of SEQ ID NO:144.

In some embodiments, the antibody or antigen binding fragment thereof comprises a VH comprising the amino acid sequence of SEQ ID NO:122 and a VL comprising the amino acid sequence of SEQ ID NO:144.

In some embodiments, the antibody or antigen binding fragment thereof comprises a VH comprising the amino acid sequence of SEQ ID NO:123 and a VL comprising the amino acid sequence of SEQ ID NO:144.

In some embodiments, the antibody or antigen binding fragment thereof comprises a VH comprising the amino acid sequence of SEQ ID NO:113 and a VL comprising the amino acid sequence of SEQ ID NO:146.

In some embodiments, the antibody or antigen binding fragment thereof comprises a VH comprising the amino acid sequence of SEQ ID NO:121 and a VL comprising the amino acid sequence of SEQ ID NO:146.

In some embodiments, the antibody or antigen binding fragment thereof comprises a VH comprising the amino acid sequence of SEQ ID NO:118 and a VL comprising the amino acid sequence of SEQ ID NO:146.

In some embodiments, the antibody or antigen binding fragment thereof comprises a VH comprising the amino acid sequence of SEQ ID NO:122 and a VL comprising the amino acid sequence of SEQ ID NO:146.

In some embodiments, the antibody or antigen binding fragment thereof comprises a VH comprising the amino acid sequence of SEQ ID NO:123 and a VL comprising the amino acid sequence of SEQ ID NO:146.

In some embodiments, the antibody or antigen binding fragment thereof comprises a VH comprising the amino acid sequence of SEQ ID NO:113 and a VL comprising the amino acid sequence of SEQ ID NO:145.

In some embodiments, the antibody or antigen binding fragment thereof comprises a VH comprising the amino acid sequence of SEQ ID NO:121 and a VL comprising the amino acid sequence of SEQ ID NO:145.

In some embodiments, the antibody or antigen binding fragment thereof comprises a VH comprising the amino acid sequence of SEQ ID NO:118 and a VL comprising the amino acid sequence of SEQ ID NO:145.

In some embodiments, the antibody or antigen binding fragment thereof comprises a VH comprising the amino acid sequence of SEQ ID NO:122 and a VL comprising the amino acid sequence of SEQ ID NO:145.

In some embodiments, the antibody or antigen binding fragment thereof comprises a VH comprising the amino acid sequence of SEQ ID NO:123 and a VL comprising the amino acid sequence of SEQ ID NO:145.

In some embodiments, the antibody or antigen binding fragment thereof comprises a VH comprising the amino acid sequence of SEQ ID NO:114 and a VL comprising the amino acid sequence of SEQ ID NO:146.

In some embodiments, the antibody or antigen binding fragment thereof comprises a VH comprising the amino acid sequence of SEQ ID NO:115 and a VL comprising the amino acid sequence of SEQ ID NO:146.

In some embodiments, the antibody or antigen binding fragment thereof comprises a VH comprising the amino acid sequence of SEQ ID NO:116 and a VL comprising the amino acid sequence of SEQ ID NO:146.

In some embodiments, the antibody or antigen binding fragment thereof comprises a VH comprising the amino acid sequence of SEQ ID NO:117 and a VL comprising the amino acid sequence of SEQ ID NO:146.

In some embodiments, the antibody or antigen binding fragment thereof comprises a VH comprising the amino acid sequence of SEQ ID NO:124 and a VL comprising the amino acid sequence of SEQ ID NO:146.

In some embodiments, the antibody or antigen binding fragment thereof comprises a VH comprising the amino acid sequence of SEQ ID NO:125 and a VL comprising the amino acid sequence of SEQ ID NO:146.

In some embodiments, the antibody or antigen binding fragment thereof comprises a VH comprising the amino acid sequence of SEQ ID NO:119 and a VL comprising the amino acid sequence of SEQ ID NO:146.

In some embodiments, the antibody or antigen binding fragment thereof comprises a VH comprising the amino acid sequence of SEQ ID NO:120 and a VL comprising the amino acid sequence of SEQ ID NO:146.

In some embodiments, the antibody or antigen binding fragment thereof comprises a VH comprising the amino acid sequence of SEQ ID NO:113 and a VL comprising the amino acid sequence of SEQ ID NO:147.

In some embodiments, the antibody or antigen binding fragment thereof comprises a VH comprising the amino acid sequence of SEQ ID NO:118 and a VL comprising the amino acid sequence of SEQ ID NO:147.

In some embodiments, the antibody or antigen binding fragment thereof comprises a VH comprising the amino acid sequence of SEQ ID NO:114 and a VL comprising the amino acid sequence of SEQ ID NO:147.

In some embodiments, the antibody or antigen binding fragment thereof comprises a VH comprising the amino acid sequence of SEQ ID NO:115 and a VL comprising the amino acid sequence of SEQ ID NO:147.

In some embodiments, the antibody or antigen binding fragment thereof comprises a VH comprising the amino acid sequence of SEQ ID NO:116 and a VL comprising the amino acid sequence of SEQ ID NO:147.

In some embodiments, the antibody or antigen binding fragment thereof comprises a VH comprising the amino acid sequence of SEQ ID NO:117 and a VL comprising the amino acid sequence of SEQ ID NO:147.

In some embodiments, the antibody or antigen binding fragment thereof comprises a VH comprising the amino acid sequence of SEQ ID NO:124 and a VL comprising the amino acid sequence of SEQ ID NO:147.

In some embodiments, the antibody or antigen binding fragment thereof comprises a VH comprising the amino acid sequence of SEQ ID NO:125 and a VL comprising the amino acid sequence of SEQ ID NO:147.

In some embodiments, the antibody or antigen binding fragment thereof comprises a VH comprising the amino acid sequence of SEQ ID NO:119 and a VL comprising the amino acid sequence of SEQ ID NO:147.

In some embodiments, the antibody or antigen binding fragment thereof comprises a VH comprising the amino acid sequence of SEQ ID NO:120 and a VL comprising the amino acid sequence of SEQ ID NO:147.

In some embodiments, the antibody or antigen binding fragment thereof comprises a VH comprising the amino acid sequence of SEQ ID NO:113 and a VL comprising the amino acid sequence of SEQ ID NO:148.

In some embodiments, the antibody or antigen binding fragment thereof comprises a VH comprising the amino acid sequence of SEQ ID NO:118 and a VL comprising the amino acid sequence of SEQ ID NO:148.

In some embodiments, the antibody or antigen binding fragment thereof comprises a VH comprising the amino acid sequence of SEQ ID NO:114 and a VL comprising the amino acid sequence of SEQ ID NO:148.

In some embodiments, the antibody or antigen binding fragment thereof comprises a VH comprising the amino acid sequence of SEQ ID NO:115 and a VL comprising the amino acid sequence of SEQ ID NO:148.

In some embodiments, the antibody or antigen binding fragment thereof comprises a VH comprising the amino acid sequence of SEQ ID NO:116 and a VL comprising the amino acid sequence of SEQ ID NO:148.

In some embodiments, the antibody or antigen binding fragment thereof comprises a VH comprising the amino acid sequence of SEQ ID NO:117 and a VL comprising the amino acid sequence of SEQ ID NO:148.

In some embodiments, the antibody or antigen binding fragment thereof comprises a VH comprising the amino acid sequence of SEQ ID NO:124 and a VL comprising the amino acid sequence of SEQ ID NO:148.

In some embodiments, the antibody or antigen binding fragment thereof comprises a VH comprising the amino acid sequence of SEQ ID NO:125 and a VL comprising the amino acid sequence of SEQ ID NO:148.

In some embodiments, the antibody or antigen binding fragment thereof comprises a VH comprising the amino acid sequence of SEQ ID NO:119 and a VL comprising the amino acid sequence of SEQ ID NO:148.

In some embodiments, the antibody or antigen binding fragment thereof comprises a VH comprising the amino acid sequence of SEQ ID NO:120 and a VL comprising the amino acid sequence of SEQ ID NO:148.

In some embodiments, the antibody or antigen binding fragment thereof comprises a VH comprising the amino acid sequence of SEQ ID NO:113 and a VL comprising the amino acid sequence of SEQ ID NO:149.

In some embodiments, the antibody or antigen binding fragment thereof comprises a VH comprising the amino acid sequence of SEQ ID NO:118 and a VL comprising the amino acid sequence of SEQ ID NO:149.

In some embodiments, the antibody or antigen binding fragment thereof comprises a VH comprising the amino acid sequence of SEQ ID NO:114 and a VL comprising the amino acid sequence of SEQ ID NO:149.

In some embodiments, the antibody or antigen binding fragment thereof comprises a VH comprising the amino acid sequence of SEQ ID NO:115 and a VL comprising the amino acid sequence of SEQ ID NO:149.

In some embodiments, the antibody or antigen binding fragment thereof comprises a VH comprising the amino acid sequence of SEQ ID NO:116 and a VL comprising the amino acid sequence of SEQ ID NO:149.

In some embodiments, the antibody or antigen binding fragment thereof comprises a VH comprising the amino acid sequence of SEQ ID NO:117 and a VL comprising the amino acid sequence of SEQ ID NO:149.

In some embodiments, the antibody or antigen binding fragment thereof comprises a VH comprising the amino acid sequence of SEQ ID NO:124 and a VL comprising the amino acid sequence of SEQ ID NO:149.

In some embodiments, the antibody or antigen binding fragment thereof comprises a VH comprising the amino acid sequence of SEQ ID NO:125 and a VL comprising the amino acid sequence of SEQ ID NO:149.

In some embodiments, the antibody or antigen binding fragment thereof comprises a VH comprising the amino acid sequence of SEQ ID NO:119 and a VL comprising the amino acid sequence of SEQ ID NO:149.

In some embodiments, the antibody or antigen binding fragment thereof comprises a VH comprising the amino acid sequence of SEQ ID NO:120 and a VL comprising the amino acid sequence of SEQ ID NO:149.

In some embodiments, the antibody or antigen binding fragment thereof comprises a VH comprising the amino acid sequence of SEQ ID NO:114 and a VL comprising the amino acid sequence of SEQ ID NO:143.

In some embodiments, the antibody or antigen binding fragment thereof comprises a VH comprising the amino acid sequence of SEQ ID NO:114 and a VL comprising the amino acid sequence of SEQ ID NO:144.

In some embodiments, the antibody or antigen binding fragment thereof comprises a VH comprising the amino acid sequence of SEQ ID NO:114 and a VL comprising the amino acid sequence of SEQ ID NO:145.

In some embodiments, the antibody or antigen binding fragment thereof comprises a VH comprising the amino acid sequence of SEQ ID NO:115 and a VL comprising the amino acid sequence of SEQ ID NO:143.

In some embodiments, the antibody or antigen binding fragment thereof comprises a VH comprising the amino acid sequence of SEQ ID NO:115 and a VL comprising the amino acid sequence of SEQ ID NO:144.

In some embodiments, the antibody or antigen binding fragment thereof comprises a VH comprising the amino acid sequence of SEQ ID NO:115 and a VL comprising the amino acid sequence of SEQ ID NO:145.

In some embodiments, the antibody or antigen binding fragment thereof comprises a VH comprising the amino acid sequence of SEQ ID NO:116 and a VL comprising the amino acid sequence of SEQ ID NO:143.

In some embodiments, the antibody or antigen binding fragment thereof comprises a VH comprising the amino acid sequence of SEQ ID NO:116 and a VL comprising the amino acid sequence of SEQ ID NO:144.

In some embodiments, the antibody or antigen binding fragment thereof comprises a VH comprising the amino acid sequence of SEQ ID NO:116 and a VL comprising the amino acid sequence of SEQ ID NO:145.

In some embodiments, the antibody or antigen binding fragment thereof comprises a VH comprising the amino acid sequence of SEQ ID NO:117 and a VL comprising the amino acid sequence of SEQ ID NO:143.

In some embodiments, the antibody or antigen binding fragment thereof comprises a VH comprising the amino acid sequence of SEQ ID NO:117 and a VL comprising the amino acid sequence of SEQ ID NO:144.

In some embodiments, the antibody or antigen binding fragment thereof comprises a VH comprising the amino acid sequence of SEQ ID NO:117 and a VL comprising the amino acid sequence of SEQ ID NO:145.

In some embodiments, the antibody or antigen binding fragment thereof comprises a VH comprising the amino acid sequence of SEQ ID NO:119 and a VL comprising the amino acid sequence of SEQ ID NO:143.

In some embodiments, the antibody or antigen binding fragment thereof comprises a VH comprising the amino acid sequence of SEQ ID NO:119 and a VL comprising the amino acid sequence of SEQ ID NO:144.

In some embodiments, the antibody or antigen binding fragment thereof comprises a VH comprising the amino acid sequence of SEQ ID NO:119 and a VL comprising the amino acid sequence of SEQ ID NO:145.

In some embodiments, the antibody or antigen binding fragment thereof comprises a VH comprising the amino acid sequence of SEQ ID NO:120 and a VL comprising the amino acid sequence of SEQ ID NO:143.

In some embodiments, the antibody or antigen binding fragment thereof comprises a VH comprising the amino acid sequence of SEQ ID NO:120 and a VL comprising the amino acid sequence of SEQ ID NO:144.

In some embodiments, the antibody or antigen binding fragment thereof comprises a VH comprising the amino acid sequence of SEQ ID NO:120 and a VL comprising the amino acid sequence of SEQ ID NO:145.

In some embodiments, the antibody or antigen binding fragment thereof comprises a VH comprising the amino acid sequence of SEQ ID NO:121 and a VL comprising the amino acid sequence of SEQ ID NO:147.

In some embodiments, the antibody or antigen binding fragment thereof comprises a VH comprising the amino acid sequence of SEQ ID NO:121 and a VL comprising the amino acid sequence of SEQ ID NO:148.

In some embodiments, the antibody or antigen binding fragment thereof comprises a VH comprising the amino acid sequence of SEQ ID NO:121 and a VL comprising the amino acid sequence of SEQ ID NO:149.

In some embodiments, the antibody or antigen binding fragment thereof comprises a VH comprising the amino acid sequence of SEQ ID NO:122 and a VL comprising the amino acid sequence of SEQ ID NO:147.

In some embodiments, the antibody or antigen binding fragment thereof comprises a VH comprising the amino acid sequence of SEQ ID NO:122 and a VL comprising the amino acid sequence of SEQ ID NO:148.

In some embodiments, the antibody or antigen binding fragment thereof comprises a VH comprising the amino acid sequence of SEQ ID NO:122 and a VL comprising the amino acid sequence of SEQ ID NO:149.

In some embodiments, the antibody or antigen binding fragment thereof comprises a VH comprising the amino acid sequence of SEQ ID NO:123 and a VL comprising the amino acid sequence of SEQ ID NO:147.

In some embodiments, the antibody or antigen binding fragment thereof comprises a VH comprising the amino acid sequence of SEQ ID NO:123 and a VL comprising the amino acid sequence of SEQ ID NO:148.

In some embodiments, the antibody or antigen binding fragment thereof comprises a VH comprising the amino acid sequence of SEQ ID NO:123 and a VL comprising the amino acid sequence of SEQ ID NO:149.

In some embodiments, the antibody or antigen binding fragment thereof comprises a VH comprising the amino acid sequence of SEQ ID NO:124 and a VL comprising the amino acid sequence of SEQ ID NO:143.

In some embodiments, the antibody or antigen binding fragment thereof comprises a VH comprising the amino acid sequence of SEQ ID NO:124 and a VL comprising the amino acid sequence of SEQ ID NO:144.

In some embodiments, the antibody or antigen binding fragment thereof comprises a VH comprising the amino acid sequence of SEQ ID NO:124 and a VL comprising the amino acid sequence of SEQ ID NO:145.

In some embodiments, the antibody or antigen binding fragment thereof comprises a VH comprising the amino acid sequence of SEQ ID NO:125 and a VL comprising the amino acid sequence of SEQ ID NO:143.

In some embodiments, the antibody or antigen binding fragment thereof comprises a VH comprising the amino acid sequence of SEQ ID NO:125 and a VL comprising the amino acid sequence of SEQ ID NO:144.

In some embodiments, the antibody or antigen binding fragment thereof comprises a VH comprising the amino acid sequence of SEQ ID NO:125 and a VL comprising the amino acid sequence of SEQ ID NO:145.

In some embodiments, the antibody or antigen binding fragment thereof comprises a VH comprising the amino acid sequence of SEQ ID NO:40, and a VL comprising the amino acid sequence of SEQ ID NO:128.

In some embodiments, the antibody or antigen binding fragment thereof comprises a VH comprising the amino acid sequence selected from any one of SEQ ID NOS:94-102, and a VL comprising the amino acid sequence selected from any one of SEQ ID NOS:138-141.

In some embodiments, the antibody or antigen binding fragment thereof comprises a VH comprising the amino acid sequence of SEQ ID NO:94 and a VL comprising the amino acid sequence of SEQ ID NO:138.

In some embodiments, the antibody or antigen binding fragment thereof comprises a VH comprising the amino acid sequence of SEQ ID NO:95 and a VL comprising the amino acid sequence of SEQ ID NO:138.

In some embodiments, the antibody or antigen binding fragment thereof comprises a VH comprising the amino acid sequence of SEQ ID NO:96 and a VL comprising the amino acid sequence of SEQ ID NO:138.

In some embodiments, the antibody or antigen binding fragment thereof comprises a VH comprising the amino acid sequence of SEQ ID NO:97 and a VL comprising the amino acid sequence of SEQ ID NO:138.

In some embodiments, the antibody or antigen binding fragment thereof comprises a VH comprising the amino acid sequence of SEQ ID NO:98 and a VL comprising the amino acid sequence of SEQ ID NO:138.

In some embodiments, the antibody or antigen binding fragment thereof comprises a VH comprising the amino acid sequence of SEQ ID NO:99 and a VL comprising the amino acid sequence of SEQ ID NO:138.

In some embodiments, the antibody or antigen binding fragment thereof comprises a VH comprising the amino acid sequence of SEQ ID NO:100 and a VL comprising the amino acid sequence of SEQ ID NO:138.

In some embodiments, the antibody or antigen binding fragment thereof comprises a VH comprising the amino acid sequence of SEQ ID NO:101 and a VL comprising the amino acid sequence of SEQ ID NO:138.

In some embodiments, the antibody or antigen binding fragment thereof comprises a VH comprising the amino acid sequence of SEQ ID NO:102 and a VL comprising the amino acid sequence of SEQ ID NO:138.

In some embodiments, the antibody or antigen binding fragment thereof comprises a VH comprising the amino acid sequence of SEQ ID NO:96 and a VL comprising the amino acid sequence of SEQ ID NO:139.

In some embodiments, the antibody or antigen binding fragment thereof comprises a VH comprising the amino acid sequence of SEQ ID NO:96 and a VL comprising the amino acid sequence of SEQ ID NO:140.

In some embodiments, the antibody or antigen binding fragment thereof comprises a VH comprising the amino acid sequence of SEQ ID NO:96 and a VL comprising the amino acid sequence of SEQ ID NO:141.

In some embodiments, the antibody or antigen binding fragment thereof comprises a VH comprising the amino acid sequence of SEQ ID NO:98 and a VL comprising the amino acid sequence of SEQ ID NO:140.

In some embodiments, the antibody or antigen binding fragment thereof comprises a VH comprising the amino acid sequence of SEQ ID NO:100 and a VL comprising the amino acid sequence of SEQ ID NO:140.

In some embodiments, the antibody or antigen binding fragment thereof comprises a VH comprising the amino acid sequence of SEQ ID NO:94 and a VL comprising the amino acid sequence of SEQ ID NO:139.

In some embodiments, the antibody or antigen binding fragment thereof comprises a VH comprising the amino acid sequence of SEQ ID NO:94 and a VL comprising the amino acid sequence of SEQ ID NO:140.

In some embodiments, the antibody or antigen binding fragment thereof comprises a VH comprising the amino acid sequence of SEQ ID NO:94 and a VL comprising the amino acid sequence of SEQ ID NO:141.

In some embodiments, the antibody or antigen binding fragment thereof comprises a VH comprising the amino acid sequence of SEQ ID NO:95 and a VL comprising the amino acid sequence of SEQ ID NO:139.

In some embodiments, the antibody or antigen binding fragment thereof comprises a VH comprising the amino acid sequence of SEQ ID NO:95 and a VL comprising the amino acid sequence of SEQ ID NO:140.

In some embodiments, the antibody or antigen binding fragment thereof comprises a VH comprising the amino acid sequence of SEQ ID NO:95 and a VL comprising the amino acid sequence of SEQ ID NO:141.

In some embodiments, the antibody or antigen binding fragment thereof comprises a VH comprising the amino acid sequence of SEQ ID NO:97 and a VL comprising the amino acid sequence of SEQ ID NO:138.

In some embodiments, the antibody or antigen binding fragment thereof comprises a VH comprising the amino acid sequence of SEQ ID NO:97 and a VL comprising the amino acid sequence of SEQ ID NO:139.

In some embodiments, the antibody or antigen binding fragment thereof comprises a VH comprising the amino acid sequence of SEQ ID NO:97 and a VL comprising the amino acid sequence of SEQ ID NO:140.

In some embodiments, the antibody or antigen binding fragment thereof comprises a VH comprising the amino acid sequence of SEQ ID NO:97 and a VL comprising the amino acid sequence of SEQ ID NO:141.

In some embodiments, the antibody or antigen binding fragment thereof comprises a VH comprising the amino acid sequence of SEQ ID NO:98 and a VL comprising the amino acid sequence of SEQ ID NO:138.

In some embodiments, the antibody or antigen binding fragment thereof comprises a VH comprising the amino acid sequence of SEQ ID NO:98 and a VL comprising the amino acid sequence of SEQ ID NO:139.

In some embodiments, the antibody or antigen binding fragment thereof comprises a VH comprising the amino acid sequence of SEQ ID NO:98 and a VL comprising the amino acid sequence of SEQ ID NO:141.

In some embodiments, the antibody or antigen binding fragment thereof comprises a VH comprising the amino acid sequence of SEQ ID NO:99 and a VL comprising the amino acid sequence of SEQ ID NO:138.

In some embodiments, the antibody or antigen binding fragment thereof comprises a VH comprising the amino acid sequence of SEQ ID NO:99 and a VL comprising the amino acid sequence of SEQ ID NO:139.

In some embodiments, the antibody or antigen binding fragment thereof comprises a VH comprising the amino acid sequence of SEQ ID NO:99 and a VL comprising the amino acid sequence of SEQ ID NO:140.

In some embodiments, the antibody or antigen binding fragment thereof comprises a VH comprising the amino acid sequence of SEQ ID NO:99 and a VL comprising the amino acid sequence of SEQ ID NO:141.

In some embodiments, the antibody or antigen binding fragment thereof comprises a VH comprising the amino acid sequence of SEQ ID NO:100 and a VL comprising the amino acid sequence of SEQ ID NO:138.

In some embodiments, the antibody or antigen binding fragment thereof comprises a VH comprising the amino acid sequence of SEQ ID NO:100 and a VL comprising the amino acid sequence of SEQ ID NO:139.

In some embodiments, the antibody or antigen binding fragment thereof comprises a VH comprising the amino acid sequence of SEQ ID NO:100 and a VL comprising the amino acid sequence of SEQ ID NO:141.

In some embodiments, the antibody or antigen binding fragment thereof comprises a VH comprising the amino acid sequence of SEQ ID NO:101 and a VL comprising the amino acid sequence of SEQ ID NO:138.

In some embodiments, the antibody or antigen binding fragment thereof comprises a VH comprising the amino acid sequence of SEQ ID NO:101 and a VL comprising the amino acid sequence of SEQ ID NO:139.

In some embodiments, the antibody or antigen binding fragment thereof comprises a VH comprising the amino acid sequence of SEQ ID NO:101 and a VL comprising the amino acid sequence of SEQ ID NO:140.

In some embodiments, the antibody or antigen binding fragment thereof comprises a VH comprising the amino acid sequence of SEQ ID NO:101 and a VL comprising the amino acid sequence of SEQ ID NO:141.

In some embodiments, the antibody or antigen binding fragment thereof comprises a VH comprising the amino acid sequence of SEQ ID NO:102 and a VL comprising the amino acid sequence of SEQ ID NO:138.

In some embodiments, the antibody or antigen binding fragment thereof comprises a VH comprising the amino acid sequence of SEQ ID NO:102 and a VL comprising the amino acid sequence of SEQ ID NO:139.

In some embodiments, the antibody or antigen binding fragment thereof comprises a VH comprising the amino acid sequence of SEQ ID NO:102 and a VL comprising the amino acid sequence of SEQ ID NO:140.

In some embodiments, the antibody or antigen binding fragment thereof comprises a VH comprising the amino acid sequence of SEQ ID NO:102 and a VL comprising the amino acid sequence of SEQ ID NO:141.

In some embodiments, the antibody or antigen binding fragment thereof comprises a VH comprising the amino acid sequence of SEQ ID NO:41, and a VL comprising the amino acid sequence of SEQ ID NO:129.

In some embodiments, the antibody or antigen binding fragment thereof comprises a VH comprising the amino acid sequence selected from any one of SEQ ID NOS:103-112, and a VL comprising the amino acid sequence of SEQ ID NO:142.

In some embodiments, the antibody or antigen binding fragment thereof comprises a VH comprising the amino acid sequence of SEQ ID NO:103 and a VL comprising the amino acid sequence of SEQ ID NO:142.

In some embodiments, the antibody or antigen binding fragment thereof comprises a VH comprising the amino acid sequence of SEQ ID NO:104 and a VL comprising the amino acid sequence of SEQ ID NO:142.

In some embodiments, the antibody or antigen binding fragment thereof comprises a VH comprising the amino acid sequence of SEQ ID NO:105 and a VL comprising the amino acid sequence of SEQ ID NO:142.

In some embodiments, the antibody or antigen binding fragment thereof comprises a VH comprising the amino acid sequence of SEQ ID NO:106 and a VL comprising the amino acid sequence of SEQ ID NO:142.

In some embodiments, the antibody or antigen binding fragment thereof comprises a VH comprising the amino acid sequence of SEQ ID NO:107 and a VL comprising the amino acid sequence of SEQ ID NO:142.

In some embodiments, the antibody or antigen binding fragment thereof comprises a VH comprising the amino acid sequence of SEQ ID NO:108 and a VL comprising the amino acid sequence of SEQ ID NO:142.

In some embodiments, the antibody or antigen binding fragment thereof comprises a VH comprising the amino acid sequence of SEQ ID NO:109 and a VL comprising the amino acid sequence of SEQ ID NO:142.

In some embodiments, the antibody or antigen binding fragment thereof comprises a VH comprising the amino acid sequence of SEQ ID NO:110 and a VL comprising the amino acid sequence of SEQ ID NO:142.

In some embodiments, the antibody or antigen binding fragment thereof comprises a VH comprising the amino acid sequence of SEQ ID NO:111 and a VL comprising the amino acid sequence of SEQ ID NO:142.

In some embodiments, the antibody or antigen binding fragment thereof comprises a VH comprising the amino acid sequence of SEQ ID NO:112 and a VL comprising the amino acid sequence of SEQ ID NO:142.

In some embodiments of the disclosure, including any of the aforementioned embodiments, the VH may be joined to a heavy chain constant region, such as a human IgG1 constant region of SEQ ID NO:230 or 231.

In some embodiments of the disclosure, including any of the aforementioned embodiments, the VL may be joined to a light chain constant region, such as a human kappa constant region of SEQ ID NO:232.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:150, and a light chain comprising an amino acid sequence that is at least 90%, 91%, 92%, 93%, 94%, 95%, 96%, 97%, 98%, or 99% identical to the amino acid sequence of SEQ ID NO:206, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence selected from any one of SEQ ID NOS:155-200, and a light chain comprising an amino acid sequence that is at least 90%, 91%, 92%, 93%, 94%, 95%, 96%, 97%, 98%, or 99% identical to the amino acid sequence selected from any one of SEQ ID NOS:211-213, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:151, and a light chain comprising an amino acid sequence that is at least 90%, 91%, 92%, 93%, 94%, 95%, 96%, 97%, 98%, or 99% identical to the amino acid sequence of SEQ ID NO:207, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence selected from any one of SEQ ID NOS:201-205, and a light chain comprising an amino acid sequence that is at least 90%, 91%, 92%, 93%, 94%, 95%, 96%, 97%, 98%, or 99% identical to the amino acid sequence selected from any one of SEQ ID NOS:214-217, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:154, and a light chain comprising an amino acid sequence that is at least 90%, 91%, 92%, 93%, 94%, 95%, 96%, 97%, 98%, or 99% identical to the amino acid sequence of SEQ ID NO:210, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:152, and a light chain comprising an amino acid sequence that is at least 90%, 91%, 92%, 93%, 94%, 95%, 96%, 97%, 98%, or 99% identical to the amino acid sequence of SEQ ID NO:208, provided that the amino acid sequences of the VH-CDRs and VL-CDRs are unchanged.

In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:153, and a light chain comprising an amino acid sequence that is at least 90%, 91%, 92%, 93%, 94%, 95%, 96%, 97%, 98%, or 99% identical to the amino acid sequence of SEQ ID NO:209, provided that the amino acid sequences of the VH-CDRs and VL-CDRs are unchanged.

In some embodiments, the antibody or antigen binding fragment thereof comprises a heavy chain comprising the amino acid sequence of SEQ ID NO:150, and a light chain comprising the amino acid sequence of SEQ ID NO:206.

In some embodiments, the antibody or antigen binding fragment thereof comprises a heavy chain comprising the amino acid sequence selected from any one of SEQ ID NOS:155-200, and a light chain comprising the amino acid sequence selected from any one of SEQ ID NOS:211-213.

In some embodiments, the antibody or antigen binding fragment thereof comprises a heavy chain comprising the amino acid sequence of SEQ ID NO:151, and a light chain comprising the amino acid sequence of SEQ ID NO:207.

In some embodiments, the antibody or antigen binding fragment thereof comprises a heavy chain comprising the amino acid sequence selected from any one of SEQ ID NOS:201-205, and a light chain comprising the amino acid sequence selected from any one of SEQ ID NOS:214-217.

In some embodiments, the antibody or antigen binding fragment thereof comprises a heavy chain comprising the amino acid sequence of SEQ ID NO:154, and a light chain comprising the amino acid sequence of SEQ ID NO:210.

In some embodiments, the antibody or antigen binding fragment thereof comprises a heavy chain comprising the amino acid sequence of SEQ ID NO:152, and a light chain comprising the amino acid sequence of SEQ ID NO:208.

In some embodiments, the antibody or antigen binding fragment thereof comprises a heavy chain comprising the amino acid sequence of SEQ ID NO:153, and a light chain comprising the amino acid sequence of SEQ ID NO:209.

In some embodiments of the disclosure, including any of the aforementioned embodiments, the anti-ASGR1 antibody or antigen binding fragment thereof is conjugated to a small molecule drug to form an antibody drug conjugate. In some embodiments, the small molecule drug is a myeloid cell agonist (e.g., TLR8 agonist, TLR7 agonist, or both) of the disclosure, thus forming a myeloid cell agonist conjugate.

In some embodiments of the disclosure, an anti-ASGR1 antibody or antigen binding fragment thereof can be chimeric or humanized. Chimeric and humanized forms of non-human (e.g., murine) antibodies can be intact (full length) chimeric immunoglobulins, immunoglobulin chains or antigen binding fragments thereof (such as Fv, Fab, Fab', F(ab')$_2$ or other target-binding subdomains of antibodies), which can contain sequences derived from non-human immunoglobulin. In some embodiments, the humanized antibody or antigen binding fragment thereof can comprise substantially all of at least one, and typically two, variable domains, in which all or substantially all of the CDR regions correspond to those of a non-human immunoglobulin and all or substantially all of the framework (FR) regions are those of a human immunoglobulin sequence. A humanized antibody can also comprise at least a portion of an immunoglobulin constant region (Fc), an Fc domain. In some embodiments, including those in which a humanized antibody can also comprise at least a portion of an Fc domain, the Fc domain comprises a human immunoglobulin sequence.

In some embodiments of the disclosure, an anti-ASGR1 antibody or antigen binding fragment thereof of the disclosure comprises a human antibody. As used throughout the disclosure, "human antibodies" can include antibodies having, for example, the amino acid sequence of a human immunoglobulin and include antibodies isolated from human immunoglobulin libraries or from animals transgenic for one or more human immunoglobulins and that typically do not express endogenous immunoglobulins. Human antibodies can be produced using transgenic mice incapable of expressing functional endogenous immunoglobulins, but capable of expressing human immunoglobulin genes. Completely human antibodies that recognize a selected epitope can be generated using guided selection. In this approach, a selected non-human monoclonal antibody, e.g., a mouse antibody, is used to guide the selection of a completely human antibody recognizing the same epitope.

In some embodiments of the disclosure, an anti-ASGR1 antibody or antigen binding fragment thereof comprises a bispecific antibody or a dual variable domain antibody (DVD). Bispecific and DVD antibodies are monoclonal, often human or humanized, antibodies that have binding specificities for at least two different antigens, one of which is ASGR1.

In some embodiments of the disclosure, an anti-ASGR1 antibody or antigen binding fragment thereof comprises a derivatized or otherwise modified sequence. In some embodiments of the disclosure, an anti-ASGR1 antibody is a derivatized antibody. In some embodiments, an anti-ASGR1 antibody comprises a derivatized antibody or an antigen binding fragment thereof. In some embodiments of the disclosure, an anti-ASGR1 antibody is a modified antibody. In some embodiments, an anti-ASGR1 antibody comprises a modified antibody or an antigen binding fragment thereof. For example, derivatized antibodies can be modified by glycosylation, acetylation, pegylation, phosphorylation, amidation, derivatization by known protecting/blocking groups, proteolytic cleavage, or the like.

Nucleic Acids, Vectors, and Host Cells

The disclosure provides an isolated nucleic acid that encodes anti-ASGR1 antibody or antigen binding fragment thereof. In some embodiments, a nucleic acid encoding an anti-ASGR1 antibody or antigen binding fragment thereof comprises a sequence encoding one or more of a CDR sequence, a framework sequence, a variable region sequence, a constant region sequence, a heavy chain sequence and a light chain sequence of the ASGR1 antibody or antibody binding fragment of the disclosure. In some embodiments, the nucleic acid encoding the anti-ASGR1 antibody or antigen binding fragment thereof is codon optimized to enhance or maximize expression in certain types of cells (e.g., Scholten et al., Clin. Immunol. 119: 135-145, 2006). As used throughout the disclosure, a "codon optimized" polynucleotide is a heterologous polypeptide having codons modified with silent mutations corresponding to the abundances of host cell tRNA levels.

In some embodiments, a nucleic acid molecule encodes an anti-ASGR1 antibody or antigen binding fragment thereof (e.g., an antibody heavy and light chains, or an antibody binding domain comprising VH and VL binding regions) wherein two or more chains or regions are separated by a cleavage site. In some embodiments, a nucleic acid encoding an anti-ASGR1 antibody or antigen binding fragment thereof comprises a sequence encoding one or more of a CDR sequence, a framework sequence, a variable region sequence, a constant region sequence, a heavy chain sequence and a light chain sequence of the ASGR1 antibody or antibody binding fragment of the disclosure. In some embodiments, the cleavage site is a self-cleaving amino acid sequence comprising a 2A peptide from porcine teschovirus-1 (P2A), equine rhinitis A virus (E2A), Thosea asigna virus (T2A), foot-and-mouth disease virus (F2A), or any combination thereof (see, e.g., Kim et al., PLOS One 6:e18556, 2011, which 2A nucleic acid and amino acid sequences are incorporated herein by reference in their entirety).

The disclosure provides an expression construct comprising a nucleic acid encoding an anti-ASGR1 antibody or antigen binding fragment thereof. In some embodiments, an expression construct comprising a nucleic acid encoding an anti-ASGR1 antibody or antigen binding fragment thereof comprises a sequence encoding one or more of a CDR sequence, a framework sequence, a variable region sequence, a constant region sequence, a heavy chain sequence and a light chain sequence of the ASGR1 antibody or antibody binding fragment of the disclosure. In some embodiments, a nucleic acid may be operably linked to an expression control sequence. As used throughout the disclosure, "expression construct" refers to a DNA construct containing a nucleic acid molecule that is operably-linked to a suitable control sequence capable of effecting the expression of the nucleic acid molecule in a suitable host. An expression construct may be present in a vector (e.g., a bacterial vector, a viral vector) or may be integrated into a genome. The term "operably linked" refers to the association of two or more nucleic acids on a single polynucleotide fragment so that the function of one is affected by the other. For example, a promoter is operably-linked with a coding sequence when it is capable of affecting the expression of that coding sequence (i.e., the coding sequence is under the transcriptional control of the promoter). The term "expression control sequence" (also called a regulatory sequence) refers to nucleic acid sequences that effect the expression and processing of coding sequences to which they are operably linked. For example, expression control sequences may include transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In some embodiments, a nucleic acid or an expression construct encoding an anti-ASGR1 antibody or antigen binding fragment thereof is present in a vector. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors). Exemplary viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). In some embodiments, a vector is a plasmid. In some embodiments, a vector is a viral vector. In some embodiments, the viral vector is a lentiviral vector or a 7-retroviral vector.

The disclosure provides an isolated host cell comprising a nucleic acid, expression construct, or vector encoding an anti-ASGR1 antibody or antigen binding fragment thereof. As used throughout the disclosure, the term "host" refers to a cell or microorganism targeted for genetic modification with a heterologous or exogenous nucleic acid molecule to produce a polypeptide of interest (e.g., an anti-ASGR1 antibody or antigen-binding fragment thereof). In some embodiments, a host cell may optionally already possess or be modified to include other genetic modifications that confer desired properties related or unrelated to biosynthesis of the heterologous or exogenous protein (e.g., inclusion of a detectable marker). More than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

Methods for Producing Anti-ASGR1 Antibodies

Anti-ASGR1 antibodies or antigen binding fragments thereof of this disclosure can be produced by any method known in the art for antibody production. As one example, an anti-ASGR1 antibody or antigen binding fragment can be produced by a method using an isolated nucleic acid sequence encoding an anti-ASGR1 antibody or antigen binding fragment thereof, vectors and host cells comprising the nucleic acid sequence, and recombinant techniques for the production of the antibody or antigen binding fragment thereof. The nucleic acid sequence encoding the anti-ASGR1 antibody or antigen binding fragment thereof can be isolated into a replicable DNA vector for further cloning or for expression. DNA encoding an anti-ASGR1 antibody or antigen binding fragment thereof can be readily isolated and sequenced using conventional procedures (e.g., by using oligonucleotide probes that are capable of binding specifically to genes encoding the heavy and light chains of the antibody). Many vectors known in the art can be used. The vector components can include, but are not limited to, one or more of the following: a signal sequence, an origin of replication, one or more marker genes, an enhancer element, a promoter, and a transcription-termination sequence.

Suitable host cells for cloning or expressing the DNA vectors of the disclosure can be prokaryote, yeast, or higher eukaryote cells of the disclosure. Suitable host cells for expression of glycosylated antibody or antigen binding fragment can be derived from multicellular organisms. Examples of invertebrate cells can include, but are not limited to, plant and insect cells. Host cells used to produce an antibody or antigen binding fragment can be cultured in a variety of commercial media. When using recombinant techniques, an antibody or antigen binding fragment can be produced, for example, intracellularly, in the periplasmic space, or directly secreted into the medium. If the antibody or antigen binding fragment is produced intracellularly, the particulate debris, either host cells or lysed fragments, can be removed, for example, by centrifugation or ultrafiltration. Where the antibody or antigen binding fragment is secreted into the medium, supernatants from such expression systems can be concentrated using a commercially available protein concentration filter. A protease inhibitor such as phenylmethylsuphonyl fluoride can be included in any of the foregoing steps to inhibit proteolysis, and antibiotics can be included to prevent the growth of adventitious contaminants.

An anti-ASGR1 antibody or antigen binding fragment thereof composition prepared from the cells can be purified using, for example, hydroxylapatite chromatography, gel electrophoresis, dialysis, and affinity chromatography. The suitability of a protein A as an affinity ligand can depend on the species and isotype of any immunoglobulin Fc domain that may be present in the antibody or antigen binding fragment. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation can also be used to recover the antibody or antigen binding fragment. Following any preliminary purification step(s), the mixture comprising the antibody or antigen binding fragment and contaminants can be subjected to low-pH hydrophobic-interaction chromatography. The methods for humanizing antibodies can include, for example, humanization uses CDR grafting (Jones et al., *Nature* 15 321:522 (1986)) and variants thereof, including "reshaping" (Verhoeyen, et al., 1988 *Science* 239: 1534-1536; Riechmann, et al., 1988 *Nature* 332:323-337; Tempest, et al., *Bio Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., B W Metcalf, B J Dalton (Eds.) Cellular adhesion: molecular definition to therapeutic potential. Plenum Press, New York; 1994:291-312). Superhumanization (Tan, et al., 2002 *J Immunol* 169: 1119-25) is another variant humanization method that can be used to graft non-human CDRs into human germline antibody sequences having similar CDR canonical structures.

In some embodiments, the anti-ASGR1 antibodies or antigen binding fragments thereof of this disclosure, or conjugates thereof having a myeloid cell agonist, are humanized.

Immune-Stimulatory Compounds

Anti-ASGR1 antibodies or antigen binding fragments thereof of this disclosure are attached to immune stimulatory compounds (e.g., TLR8 agonist), generally via a linker(s) to form immune-stimulatory conjugates. An anti-ASGR1 antibody or antigen binding fragment thereof of this disclosure can be attached to one or more immune-stimulatory compounds, generally from about 1 to about 10 compounds per antibody or antigen binding fragment thereof, and preferably from about 2 to about 4 compounds per antibody or antigen binding fragment thereof.

In some embodiments, an immune stimulatory compound activates human immune cells, such as dendritic cells, macrophages, monocytes, myeloid-derived suppressor cells, NK cells, B cells, T cells, or a combination thereof. In some embodiments, an immune-stimulatory compound is a myeloid cell agonist. A myeloid cell agonist is a compound that activates or stimulates an immune response by a myeloid cell. For example, a myeloid cell agonist can stimulate an immune response by causing the release of cytokines by myeloid cells, which results in the activation of immune cells. The stimulation of an immune response by a myeloid cell agonist can be measured in vitro by co-culturing immune cells (e.g., peripheral blood mononuclear cells (PBMCs)) with cells targeted by the conjugate and measuring cytokine release, chemokine release, proliferation of immune cells, upregulation of immune cell activation markers, ADCP, and/or ADCC. Exemplary assays are described in the Examples. ADCC can be measured by determining the percentage of remaining target cells in the co-culture after administration of the conjugate with the target cells and PBMCs.

For example, an immune stimulatory compound can act on toll like receptors (TLRs), nucleotide-oligomerization domain-like receptors (NOD), RIG-I-Like receptors (RLR), c-type lectin receptors (CLR), or cytosolic DNA Sensors (CDS), or a combination thereof.

In some embodiments, an immune stimulatory compound comprises a ligand of one or more TLRs selected from the group consisting of: TLR2, TLR3, TLR4, TLR5, TLR7, TLR8, TLR7/TLR8, TLR9, and TLR10.

In some embodiments, an immune-stimulatory compound is a myeloid cell agonist. In some embodiments, a myeloid cell agonist is a ligand of TLR2 selected from the group consisting of: (a) a heat killed bacteria product, preferably HKAL, HKEB, HKHP, HKLM, HKLP, HKLR, HKMF, HKPA, HKPG, or HKSA, HKSP, and (b) a cell-wall components product, preferably LAM, LM, LPS, LIA, LIA, PGN, FSL, Pam2CSK4, Pam3CSK4, or Zymosan.

In some embodiments, a myeloid cell agonist is a ligand of TLR3 selected from the group consisting of: rintatolimod, poly-ICLC, RIBOXXON®, Apoxxim, RIBOXXIM®, IPH-33, MCT-465, MCT-475, and ND-1.1.

In some embodiments, a myeloid cell agonist is a ligand of TLR4 selected from the group consisting of LPS, MPLA or a pyrimido[5,4-b]indole such as those described in International Publication No. WO 2014/052828 (Regents of the University of California).

In some embodiments, the myeloid cell agonist is a ligand of TLR5 selected from the group consisting of: FLA and Flagellin.

In some embodiments, the myeloid cell agonist is a ligand of TLR6.

In some embodiments, a myeloid cell agonist is a TLR7 agonist and/or a TLR8 agonist. In some embodiments, the myeloid cell agonist is a TLR7 agonist. In some embodiments, the myeloid cell agonist is a TLR8 agonist. In some embodiments, the myeloid cell agonist selectively agonizes TLR7 and not TLR8. In some embodiments, the myeloid cell agonist selectively agonizes TLR8 and not TLR7.

In some embodiments, a myeloid cell agonist is a TLR7 agonist. In some embodiments, the TLR7 agonist is selected from an imidazoquinoline, an imidazoquinoline amine, a thiazoquinoline, an aminoquinoline, an aminoquinazoline, a pyrido[3,2-d]pyrimidine-2,4-diamine, a pyrimidine-2,4-diamine, a 2-aminoimidazole, an 1-alkyl-1H-benzimidazol-2-amine, a tetrahydropyridopyrimidine, a heteroarothiadiazide-2,2-dioxide, a benzonaphthyridine, a thieno[3,2-d]pyrimidine, a 4-amino-imidazoquinoline, an imidazo-pyridinone, an imidazo-pyrimidinone, a purine, a fused pyrimidine-lactam, an imidazo[4,5-c]quinoline-4-amine, an imidazo[4,5-c]quinoline, a pyrimidine, a benzazepine, an imidazo-pyridine, a pyrrolo-pyrimidine, a 2-amino-quinazoline, a guanosine analog, an adenosine analog, a thymidine homopolymer, an ssRNA, CpG-A, PolyG10, and PolyG3. In some embodiments, the TLR7 agonist is selected from an imidazoquinoline, an imidazoquinoline amine, a thiazoquinoline, an aminoquinoline, an aminoquinazoline, a pyrido[3,2-d]pyrimidine-2,4-diamine, a pyrimidine-2,4-diamine, a 2-aminoimidazole, a 1-alkyl-1H-benzimidazol-2-amine, a tetrahydropyridopyrimidine, a heteroarothiadiazide-2,2-dioxide, a benzonaphthyridine, a thieno[3,2-d]pyrimidine, a 4-amino-imidazoquinoline, an imidazo-pyridinone, an imidazo-pyrimidinone, a purine, a fused pyrimidine-lactam, an imidazo[4,5-c]quinoline-4-amine, an imidazo[4,5-c]quinoline, a pyrimidine, a benzazepine, an imidazo-pyridine, a pyrrolo-pyrimidine, and a 2-amino-quinazoline, but is other than a guanosine analog, an adenosine analog, a thymidine homopolymer, an ssRNA, CpG-A, PolyG10, and PolyG3. In some embodiments, a TLR7 agonist is a non-naturally occurring compound. Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the TLR7 modulator compounds disclosed in US Patent Application Publication No. US 2016/0168164 (Janssen, thieno[3,2-d]pyrimidine derivatives), US Patent Application Publication No. US 2015/0299194 (Roche, 4-amino-imidazoquinoline derivatives), US Patent Application Publication No. US 2011/0098248 (Gilead Sciences, imidazo-pyridinone, imidazo-pyrimidinone, and purine derivatives), US Patent Application Publication No. US 2010/0143301 (Gilead Sciences, fused pyrimidine-lactam derivatives), and US Patent Application Publication No. US 20090047249 (Gilead Sciences, purine derivatives), and these publications are incorporated by reference herein. Further examples of TLR7 modulators include compounds disclosed in International Publication No. WO 2018/009916 (Stanford University/Bolt Biotherapeutics, imidazo[4,5-c]quinolin-4-amine derivatives), International Publication No. WO 2018/112108 (Bolt Biotherapeutics, imidazo[4,5-c]quinoline, pyrimidine, benzazepine, imidazo-pyridine, pyrrolo-pyrimidine, and purine derivatives), US Patent Application Publication No. US 2019/0055247 (Bristol-Myers Squibb, purine derivatives), International Publication No. WO 2018/198091 (Novartis, pyrrolo-pyrimidine derivatives), US Patent Application Publication No. US 2017/0121421 (Novartis, pyrrolo-pyrimidine derivatives), U.S. Pat. No. 10,253,003 (Janssen, 2-amino-quinazoline derivatives), and U.S. Pat. No. 10,233, 184 (Roche, imidazo-pyrimidinone derivatives), and these publications are incorporated by reference herein. In some embodiments, a TLR7 agonist has an EC50 value of 500 nM or less by PBMC assay measuring TNFalpha or IFNalpha production. In some embodiments, a TLR7 agonist has an EC50 value of 100 nM or less by PBMC assay measuring TNFalpha or IFNalpha production. In some embodiments, a TLR7 agonist has an EC50 value of 50 nM or less by PBMC assay measuring TNFalpha or IFNalpha production. In some embodiments, a TLR7 agonist has an EC50 value of 10 nM or less by PBMC assay measuring TNFalpha or IFNalpha production.

In some embodiments the myeloid cell agonist is a TLR8 agonist. In some embodiments, a TLR8 agonist is selected from the group consisting of a benzazepine, an imidazoquinoline, a thiazoloquinoline, an aminoquinoline, an aminoquinazoline, a pyrido[3,2-d]pyrimidine-2,4-diamine, a pyrimidine-2,4-diamine, a 2-aminoimidazole, an 1-alkyl-1H-benzimidazol-2-amine, a tetrahydropyridopyrimidine, a pyrido[3,2-d]pyrimidine, a dihydropyrimidinyl benzazepine carboxamide, a benzo[b]azepine, benzazepine dicarboxamide derivatives with a tertiary amide, benzazepine dicarboxamide derivatives with a secondary amide, a quinazoline, a pyrido[3,2-d]pyrimidine, a diamino-pyrimidine, an aminoquinazoline, a heterocyclic-substituted 2-amino-quinazoline, a diamino-pyrimidine, a piperidino-pyrimidine, an alkylamino-pyrimidine, an 8-substituted benzoazepine, an amino-diazepine, an amino-benzo-diazepine, an amido-indole, an amido-benzimidazole, a phenyl sulfonamide, a dihydropteridinone, a fused amino-pyrimidine, a quinazoline, a pyrido-pyrimidine, an amino-substituted benzazepine, a pyrrolo-pyridine, an imidazo-pyridine derivatives, and an amino-benzazepine, and is other than a ssRNA. In some embodiments, a TLR8 agonist is a non-naturally occurring compound. Examples of TLR8 agonists include motolimod, resiquimod, 3M-051, 3M-052, MCT-465, IMO-4200, VTX-763, VTX-1463, and the TLR8 modulator compounds disclosed in US Patent Application Publication No. US 2018/0086755 (Gilead, pyrido[3,2-d]pyrimidine derivatives), International Publication No. WO 2017216054 (Roche, dihydropyrimidinyl benzazepine carboxamide derivatives), International Publication No. WO 2017/190669 (Shanghai De Novo Pharmatech, benzo[b]azepine derivatives), International Publication No. WO 2016/142250 (Roche, benzazepine dicarboxamide derivatives), International Publication No. WO 2017/202704 (Roche, benzazepine dicarboxamide derivatives with a tertiary amide), International Publication No. WO2017/202703 (Roche, benzazepine dicarboxamide derivatives with a secondary amide), US Patent Application Publication No. US 2017/0071944 (Gilead, quinazoline and pyrido[3,2-d]pyrimdine derivatives), US Patent Application Publication No. US 2014/0045849 (Janssen, diamino-pyrimidine derivatives), US Patent Application Publication No. US 2014/0073642 (Janssen, amino-quinazoline derivatives), International Publication No. WO 2014/056953 (Janssen, pyrrolo[3,2-d]pyrimidine derivatives), International Publication No. WO 2014/076221 (Janssen, heterocyclic substituted 2-amino-quinazoline derivatives), International Publication No. WO 2014/128189 (Janssen, diamino-pyrimidine derivatives), US Patent Application Publication No. 2014/0350031 (Janssen, piperidino-pyrimidine derivatives), International Publication No. WO2014/023813 (Janssen, alkyl-aminopyrimidine derivatives), US Patent Application Publication No. US 2008/0234251 (Array Biopharma, 8-substituted benzoazepine derivatives), US Patent Application Publication No. US 2008/0306050 (Array Biopharma, amino-diazepine derivatives), US Patent Application Publication No. US 2010/0029585 (VentiRx Pharma, amino-benzazepine derivatives), US Patent Application Publication No. US 2011/0092485 (VentiRx Pharma, amino-benzazepine derivatives), US Patent Application Publication No. US 2011/0118235 (VentiRx Pharma, amino-benzazepine derivatives), US Patent Application Publication No. US 2012/0082658 (VentiRx Pharma, amino-benzazepine VTX-378), US Patent Application Publication No. US 2012/0219615 (VentiRx Pharma), US Patent Application Publication No. US 2014/0066432 (VentiRx Pharma, amino-benzazepine VTX-2337), US Patent Application Publication No. US 2014/0088085 (VentiRx Pharma, amino-benzazepine and amino-benzo-diazepine derivatives), US Patent Application Publication No. US 2014/0275167 (Novira Therapeutics, amido-indole and amido-benzimidazole derivatives), and US Patent Application Publication No. US 2013/0251673 (Novira Therapeutics, phenyl sulfonamide derivatives), and these publications are incorporated by reference herein. Further examples of TLR8 modulators include compounds disclosed in US Patent Application Publication No. US 2016/0108045 (Gilead, dihydropteridinone derivatives), US Patent Application Publication No. US 2018/0065938 (Gilead, fused amino-pyrimidine derivatives), US Patent Application Publication No. US 2018/0263985 (Gilead, quinazoline and pyrido-pyrimidine derivatives), International Publication No. WO 2017/046112 (Roche, amino-substituted benzazepine derivatives), International Publication No. WO 2016/096778 (Roche, amino-substituted benzazepine derivatives), US Patent Application Publication No. 2019/0016808 (Birdie Biopharmaceuticals, pyrrolo- or imidazo-pyridine derivatives or amino-benzazepine derivatives), and these publications are incorporated by reference herein. In some embodiments, the TLR8 agonist comprises the structure:

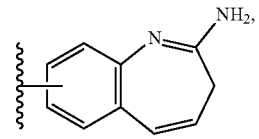

wherein the structure is optionally substituted at any position other than the —NH$_2$ position. In some embodiments, a TLR8 agonist has an EC50 value of 500 nM or less by PBMC assay measuring TNFalpha production. In some embodiments, a TLR8 agonist has an EC50 value of 100 nM or less by PBMC assay measuring TNFalpha production. In some embodiments, a TLR8 agonist has an EC50 value of 50 nM or less by PBMC assay measuring TNFalpha production. In some embodiments, a TLR8 agonist has an EC50 value of 10 nM or less by PBMC assay measuring TNFalpha production.

In some embodiments, a TLR8 agonist is a benzazepine selected from compounds provided throughout the disclosure.

In some embodiments, a myeloid cell agonist is a ligand of TLR9 selected from the group consisting of: ODN1585, ODN1668, ODN1826, PF-3512676 (ODN2006), ODN2007, ODN2216, ODN2336, ODN2395, BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

In some embodiments, the myeloid agonist selectively agonizes TLR9, TLR3, TLR4, TLR2, TLR5, RIG-I, STING, cGAS, NOD1, NOD2, NOD1/NOD2, NRLP3, ALPK1, MDA5 AIM2, IRE1 and PERK.

In some embodiments, a myeloid cell agonist is a ligand of TLR10.

In some embodiments, a myeloid cell agonist is a ligand of a ligand of nucleotide-oligomerization domain (NOD)-like selected from the group consisting of: NOD1 agonist (C12-iE-DAP, iE-DAP, Tri-DAP), NOD2 agonist (L18-MDP, MDP, M-TriLYS, M-TriLYS-D-ASN, Murabutide, N-Glycolyl-MDP), and NOD1/NOD2 agonists (M-TriDAP, PGN).

In some embodiments, a myeloid cell agonist is a ligand of one or more RIG-I-Like receptors (RLR) selected from the group consisting of: 5'ppp-dsRNA, Poly (dA:dT), Poly (dG:dC), and Poly (I:C).

In some embodiments, a myeloid cell agonist is a ligand of one or more C-type lectin receptors (CLR) selected from the group consisting of: Cnrdlan AL, HKCA, HKSC, WGP, Zymosan, and Trehalose-6,6-dibehenate.

In some embodiments, a myeloid cell agonist is a ligand of one or more Cytosolic DNA Sensors (CDS) selected from the group consisting of: ADU-S100, c-GMP, c-G-AMP, c-G-GMP, c-A-AMP, c-di-AMP, c-di-IMP, c-di-GMP, c-di-UMP, HSV-60, ISD, pCpG, Poly (dA:dT), Poly(dG:dC), Poly (dA), VACV-70 and a-mangostin and the compounds disclosed in International Publication No. WO 2018/156625 (U of Texas), International Publication No. WO 2018/152453 (Eisai), International Publication No. WO 2018/138685 (Janssen), International Publication No. WO 2018/100558 (Takeda), International Publication No. WO 2018/098203 (Janssen), International Publication No. WO 2018/065360 (Biolog Life Sciences), International Publication No. WO 2018/060323 (Boehringer Ingelheim), International Publication No. WO 2018/045204 (IFM Therapeutics), International Publication No. WO 2018/009466 (Aduro), International Publication No. WO 2017/161349 (Immune Sensor), International Publication No. WO 2017/123669, International Publication No. WO 2017/123657, International Publication No. WO 2017/027646 (Merck), International Publication No. WO 2017/027645 (Merck), International Publication No. WO2016/120305 (GSK), International Publication No. WO 2016/096174 (Invivo-Gen), and US Patent Application Publication No. US 2014/0341976 (Aduro).

In some embodiments, the myeloid cell agonist is a ligand of an inflammasome inducer selected from the group consisting of: (a) NLRP3 inflammasome protein complex, preferably alum Crystals, ATP, CPPD Crystals, Hennozoin, MSU Crystals, Nano-Si 02, Nigericin, and (b) AIM2 inflammasome protein complex, such as Poly (dA:dT).

In some embodiments of the disclosure, a TLR8 agonist is selected from Category A or Category C, or a TLR7 agonist is selected from Category B. Variables and Formula of the Compounds of Category A (TLR8 agonists) are described in the section entitled Compounds of Category A; variables and Formula of the Compounds of Category B (TLR7 agonists) are described in section entitled Compounds of Category B; and variables and Formula of the Compounds of Category C (TLR8 agonists) are described in section entitled Compounds of Category C. Formulas and variables of the Compounds of Category A, the Compounds of Category B and the Compounds of Category C may overlap in nomenclature, e.g., Formula IA for Compounds of each of Category A, Category B and Category C; however, variables and Formula descriptions are not intended to be interchangeable between the categories.

Compounds of Category A, TLR8 Agonists

In some embodiments, the myeloid cell agonist is a benzazepine-4-carboxamide compound. In some embodiments, the benzazepine-4-carboxamide compound has the structure of Formula X-1:

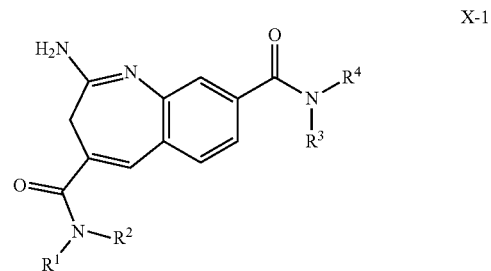

wherein:
$R^1$ is $C_{3-7}$ alkyl;
$R^2$ is $C_{3-7}$ alkyl or $C_{3-7}$ cycloalkyl-$C_{1-7}$ alkyl;
$R^3$ is hydrogen;
$R^4$ is selected from the group consisting of
$C_{1-7}$ alkyl, said $C_{1-7}$ alkyl being unsubstituted or substituted by one or two groups selected from the group consisting of phenyl and heteroaryl, said heteroaryl being an aromatic 5- or 6-membered ring which comprises one, two, or three atoms selected from nitrogen, oxygen, and/or sulfur;
$C_{3-7}$ cycloalkyl, said $C_{3-7}$ cycloalkyl being unsubstituted or substituted by phenyl or phenylamino-$C_{1-4}$ alkyl, and
heterocyclyl, said heterocyclyl being a saturated 3- to 7-membered ring containing one heteroatom selected from N and O and being unsubstituted or substituted by phenyl.

Structures of Formula X-1 are described, for example, in International Publication No. WO 2017/202703.

In some embodiments, the myeloid cell agonist is a benzazepine-dicarboxamide compound. In some embodiments, the benzazepine-dicarboxamide compound has the structure of Formula X-2:

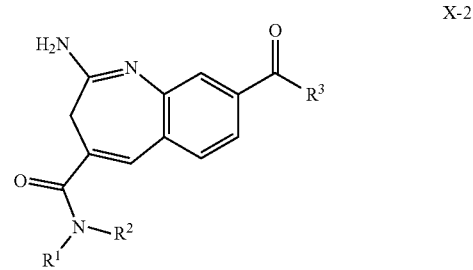

wherein:
$R^1$ is $C_{3-7}$ alkyl;
$R^2$ is $C_{3-7}$ alkyl or $C_{3-7}$ cycloalkyl-$C_{1-7}$ alkyl;
$R^3$ is a heterocycle selected from

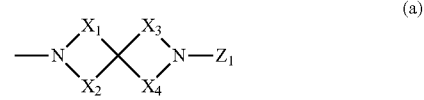

(a)

wherein

X$_1$ is (CH$_2$)$_m$ wherein m is 1 or 2;
X$_2$ is (CH$_2$)$_n$ wherein n is 1 or 2;
X$_3$ is (CH$_2$)$_o$ wherein o is 1 or 2;
X$_4$ is (CH$_2$)$_p$ wherein p is 1 or 2; and
Z$_1$ is phenyl, wherein phenyl is unsubstituted or substituted by one or two groups selected from the group consisting of C$_{1-7}$ alkyl, halogen, halogen-C$_{1-7}$ alkyl, C$_{1-7}$ alkoxy, hydroxy-C$_{1-7}$ alkyl, amino-C$_{1-7}$ alkyl, C$_{1-7}$ alkyl-amino-C$_{1-7}$ alkyl, and di-C$_{1-7}$ alkyl-amino-C$_{1-7}$ alkyl; or (b)

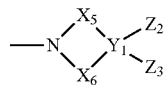

wherein

X$_5$ is (CH$_2$)$_q$ wherein q is 1 or 2;
X$_6$ is (CH$_2$)$_r$ wherein r is 1 or 2;
Y$_1$ is a carbon or nitrogen atom;
Z$_2$ is hydrogen; and
Z$_3$ is selected from the group consisting of hydrogen, C$_{1-7}$ alkoxy, C$_{2-7}$ alkenyloxy, phenyl, phenyl-C$_{1-7}$ alkyl, phenyl-C$_{1-7}$ alkyloxy, phenyl-C$_{1-7}$ alkylamino, phenylamino-C$_{1-7}$ alkyl, phenylamino, wherein phenyl is unsubstituted or substituted by one or two groups selected from the group consisting of C$_{1-7}$ alkyl, halogen, halogen-C$_{1-7}$ alkyl, C$_{1-7}$ alkoxy, hydroxy-C$_{1-7}$ alkyl, amino-C$_{1-7}$ alkyl, C$_{1-7}$ alkyl-amino-C$_{1-7}$ alkyl, and di-C$_{1-7}$ alkyl-amino-C$_{1-7}$ alkyl; or (c)

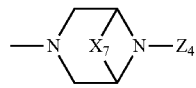

wherein

X$_7$ is (CH$_2$)$_s$ wherein s is 1 or 2; and
Z$_4$ is phenyl, wherein phenyl is unsubstituted or substituted by one or two groups selected from the group consisting of C$_{1-7}$ alkyl, halogen, halogen-C$_{1-7}$ alkyl, C$_{1-7}$ alkoxy, hydroxy-C$_{1-7}$ alkyl, amino-C$_{1-7}$ alkyl, C$_{1-7}$ alkyl-amino-C$_{1-7}$ alkyl, and di-C$_{1-7}$ alkyl-amino-C$_{1-7}$ alkyl; or (d)

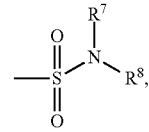

wherein

X$_8$ is (CH$_2$)$_t$ wherein t is 1 or 2; and
Z$_5$ is phenyl, wherein phenyl is unsubstituted or substituted by one or two groups selected from the group consisting of C$_{1-7}$ alkyl, halogen, halogen-C$_{1-7}$ alkyl, C$_{1-7}$ alkoxy, hydroxy-C$_{1-7}$ alkyl, amino-C$_{1-7}$ alkyl, C$_{1-7}$ alkyl-amino-C$_{1-7}$ alkyl, and di-C$_{1-7}$ alkyl-amino-C$_{1-7}$ alkyl.

Compounds of Formula X-2 are described, for example, in International Publication No. WO 2017/202704.

In some embodiments, the myeloid cell agonist is a benzazepine sulfonamide compound. In some embodiments, the benzazepine sulfonamide compound has the structure of Formula X-3:

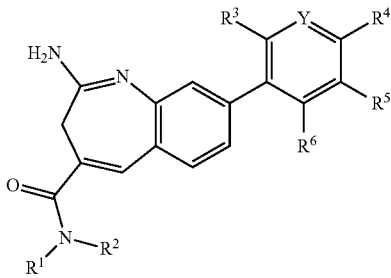

X-3 wherein

R$^1$ and R$^2$ are the same or different and are selected from the group consisting of C$_{1-7}$ alkyl, hydroxy-C$_{2-7}$ alkyl, amino-C$_{2-7}$ alkyl, C$_{2-7}$ alkenyl, and C$_{3-7}$ alkynyl;

R$^3$ is hydrogen or C$_{1-7}$ alkyl;

R$^6$ is hydrogen or C$_{1-7}$ alkyl;

one of R$^4$ and R$^5$ is selected from the group consisting of hydrogen, C$_{1-7}$ alkyl, halogen-C$_{1-7}$ alkyl, and C$_{1-7}$ alkoxy, and the other one of R$^4$ and R$^5$ is

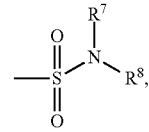

wherein R$^7$ and R$^8$ are the same or different and are selected from the group consisting of hydrogen, C$_{1-7}$ alkyl, halogen-C$_{1-7}$ alkyl, hydroxy-C$_{1-7}$ alkyl, hydroxy-C$_{1-7}$ alkoxy-C$_{1-7}$ alkyl, amino-C$_{1-7}$ alkyl, C$_{1-7}$ alkyl-amino-C$_{1-7}$ alkyl, amino-C$_{1-7}$ alkoxy-C$_{1-7}$ alkyl, C$_{1-7}$ alkyl-amino-C$_{1-7}$ alkoxy-C$_{1-7}$ alkyl, amino-C$_{1-7}$ alkyl-carbonyl, and C$_{1-7}$ alkyl-amino-C$_{1-7}$ alkyl-carbonyl; or R$^7$ and R$^8$ together with the nitrogen atom they are attached to form a 4- to 6-membered heterocycle which is unsubstituted or substituted with a group selected from the group consisting of amino, C$_{1-7}$ alkyl-amino, hydroxy, and hydroxy-C$_{1-7}$ alkyl, and which may contain an additional N—R$^{10}$ group, wherein R$^{10}$ is selected from the group consisting of hydrogen, amino-C$_{1-7}$ alkyl, and C$_{1-7}$ alkyl-amino-C$_{1-7}$ alkyl; and Y is N or CR$^9$;

wherein R$^9$ is selected from the group consisting of hydrogen, C$_{1-7}$ alkyl, and halogen-C$_{1-7}$ alkyl.

Compounds of Formula X-3 are described, for example, in International Publication No. WO 2016/096778.

In some embodiments, the myeloid cell agonist is a dihydropyrimidinyl benzazepine carboxamide compound. In some embodiments, the dihydropyrimidinyl benzazepine carboxamide compound has the structure of Formula X-4:

83

X-4 wherein
- $R^1$ is $C_{3-7}$ alkyl;
- $R^2$ is $C_{3-7}$ alkyl or $C_{3-7}$ cycloalkyl-$C_{1-7}$ alkyl;
- $R^3$ is hydrogen or $C_{1-7}$ alkyl;
- $R^4$ is hydrogen or $C_{1-7}$ alkyl;
- $R^5$ is selected from the group consisting of hydrogen, halogen, $C_{1-7}$ alkyl, and $C_{1-7}$ alkoxy;
- $R^6$ is selected from the group consisting of hydrogen, halogen, $C_{1-7}$ alkyl, and $C_{1-7}$ alkoxy; and
- X is N or $CR^7$, wherein $R^7$ is selected from the group consisting of hydrogen, halogen, $C_{1-7}$ alkyl, and $C_{1-7}$ alkoxy.

Compounds of Formula X-4 are described, for example, in International Publication No. WO2017/216054.

In some embodiments, the myeloid cell agonist is a sulfinylphenyl or sulfonimidoylphenyl benzazepine compound. In some embodiments, the sulfinylphenyl or sulfonimidoylphenyl benzazepine compound has the structure of Formula X-5:

X-5 wherein
- X is $CR^7$ or N;
- $R^1$ is $C_{3-7}$ alkyl or $C_{3-7}$ cycloalkyl;
- $R^2$ is selected from the group consisting of $C_{3-7}$ alkyl, hydroxy-$C_{1-7}$ alkyl, $C_{3-7}$-alkynyl, amino-$C_{1-7}$ alkoxy-$C_{1-7}$ alkoxy-$C_{1-7}$ alkyl, halogen-$C_{1-7}$ alkyl, and $C_{3-7}$ cycloalkyl-$C_{1-7}$ alkyl;
- one of $R^3$ and $R^4$ is $$-\underset{\underset{R^9}{|}}{\overset{\overset{O}{\|}}{S}}-R^8,$$

and the other one of $R^3$ and $R^4$ is selected from the group consisting of hydrogen, $C_{1-7}$ alkyl, and halogen;

$R^5$, $R^6$, and $R^7$ are independently from each other selected from hydrogen, $C_{1-7}$ alkyl, and halogen;

$R^8$ is $C_{1-7}$ alkyl; and $R^9$ is absent or is $=N-R^{10}$, wherein $R^{10}$ is selected from the group consisting of hydrogen, $C_{1-7}$ alkyl, halogen-$C_{1-7}$ alkyl, hydroxy-$C_{1-7}$ alkyl, and hydroxy-$C_{1-7}$ alkoxy-$C_{1-7}$ alkyl.

Compounds of Formula X-5 are described, for example, in International Publication No. WO 2017/046112.

In some embodiments, the myeloid cell agonist is a TLR modulator compound that has the structure of Formula X-6:

X-6 wherein
- === (1) is a double bond or a single bond;
- === (2) is a single bond or is double bond and $R_1$ is absent;
- $R_2$ and $R_3$ are independently selected from H and lower alkyl, or $R_2$ and $R_3$ are connected to form a saturated carbocycle having from 3 to 7 ring members;
- one of $R_7$ and $R_8$ is $-NR_fR_g$, , or and the other is hydrogen;
- where $R_f$ and $R_g$ are lower alkyl or $R_f$ and $R_g$ together with the nitrogen to which they are attached form a saturated heterocyclic ring having 4 to 6 ring members;
- $R_4$ is $-NR_cR_d$ or $-OR_{10}$;
- $R_c$ and $R_d$ are lower alkyl, where the alkyl is optionally substituted with one or more $-OH$;
- $R_{10}$ is alkyl, where the alkyl is optionally substituted with one or more $-OH$;
- Z is C and === (1) is a double bond, or Z is N and === (1) is a single bond;
- $R_a$ and $R_b$ are independently selected from H, alkyl, alkenyl, alkynyl, and $R^e$, wherein the alkyl is optionally substituted with one or more $-OR^{10}$, or $R^e$;
- $R^e$ is selected from $-NH_2$, $-NH(alkyl)$, and $-N(alkyl)_2$;
- $R^1$ is absent when === (2) is a double bond, or when === (2) is a single bond, $R^1$ and one of $R^a$ or $R^b$ are taken together with the atoms to which they are attached to form a saturated, partially unsaturated, or unsaturated heterocycle having 5-7 ring members, and the other of $R^a$ or $R^b$ is hydrogen or is absent as necessary to accommodate ring unsaturation.

In some embodiments, the myeloid cell agonist is a TLR modulator compound that has the structure of Formula X-7:

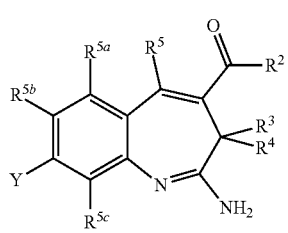

X-7 wherein

Y is $CF_2CF_3$, $CF_2CF_7R^6$, or an aryl or heteroaryl ring, wherein said aryl and heteroaryl rings are substituted with one or more groups independently selected from alkenyl, alkynyl, Br, CN, OH, $NR^6R^7$, $C(=O)R^8$, $NR^6SO_2R^7$, ($C_1$-$C_6$ alkyl)amino, $R^6OC(=O)CH=CH_2$—, $SR^6$ and $SO_2R^6$, and wherein the aryl and heteroaryl rings are optionally further substituted with one or more groups independently selected from F, Cl, $CF_3$, $CF_3O$—, $HCF_2O$—, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein the alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O$—, $R^6OC(O)CH=CH_2$—, $NR^6SO_2R^7$, $SR^6$ and $SO_2R^6$, or $R^3$ and $R^4$ together with the atom to which they are attached form a saturated or partially unsaturated carbocyclic ring, wherein the carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O$, $R^6OC(=O)CH=CH_2$—, $NR^6SO_2R^7$, $SR^6$ and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein the alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(O)NR^6R^7$, ($C_1$-$C_6$ alkyl)amino, $CH_3OCH_2O$—, $R^6OC(=O)CH=CH_2$—, $NR^6SO_2R^7$, $SR^6$ and $SO_2R^6$;

$R^{5a}$, $R^{5b}$, and $R^{5c}$ are independently H, F, Cl, Br, I, OMe, $CH_3$, $CH_2F$, $CHF_2$ or $CF_3$; and $R^6$ and $R^7$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl) amino, $CH_3OCH_2O$—, $R^6OC(O)CH=CH_2$—, $NR^6SO_2R^7$, $SR^6$ and $SO_2R^6$, or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O$—, $R^6OC(=O)CH=CH_2$—, $NR^6SO_2R^7$, $SR^6$ and $SO_2R^6$.

In some embodiments, the myeloid cell agonist is a TLR modulator compound that has the structure of Formula X-8:

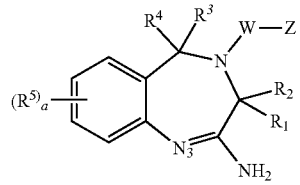

X-8 wherein

W is —C(O)—;

Z is H, alkyl, alkenyl, alkynyl, heteroalkyl, cycloalkyl, heterocycloalkyl, aryl, heteroaryl, $OR^6$ or $NR^6R^7$, wherein the alkyl, alkenyl, alkynyl, heteroalkyl, cycloalkyl, heterocycloalkyl, aryl and heteroaryl are optionally substituted with one or more groups independently selected from alkyl, alkenyl, alkynyl. F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl) amino, $CH_3OCH_2O$—, $R^6OCC=O)CH=CH_2$—, $NR^6SO_2R^7$, $SR^6$ and $SO_2R^6$;

$R^1$, $R^2$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl, and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O$—, $R^6OC(C=O)CH=CH_2$—, $NR^6SO_2R^7$, $SR_6$ and $SO_2R^6$, or $R^1$ and $R^2$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O$—, $R^6OC(=O)CH=CH_2$—, $NR^6SO_2R^7$, $SR^6$ and $SO_2R^6$, or $R^3$ and $R^4$ together are oxo;

$R^5$ is H, F, Cl, Br, I, OMe, $CH_3$, $CH_2F$, $CHF_2$, $CF_3$ or $CF_2CF_3$;

$R^6$ and $R^7$ are independently selected from H, alkyl, alkenyl, alkynyl, heteroalkyl, cycloalkyl, cycloalkenyl, heterocycloalkyl, aryl, and heteroaryl, wherein said alkyl, alkenyl, alkynyl, heteroalkyl, cycloalkyl cycloalkenyl, heterocycloalkyl, aryl, and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl) amino, $CH_3OCH_2O$—, $R^6OC(=O)CH=CH_2$—, $NR^6SO_2R^7$, $SR^6$ and $SO_2R^6$;

or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, ($C_1$-$C_6$ alkyl)amino, $CH_3OCH_2O-$, $R^6OC(=O)CH=CH_2-$, $NR^6SO_2R^7$, $SR^6$ and $SO_2R^6$; and n is 0, 1, 2, 3 or 4.

Compounds of Formula X-6, X-7, and X-8 are described, for example, in U.S. Publication Nos. US 2019/0016808 and US 2014/0088085.

In some embodiments, the myeloid cell agonist is a TLR modulator compound that has the structure of Formula X-9:

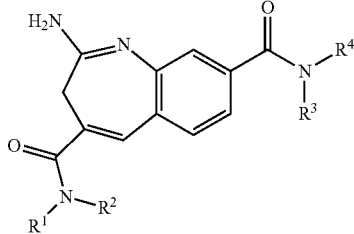

X-9 wherein $R^1$ is $C_{3-7}$ alkyl or $C_{3-7}$ cycloalkyl;

$R^2$ is selected from the group consisting of $C_{1-7}$ alkyl, hydroxy-$C_{1-7}$ alkyl, $C_{2-7}$ alkenyl, $C_{3-7}$ alkynyl, amino-$C_{1-7}$ alkoxy-$C_{1-7}$alkyl, amino-$C_{1-7}$ alkoxy-$C_{1-7}$ alkoxy-$C_{1-7}$ alkyl, halogen-$C_{1-7}$ alkyl, $C_{3-7}$ cycloalkyl-$C_{1-7}$ alkyl, and phenyl-$C_{1-7}$ alkyl, wherein phenyl is unsubstituted or substituted by amino-$C_{1-7}$ alkyl;

$R^3$ is hydrogen;

$R^4$ is selected from the group consisting of phenyl, said phenyl being unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, di-$C_{1-7}$ alkyl-amino-$C_{1-7}$ alkyl, amino-$C_{2-7}$ alkenyl, $C_{1-7}$ alkyl-amino-$C_{2-7}$ alkenyl, di-$C_{1-7}$ alkyl-amino-$C_{2-7}$ alkenyl, amino-$C_{2-7}$ alkynyl, $C_{1-7}$ alkyl-amino-$C_{2-7}$ alkynyl, di-$C_{1-7}$ alkyl-amino-$C_{2-7}$ alkynyl, benzyloxycarbonylamino-$C_{1-7}$ alkyl, amino-$C_{1-7}$ alkoxy, amino-$C_{1-7}$ alkoxy-$C_{1-7}$ alkoxy, amino-$C_{1-7}$ alkoxy-$C_{1-7}$ alkyl, amino-$C_{1-7}$ alkoxy-$C_{1-7}$ alkoxy-$C_{1-7}$ alkyl, $C_{1-7}$ alkylsulfonyl, heterocyclylcarbonyl, and phenyl-$C_{1-7}$ alkyl, wherein phenyl is unsubstituted or substituted by $C_{1-7}$ alkoxy or amino-$C_{1-7}$ alkyl; or heteroaryl, said heteroaryl being a 5- or 6-membered aromatic ring containing one, two, or three heteroatoms selected from N, O, or S, and being unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, di-$C_{1-7}$ alkyl-amino-$C_{1-7}$ alkyl, amino-$C_{2-7}$ alkenyl, $C_{1-7}$ alkyl-amino-$C_{2-7}$ alkenyl, di-$C_{1-7}$ alkyl-amino-$C_{2-7}$ alkenyl, amino-$C_{2-7}$ alkynyl, $C_{1-7}$ alkyl-amino-$C_{2-7}$ alkynyl, di-$C_{1-7}$ alkyl-amino-$C_{2-7}$ alkynyl, benzyloxycarbonylamino-$C_{1-7}$ alkyl, amino-$C_{1-7}$ alkoxy, amino-$C_{1-7}$ alkoxy-$C_{1-7}$ alkoxy, amino-$C_{1-7}$ alkoxy-$C_{1-7}$ alkyl, amino-$C_{1-7}$ alkoxy-$C_{1-7}$ alkoxy-$C_{1-7}$ alkyl, $C_{1-7}$ alkylsulfonyl, heterocyclylcarbonyl, and phenyl-$C_{1-7}$ alkyl, wherein phenyl is unsubstituted or substituted by $C_{1-7}$ alkoxy or amino-$C_{1-7}$ alkyl.

Compounds of Formula X-9 are described, for example, in International Publication No. WO 2016/142250.

In some embodiments, the disclosure provides a TLR8 agonist represented by the structure of Formula (IIA):

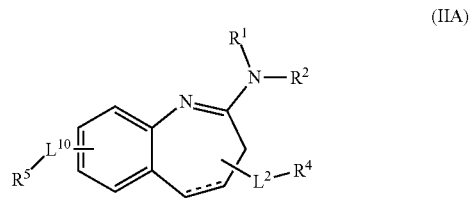

(IIA)

or a pharmaceutically acceptable salt thereof, wherein:

--- represents an optional double bond;

$L^{10}$ is $-X^{10}-$;

$L^2$ is selected from $-X^2-$, $-X^2-C_{1-6}$ alkylene-$X^2-$, $-X^2-C_{2-6}$ alkenylene-$X^2-$, and $-X^2-C_{2-6}$ alkynylene-$X^2-$, each of which is optionally substituted on alkylene, alkenylene or alkynylene with one or more $R^{12}$;

$X^{10}$ is selected from $-C(O)-$, and $-C(O)N(R^{10})-*$, wherein * represents where $X^{10}$ is bound to $R^5$;

$X^2$ at each occurrence is independently selected from a bond, $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, $-N(R^{10})C(O)O-$, $-OC(O)N(R^{10})-$, $-C(NR^{10})-$, $-N(R^{10})C(NR^{10})-$, $-C(NR^{10})N(R^{10})-$, $-N(R^{10})C(NR^{10})N(R^{10})-$, $-S(O)_2-$, $-OS(O)-$, $-S(O)O-$, $-S(O)$, $-OS(O)_2-$, $-S(O)_2O$, $-N(R^{10})S(O)_2-$, $-S(O)_2N(R^{10})-$, $-N(R^{10})S(O)-$, $-S(O)N(R^{10})-$, $-N(R^{10})S(O)_2N(R^{10})-$, and $-N(R^{10})S(O)N(R^{10})-$;

$R^1$ and $R^8$ are independently selected from hydrogen; and $C_{1-10}$ alkyl, $C_{2-10}$ alkenyl, and $C_{2-10}$ alkynyl, each of which is optionally substituted with one or more substituents independently selected from halogen, $-OR^{10}$, $-SR^{10}$, $-C(O)N(R^{10})_2$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, and $-CN$;

$R^4$ is selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R_{10}$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl;

$R^5$ is selected from unsaturated $C_{4-8}$ carbocycle; bicyclic carbocycle; and fused 5-5, fused 5-6, and fused 6-6 bicyclic heterocycle, wherein $R^5$ is optionally substituted and wherein substituents are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^5$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl; and R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl; wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IIA) is represented by Formula (IIB):

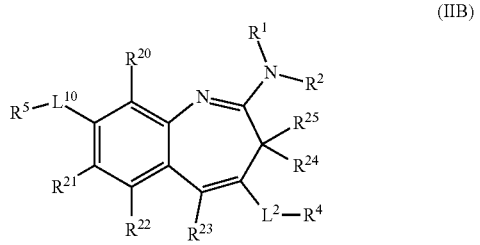

(IIB)

or a pharmaceutically acceptable salt thereof, wherein:

R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —OR$^{10}$, —NO$_2$, —CN, and C$_{1-10}$ alkyl. R$^{20}$, R$^{21}$, R$^{22}$, and R$^{23}$ may be each hydrogen. In some embodiments, R$^{21}$ is halogen. In some embodiments, R$^{21}$ is hydrogen. In some embodiments, R$^{21}$ is —OR$^{10}$. For example, R$^{21}$ may be —OCH$_3$.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In some embodiments, R$^{24}$ and R$^{25}$ are each hydrogen. In some embodiments, R$^{24}$ and R$^{25}$ taken together form an optionally substituted saturated C$_{3-5}$ carbocycle, wherein substituents are selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; and C$_{1-10}$ alkyl, C$_{2-10}$ alkenyl, C$_{2-10}$ alkynyl, each of which is independently optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^1$ is hydrogen. In some embodiments, R$^2$ is hydrogen. In some embodiments, R$^2$ is —C(O)—.

In some embodiments, L$^{10}$ is selected from —C(O)N(R$^{10}$)—*. In some embodiments, R$^{10}$ of —C(O)N(R$^{10}$)—* is selected from hydrogen and C$_{1-6}$ alkyl. For example, L$^{10}$ may be —C(O)NH—*.

In some embodiments, R$^5$ is an optionally substituted bicyclic carbocycle. In some embodiments, R$^5$ is an optionally substituted 8- to 12-membered bicyclic carbocycle. R$^5$ may be an optionally substituted 8- to 12-membered bicyclic carbocycle substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In some embodiments, R$^5$ is an optionally substituted 8- to 12-membered bicyclic carbocycle substituted with one or more substituents independently selected from —OR$^{10}$, —N(R$^{10}$)$_2$, and =O. In some embodiments, R$^5$ is an optionally substituted indane, and optionally substituted tetrahydronaphthalene. R$^5$ may be selected from:

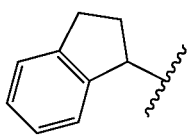 [SMILES: *C1CCc2ccccc21]

and

any one of which is optionally substituted. For example, the $R^5$ is selected from:

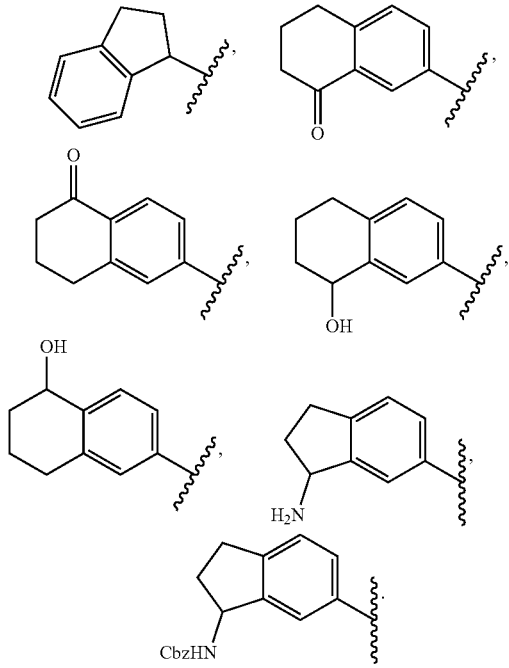

In some embodiments, $R^5$ is an optionally substituted unsaturated $C_{4-8}$ carbocycle. In some embodiments, $R^5$ is an optionally substituted unsaturated $C_{4-6}$ carbocycle. In some embodiments, $R^5$ is an optionally substituted unsaturated $C_{4-6}$ carbocycle with one or more substituents independently selected from optionally substituted $C_{3-12}$ carbocycle, and optionally substituted 3- to 12-membered heterocycle. $R^5$ may be an optionally substituted unsaturated $C_{4-6}$ carbocycle with one or more substituents independently selected from optionally substituted phenyl, optionally substituted 3- to 12-membered heterocycle, optionally substituted $C_{1-10}$ alkyl, optionally substituted $C_{2-10}$ alkenyl, and halogen.

In some embodiments, $R^5$ is selected from an optionally substituted fused 5-5, fused 5-6, and fused 6-6 bicyclic heterocycle. In some embodiments, $R^5$ is an optionally substituted fused 5-5, fused 5-6, and fused 6-6 bicyclic heterocycle with one or more substituents independently selected from —C(O)OR$^{10}$, —N(R$^{10}$)$_2$, —OR$^{10}$, and optionally substituted $C_{1-10}$ alkyl. In some embodiments, $R^5$ is an optionally substituted fused 5-5, fused 5-6, and fused 6-6 bicyclic heterocycle substituted with —C(O)OR$^{10}$. In some embodiments, $R^5$ is an optionally substituted fused 6-6 bicyclic heterocycle. For example, the fused 6-6 bicyclic heterocycle may be an optionally substituted pyridine-piperidine. In some embodiments, $L^{10}$ is bound to a carbon atom of the pyridine of the fused pyridine-piperidine. In some embodiments, $R^5$ is selected from tetrahydroquinoline, tetrahydroisoquinoline, tetrahydronaphthyridine, cyclopentapyridine, and dihydrobenzoxaborole, any one of which is optionally substituted. $R^5$ may be an optionally substituted tetrahydronaphthyridine. In some embodiments, $R^5$ is selected from:

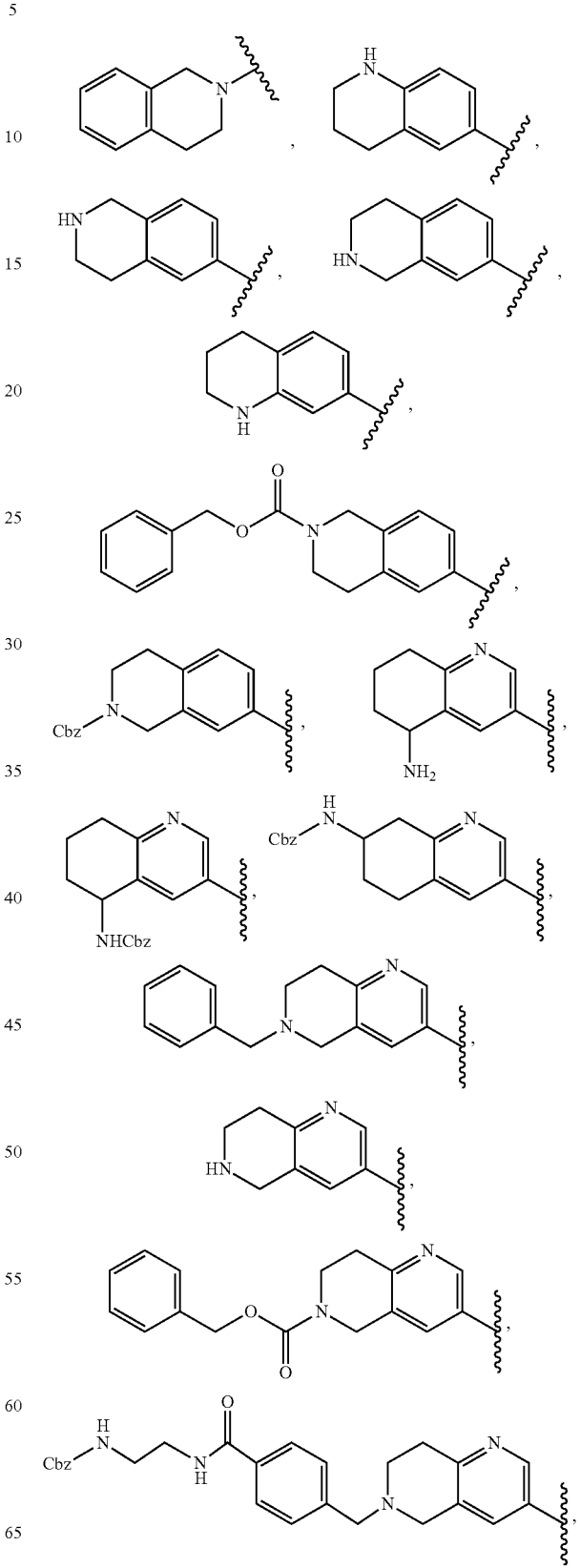

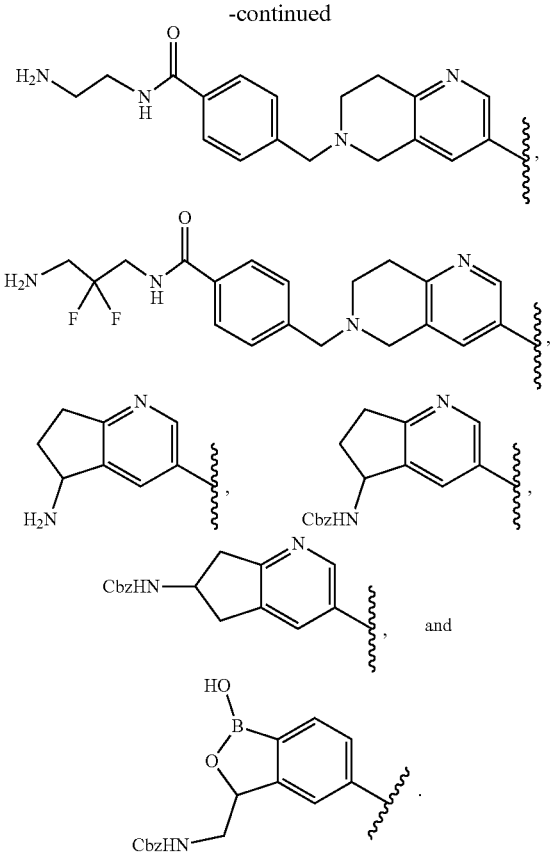

In some embodiments, when $R^5$ is substituted, substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl. In some embodiments, the substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle. In some embodiments, the substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})_2$, $-C(O)R^{10}$, $-C(O)OR^{10}$, $-OC(O)R^{10}$, $-NO_2$, $=O$, and $-CN$; and $C_{1-10}$ alkyl optionally substituted with one or more substituents independently selected from halogen, $-OR^{10}$, $-SR^{10}$, $-N(R^{10})_2$, $-C(O)R^{10}$, $-C(O)OR^{10}$, $-NO_2$, $=O$, and $-CN$. In some embodiments, $R^5$ is not substituted.

In some embodiments, $L^2$ is selected from $-C(O)-$, and $-C(O)NR^{10}-$. In some embodiments, $L^2$ is $-C(O)-$. In some embodiments, $L^2$ is $-C(O)NR^{10}-$. $R^{10}$ of $-C(O)NR^{10}-$ may be selected from hydrogen and $C_{1-6}$ alkyl. For example, $L^2$ may be $-C(O)NH-$.

In some embodiments, $R^4$ is selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle and 3- to 12-membered, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl. In some embodiments, $R^4$ is selected from: $-OR^{10}$, and $-N(R^{10})_2$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, $-OR^{10}$, $-SR^{10}$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl. In some embodiments, $R^4$ is $-N(R^{10})_2$. $R^{10}$ of $-N(R^{10})_2$ may be independently selected at each occurrence from optionally substituted $C_{1-6}$ alkyl. In some embodiments, $R^{10}$ of $-N(R^{10})_2$ is independently selected at each occurrence from methyl, ethyl, propyl, and butyl, any one of which is optionally substituted. For example, $R^4$ may be

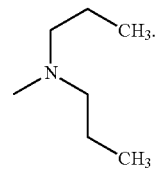

In some embodiments, -$L^2$-$R^4$ is

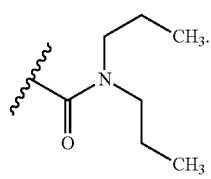

In some embodiments, $R^{12}$ is independently selected at each occurrence from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl. In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; and C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle.

In some embodiments, the compound of Formula (IIB) is a compound of Formula (IIC):

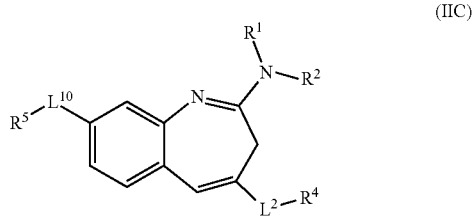

(IIC)

or a pharmaceutically acceptable salt thereof,
wherein:
R$^1$ and R$^2$ are hydrogen;
L$^2$ is —C(O)—;
R$^4$ is —N(R$^{10}$)$_2$;
R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl;

L$^{10}$ is —C(O)N(R$^{10}$)—*, wherein * represents where L$^{10}$ is bound to R$^5$; and R$^5$ is a fused 5-5, fused 5-6, or fused 6-6 bicyclic heterocycle, wherein R$^5$ is optionally substituted and wherein substituents are independently selected at each occurrence from:

halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN;

C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments, R$^{10}$ of —N(R$^{10}$)$_2$ is independently selected at each occurrence from methyl, ethyl, propyl, and butyl, any one of which is optionally substituted; and/or R$^{10}$ of —C(O)N(R$^{10}$)—* is hydrogen.

In some embodiments, R$^4$ is

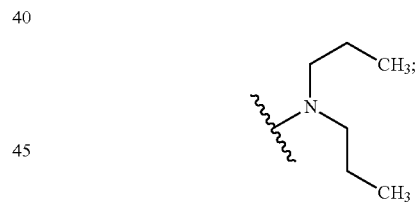

and/or R$^{10}$ of —C(O)N(R$^{10}$)—* is hydrogen.

In some embodiments, the compound is selected from:

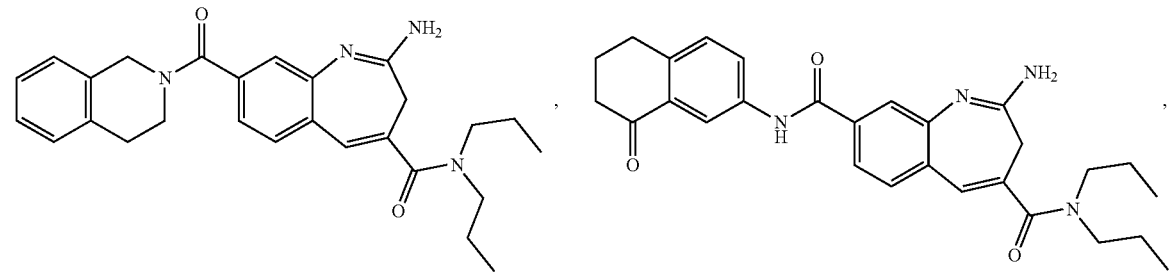

,

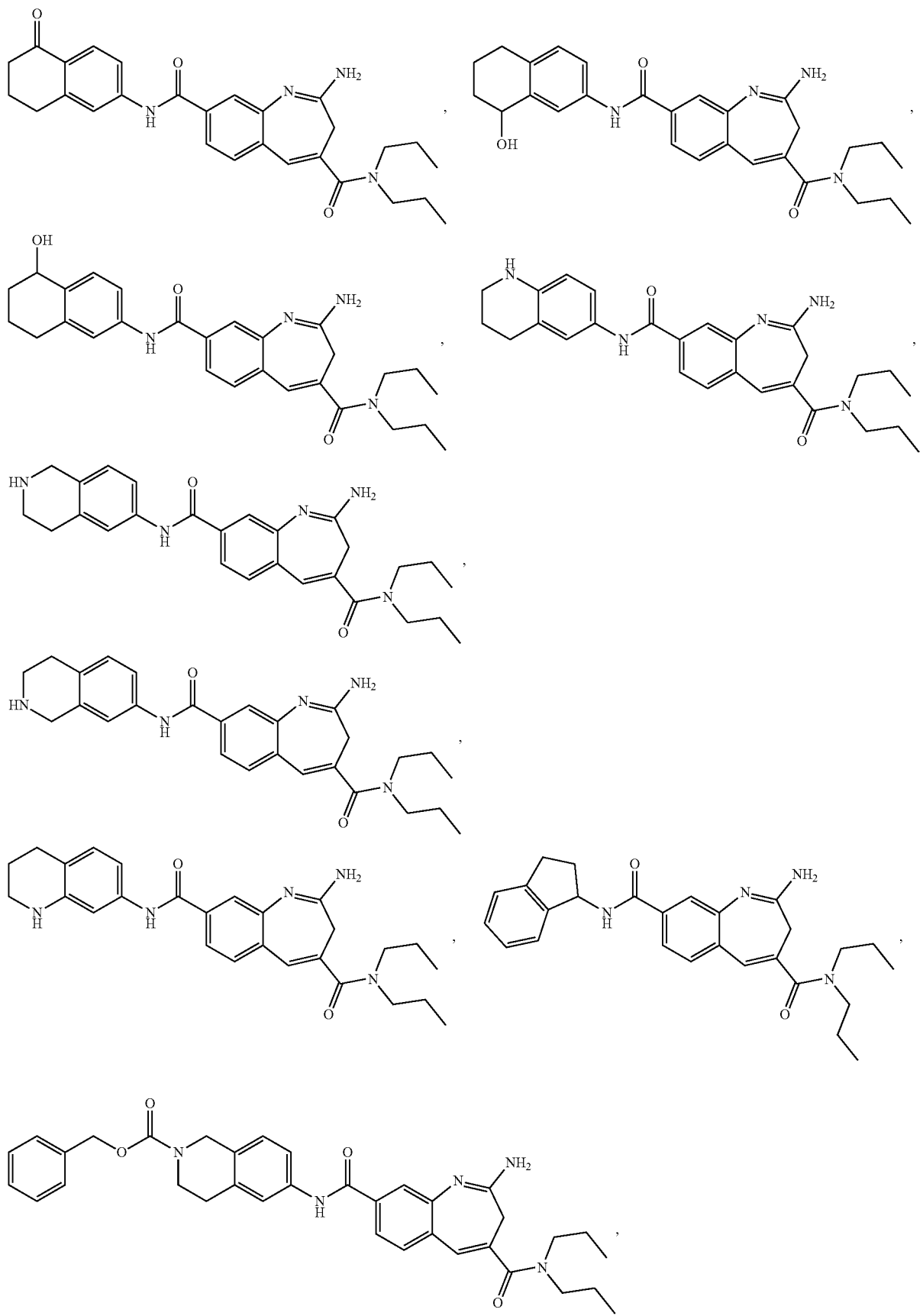

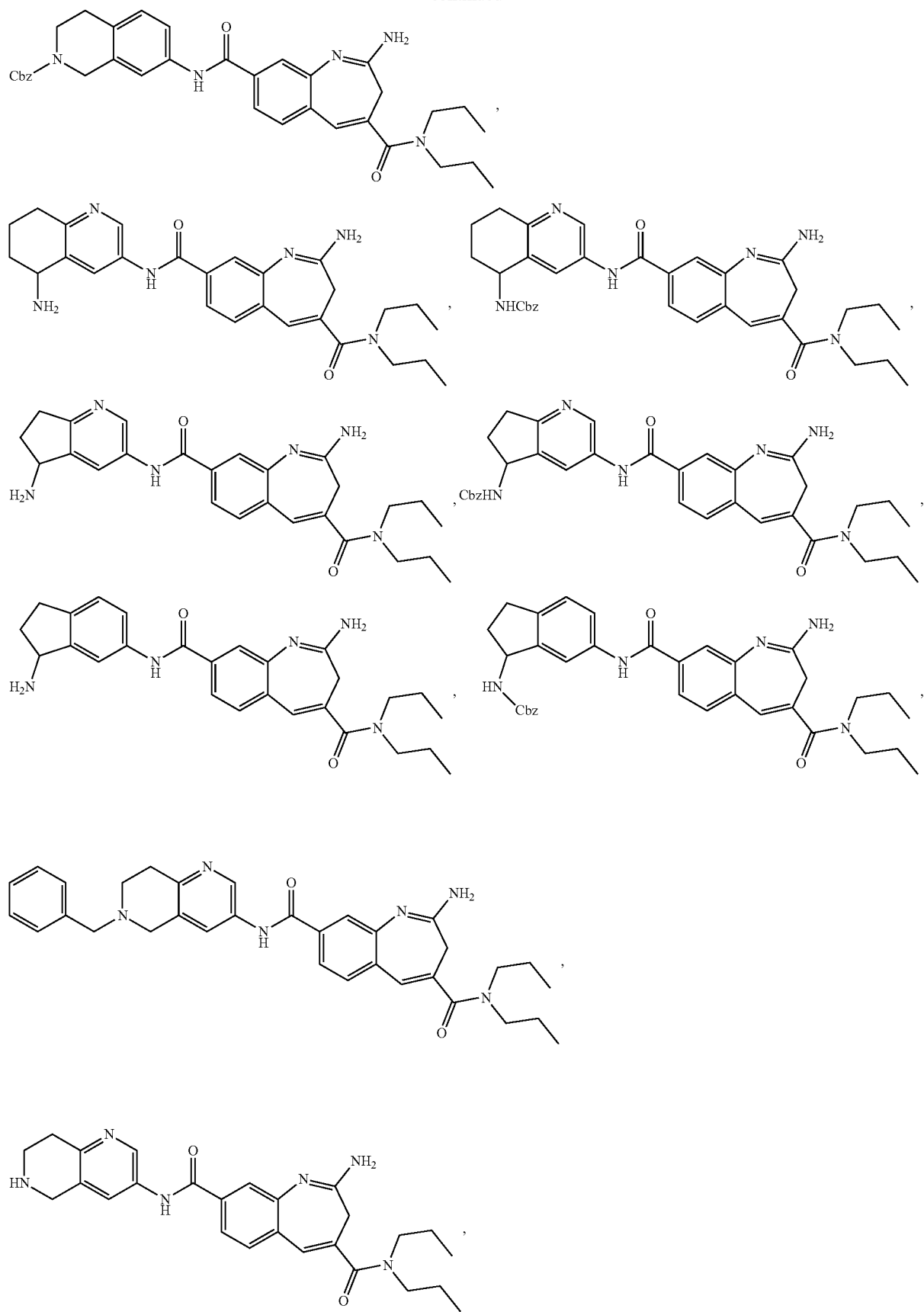

-continued
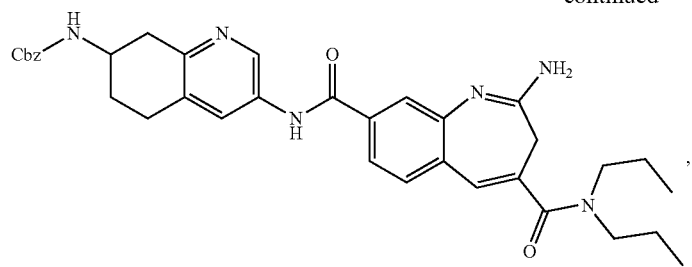
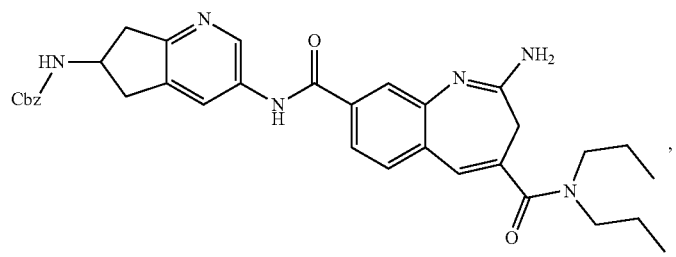
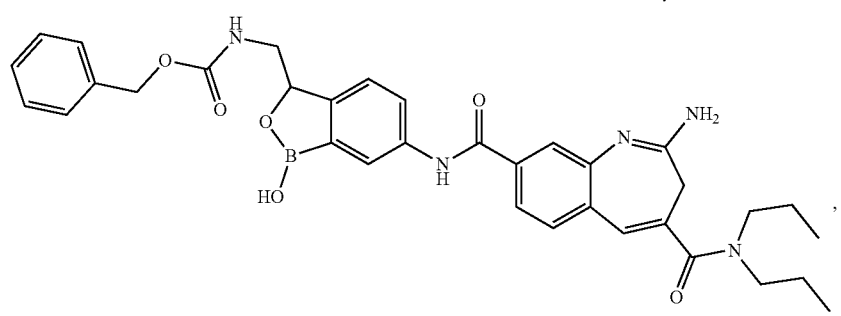
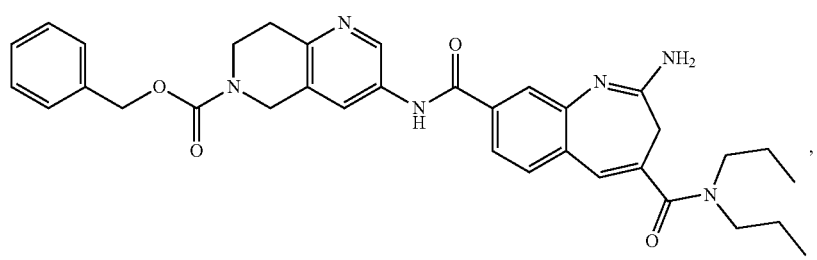
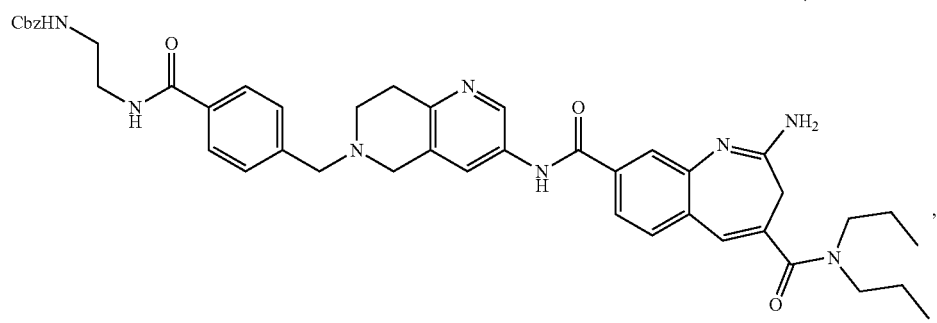
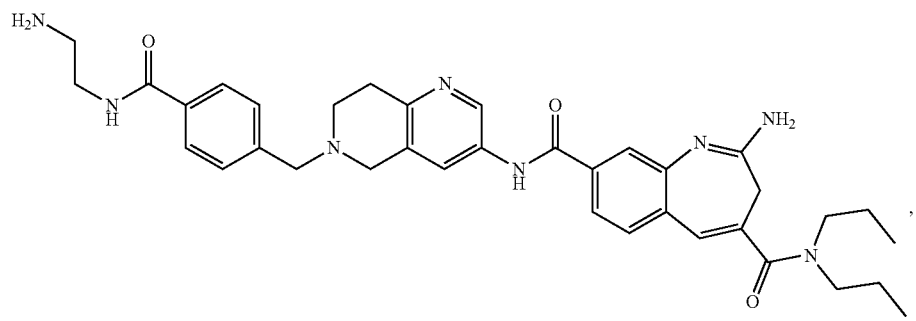

-continued

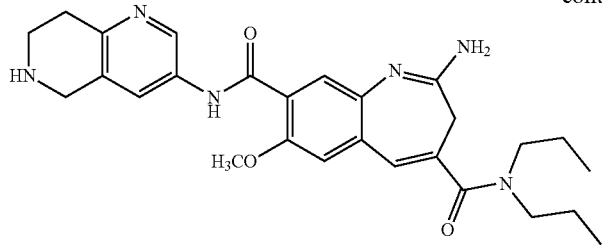

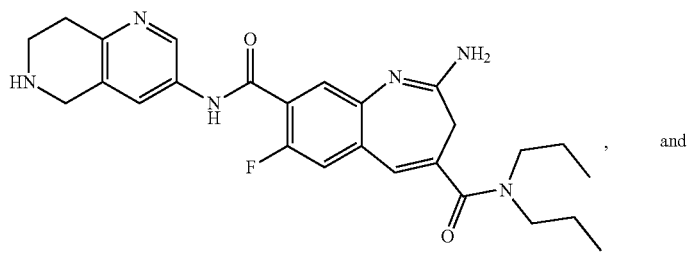

, and

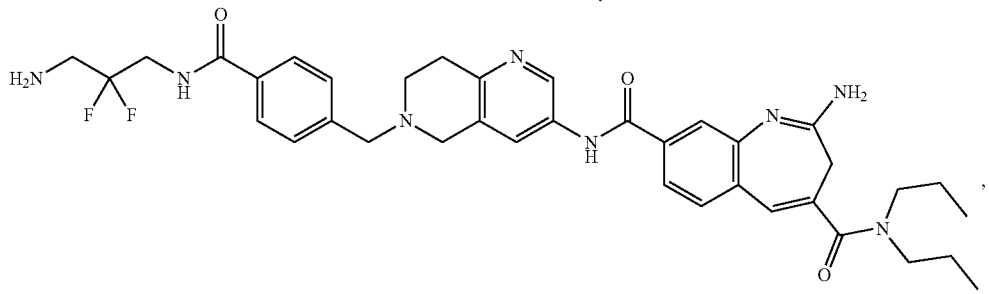

and a salt of any one thereof.

In some embodiments, the disclosure provides a compound represented by the structure of Formula (IIIA):

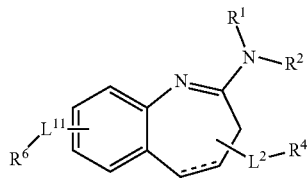

(IIIA)

or a pharmaceutically acceptable salt thereof, wherein:

--- represents an optional double bond;

$L^{11}$ is —$X^{11}$—;

$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^2$;

$X^{11}$ is selected from —C(O)— and —C(O)N($R^{10}$)—*, wherein * represents where $X^{11}$ is bound to $R^6$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —S(O)—, —S(O)O—, —S(O)—, —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from: —$OR^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R_{10}$; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^6$ is selected from phenyl and 5- or 6-membered heteroaryl, any one of which is substituted with one or more substituents selected from $R^7$ and $R^6$ is further optionally substituted by one or more additional substituents independently selected from $R^{12}$;

$R^7$ is selected from —C(O)NHNH$_2$, —C(O)NH—$C_{1-3}$ alkylene-NH($R^{10}$), —C(O)CH$_3$, —$C_{1-3}$ alkylene-NHC(O)OR$^{11}$, —$C_{1-3}$ alkylene-NHC(O)$R^{10}$, —$C_{1-3}$ alkylene-NHC(O)NHR$^{10}$, —$C_{1-3}$ alkylene-NHC(O)—$C_{1-3}$ alkylene-$R^{10}$, and a 3- to 12-membered heterocycle optionally substituted with one or more substituents independently selected from $R^{12}$;

$R^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, —C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

$R^{11}$ is selected from C$_{3-12}$ carbocycle and 3- to 12-membered heterocycle, each of which is optionally substituted with one or more substituents independently selected from $R^{12}$; and $R^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$), —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in $R^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$), —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from $R^{12}$ or two substituents on a single carbon atom combine to form a 3- to 7-membered carbocycle.

In some embodiments, the compound of Formula (IIIA) is represented by Formula (IIIB):

(IIIB)

or a pharmaceutically acceptable salt thereof, wherein:
$R^{20}$, $R^{21}$, $R^{22}$, and $R^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and $R^{24}$ and $R^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or $R^{24}$ and $R^{25}$ taken together form an optionally substituted saturated C$_{3-7}$ carbocycle.

In some embodiments, $R^{20}$, $R^{21}$, $R^{22}$, and $R^{23}$ are independently selected from hydrogen, halogen, —OH, —NO$_2$, —CN, and C$_{1-10}$ alkyl. In some embodiments, $R^{20}$, $R^{21}$, $R^{22}$, and $R^{23}$ are each hydrogen. In some embodiments, $R^{24}$ and $R^{25}$ are independently selected from hydrogen, halogen, —OH, —NO$_2$, —CN, and C$_{1-10}$ alkyl, or $R^{24}$ and $R^{25}$ taken together form an optionally substituted saturated C$_{3-7}$ carbocycle. In some embodiments, $R^{24}$ and $R^{25}$ are each hydrogen. In some embodiments, $R^{24}$ and $R^{25}$ taken together form an optionally substituted saturated C$_{3-5}$ carbocycle.

In some embodiments, $R^1$ is hydrogen. In some embodiments, $R^2$ is hydrogen.

In some embodiments, $L^{11}$ is selected from —C(O)N(R$^{10}$)—*. In some embodiments, $R^{10}$ of —C(O)N(R$^{10}$)—* is selected from hydrogen and C$_{1-6}$ alkyl. For example, $L^{11}$ may be —C(O)NH—*.

In some embodiments, $R^6$ is phenyl substituted with $R^7$ and $R^6$ is further optionally substituted with one or more additional substituents independently selected from $R^{12}$. In some embodiments, $R^6$ is selected from phenyl substituted with one or more substituents independently selected from —C(O)NHNH$_2$, —C(O)NH—C$_{1-3}$ alkylene-NH(R$^{11}$), —C$_{1-3}$ alkylene-NHC(O)R$^{10}$, and —C(O)CH$_3$; and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$ alkylene-(R$^{10}$) and $R^6$ is further optionally substituted with one or more additional substituents independently selected from $R^{12}$. For example, $R^6$ may be selected from:

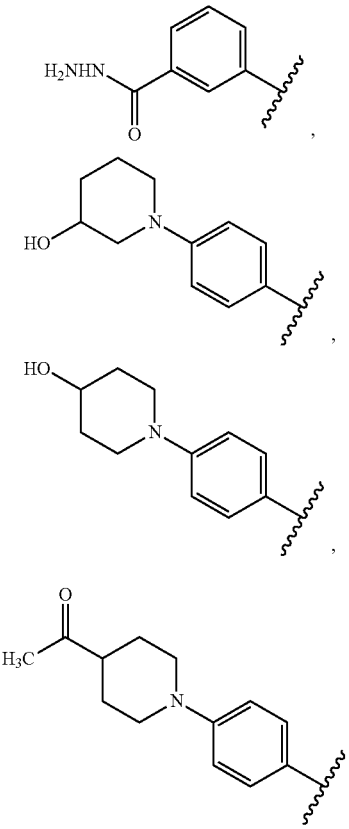

-continued

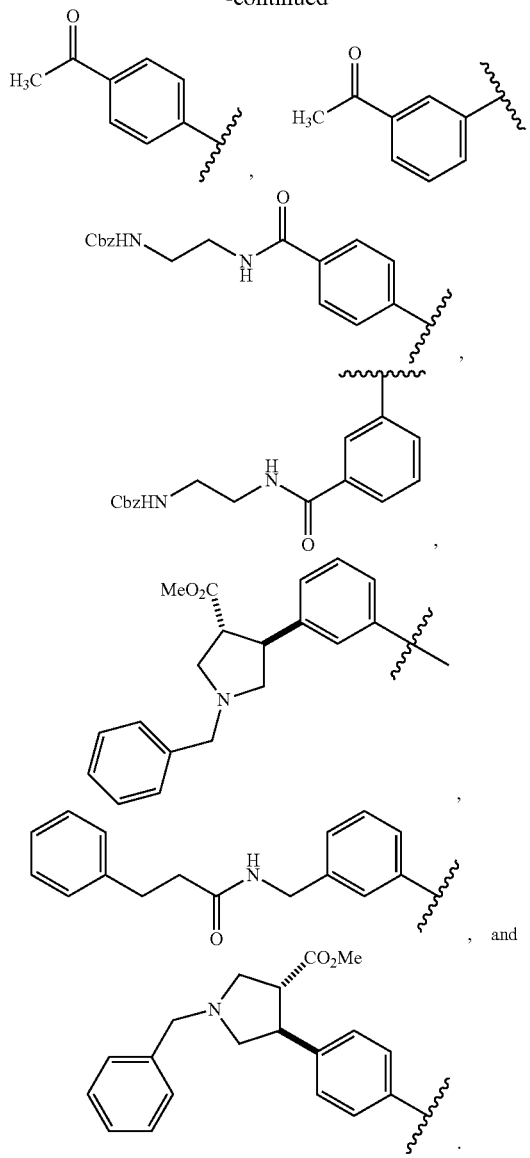

In some embodiments, $R^6$ is selected from a 5- and 6-membered heteroaryl substituted with one or more substituents independently selected from $R^7$, and $R^6$ is further optionally substituted with one or more additional substituents selected from $R^{12}$. In some embodiments, $R^6$ is selected from 5- and 6-membered heteroaryl substituted with one or more substituents independently selected from —C(O)CH$_3$, —C$_{1-3}$ alkylene-NHC(O)OR$^{10}$, —C$_{1-3}$ alkylene-NHC(O)R$^{10}$, —C$_{1-3}$ alkylene-NHC(O)NHR$^{10}$, and —C$_{1-3}$ alkylene-NHC(O)—C$_{1-3}$ alkylene-(R$^{10}$); and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$ alkylene-(R$^{10}$), and $R^6$ is optionally further substituted with one or more additional substituents independently selected from $R^{12}$. $R^6$ may be selected from substituted pyridine, pyrazine, pyrimidine, pyridazine, furan, pyran, oxazole, thiazole, imidazole, pyrazole, oxadiazole, oxathiazole, and triazole, and $R^6$ is optionally further substituted with one or more additional substituents independently selected from $R^{12}$. In some embodiments, $R^6$ is substituted pyridine and $R^6$ is optionally further substituted with one or more additional substituents independently selected from $R^{12}$. $R^6$ may be represented as follows:

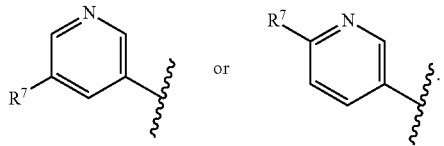

In some embodiments, $R^6$ is substituted pyridine, and wherein $R^7$ is —C$_{1-3}$ alkylene-NHC(O)—C$_{1-3}$ alkylene-R$^{10}$. In some embodiments, $R^7$ is —C$_1$ alkylene-NHC(O)—C$_1$ alkylene-R$^{10}$. In some embodiments, $R^7$ is —C$_1$ alkylene-NHC(O)—C$_1$ alkylene-NH$_2$. In some embodiments, $R^6$ is selected from:

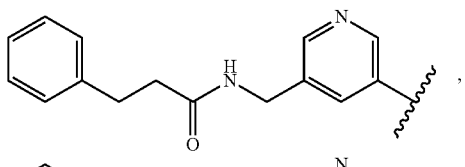

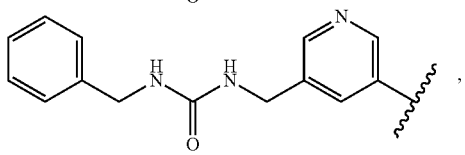

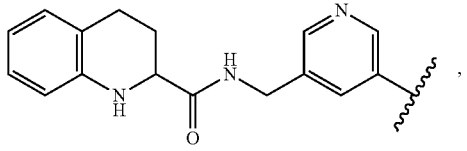

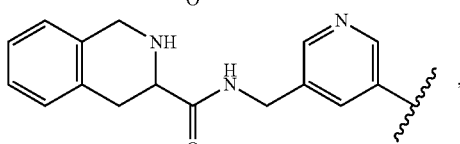

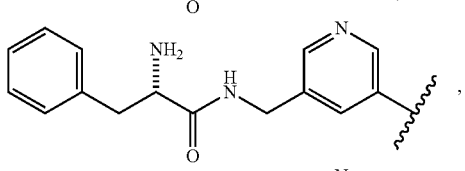

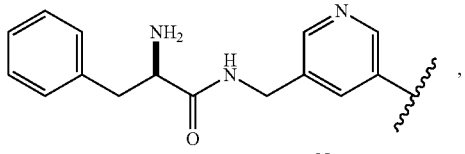

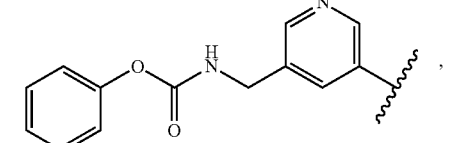

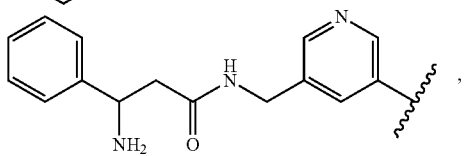

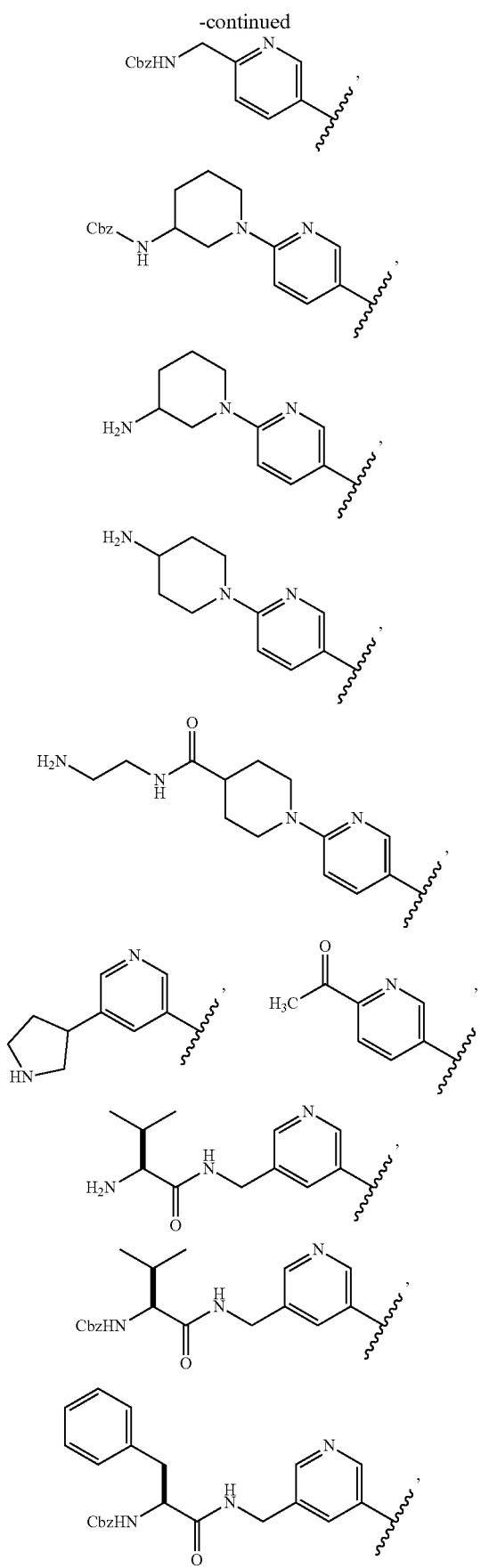

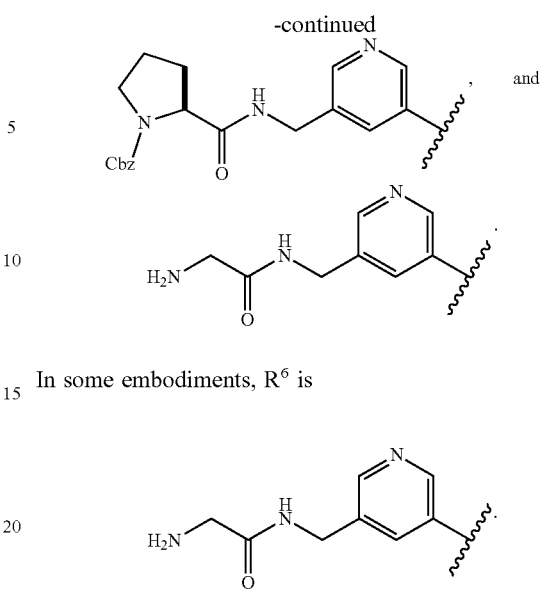

In some embodiments, $R^6$ is

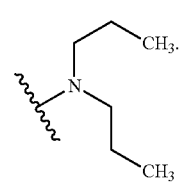

In some embodiments, $L^2$ is selected from —C(O)—, and —C(O)NR$^{10}$—. In some embodiments, $L^2$ is selected from —C(O)NR$^{10}$—. $R^{10}$ of —C(O)NR$^{10}$— may be selected from hydrogen and $C_{1-6}$ alkyl. For example, $L^2$ may be —C(O)NH—. In some embodiments, $L^2$ is —C(O)—.

In some embodiments, $R^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle; and $C_{3-12}$ carbocycle and 3- to 12-membered, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{1-6}$ alkyl, $C_{2-6}$ alkenyl, and $C_{2-6}$ alkynyl. In some embodiments, $R^4$ is selected from: —OR$^{10}$ and —N(R$^{10}$)$_2$; and $C_{1-10}$ alkyl, $C_{2-10}$ alkenyl, $C_{2-10}$ alkynyl, $C_{3-12}$ carbocycle and 3- to 12-membered heterocycle, each of which is independently optionally substituted at each occurrence with one or more substituents selected from halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, $C_{1-10}$ alkyl, $C_{2-10}$ alkenyl, and $C_{2-10}$ alkynyl. In some embodiments, $R^4$ is —N(R$^{10}$)$_2$. $R^{10}$ of —N(R$^{10}$)$_2$ may be independently selected at each occurrence from optionally substituted $C_{1-6}$ alkyl. In some embodiments, $R^{10}$ of —N(R$^{10}$)$_2$ is independently selected at each occurrence from methyl, ethyl, propyl, and butyl, any of which are optionally substituted. For example, $R^4$ may be In some embodiments, -L²-R⁴ is

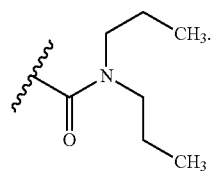

In some embodiments, R¹² is independently selected at each occurrence from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), and —CN; C₁₋₁₀ alkyl, C₂₋₁₀ alkenyl, C₂₋₁₀ alkynyl, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), —CN, C₃₋₁₀ carbocycle and 3- to 10-membered heterocycle; and C₃₋₁₀ carbocycle and 3- to 10-membered heterocycle, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), —CN, C₁₋₆ alkyl, C₂₋₆ alkenyl, and C₂₋₆ alkynyl.

In some embodiments, R¹² is independently selected at each occurrence from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), and —CN; C₁₋₁₀ alkyl, C₂₋₁₀ alkenyl, C₂₋₁₀ alkynyl, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), —CN, C₃₋₁₀ carbocycle and 3- to 10-membered heterocycle.

In some embodiments, the compound is selected from:

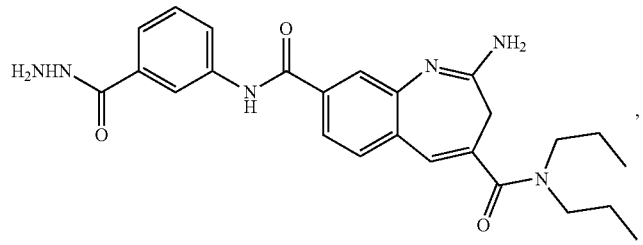

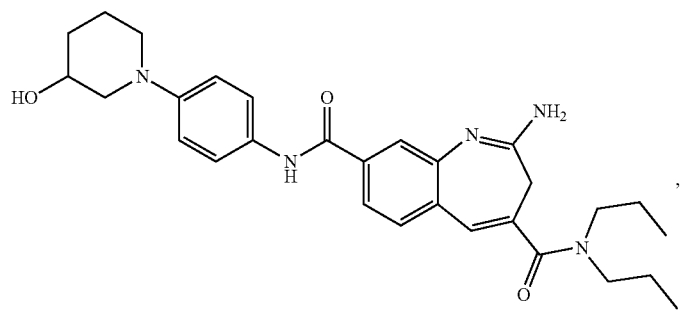

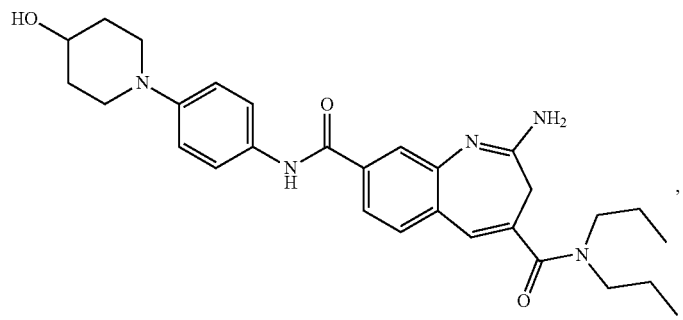

-continued
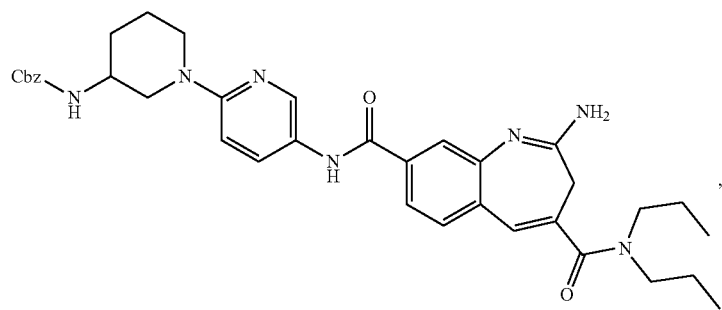
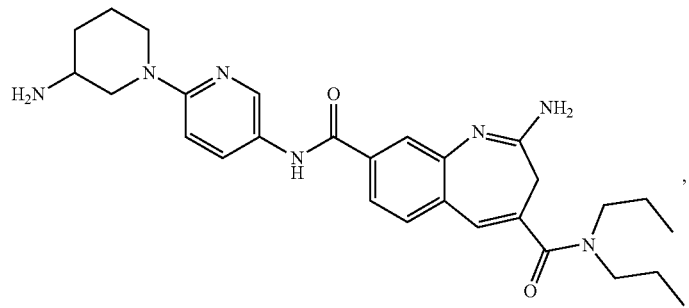
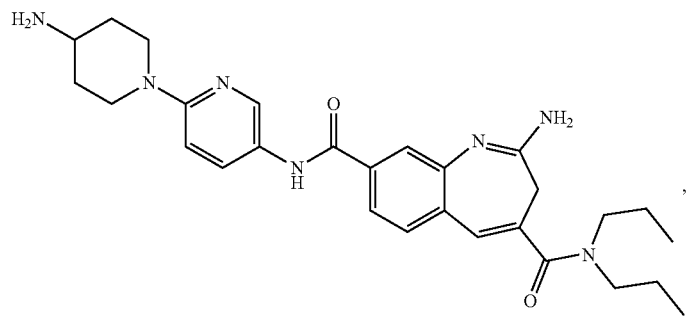
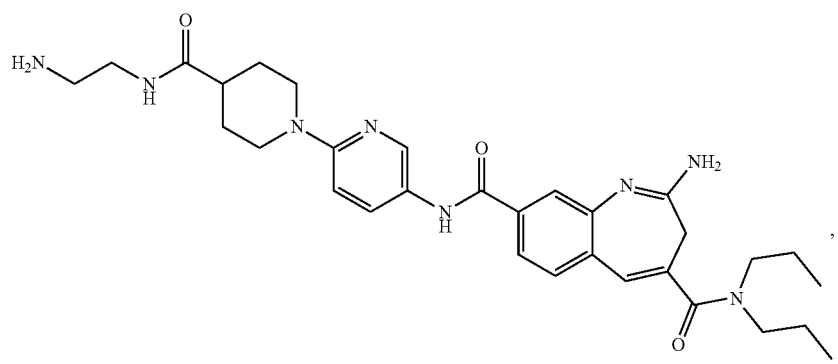
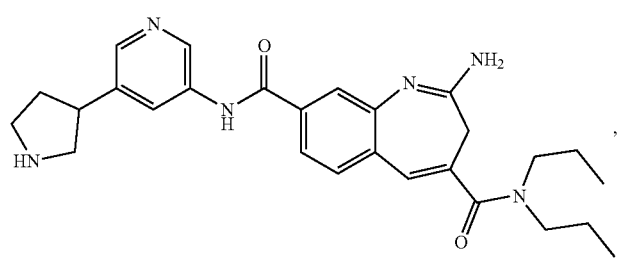

-continued
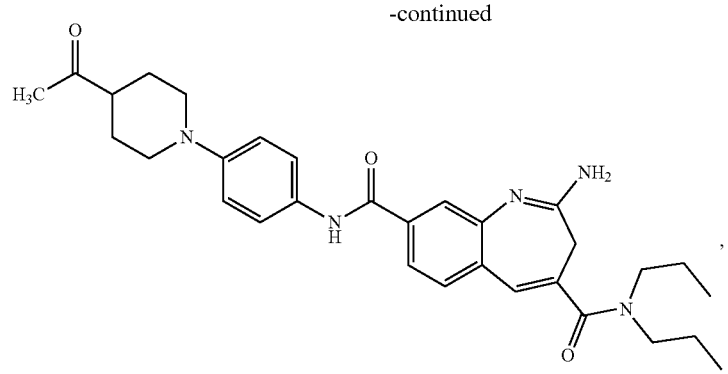
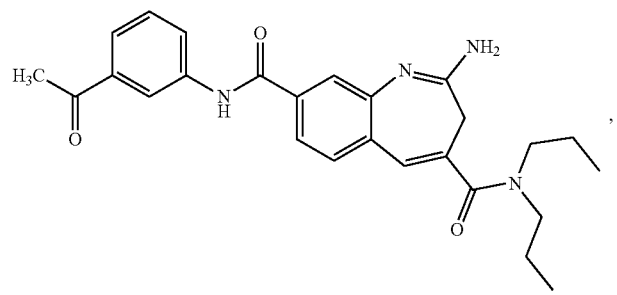
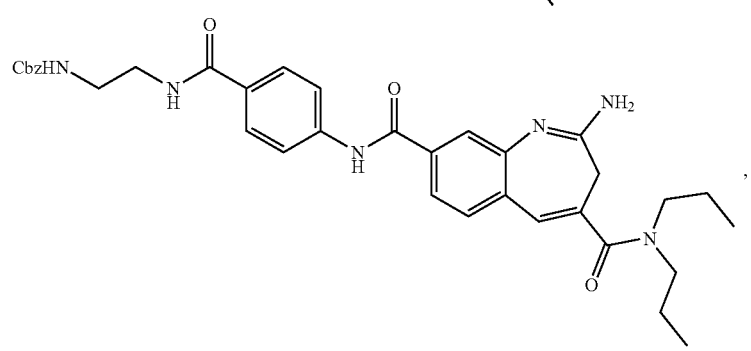
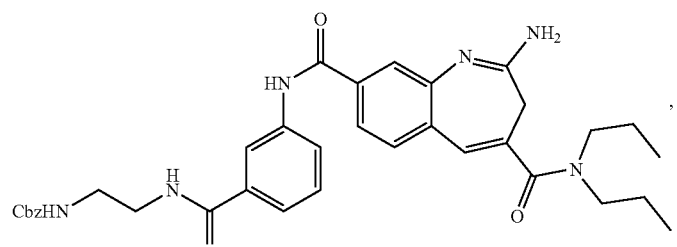
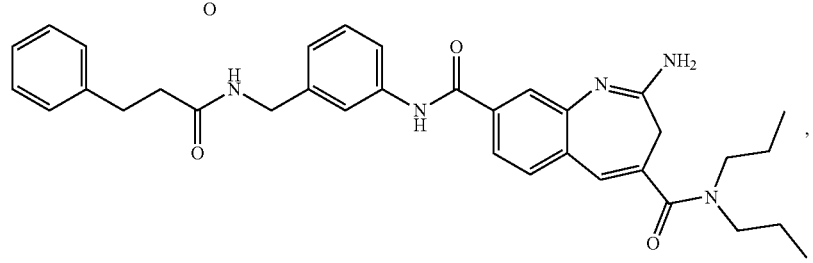
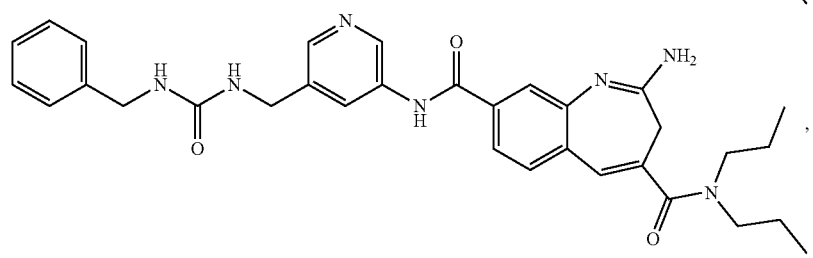

-continued
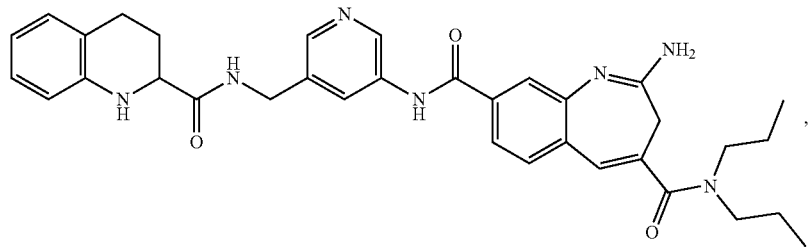
,
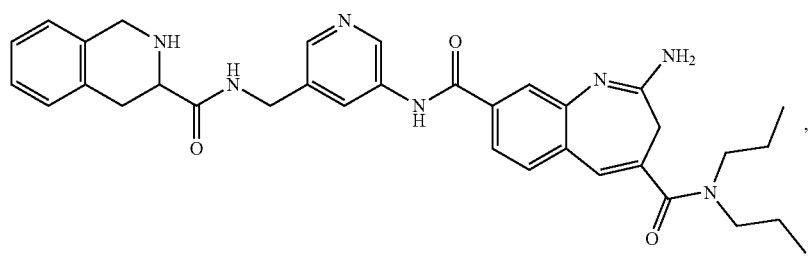
,
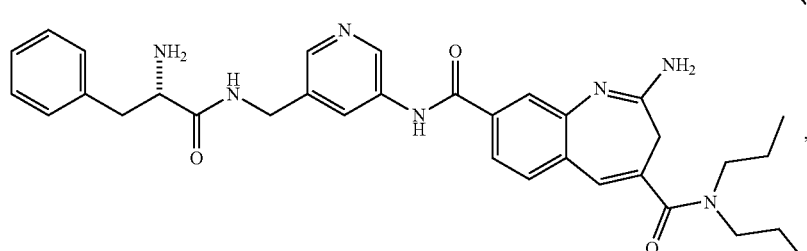
,
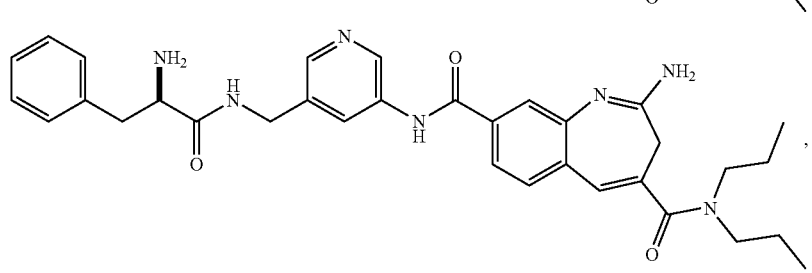
,
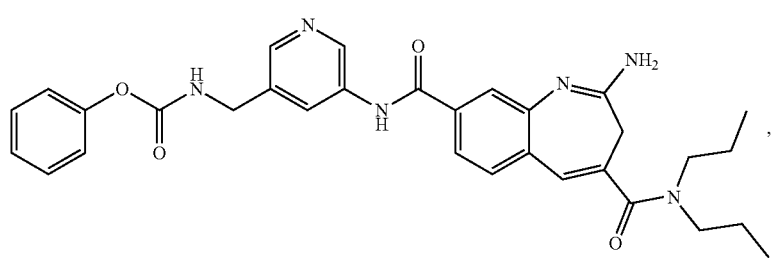
,
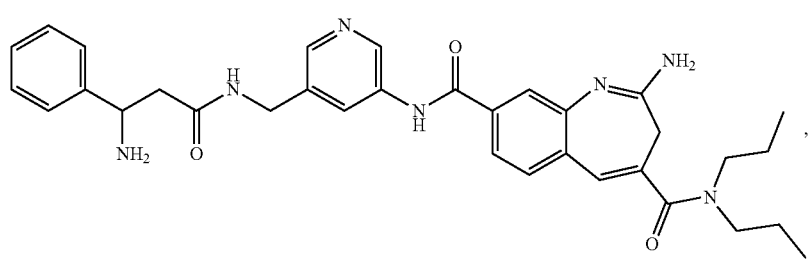
, -continued
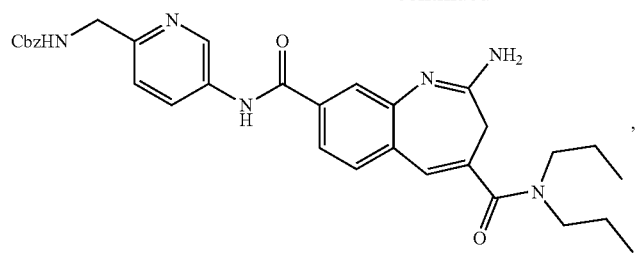,
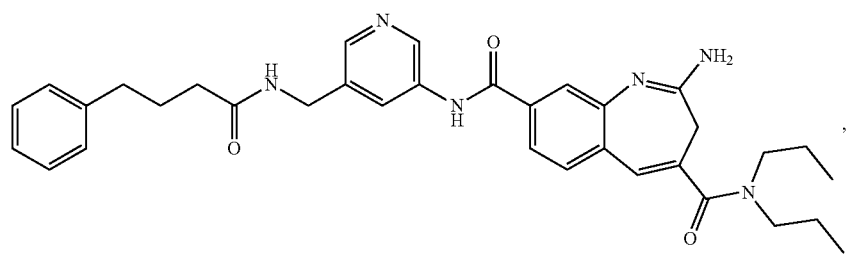,
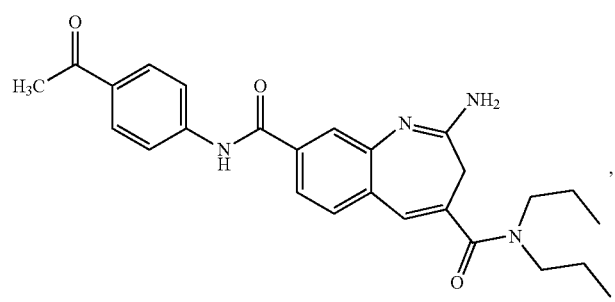,
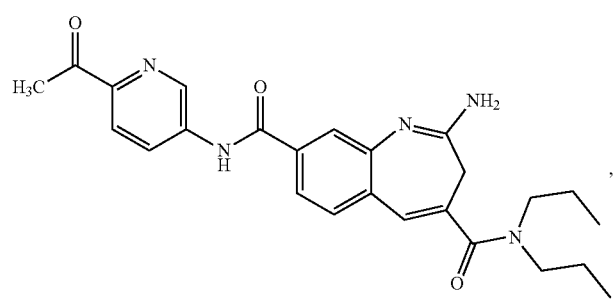,
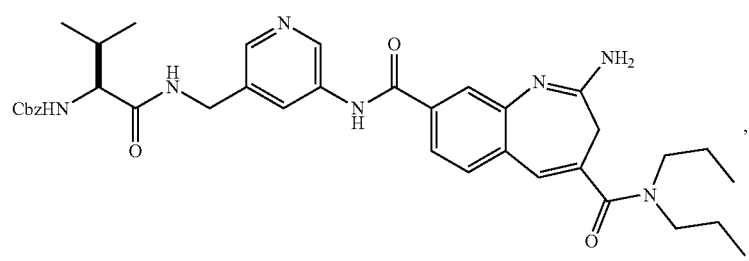,
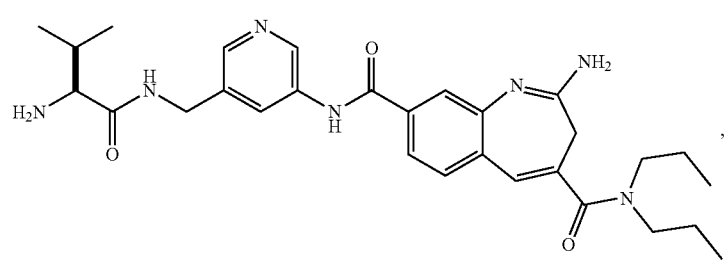, -continued
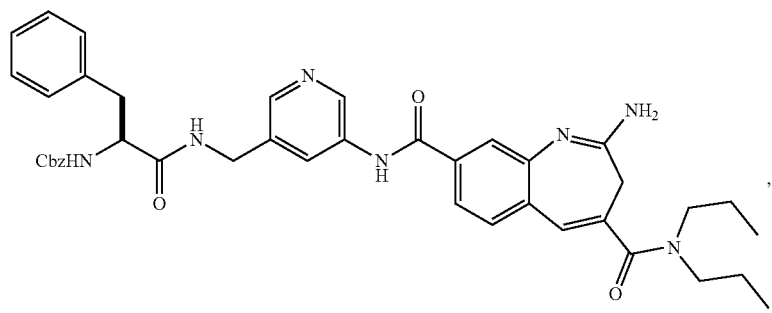
,
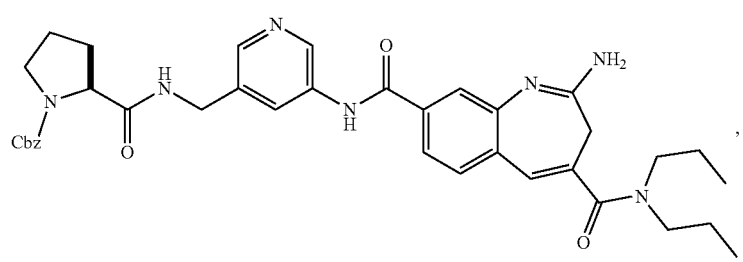
,
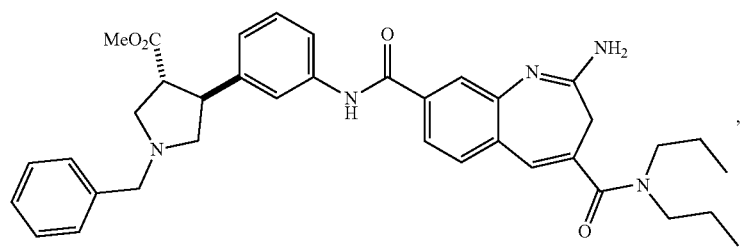
,
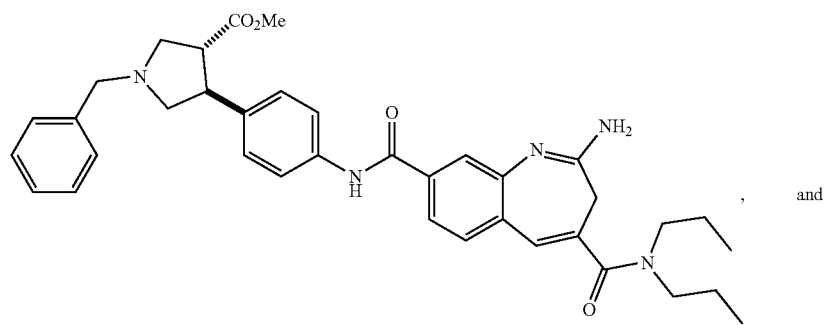
, and -continued

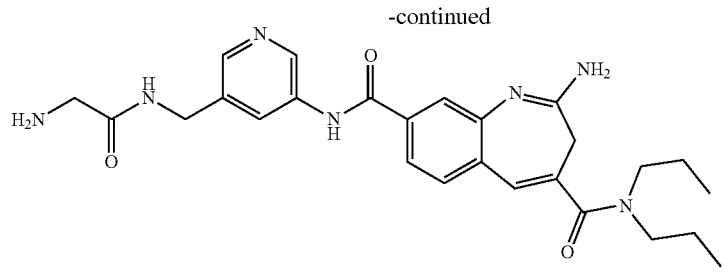

and a salt of any one thereof.

In some embodiments, the disclosure provides a compound represented by the structure of Formula (IA):

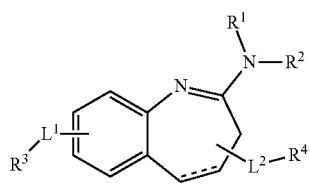

(IA)

or a pharmaceutically acceptable salt thereof, wherein:

--- represents an optional double bond;

$L^1$ is selected from —$X^1$—, —$X^2$—$C_{1-6}$ alkylene-$X^2$—, $C_{1-6}$ alkylene-, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^1$ is selected from —S—*, —N($R^{10}$)—*, —C(O)O—*, —OC(O)—*, —OC(O)O—*, —C(O)N($R^{10}$)C(O)—*, —C(O)N($R^{10}$)C(O)N($R^{10}$)*, —N($R^{10}$)C(O)—*, —$CR^{10}_2$N($R^{10}$)C(O)—*, —N($R^{10}$)C(O)N($R^{10}$)—*, —N($R^{10}$)C(O)O—*, —OC(O)N($R^{10}$)—*, —C(NR)—*, —N($R^{10}$)C(NR$^{10}$)—*, —C(NR$^{10}$)N($R^{10}$)—*, —N($R^{10}$)C(NR$^{10}$)N($R^{15}$)—*, —S(O)—*, —OS(O)—*, —S(O)O—*, —S(O), —N($R^{10}$)S(O)$_2$N($R^{10}$)—*, and —N($R^{10}$)S(O)N($R^{10}$)—*, wherein * represents where $X^1$ is bound to $R^3$;

$X^2$ is independently selected at each occurrence from —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(NR$^{10}$)—, —N($R^{10}$)C(NR$^{10}$)—, —C(NR$^{10}$)N($R^{10}$)—, —N($R^{10}$)C(NR$^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —OR$^{10}$, —SR$^{10}$, —C(O)N($R^{10}$)$_2$, —N($R^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N($R^{10}$), and —CN;

$R^3$ is selected from optionally substituted $C_{3-12}$ carbocycle, and optionally substituted 3- to 12-membered heterocycle, wherein substituents on $R^3$ are independently selected at each occurrence from: halogen, —OR$^{10}$, —SR$^{10}$, —C(O)N($R^{10}$)$_2$, —N($R^{10}$)C(O)R$^{10}$, —N($R^{10}$)C(O)N($R^{10}$)$_2$, —N($R^{10}$)$_2$, —C(O)R$^{10}$, —C(O)OR$^{10}$, —OC(O)R$^{10}$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N($R^{10}$), —N($R^{10}$)C(O)R$^{10}$, —N($R^{10}$)C(O)N($R^{10}$)$_2$, —N($R^{10}$)$_2$, —C(O)R$^{10}$, —C(O)OR$^{10}$, —OC(O)R$^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^3$ is optionally substituted with one or more substituents independently selected from halogen, —OR$^{10}$, —SR$^{10}$, —C(O)N($R^{10}$)$_2$, —N($R^{10}$)C(O)R$^{10}$, —N($R^{10}$)C(O)N($R^{10}$)$_2$, —N($R^{10}$)$_2$, —C(O)R$^{10}$, —C(O)OR$^{10}$, —OC(O)R$^{10}$, —NO$_2$, =O, =S, =N($R^{10}$), —CN, $C_{1-6}$ alkyl, $C_{2-6}$ alkenyl, and $C_{2-6}$ alkynyl;

$R^4$ is selected from: —OR$^{10}$, —N($R^{10}$)$_2$, —C(O)N($R^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N($R^{10}$)$_2$, —N($R^{10}$)C(O)R$^{10}$, —N($R^{10}$)C(O)N($R^{10}$)$_2$, —N($R^{10}$)$_2$, —C(O)R$^{10}$, —C(O)OR$^{10}$, —OC(O)R$^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —OR$^{10}$, —SR$^{10}$, —C(O)N($R^{10}$)$_2$, —N($R^{10}$)C(O)R$^{10}$, —N($R^{10}$)C(O)N($R^{10}$)$_2$, —N($R^{10}$)$_2$, —C(O)R$^{10}$, —C(O)OR$^{10}$, —OC(O)R$^{10}$, —NO$_2$, =O, =S, =N($R^{10}$), —CN, $C_{1-6}$ alkyl, $C_{2-6}$ alkenyl, and $C_{2-6}$ alkynyl;

$R^{10}$ is independently selected at each occurrence from: hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl; and $R^{12}$ is independently selected at each occurrence from halogen, —OR$^{10}$, —SR$^{10}$, —N($R^{10}$)$_2$, —C(O)R$^{10}$, —C(O)N($R^{10}$)$_2$, —N($R^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N($R^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IA) is represented by Formula (IB):

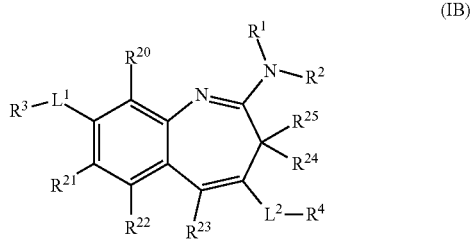

(IB)

or a pharmaceutically acceptable salt thereof, wherein:

R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —NO$_2$, —CN, and C$_{1-10}$ alkyl. In some embodiments, R$^{20}$, R$^{21}$, R$^{22}$, and R$^{23}$ are each hydrogen.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In some embodiments, R$^{24}$ and R$^{25}$ are each hydrogen. In some embodiments, R$^{24}$ and R$^{25}$ taken together form an optionally substituted saturated C$_{3-5}$ carbocycle.

In some embodiments, R$^1$ is hydrogen. In some embodiments, R$^2$ is hydrogen.

In some embodiments, L$^1$ is selected from —N(R$^{10}$)C(O)—*, —S(O)$_2$N(R$^{10}$)—*, —CR$^{10}$$_2$N(R$^{10}$)C(O)—* and —X$^2$—C$_{1-6}$ alkylene-X$^2$—C$_{1-6}$ alkylene-. In some embodiments, L$^1$ is selected from —N(R$^{10}$)C(O)—*. In some embodiments, R$^{10}$ of —N(R$^{10}$)C(O)—* is selected from hydrogen and C$_{1-6}$ alkyl. For example, L$^1$ may be —NHC(O)—*. In some embodiments, L$^1$ is selected from —S(O)$_2$N(R$^{10}$)—*. In some embodiments, R$^{10}$ of —S(O)$_2$N(R$^{10}$)—* is selected from hydrogen and C$_{1-6}$ alkyl. For example, L$^1$ is —S(O)$_2$NH—*. In some embodiments, L$^1$ is —CR$^{10}$$_2$N(R$^{10}$)C(O)—*. In some embodiments, L$^1$ is selected from —CH$_2$N(H)C(O)—* and —CH(CH$_3$)N(H)C(O)—*.

In some embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$), —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$), —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^3$ is selected from an optionally substituted aryl and an optionally substituted heteroaryl. In some embodiments, R$^3$ is an optionally substituted heteroaryl. R$^3$ may be an optionally substituted heteroaryl substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In some embodiments, R$^3$ is selected from an optionally substituted 6-membered heteroaryl. For example, R$^3$ may be an optionally substituted pyridine. In some embodiments, R$^3$ is an optionally substituted aryl. In some embodiments, R$^3$ is an optionally substituted aryl substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. R$^3$ may be an optionally substituted phenyl. In some embodiments, R$^3$ is selected from pyridine, phenyl, tetrahydronaphthalene, tetrahydroquinoline, tetrahydroisoquinoline, indane, cyclopropylbenzene, cyclopentapyridine, and dihydrobenzoxaborole, any one of which is optionally substituted. R$^3$ may be selected from:

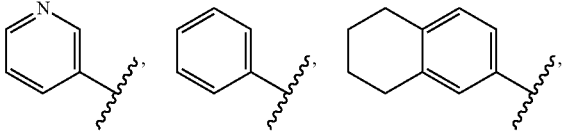

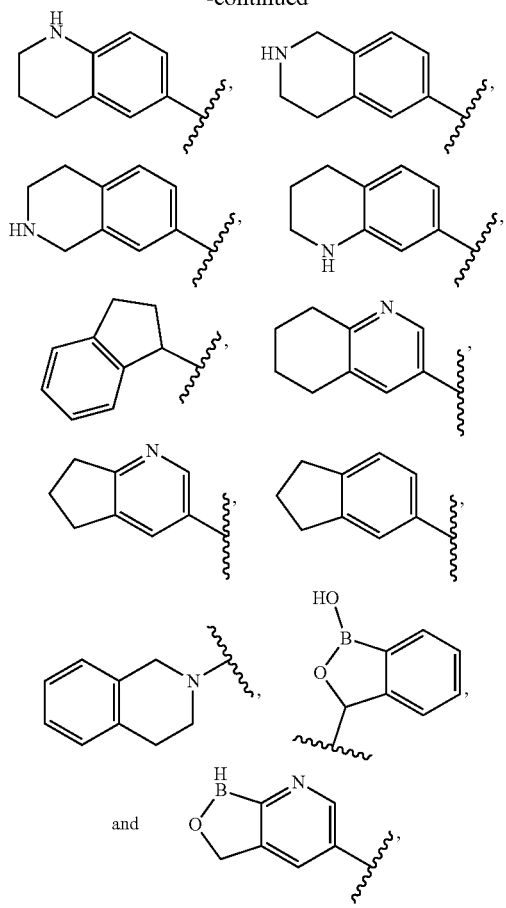
any one of which is optionally substituted. For example, $R^3$ may be selected from:
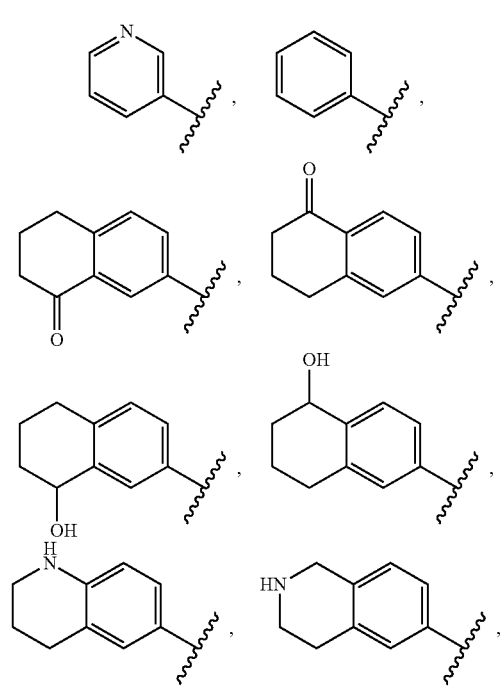
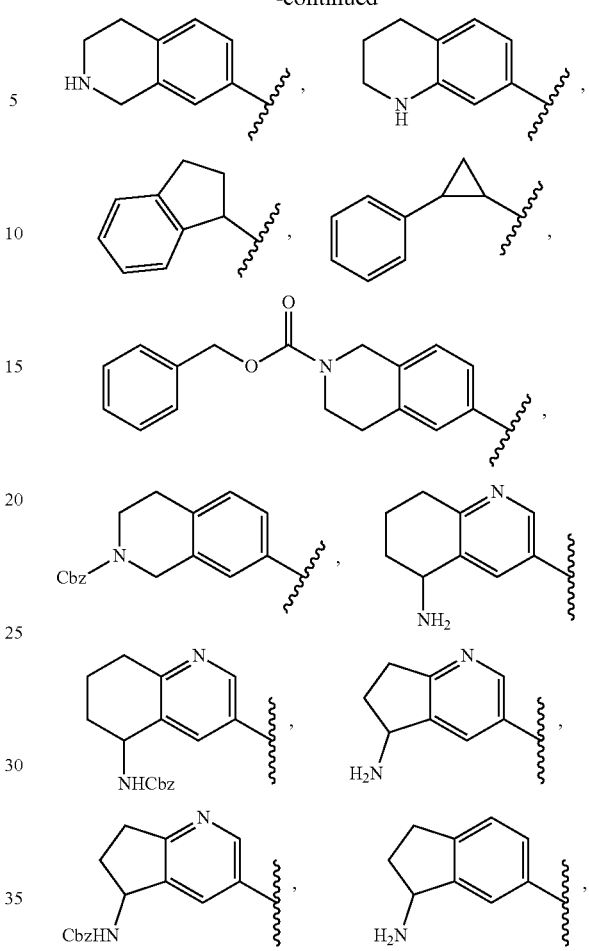

129
-continued
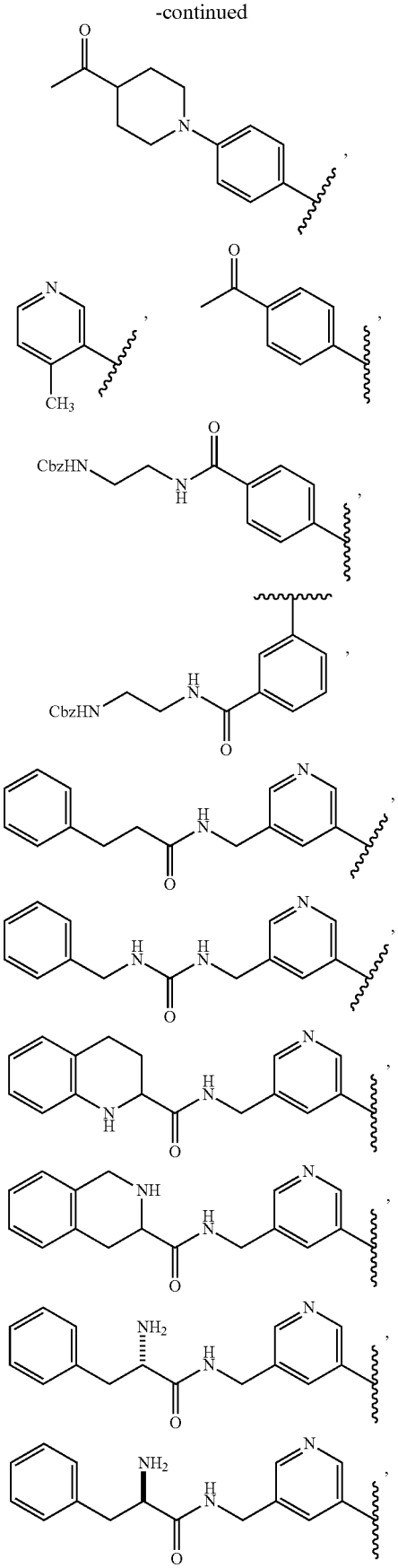
130
-continued
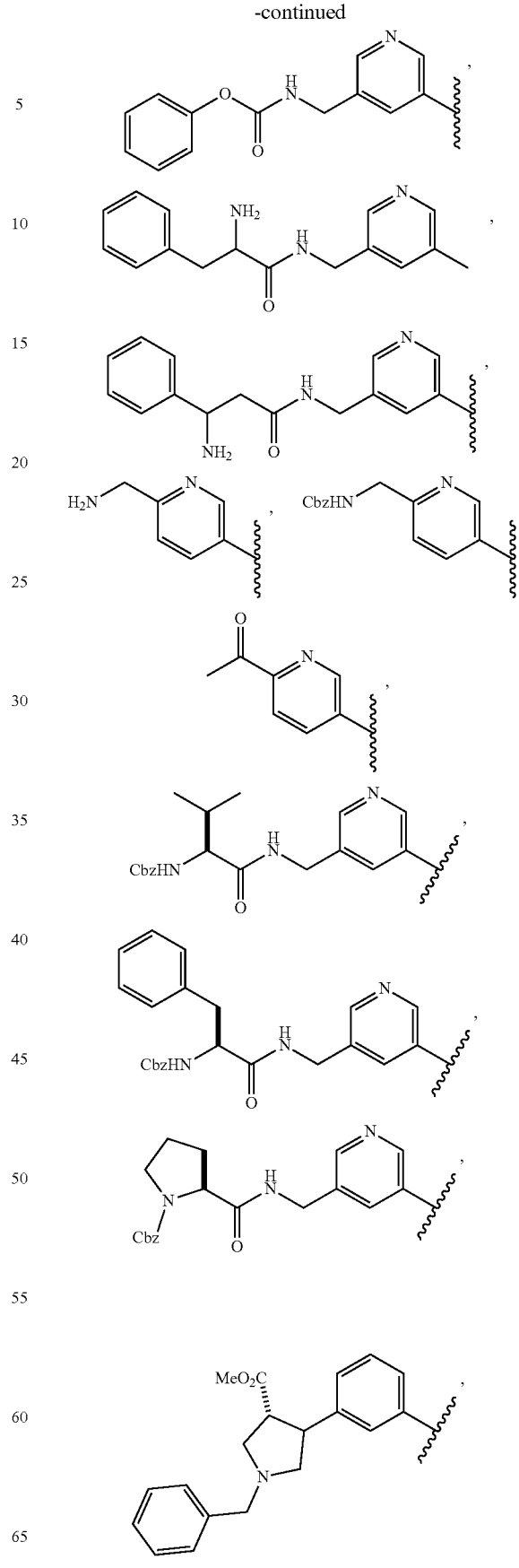

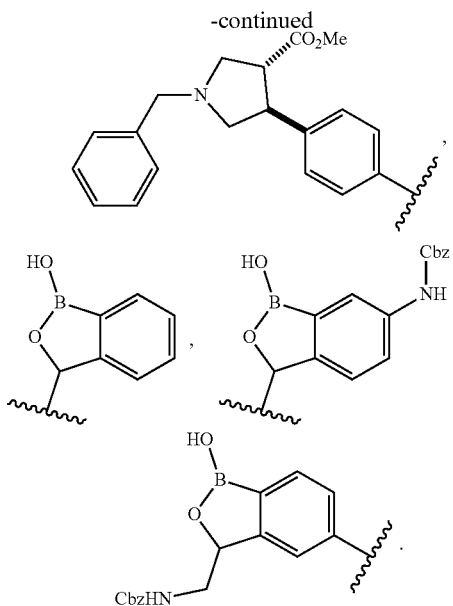

In some embodiments, $L^2$ is selected from —C(O)—, and —C(O)NR$^{10}$—. In some embodiments, $L^2$ is —C(O)—. In some embodiments, $L^2$ is selected from —C(O)NR$^{10}$—. R$^{10}$ of —C(O)NR$^{10}$— may be selected from hydrogen and C$_{1-6}$ alkyl. For example, $L^2$ may be —C(O)NH—.

In some embodiments, R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$_{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments, R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle. In some embodiments, R$^4$ is selected from: —OR$^{10}$, and —N(R$^{10}$)$_2$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl. In some embodiments, R$^4$ is —N(R$^{10}$)$_2$. R$^{10}$ of —N(R$^{10}$)$_2$ may be independently selected at each occurrence from optionally substituted C$_{1-6}$ alkyl. In some embodiments, R$^{10}$ of —N(R$^{10}$)$_2$ is independently selected at each occurrence from methyl, ethyl, propyl and butyl, any one of which is optionally substituted. For example, R$^4$ may be

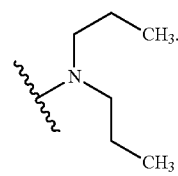

In some embodiments, $L^2$-R$^4$ is

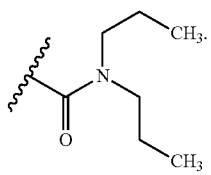 [SMILES: *C(=O)N(CCC)CCC]

In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(ORIO)$_2$, —NO$_2$, =O, =S, =N(R$^{10}$), —CN, C$_{1-6}$ alkyl, C$_{2-6}$ alkenyl, C$_{2-6}$ alkynyl. In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{0}$, —S(O)R$^{10}$, —S(O)$_2$R$^{10}$, —P(O)(OR$^{10}$)$_2$, —OP(O)(OR$^{0}$)$_2$, —NO$_2$, =O, =S, =N(R$^{10}$), —CN, C$_{3-10}$ carbocycle and 3- to 10-membered heterocycle.

In some embodiments, the compound is selected from:

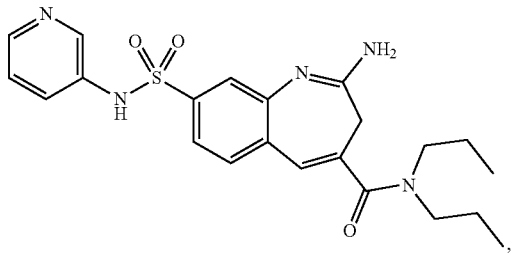

-continued

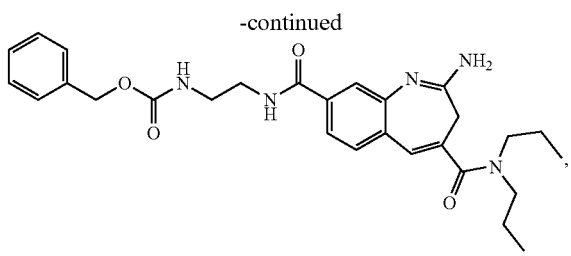

of any one thereof.

In some embodiments, the disclosure provides a compound represented by the structure of Formula (IVA):

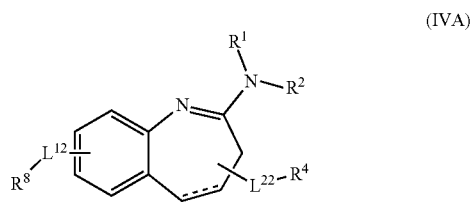

or a pharmaceutically acceptable salt thereof, wherein:

═══ represents an optional double bond;

$L^{12}$ is selected from —$X^3$—, —$X^3$—$C_{1-6}$ alkylene-$X^3$—, —$X^3$—$C_{2-6}$ alkenylene-$X^3$—, and —$X^3$—$C_{2-6}$ alkynylene-$X^3$—, each of which is optionally substituted on alkylene, alkenylene, or alkynylene with one or more substituents independently selected from $R^{12}$;

$L^{22}$ is independently selected from —$X^4$—, —$X^4$—$C_{1-6}$ alkylene-$X^4$—, —$X^4$—$C_{2-6}$ alkenylene-$X^4$—, and —$X^4$—$C_{2-6}$ alkynylene-$X^4$—, each of which is optionally substituted on alkylene, alkenylene, or alkynylene with one or more substituents independently selected from $R_{10}$;

$X^3$ and $X^4$ are independently selected at each occurrence from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O)—, —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from $L^3$, and hydrogen; and $C_{1-10}$ alkyl, $C_{2-10}$ alkenyl, and $C_{2-10}$ alkynyl, each of which is optionally bound to $L^3$ and each of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, ═O, ═S, ═N($R^{10}$), and —CN;

$R^4$ and $R^8$ are independently selected from: —$OR^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R_{10}$; $C_{1-10}$ alkyl, $C_{2-10}$ alkenyl, $C_{2-10}$ alkynyl, each of which is optionally bound to $L^3$ and each of which is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, ═O, ═S, ═N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ and $R^8$ is optionally bound to $L^3$ and each of which is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, ═O, ═S, ═N($R^{10}$), —CN, $C_{1-6}$ alkyl, $C_{2-6}$ alkenyl, and $C_{2-6}$ alkynyl;

$R^{10}$ is independently selected at each occurrence from $L^3$, hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, ═O, ═S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$L^3$ is a linker moiety, wherein there is at least one occurrence of $L^3$; and $R^{12}$ is independently selected at each occurrence from halogen, —$OR^{10}$, —$SR^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, ═O, ═S, ═N($R^{10}$), and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, ═O, ═S, ═N($R^{10}$), —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, —$OR^{10}$, —$SR^{10}$, —N($R^{10}$)$_2$, —C(O)$R^{10}$, —C(O)N($R^{10}$), —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, ═O, ═S, ═N($R^{10}$), —CN, $C_{1-6}$ alkyl, $C_{2-6}$ alkenyl, $C_{2-6}$ alkynyl; wherein any substitutable carbon on the benzazepine core is optionally substituted by a substituent independently selected from $R^{12}$ or two substituents on a single carbon atom combine to form a 3- to 7-membered carbocycle.

In some embodiments, the compound of Formula (IVA) is represented by Formula (IVB):

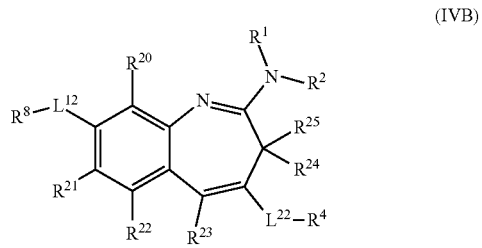

or a pharmaceutically acceptable salt thereof, wherein:

$R^{20}$, $R^{21}$, $R^{22}$, and $R^{23}$ are independently selected from hydrogen, halogen, —$OR^{10}$, —$SR^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, ═O, ═S, ═N($R^{10}$), —CN, $C_{1-10}$ alkyl, $C_{2-10}$ alkenyl, and $C_{2-10}$ alkynyl; and $R^{24}$, and $R^{25}$ are independently selected from hydrogen, halogen, —$OR^{10}$, —$SR^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, ═O, ═S, ═N($R^{10}$), —CN, $C_{1-10}$ alkyl, $C_{2-10}$ alkenyl, and $C_{2-10}$ alkynyl; or $R^{24}$ and $R^{21}$ taken together form an optionally substituted saturated $C_{3-7}$ carbocycle.

In some embodiments, $R^1$ is $L^3$. In some embodiments, $R^2$ is $L^3$.

In some embodiments, $L^{12}$ is —C(O)N($R^{10}$)—. In some embodiments, $R^{10}$ of —C(O)N($R^{10}$)— is selected from hydrogen, $C_{1-6}$ alkyl, and $L^3$. For example, $L^{12}$ may be —C(O)NH—.

In some embodiments, $R^8$ is an optionally substituted 5- or 6-membered heteroaryl. $R^8$ may be an optionally substituted 5- or 6-membered heteroaryl, bound to $L^3$. In some embodiments, $R^8$ is an optionally substituted pyridine, bound to $L^3$.

In some embodiments, $L^{22}$ is selected from —C(O)—, and —C(O)N$R^{10}$—. In some embodiments, $L^{22}$ is —C(O)—. In some embodiments, $L^{22}$ is —C(O)N$R^{10}$—. $R^{10}$ of —C(O)N$R^{10}$— may be selected from hydrogen, $C_{1-6}$ alkyl, and -$L^3$. For example, $L^{22}$ may be —C(O)NH—.

In some embodiments, $R^4$ is selected from: —O$R^{10}$, and —N($R^{10}$)$_2$; and $C_{1-10}$ alkyl, $C_{2-10}$ alkenyl, $C_{2-10}$ alkynyl, $C_{3-12}$ carbocycle, 3- to 12-membered heterocycle, aryl, and heteroaryl, each of which is optionally substituted with one or more substituents independently selected from halogen, —O$R^{10}$, —S$R^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), —CN, $C_{1-10}$ alkyl, $C_{2-10}$ alkenyl, and $C_{2-10}$ alkynyl and each of which is further optionally bound to $L^3$. In some embodiments, $R^4$ is —N($R^{10}$)$_2$ and $R^{10}$ of —N($R^{10}$)$_2$ is selected from $L^3$ and hydrogen, and wherein at least one $R^{10}$ of —N($R^{10}$)$_2$ is $L^3$.

In some embodiments, the compound of Formula (IVB) is a compound of Formula (IVC):

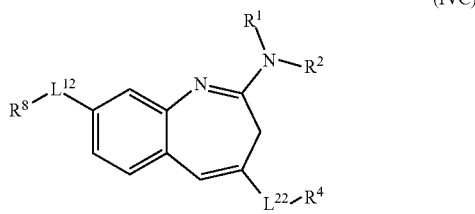

(IVC)

or a pharmaceutically acceptable salt thereof,
wherein:
$R^1$ and $R^2$ are hydrogen;
$L^{22}$ is —C(O)—;
$R^4$—N($R^{10}$)$_2$;
$R^{10}$ is independently selected at each occurrence from hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;
$L^{12}$ is —C(O)N($R^{10}$)—*, wherein * represents where $L^{12}$ is bound to $R^8$;
$R^8$ is an optionally substituted fused 5-5, fused 5-6, or fused 6-6 bicyclic heterocycle bound to linker moiety, $L^3$, and wherein optional substituents are independently selected at each occurrence from:
halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN;

$C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl.

In some embodiments: $R^{10}$ of —N($R^{10}$)$_2$ is independently selected at each occurrence from methyl, ethyl, propyl, and butyl, any one of which is optionally substituted. In some embodiments, $R^{10}$ of —C(O)N($R^{10}$)—* is hydrogen.

In some embodiments, the compound is further covalently bound to a linker, $L^3$. In some embodiments, $L^3$ is a noncleavable linker. In some embodiments, $L^3$ is a cleavable linker. $L^3$ may be cleavable by a lysosomal enzyme. In some embodiments, the compound is covalently attached to an antibody or antigen binding fragment thereof.

In some embodiments, $L^3$ is represented by the formula:

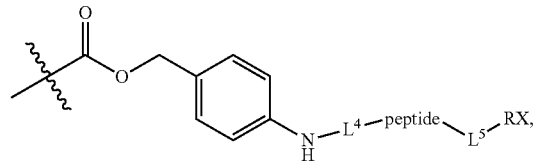

wherein:
$L^4$ represents the C-terminus of the peptide and $L^5$ is selected from a bond, alkylene and heteroalkylene, wherein $L^5$ is optionally substituted with one or more groups independently selected from $R^{32}$, and RX is a reactive moiety; and $R^{32}$ is independently selected at each occurrence from halogen, —OH, —CN, —O-alkyl, —SH, =O, =S, —NH$_2$, —NO$_2$; and $C_{1-10}$ alkyl, $C_{2-10}$ alkenyl, $C_{2-10}$ alkynyl, each of which is optionally substituted with one or more substituents independently selected from halogen, —OH, —CN, —O-alkyl, —SH, =O, =S, —NH$_2$, —NO$_2$.

In some embodiments, RX comprises a leaving group. In some embodiments, RX comprises a maleimide. In some embodiments, $L^3$ is further covalently bound to an antibody or antigen binding fragment thereof.

In some embodiments, $L^3$ is represented by the formula:

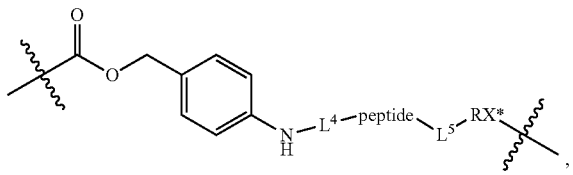

wherein
$L^4$ represents the C-terminal of the peptide and
$L^5$ is selected from a bond, alkylene and heteroalkylene, wherein $L^5$ is optionally substituted with one or more groups independently selected from $R^{32}$;

RX* comprises a bond, a succinimide moiety, or a hydrolyzed succinimide moiety bound to a residue of an antibody or antigen binding fragment thereof, wherein on RX* represents the point of attachment to the residue of the antibody or antigen binding fragment thereof; and, $R^{32}$ is independently selected at each occurrence from halogen, —OH, —CN, —O-alkyl, —SH, =O, =S, —NH$_2$, —NO$_2$; and C$_{1-10}$ alkyl, C$_{2-10}$ alkenyl, C$_{2-10}$ alkynyl, each of which is optionally substituted with one or more substituents independently selected from halogen, —OH, —CN, —O-alkyl, —SH, =O, =S, —NH$_2$, —NO$_2$. In some embodiments, the peptide of $L^3$ comprises Val-Cit or Val-Ala.

In some embodiments, the disclosure provides a compound or salt selected from:

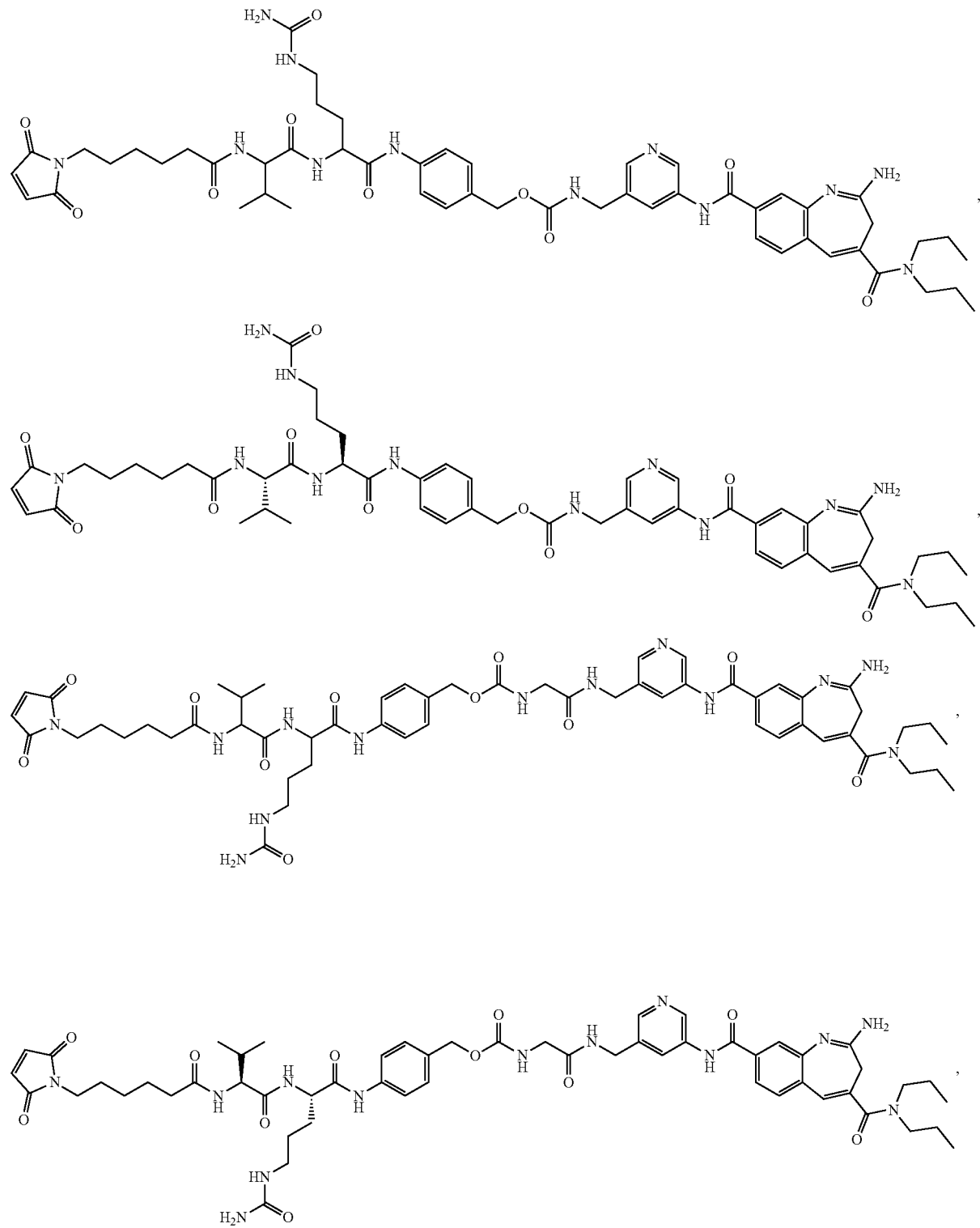

-continued
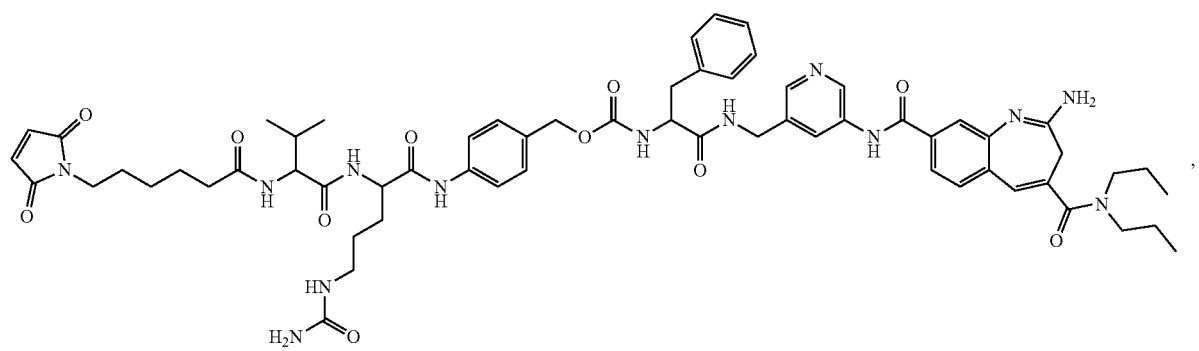
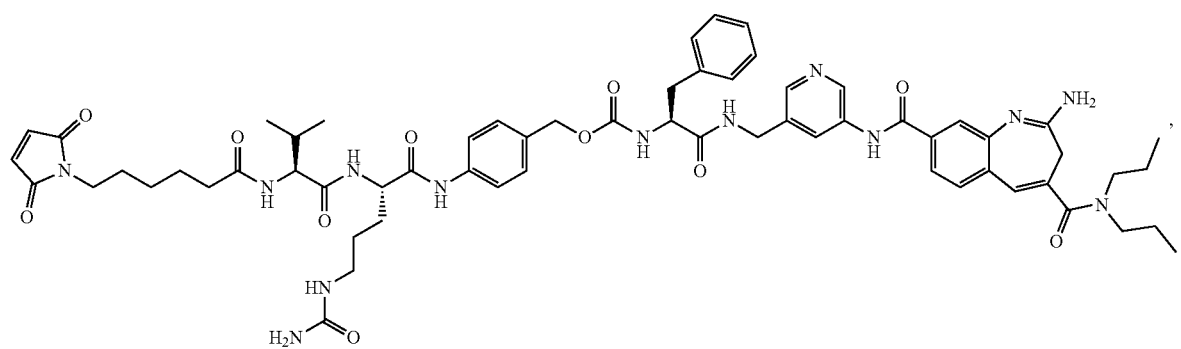
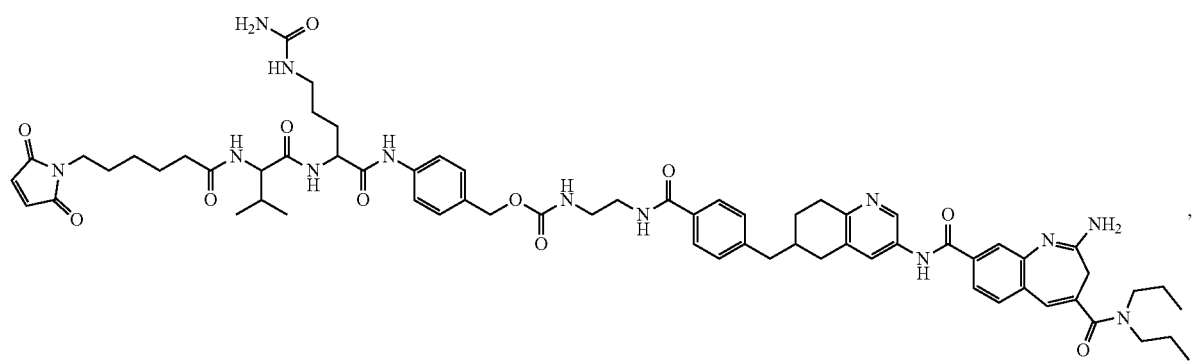
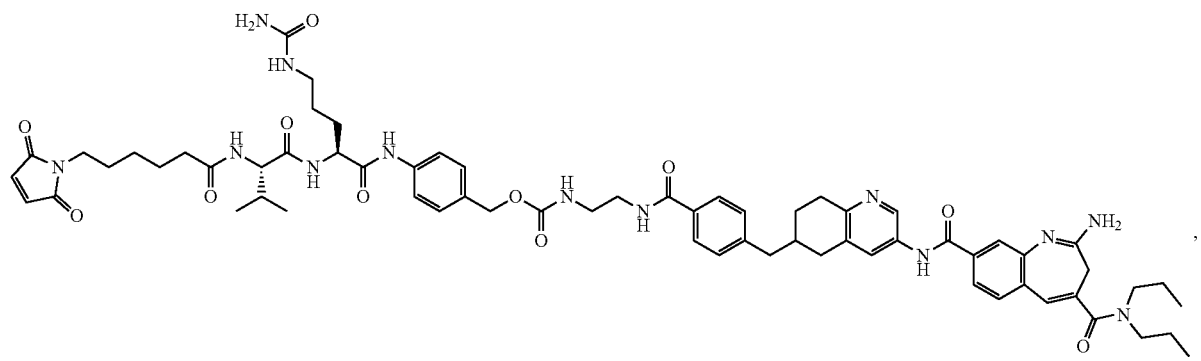

-continued
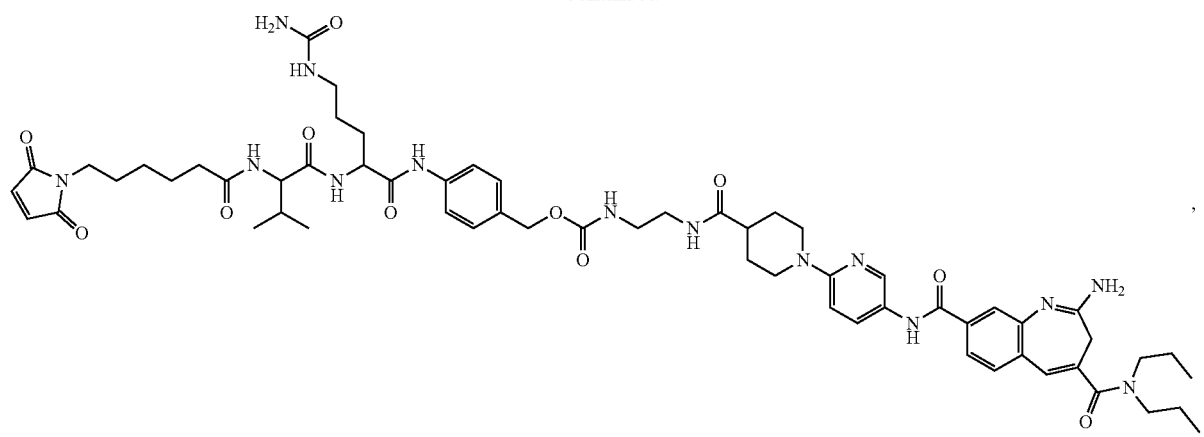
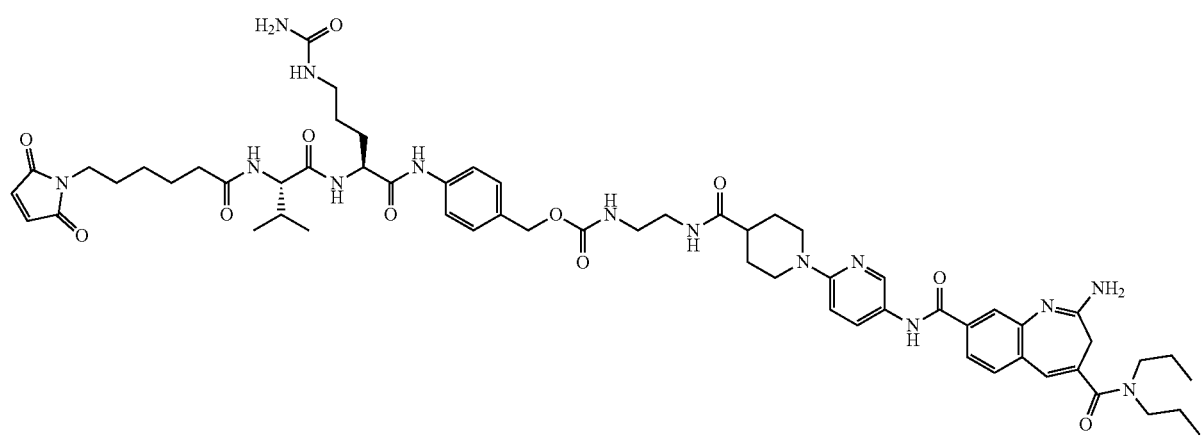
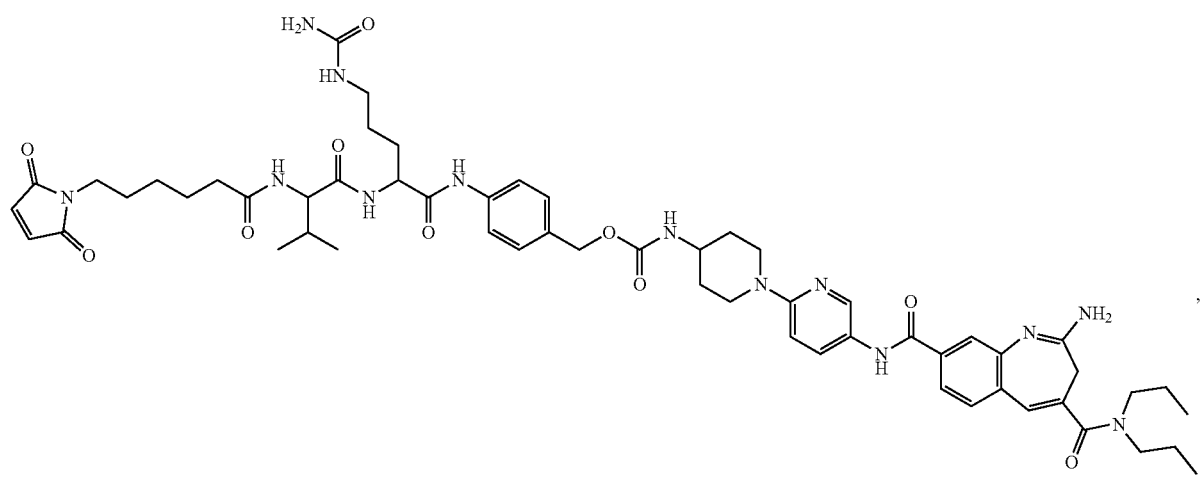

-continued
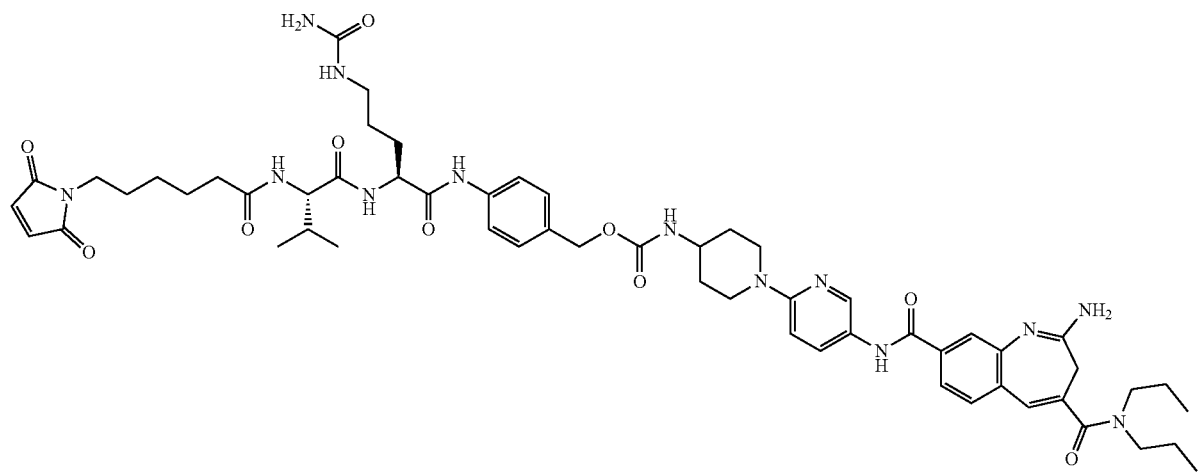
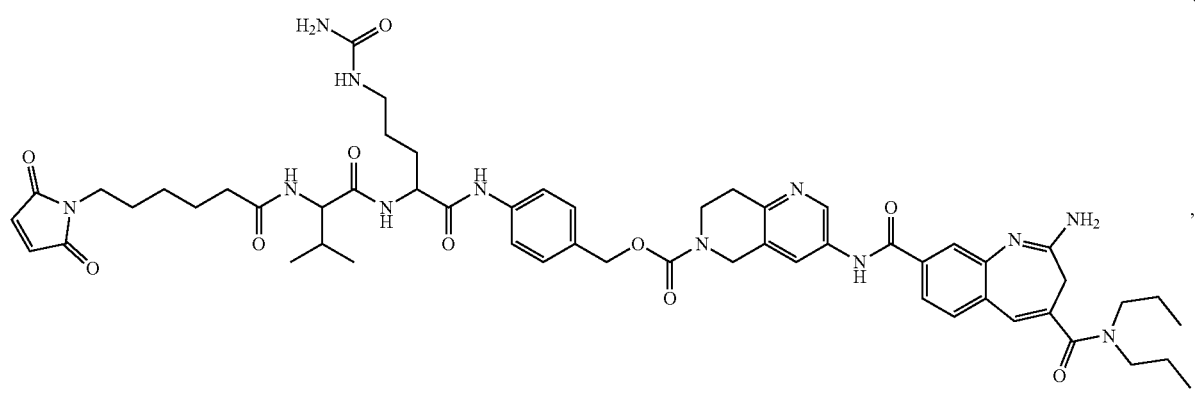
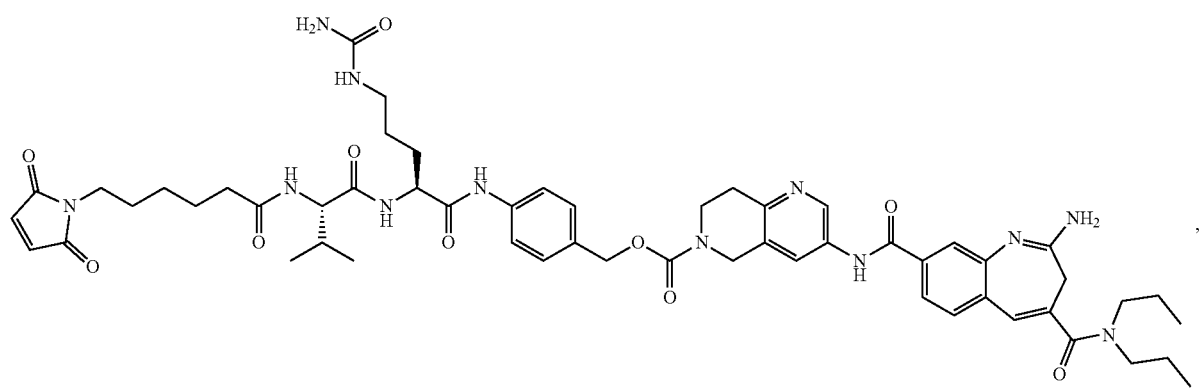
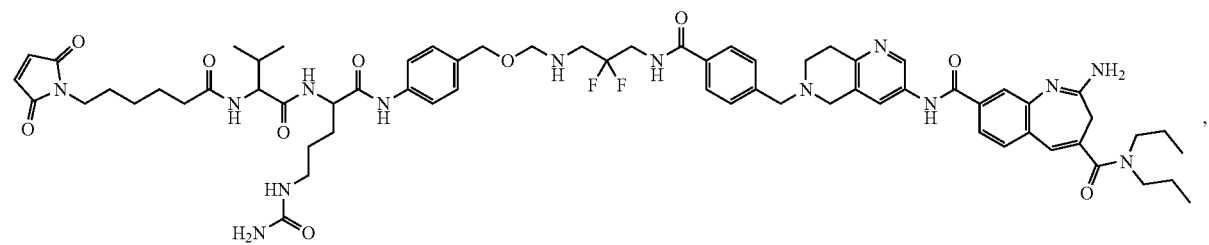

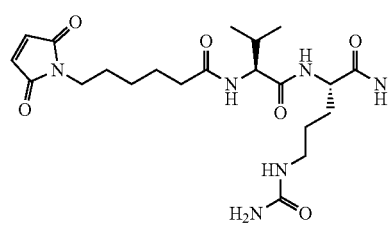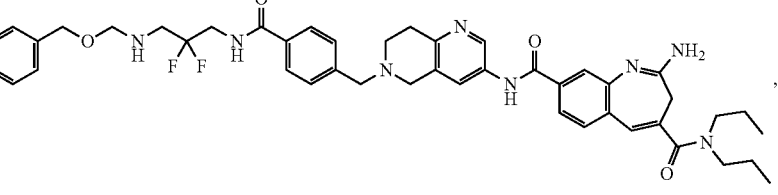
and a salt of any one thereof.
In some embodiments, the disclosure provides a compound or salt selected from:
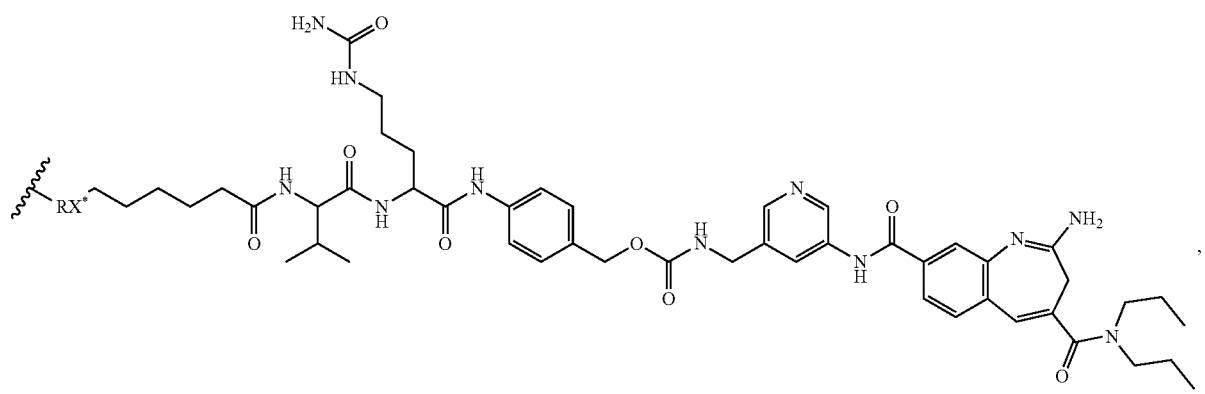
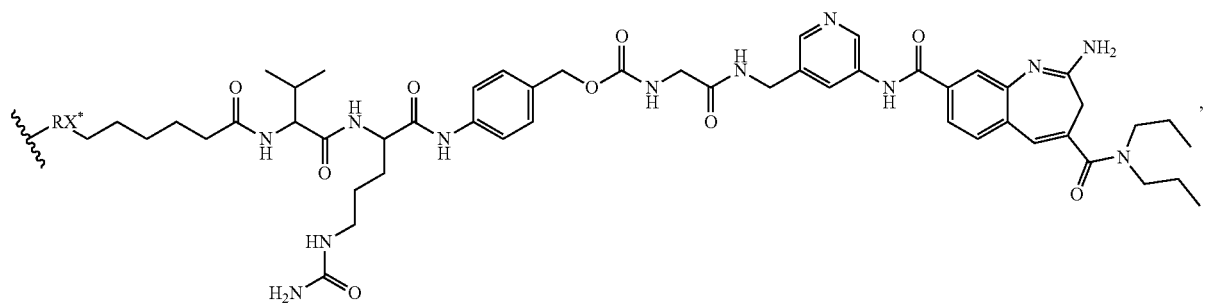

-continued
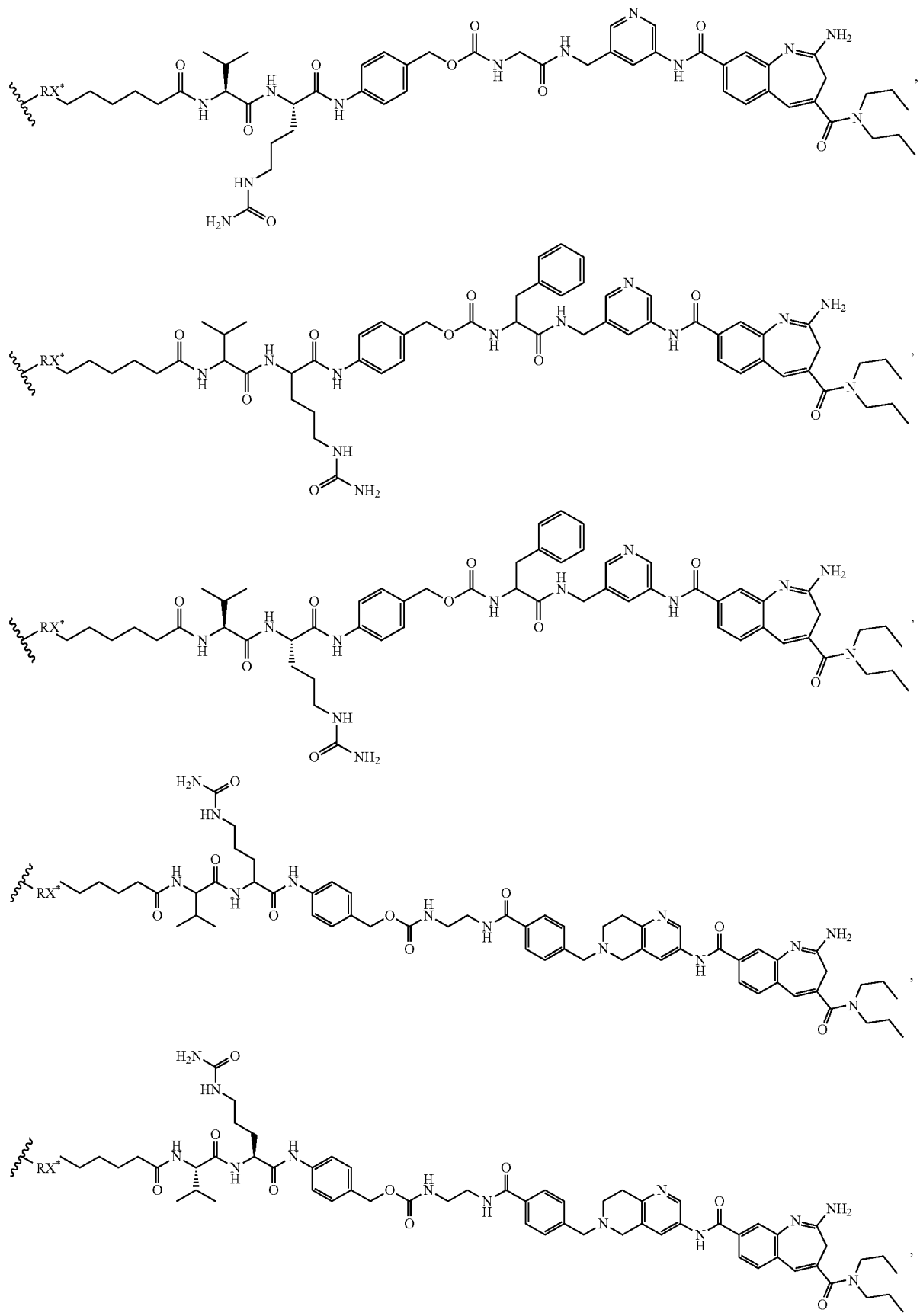

-continued
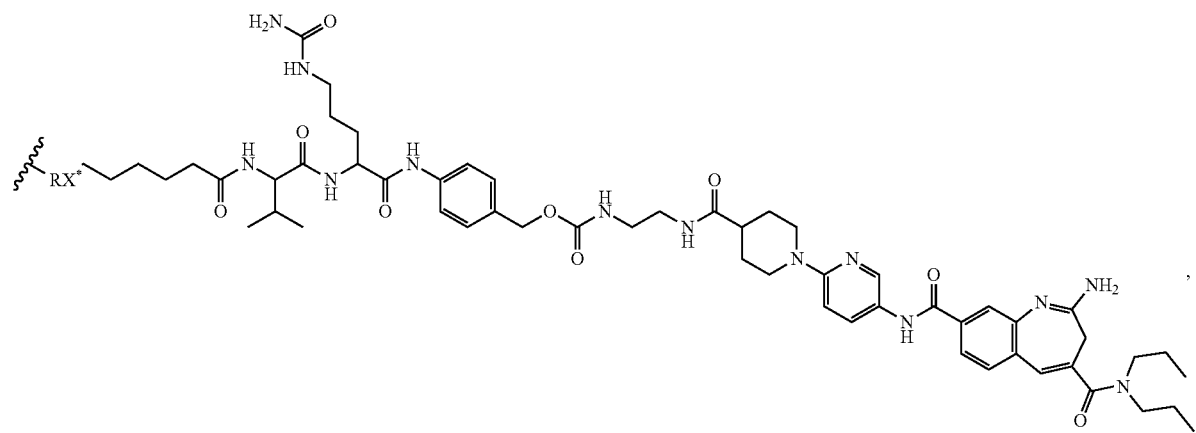
,
,
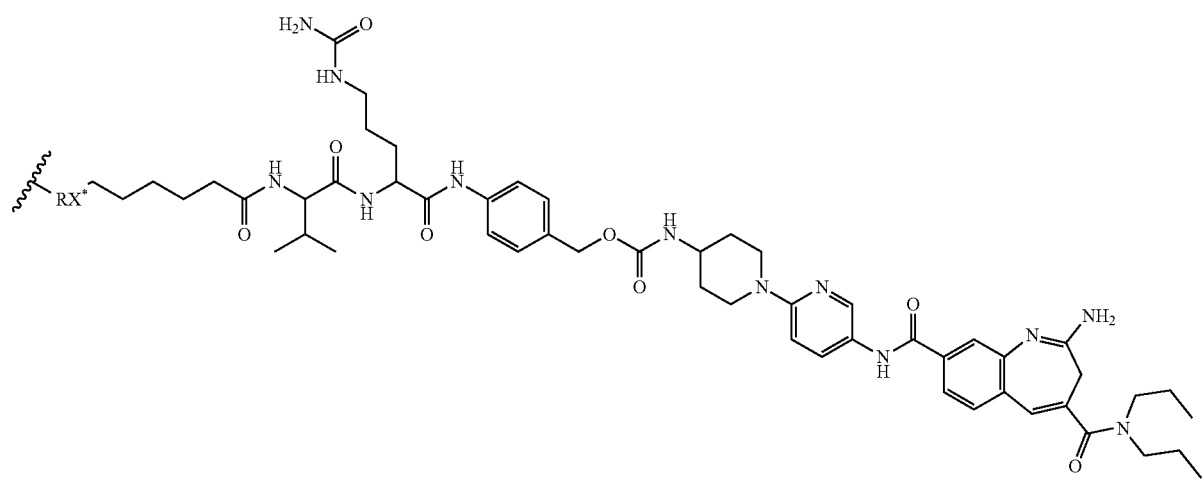
,

-continued
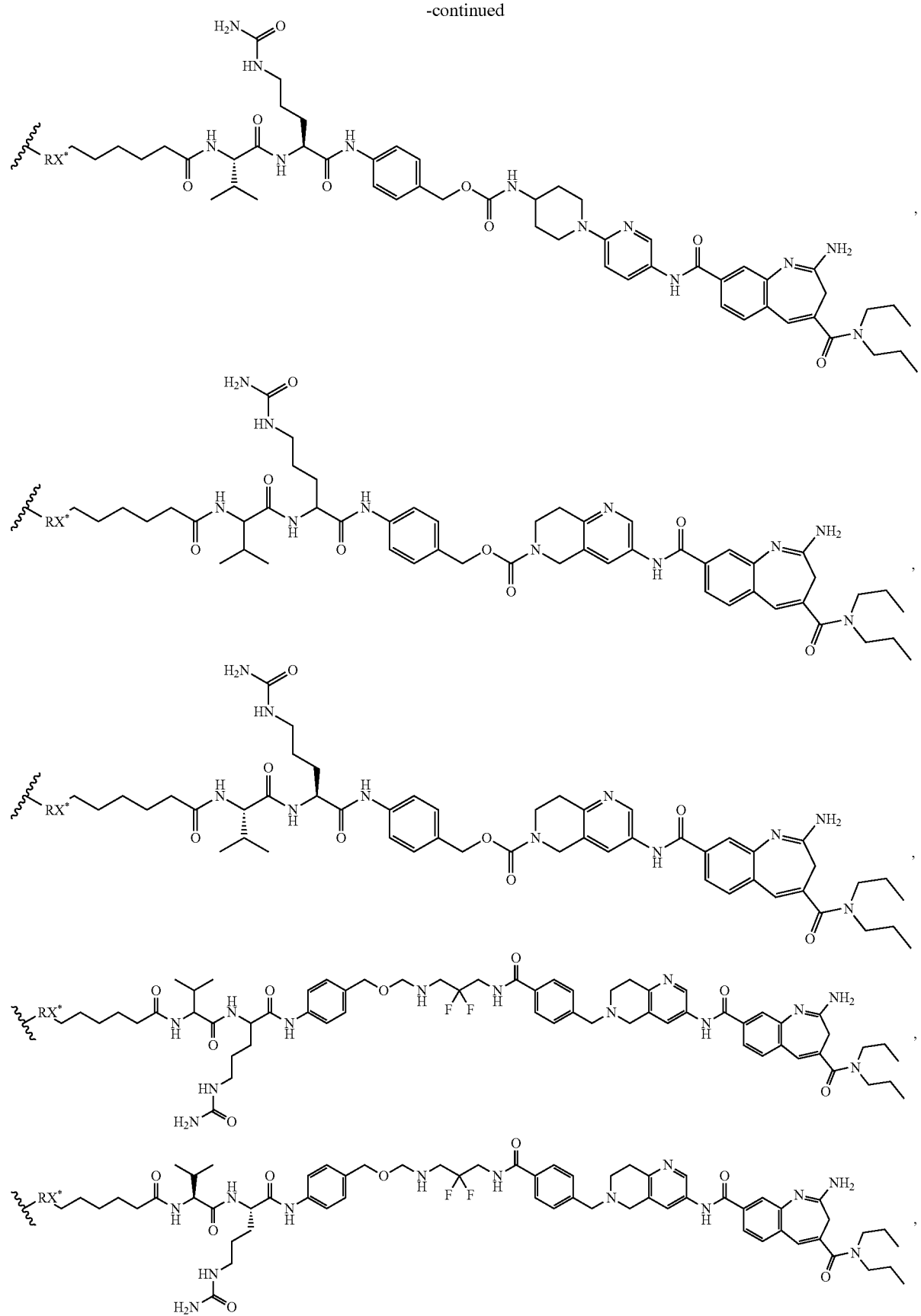

and a salt of any one thereof, wherein the RX* is a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof.

In some embodiments, $L^3$ is represented by the formula:

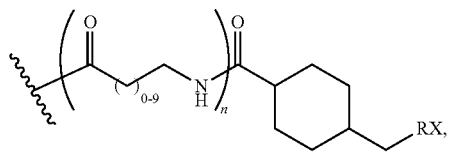

wherein RX comprises a reactive moiety, and n=0-9. In some embodiments, RX comprises a leaving group. In some embodiments, RX comprises a maleimide. In some embodiments, $L^3$ is represented as follows:

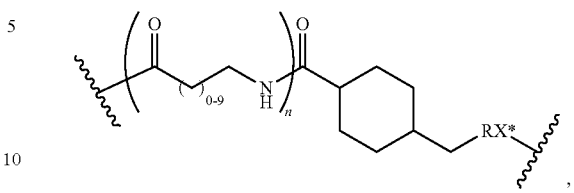

wherein RX* comprises a bond, a succinimide moiety, or a hydrolyzed succinimide moiety bound to a residue of an antibody or antigen binding fragment, wherein

on RX* represents the point of attachment to the residue of the antibody or antigen binding fragment thereof, and n=0-9.

In some embodiments, the disclosure provides a compound or salt selected from:

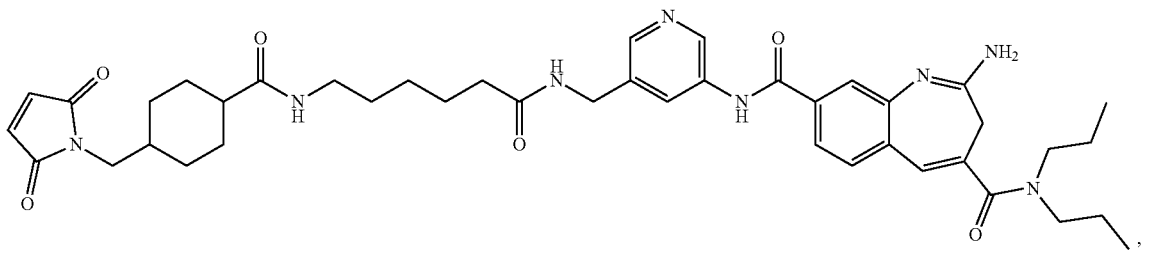

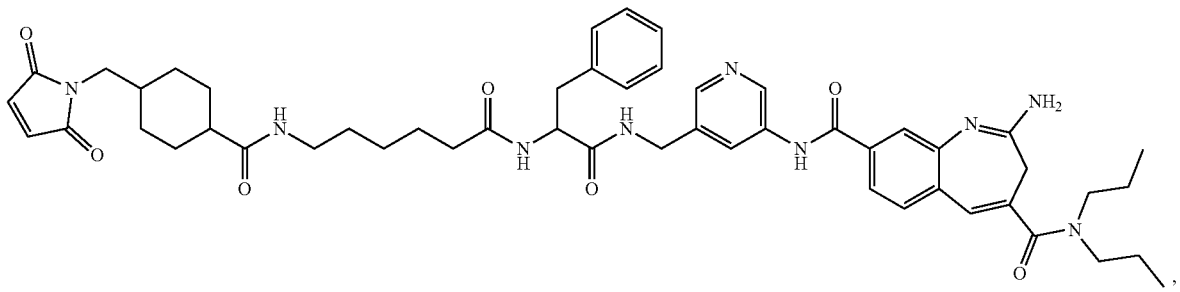

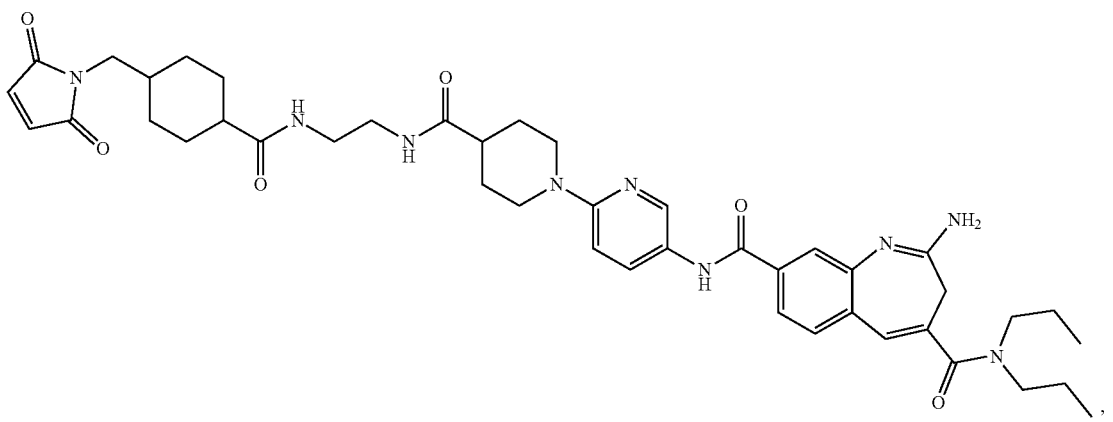

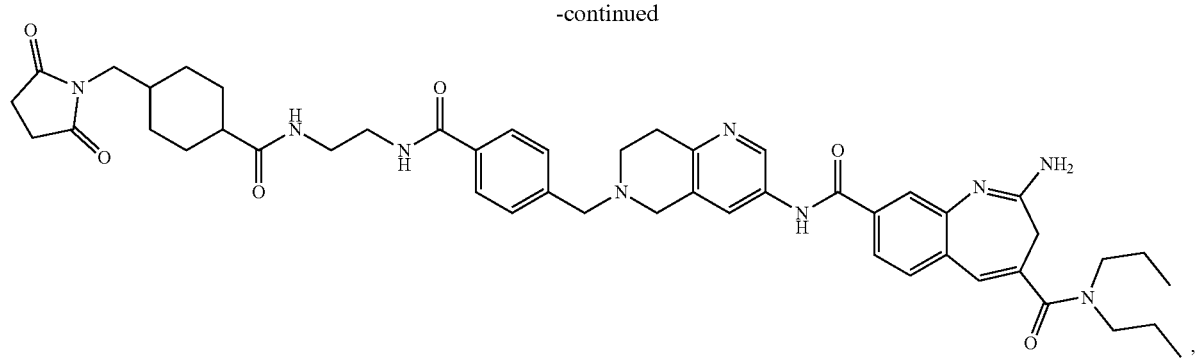
and a salt of any one thereof.
In some embodiments, the disclosure provides a compound or salt selected from:
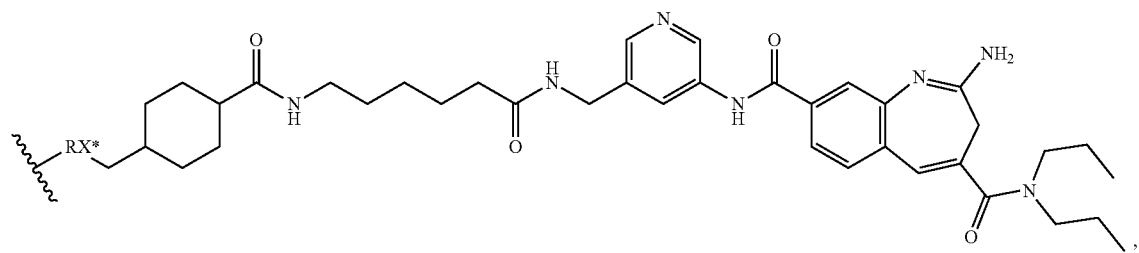
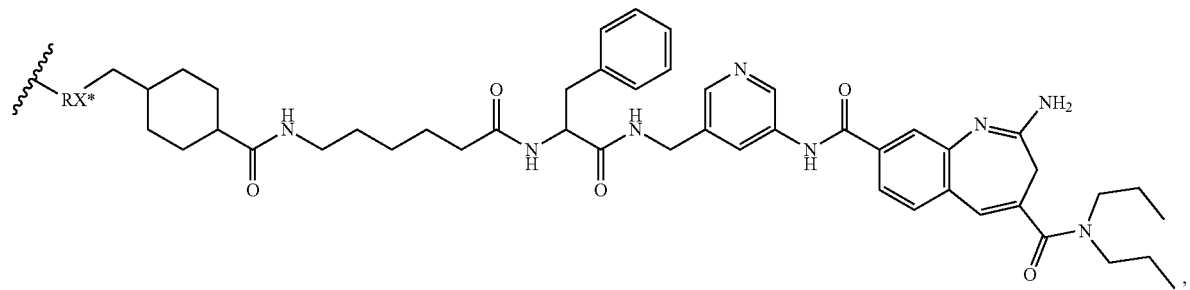
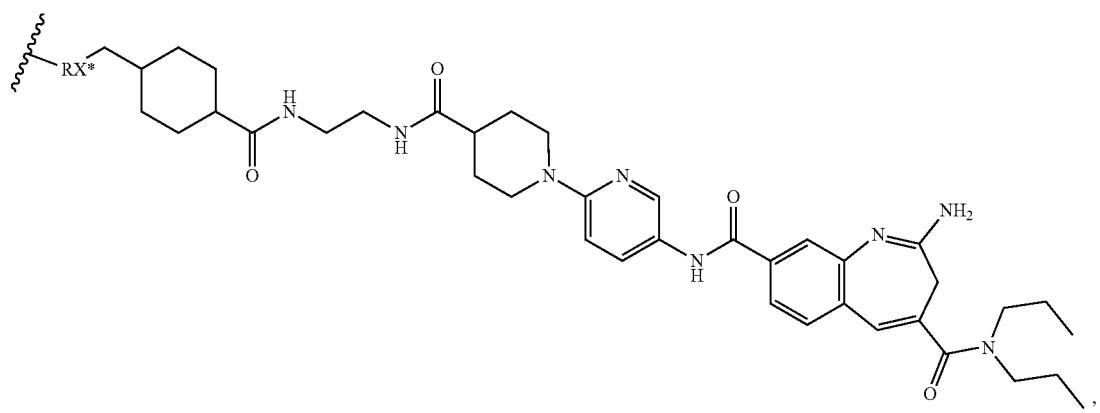

-continued

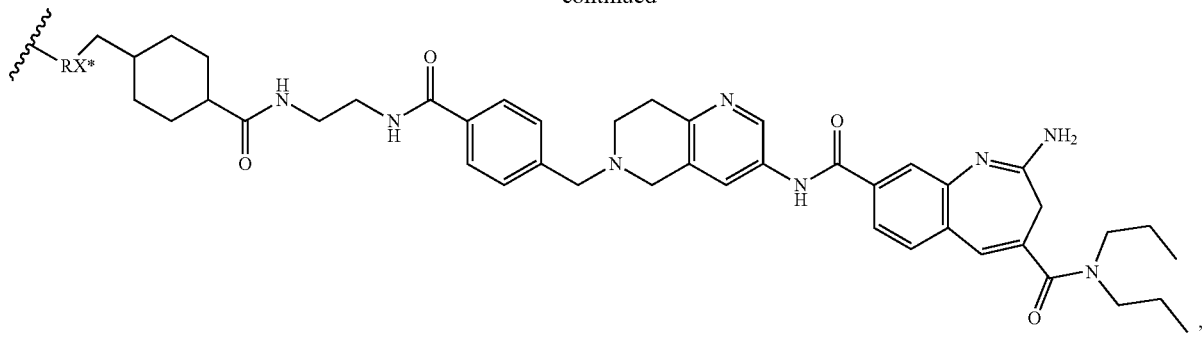

and a salt of any one thereof, wherein the RX* comprises a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof.

In some embodiments, RX* comprises a succinamide moiety and is bound to a cysteine residue of an antibody or antigen binding fragment thereof. In some embodiments, RX* comprises a hydrolyzed succinamide moiety and is bound to a cysteine residue of an antibody or antigen binding fragment thereof.

In some embodiments, the disclosure provides a conjugate represented by the formula: $(D-L^3)_{1-8}$, wherein Antibody is an anti-ASGR1 antibody or antigen binding fragment thereof of the disclosure, D is a Category A compound or salt of the disclosure, and $L^3$ is a linker moiety.

In some embodiments, the disclosure provides a conjugate represented by the formula:

$$(D-L^3)_{1-8}\text{—Antibody,}$$

wherein Antibody is an anti-ASGR1 antibody or antigen binding fragment thereof of the disclosure, and $D-L^3$ is a Category A compound or salt of the disclosure.

In some embodiments, the disclosure provides a pharmaceutical composition, comprising the conjugate of the disclosure and at least one pharmaceutically acceptable excipient.

In some embodiments, the average DAR of the conjugate is from about 2 to about 8, or about 1 to about 3, or about 3 to about 5.

Examples of TLR8 agonist compounds according to Category A are provided in Table 1a and their stereoisomers. It is understood that a compound is provided in Table 1a, salts of that compound are envisioned by Table 1a.

TABLE 1a

Compounds 1.1-1.69

| Compound | Structure and IUPAC |
|---|---|
| 1.1 | 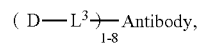<br>2-amino-N4,N4-dipropyl-N8-(1,2,3,4-tetrahydroquinolin-7-yl)-3H-benzo[b]azepine-4,8-dicarboxamide |
| 1.2 | <br>N⁸-(3-acetylphenyl)-2-amino-N⁴,N⁴-dipropyl-3H-benzo[b]azepine-4,8-dicarboxamide |

TABLE 1a-continued

Compounds 1.1-1.69

| Compound | Structure and IUPAC |
|---|---|
| 1.3 | 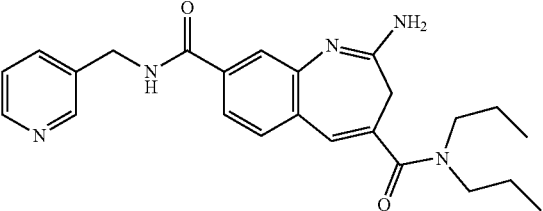
2-amino-$N^4,N^4$-dipropyl-$N^8$-(pyridin-3-ylmethyl)-3H-benzo[b]azepine-4,8-dicarboxamide |
| 1.4 | 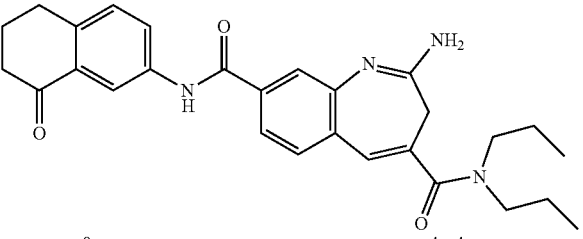
2-amino-$N^8$-(8-oxo-5,6,7,8-tetrahydronaphthalen-2-yl)-$N^4,N^4$-dipropyl-3H-benzo[b]azepine-4,8-dicarboxamide |
| 1.5 | 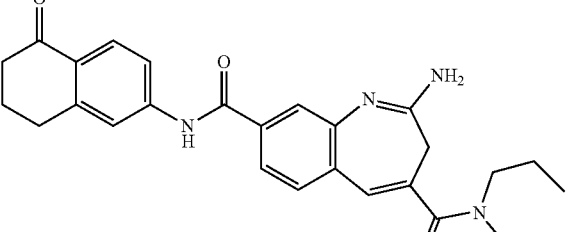
2-amino-$N^8$-(5-oxo-5,6,7,8-tetrahydronaphthalen-2-yl)-$N^4,N^4$-dipropyl-3H-benzo[b]azepine-4,8-dicarboxamide |
| 1.6 | 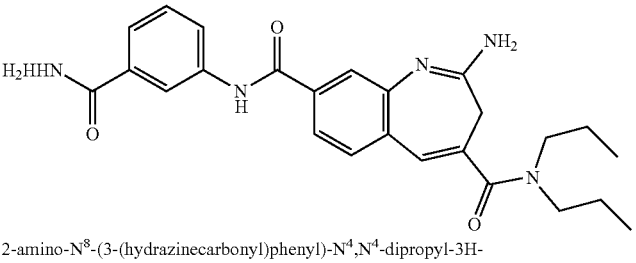
2-amino-$N^8$-(3-(hydrazinecarbonyl)phenyl)-$N^4,N^4$-dipropyl-3H-benzo[b]azepine-4,8-dicarboxamide |
| 1.7 | 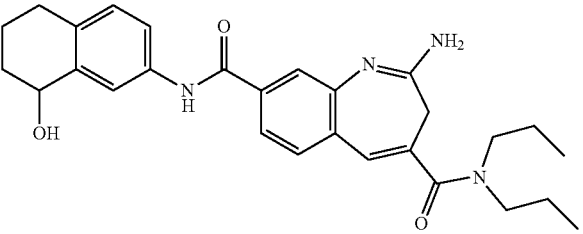
2-amino-$N^8$-(8-hydroxy-5,6,7,8-tetrahydronaphthalen-2-yl)-N4,N4-dipropyl-3H-benzo[b]azepine-4,8-dicarboxamide |

TABLE 1a-continued

Compounds 1.1-1.69

| Compound | Structure and IUPAC |
|---|---|
| 1.8 | 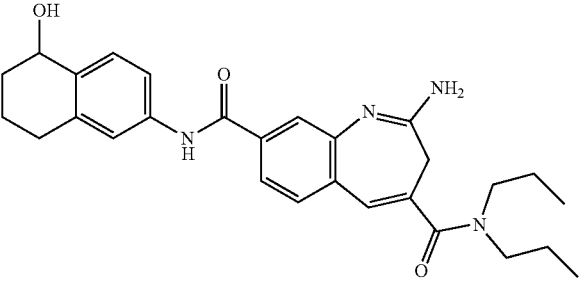
2-amino-N$^8$-(5-hydroxy-5,6,7,8-tetrahydronaphthalen-2-yl)-N$^4$,N$^4$-dipropyl-3H-benzo[b]azepine-4,8-dicarboxamide |
| 1.9 | 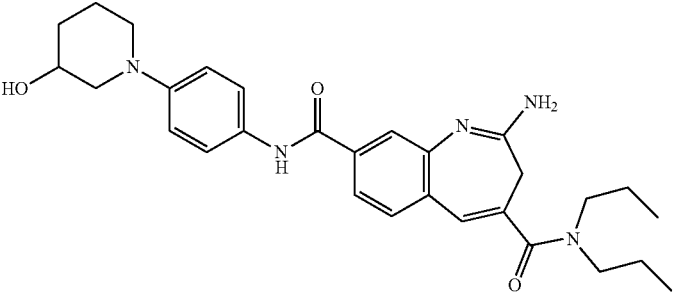
2-amino-N$^8$-(4-(3-hydroxypiperidin-1-yl)phenyl)-N$^4$,N$^4$-dipropyl-3H-benzo[b]azepine-4,8-dicarboxamide |
| 1.10 | 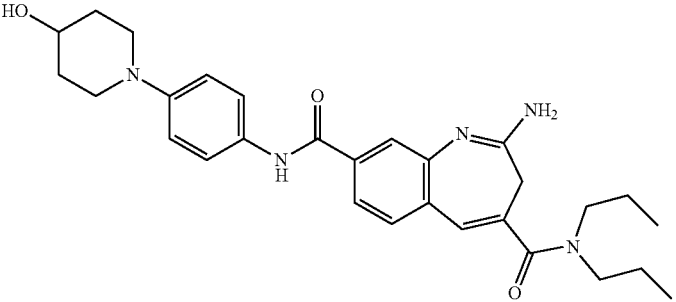
2-amino-N$^8$-(4-(4-hydroxypiperidin-1-yl)phenyl)-N$^4$,N$^4$-dipropyl-3H-benzo[b]azepine-4,8-dicarboxamide |
| 1.11 | 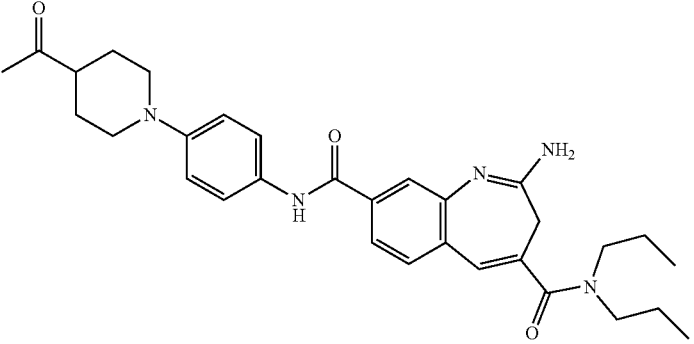
N$^8$-(4-(4-acetylpiperidin-1-yl)phenyl)-2-amino-N$^4$,N$^4$-dipropyl-3H-benzo[b]azepine-4,8-dicarboxamide |

TABLE 1a-continued

Compounds 1.1-1.69

| Compound | Structure and IUPAC |
|---|---|
| 1.12 | 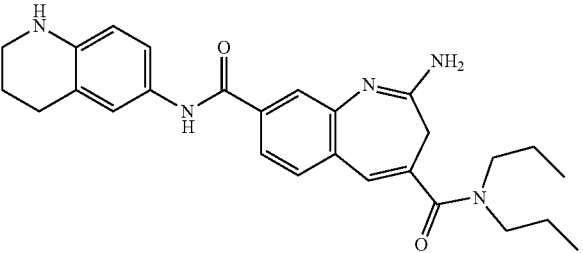
2-amino-$N^4,N^4$-dipropyl-$N^8$-(1,2,3,4-tetrahydroquinolin-6-yl)-3H-benzo[b]azepine-4,8-dicarboxamide |
| 1.13 | 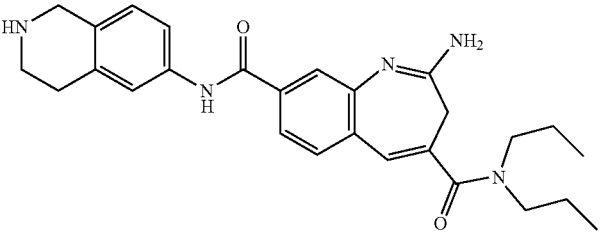
2-amino-$N^4,N^4$-dipropyl-$N^8$-(1,2,3,4-tetrahydroisoquinolin-6-yl)-3H-benzo[b]azepine-4,8-dicarboxamide |
| 1.14 | 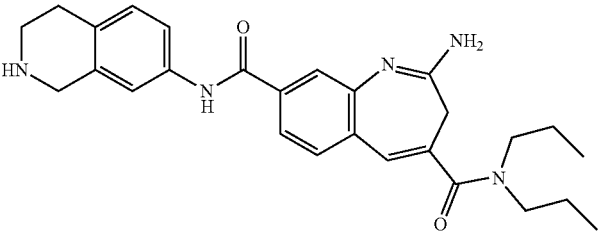
2-amino-$N^4,N^4$-dipropyl-$N^8$-(1,2,3,4-tetrahydro-isoquinolin-7-yl)-3H-benzo[b]azepine-4,8-dicarboxamide trifluoroacetate salt |
| 1.15 | 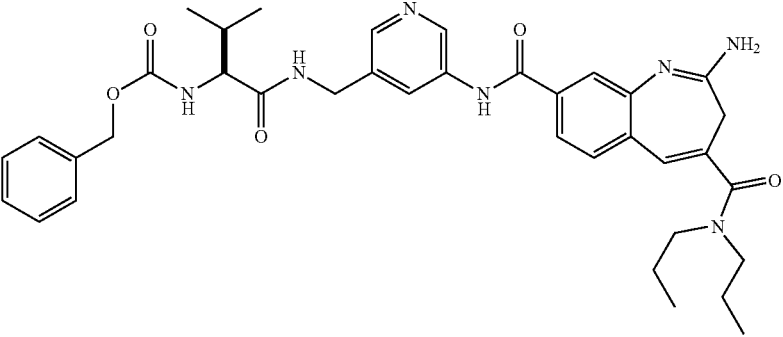
benzyl (S)-(1-(((5-(2-amino-4-(dipropyl-carbamoyl)-3H-benzo[b]azepine-8-carboxamido)pyridin-3-yl)methyl)amino)-3-methyl-1-oxobutan-2-yl)carbamate |

TABLE 1a-continued

Compounds 1.1-1.69

| Compound | Structure and IUPAC |
|---|---|
| 1.16 | 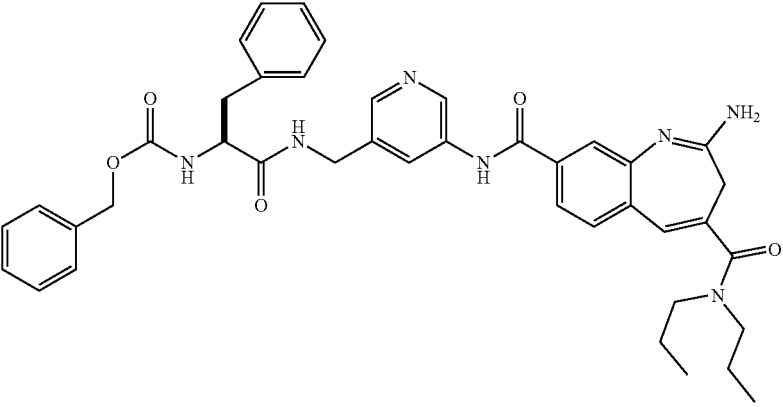 [SMILES: CCCN(CCC)C(=O)C1=Cc2ccc(C(=O)Nc3cncc(CNC(=O)[C@H](Cc4ccccc4)NC(=O)OCc4ccccc4)c3)cc2N=C(N)C1] benzyl (S)-(1-(((5-(2-amino-4-(dipropyl-carbamoyl)-3H-benzo[b]azepine-8-carboxamido)pyridin-3-yl)methyl)amino)-1-oxo-3-phenylpropan-2-yl)carbamate |
| 1.17 | 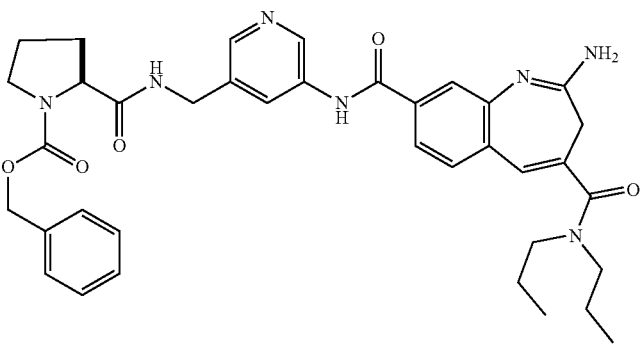 [SMILES: CCCN(CCC)C(=O)C1=Cc2ccc(C(=O)Nc3cncc(CNC(=O)[C@@H]4CCCN4C(=O)OCc4ccccc4)c3)cc2N=C(N)C1] benzyl (S)-2-(((5-(2-amino-4-(dipropyl-carbamoyl)-3H-benzo[b]azepine-8-carboxamido)pyridin-3-yl)methyl)carbamoyl)pyrrolidine-1-carboxylate |
| 1.18 | 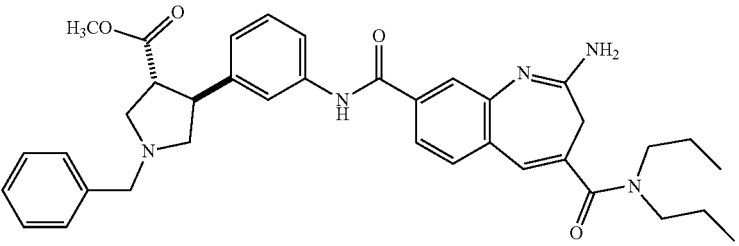 methyl (3R,4S)-4-(3-(2-amino-4-(dipropylcarbamoyl)-3H-benzo[b]azepine-8-carboxamido)phenyl)-1-benzylpyrrolidine-3-carboxylate |

TABLE 1a-continued

Compounds 1.1-1.69

| Compound | Structure and IUPAC |
|---|---|
| 1.19 | 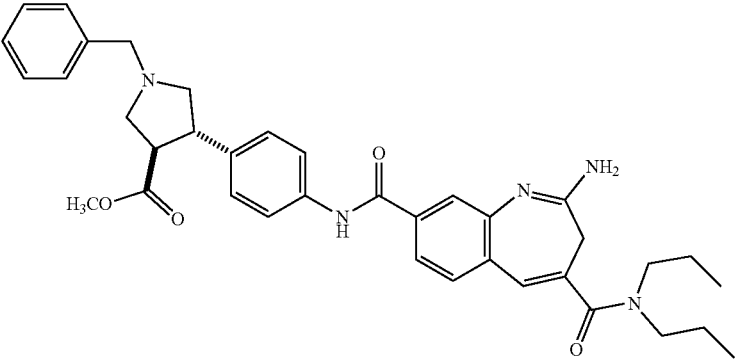<br>methyl (3R,4S)-4-(4-(2-amino-4-(dipropyl-carbamoyl)-3H-benzo[b]azepine-8-carboxamido)phenyl)-1-benzylpyrrolidine-3-carboxylate |
| 1.20 | 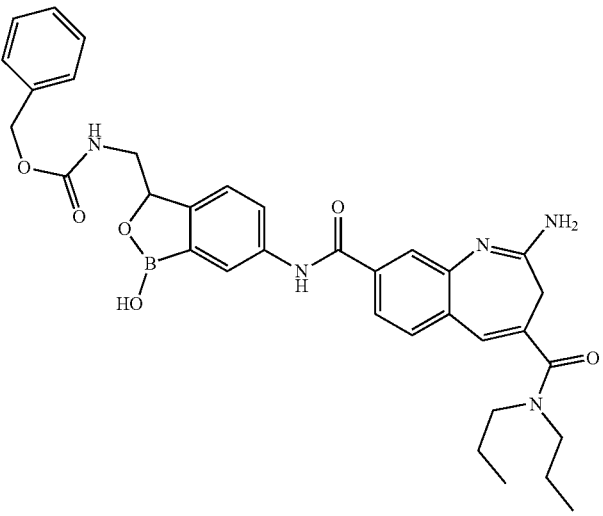 [SMILES: CCCN(CCC)C(=O)C1=Cc2ccc(C(=O)Nc3ccc4c(c3)B(O)OC4CNC(=O)OCc3ccccc3)cc2N=C(N)C1]<br>benzyl ((6-(2-amino-4-(dipropylcarbamoyl)-3H-benzo[b]azepine-8-carboxamido)-1-hydroxy-1,3-dihydrobenzo[c][1,2]oxaborol-3-yl)methyl)carbamate |
| 1.21 | 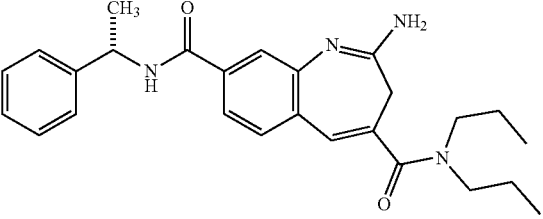 [SMILES: CCCN(CCC)C(=O)C1=Cc2ccc(C(=O)N[C@@H](C)c3ccccc3)cc2N=C(N)C1]<br>(S)-2-amino-$N^8$-(1-phenylethyl)-$N^4$,$N^4$-dipropyl-3H-benzo[b]azepine-4,8-dicarboxamide |
| 1.22 | 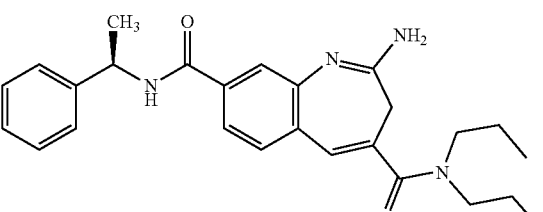<br>(R)-2-amino-$N^8$-(1-phenylethyl)-$N^4$,$N^4$-dipropyl-3H-benzo[b]azepine-4,8-dicarboxamide |

TABLE 1a-continued

Compounds 1.1-1.69

| Compound | Structure and IUPAC |
|---|---|

1.23

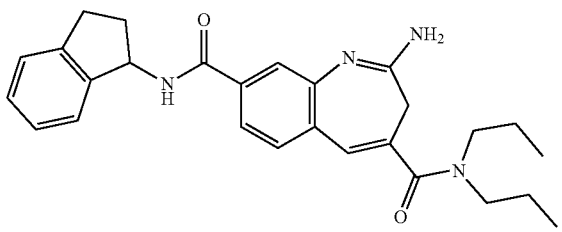 [SMILES: CCCN(CCC)C(=O)C1=Cc2ccc(C(=O)NC3CCc4ccccc43)cc2N=C(N)C1]

2-amino-$N^8$-(2,3-dihydro-1H-inden-1-yl)-$N^4,N^4$-dipropyl-3H-benzo[b]azepine-4,8-dicarboxamide 1.24

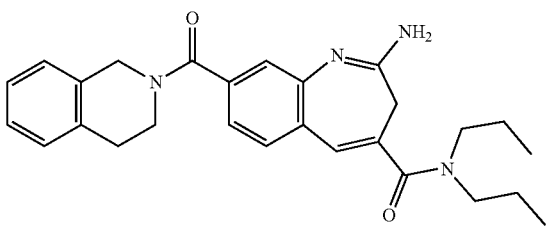 [SMILES: CCCN(CCC)C(=O)C1=Cc2ccc(C(=O)N3CCc4ccccc4C3)cc2N=C(N)C1]

2-amino-N,N-dipropyl-8-(1,2,3,4-tetrahydroisoquinoline-2-carbonyl)-3H-benzo[b]azepine-4-carboxamide 1.25

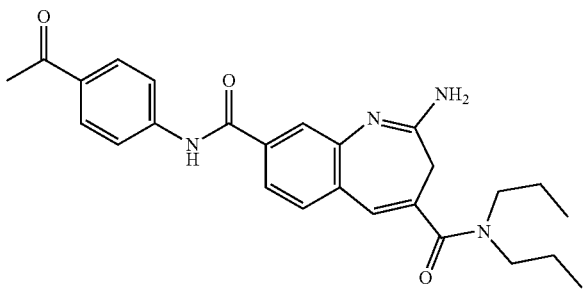 [SMILES: CCCN(CCC)C(=O)C1=Cc2ccc(C(=O)Nc3ccc(C(C)=O)cc3)cc2N=C(N)C1]

$N^8$-(4-acetylphenyl)-2-amino-$N^4,N^4$-dipropyl-3H-benzo[b]azepine-4,8-dicarboxamide 1.26

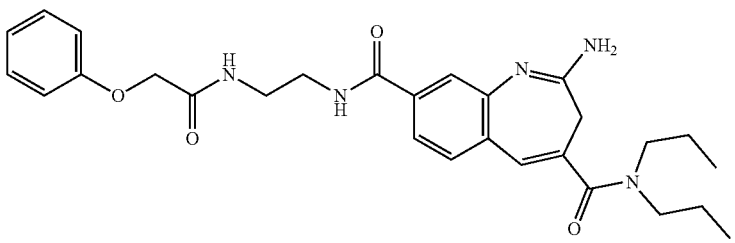 [SMILES: CCCN(CCC)C(=O)C1=Cc2ccc(C(=O)NCCNC(=O)COc3ccccc3)cc2N=C(N)C1]

benzyl (2-(2-amino-4-(dipropylcarbamoyl)-3H-benzo[b]azepine-8-carboxamido)ethyl)carbamate TABLE 1a-continued
Compounds 1.1-1.69
| Compound | Structure and IUPAC |
|---|---|
| 1.27 | 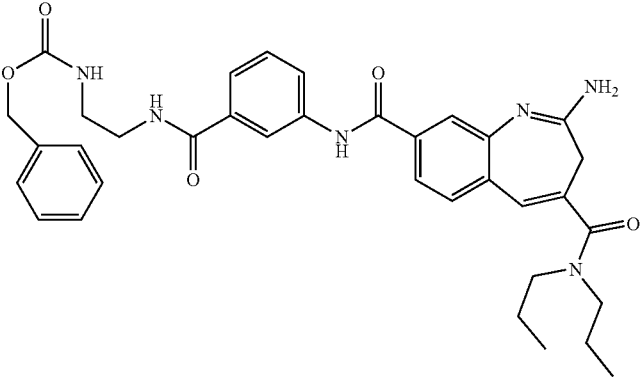 [SMILES: CCCN(CCC)C(=O)C1=Cc2ccc(C(=O)Nc3cccc(C(=O)NCCNC(=O)OCc4ccccc4)c3)cc2N=C(N)C1] benzyl (2-(3-(2-amino-4-(dipropylcarbamoyl)-3H-benzo[b]azepine-8-carboxamido)benzamido)ethyl)carbamate |
| 1.28 | 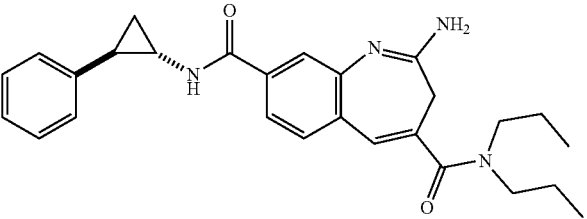 2-amino-$N^8$-((1S,2R)-2-phenylcyclopropyl)-$N^4$,$N^4$-dipropyl-3H-benzo[b]azepine-4,8-dicarboxamide |
| 1.29 | 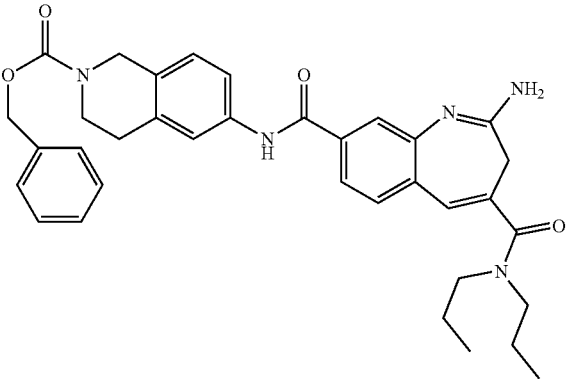 [SMILES: CCCN(CCC)C(=O)C1=Cc2ccc(C(=O)Nc3ccc4c(c3)CCN(C(=O)OCc3ccccc3)C4)cc2N=C(N)C1] benzyl 6-(2-amino-4-(dipropylcarbamoyl)-3H-benzo[b]azepine-8-carboxamido)-3,4-dihydroisoquinoline-2(1H)-carboxylate |

TABLE 1a-continued

Compounds 1.1-1.69

| Compound | Structure and IUPAC |
|---|---|
| 1.30 | 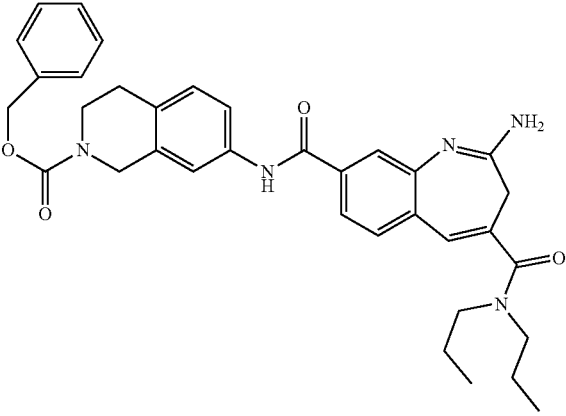 [SMILES: CCCN(CCC)C(=O)C1=Cc2ccc(C(=O)Nc3ccc4c(c3)CN(C(=O)OCc3ccccc3)CC4)cc2N=C(N)C1]<br>benzyl 7-(2-amino-4-(dipropylcarbamoyl)-3H-benzo[b]azepine-8-carboxamido)-3,4-dihydroisoquinoline-2(1H)-carboxylate |
| 1.31 | 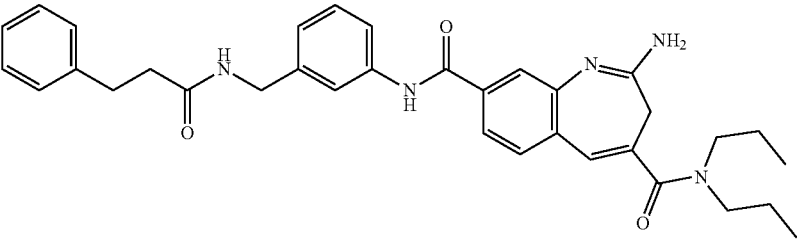 [SMILES: CCCN(CCC)C(=O)C1=Cc2ccc(C(=O)Nc3cccc(CNC(=O)CCc4ccccc4)c3)cc2N=C(N)C1]<br>2-amino-$N^8$-(3-((3-phenylpropanamido)methyl)phenyl)-$N^4,N^4$-dipropyl-3H-benzo[b]azepine-4,8-dicarboxamide |
| 1.32 | 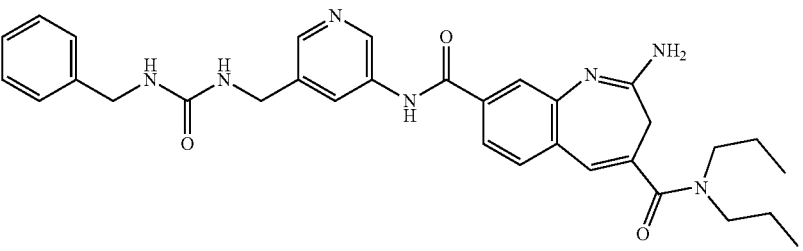 [SMILES: CCCN(CCC)C(=O)C1=Cc2ccc(C(=O)Nc3cncc(CNC(=O)NCc4ccccc4)c3)cc2N=C(N)C1]<br>2-amino-$N^8$-(5-((3-benzylureido)methyl)pyridin-3-yl)-$N^4,N^4$-dipropyl-3H-benzo[b]azepine-4,8-dicarboxamide |
| 1.33 | 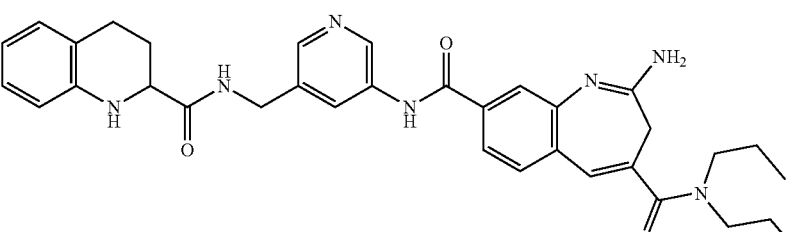<br>2-amino-$N^4,N^4$-dipropyl-$N^8$-(5-((1,2,3,4-tetrahydroquinoline-2-carboxamido)methyl)pyridin-3-yl)-3H-benzo[b]azepine-4,8-dicarboxamide |

TABLE 1a-continued

Compounds 1.1-1.69

| Compound | Structure and IUPAC |
|---|---|
| 1.34 | 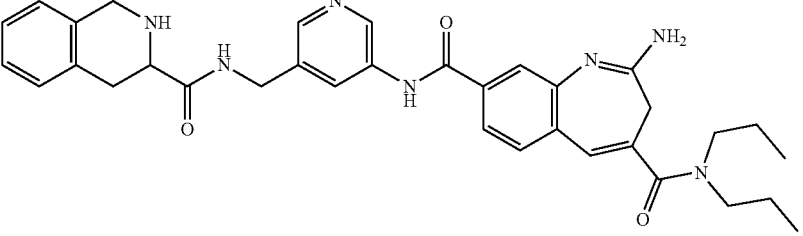<br>2-amino-$N^4$,$N^4$-dipropyl-$N^8$-(5-((1,2,3,4-tetrahydroisoquinoline-3-carboxamido)-methyl)pyridin-3-yl)-3H-benzo[b]azepine-4,8-dicarboxamide |
| 1.35 | 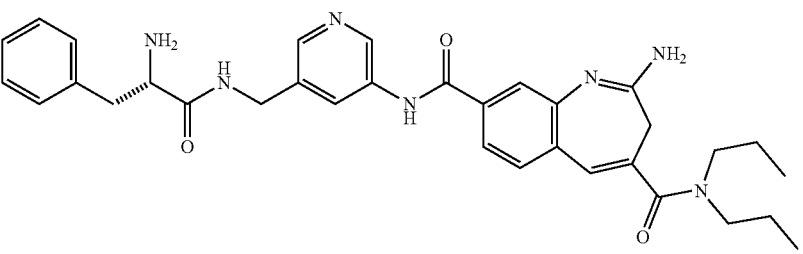 [SMILES: CCCN(CCC)C(=O)C1=Cc2ccc(C(=O)Nc3cncc(CNC(=O)[C@@H](N)Cc4ccccc4)c3)cc2N=C(N)C1]<br>(S)-2-amino-$N^8$-(5-((2-amino-3-phenylpropanamido)methyl)pyridin-3-yl)-$N^4$,$N^4$-dipropyl-3H-benzo[b]azepine-4,8-dicarboxamide |
| 1.36 | 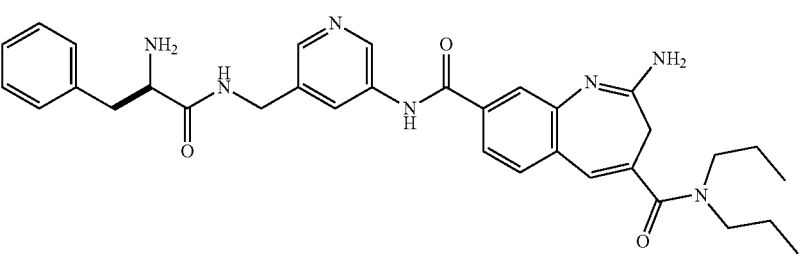 [SMILES: CCCN(CCC)C(=O)C1=Cc2ccc(C(=O)Nc3cncc(CNC(=O)[C@H](N)Cc4ccccc4)c3)cc2N=C(N)C1]<br>(R)-2-amino-$N^8$-(5-((2-amino-3-phenyl-propanamido)-methyl)pyridine-3-yl)-$N^4$,$N^4$-dipropyl-3H-benzo[b]azepine-4,8-dicarboxamide |
| 1.37 | 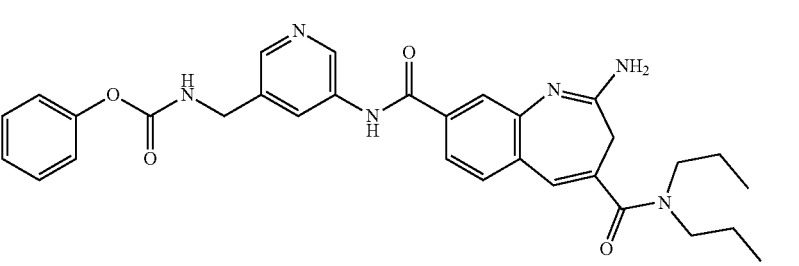 [SMILES: CCCN(CCC)C(=O)C1=Cc2ccc(C(=O)Nc3cncc(CNC(=O)Oc4ccccc4)c3)cc2N=C(N)C1]<br>Phenyl ((5-(2-amino-4-(dipropylcarbamoyl)-3H-benzo[b]azepine-8-carboxamido)pyridin-3-yl)methyl)carbamate |
| 1.38 | 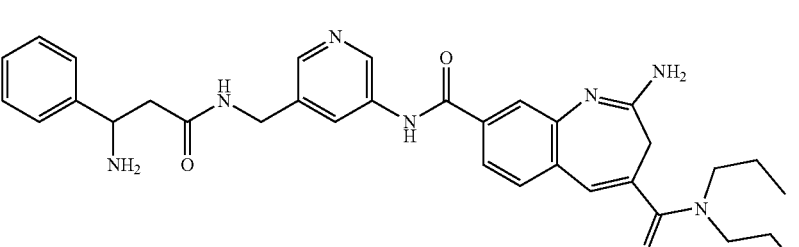<br>2-amino-$N^8$-(5-((3-amino-3-phenyl-propanamido)methyl)-pyridin-3-yl)-$N^4$,$N^4$-dipropyl-3H-benzo[b]azepine-4,8-dicarboxamide |

TABLE 1a-continued

Compounds 1.1-1.69

| Compound | Structure and IUPAC |
|---|---|
| 1.39 | 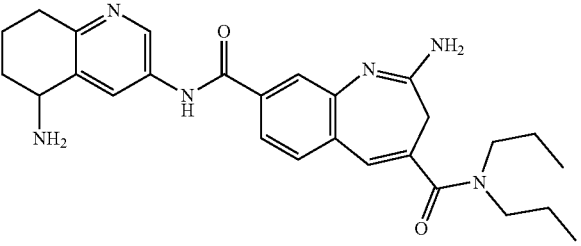 [SMILES: CCCN(CCC)C(=O)C1=Cc2ccc(C(=O)Nc3cnc4c(c3)C(N)CCC4)cc2N=C(N)C1]<br>2-amino-$N^8$-(5-amino-5,6,7,8-tetrahydro-quinolin-3-yl)-$N^4,N^4$-dipropyl-3H-benzo-[b]azepine-4,8-dicarboxamide |
| 1.40 | 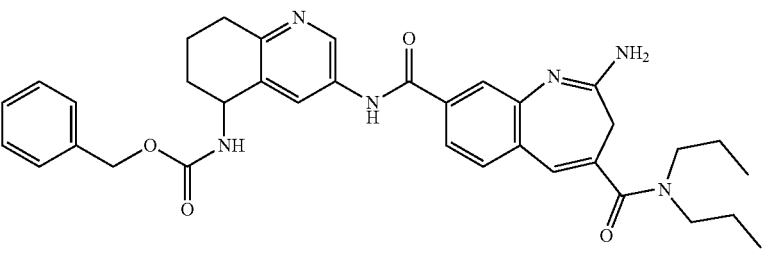 [SMILES: CCCN(CCC)C(=O)C1=Cc2ccc(C(=O)Nc3cnc4c(c3)C(NC(=O)OCc3ccccc3)CCC4)cc2N=C(N)C1]<br>Benzyl (3-(2-amino-4-(dipropylcarbamoyl)-3H-benzo[b]azepine-8-carboxamido)-5,6,7,8-tetrahydroquinolin-5-yl)carbamate |
| 1.41 | 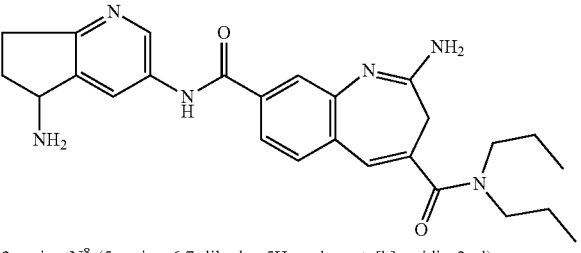<br>2-amino-$N^8$-(5-amino-6,7-dihydro-5H-cyclopenta[b]pyridin-3-yl)-$N^4,N^4$-dipropyl-3H-benzo[b]azepine-4,8-dicarboxamide |
| 1.42 | 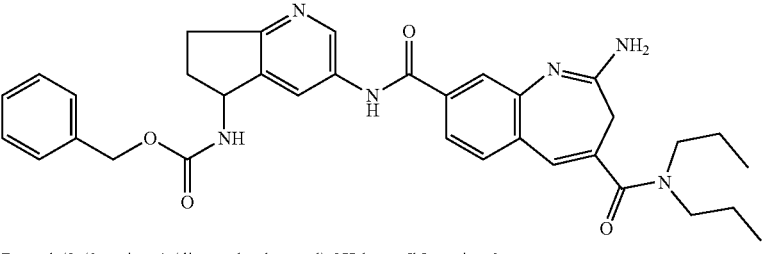<br>Benzyl (3-(2-amino-4-(dipropylcarbamoyl)-3H-benzo[b]azepine-8-carboxamido)-6,7-dihydro-5H-cyclopenta[b]pyridin-5-yl)carbamate |
| 1.43 | 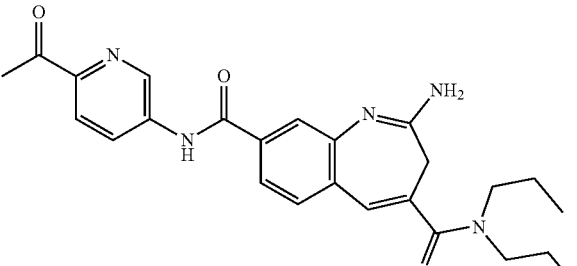<br>$N^8$-(6-acetylpyridin-3-yl)-2-amino-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.44 | 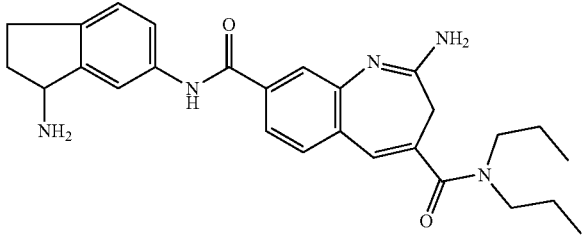 [SMILES: CCCN(CCC)C(=O)C1=Cc2ccc(C(=O)Nc3ccc4c(c3)C(N)CC4)cc2N=C(N)C1]
2-amino-$N^8$-(3-amino-2,3-dihydro-1H-inden-5-yl)-$N^4,N^4$-dipropyl-3H-benzo[b]azepine-4,8-dicarboxamide |
| 1.45 | 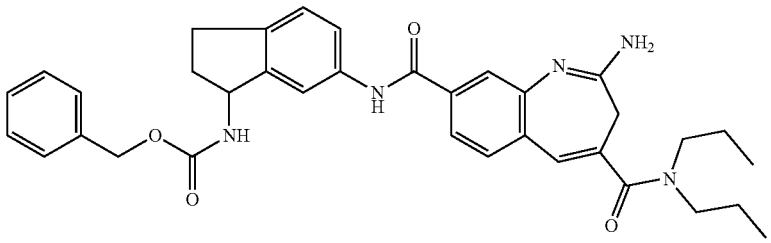 [SMILES: CCCN(CCC)C(=O)C1=Cc2ccc(C(=O)Nc3ccc4c(c3)C(NC(=O)OCc3ccccc3)CC4)cc2N=C(N)C1]
Benzyl (6-(2-amino-4-(dipropylcarbamoyl)-3H-benzo[b]azepine-8-carboxamido)-2,3-dihydro-1H-inden-1-yl)carbamate |
| 1.46 | 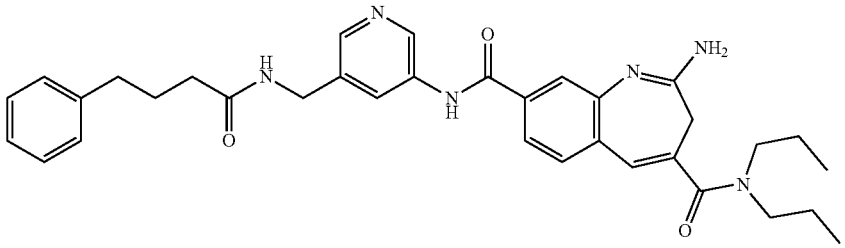 [SMILES: CCCN(CCC)C(=O)C1=Cc2ccc(C(=O)Nc3cncc(CNC(=O)CCCc4ccccc4)c3)cc2N=C(N)C1]
2-amino-$N^8$-(5-((4-phenylbutanamido)methyl)pyridin-3-yl)-$N^4,N^4$-dipropyl-3H-benzo[b]azepine-4,8-dicarboxamide |
| 1.47 | 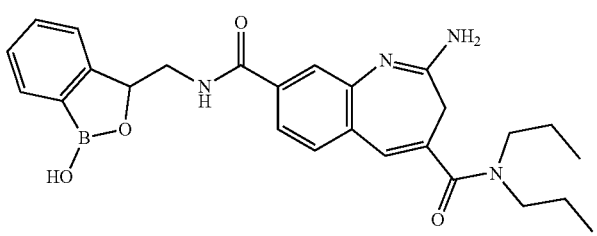 [SMILES: CCCN(CCC)C(=O)C1=Cc2ccc(C(=O)NCC3OB(O)c4ccccc43)cc2N=C(N)C1]
2-amino-$N^8$-((1-hydroxy-1,3-dihydro-benzo[c][1,2]oxaborol-3-yl)methyl)-N4,N4-dipropyl-3H-benzo[b]azepine-4,8-dicarboxamide |
| 1.48 | 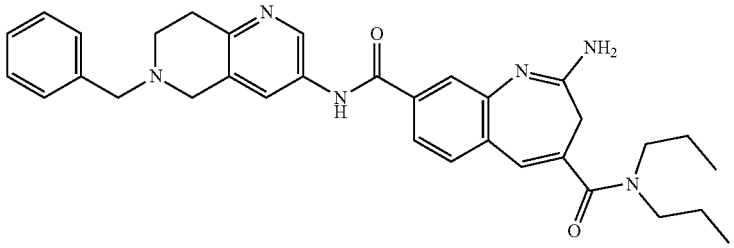 [SMILES: CCCN(CCC)C(=O)C1=Cc2ccc(C(=O)Nc3cnc4c(c3)CN(Cc3ccccc3)CC4)cc2N=C(N)C1]
2-amino-$N^8$-(6-benzyl-5,6,7,8-tetrahydro-1,6-naphthyridin-3-yl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.49 | 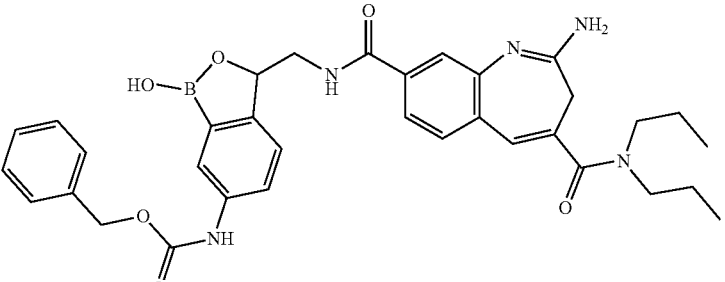<br>benzyl (3-((2-amino-4-(dipropylcarbamoyl)-3H-benzo[b]azepine-8-carboxamido)methyl)-1-hydroxy-1,3-dihydrobenzo[c][1,2]oxaborol-6-yl)carbamate |
| 1.50 | 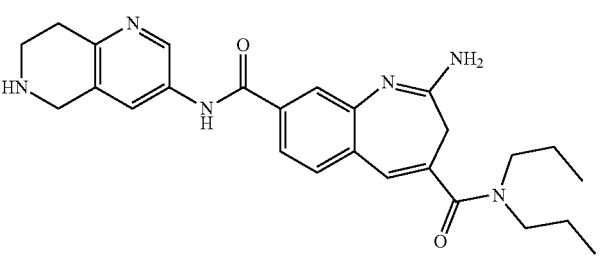 [SMILES: CCCN(CCC)C(=O)C1=Cc2ccc(C(=O)Nc3cnc4c(c3)CNCC4)cc2N=C(N)C1]<br>2-amino-$N^4,N^4$-dipropyl-$N^8$-(5,6,7,8-tetrahydro-1,6-naphthyridin-3-yl)-3H-benzo[b]azepine-4,8-dicarboxamide |
| 1.51 | 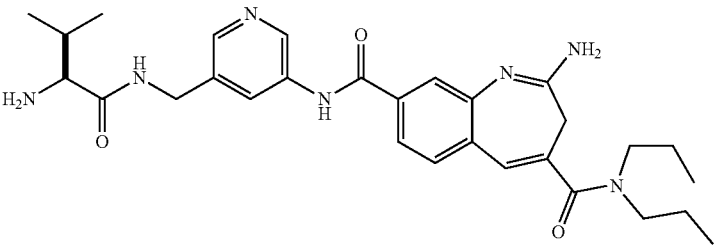 [SMILES: CCCN(CCC)C(=O)C1=Cc2ccc(C(=O)Nc3cncc(CNC(=O)[C@@H](N)C(C)C)c3)cc2N=C(N)C1]<br>(S)-2-amino-$N^8$-(5-((2-amino-3-methylbutanamido)methyl)pyridin-3-yl)-$N^4,N^4$-dipropyl-3H-benzo[b]azepine-4,8-dicarboxamide |
| 1.52 | 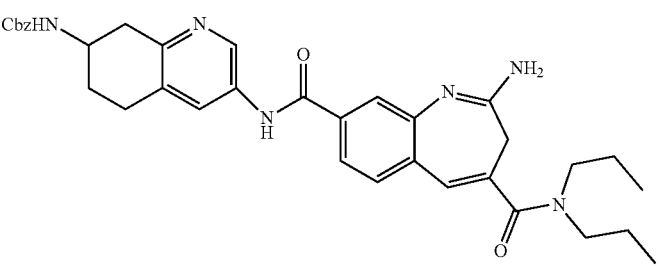 [SMILES: CCCN(CCC)C(=O)C1=Cc2ccc(C(=O)Nc3cnc4c(c3)CCC(NC(=O)OCc3ccccc3)C4)cc2N=C(N)C1]<br>benzyl (3-(2-amino-4-(dipropylcarbamoyl)-3H-benzo[b]azepine-8-carboxamido)-5,6,7,8-tetrahydroquinolin-7-yl)carbamate |
| 1.53 | 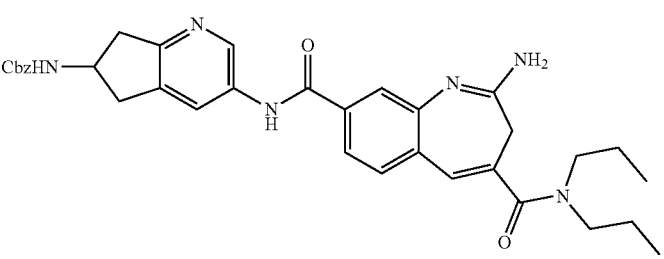 [SMILES: CCCN(CCC)C(=O)C1=Cc2ccc(C(=O)Nc3cnc4c(c3)CC(NC(=O)OCc3ccccc3)C4)cc2N=C(N)C1]<br>benzyl (3-(2-amino-4-(dipropylcarbamoyl)-3H-benzo[b]azepine-8-carboxamido)-6,7-dihydro-5H-cyclopenta[b]pyridin-6-yl)carbamate |

TABLE 1a-continued

Compounds 1.1-1.69

| Compound | Structure and IUPAC |
|---|---|
| 1.54 | 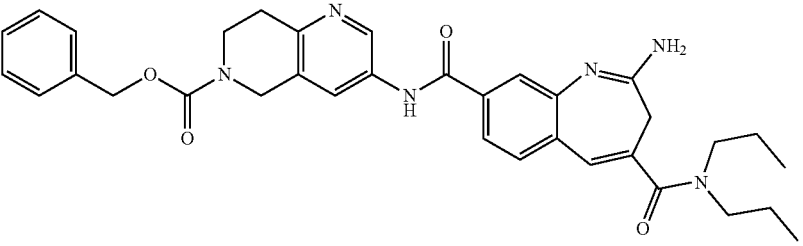 [SMILES: CCCN(CCC)C(=O)C1=Cc2ccc(C(=O)Nc3cnc4c(c3)CN(C(=O)OCc3ccccc3)CC4)cc2N=C(N)C1]<br>benzyl 3-(2-amino-4-(dipropylcarbamoyl)-3H-benzo[b]azepine-8-carboxamido)-7,8-dihydro-1,6-naphthyridine-6(5H)-carboxylate |
| 1.55 | 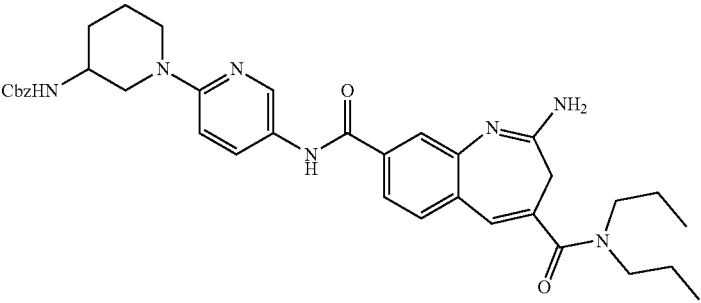 [SMILES: CCCN(CCC)C(=O)C1=Cc2ccc(C(=O)Nc3ccc(N4CCCC(NC(=O)OCc5ccccc5)C4)nc3)cc2N=C(N)C1]<br>benzyl (1-(5-(2-amino-4-(dipropylcarbamoyl)-3H-benzo[b]azepine-8-carboxamido)pyridin-2-yl)piperidin-3-yl)carbamate |
| 1.56 | 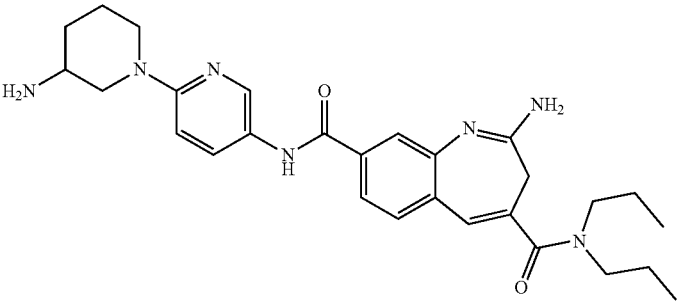 [SMILES: CCCN(CCC)C(=O)C1=Cc2ccc(C(=O)Nc3ccc(N4CCCC(N)C4)nc3)cc2N=C(N)C1]<br>2-amino-$N^8$-(6-(3-aminopiperidin-1-yl)pyridin-3-yl)-$N^4,N^4$-dipropyl-3H-benzo[b]azepine-4,8-dicarboxamide |
| 1.57 | 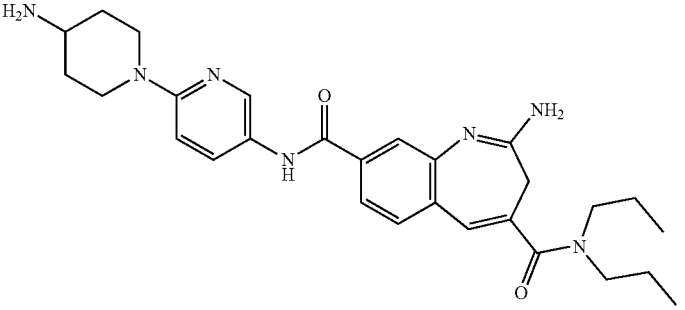 [SMILES: CCCN(CCC)C(=O)C1=Cc2ccc(C(=O)Nc3ccc(N4CCC(N)CC4)nc3)cc2N=C(N)C1]<br>2-amino-$N^8$-(6-(4-aminopiperidin-1-yl)pyridin-3-yl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.58 | 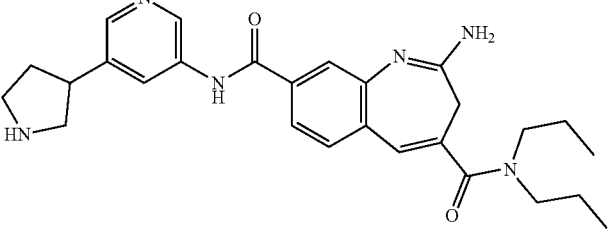<br>2-amino-$N^4,N^4$-dipropyl-$N^8$-(5-(pyrrolidin-3-yl)pyridin-3-yl)-3H-benzo[b]azepine-4,8-dicarboxamide |
| 1.59 | 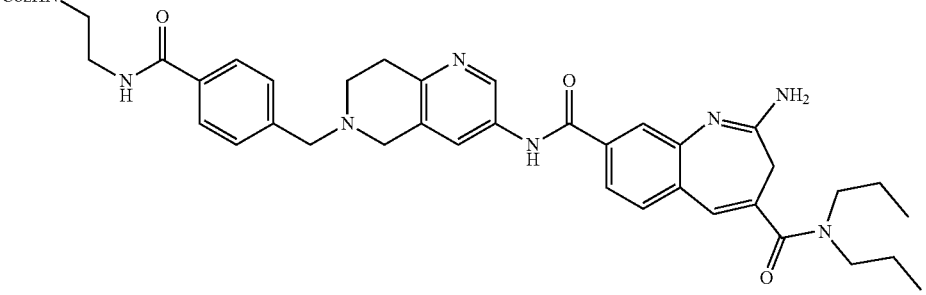<br>benzyl (2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)carbamate |
| 1.60 | 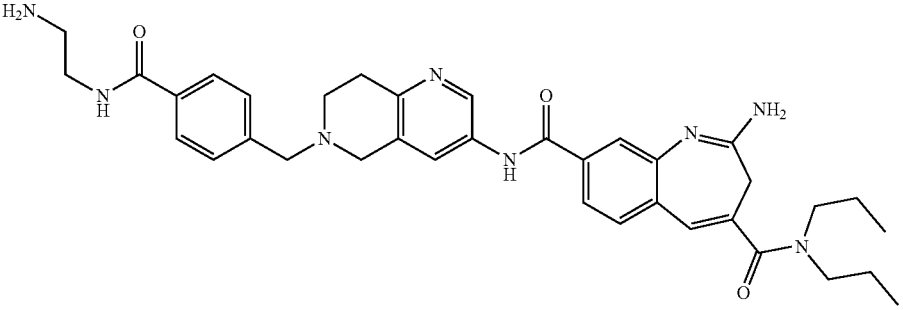 [SMILES: CCCN(CCC)C(=O)C1=Cc2ccc(C(=O)Nc3cnc4c(c3)CN(Cc3ccc(C(=O)NCCN)cc3)CC4)cc2N=C(N)C1]<br>2-amino-$N^8$-(6-(4-((2-aminoethyl)carbamoyl)benzyl)-5,6,7,8-tetrahydro-1,6-naphthyridin-3-yl)-$N^4,N^4$-dipropyl-3H-benzo[b]azepine-4,8-dicarboxamide |
| 1.61 | 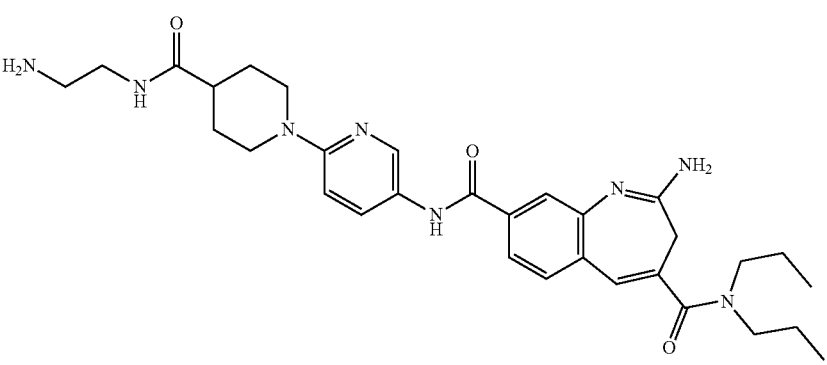 [SMILES: CCCN(CCC)C(=O)C1=Cc2ccc(C(=O)Nc3ccc(N4CCC(C(=O)NCCN)CC4)nc3)cc2N=C(N)C1]<br>2-amino-$N^8$-(6-(4-((2-aminoethyl)carbamoyl)piperidin-1-yl)pyridin-3-yl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.62 | 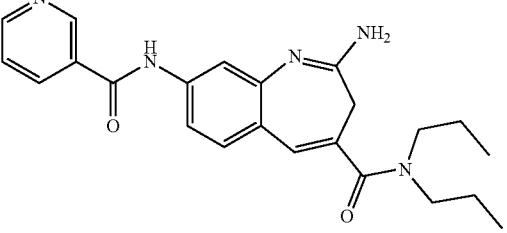

2-amino-8-(nicotinamido)-N,N-dipropyl-3H-benzo[b]azepine-4-carboxamide |
| 1.63 | 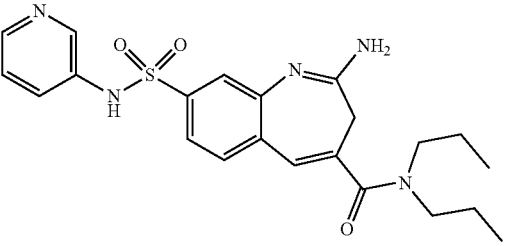 [SMILES: CCCN(CCC)C(=O)C1=Cc2ccc(S(=O)(=O)Nc3cccnc3)cc2N=C(N)C1]

2-amino-N,N-dipropyl-8-(N-(pyridin-3-yl)sulfamoyl)-3H-benzo[b]azepine-4-carboxamide |
| 1.64 | 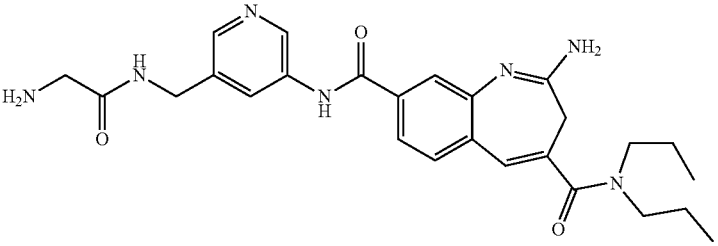 [SMILES: CCCN(CCC)C(=O)C1=Cc2ccc(C(=O)Nc3cncc(CNC(=O)CN)c3)cc2N=C(N)C1]

2-amino-N8-(5-((2-aminoacetamido)methyl)pyridin-3-yl)-N4,N4-dipropyl-3H-benzo[b]azepine-4,8-dicarboxamide |
| 1.65 | 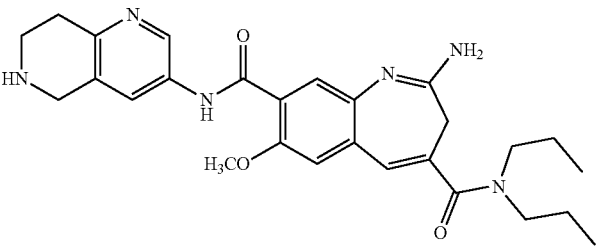 [SMILES: CCCN(CCC)C(=O)C1=Cc2cc(OC)c(C(=O)Nc3cnc4c(c3)CNCC4)cc2N=C(N)C1]

2-amino-7-methoxy-N4,N4-dipropyl-N8-(5,6,7,8-tetrahydro-1,6-naphthyridin-3-yl)-3H-benzo[b]azepine-4,8-dicarboxamide |
| 1.66 | 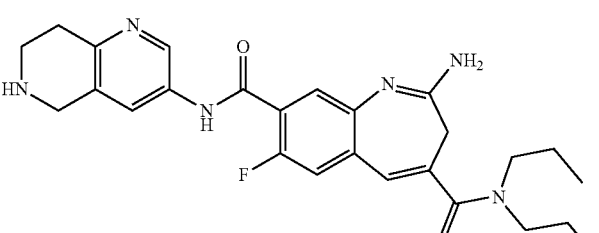

2-amino-7-fluoro-N4,N4-dipropyl-N8-(5,6,7,8-tetrahydro-1,6-naphthyridin-3-yl)-3H-benzo[b]azepine-4,8-dicarboxamide |

TABLE 1a-continued

Compounds 1.1-1.69

| Compound | Structure and IUPAC |
|---|---|
| 1.67 | [Structure]<br>2-amino-N8-(6-(4-((3-amino-2,2-difluoropropyl)carbamoyl)benzyl)-5,6,7,8-tetrahydro-1,6-naphthyridin-3-yl)-N4,N4-dipropyl-3H-benzo[b]azepine-4,8-dicarboxamide |
| 1.68 | [Structure] |
| 1.69 | [Structure] |

Compounds of Category B, TLR7 Agonists

In some embodiments, the disclosure provides a compound represented by the structure of Formula (IA):

(IA)

or a pharmaceutically acceptable salt thereof, wherein:

$R^1$, $R^2$, $R^3$, $R^4$, and $R^5$ are independently selected from hydrogen; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN; or $R^3$ and $R^{11}$ taken together form a 5- to 10-membered heterocycle optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN;

$R^6$ is selected from halogen, —$OR^{20}$, —$N(R^{20})_2$, —$C(O)N(R^{20})_2$, —$C(O)R^{20}$, —$C(O)OR^{20}$, —$S(O)R^{20}$, and —$S(O)_2R^{20}$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN;

$R^7$, $R^8$, $R^9$, and $R^{10}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen;

$R^{11}$ and $R^{12}$ are independently selected from hydrogen, halogen, —$OR^{20}$, —$SR^{20}$, —$C(O)N(R^{20})_2$, —$N(R^{20})_2$, —S(O)R$^{20}$, —S(O)$_2$R$^{20}$, —C(O)R$^{20}$, —C(O)OR$^{20}$, —OC(O)R$^{20}$, —NO$_2$, and —CN; and C$_{1-6}$ alkyl, C$_{2-6}$ alkenyl, and C$_{2-6}$ alkynyl, each of which is optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), —CN, C$_{3-12}$ carbocycle, and 3- to 12-membered heterocycle; or R$^{11}$ and R$^{12}$ taken together form a C$_{3-6}$ carbocycle optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), and —CN;

R$^{13}$ and R$^{14}$ are independently selected at each occurrence from hydrogen, halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, and —CN; C$_{1-6}$ alkyl, C$_{2-6}$ alkenyl, and C$_{2-6}$ alkynyl, each of which is optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), —CN, C$_{3-12}$ carbocycle, and 3- to 12-membered heterocycle; and C$_{3-12}$ carbocycle and 3- to 12-membered heterocycle, each of which is optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), —CN, C$_{1-6}$ alkyl, C$_{2-6}$ alkenyl, and C$_{2-6}$ alkynyl;

R$^{15}$ is independently selected at each occurrence from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), —CN, C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

R$^{16}$ is selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

R$^{20}$ is independently selected at each occurrence from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

X$^1$ is O, S, or NR$^{16}$;
X$^2$ is C(O) or S(O)$_2$;
n is 1, 2, or 3;
x is 1, 2, or 3;
w is 0, 1, 2, 3, or 4; and
z is 0, 1, or 2.

In some embodiments, for a compound of Formula (IA), wherein X$^1$ is O. In some embodiments, for a compound of Formula (IA), n is 2. In some embodiments, for a compound of Formula (IA), x is 2. In some embodiments, for a compound of Formula (IA), z is 0. In some embodiments, for a compound of Formula (IA), z is 1.

In some embodiments, a compound of Formula (IA) is represented by Formula (IB).

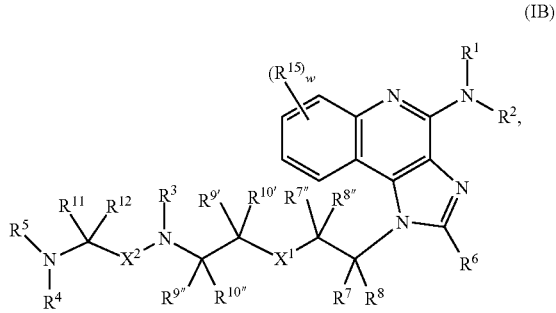

(IB)

or a pharmaceutically acceptable salt thereof, wherein R$^{7'}$, R$^{7''}$, R$^{8'}$, R$^{8''}$, R$^{9'}$, R$^{9''}$, R$^{10'}$, and R$^{10''}$ are independently selected at each occurrence from hydrogen and halogen; and C$_{1-6}$ alkyl, C$_{2-6}$ alkenyl, and C$_{2-6}$ alkynyl, each of which is optionally substituted with one or more substituents independently selected from halogen.

In some embodiments, a compound of Formula (IA) is represented by Formula (IC):

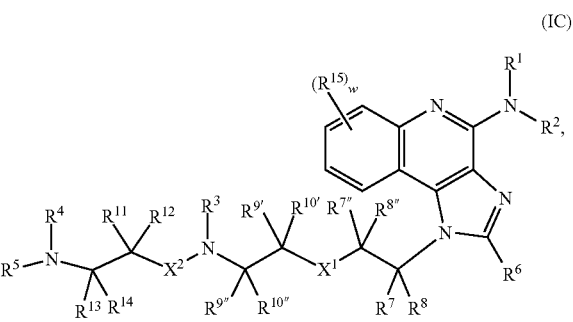

(IC)

or a pharmaceutically acceptable salt thereof, wherein R$^{7'}$, R$^{7''}$, R$^{8'}$, R$^{8''}$, R$^{9'}$, R$^{9''}$, R$^{10'}$, and R$^{10''}$ are independently selected at each occurrence from hydrogen and halogen; and C$_{1-6}$ alkyl, C$_{2-6}$ alkenyl, and C$_{2-6}$ alkynyl, each of which is optionally substituted with one or more substituents independently selected from halogen.

In some embodiments, for a compound or salt of any one of Formulas (IA), (IB), or (IC), R$^1$, R$^2$, R$^3$, R$^4$, and R$^5$ are independently selected from hydrogen and C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), and —CN.

In some embodiments, for a compound or salt of any one of Formulas (IA), (IB), or (IC), R$^1$ and R$^2$ are independently selected from hydrogen and C$_{1-6}$ alkyl. In some embodiments, for a compound or salt of any one of Formulas (IA), (IB), or (IC), R$^1$ and R$^2$ are each hydrogen.

In some embodiments, for a compound or salt of any one of Formulas (IA), (IB), or (IC), R$^3$ is selected from hydrogen and C$_{1-6}$ alkyl optionally substituted with one or more halogens.

In some embodiments, for a compound or salt of any one of Formulas (IA), (IB), or (IC), $R^3$ is hydrogen.

In some embodiments, for a compound or salt of any one of Formulas (IA), (IB), or (IC), $R^4$ is selected from hydrogen and $C_{1-6}$ alkyl optionally substituted with one or more halogens.

In some embodiments, for a compound or salt of any one of Formulas (IA), (IB), or (IC), $R^4$ is hydrogen.

In some embodiments, for a compound or salt of any one of Formulas (IA), (IB), or (IC), $R^5$ is selected from hydrogen and $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, $=O$, $=S$, $=N(R^{20})$, and —CN. In some embodiments, for a compound or salt of any one of Formulas (IA), (IB), or (IC), $R^5$ is hydrogen.

In some embodiments, for a compound or salt of any one of Formulas (IA), (IB), or (IC), $R^6$ is selected from halogen, —$OR^{20}$, and —$N(R^{20})_2$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, $=O$, $=S$, $=N(R^{20})$, and —CN; and $R^{20}$ is independently selected at each occurrence from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, $=O$, $=S$, —$C(O)OCH_2C_6H_5$, —$NHC(O)OCH_2C_6H_5$, $C_{1-6}$ alkyl, —$C_{1-6}$ haloalkyl, —O—$C_{1-6}$ alkyl, $C_{2-6}$ alkenyl, $C_{2-6}$ alkynyl, $C_{3-12}$ carbocycle, and 3- to 12-membered heterocycle.

In some embodiments, for a compound or salt of any one of Formulas (IA), (IB), or (IC), $R^6$ is $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$; and $R^{20}$ is independently selected at each occurrence from hydrogen; $C_{1-6}$ alkyl, $C_{3-12}$ carbocycle, and 3- to 12-membered heterocycle, each of which is optionally substituted with one or more substituents independently selected from halogen, —OH, —CN, —$NO_2$, —$NH_2$, $=O$, $=S$, —$C(O)OCH_2C_6H_5$, —$NHC(O)OCH_2C_6H_5$, $C_{1-6}$ alkyl, —$C_{1-6}$ haloalkyl, —O—$C_{1-6}$ alkyl, $C_{2-6}$ alkenyl, $C_{2-6}$ alkynyl, $C_{3-12}$ carbocycle, and 3- to 12-membered heterocycle.

In some embodiments, for a compound or salt of any one of Formulas (IA), (IB), or (IC), $R^6$ is $C_{1-6}$ alkyl substituted with —$OR^{20}$, and $R^{20}$ is selected from hydrogen and $C_{1-6}$ alkyl optionally substituted with one or more substituents independently selected from halogen, —OH, and —$NH_2$.

In some embodiments, for a compound or salt of any one of Formulas (IA), (IB), or (IC), $R^{7'}$, $R^{7''}$, $R^{8'}$, $R^{8''}$, $R^{9'}$, $R^{9''}$, $R^{10'}$, and $R^{10''}$ are independently selected at each occurrence from hydrogen and halogen; and $C_{1-6}$ alkyl, optionally substituted with one or more substituents independently selected from halogen.

In some embodiments, for a compound or salt of any one of Formulas (IB) or (IC), wherein $R^{7'}$ and $R^{8'}$ are each hydrogen. In some embodiments, for a compound or salt of any one of Formulas (IB) or (IC), wherein $R^{7''}$ and $R^{8''}$ are each $C_{1-6}$ alkyl. In some embodiments, for a compound or salt of any one of Formulas (IB) or (IC), $R^{7''}$ and $R^{8''}$ are each methyl.

In some embodiments, for a compound or salt of any one of Formulas (IB) or (IC), $R^{9'}$, $R^{9''}$, $R^{10'}$, and $R^{10''}$ are independently selected at each occurrence from hydrogen and $C_{1-6}$ alkyl.

In some embodiments, for a compound or salt of any one of Formulas (IB) or (IC), $R^{9'}$, $R^{9''}$, $R^{10'}$, and $R^{10''}$ are each hydrogen.

In some embodiments, for a compound or salt of any one of Formulas (IA), (IB), or (IC), $R^{11}$ and $R^{12}$ are independently selected from hydrogen, halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$; and $C_{1-6}$ alkyl, optionally substituted with one or more substituents independently selected from halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$, $C_{3-12}$ carbocycle, and 3- to 12-membered heterocycle.

In some embodiments, for a compound or salt of any one of Formulas (IA) or (IC), $R^{13}$ and $R^{14}$ are independently selected from hydrogen, halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$; and $C_{1-6}$ alkyl optionally substituted with one or more substituents independently selected from halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$, $C_{3-12}$ carbocycle, and 3- to 12-membered heterocycle.

In some embodiments, for a compound or salt of any one of Formulas (IA), (IB), or (IC), $R^3$ and $R^{11}$ taken together form an optionally substituted 5- to 6-membered heterocycle.

In some embodiments, for a compound or salt of any one of Formulas (IA), (IB), or (IC), $R^{11}$ and $R^{12}$ taken together form an optionally substituted $C_{3-6}$ carbocycle.

In some embodiments, for a compound or salt of any one of Formulas (IA), (IB), or (IC), $X^2$ is C(O).

In some embodiments, the compound is represented by:

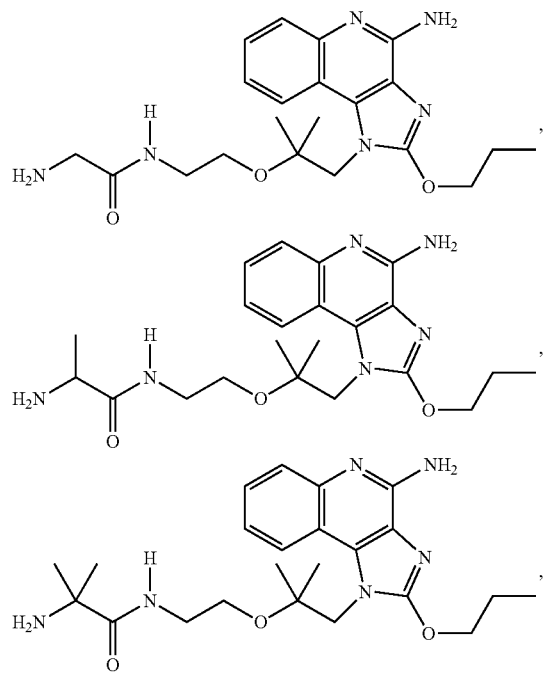

-continued

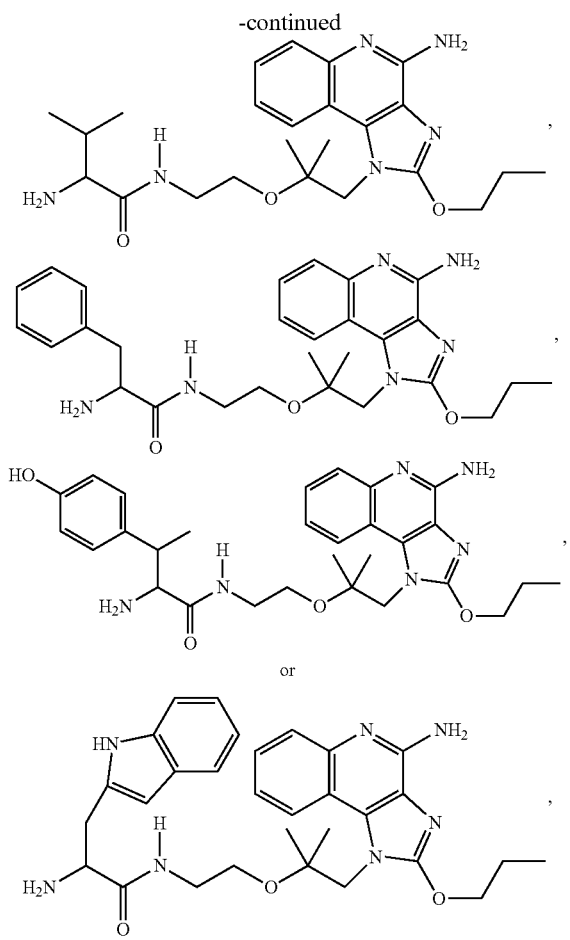

or a pharmaceutically acceptable salt of any one thereof.

In certain aspects, the disclosure provides a pharmaceutical composition of a compound or pharmaceutically acceptable salt of any one of Formulas (IA), (IB), or (IC), and a pharmaceutically acceptable excipient.

In some embodiments, for a compound or salt of any one of Formulas (IA), (IB), or (IC), the compound or salt is further covalently bound to a linker, $L^3$.

In certain aspects the disclosure provides a compound represented by Formula (IIA):

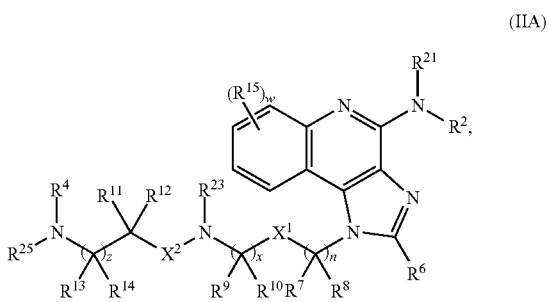

(IIA)

or a pharmaceutically acceptable salt thereof, wherein:

$R^2$ and $R^8$ are independently selected from hydrogen; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), and —CN;

$R^{21}$, $R^{23}$, and $R^{25}$ are independently selected from hydrogen; $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), and —CN; and $L^3$; or $R^{23}$ and $R^{11}$ taken together form a 5- to 10-membered heterocycle optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), and —CN; and wherein one of $R^{21}$, $R^{23}$, and $R^{25}$ is $L^3$;

$R^6$ is selected from halogen, —$OR^{20}$, —N($R^{20}$)$_2$, —C(O)N($R^{20}$)$_2$, —C(O)$R^{20}$, —C(O)O$R^{20}$, —S(O)$R^{20}$, and —S(O)$_2R^{20}$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), and —CN;

$R^7$, $R^8$, $R^9$, and $R^{10}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen;

$R^{11}$ and $R^{12}$ are independently selected from hydrogen, halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, and —CN; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), —CN, $C_{3-12}$ carbocycle, and 3- to 12-membered heterocycle; or $R^{11}$ and $R^{12}$ taken together form a $C_{3-6}$ carbocycle optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), and —CN;

$R^{13}$ and $R^{14}$ are independently selected at each occurrence from hydrogen, halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, —CN, $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), —CN, $C_{3-12}$ carbocycle, and 3- to 12-membered heterocycle; and $C_{3-12}$ carbocycle and 3- to 12-membered heterocycle, each of which is optionally substituted with one or more substituents independently selected from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), —CN, $C_{1-6}$ alkyl, $C_{2-6}$ alkenyl, and $C_{2-6}$ alkynyl;

$R^{15}$ is independently selected at each occurrence from halogen, —$OR^{20}$, —$SR^{20}$, —C(O)N($R^{20}$)$_2$, —N($R^{20}$)$_2$, —S(O)$R^{20}$, —S(O)$_2R^{20}$, —C(O)$R^{20}$, —C(O)O$R^{20}$, —OC(O)$R^{20}$, —NO$_2$, =O, =S, =N($R^{20}$), —CN, $C_{1-6}$ alkyl, $C_{2-6}$ alkenyl, and $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, —C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

R$^{16}$ is selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

R$^{20}$ is independently selected at each occurrence from hydrogen; C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle;

L$^3$ is a linker;
X$^1$ is O, S, or NR$^{16}$;
X$^2$ is C(O) or S(O)$_2$;
n is 1, 2, or 3;
x is 1, 2, or 3;
w is 0, 1, 2, 3, or 4; and
z is 0, 1, or 2.

In some embodiments, for a compound or salt of Formula (IIA), X$^1$ is O. In some embodiments, for a compound or salt of Formula (IIA), n is 2. In some embodiments, for a compound or salt of Formula (IIA), x is 2. In some embodiments, for a compound or salt of Formula (IIA), z is 0. In some embodiments, for a compound or salt of Formula (IIA), z is 1.

In some embodiments, the compound of Formula (IIA) is represented by (IIB) or (IIC):

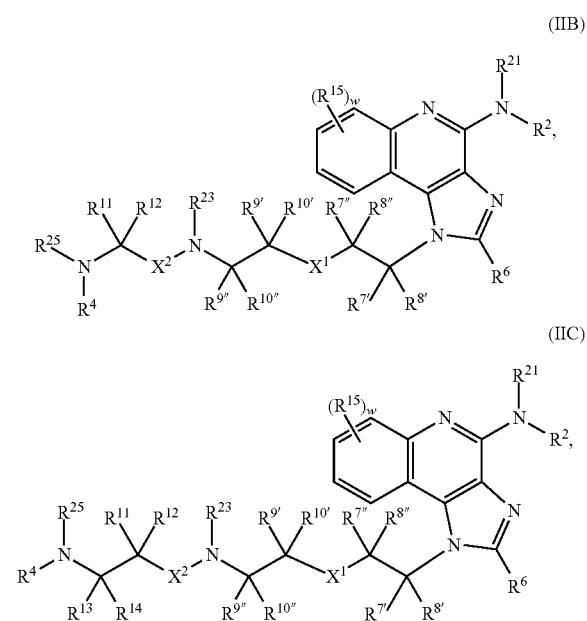

or a pharmaceutically acceptable salt thereof, wherein R$^{7'}$, R$^{7''}$, R$^{8'}$, R$^{8''}$, R$^{9'}$, R$^{9''}$, R$^{10'}$, and R$^{10'''}$ are independently selected at each occurrence from hydrogen and halogen; and C$_{1-6}$ alkyl, C$_{2-6}$ alkenyl, and C$_{2-6}$ alkynyl, each of which is optionally substituted with one or more substituents independently selected from halogen.

In some embodiments, for a compound or salt of any one of Formulas (IIA), (IIB), or (IIC), R$^2$ and R$^4$ are independently selected from hydrogen and C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), and —CN.

In some embodiments, for a compound or salt of any one of Formulas (IIA), (IIB), or (IIC), R$^2$ and R$^4$ are independently selected from hydrogen and C$_{1-6}$ alkyl. In some embodiments, for a compound or salt of any one of Formulas (IIA), (IIB), or (IIC), R$^2$ and R$^4$ are each hydrogen.

In some embodiments, for a compound or salt of any one of Formulas (IIA), (IIB), or (IIC), R$^{23}$ is selected from hydrogen and C$_{1-6}$ alkyl optionally substituted with one or more halogens. In some embodiments, for a compound or salt of any one of Formulas (IIA), (IIB), or (IIC), R$^{23}$ is hydrogen.

In some embodiments, for a compound or salt of any one of Formulas (IIA), (IIB), or (IIC), R$^{21}$ is selected from hydrogen and C$_{1-6}$ alkyl optionally substituted with one or more halogens. In some embodiments, for a compound or salt of any one of Formulas (IIA), (IIB), or (IIC), R$^{21}$ is hydrogen.

In some embodiments, for a compound or salt of any one of Formulas (IIA), (IIB), or (IIC), R$^{21}$ is L$^3$.

In some embodiments, for a compound or salt of any one of Formulas (IIA), (IIB), or (IIC), R$^{25}$ is selected from hydrogen and C$_{1-6}$ alkyl, optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), and —CN. In some embodiments, for a compound or salt of any one of Formulas (IIA), (IIB), or (IIC), R$^{25}$ is hydrogen.

In some embodiments, for a compound or salt of any one of Formulas (IIA), (IIB), or (IIC), R$^{25}$ is L$^3$.

In some embodiments, for a compound or salt of any one of Formulas (IIA), (IIB), or (IIC), R$^6$ is selected from halogen, —OR$^{20}$, and —N(R$^{20}$)$_2$; and C$_{1-6}$ alkyl, C$_{2-6}$ alkenyl, C$_{2-6}$ alkynyl, each of which is optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$, —NO$_2$, =O, =S, =N(R$^{20}$), and —CN; and R$^{20}$ is independently selected at each occurrence from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle.

In some embodiments, for a compound or salt of any one of Formulas (IIA), (IIB), or (IIC), R$^6$ is C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$; and R$^{20}$ is independently selected at each occurrence from hydrogen, —NH$_2$, —C(O)OCH$_2$C$_6$H$_5$; C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$ haloalkyl, —O—C$_{1-6}$ alkyl, C$_{2-6}$ alkenyl, C$_{2-6}$ alkynyl, C$_{3-12}$ carbocycle, and 3- to 12-membered heterocycle.

In some embodiments, for a compound or salt of any one of Formulas (IIA), (IIB), or (IIC), R$^6$ is C$_{1-6}$ alkyl substituted with —OR$^{20}$, and R$^{20}$ is selected from hydrogen and C$_{1-6}$ alkyl, which is optionally substituted with one or more substituents independently selected from halogen, —OH, and —NH$_2$.

In some embodiments, for a compound or salt of any one of Formulas (IIB) or (IIC), R$^{7'}$, R$^{7''}$, R$^{8'}$, R$^{8''}$, R$^{9'}$, R$^{9'''}$, R$^{10'}$, and R$^{10''}$ are independently selected at each occurrence from hydrogen and halogen; and C$_{1-6}$ alkyl optionally substituted with one or more substituents independently selected from halogen.

In some embodiments, for a compound or salt of any one of Formulas (IIB) or (IIC), R$^{7''}$ and R$^{8''}$ are hydrogen.

In some embodiments, for a compound or salt of any one of Formulas (IIB) or (IIC), R$^{7''}$ and R$^{8''}$ are C$_{1-6}$ alkyl.

In some embodiments, for a compound or salt of any one of Formulas (IIB) or (IIC), R$^{7''}$ and R$^{8''}$ are methyl.

In some embodiments, for a compound or salt of any one of Formulas (IIB) or (IIC), R$^{9'}$, R$^{9'''}$, R$^{10'}$, and R$^{10''}$ are independently selected at each occurrence from hydrogen and C$_{1-6}$ alkyl.

In some embodiments, for a compound or salt of any one of Formulas (IIB) or (IIC), R$^{9'}$, R$^{9'''}$, R$^{10'}$, and R$^{10''}$ are each hydrogen.

In some embodiments, for a compound or salt of any one of Formulas (IIA), (IIB), or (IIC), R$^{11}$ and R$^{12}$ are independently selected from hydrogen, halogen, —OR$^{20}$, —SR$^{20}$, —C(O)N(R$^{20}$)$_2$, —N(R$^{20}$)$_2$, —C(O)R$^{20}$, —C(O)OR$^{20}$, and —OC(O)R$^{20}$; and C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$, C$_{3-12}$ carbocycle, and 3- to 12-membered heterocycle.

In some embodiments, for a compound or salt of any one of Formulas (IIA) or (IIC), R$^{13}$ and R$^{14}$ are independently selected from hydrogen, halogen, —OR$^{20}$, —SR$^{20}$, —C(O)N(R$^{20}$)$_2$, —N(R$^{20}$)$_2$, —C(O)R$^{20}$, —C(O)OR$^{20}$, and —OC(O)R$^{20}$; and C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$, C$_{3-12}$ carbocycle, and 3- to 12-membered heterocycle.

In some embodiments, for a compound or salt of any one of Formulas (IIA), (IIB), or (IIC), R$^{23}$ and R$^{11}$ taken together form an optionally substituted 5- to 6-membered heterocycle.

In some embodiments, for a compound or salt of any one of Formulas (IIA), (IIB), or (IIC), R$^{11}$ and R$^{12}$ taken together form an optionally substituted C$_{3-6}$ carbocycle.

In some embodiments, for a compound or salt of any one of Formulas (IIA), (IIB), or (IIC), X$^2$ is C(O).

In some embodiments, for a compound or salt of any one of Formulas (IIA), (IIB), or (IIC), L$^3$ is a cleavable linker. In some embodiments, for a compound or salt of any one of Formulas (IIA), (IIB), or (IIC), L$^3$ is cleavable by a lysosomal enzyme.

In some embodiments, for a compound or salt of any one of Formulas (IIA), (IIB), or (IIC), L$^3$ is represented by the formula:

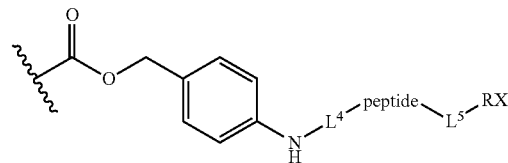

wherein:
L$^4$ represents the C-terminus of the peptide and L$^5$ is selected from a bond, alkylene and heteroalkylene, wherein L$^5$ is optionally substituted with one or more groups independently selected from R$^{30}$, and RX is a reactive moiety; and R$^{30}$ is independently selected at each occurrence from halogen, —OH, —CN, —O-alkyl, —SH, =O, =S, —NH$_2$, —NO$_2$; and C$_1$-C$_{10}$ alkyl, C$_2$-C$_{10}$ alkenyl, and C$_2$-C$_{10}$ alkynyl, each of which is independently optionally substituted at each occurrence with one or more substituents selected from halogen, —OH, —CN, —O-alkyl, —SH, =O, =S, —NH$_2$, and —NO$_2$.

In some embodiments, for a compound or salt of any one of Formulas (IIA), (IIB), or (IIC), RX comprises a leaving group. In some embodiments, for a compound or salt of any one of Formulas (IIA), (IIB), or (IIC), RX is a maleimide or an alpha-halo carbonyl. In some embodiments, for a compound or salt of any one of Formulas (IIA), (IIB), or (IIC), the peptide of L$^3$ comprises Val-Cit or Val-Ala.

In some embodiments, for a compound or salt of any one of Formulas (IIA), (IIB), or (IIC), L$^3$ is represented by the formula:

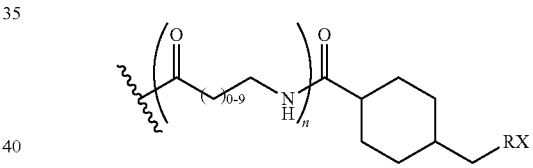

wherein:
RX comprises a reactive moiety; and
n is 0-9.

In some embodiments, for a compound or salt of any one of Formulas (IIA), (IIB), or (IIC), RX comprises a leaving group. In some embodiments, for a compound or salt of any one of Formulas (IIA), (IIB), or (IIC), RX is a maleimide or an alpha-halo carbonyl. In some embodiments, for a compound or salt of any one of Formulas (IIA), (IIB), or (IIC), L$^3$ is further covalently bound to an antibody or antigen binding fragment thereof to form a conjugate.

In some embodiments, the disclosure provides a conjugate represented by the formula:

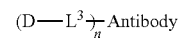

wherein:
Antibody is an anti-ASGR1 antibody or an antigen-binding fragment thereof of the disclosure;
n is 1 to 20;
D is a compound or salt of any one of a Category B compound of Formulas (IA), (IB), or (IC); and L$^3$ is a linker moiety; or D-L³ is a compound or salt of any one of a Category B compound of Formulas (IIA), (IIB), or (IIC).

In some embodiments, for a conjugate of a compound or salt of any one of Formulas (IA), (IB), (IC), (IIA), (IIB), and (IIC), n is selected from 1 to 8. In some embodiments, for a conjugate of a compound or salt of any one of Formulas (IA), (IB), (IC), (IIA), (IIB), and (IIC), n is selected from 2 to 5. In some embodiments, for a conjugate of a compound or salt of any one of Formulas (IA), (IB), (IC), (IIA), (IIB), and (IIC), n is 2.

In some embodiments, for a compound or salt of any one of Formulas (IIA), (IIB), and (IIC), -L³ is represented by the formula:

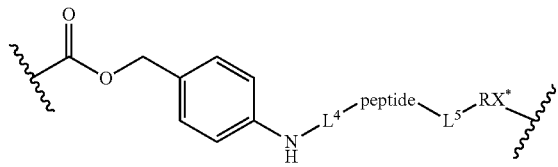

wherein:

L⁴ represents the C-terminus of the peptide and L⁵ is selected from a bond, alkylene and heteroalkylene, wherein L⁵ is optionally substituted with one or more groups independently selected from R³⁰;

RX* is a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof; and R³⁰ is independently selected at each occurrence from halogen, —OH, —CN, —O-alkyl, —SH, =O, =S, —NH₂, —NO₂; and C₁-C₁₀ alkyl, C₂-C₁₀ alkenyl, and C₂-C₁₀ alkynyl, each of which is independently optionally substituted at each occurrence with one or more substituents selected from halogen, —OH, —CN, —O-alkyl, —SH, =O, =S, —NH₂, and —NO₂.

In some embodiments, for a compound or salt of any one of Formulas (IIA), (IIB), or (IIC), RX* is a succinamide moiety, hydrolyzed succinamide moiety or a mixture thereof and is bound to a cysteine residue of an antibody.

In some embodiments for a compound of Formulas (IIA), (IIB) and (IIC), -L³ is represented by the formula:

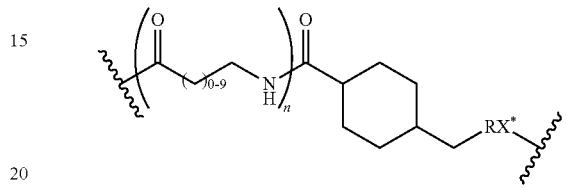

wherein:

RX* is a bond, a succinimide moiety, or a hydrolyzed succinimide moiety bound to a residue of an antibody, wherein

on RX* represents the point of attachment to the residue of the antibody; and n is 0-9.

Examples of TLR7 agonist compounds according to Category B are provided in Table 3 and their stereoisomers. It is understood that salts of the compounds provided in Table 3 are also envisioned by Table 3.

TABLE 3

| Compounds 3.1-3.14 | |
|---|---|
| Compound | Structure |
| 3.1 | ![structure] | benzyl (1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)carbamate TABLE 3-continued
Compounds 3.1-3.14
| Compound | Structure |
|---|---|
| 3.2 | 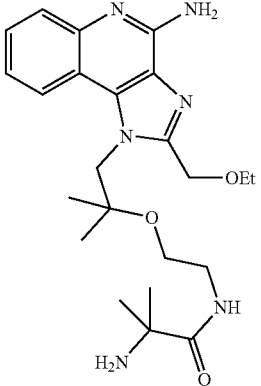 [SMILES: CCOCc1nc2c(N)nc3ccccc3c2n1CC(C)(C)OCCNC(=O)C(C)(C)N]<br>2-amino-N-(2-((1-(4-amino-2-(ethoxymethyl)-1H-imidazo[4,5-c]quinolin-1-yl)-2-methylpropan-2-yl)oxy)ethyl)-2-methylpropanamide |
| 3.3 | 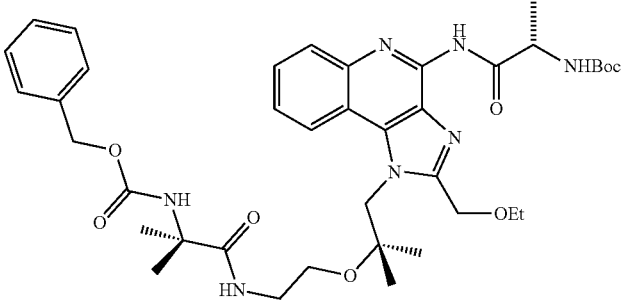<br>benzyl (S)-(1-((2-((1-(4-(2-((tert-butoxycarbonyl)amino)propanamido)-2-(ethoxymethyl)-1H-imidazo[4,5-c]quinolin-1-yl)-2-methylpropan-2-yl |
| 3.4 | 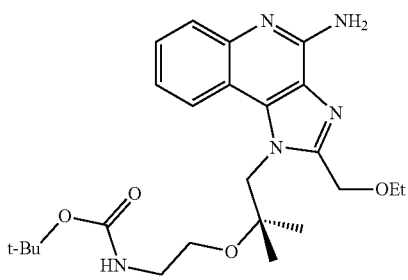<br>tert-butyl (2-((1-(4-amino-2-(ethoxymethyl)-1H-imidazo[4,5-c]quinolin-1-yl)-2-methylpropan-2-yl)oxy)ethyl)carbamate |

TABLE 3-continued
Compounds 3.1-3.14
| Compound | Structure |
|---|---|
| 3.5 | <br>tert-butyl (2-((1-(4-((S)-2-((S)-2-amino-3-methylbutanamido)-5-ureidopentanamido)-2-(ethoxymethyl)-1H-imidazo[4,5-c]quinolin-1-yl)-2-methylpropan-2-yl)oxy)ethyl)carbamate |
| 3.6 | 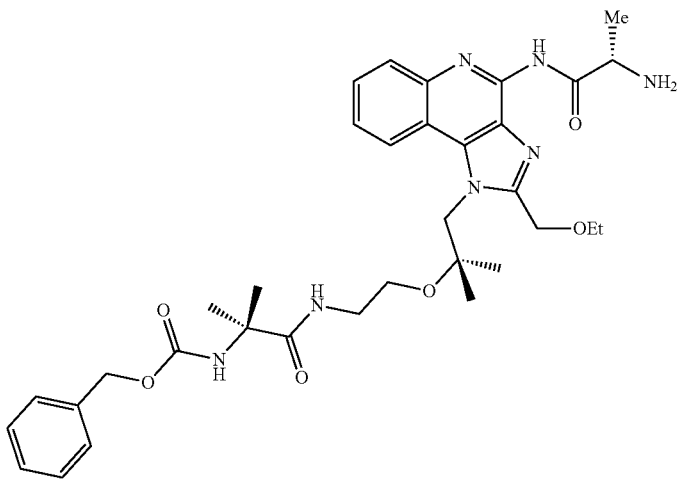<br>benzyl (S)-(1-((2-((1-(4-(2-aminopropanamido)-2-(ethoxymethyl)-1H-imidazo[4,5-c]quinolin-1-yl)-2-methylpropan-2-yl)oxy)ethyl)amino)-2-methyl-1-oxopropan-2-yl)carbamate |

TABLE 3-continued

Compounds 3.1-3.14

| Compound | Structure |
|---|---|
| 3.7 | 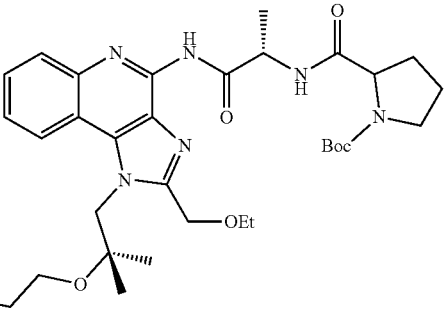<br>tert-butyl 2-(((S)-1-((2-(ethoxymethyl)-1-(5,5,11,11-tetramethyl-3,6-dioxo-1-phenyl-2,10-dioxa-4,7-diazadodecan-12-yl)-1H-imidazo[4,5-c]quinolin-4-yl)amino)-1-oxopropan-2-yl)carbamoyl)pyrrolidine-1-carboxylate |
| 3.8 | 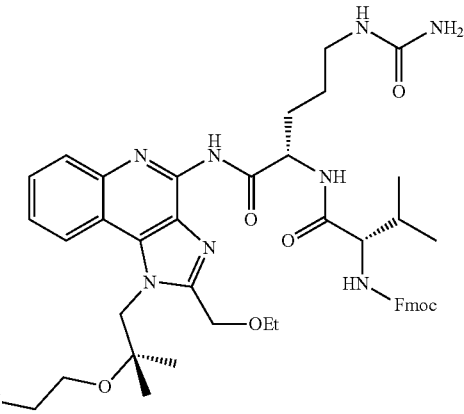<br>(9H-fluoren-9-yl)methyl ((S)-1-(((S)-1-((1-(2-(2-((tert-butoxycarbonyl)amino)ethoxy)-2-methylpropyl)-2-(ethoxymethyl)-1H-imidazo[4,5-c]quinolin-4-yl)amino)-1-oxo-5-ureidopentan-2-yl)amino)-3-methyl-1-oxobutan-2-yl)carbamate |
| 3.9 | 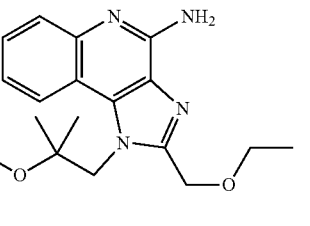 |
| 3.10 | 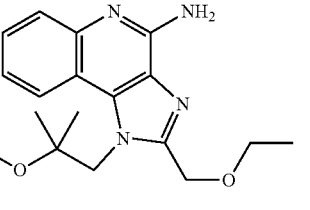 |

TABLE 3-continued

Compounds 3.1-3.14

| Compound | Structure |
|---|---|
| 3.11 | 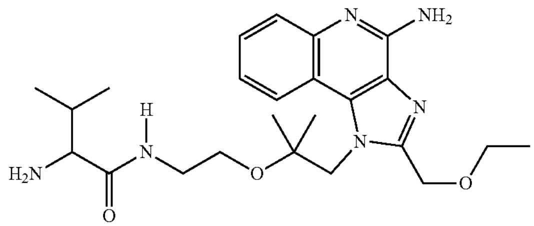 [SMILES: CCOCc1nc2c(N)nc3ccccc3c2n1CC(C)(C)OCCNC(=O)C(N)C(C)C] |
| 3.12 | 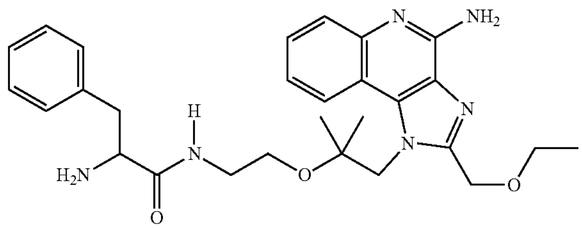 [SMILES: CCOCc1nc2c(N)nc3ccccc3c2n1CC(C)(C)OCCNC(=O)C(N)Cc1ccccc1] |
| 3.13 | 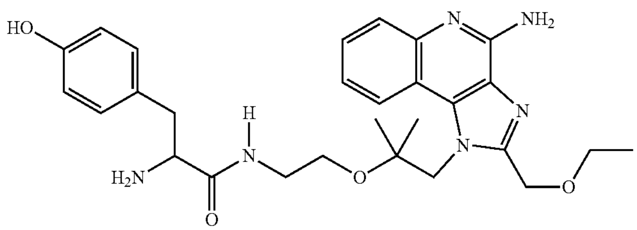 [SMILES: CCOCc1nc2c(N)nc3ccccc3c2n1CC(C)(C)OCCNC(=O)C(N)Cc1ccc(O)cc1] |
| 3.14 | 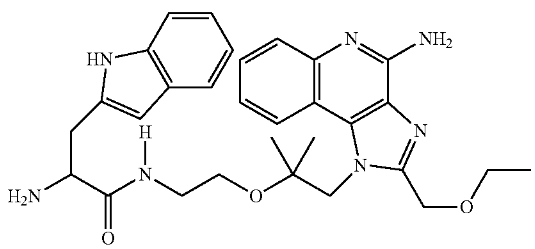 [SMILES: CCOCc1nc2c(N)nc3ccccc3c2n1CC(C)(C)OCCNC(=O)C(N)Cc1cc2ccccc2[nH]1] |

In some embodiments, the disclosure provides a conjugate represented by the following structure:

or a pharmaceutically acceptable salt thereof, wherein Ab comprises an anti-ASGR1 antibody or an antigen-binding fragment thereof of the disclosure, D is a compound or salt of a Category B compound of Formula (IID):

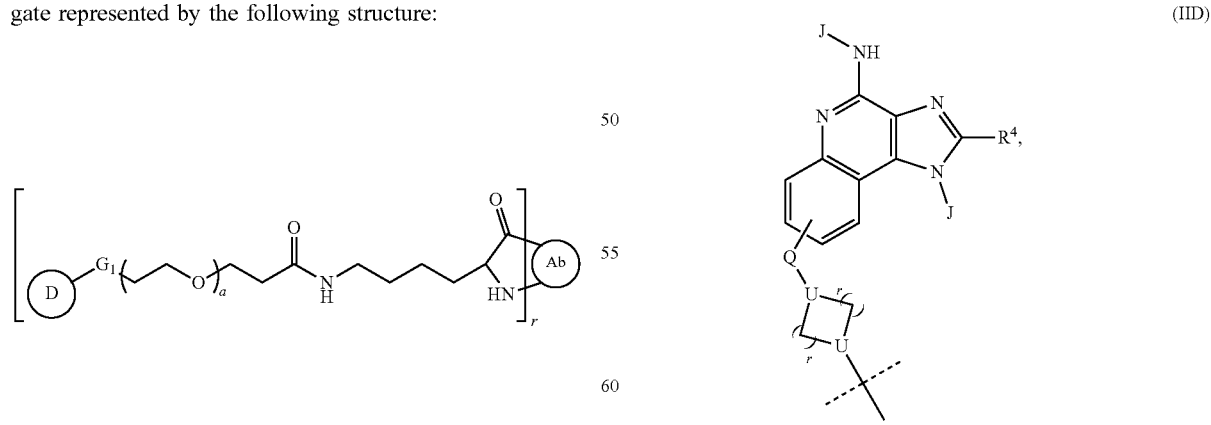

(IID)

wherein $R^4$ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10.

In some embodiments, D has the following structure:

In some embodiments, the conjugate has the following structure:

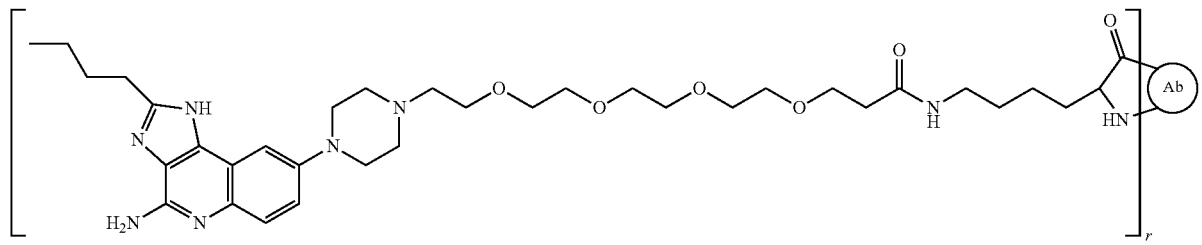

In any of the aforementioned embodiments having a conjugate structure of:

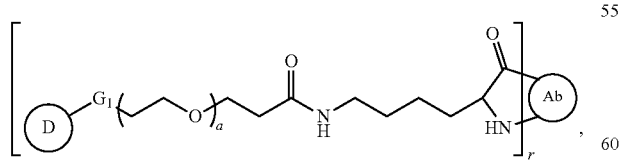

wherein D is a compound or salt of a Category B compound of Formula (IID):

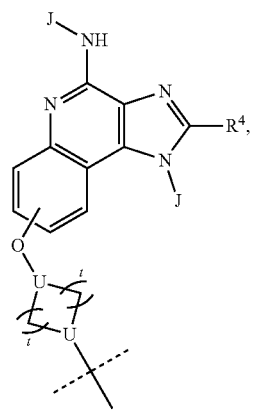

(IID)

wherein R⁴ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10; or

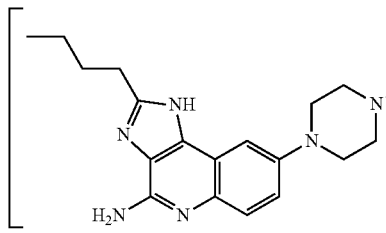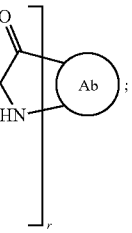

the antibody of the conjugate comprises a heavy chain variable region (VH) and a light chain variable region (VL), (1) wherein the VH comprises a CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8;

(2) wherein the VH comprises a CDR1 (VH-CDR1) comprising the amino acid sequence of SEQ ID NO:33, a VH-CDR2 comprising the amino acid sequence of SEQ ID NO:34, a VH-CDR3 comprising the amino acid sequence of SEQ ID NO:35; and the VL comprises a CDR1 (VL-CDR1) comprising the amino acid sequence of SEQ ID NO:36, a VL-CDR2 comprising the amino acid sequence of SEQ ID NO:37, and a VL-CDR3 comprising the amino acid sequence of SEQ ID NO:38;

(3) wherein the VH comprises a CDR1 (VH-CDR1) comprising the amino acid sequence of SEQ ID NO:39, a VH-CDR2 comprising the amino acid sequence of SEQ ID NO:40, a VH-CDR3 comprising the amino acid sequence of SEQ ID NO:41; and the VL comprises a CDR1 (VL-CDR1) comprising the amino acid sequence of SEQ ID NO:42, a VL-CDR2 comprising the amino acid sequence of SEQ ID NO:43, and a VL-CDR3 comprising the amino acid sequence of SEQ ID NO:44;

(4) wherein the VH comprises a CDR1 (VH-CDR1) comprising the amino acid sequence of SEQ ID NO:45, a VH-CDR2 comprising the amino acid sequence of SEQ ID NO:46, a VH-CDR3 comprising the amino acid sequence of SEQ ID NO:47; and the VL comprises a CDR1 (VL-CDR1) comprising the amino acid sequence of SEQ ID NO:48, a VL-CDR2 comprising the amino acid sequence of SEQ ID NO:49, and a VL-CDR3 comprising the amino acid sequence of SEQ ID NO:50;

(5) wherein the VH comprises a CDR1 (VH-CDR1) comprising the amino acid sequence of SEQ ID NO:51, a VH-CDR2 comprising the amino acid sequence of SEQ ID NO:52, a VH-CDR3 comprising the amino acid sequence of SEQ ID NO:53; and the VL comprises a CDR1 (VL-CDR1) comprising the amino acid sequence of SEQ ID NO:54, a VL-CDR2 comprising the amino acid sequence of SEQ ID NO:55, and a VL-CDR3 comprising the amino acid sequence of SEQ ID NO:56;

(6) wherein the VH comprises a CDR1 (VH-CDR1) comprising the amino acid sequence of SEQ ID NO:57, a VH-CDR2 comprising the amino acid sequence of SEQ ID NO:58, a VH-CDR3 comprising the amino acid sequence of SEQ ID NO:59; and the VL comprises a CDR1 (VL-CDR1) comprising the amino acid sequence of SEQ ID NO:60, a VL-CDR2 comprising the amino acid sequence of SEQ ID NO:61, and a VL-CDR3 comprising the amino acid sequence of SEQ ID NO:62;

(7) wherein VH comprises the amino acid sequence of SEQ ID NO:10, and VL comprises the amino acid sequence selected from any one of SEQ ID NOS:12-17; or (8) wherein VH comprises the amino acid of SEQ ID NO:24, and VL comprises the amino acid sequence selected from any one of SEQ ID NOS:26-31.

In another aspect, the disclosure provides a conjugate represented by the following structure:

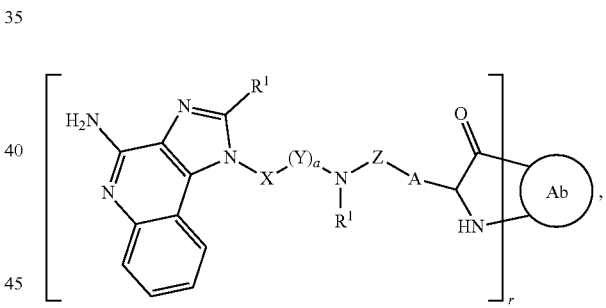

or a pharmaceutically acceptable salt thereof, wherein Ab comprises an anti-ASGR1 antibody or an antigen-binding fragment thereof of the disclosure; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$, $R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy; X is selected from O and $CH_2$; subscript n is an integer from 1 to 12; and subscript r is an integer from 1 to 10.

In some embodiments, the conjugate is represented by the following structure:

or a pharmaceutically acceptable salt thereof, wherein Ab comprises an anti-ASGR1 antibody or an antigen-binding fragment thereof of the disclosure; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$; X is selected from O and $CH_2$; subscript n is an integer from 1 to 12; and W is selected from the group consisting of O and $CH_2$.

In some embodiments, the conjugate is represented by the following structure:

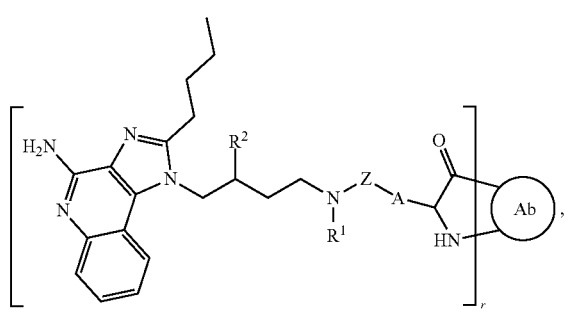

or a pharmaceutically acceptable salt thereof, wherein Ab comprises an anti-ASGR1 antibody or antigen-binding fragment thereof of the disclosure; subscript r is an integer from 1 to 10; A is an unmodified amino acid sidechain in the antibody or a modified amino acid sidechain in the antibody; Z is a linking moiety; and $R^1$ is selected from H and $C_{1-4}$ alkyl; or Z, $R^1$, and the nitrogen atom to which they are attached form a linking moiety comprising a 5- to 8-membered heterocycle; and $R^2$ is selected from H, OH, and $NH_2$.

In some embodiments, the conjugate is represented by the following structure:

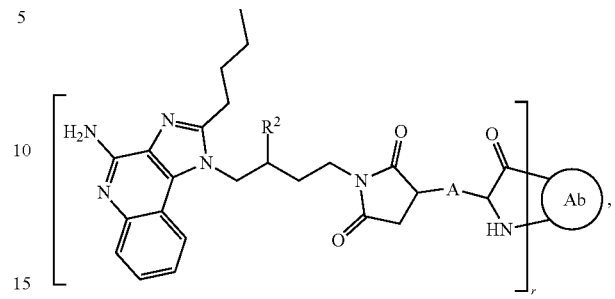

or a pharmaceutically acceptable salt thereof, wherein Ab comprises an anti-ASGR1 antibody or antigen-binding fragment thereof of the disclosure; A is an unmodified amino acid sidechain in the antibody or a modified amino acid sidechain in the antibody; $R^2$ is selected from H, OH, and $NH_2$; and subscript r is an integer from 1 to 10.

In any of the aforementioned embodiments having a conjugate structure of:

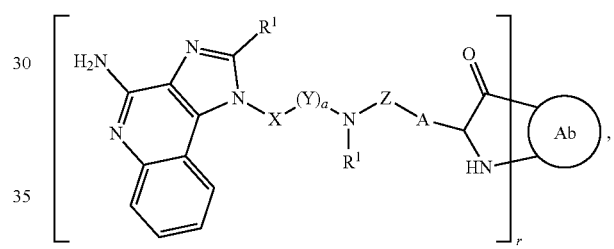

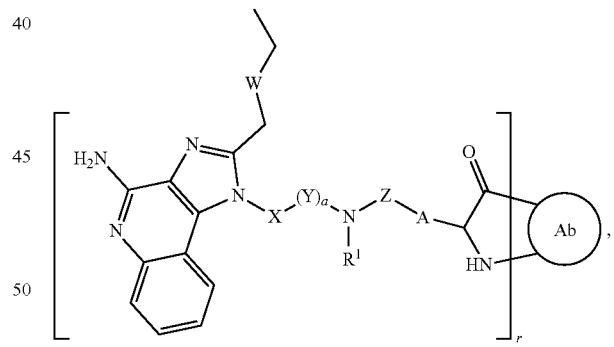

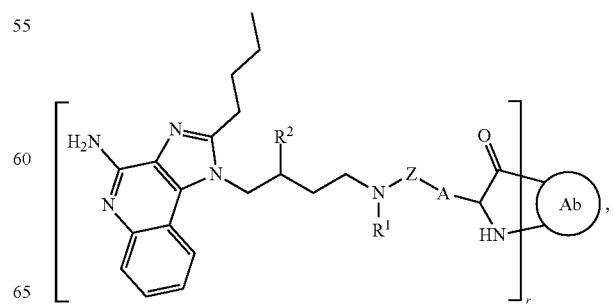

-continued
or

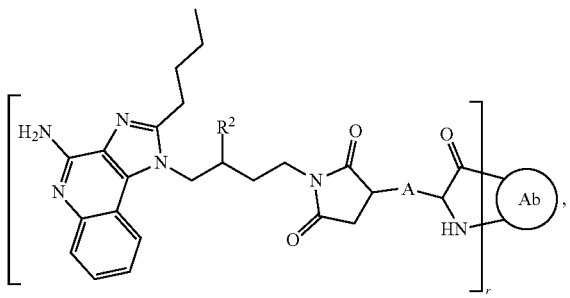

the antibody of the conjugate comprises a heavy chain variable region (VH) and a light chain variable region (VL), (1) wherein the VH comprises a CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8;

(2) wherein the VH comprises a CDR1 (VH-CDR1) comprising the amino acid sequence of SEQ ID NO:33, a VH-CDR2 comprising the amino acid sequence of SEQ ID NO:34, a VH-CDR3 comprising the amino acid sequence of SEQ ID NO:35; and the VL comprises a CDR1 (VL-CDR1) comprising the amino acid sequence of SEQ ID NO:36, a VL-CDR2 comprising the amino acid sequence of SEQ ID NO:37, and a VL-CDR3 comprising the amino acid sequence of SEQ ID NO:38;

(3) wherein the VH comprises a CDR1 (VH-CDR1) comprising the amino acid sequence of SEQ ID NO:39, a VH-CDR2 comprising the amino acid sequence of SEQ ID NO:40, a VH-CDR3 comprising the amino acid sequence of SEQ ID NO:41; and the VL comprises a CDR1 (VL-CDR1) comprising the amino acid sequence of SEQ ID NO:42, a VL-CDR2 comprising the amino acid sequence of SEQ ID NO:43, and a VL-CDR3 comprising the amino acid sequence of SEQ ID NO:44;

(4) wherein the VH comprises a CDR1 (VH-CDR1) comprising the amino acid sequence of SEQ ID NO:45, a VH-CDR2 comprising the amino acid sequence of SEQ ID NO:46, a VH-CDR3 comprising the amino acid sequence of SEQ ID NO:47; and the VL comprises a CDR1 (VL-CDR1) comprising the amino acid sequence of SEQ ID NO:48, a VL-CDR2 comprising the amino acid sequence of SEQ ID NO:49, and a VL-CDR3 comprising the amino acid sequence of SEQ ID NO:50;

(5) wherein the VH comprises a CDR1 (VH-CDR1) comprising the amino acid sequence of SEQ ID NO:51, a VH-CDR2 comprising the amino acid sequence of SEQ ID NO:52, a VH-CDR3 comprising the amino acid sequence of SEQ ID NO:53; and the VL comprises a CDR1 (VL-CDR1) comprising the amino acid sequence of SEQ ID NO:54, a VL-CDR2 comprising the amino acid sequence of SEQ ID NO:55, and a VL-CDR3 comprising the amino acid sequence of SEQ ID NO:56;

(6) wherein the VH comprises a CDR1 (VH-CDR1) comprising the amino acid sequence of SEQ ID NO:57, a VH-CDR2 comprising the amino acid sequence of SEQ ID NO:58, a VH-CDR3 comprising the amino acid sequence of SEQ ID NO:59; and the VL comprises a CDR1 (VL-CDR1) comprising the amino acid sequence of SEQ ID NO:60, a VL-CDR2 comprising the amino acid sequence of SEQ ID NO:61, and a VL-CDR3 comprising the amino acid sequence of SEQ ID NO:62;

(7) wherein VH comprises the amino acid sequence of SEQ ID NO:10, and VL comprises the amino acid sequence selected from any one of SEQ ID NOS:12-17; or (8) wherein VH comprises the amino acid of SEQ ID NO:24, and VL comprises the amino acid sequence selected from any one of SEQ ID NOS:26-31.

Compounds of Category C, TLR8 Agonists

In some embodiments, the myeloid cell agonist is a benzazepine compound (Bza). In some embodiments, the disclosure provides a conjugate represented by Formula I:

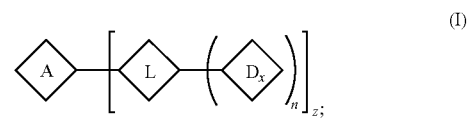

(I)

wherein: A is an anti-ASGR1 antibody or an antigen-binding fragment thereof, L is a linker; $D_x$ is an immune-stimulatory compound; n is selected from 1 to 20; and z is selected from 1 to 20.

In some embodiments of the conjugates of the disclosure, $D_x$ is selected from a compound or salt of a compound of the disclosure, including, but not limited to Category C (e.g., Formulas (Ia), (Ib), (Ic), (Id), (Ie), (If), (Ig) and (Ih)).

In some embodiments, L is represented by the formula:

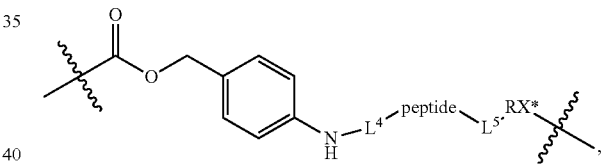

wherein
$L^4$ represents the C-terminal of the peptide and
$L^5$ is selected from a bond, alkylene and heteroalkylene,
wherein L is optionally substituted with one or more groups independently selected from $R^{32}$;
RX* comprises a bond, a succinimide moiety, or a hydrolyzed succinimide moiety bound to a residue of an antibody or antigen binding fragment thereof,
wherein

on RX* represents the point of attachment to the residue of the antibody or antigen binding fragment thereof, and,
$R^{32}$ is independently selected at each occurrence from halogen, —OH, —CN, —O-alkyl, —SH, =O, =S, —NH$_2$, —NO$_2$; and $C_{1-10}$ alkyl, $C_{2-10}$ alkenyl, $C_{2-10}$ alkynyl, each of which is optionally substituted with one or more substituents independently selected from halogen, —OH, —CN, —O-alkyl, —SH, =O, =S, —NH$_2$, —NO$_2$. In some embodiments, the peptide of L comprises Val-Cit or Val-Ala.

In some embodiments of the Category C compounds of the disclosure, $D_x$ comprises an aminobenzazepine moiety having the formula:

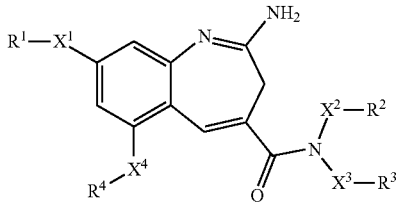

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from: —($C_1$-$C_{12}$ alkyldiyl)-N($R^5$)—*; —($C_1$-$C_{12}$ alkyldiyl)-N($R^5$)$_2$; —($C_3$-$C_{12}$ carbocyclyl); —($C_3$-$C_{12}$ carbocyclyl)-*; —($C_3$-$C_{12}$ carbocyclyl)-($C_1$-$C_{12}$ alkyldiyl)-NR$^5$—*; —($C_3$-$C_{12}$ carbocyclyl)-($C_1$-$C_{12}$ alkyldiyl)-N($R^5$)$_2$; —($C_3$-$C_{12}$ carbocyclyl)-NR$^5$—C(=NR$^5$)NR$^5$—*; —($C_6$-$C_{20}$ aryl); —($C_6$-$C_{20}$ aryl)-*; —($C_6$-$C_{20}$ aryldiyl)-N($R^5$)—*; —($C_6$-$C_{20}$ aryldiyl)-($C_1$-$C_{12}$ alkyldiyl)-N($R^5$)—*; —($C_6$-$C_{20}$ aryldiyl)-($C_1$-$C_{12}$ alkyldiyl)-N($R^5$)$_2$; —($C_6$-$C_{20}$ aryldiyl)-($C_1$-$C_{12}$ alkyldiyl)-NR$^5$—C(=NR$^{5a}$)N($R^5$)—*; —($C_2$-$C_{20}$ heterocyclyl); —($C_2$-$C_{20}$ heterocyclyl)-*; —($C_2$-$C_9$ heterocyclyl)-($C_1$-$C_{12}$ alkyldiyl)-NR5-*; —($C_2$-$C_9$ heterocyclyl)-($C_1$-$C_{12}$ alkyldiyl)-N(R5)$_2$; —($C_2$-$C_9$ heterocyclyl)-NR$^5$—C(=NR$^{5a}$)NR$^5$—*; —($C_1$-$C_{20}$ heteroaryl); —($C_1$-$C_{20}$ heteroaryl)-*; —($C_1$-$C_{20}$ heteroaryl)-($C_1$-$C_{12}$ alkyldiyl)-N($R^5$)—*; —($C_1$-$C_{20}$ heteroaryl)-($C_1$-$C_{12}$ alkyldiyl)-N($R^5$)$_2$; —($C_1$-$C_{20}$ heteroaryl)-NR$^5$—C(=NR$^{5a}$)N($R^5$)—*; —C(=O)—*; —C(=O)—($C_2$-$C_{20}$ heterocyclyldiyl)-*; —C(=O)N($R^5$)$_2$; —C(=O)N($R^5$)—*; —C(=O)N($R^5$)—($C_1$-$C_{12}$ alkyldiyl)-N($R^5$)C(=O)R$^5$; —C(=O)N($R^5$)—($C_1$-$C_{12}$ alkyldiyl)-N($R^5$)C(=O)N($R^5$)$_2$; —C(=O)NR$^5$—($C_1$-$C_{12}$ alkyldiyl)-N($R^5$)CO$_2$R$^5$; —C(=O)NR$^5$—($C_1$-$C_{12}$ alkyldiyl)-N($R^5$)C(=NR$^{5a}$)N($R^5$)$_2$; —C(=O)NR$^5$—($C_1$-$C_{12}$ alkyldiyl)-NR$^5$C(=NR$^{5a}$)R$^5$; —C(=O)NR$^5$—($C_1$-$C_5$ alkyldiyl)-NR$^5$($C_2$-$C_5$ heteroaryl); —C(=O)NR$^5$—($C_1$-$C_{20}$ heteroaryldiyl)-N($R^5$)—*; —C(=O)NR$^5$, —($C_1$-$C_{20}$ heteroaryldiyl)-*; —C(=O)NR$^5$—($C_1$-$C_{20}$ heteroaryldiyl)-($C_1$-$C_{12}$ alkyldiyl)-N($R^5$)$_2$; —C(=O)NR$^5$—($C_1$-$C_{20}$ heteroaryldiyl)-($C_2$-$C_{20}$ heterocyclyldiyl)-C(=O)NR$^5$—($C_1$-$C_{12}$ alkyldiyl)-NR*; —N($R^5$)$_2$; —N($R^5$)—*; —N($R^5$)C(=O) R$^5$; —N($R^5$)C(=O)—*; —N($R^5$)C(=O)N($R^5$)$_2$; —N($R^5$)C(=O)N($R^5$)—*; —N($R^5$)CO$_2$R$^5$; —NR$^5$C(=NR$^{5a}$)N($R^5$)$_2$; —NR$^5$C(=NR$^{5a}$)N($R^5$)—*; —NR$^5$C(=NR$^{5a}$)R$^5$; —N($R^5$)—($C_2$-$C_5$ heteroaryl); —O—($C_1$-$C_{12}$ alkyl); —O—($C_1$-$C_{12}$ alkyldiyl)-N($R^5$)$_2$; —O—($C_1$-$C_{12}$ alkyldiyl)-N($R^5$)—*; —S(=O)$_2$—($C_2$-$C_{20}$ heterocyclyldiyl)-*; —S(=O)$_2$—($C_2$-$C_{20}$ heterocyclyldiyl)-($C_1$-$C_{12}$ alkyldiyl)-N($R^5$)$_2$; —S(=O)$_2$—($C_2$-$C_{20}$ heterocyclyldiyl)-($C_1$-$C_{12}$ alkyldiyl)-NR$^5$*; and —S(=O)$_2$—($C_2$-$C_{20}$ heterocyclyldiyl)-($C_1$-$C_{12}$ alkyldiyl)-OH; or $R^2$ and $R^3$ together form a 5- or 6-membered heterocyclyl ring;

$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$);

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two Rs groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk* indicates the attachment site of L, and where one of $R^1$, $R^2$, $R^3$ and $R^4$ is attached to L;

L is the linker selected from the group consisting of: —C(=O)-(PEG)-; —C(=O)-(PEG)-C(=O)—; —C(=O)-(PEG)-O—; —C(=O)-(PEG)-C(=O)-(PEP)-; —C(=O)-(PEG)-C(=O)N($R^5$)—($C_1$-$C_{12}$ alkyldiyl)-; —C(=O)-(PEG)-C(=O)N($R^5$)—($C_1$-$C_{12}$ alkyldiyl)-N($R^5$)C(=O)—($C_2$-$C_5$ monoheterocyclyldiyl)-; —C(=O)-(PEG)-C(=O)N($R^5$)—($C_1$-$C_{12}$ alkyldiyl)-(MCgluc)-; —C(=O)-(PEG)-C(=O)-(MCgluc)-; —C(=O)-(PEG)-C(=O)-(PEP)—N($R^5$)—($C_1$-$C_{12}$ alkyldiyl)-; —C(=O)-(PEG)-C(=O)-(PEP)—N($R^5$)—($C_1$-$C_{12}$ alkyldiyl)-N($R^5$)C(=O)—($C_2$-$C_5$ monoheterocyclyldiyl)-; —C(=O)-(PEG)-N($R^5$)—; —C(=O)-(PEG)-N($R^5$)—(PEG)-C(=O)-(PEP)-; —C(=O)-(PEG)-N+($R^5$)$_2$-(PEG)-C(=O)-(PEP)-; —C(=O)-(PEG)-C(=O)—N($R^5$)CH(AA$_1$)C(=O)-(PEG)-C(=O)-(PEP)-; —C(=O)-(PEG)-C(=O)—N($R^5$)CH(AA$_1$)C(=O)—N($R^5$)—($C_1$-$C_{12}$ alkyldiyl)-; —C(=O)-(PEG)-SS—($C_1$-$C_{12}$ alkyldiyl)-OC(=O)—; —C(=O)-(PEG)-SS—($C_1$-$C_{12}$ alkyldiyl)-C(=O)—; —C(=O)—($C_1$-$C_{12}$ alkyldiyl)-C(=O)-(PEP)-; —C(=O)—($C_1$-$C_{12}$ alkyldiyl)-C(=O)-(PEP)-N($R^5$)—($C_1$-$C_{12}$ alkyldiyl)-; —C(=O)—($C_1$-$C_{12}$ alkyldiyl)-C(=O)-(PEP)—N($R^5$)—($C_1$-$C_{12}$ alkyldiyl)-N($R^5$)—C(=O); —C(=O)—($C_1$-$C_{12}$ alkyldiyl)-C(=O)-(PEP)—N($R^5$)—($C_1$-$C_{12}$ alkyldiyl)-N($R^5$)C(=O)—($C_2$-$C_5$ monoheterocyclyldiyl)-; —C(=O)—CH$_2$CH$_2$OCH$_2$CH$_2$—($C_1$-$C_{20}$ heteroaryldiyl)-CH$_2$O-(PEG)-C(=O)(MCgluc)-; —C(=O)—CH$_2$CH$_2$OCH$_2$CH$_2$—($C_1$-$C_{20}$ heteroaryldiyl)-CH$_2$O-(PEG)-C(=O)(MCgluc)-N($R^5$)—($C_1$-$C_{12}$ alkyldiyl)-N($R^5$)C(=O)—($C_2$-$C_5$ monoheterocyclyldiyl)-; and -(succinimidyl)-(CH$_2$)$_m$—C(=O)-(PEP)—N($R^5$)—($C_1$-$C_{12}$ alkyldiyl)-N($R^5$)C(=O)—($C_2$-$C_5$ monoheterocyclyldiyl)-;

PEG has the formula: —(CH$_2$CH$_2$O)$_n$—(CH$_2$)$_m$—; m is an integer from 1 to 5, and n is an integer from 2 to 50;

PEP has the formula:

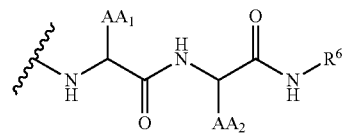

where AA$_1$ and AA$_2$ are independently selected from an amino acid side chain, or AA$_1$ or AA$_2$ and an adjacent nitrogen atom form a 5-membered ring praline amino acid, and the wavy line indicates a point of attachment;

$R^6$ is selected from the group consisting of $C_6$-$C_{20}$ aryldiyl and $C_1$-$C_{20}$ heteroaryldiyl, substituted with —CH$_2$O—C(=O)— and optionally with:

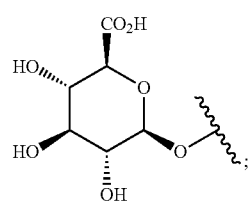 [SMILES: *O[C@@H]1O[C@H](C(=O)O)[C@@H](O)[C@H](O)[C@H]1O]

221 and
MCgluc is selected from the groups:

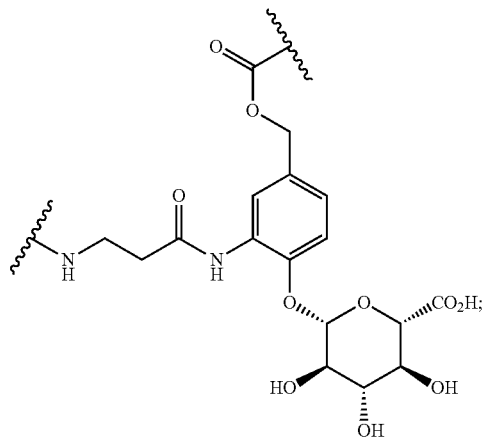

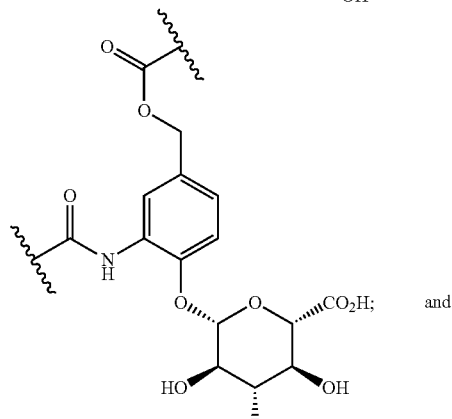 and

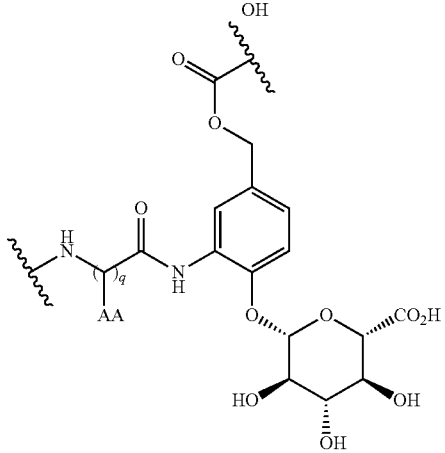

where q is 1 to 8, and AA is an amino acid side chain; and
alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —CH$_3$, —CH$_2$CH$_3$, —CH=CH$_2$, —C≡CH, —C≡CCH$_3$, —CH$_2$CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN,

222

—C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NHC(=NH)H, —NHC(=NH)CH$_3$, —NHC(=NH)NH$_2$, —NHC(=O)NH$_2$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —O(CH$_2$CH$_2$O)$_n$—(CH$_2$)mCO$_2$H, —O(CH$_2$CH$_2$O)$_n$H, —OP(O)(OH)$_2$, —S(O)$_2$N(CH$_3$)$_2$, —SCH$_3$, —S(O)$_2$CH$_3$, and —S(O)$_3$H.

In some embodiments, the PEP is selected from the groups:

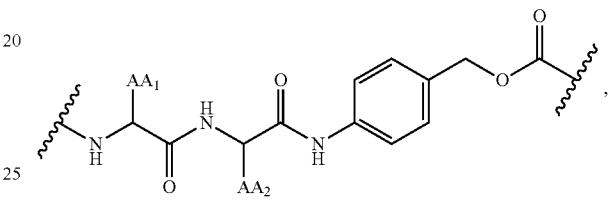

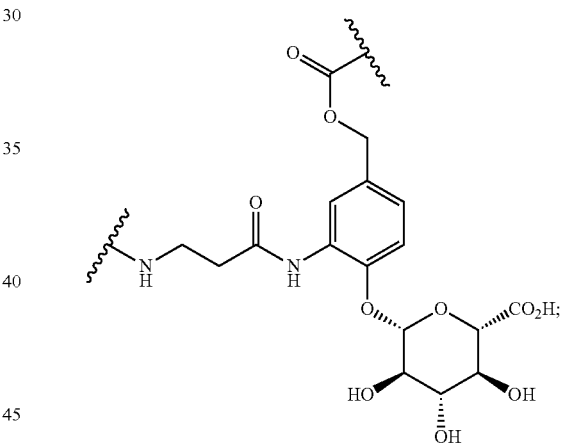

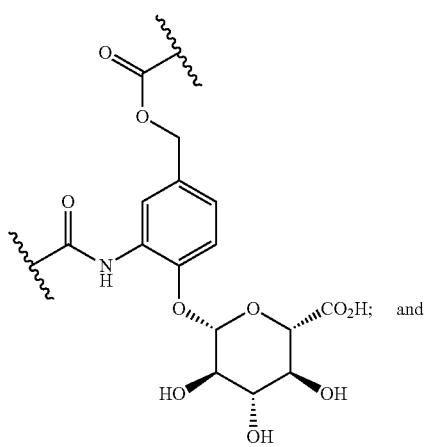 and

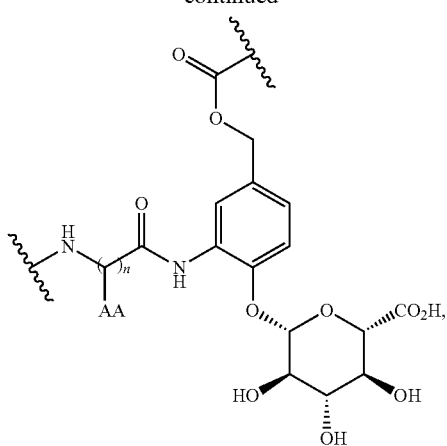

wherein n is 1 or more and AA is an amino acid side chain. In some embodiments of Formula I, each of $AA_1$ and $AA_2$ are independently selected from a side chain of a naturally-occurring amino acid. In some embodiments of Formula I, each of $AA_1$ and $AA_2$ are independently selected from H, —$CH_3$, —$CH(CH_3)_2$, —$CH_2(C_6H_5)$, —$CH_2CH_2CH_2CH_2NH_2$, —$CH_2CH_2CH_2NHC(NH)NH_2$, —$CH_2CH(CH_3)_2$, —$CH_2SO_3H$, and —$CH_2CH_2CH_2NHC(O)NH_2$. In some embodiments of Formula I, $AA_1$ is —$CH(CH_3)_2$ and $AA_2$ is —$CH_2CH_2CH_2NHC(O)NH_2$. In some embodiments of Formula I, each of $AA_1$ and $AA_2$ are independently selected from GlcNAc, aspartic acid, —$CH_2SO_3H$ and —$CH_2OPO_3H$.

In some embodiments of the formulas of the disclosure, including Formula I of Category C, L-$D_x$ is selected from Formulas Ia-Id:

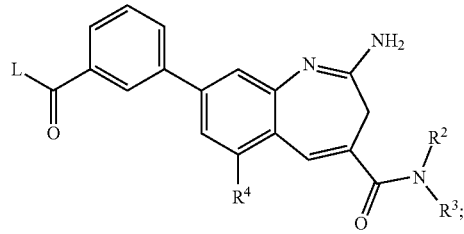

Ia

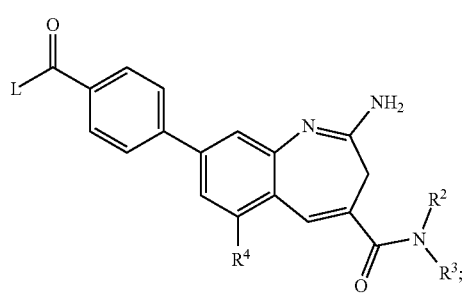

Ib

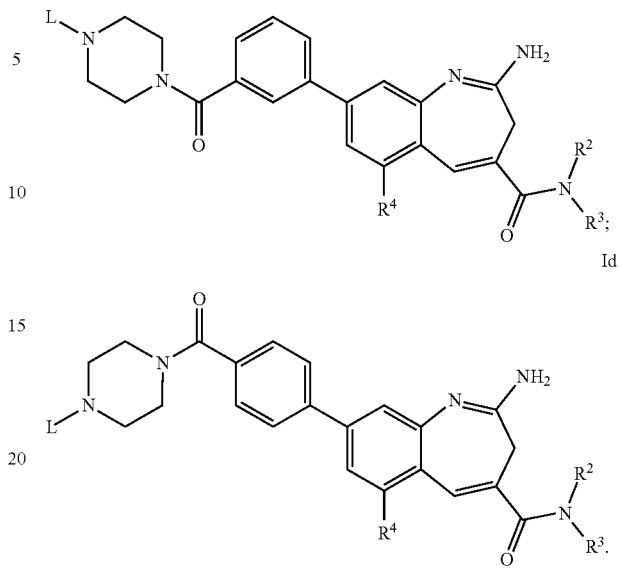

Ic

Id

In some embodiments of the formulas of the disclosure, including Formula I of Category C, L is —C(=O)-(PEG)- or —C(=O)-(PEG)-C(=O)—. In some embodiments of the formulas of the disclosure, including Formula I of Category C, L-D is selected from Formulas Ie and If:

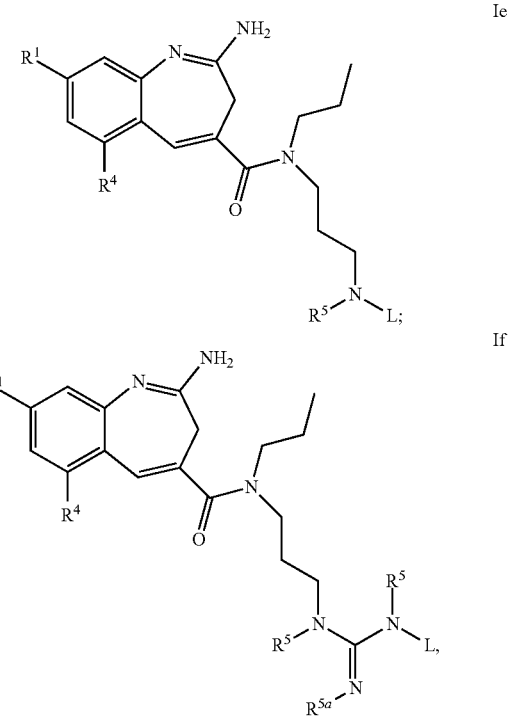

Ie

If wherein $R^{5a}$ of Formula If is phenyl, optionally substituted with one or more groups selected from F, Cl, Br, I, —CN, and —$NO_2$. In some embodiments of the formulas of the disclosure, including Formula I of Category C, L-$D_x$ is selected from Formulas Ig and Ih:

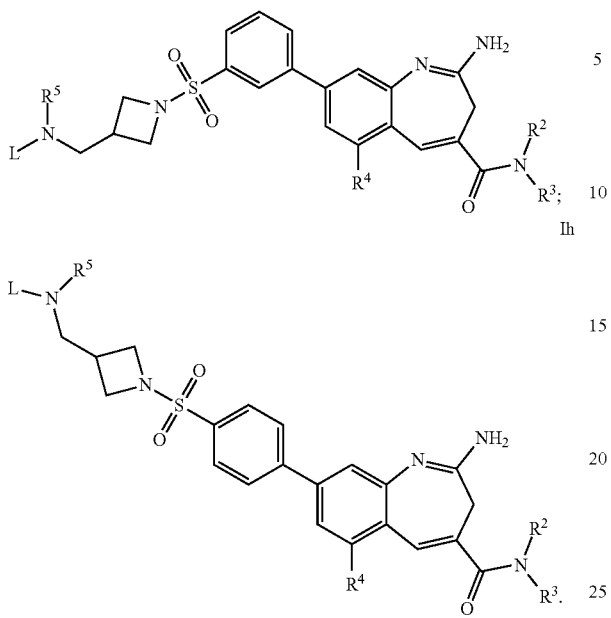

In some embodiments of the formulas of the disclosure, including Formula I of Category C, L is —C(=O)-(PEG)-C(=O)-(PEP)-.

In some embodiments of the formulas of the disclosure, including Formula I of Category C, $R^2$ and $R^3$ are each $C_1$-$C_5$ alkyl.

In some embodiments of the formulas of the disclosure, including Formula I of Category C, $R^2$ and $R^3$ are each —CH$_2$CH$_2$CH$_3$.

In some embodiments of the formulas of the disclosure, including Formula I of Category C, $R^2$ and $R^3$ are each a bond, and $R^2$ or $R^3$ is —O—($C_1$-$C_{12}$ alkyl).

In some embodiments of the formulas of the disclosure, including Formula I of Category C, $R^2$ and $R^3$ are each a bond, and $R^2$ or $R^3$ is —OCH$_2$CH$_3$.

In some embodiments of the formulas of the disclosure, including Formula I of Category C, one of $R^1$ and $R^4$ is selected from: —($C_1$-$C_{12}$ alkyldiyl)-N($R^5$)—*; —($C_1$-$C_{12}$ alkyldiyl)-N($R^5$)C(=N$R^5$)N($R^5$)—*; —($C_6$-$C_{20}$ aryldiyl)-S(=O)$_2$—($C_2$-$C_{20}$ heterocyclyldiyl)-*; —($C_6$-$C_{20}$ aryldiyl)-S(=O)$_2$—($C_2$-$C_{20}$ heterocyclyldiyl)-($C_1$-$C_{12}$ alkyldiyl)-N($R^5$)—*; —($C_6$-$C_{20}$ aryldiyl)-C(=O)—*; —($C_6$-$C_{20}$ aryldiyl)-($C_1$-$C_{12}$ alkyldiyl)-N($R^5$)—*; —($C_6$-$C_{20}$ aryldiyl)-C(=O)—($C_2$-$C_{20}$ heterocyclyldiyl)-*; —C(=O)N$R^5$—($C_1$-$C_{20}$ heteroaryldiyl)-*; and —C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$—*.

In some embodiments of the formulas of the disclosure, including Formula I of Category C, one of $R^2$ and $R^3$ is selected from: —($C_1$-$C_{12}$ alkyldiyl)-N($R^5$)—*; —($C_1$-$C_{12}$ alkyldiyl)-O—($C_1$-$C_{12}$ alkyldiyl)-N($R^5$)—*; —($C_1$-$C_{12}$ alkyldiyl)-N($R^5$)C(=N$R^5$)—N($R^5$)—*; —($C_1$-$C_{12}$ alkyldiyl)-($C_6$-$C_{20}$ aryldiyl)-($C_1$-$C_{12}$ alkyldiyl)-N($R^5$)—*; —($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*; —($C_2$-$C_6$ alkynyldiyl)-N($R^5$)—*; and —($C_2$-$C_6$ alkynyldiyl)-N($R^5$)C(=N$R^5$)N($R^5$)—*; $X^2$ and $X^3$ are a bond, and where the asterisk* indicates the attachment site of L.

In some embodiments of the formulas of the disclosure, including Formula I of Category C, one of $R^1$ and $R^4$ is selected from —($C_6$-$C_{20}$ aryldiyl)-S(=O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(=O)$_2$—($C_2$-$C_{20}$ heterocyclyldiyl)-($C_1$-$C_{12}$ alkyldiyl)-OH.

In some embodiments of the formulas of the disclosure, including Formula I of Category C, $C_6$-$C_{20}$ aryldiyl is phenyldiyl and $C_2$-$C_{20}$ heterocyclyldiyl is azetidindiyl.

In some embodiments of the formulas of the disclosure, including Formula I of Category C, one of $R^1$ and $R^4$ is selected from the formulas:

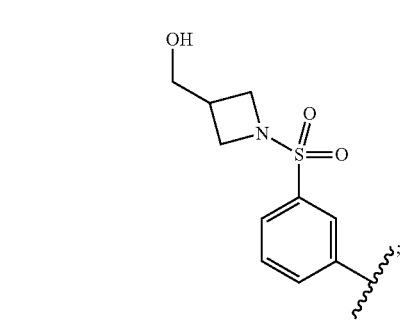

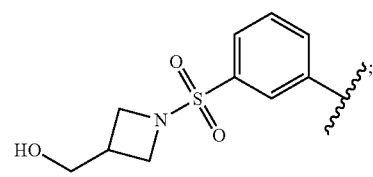

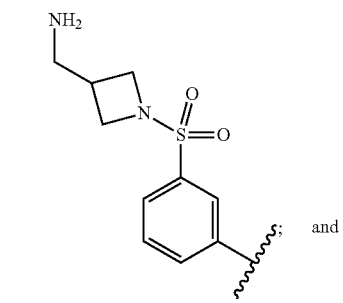

and

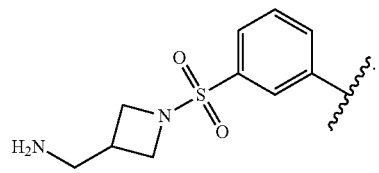

In some embodiments of the formulas of the disclosure, including Formula I of Category C, one of $R^1$ and $R^4$ is —C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$-L.

In some embodiments of the formulas of the disclosure, including Formula I of Category C, $C_1$-$C_{20}$ heteroaryldiyl is pyridindiyl and $C_2$-$C_{20}$ heterocyclyldiyl is piperidiyl.

In some embodiments, the disclosure provides a conjugate comprising a benzazepine according to Formula (II):

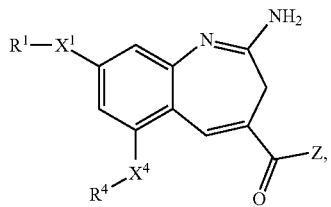

wherein

Z is selected from H, —O(C$_1$-C$_8$ alkyl), and N(X$^2$R$^2$)(X$^3$R$^3$);

R$^1$, R$^2$, R$^3$, and R$^4$ are independently selected from the group consisting of H, C$_1$-C$_{12}$ alkyl, C$_2$-C$_6$ alkenyl, C$_2$-C$_6$ alkynyl, C$_3$-C$_{12}$ carbocyclyl, C$_6$-C$_{20}$ aryl, C$_2$-C$_9$ heterocyclyl, and C$_1$-C$_{20}$ heteroaryl, where alkyl, alkenyl, alkynyl, carbocyclyl, aryl, heterocyclyl, and heteroaryl are independently and optionally substituted with one or more groups selected from: —(C$_1$-C$_{12}$ alkyldiyl)-N(R$^5$)—*; —(C$_1$-C$_{12}$ alkyldiyl)-N(R$^5$)$_2$; —(C$_3$-C$_{12}$ carbocyclyl); —(C$_3$-C$_{12}$ carbocyclyl)-*; —(C$_3$-C$_{12}$ carbocyclyl)-(C$_1$-C$_{12}$ alkyldiyl)-NR$^5$—*; —(C$_3$-C$_{12}$ carbocyclyl)-(C$_1$-C$_{12}$ alkyldiyl)-N(R$^5$)$_2$; —(C$_3$-C$_{12}$ carbocyclyl)-NR$^5$—C(=NR$^5$)NR$^5$—*; —(C$_6$-C$_{20}$ aryl); —(C$_6$-C$_{20}$ aryl)-*; —(C$_6$-C$_{20}$ aryldiyl)-N(R$^5$)—*; —(C$_6$-C$_{20}$ aryldiyl)-(C$_1$-C$_{12}$ alkyldiyl)-N(R$^5$)—*; —(C$_6$-C$_{20}$ aryldiyl)-(C$_1$-C$_{12}$ alkyldiyl)-N(R$^5$)$_2$; —(C$_6$-C$_{20}$ aryldiyl)-(C$_1$-C$_{12}$ alkyldiyl)-NR$^5$—C(=NR$^{5a}$)N(R$^5$)—*; —(C$_2$-C$_{20}$ heterocyclyl); —(C$_2$-C$_{20}$ heterocyclyl)-*; —(C$_2$-C$_9$ heterocyclyl)-(C$_1$-C$_{12}$ alkyldiyl)-NR$^5$—*; —(C$_2$-C$_9$ heterocyclyl)-(C$_1$-C$_{12}$ alkyldiyl)-N(R$^5$)$_2$; —(C$_2$-C$_9$ heterocyclyl)-NR$^5$—C(=NR$^{5a}$)NR$^5$—*; —(C$_1$-C$_{20}$ heteroaryl); —(C$_1$-C$_{20}$ heteroaryl)-*; —(C$_1$-C$_{20}$ heteroaryl)-(C$_1$-C$_{12}$ alkyldiyl)-N(R$^5$)—*; —(C$_1$-C$_{20}$ heteroaryl)-(C$_1$-C$_{12}$ alkyldiyl)-N(R$^5$)$_2$; —(C$_1$-C$_{20}$ heteroaryl)-NR$^5$—C(=NR$^{5a}$)N(R$^5$)—*; —C(=O)—*; —C(=O)—(C$_2$-C$_{20}$ heterocyclyldiyl)-*; —C(=O)N(R$^5$)$_2$; —C(=O)N(R$^5$)—*; —C(=O)N(R$^5$)—(C$_1$-C$_{12}$ alkyldiyl)-N(R$^5$)C(=O)R$^5$; —C(=O)N(R$^5$)—(C$_1$-C$_{12}$ alkyldiyl)-N(R$^5$)C(=O)N(R$^5$)$_2$; —C(=O)NR$^5$—(C$_1$-C$_{12}$ alkyldiyl)-N(R$^5$)CO$_2$R$^5$; —C(=O)NR$^5$—(C$_1$-C$_{12}$ alkyldiyl)-N(R$^5$)C(=NR$^{5a}$)N(R$^5$)$_2$; —C(=O)NR$^5$—(C$_1$-C$_{12}$ alkyldiyl)-NR$^5$C(=NR$^{5a}$)R$^5$; —C(=O)NR$^5$—(C$_1$-C$_8$ alkyldiyl)-NR$^5$ (C$_2$-C$_8$ heteroaryl); —C(=O)NR$^5$—(C$_1$-C$_{20}$ heteroaryldiyl)-N(R$^5$)—*; —C(=O)NR$^5$—(C$_1$-C$_{20}$ heteroaryldiyl)-*; —C(=O)NR$^5$—(C$_1$-C$_{20}$ heteroaryldiyl)-(C$_1$-C$_{12}$ alkyldiyl)-N(R$^5$)$_2$; —C(=O)NR$^5$—(C$_1$-C$_{20}$ heteroaryldiyl)-(C$_2$-C$_{20}$ heterocyclyldiyl)-C(=O)NR$^5$—(C$_1$-C$_{12}$ alkydiyl)-NR$^5$—*; —N(R$^5$)$_2$; —N(R$^5$)—*; —N(R$^5$)C(=O)R$^5$; —N(R$^5$)C(=O)—*; —N(R$^5$)C(=O)N(R$^5$)$_2$; —N(R$^5$)C(=O)N(R$^5$)—*; —N(R$^5$)CO$_2$R$^5$; —NR$^5$C(=NR$^{5a}$)N(R$^5$)$_2$; —NR$^5$C(=NR$^{5a}$)N(R$^5$)—*; —NR$^5$C(=NR$^{5a}$)R$^5$; —N(R$^5$)—(C$_2$-C$_8$ heteroaryl); —O—(C$_1$-C$_{12}$ alkyl); —O—(C$_1$-C$_{12}$ alkyldiyl)-N(R$^5$)$_2$; —O—(C$_1$-C$_{12}$ alkyldiyl)-N(R$^5$)—*; —S(=O)$_2$—(C$_2$-C$_{20}$ heterocyclyldiyl)-*; —S(=O)$_2$—(C$_2$-C$_{20}$ heterocyclyldiyl)-(C$_1$-C$_{12}$ alkyldiyl)-N(R$^5$)$_2$; —S(=O)$_2$—(C$_2$-C$_{20}$ heterocyclyldiyl)-(C$_1$-C$_{12}$ alkyldiyl)-NR$^5$—*; and —S(=O)$_2$—(C$_2$-C$_{20}$ heterocyclyldiyl)-(C$_1$-C$_{12}$ alkyldiyl)-OH; or R$^2$ and R$^3$ together form a 5- or 6-membered heterocyclyl ring;

X$^1$, X$^2$, X$^3$, and X$^4$ are independently selected from the group consisting of a bond, C(=O), C(=O)N(R$^5$), O, N(R$^5$), S, S(O)$_2$, and S(O)$_2$N(R$^5$);

R$^5$ is selected from the group consisting of H, C$_6$-C$_{20}$ aryl, C$_6$-C$_{20}$ aryldiyl, C$_1$-C$_{12}$ alkyl, and C$_1$-C$_{12}$ alkyldiyl, or two R$^5$ groups together form a 5- or 6-membered heterocyclyl ring;

R$^{5a}$ is selected from the group consisting of C$_6$-C$_{20}$ aryl and C$_1$-C$_{20}$ heteroaryl; where the asterisk* indicates the attachment site of L, and where one of R$^{10}$, R$^2$, R$^3$ and R$^4$ is attached to L;

L is the linker selected from the group consisting of: Q-C(=O)-(PEG)-; Q-C(=O)-(PEG)-C(=O)—; Q-C(=O)-(PEG)-O—; Q-C(=O)-(PEG)-C(=O)-(PEP)-; Q-C(=O)-(PEG)-C(=0)N(R$^5$)—(C$_1$-C$_{12}$ alkyldiyl)-; Q-C(=O)-(PEG)-C(=O)N(R$^5$)—(C$_1$-C$_{12}$ alkyldiyl)-N(R$^5$)C(=O)—(C$_2$-C$_8$ monoheterocyclyldiyl)-; Q-C(=O)-(PEG)-C(=O)N(R$^5$)—(C$_1$-C$_{12}$ alkyldiyl)-(MCgluc)-; Q-C(=O)-(PEG)-C(=O)-(MCgluc)-; Q-C(=O)-(PEG)-C(=O)-(PEP)-N(R$^5$)—(C$_1$-C$_{12}$ alkyldiyl)-; Q-C(=O)-(PEG)-C(=O)-(PEP)—N(R$^5$)—(C$_1$-C$_{12}$ alkyldiyl)-N(R$^5$)C(=O)—(C$_2$-C$_8$ monoheterocyclyldiyl)-; Q-C(=O)-(PEG)-N(R$^5$)—; Q-C(=O)-(PEG)-N(R$^5$)-(PEG)-C(=O)-(PEP)-; Q-C(=O)-(PEG)-N+(R$^5$)$_2$-(PEG)-C(=O)-(PEP)-; Q-C(=O)-(PEG)-C(=O)—N(R$^5$)CH(AA$_1$)C(=O)-(PEG)-C(=O)-(PEP)-; Q-C(=O)-(PEG)-C(=O)—N(R$^5$)CH(AA$_1$)C(=O)—N(R$^5$)—(C$_1$-C$_{12}$ alkyldiyl)-; Q-C(=O)-(PEG)-SS—(C$_1$-C$_{12}$ alkyldiyl)-OC(=O)—; Q-C(=O)-(PEG)-SS—(C$_1$-C$_{12}$ alkyldiyl)-C(=O)—; Q-C(=O)—(C$_1$-C$_{12}$ alkyldiyl)-C(=O)-(PEP)-; Q-C(=O)—(C$_1$-C$_{12}$ alkyldiyl)-C(=O)-(PEP)—N(R$^5$)—(C$_1$-C$_{12}$ alkyldiyl)-; Q-C(=O)—(C$_1$-C$_{12}$ alkyldiyl)-C(=O)-(PEP)—N(R$^5$)—(C$_1$-C$_{12}$ alkyldiyl)-N(R$^5$)—C(=O); Q-C(=O)—(C$_1$-C$_{12}$ alkyldiyl)-C(=O)-(PEP)—N(R$^5$)—(C$_1$-C$_{12}$ alkyldiyl)-N(R$^5$)C(=O) (C$_2$-C$_5$ monoheterocyclyldiyl)-; Q-C(=O)—CH$_2$CH$_2$OCH$_2$CH$_2$—(C$_1$-C$_{20}$ heteroaryldiyl)-CH$_2$O-(PEG)-C(=O)(MCgluc)-; Q-C(=O)—CH$_2$CH$_2$OCH$_2$CH$_2$—(C$_1$-C$_{20}$ heteroaryldiyl)-CH$_2$O-(PEG)-C(=O)(MCgluc)-N(R$^5$)—(C$_1$-C$_{12}$ alkyldiyl)-N(R$^5$)C(=O)—(C$_2$-C$_5$ monoheterocyclyldiyl)-; and Q-(CH$_2$)$_m$—C(=O)-(PEP)—N(R$^5$)—(C$_1$-C$_{12}$ alkyldiyl)-N(R$^5$)C(=O)—(C$_2$-C$_5$ monoheterocyclyldiyl)-;

where PEG has the formula: —(CH$_2$CH$_2$O)$_n$—(CH$_2$)$_m$—;
m is an integer from 1 to 5, and n is an integer from 2 to 50;
PEP has the formula:

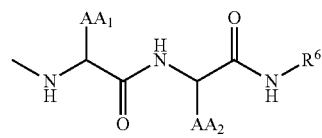

where AA$_1$ and AA$_2$ are independently selected from an amino acid side chain, or AA$_1$ or AA$_2$ and an adjacent nitrogen atom form a 5-membered ring praline amino acid, and the wavy line indicates a point of attachment and;

R$^6$ is selected from the group consisting of C$_6$-C$_{20}$ aryldiyl and C$_1$-C$_{20}$ heteroaryldiyl, substituted with —CH$_2$O—C(=O)— and optionally with:

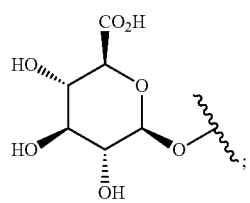 [SMILES: *O[C@@H]1O[C@H](C(=O)O)[C@@H](O)[C@H](O)[C@H]1O]

and
MCgluc is selected from the groups:

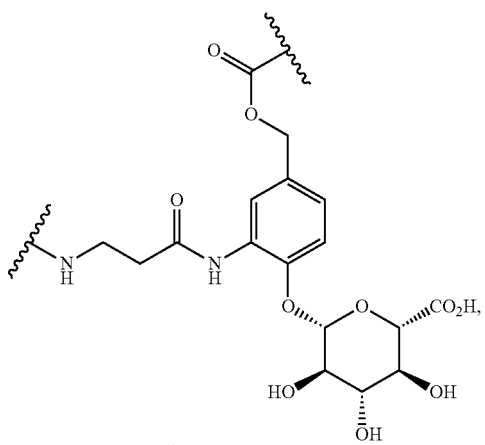

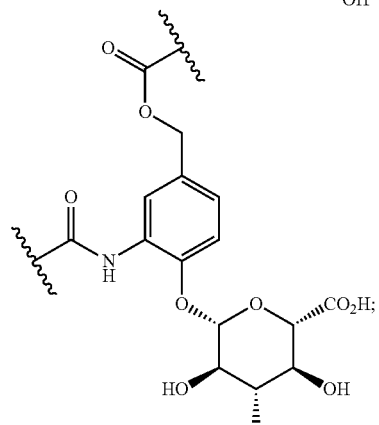
and

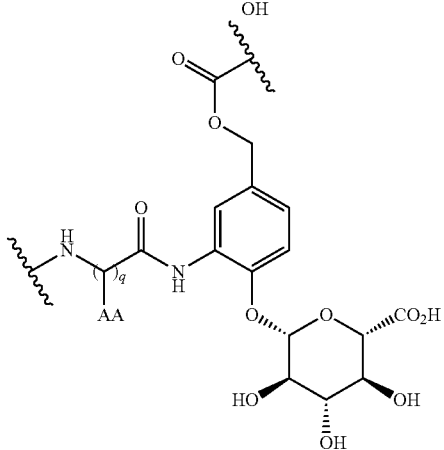

where q is 1 to 8, and AA is an amino acid side chain; and

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —CH($CH_3$)$_2$, —$CH_2$CH($CH_3$)$_2$, —$CH_2$OH, —$CH_2$O$CH_3$, —$CH_2CH_2$OH, —C($CH_3$)$_2$OH, —CH(OH)CH($CH_3$)$_2$, —C($CH_3$)$_2CH_2$OH, —$CH_2CH_2SO_2CH_3$, —$CH_2$OP(O)(OH)$_2$, —$CH_2$F, —$CHF_2$, —$CF_3$, —$CH_2CF_3$, —$CH_2CHF_2$, —CH($CH_3$)CN, —C($CH_3$)$_2$CN, —$CH_2$CN, —$CH_2NH_2$, —$CH_2NHSO_2CH_3$, —$CH_2NHCH_3$, —$CH_2$N($CH_3$)$_2$, —$CO_2$H, —$COCH_3$, —$CO_2CH_3$, —$CO_2$C($CH_3$)$_3$, —COCH(OH)$CH_3$, —$CONH_2$, —$CONHCH_3$, —CON($CH_3$)$_2$, —C($CH_3$)$_2CONH_2$, —$NH_2$, —$NHCH_3$, —N($CH_3$)$_2$, —$NHCOCH_3$, —N($CH_3$)$COCH_3$, —NHS(O)$_2CH_3$, —N($CH_3$)C($CH_3$)$_2CONH_2$, —N($CH_3$)$CH_2CH_2$S(O)$_2CH_3$, —NHC(=NH)H, —NHC(=NH)$CH_3$, —NHC(=NH)$NH_2$, —NHC(=O)$NH_2$, —$NO_2$, =O, —OH, —$OCH_3$, —$OCH_2CH_3$, —$OCH_2CH_2OCH_3$, —$OCH_2CH_2$OH, —$OCH_2CH_2$N($CH_3$)$_2$, —O($CH_2CH_2$O)$_n$—($CH_2$)$_m$$CO_2$H, —O($CH_2CH_2$O)$_n$H, —OP(O)(OH)$_2$, —S(O)$_2$N($CH_3$)$_2$, —$SCH_3$, —S(O)$_2CH_3$, and —S(O)$_3$H.

In some embodiments of the formulas of the disclosure, including Formula (II) of Category C, PEP is selected from the groups:

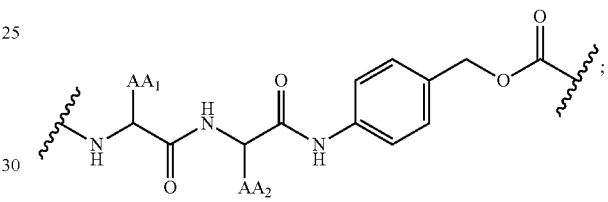

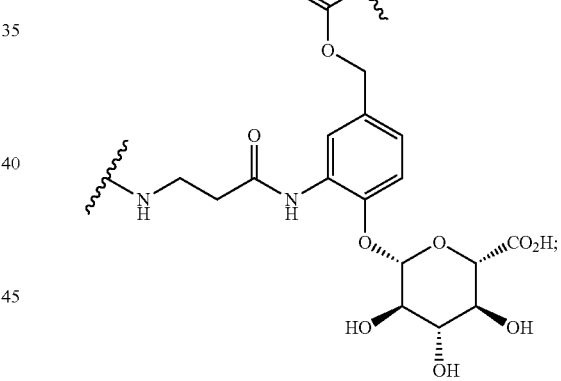

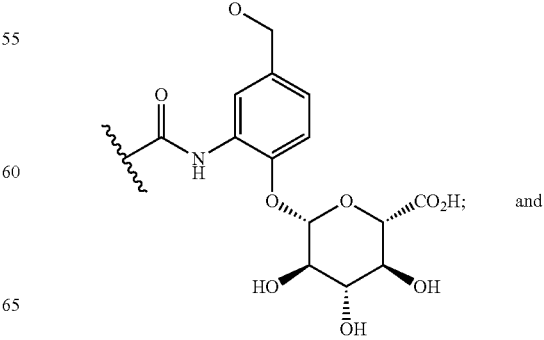
and

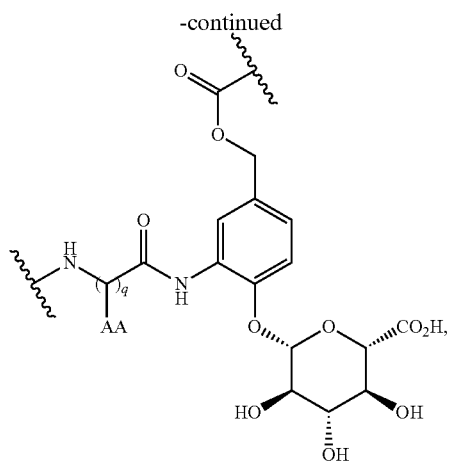

wherein n is 1 or more and AA is an amino acid side chain.

In some embodiments of the formulas of the disclosure, including Formula (II) of Category C, each $AA_1$ and $AA_2$ are independently selected from a side chain of a naturally-occurring amino acid.

In some embodiments of the formulas of the disclosure, including Formula (II) of Category C, $AA_1$ and $AA_2$ are independently selected from H, —$CH_3$, —$CH(CH_3)_2$, —$CH_2(C_6H_5)$, —$CH_2CH_2CH_2CH_2NH_2$, —$CH_2CH_2CH_2NHC(NH)NH_2$, —$CH_2CH(CH_3)_2$, —$CH_2SO_3H$, and —$CH_2CH_2CH_2NHC(O)NH_2$.

In some embodiments of the formulas of the disclosure, including Formula (II) of Category C, each $AA_1$ is —CH$(CH_3)_2$, and $AA_2$ is —$CH_2CH_2CH_2NHC(O)NH_2$.

In some embodiments of the formulas of the disclosure, including Formula (II) of Category C, each $AA_1$ and $AA_2$ are independently selected from GlcNAc aspartic acid, —$CH_2SO_3H$, and —$CH_2OPO_3H$.

In some embodiments of the formulas of the disclosure, including Formula II of Category C, the aminobenzazepine-linker compound of Formula (II) is selected from Formulas IIa-IId:

IIa
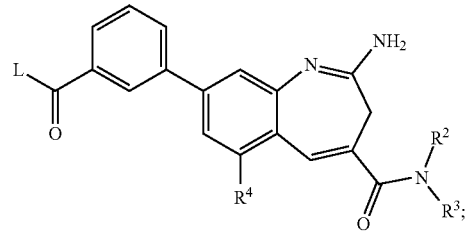

IIb
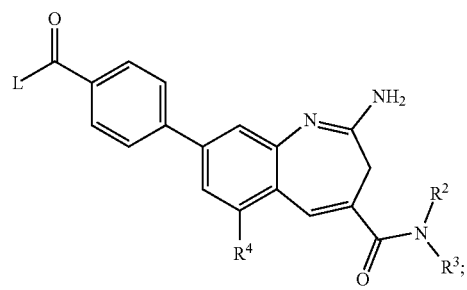

IIc
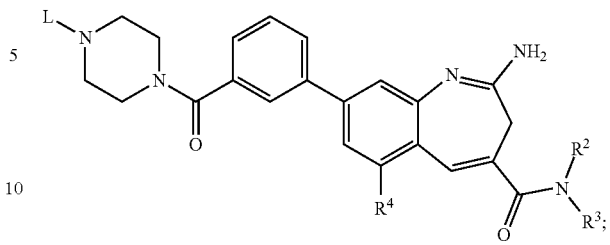

and

IId
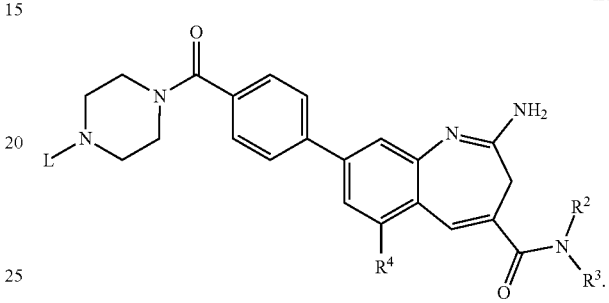

In some embodiments of the formulas of the disclosure, including Formula II of Category C, the aminobenzazepine-linker compound of Formula (II) is selected from Formulas IIe and IIf:

IIe
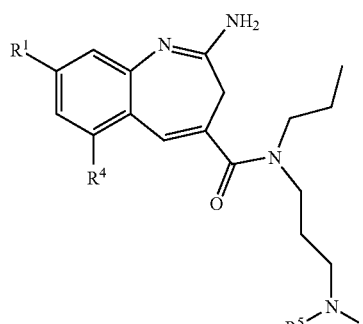

and

IIf
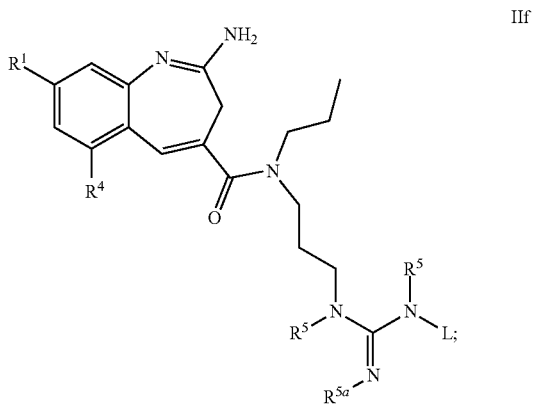

wherein $R^{5a}$ of formula IIf is phenyl, optionally substituted with one or more groups selected from F, Cl, Br, I, —CN, and —$NO_2$.

In some embodiments of the formulas of the disclosure, including Formula II of Category C, L is Q-C(=O)-(PEG)- or Q-C(=O)-(PEG)-C(=O)—.

In some embodiments of the formulas of the disclosure, including Formula II of Category C, the aminobenzazepine-linker compound of Formula II is selected from Formulas IIg and IIh:

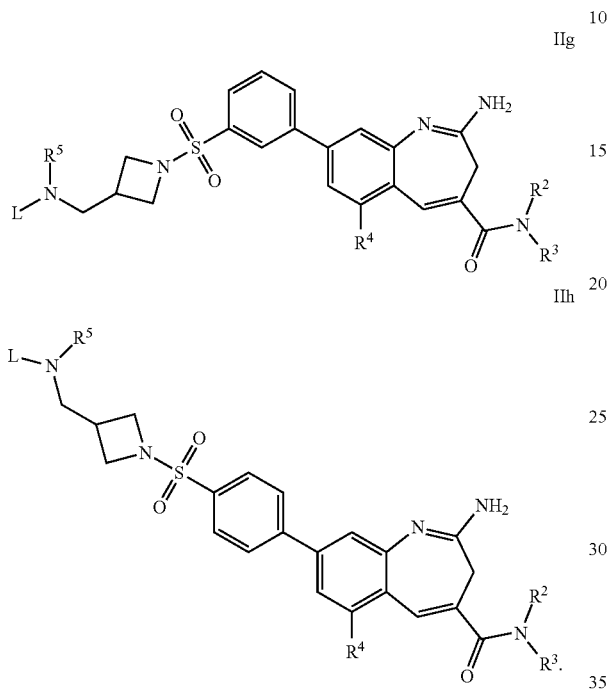

In some embodiments of the formulas of the disclosure, including Formula II of Category C, L is —C(=O)-(PEG)-C(=O)-(PEP)-.

In some embodiments of the formulas of the disclosure, including Formula II of Category C, $R^2$ and $R^3$ are each $C_1$-$C_8$ alkyl.

In some embodiments of the formulas of the disclosure, including Formula II of Category C, $R^2$ and $R^3$ are each —$CH_2CH_2CH_3$.

In some embodiments of the formulas of the disclosure, including Formula II of Category C, $X^2$ and $X^3$ are each a bond, and $R^2$ and $R^3$ is —O—($C_1$-$C_{12}$ alkyl).

In some embodiments of the formulas of the disclosure, including Formula II of Category C, $X^2$ and $X^3$ are each a bond, and $R^2$ and $R^3$ is —$OCH_2CH_3$.

In some embodiments of the formulas of the disclosure, including Formula II of Category C, one of $R^1$ and $R^4$ is selected from —($C_6$-$C_{20}$ aryldiyl)-S(=O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(=O)$_2$—($C_2$-$C_{20}$ heterocyclyldiyl)-($C_1$-$C_{12}$ alkyldiyl)-OH.

In some embodiments of the formulas of the disclosure, including Formula II of Category C, $C_6$-$C_{20}$ aryldiyl is phenyldiyl and $C_2$-$C_{20}$ heterocyclyldiyl is azetidindiyl.

In some embodiments of the formulas of the disclosure, including Formula II of Category C, the aminobenzazepine-linker compound of Formula II is selected from Formulas:

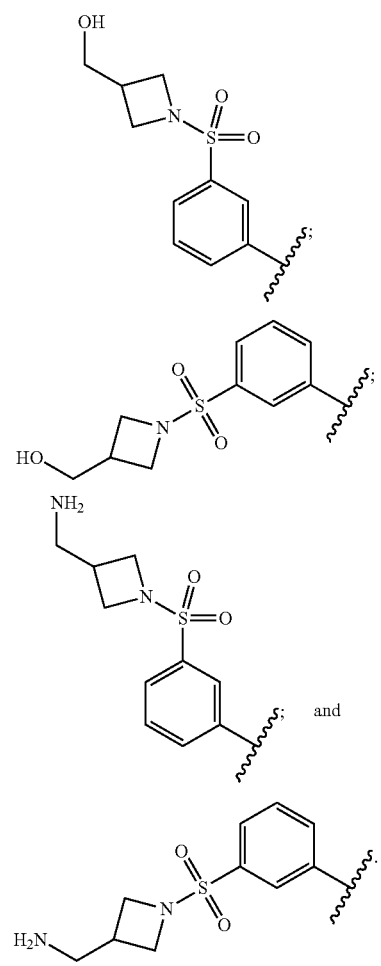

In some embodiments of the formulas of the disclosure, including Formula II of Category C, one of $R^1$ and $R^4$ is —C(=O)NR$^5$—($C_1$-$C_{20}$ heteroaryldiyl)-($C_2$-$C_{20}$ heterocyclyldiyl)-C(=O)NR$^5$—($C_1$-$C_{12}$ alkyldiyl)-NR$^5$-L.

In some embodiments of the formulas of the disclosure, including Formula II of Category C, $C_1$-$C_{20}$ heteroaryldiyl is pyridindiyl and $C_2$-$C_{20}$ heterocyclyldiyl is piperidiyl.

In some embodiments of the formulas of the disclosure, including Formula II of Category C, Q is selected from:

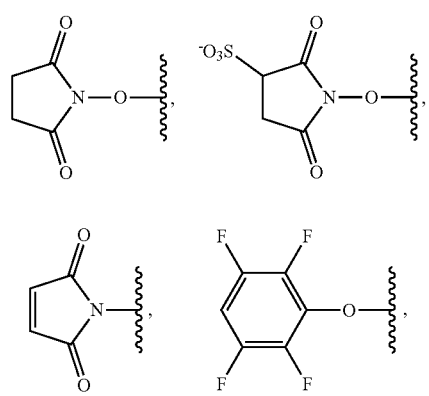

-continued

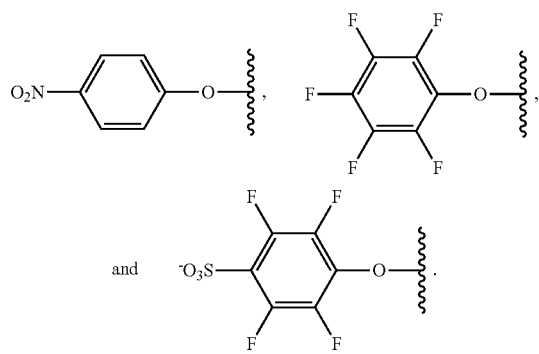

In some embodiments, the disclosure provides a conjugate comprising a benzazepine according to Formula III:

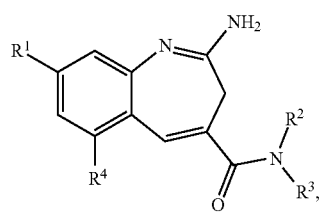

a pharmaceutically acceptable salt thereof, or a quaternary ammonium salt thereof, wherein $R^1$, $R^2$, $R^3$, and $R^4$ are independently Y or Z, wherein one of $R^1$, $R^2$, $R^3$, and $R^4$ is Y, having the formula:

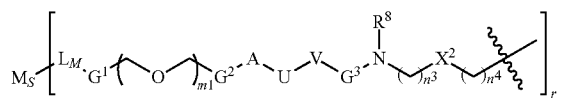

or

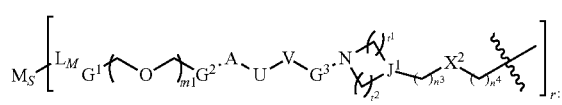

each Z independently is hydrogen or selected from the formulas:

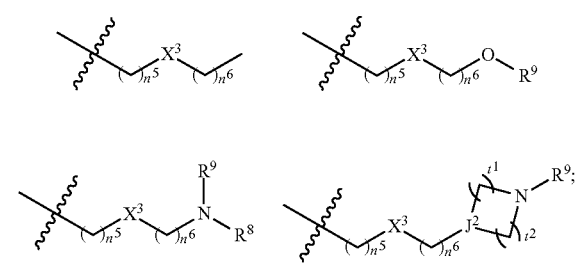

U is optionally present and is $CH_2$, $C(=O)$, $CH_2C(=O)$, or $C(=O)CH_2$,

A is optionally present and is $NR^{10}$ or selected from the formulas:

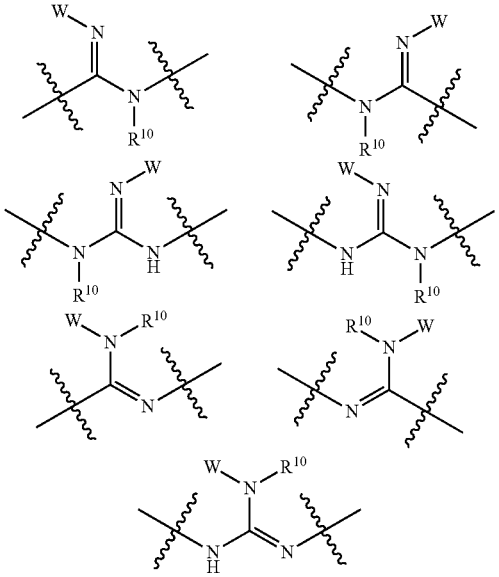

$R^{10}$ and W independently are hydrogen, $Ar^1$, or of formula:

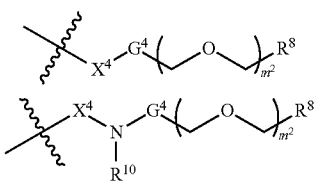

V is optionally present and is of formula:

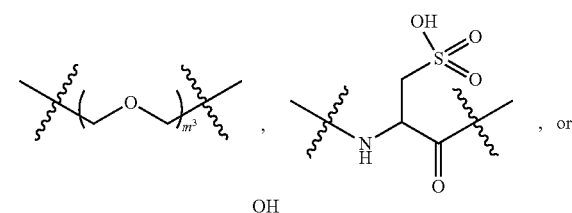

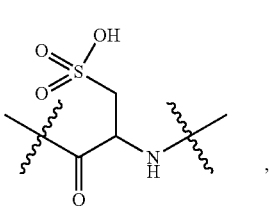

$J^1$ and $J^2$ independently are CH or N, $m^1$, $m^2$, and $m^3$ independently are an integer from 0 to 25, except that at least one of $m^1$, $m^2$, and $m^3$ is a non-zero integer, $n^1$, $n^2$, $n^3$, $n^4$, $n^5$, and $n^6$ independently are an integer from 0 to 10, $t_1$ and $t_2$ independently are an integer from 1 to 3, $G_1$, $G_2$, $G_3$, and $G_4$ independently are $CH_2$, $C(=O)$, $CH_2C(=O)$, $C(=O)CH_2$, or a bond, $X^1$, $X^2$, $X^3$, and $X^4$ are each optionally present and independently are O, $NR^7$, $CHR^7$, $SO_2$, S, or one or two cycloalkyldiyl, heterocycloalkyldiyl, aryldiyl, or heteroaryldiyl groups, and when more than one cycloalkyldiyl, heterocycloalkyldiyl, aryldiyl, or heteroaryldiyl group is present, the more than one cycloalkyldiyl, heterocycloalkyldiyl, aryldiyl, or heteroaryldiyl groups are linked or fused, wherein linked cycloalkyldiyl, heterocycloalkyldiyl, aryldiyl, or heteroaryldiyl groups are linked through a bond or —CO—, $R^9$ is hydrogen, $C_1$-$C_4$ alkyl, or selected from the formulas:

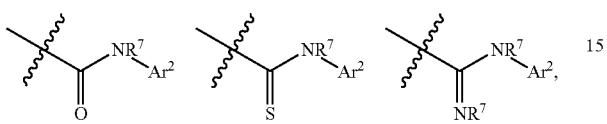

$R^8$ is independently hydrogen or $C_1$-$C_4$ alkyl, $Ar^1$ and $Ar^2$ independently are an aryl or heteroaryl group, optionally substituted with one or more halogens (e.g., fluorine, chlorine, bromine, or iodine), nitriles, hydroxyls, $C_1$-$C_4$ alkyl groups, or a combination thereof, $L_M$ is a linking moiety that comprises a functional group selected from an amide, amine, ester, carbamate, urea, thioether, thiocarbamate, thiocarbonate, and thiourea, r is an integer from 1 to 50, "Ms" is a macromolecular support, and each wavy line (~) represents a point of attachment.

Nonlimiting examples of TLR8 agonist compounds of Category C are provided in Table 1b.

TABLE 1b

Compounds 1.70-1.74

| Compound | Structure |
|---|---|
| 1.70 | |
| 1.71 | 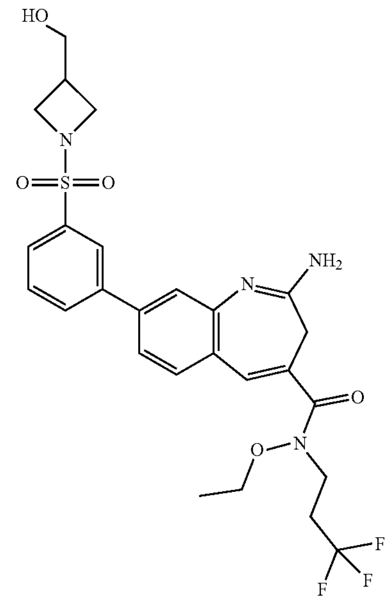 [SMILES: CCON(CCC(F)(F)F)C(=O)C1=Cc2ccc(-c3cccc(S(=O)(=O)N4CC(CO)C4)c3)cc2N=C(N)C1] |
| 1.72 | 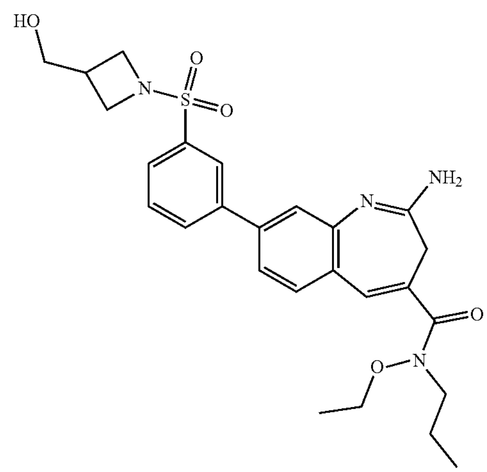 [SMILES: CCCN(OCC)C(=O)C1=Cc2ccc(-c3cccc(S(=O)(=O)N4CC(CO)C4)c3)cc2N=C(N)C1] |
| 1.73 | 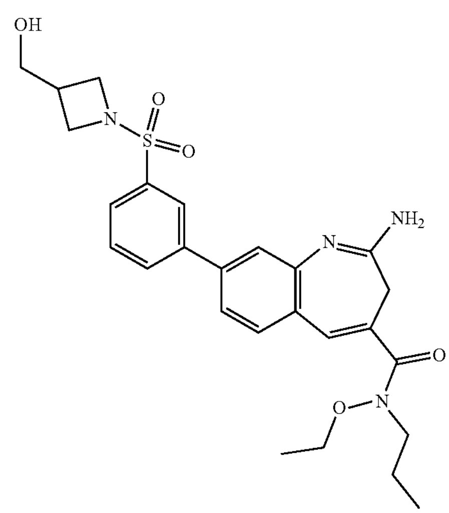 [SMILES: CCCN(OCC)C(=O)C1=Cc2ccc(-c3cccc(S(=O)(=O)N4CC(CO)C4)c3)cc2N=C(N)C1] |

TABLE 1b-continued

Compounds 1.70-1.74

| Compound | Structure |
|---|---|
| 1.74 | (structure depicted) |

Linkers

The conjugates include a linker(s) that attaches an anti-ASGR1 antibody or antigen-binding fragment thereof to at least one immune-stimulatory compound, such as a myeloid cell agonist. A linker can be, for example, a cleavable or a non-cleavable linker. A conjugate can comprise multiple linkers. The linkers in a conjugate can be the same linkers or different linkers.

As will be appreciated by skilled artisans, a linker connects an immune-stimulatory compound(s), such as a myeloid cell agonist, to the antibody or antigen-binding fragment thereof by forming a covalent linkage to the compound at one location and a covalent linkage to the antibody or antigen-binding fragment thereof at another location. The covalent linkages can be formed by reaction between functional groups on the linker and functional groups on the immune-stimulatory compound and on the antibody or antigen-binding fragment thereof. As used throughout the disclosure, the expression "linker" can include (i) unattached forms of the linker that can include a functional group capable of covalently attaching the linker to an immune-stimulatory compound and a functional group capable of covalently attached the linker to an antibody or antigen-binding fragment thereof; (ii) partially attached forms of the linker that can include a functional group capable of covalently attaching the linker to an antibody or antigen-binding fragment thereof and that can be covalently attached to an immune-stimulatory compound, or vice versa; and (iii) fully attached forms of the linker that can be covalently attached to both an immune stimulatory compound and to an antibody or antigen-binding fragment thereof. In some specific embodiments, the functional groups on a linker and covalent linkages formed between the linker and an antibody or antigen-binding fragment thereof can be specifically illustrated as Rx and Rx', respectively.

A linker can be short, long, flexible, rigid, cleavable, non-cleavable, hydrophilic, hydrophobic, unbranched (e.g., where z is 1), or branched (e.g., where z is greater than 1). A linker can contain segments that have different characteristics, such as segments of flexibility or segments of rigidity, segments of hydrophilicity, and/or segments of hydrophobicity. A linker can be chemically stable to extracellular environments, for example, chemically stable in the blood stream, and/or may include linkages that are not stable or selectively stable. A linker can include linkages that are designed to cleave and/or immolate or otherwise breakdown specifically or non-specifically inside cells. A cleavable linker can be sensitive to enzymes at a specific site, such as the lysosome or the extracellular space adjacent target cells. A cleavable linker can be cleaved by enzymes such as proteases.

A cleavable linker can include a valine-citrulline (Val-Cit) peptide, a valine-alanine peptide (Val-Ala), a phenylalanine-lysine (Phe-Lys) or other peptide, such as a peptide that forms a protease recognition and cleavage site. Such a peptide-containing linker can contain a pentafluorophenyl group. A peptide-containing linker can include a succimide or a maleimide group. A peptide-containing linker can include a para aminobenzoic acid (PABA) group. A peptide-containing linker can include an aminobenzyloxycarbonyl (PABC) group. A peptide-containing linker can include a PABA or PABC group and a pentafluorophenyl group. A peptide-containing linker can include a PABA or PABC group and a succinimide group. A peptide-containing linker can include a PABA or PABC group and a maleimide group.

A non-cleavable linker is generally protease-insensitive and insensitive to intracellular processes. A non-cleavable linker can include a maleimide group. A non-cleavable linker can include a succinimide group. A non-cleavable linker can be maleimido-alkyl-C(O)— linker. A non-cleavable linker can be maleimidocaproyl linker. A maleimidocaproyl linker can be N-maleimidomethylcyclohexane-1-carboxylate. A maleimidocaproyl linker can include a succinimide group. A maleimidocaproyl linker can include pentafluorophenyl group.

A linker can be a combination of a maleimidocaproyl group and one or more polyethylene glycol molecules. A linker can be a maleimide-PEG4 linker. A linker can be a combination of a maleimidocaproyl linker containing a succinimide group and one or more polyethylene glycol molecules. A linker can be a combination of a maleimidocaproyl linker containing a pentafluorophenyl group and one or more polyethylene glycol molecules. A linker can contain a maleimide(s) linked to polyethylene glycol molecules in which the polyethylene glycol can allow for more linker flexibility or can be used lengthen the linker.

A linker can be a (maleimidocaproyl)-(valine-alanine)-(para-aminobenzyloxycarbonyl) linker. A linker can be a (maleimidocaproyl)-(valine-citrulline)-(para-aminobenzyloxycarbonyl) linker. A linker can be a (maleimidocaproyl)-(phenylalanine-lysine)-(para-aminobenzyloxycarbonyl) linker. A linker can be a linker suitable for attachment to an engineered cysteine (THIOMAB). A THIOMAB linker can be a (maleimidocaproyl)-(valine-citrulline)-(para-aminobenzyloxycarbonyl)-linker.

A linker can also contain segments of alkylene, alkenylene, alkynylene, polyether, polyester, polyamide, polyamino acids, peptides, polypeptides, cleavable peptides, and/or aminobenzyl-carbamates. A linker can contain a maleimide at one end and an N-hydroxysuccinimidyl ester at the other end. A linker can contain a lysine with an N-terminal amine acetylated, and a valine-citrulline, valine-alanine or phenylalanine-lysine cleavage site. A linker can be a link created by a microbial transglutaminase, wherein the link can be created between an amine-containing moiety and a moiety engineered to contain glutamine as a result of the enzyme catalyzing a bond formation between the acyl group of a glutamine side chain and the primary amine of a lysine chain. A linker can contain a reactive primary amine. A linker can be a Sortase A linker. A Sortase A linker can be created by a Sortase A enzyme fusing an LPXTG recognition motif (SEQ ID NO:237) to an N-terminal GGG motif to regenerate a native amide bond. The linker created can therefore link to a moiety attached to the LPXTG recognition motif (SEQ ID NO:237) with a moiety attached to the N-terminal GGG motif A linker can be a link created between an unnatural amino acid on one moiety reacting with oxime bond that was formed by modifying a ketone group with an alkoxyamine on another moiety. A moiety can be part of a conjugate. A moiety can be part of an antibody. A moiety can be part of an immune-stimulatory compound, such as a myeloid cell agonist. A moiety can be part of a binding domain. A linker can be unsubstituted or substituted, for example, with a substituent. A substituent can include, for example, hydroxyl groups, amino groups, nitro groups, cyano groups, azido groups, carboxyl groups, carboxaldehyde groups, imine groups, alkyl groups, alkenyl groups, alkynyl groups, alkoxy groups, acyl groups, acyloxy groups, amide groups, and ester groups.

A linker can be polyvalent such that it covalently links more than one immune-stimulatory compound to a single site on the antibody or antigen-binding fragment thereof, or monovalent such that it covalently links a single immune-stimulatory compound to a single site on the antibody or antigen-binding fragment thereof.

Exemplary polyvalent linkers that may be used to attach many immune-stimulatory compounds to an antibody or antigen-binding fragment thereof of the conjugate are described. For example, Fleximer® linker technology has the potential to enable high-DAR conjugate with good physicochemical properties. As shown below, the Fleximer® linker technology is based on incorporating molecules into a solubilizing poly-acetal backbone via a sequence of ester bonds. The methodology renders highly-loaded conjugates (DAR up to 20) whilst maintaining good physicochemical properties. This methodology can be utilized with an immune-stimulatory compound as shown in the scheme below, where Drug' refers to the immune-stimulatory compound.

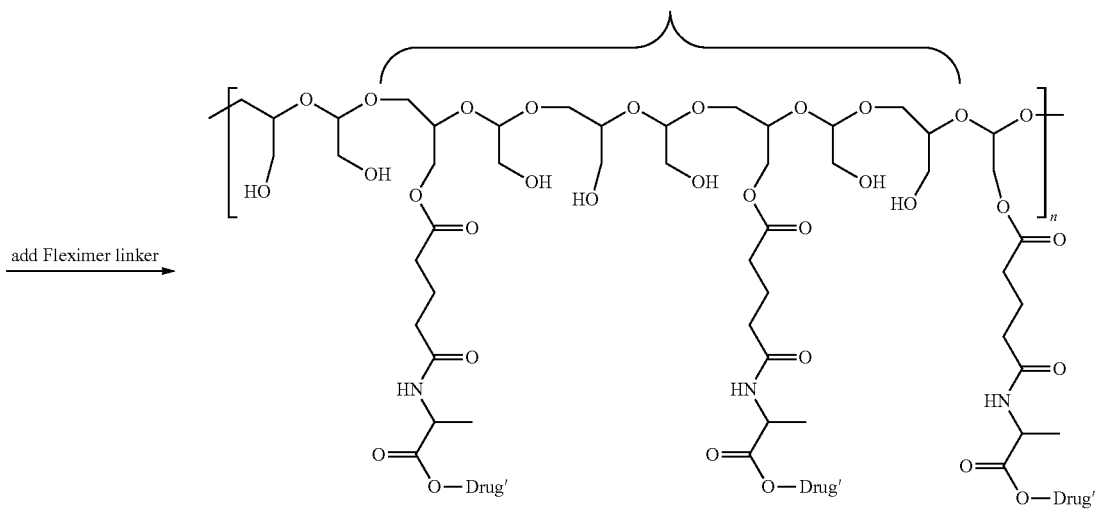

To utilize the Fleximer® linker technology depicted in the scheme above, an aliphatic alcohol can be present or introduced into the immune-stimulatory compound. The alcohol moiety is then attached to an alanine moiety, which is then synthetically incorporated into the Fleximer® linker. Liposomal processing of the conjugate in vitro releases the parent alcohol-containing drug.

In some embodiments, a moiety, construct, or conjugate of the disclosure includes the symbol

which indicates the point of attachment, e.g., the point of attachment of a chemical or functional moiety to the compound, the point of attachment of a linker to a compound of the disclosure, or the point of attachment of a linker to an antibody, an antibody construct, or a targeting moiety.

By way of example and not limitation, some cleavable and noncleavable linkers that may be included in the conjugates of the disclosure are provided in the disclosure.

Sulfamide linkers may be used to link many compounds of the disclosure to an antibody, an antibody construct, or a targeting moiety. Sulfamide linkers are as described in the disclosure and e.g., U.S. Patent Publication Number 2019/0038765, the linkers of which are incorporated by reference herein.

Cleavable linkers can be cleavable in vitro, in vivo, or both. Cleavable linkers can include chemically or enzymatically unstable or degradable linkages. Cleavable linkers can rely on processes inside the cell to liberate an immune-stimulatory compound, such as reduction in the cytoplasm, exposure to acidic conditions in the lysosome, or cleavage by specific proteases or other enzymes within the cell. Cleavable linkers can incorporate one or more chemical bonds that are chemically or enzymatically cleavable while the remainder of the linker can be non-cleavable.

A linker can contain a chemically labile group such as hydrazone and/or disulfide group. Linkers comprising chemically labile groups can exploit differential properties between the plasma and some cytoplasmic compartments. The intracellular conditions that can facilitate immune-stimulatory compound release for hydrazine-containing linkers can be the acidic environment of endosomes and lysosomes, while disulfide-containing linkers can be reduced in the cytosol, which can contain high thiol concentrations, e.g., glutathione. The plasma stability of a linker containing a chemically labile group can be increased by introducing steric hindrance using substituents near the chemically labile group.

Acid-labile groups, such as hydrazones, can remain intact during systemic circulation in the blood's neutral pH environment (pH 7.3-7.5) and can undergo hydrolysis and can release an immune-stimulatory compound once the conjugate is internalized into mildly acidic endosomal (pH 5.0-6.5) and lysosomal (pH 4.5-5.0) compartments of the cell. This pH dependent release mechanism can be associated with nonspecific release of the immune-stimulatory compound. To increase the stability of the hydrazone group of the linker, the linker can be varied by chemical modification, e.g., substitution, allowing tuning to achieve more efficient release in the lysosome with a minimized loss in circulation.

Hydrazone-containing linkers can contain additional cleavage sites, such as additional acid-labile cleavage sites and/or enzymatically labile cleavage sites. Conjugates including exemplary hydrazone-containing linkers can include, for example, the following structures:

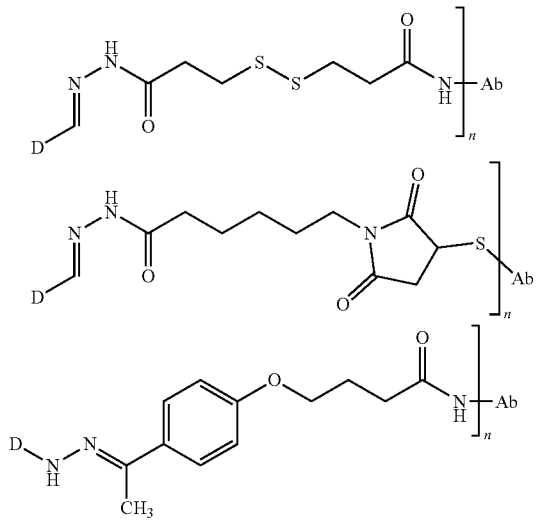

wherein D is an immune-stimulatory compound and Ab is an antibody or antigen-binding fragment thereof, respectively, and n represents the number of compound-bound linkers (LP) bound to the antibody or antigen-binding fragment thereof. In certain linkers, such as linker (Ia), the linker can comprise two cleavable groups, a disulfide and a hydrazone moiety. For such linkers, effective release of the unmodified free immune-stimulatory compound can require acidic pH or disulfide reduction and acidic pH. Linkers such as (Ib) and (Ic) can be effective with a single hydrazone cleavage site.

Other acid-labile groups that can be included in linkers include cis-aconityl-containing linkers. cis-Aconityl chemistry can use a carboxylic acid juxtaposed to an amide bond to accelerate amide hydrolysis under acidic conditions.

Cleavable linkers can also include a disulfide group. Disulfides can be thermodynamically stable at physiological pH and can be designed to release an immune-stimulatory compound upon internalization inside cells, wherein the cytosol can provide a significantly more reducing environment compared to the extracellular environment. Scission of disulfide bonds can require the presence of a cytoplasmic thiol cofactor, such as (reduced) glutathione (GSH), such that disulfide-containing linkers can be reasonably stable in circulation, selectively releasing the immune-stimulatory compound in the cytosol. The intracellular enzyme protein disulfide isomerase, or similar enzymes capable of cleaving disulfide bonds, can also contribute to the preferential cleavage of disulfide bonds inside cells. GSH can be present in cells in the concentration range of 0.5-10 mM compared with a significantly lower concentration of GSH or cysteine, the most abundant low-molecular weight thiol, in circulation at approximately 5 μM. Tumor cells, where irregular blood flow can lead to a hypoxic state, can result in enhanced activity of reductive enzymes and therefore even higher glutathione concentrations. The in vivo stability of a disulfide-containing linker can be enhanced by chemical modification of the linker, e.g., use of steric hindrance adjacent to the disulfide bond.

Immune-stimulatory conjugates including disulfide-containing linkers can include the following structures:

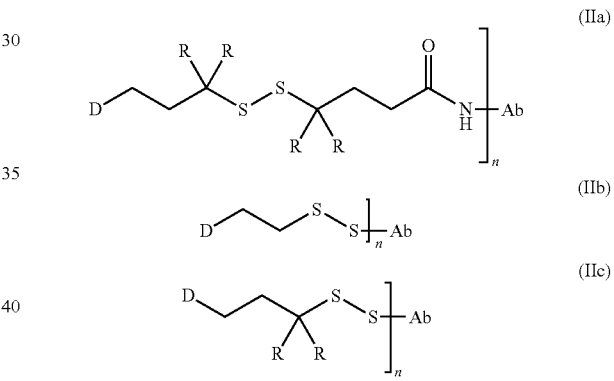

wherein D is an immune-stimulatory compound and Ab is an antibody or antigen-binding fragment thereof, respectively, n represents the number of compounds bound to linkers bound to the antibody or antigen-binding fragment thereof and R is independently selected at each occurrence from hydrogen or alkyl, for example. Increasing steric hindrance adjacent to the disulfide bond can increase the stability of the linker. Structures such as (IIa) and (IIc) can show increased in vivo stability when one or more R groups is selected from a lower alkyl such as methyl.

Another type of linker that can be used is a linker that is specifically cleaved by an enzyme. For example, the linker can be cleaved by a lysosomal enzyme. Such linkers can be peptide-based or can include peptidic regions that can act as substrates for enzymes. Peptide based linkers can be more stable in plasma and extracellular milieu than chemically labile linkers.

Peptide bonds can have good serum stability, as lysosomal proteolytic enzymes can have very low activity in blood due to endogenous inhibitors and the unfavorable pH value of blood compared to lysosomes. Release of an immune-stimulatory compound from an antibody or antigen-binding fragment thereof can occur due to the action of lysosomal proteases, e.g., cathepsin and plasmin. These proteases can be present at elevated levels in certain tumor tissues. A linker can be cleavable by a lysosomal enzyme. The lysosomal enzyme can be, for example, cathepsin B, cathepsin S, P-glucuronidase, or p-galactosidase.

The cleavable peptide can be selected from tetrapeptides such as Gly-Phe-Leu-Gly, Ala-Leu-Ala-Leu, dipeptides such as Val-Cit, Val-Ala, and Phe-Lys, or other peptides. Dipeptides can have lower hydrophobicity compared to longer peptides, depending on the composition of the peptide. A variety of dipeptide-based cleavable linkers can be used in the immune-stimulatory conjugates of the disclosure.

In some embodiments, the cleavable linker comprises a cleavable peptide. In some embodiments, a peptide can be selected to contain natural amino acids, unnatural amino acids, or any combination thereof. In some embodiments, the cleavable peptide is a dipeptide, tripeptide, or tetrapeptide. In some embodiments, the cleavable peptide is Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; Trp-Cit; Ala-Ala-Asn; Gly-Phe-Leu-Gly; Gly-Gly-Phe-Gly; or Ala-Leu-Ala-Leu.

In some embodiments, the cleavable linker comprises a structure of formula:

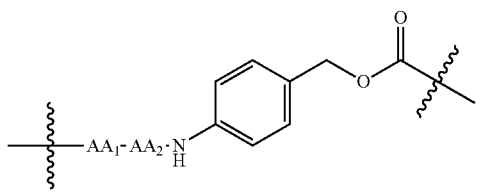

wherein -AA$_1$-AA$_2$- is the cleavable dipeptide and AA$_1$ and AA$_2$ are each an amino acid.

In some embodiments, the cleavable dipeptide is Val-Cit.

Enzymatically cleavable linkers can include a self-immolative spacer to spatially separate the immune-stimulatory compound from the site of enzymatic cleavage. The direct attachment of an immune-stimulatory compound to a peptide linker can result in proteolytic release of the immune-stimulatory compound or of an amino acid adduct of the immune-stimulatory compound, thereby impairing its activity. The use of a self-immolative spacer can allow for the elimination of the fully active, chemically unmodified immune-stimulatory compound upon amide bond hydrolysis.

One self-immolative spacer can be a bifunctional para-aminobenzyl alcohol group (PABA), which can link to the peptide through the amino group, forming an amide bond, while amine containing immune-stimulatory compounds can be attached through carbamate functionalities to the benzylic hydroxyl group of the linker (to give a p-amido-benzylcarbamate, PABC). The resulting pro-immune-stimulatory compound can be activated upon protease-mediated cleavage, leading to a 1,6-elimination reaction releasing the unmodified immune-stimulatory compound, carbon dioxide, and remnants of the linker. The following scheme depicts the fragmentation of p-amidobenzyl carbamate and release of the immune-stimulatory compound:

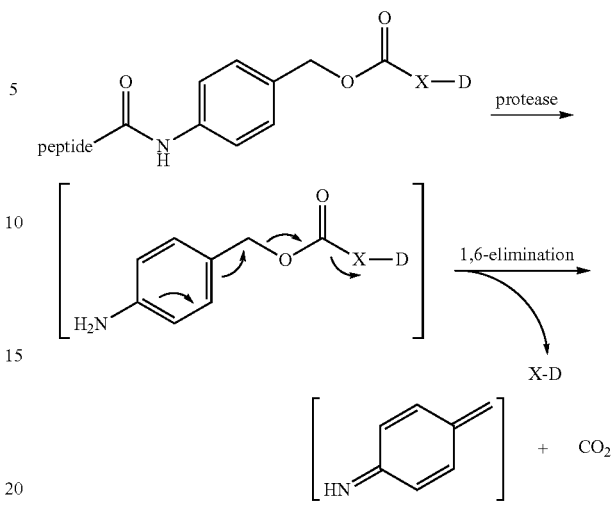

wherein X-D represents the unmodified immune-stimulatory compound and the carbonyl group adjacent "peptide" is part of the peptide. Heterocyclic variants of this self-immolative group have also been described.

An enzymatically cleavable linker can be a β-glucuronic acid-based linker. Facile release of an immune-stimulatory compound can be realized through cleavage of the β-glucuronide glycosidic bond by the lysosomal enzyme β-glucuronidase. This enzyme can be abundantly present within lysosomes and can be overexpressed in some tumor types, while the enzyme activity outside cells can be low. β-Glucuronic acid-based linkers can be used to circumvent the tendency of an immune-stimulatory conjugate to undergo aggregation due to the hydrophilic nature of β-glucuronides. In some embodiments, β-glucuronic acid-based linkers can link an antibody or antigen-binding fragment thereof to a hydrophobic immune-stimulatory compound. The following scheme depicts the release of an immune-stimulatory compound (D) from an immune-stimulatory conjugate containing a P-glucuronic acid-based linker shown below, wherein Ab indicates the antibody or antigen-binding fragment thereof.

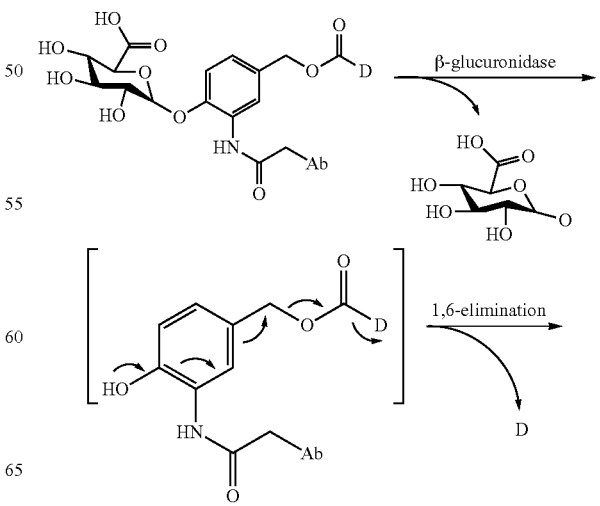

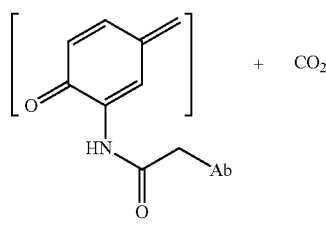 + $CO_2$

A variety of cleavable β-glucuronic acid-based linkers useful for linking drugs such as auristatins, camptothecin and doxorubicin analogues, CBI minor-groove binders, and psymberin to antibodies have been described. These β-glucuronic acid-based linkers may be used in the conjugates of the disclosure. In some embodiments, the enzymatically cleavable linker is a P-galactoside-based linker. P-Galactoside is present abundantly within lysosomes, while the enzyme activity outside cells is low.

Additionally, immune-stimulatory compounds containing a phenol group can be covalently bonded to a linker through the phenolic oxygen. One such linker relies on a methodology in which a diamino-ethane "Space Link" is used in conjunction with traditional "PABO"-based self-immolative groups to deliver phenols.

Cleavable linkers can include non-cleavable portions or segments, and/or cleavable segments or portions can be included in an otherwise non-cleavable linker to render it cleavable. By way of example only, polyethylene glycol (PEG) and related polymers can include cleavable groups in the polymer backbone. For example, a polyethylene glycol or polymer linker can include one or more cleavable groups such as a disulfide, a hydrazone or a dipeptide.

Other degradable linkages that can be included in linkers can include ester linkages formed by the reaction of PEG carboxylic acids or activated PEG carboxylic acids with alcohol groups on an immune-stimulatory compound, wherein such ester groups can hydrolyze under physiological conditions to release the immune-stimulatory compound. Hydrolytically degradable linkages can include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

A linker can contain an enzymatically cleavable peptide, for example, a linker comprising structural formula (CIIIa), (CIIIb), (CIIIc), or (CIIId):

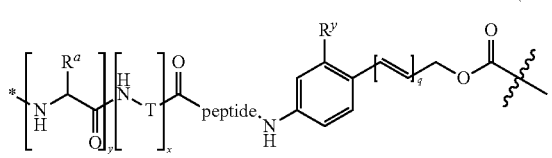 (CIIIa)

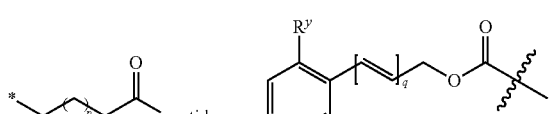 (CIIIb)

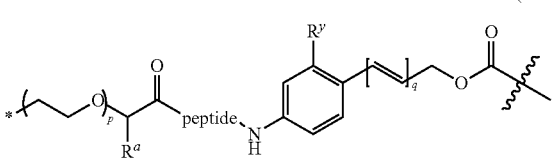 (CIIIc)

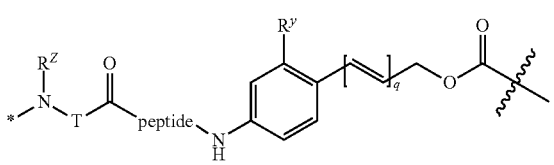 (CIIId)

or a salt thereof, wherein: "peptide" represents a peptide (illustrated in N→C orientation, wherein peptide includes the amino and carboxy "termini") that is cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; $R^y$ is hydrogen or $C_{1-4}$ alkyl-$(O)_r$—$(C_{1-4}$ alkylene$)_s$-$G^1$ or $C_{1-4}$ alkyl-$(N)$—$[(C_{1-4}$ alkylene)-$G^1]_2$; $R^z$ is $C_{1-4}$ alkyl-$(O)_r$—$(C_{1-4}$ alkylene$)_s$-$G^2$; $G^1$ is —$SO_3H$, —$CO_2H$, PEG 4-32, or a sugar moiety; $G^2$ is —$SO_3H$, —$CO_2H$, or a PEG 4-32 moiety; r is 0 or 1; s is 0 or 1; p is an integer ranging from 0 to 5; q is 0 or 1; x is 0 or 1; y is 0 or 1;

represents the point of attachment of the linker to an immune stimulatory compound; and * represents the point of attachment to the remainder of the linker.

Exemplary embodiments of linkers according to structural formula (CIIa) are illustrated below (as illustrated, the linkers include a reactive group suitable for covalently linking the linker to an antibody, an antibody construct, or a targeting moiety):

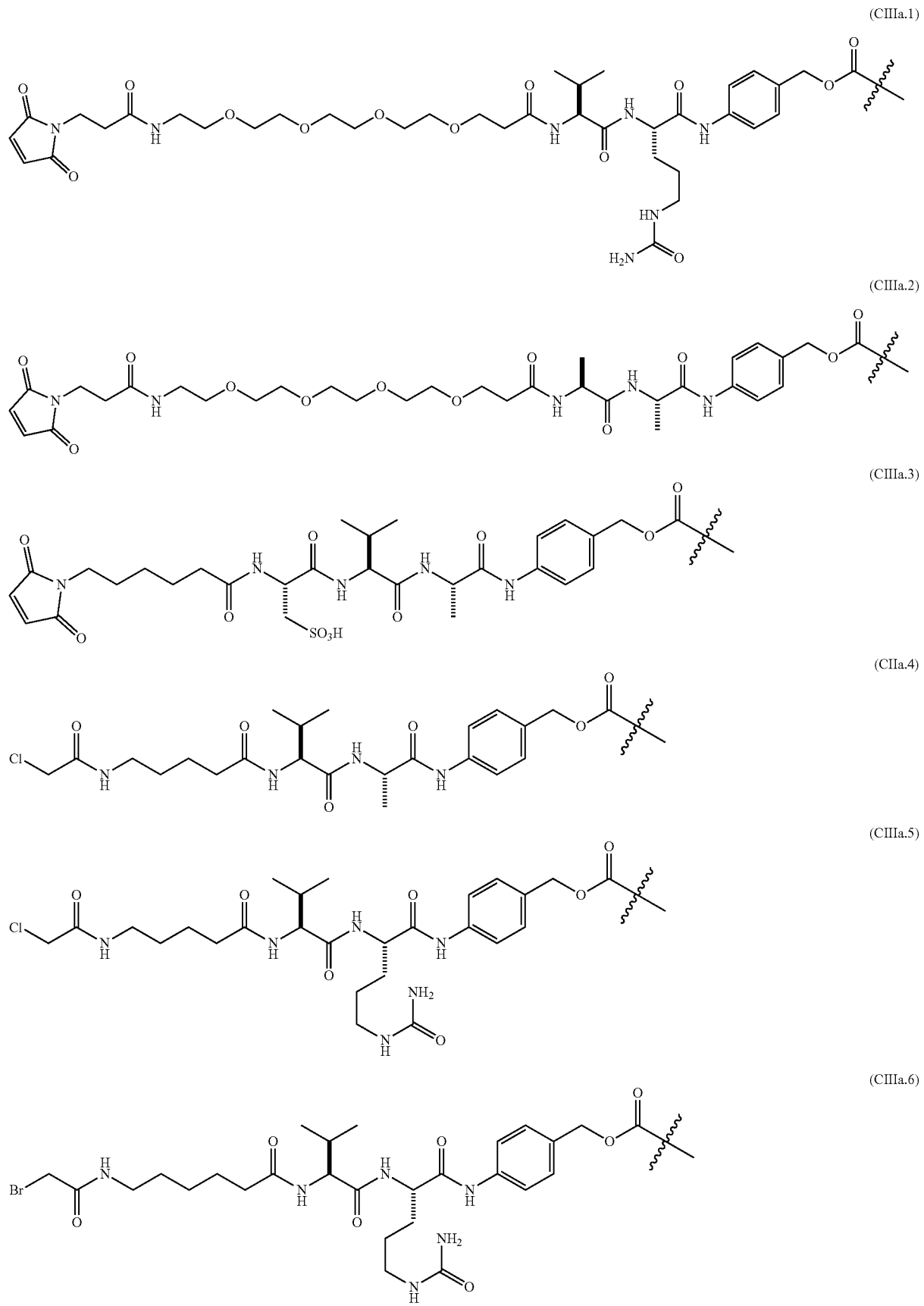

(CIIIa.7)
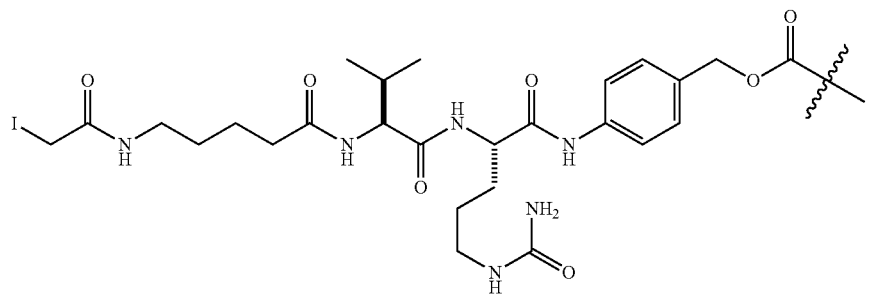

(CIIIa.8)
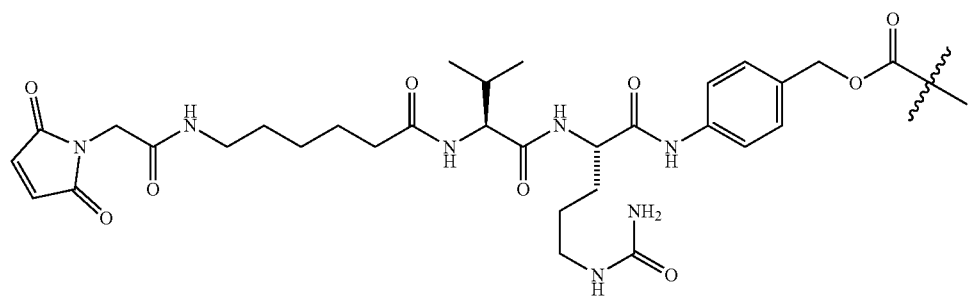

(CIIIa.9)
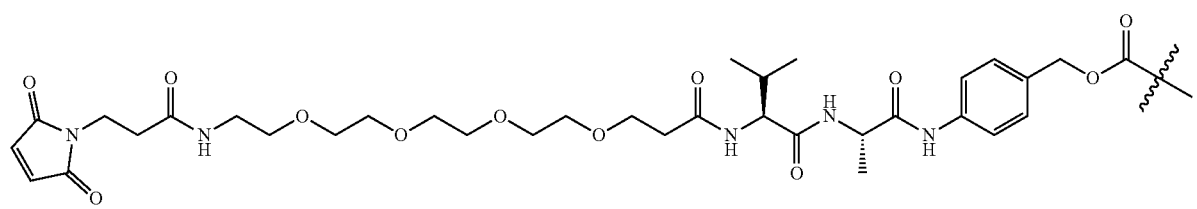

(CIIIa.10)
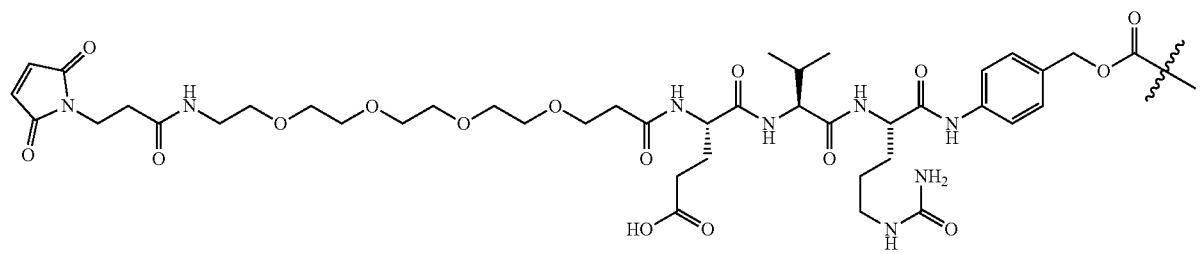

wherein

indicates an attachment site of a linker (L) to an immune stimulatory compound.

Exemplary embodiments of linkers according to structural formula (CIIIb), (CIIIc), or (CIIId) that can be included in the conjugates can include the linkers illustrated below (as illustrated, the linkers include a reactive group suitable for covalently linking the linker to an antibody, an antibody construct, or a targeting moiety):

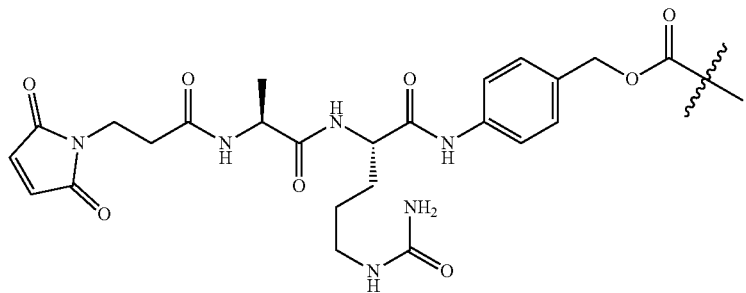
(CIIIb.1)
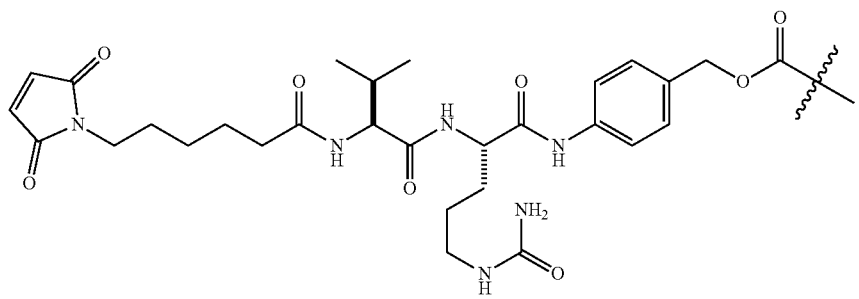
(CIIIb.2)
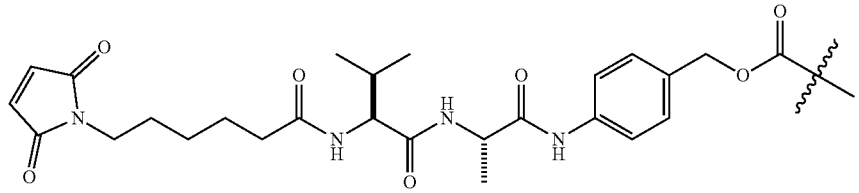
(CIIIb.3)
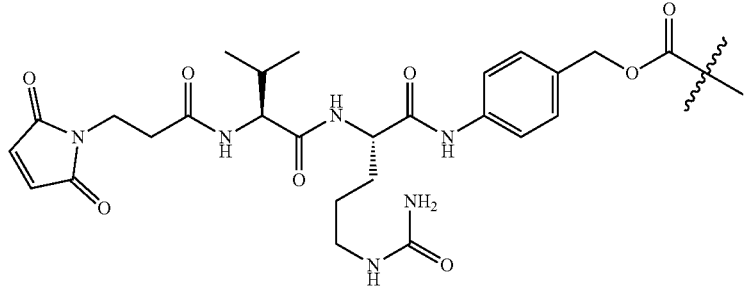
(CIIIb.4)
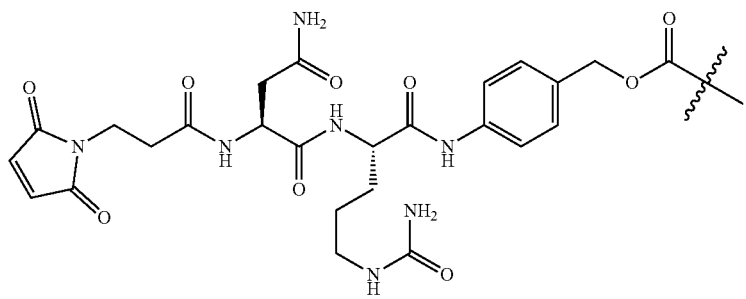
(CIIIb.5)
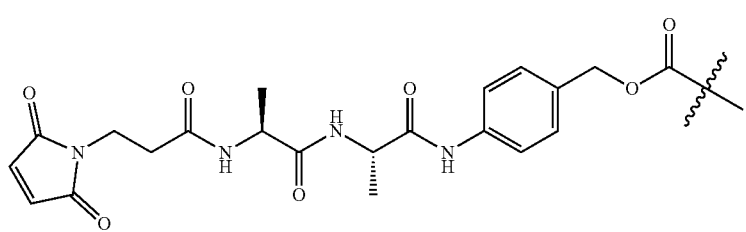
(CIIIb.6)

(CIIIb.7)
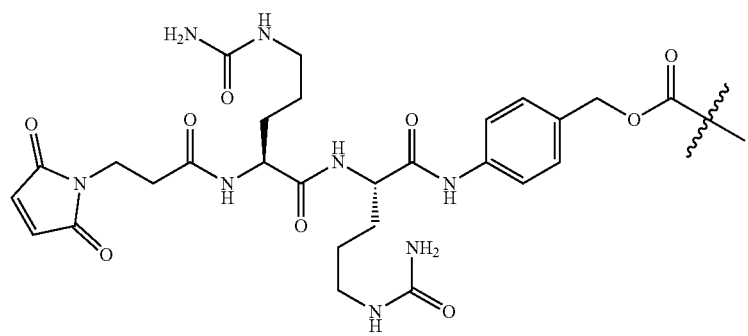
(CIIIb.8)
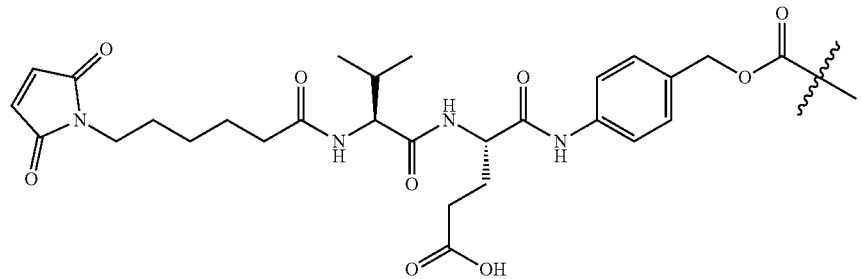
(CIIIb.9)
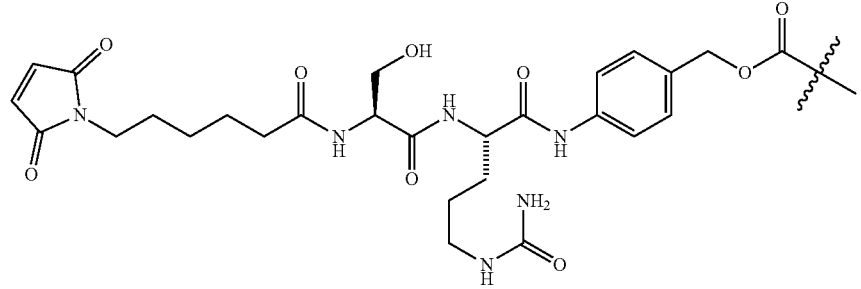
(CIIIb.10)
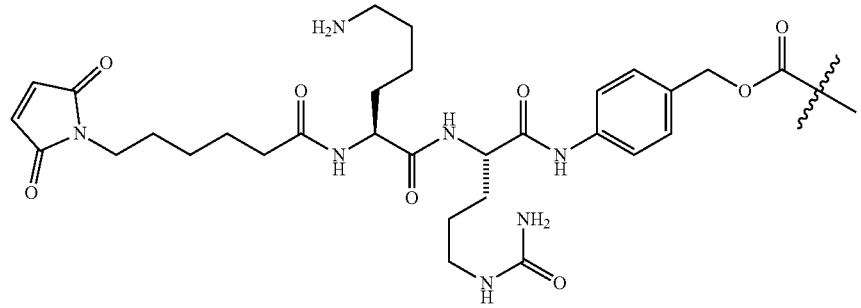
(CIIIb.11)
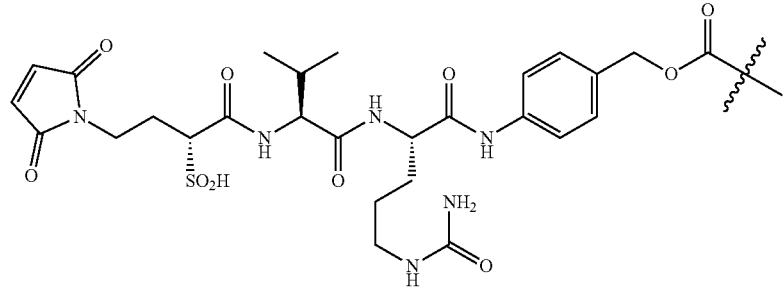

-continued
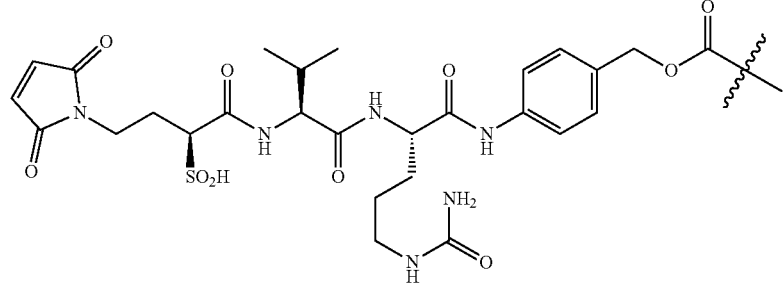 (CIIIb.12)
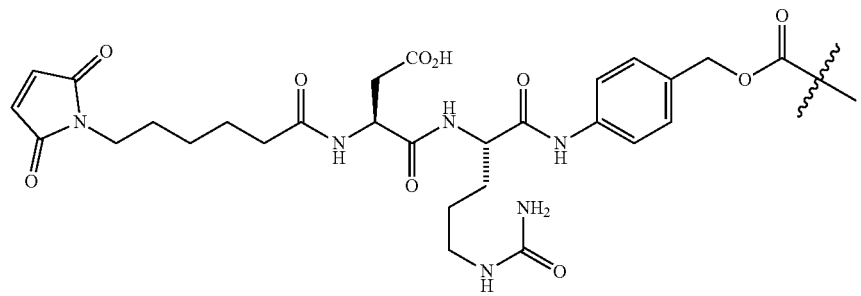 (CIIIb.13)
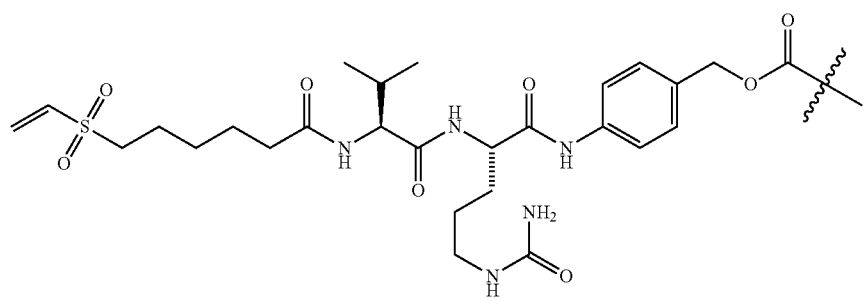 (CIIIb.14)
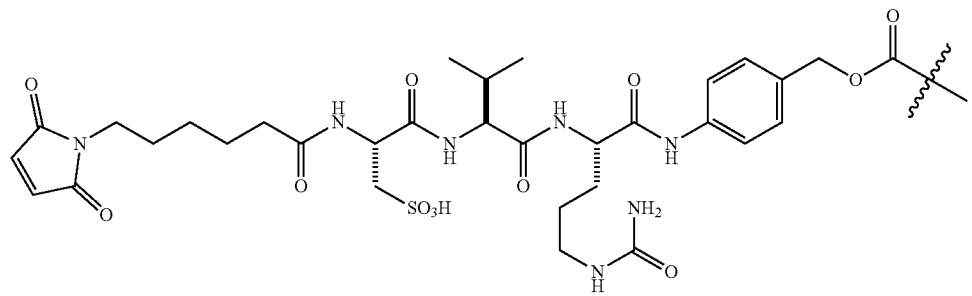 (CIIIb.15)
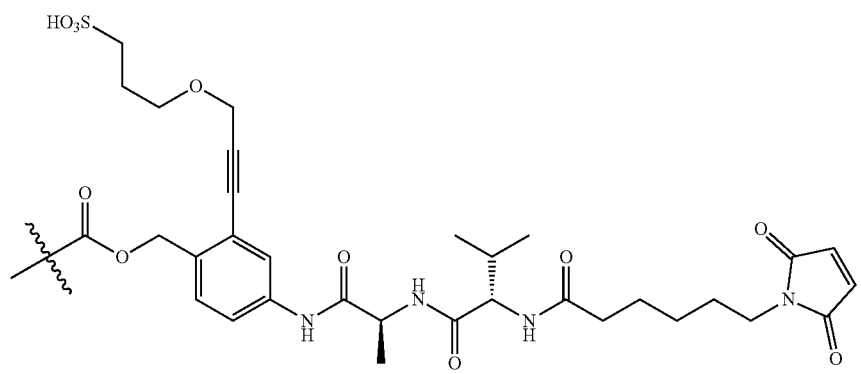 (CIIIb.16)

-continued
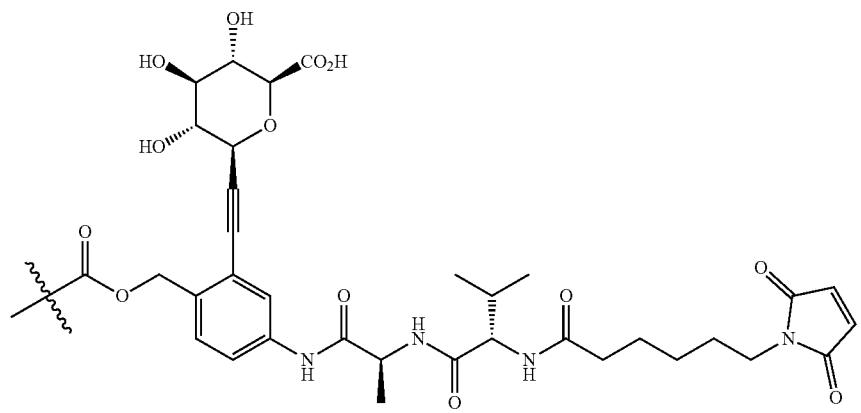
(CIIIb.17)
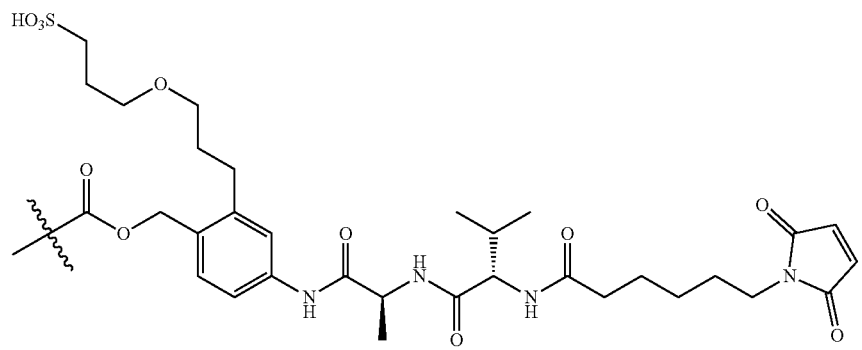
(CIIIb.18)
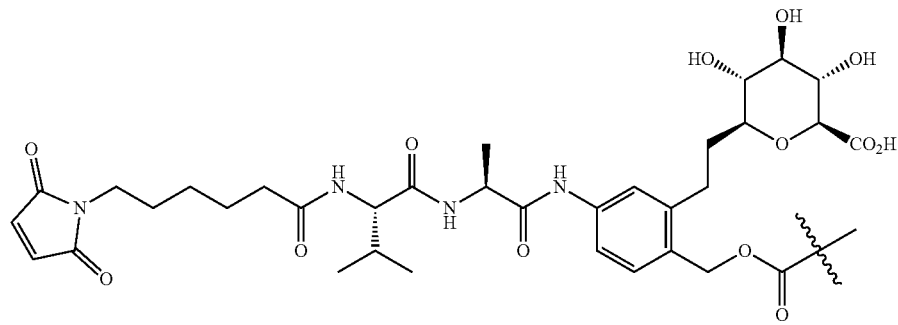
(CIIIb.19)
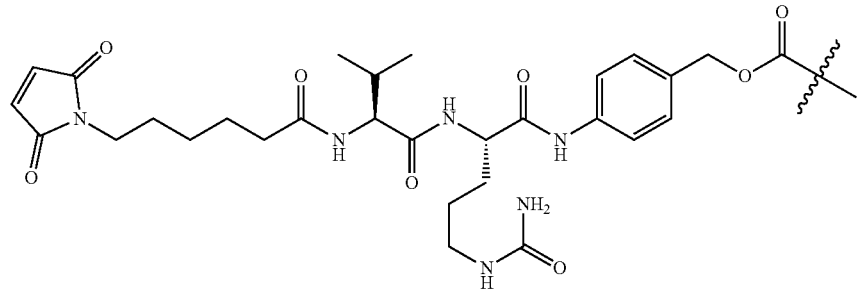
(CIIIb.20)

-continued
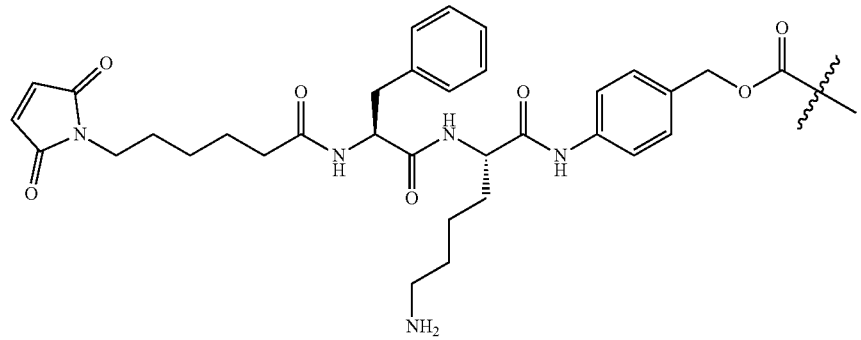
(CIIIb.21)
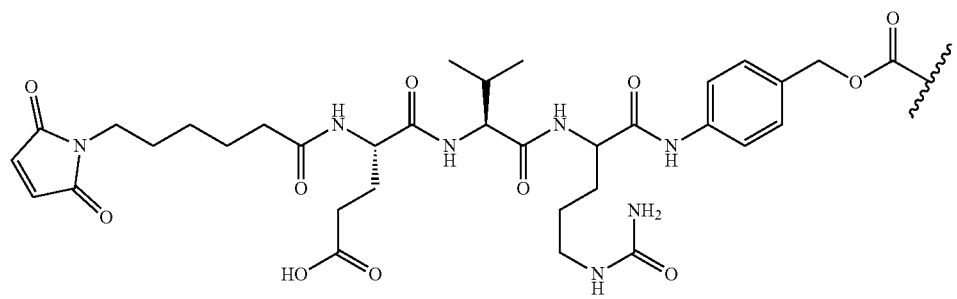
(CIIIb.22)
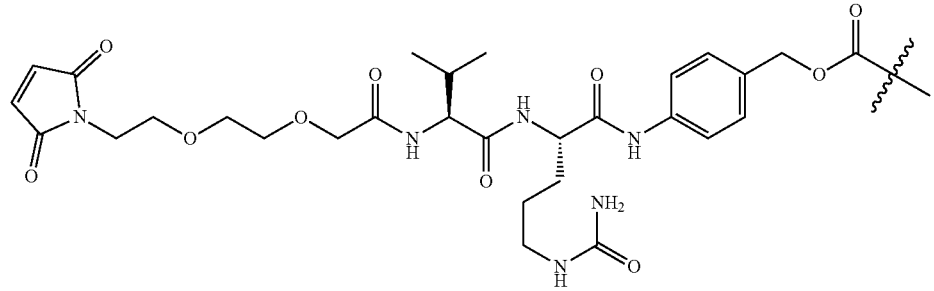
(CIIIc.1)
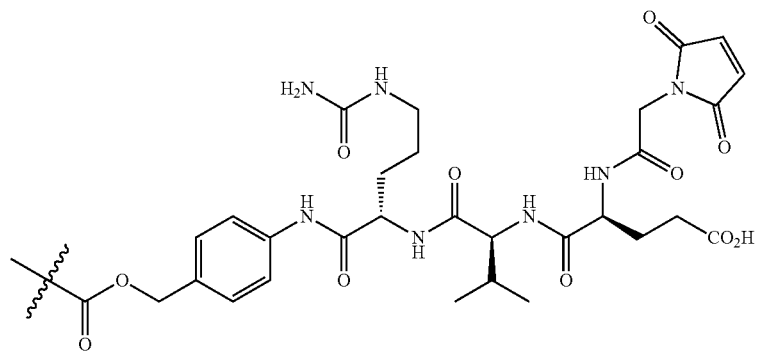
(CIIIc.2)
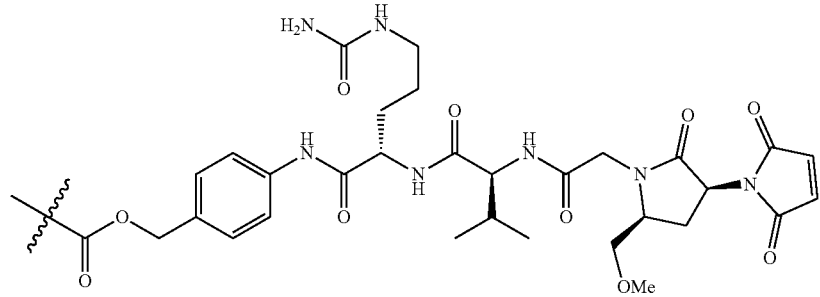
(CIIIc.3)

-continued
(CIIIc.4)
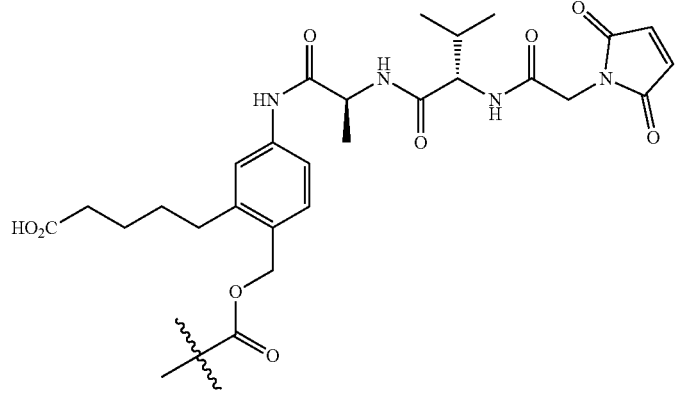
(CIIIc.5)
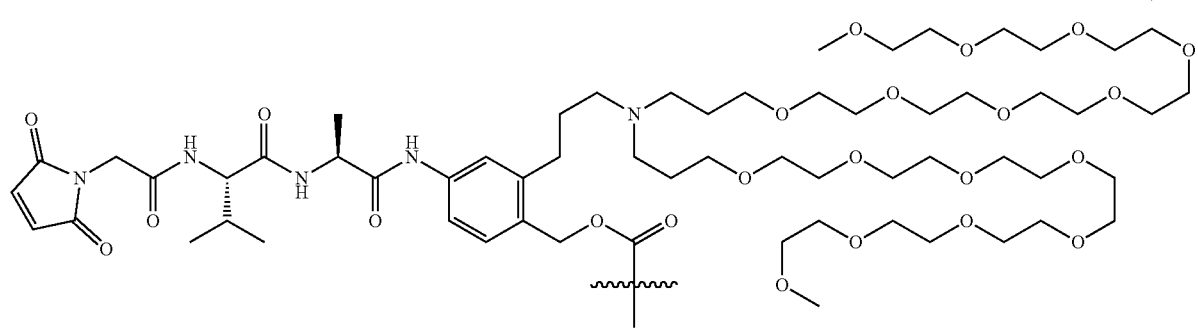
(CIIIc.6)
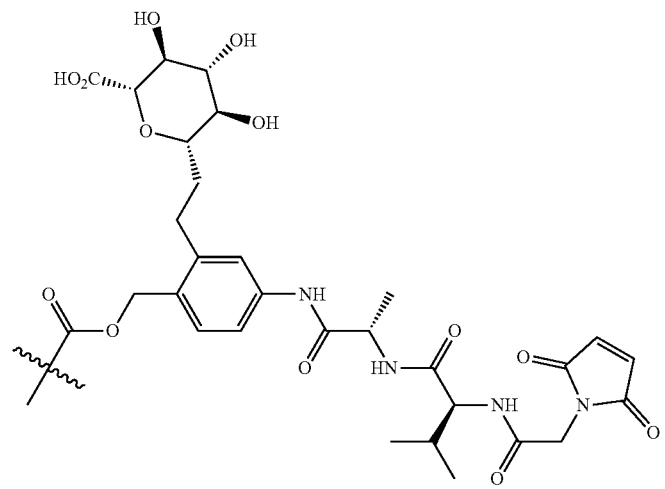
(CIIIc.7)
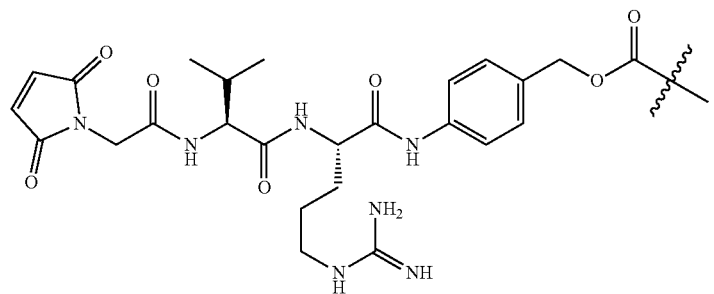

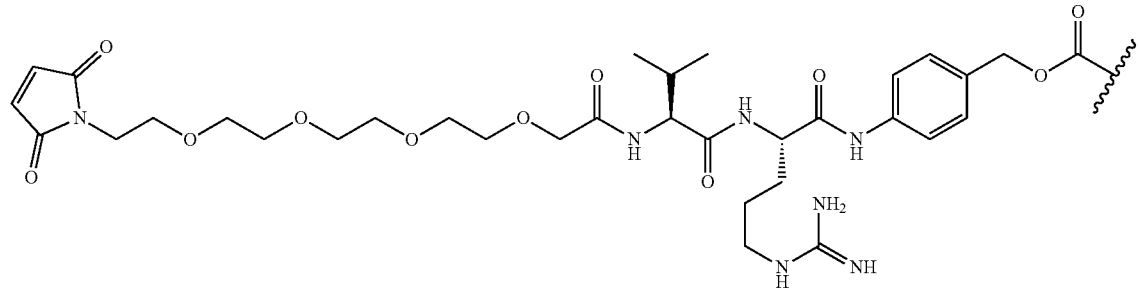
(CIIIc.8)
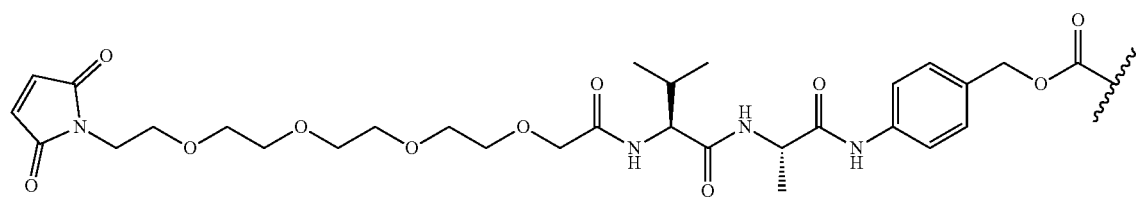
(CIIIc.9)
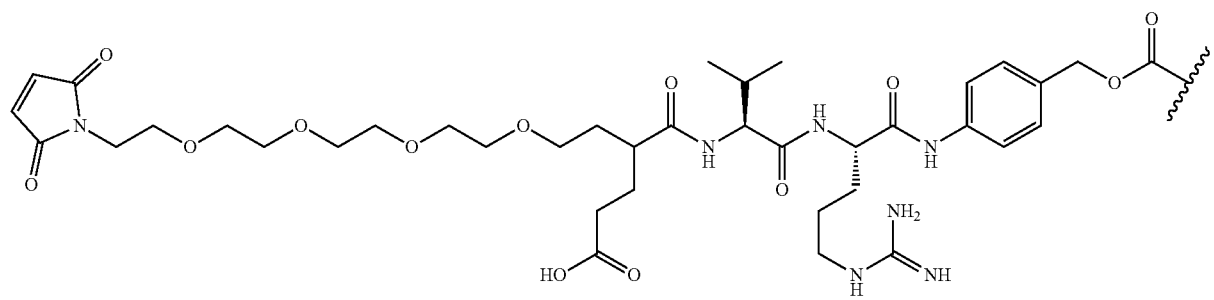
(CIIIc.10)
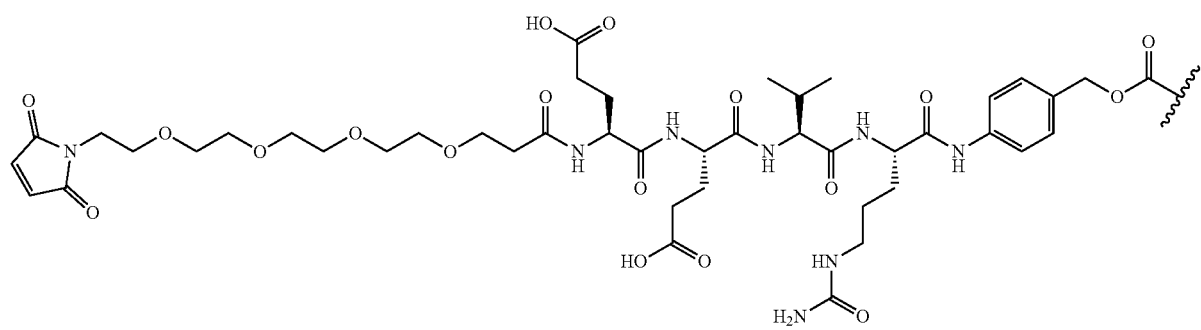
(CIIIc.11)
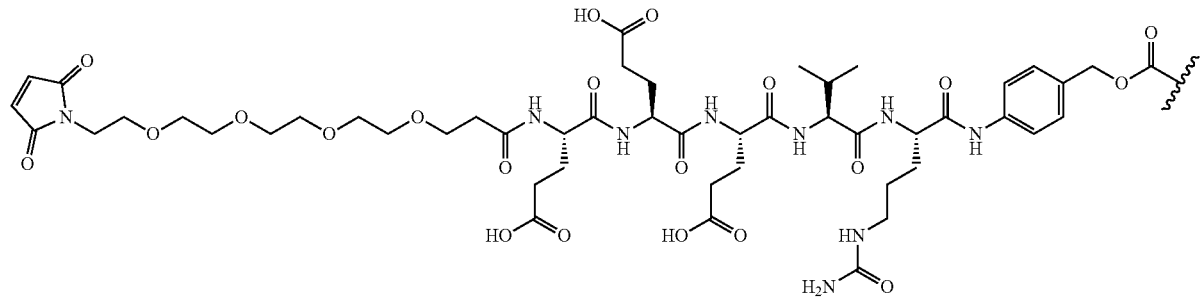
(CIIIc.12)

(CIIId.1)
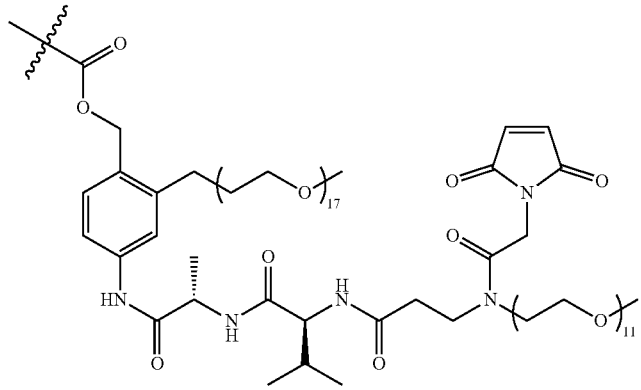
(CIIId.2)
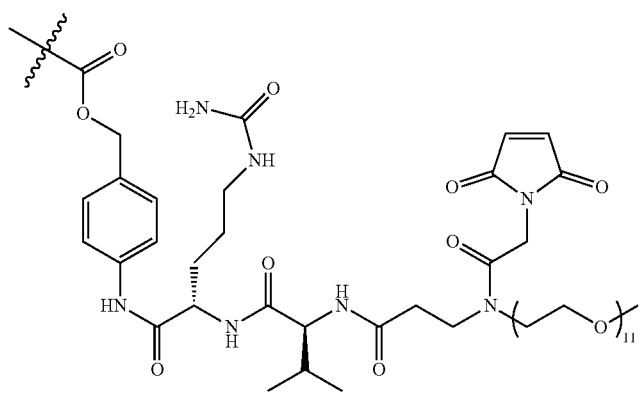
(CIIId.3)
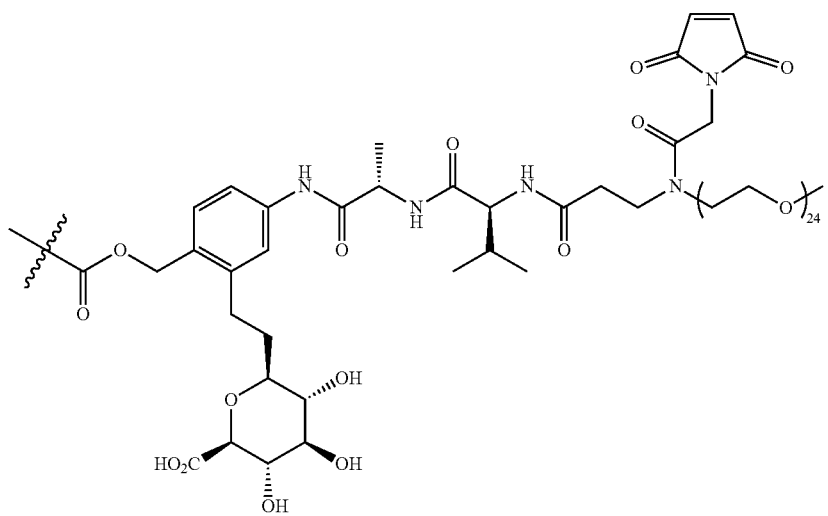

(CIIId.4)
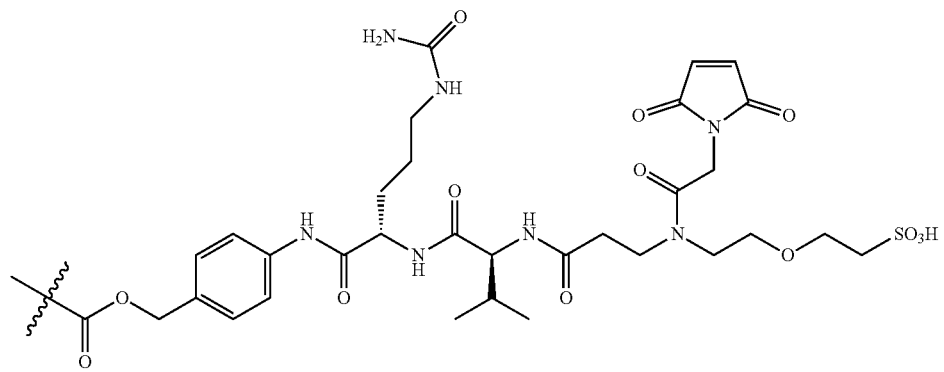
wherein
~~~
indicates an attachment site to an immune stimulatory compound.
The linker can contain an enzymatically cleavable sugar moiety, for example, a linker comprising structural formula (IVa), (IVb), (IVc), (IVd), or (IVe):
(IVa)
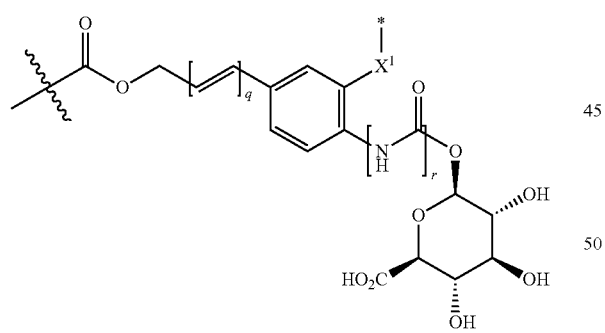
(IVb)
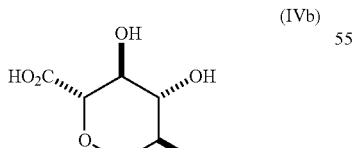
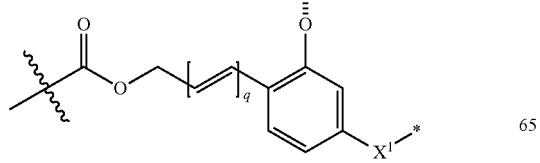
(IVc)
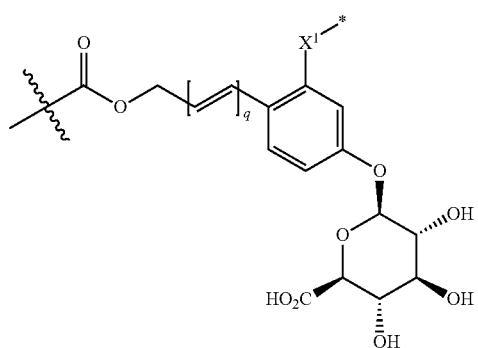
(IVd)
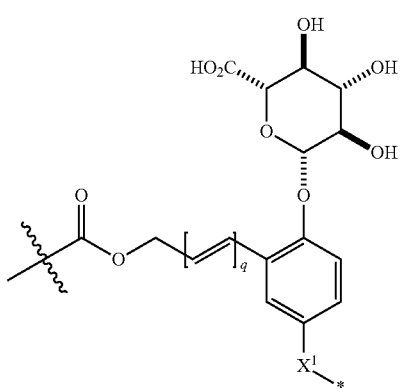

-continued (IVe)

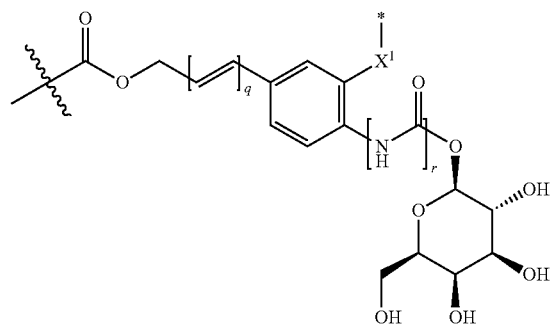

or a pharmaceutically acceptable salt thereof, wherein: q is 0 or 1; r is 0 or 1; $X^1$ is $CH_2$, O or NH;

represents the point of attachment of the linker to an immune-stimulatory compound; and * represents the point of attachment to the remainder of the linker.

Exemplary embodiments of linkers according to structural formula (IVa) that may be included in the immune-stimulatory conjugates of the disclosure can include the linkers illustrated below (as illustrated, the linkers include a group suitable for covalently linking the linker to an antibody or antigen-binding fragment thereof):

(IVa.1)

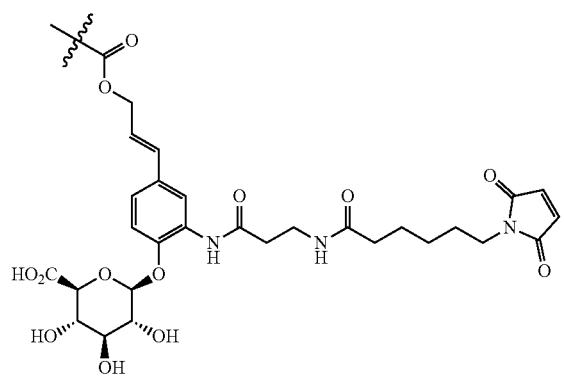

(IVa.2)

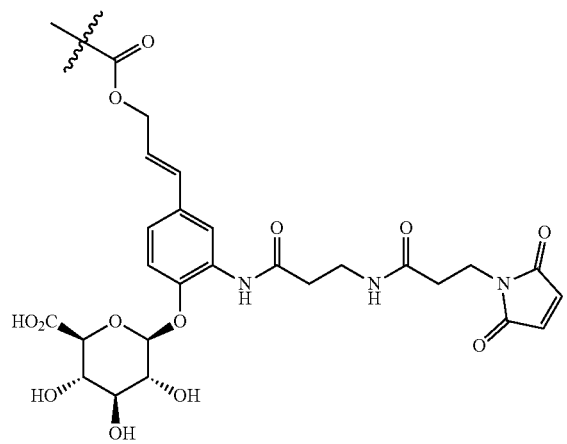

(IVa.3)

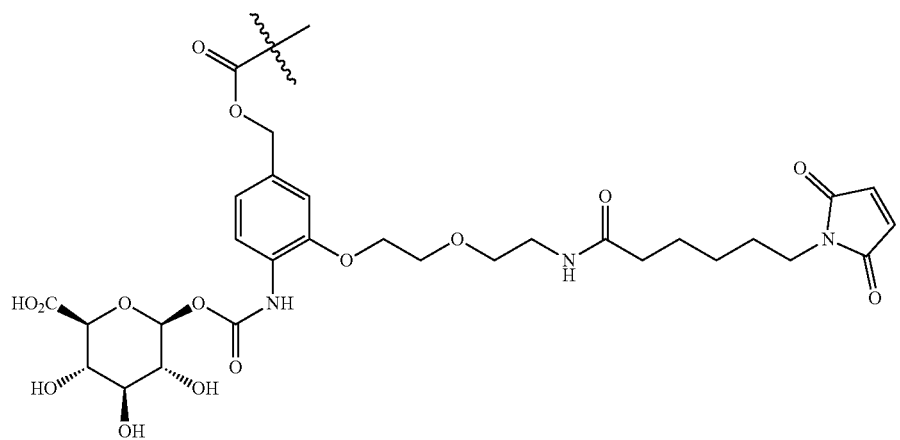

(IVa.4)
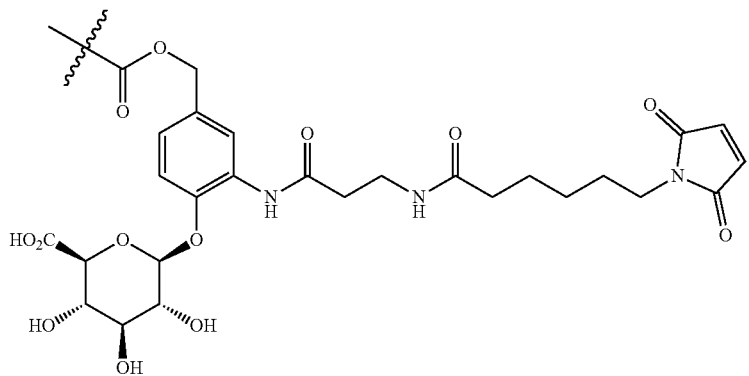
(IVa.5)
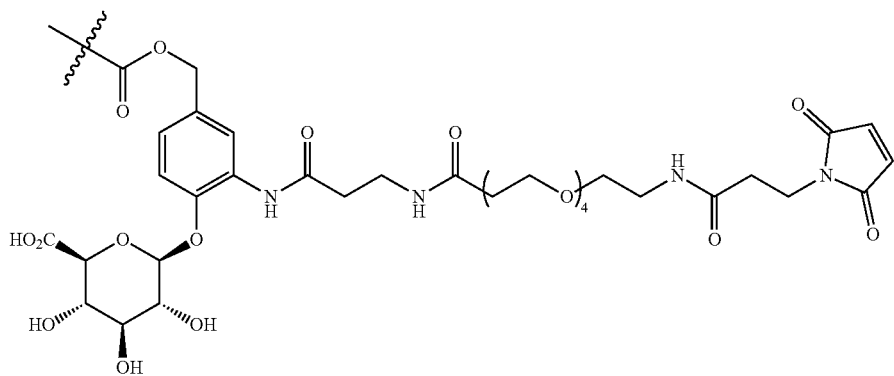
(IVa.6)
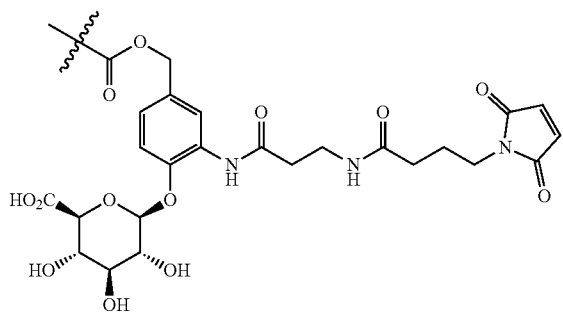
(IVa.7)
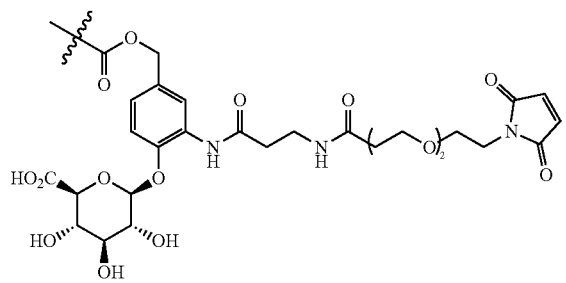
(IVa.8)
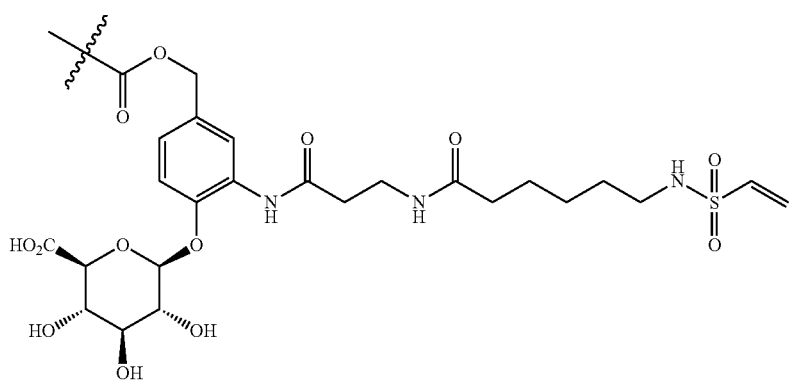

(IVa.9)

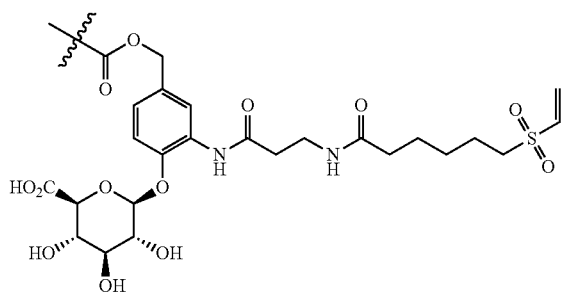

(IVa.10)

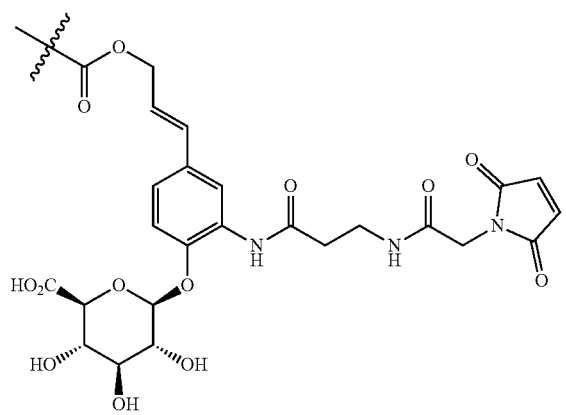

(IVa.11)

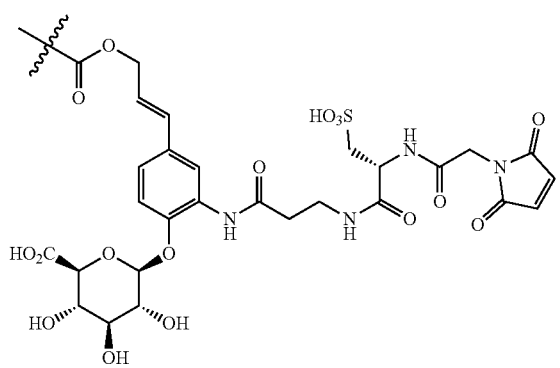

(IVa.12)

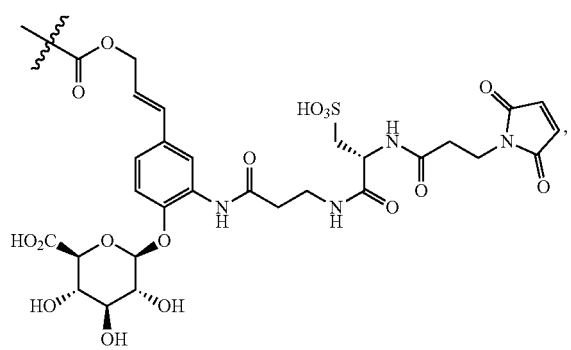

wherein

represents the point of attachment of a linker to an immune-stimulatory.

Exemplary embodiments of linkers according to structural formula (IVb) that may be included in the conjugates of the disclosure include the linkers illustrated below (as illustrated, the linkers include a group suitable for covalently linking the linker to an antibody or antigen-binding fragment thereof):

(IVb.1)

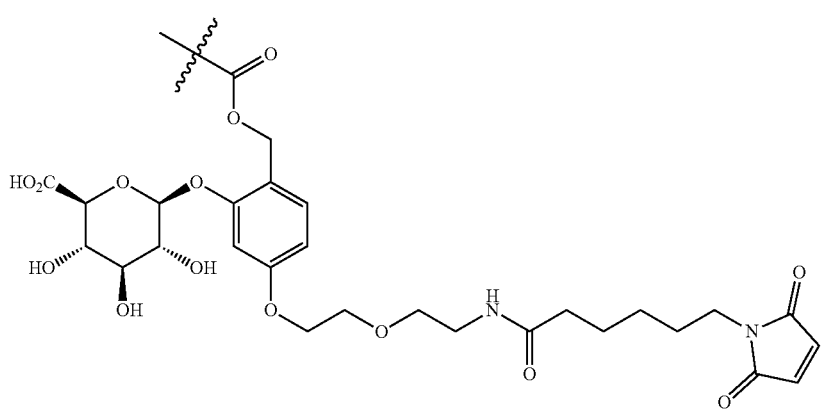

(IVb.1)
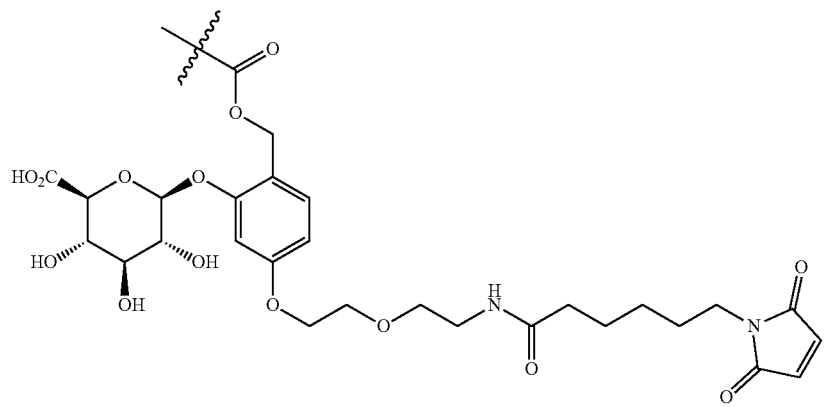
(IVb.2)
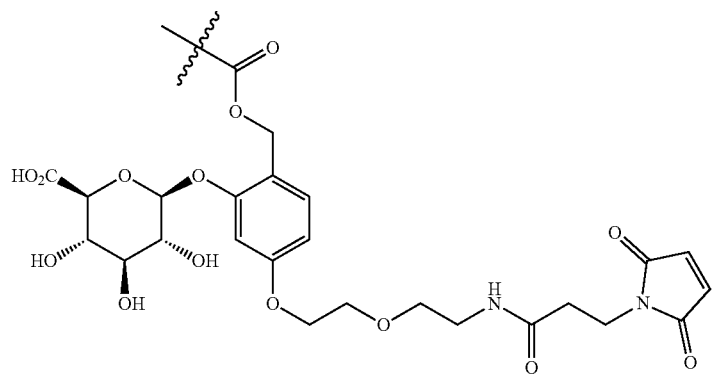
(IVb.3)
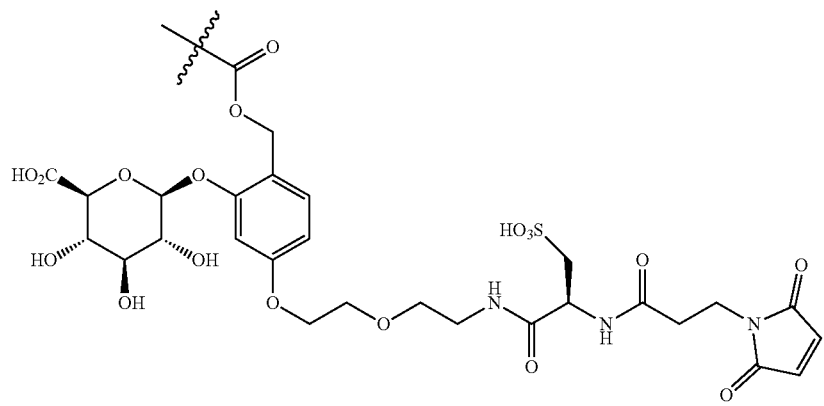
(IVb.4)
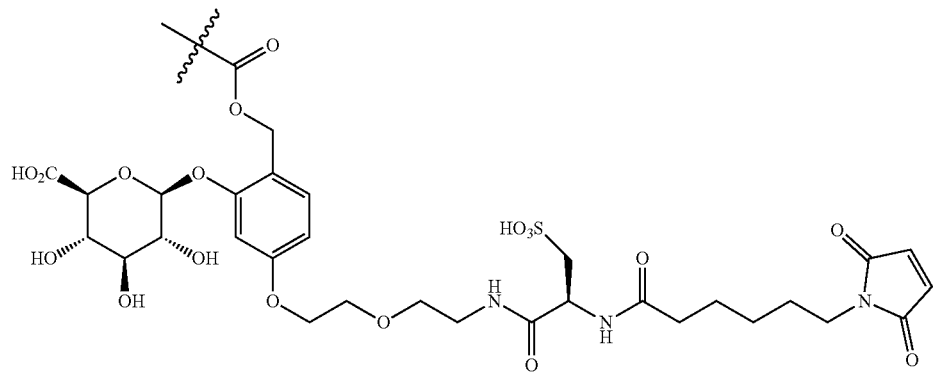

(IVb.5)
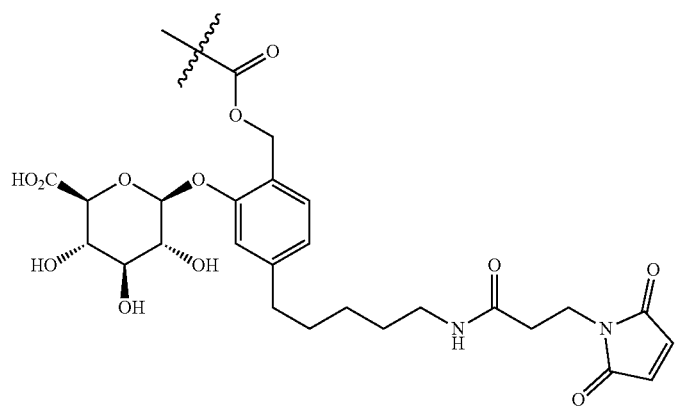
(IVb.6)
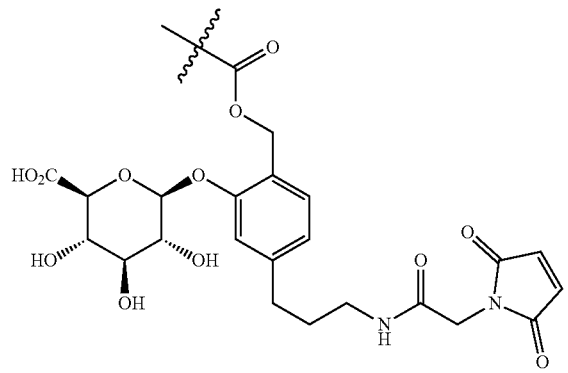
(IVb.7)
(IVb.8)
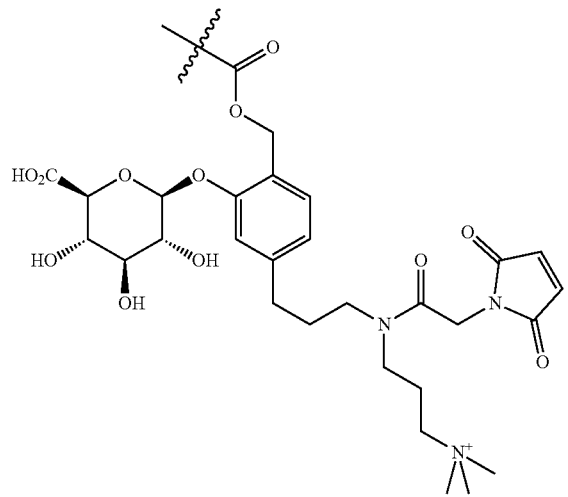

(IVb.9)

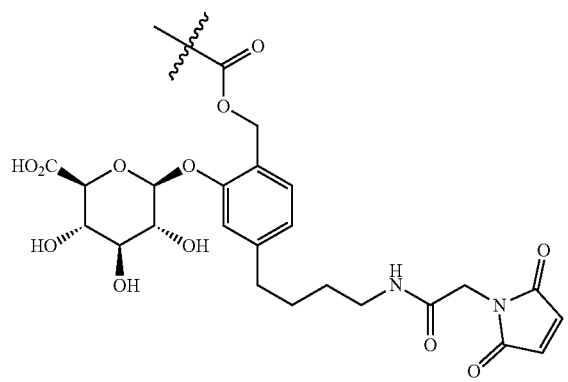

(IVb.10)

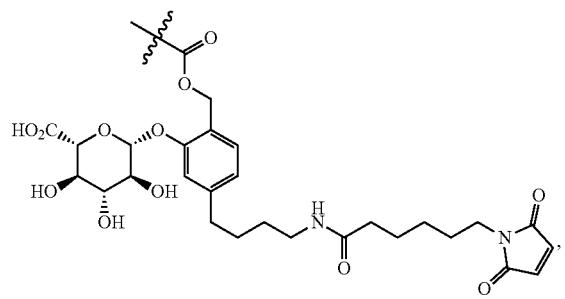

wherein

represents the point of attachment of a linker to an immunestimulatory compound.

Exemplary embodiments of linkers according to structural formula (IVc) that may be included in the conjugates of the disclosure include the linkers illustrated below (as illustrated, the linkers include a group suitable for covalently linking the linker to an antibody or antigen-binding fragment thereof):

(IVc.1)

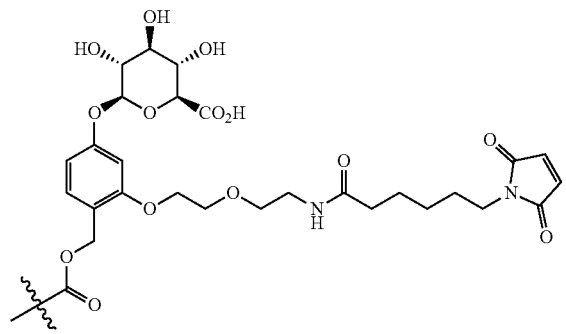

(IVc.2)

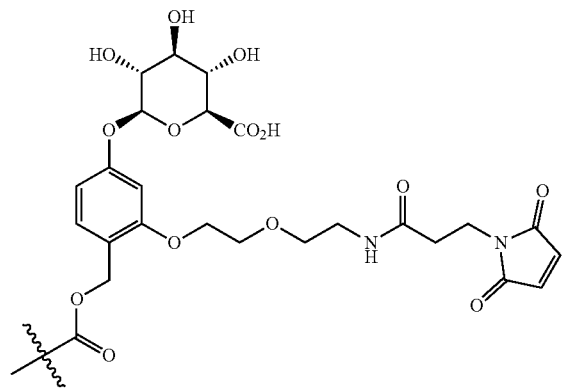

(IVc.3)

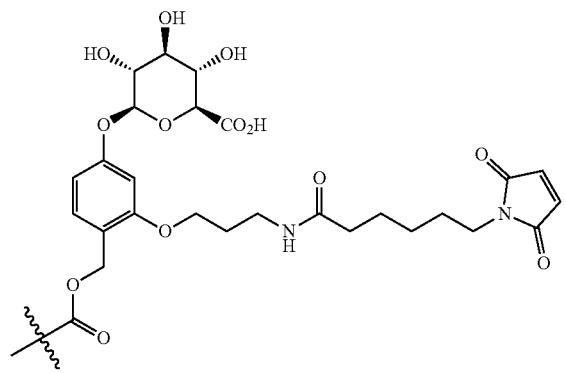

(IVc.4)
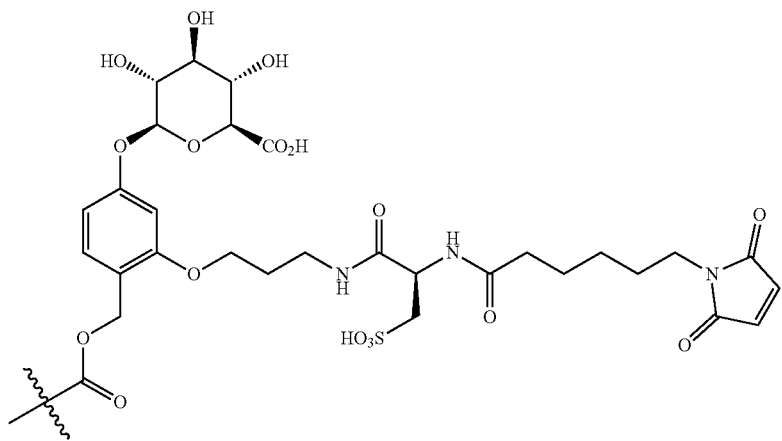
(IVc.5)
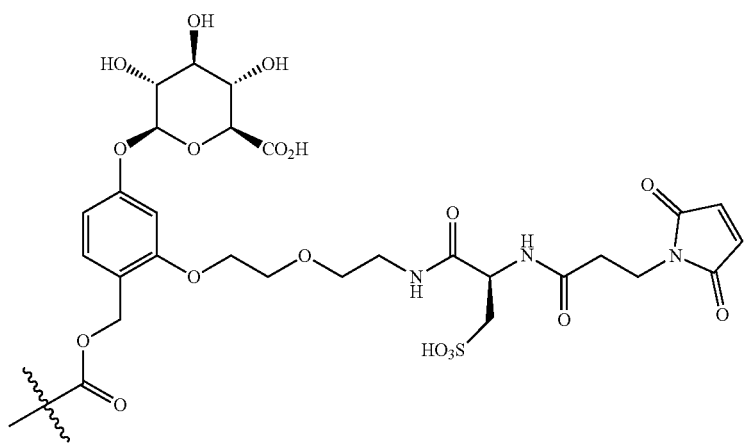
(IVc.6)
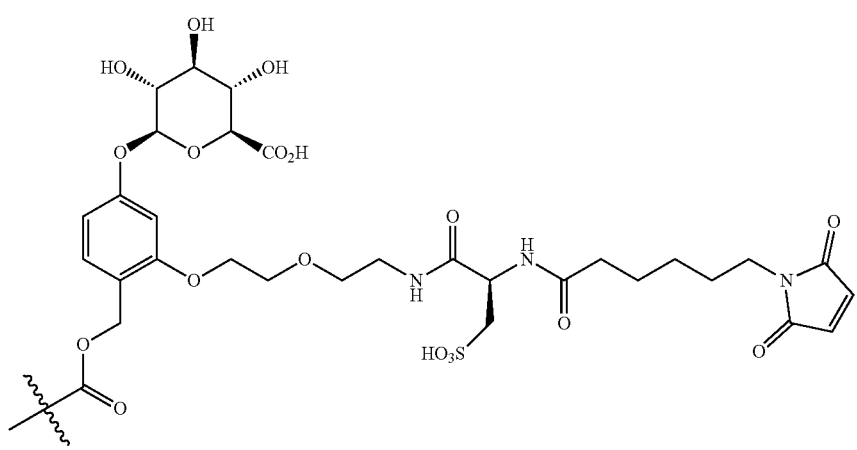

-continued
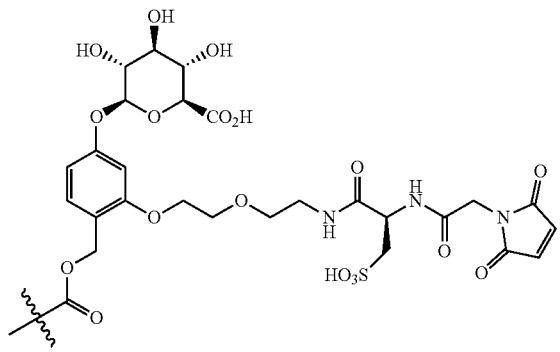
(IVc.7)
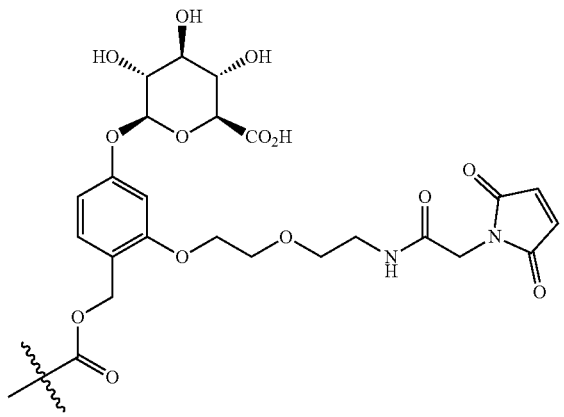
(IVc.8)
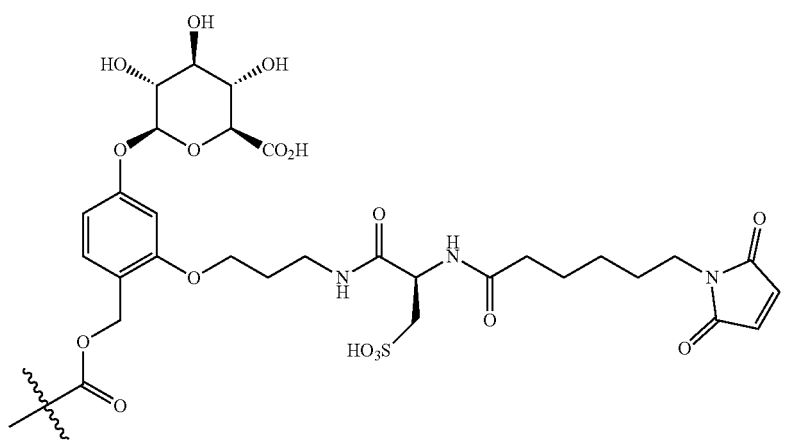
(IVc.9)
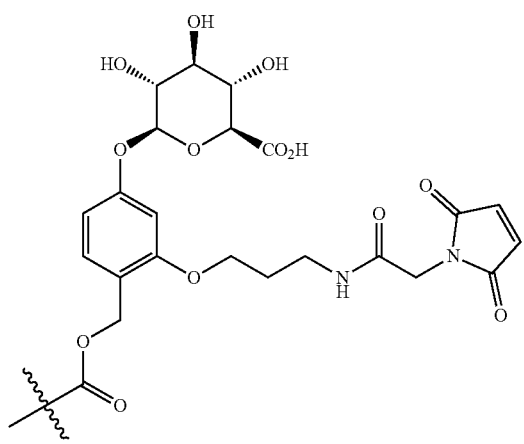
(IVc.10)

(IVc.11)

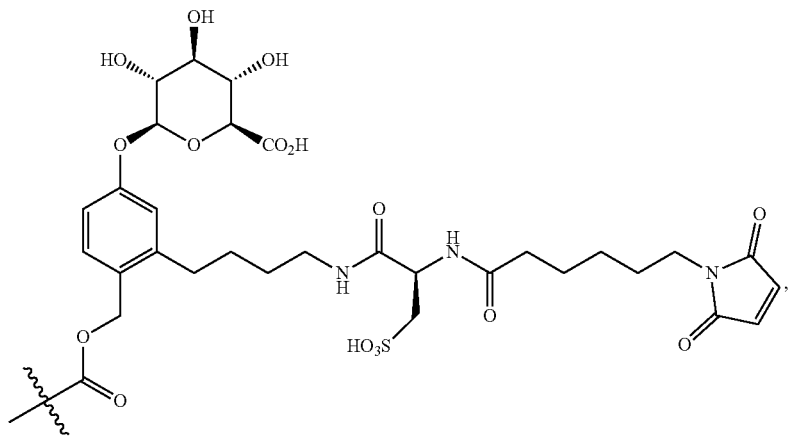

wherein

represents the point of attachment of a linker to an immune-stimulatory compound.

Exemplary embodiments of linkers according to structural formula (IVd) that may be included in the conjugates of the disclosure include the linkers illustrated below (as illustrated, the linkers include a group suitable for covalently linking the linker to an antibody or antigen-binding fragment thereof):

(IVd.1)

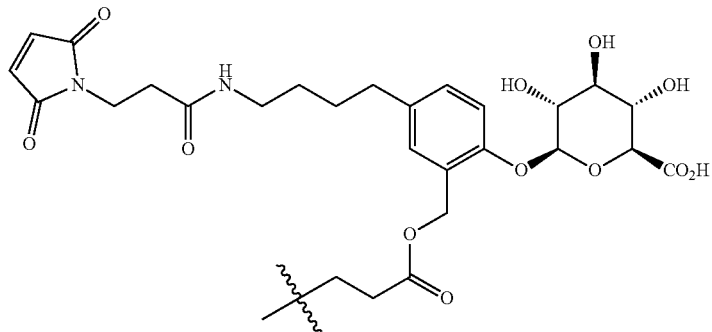

(IVd.2)

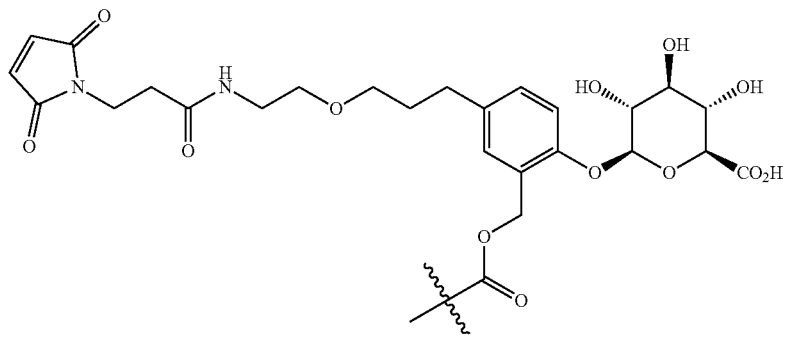

-continued (IVd.3)
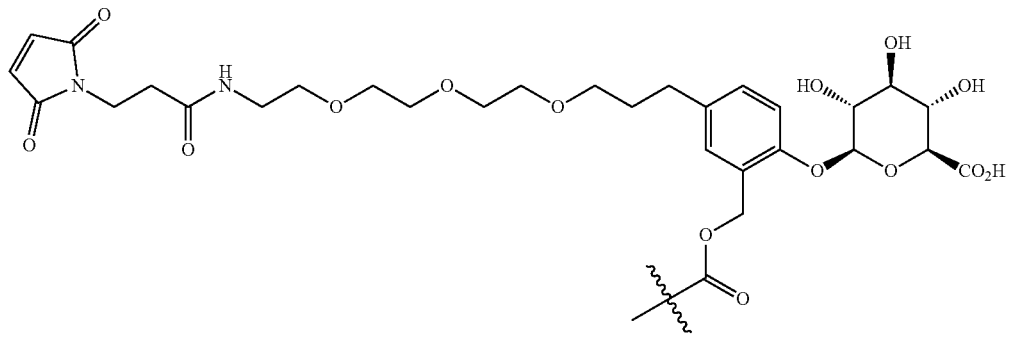

(IVd.4)
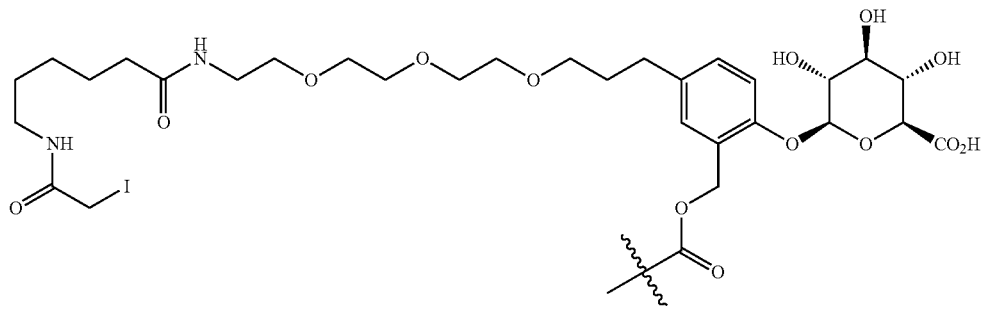

(IVd.5)
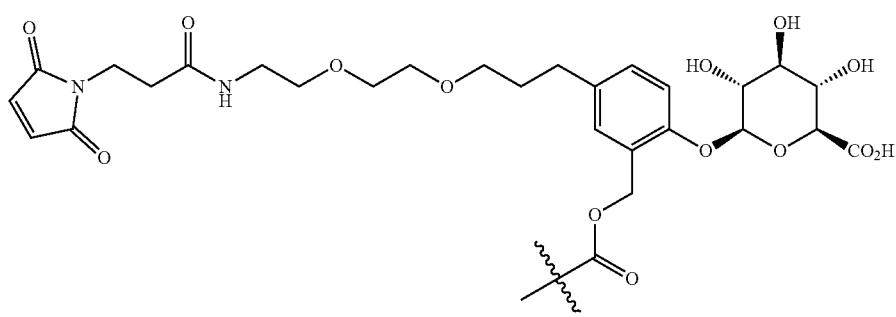

(IVd.6)
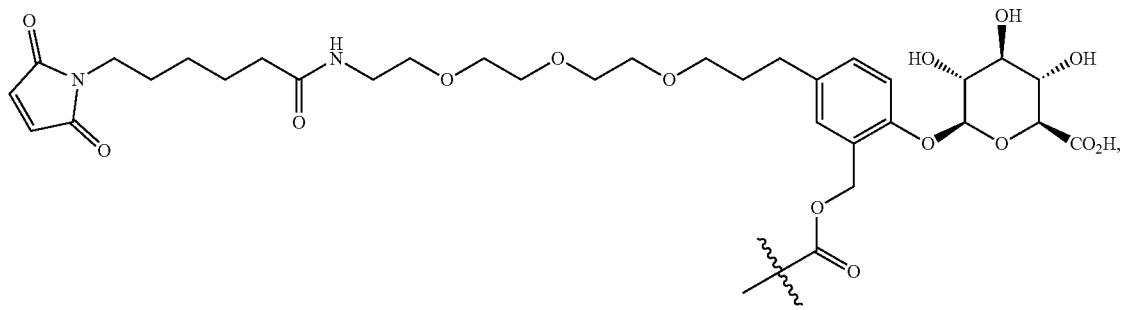

wherein

represents the point of attachment of a linker to an immune-stimulatory compound.

Exemplary embodiments of linkers according to structural formula (IVe) that may be included in the conjugates of the disclosure include the linkers illustrated below (as illustrated, the linkers include a group suitable for covalently linking the linker to an antibody or antigen-binding fragment thereof):

wherein represents the point of attachment of a linker to an immune-stimulatory compound.

Although cleavable linkers can provide certain advantages, the linkers comprising the conjugate of the disclosure need not be cleavable. For non-cleavable linkers, the immune-stimulatory compound release may not depend on the differential properties between the plasma and some cytoplasmic compartments. The release of the immune-stimulatory compound can occur after internalization of the immune-stimulatory conjugate via antigen-mediated endocytosis and delivery to lysosomal compartment, where the antibody or antigen-binding fragment thereof can be degraded to the level of amino acids through intracellular proteolytic degradation. This process can release an immune-stimulatory compound derivative, which is formed by the immune-stimulatory compound, the linker, and the amino acid residue or residues to which the linker was covalently attached. The immune-stimulatory compound derivative from immune-stimulatory conjugates with non-cleavable linkers can be more hydrophilic and less membrane permeable, which can lead to less bystander effects and less nonspecific toxicities compared to immune-stimulatory conjugates with a cleavable linker. Immune-stimulatory conjugates with non-cleavable linkers can have greater stability in circulation than immune-stimulatory conjugates with cleavable linkers. Non-cleavable linkers can include alkylene chains, or can be polymeric, such as, for example, based upon polyalkylene glycol polymers, amide polymers, or can include segments of alkylene chains, polyalkylene glycols and/or amide polymers. The linker can contain a polyethylene glycol segment having from 1 to 6 ethylene glycol units.

The linker can be non-cleavable in vivo, for example, a linker according to the formulations below:

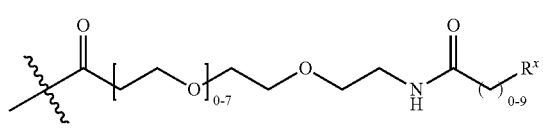

(Va)

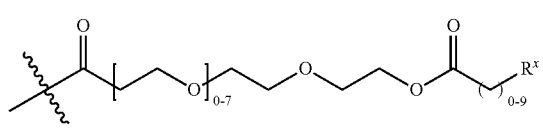

(Vb)

(Vc)

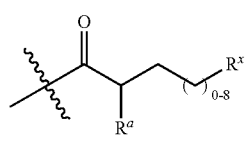

(Vd)

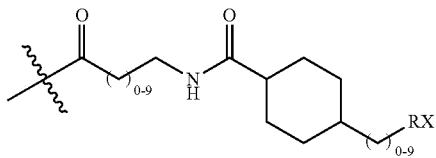

(Ve)

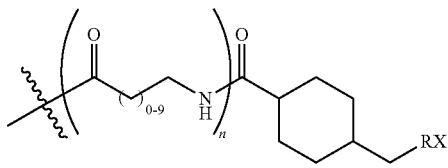

(Vf)

or salts thereof, wherein: $R^a$ is selected from hydrogen, alkyl, sulfonate and methyl sulfonate; $R^x$ is a reactive moiety including a functional group capable of covalently linking the linker to an antibody or antigen-binding fragment thereof; and represents the point of attachment of the linker to an immune-stimulatory compound.

In some embodiments, a linker is represented by formula (V):

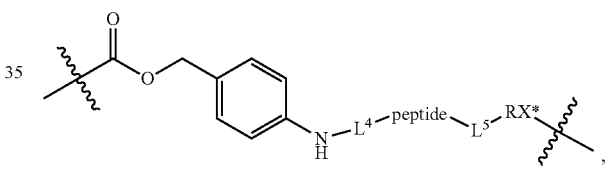

wherein:
$L^4$ represents the C-terminus of the peptide;
$L^5$ is selected from a bond, alkylene and heteroalkylene, wherein $L^5$ is optionally substituted with one or more groups independently selected from $R^{32}$;
RX* comprises a bond, a succinimide moiety, or a hydrolyzed succinimide moiety bound to a residue of a polypeptide, such as an antibody, wherein

on RX* represents the point of attachment to the residue of the polypeptide, such as the antibody, and the other

represents the point of attachment to the myeloid cell agonist, such as a TLR8 or TLR7 agonist; and
$R^{32}$ is independently selected at each occurrence from halogen, —OH, —CN, —O— alkyl, —SH, =O, =S, —NH$_2$, —NO$_2$; C$_{1-10}$ alkyl, C$_{2-10}$ alkenyl, and C$_{2-10}$ alkynyl, each of which is optionally substituted with one or more substituents independently selected from halogen, —OH, —CN, —O-alkyl, —SH, =O, =S, —NH$_2$, and —NO$_2$.

Exemplary embodiments of linkers according to structural formula (Va)-(Vf) that may be included in the conjugates of the disclosure include the linkers illustrated below (as illustrated, the linkers include a group suitable for covalently linking the linker to an antibody or antigen-binding fragment thereof; and

represents the point of attachment of the linker to an immune-stimulatory compound:

or antigen-binding fragment thereof of a conjugate. The reaction between a thiol group of an antibody or antigen-binding fragment thereof and a drug with a linker including a maleimide group proceeds according to the following scheme:

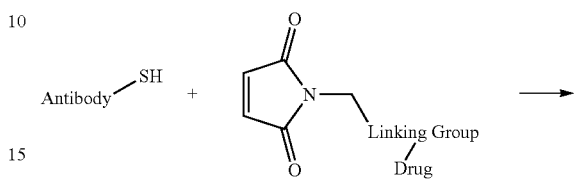

(Va.1)

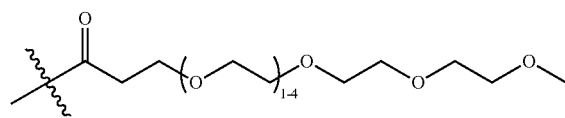

(Vc.1) (Vc.2)

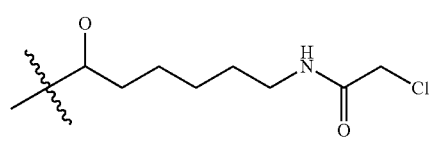

(Vd.1) (Vd.2)

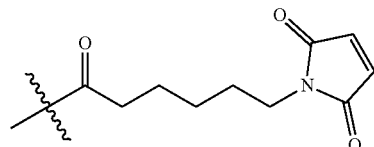

(Vd.3) (Vd.4)

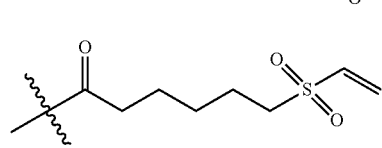

(Ve.1)

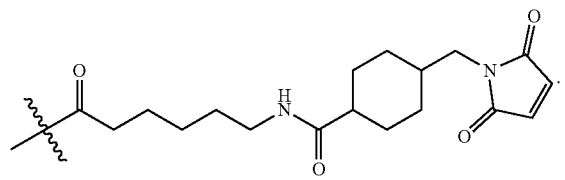

Attachment groups that are used to attach the linkers to an antibody or antigen-binding fragment thereof can be electrophilic in nature and include, for example, maleimide groups, alkynes, alkynoates, allenes and allenoates, activated disulfides, active esters such as NHS esters and HOBt esters, haloformates, acid halides, alkyl, and benzyl halides such as haloacetamides. There are also emerging technologies related to "self-stabilizing" maleimides and "bridging disulfides" that can be used in accordance with the disclosure.

Maleimide groups are frequently used in the preparation of conjugates because of their specificity for reacting with thiol groups of, for example, cysteine groups of the antibody -continued

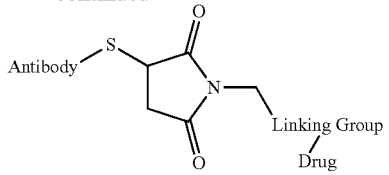

The reverse reaction leading to maleimide elimination from a thio-substituted succinimide may also take place. This reverse reaction is undesirable as the maleimide group may subsequently react with another available thiol group such as other proteins in the body having available cysteines. Accordingly, the reverse reaction can undermine the specificity of a conjugate. One method of preventing the reverse reaction is to incorporate a basic group into the linking group shown in the scheme above. Without wishing to be bound by theory, the presence of the basic group may increase the nucleophilicity of nearby water molecules to promote ring-opening hydrolysis of the succinimide group. The hydrolyzed form of the attachment group is resistant to deconjugation in the presence of plasma proteins. So-called "self-stabilizing" linkers provide conjugates with improved stability. A representative schematic is shown below:

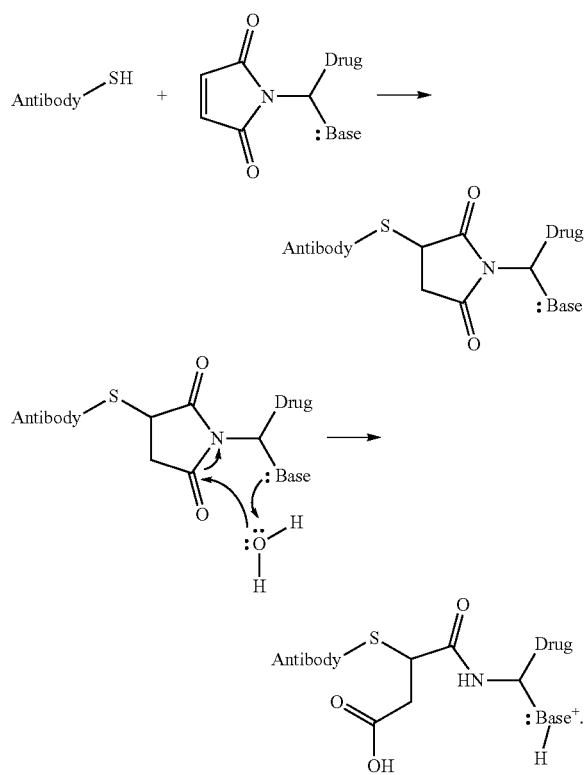

The hydrolysis reaction schematically represented above may occur at either carbonyl group of the succinimide group. Accordingly, two possible isomers may result, as shown below:

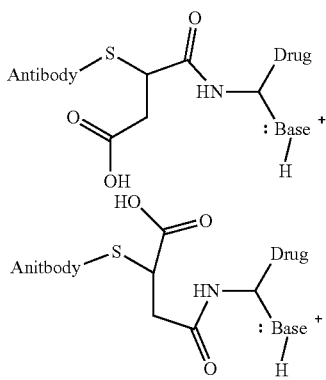

The identity of the base as well as the distance between the base and the maleimide group can be modified to tune the rate of hydrolysis of the thio-substituted succinimide group and optimize the delivery of a conjugate to a target by, for example, improving the specificity and stability of the conjugate.

Bases suitable for inclusion in a linker of the disclosure, e.g., any linker of the disclosure with a maleimide group prior to conjugating to an antibody or antigen-binding fragment thereof, may facilitate hydrolysis of a nearby succinimide group formed after conjugation of the antibody or antigen-binding fragment thereof to the linker. Bases may include, for example, amines (e.g., —N($R^{26}$)($R^{27}$), where $R^{26}$ and $R^{27}$ are independently selected from H and $C_{1-6}$ alkyl), nitrogen-containing heterocycles (e.g., a 3- to 12-membered heterocycle including one or more nitrogen atoms and optionally one or more double bonds), amidines, guanidines, and carbocycles or heterocycles substituted with one or more amine groups (e.g., a 3- to 12-membered aromatic or non-aromatic cycle optionally including a heteroatom such as a nitrogen atom and substituted with one or more amines of the type —N($R^{26}$)($R^{27}$), where $R^{26}$ and $R^{27}$ are independently selected from H or $C_{1-6}$ alkyl). A basic unit may be separated from a maleimide group by, for example, an alkylene chain of the form —$(CH_2)_m$—, where m is an integer from 0 to 10. An alkylene chain may be optionally substituted with other functional groups as described in the disclosure.

A linker of the disclosure with a maleimide group may include an electron withdrawing group such as, but not limited to, —C(O)R, =O, —CN, —$NO_2$, —$CX_3$, —X, —COOR, —$CONR_2$, —COR, —COX, —$SO_2R$, —$SO_2OR$, —$SO_2NHR$, —$SO_2NR_2$, $PO_3R_2$, —P(O)($CH_3$)NHR, —NO, —$NR_3^+$, —CR=$CR_2$, and —C≡CR, where each R is independently selected from H and $C_{1-6}$ alkyl and each X is independently selected from F, Br, Cl, and I. Self-stabilizing linkers may also include aryl, e.g., phenyl, or heteroaryl, e.g., pyridine, groups optionally substituted with electron withdrawing groups such as those of the disclosure.

Examples of self-stabilizing linkers are provided in, e.g., U.S. Patent Publication No. US 2013/0309256, the linkers of which are incorporated by reference herein. It will be understood that a self-stabilizing linker useful in conjunction with immune-stimulatory compounds may be equivalently described as unsubstituted maleimide-including linkers, thio-substituted succinimide-including linkers, or hydrolyzed, ring-opened thio-substituted succinimide-including linkers.

In some embodiments, a linker comprises a stabilizing linker moiety selected from:

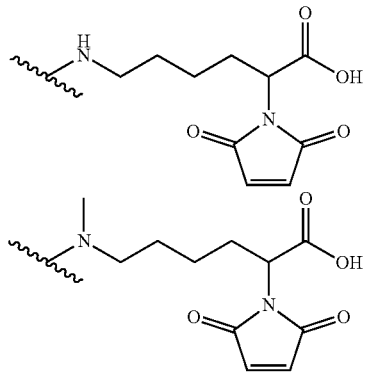

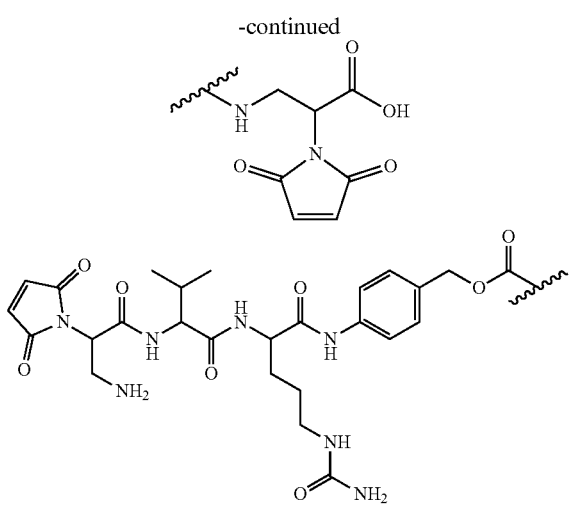

In the scheme provided above, the bottom structure may be referred to as (maleimido)-DPR-Val-Cit-PAB, where DPR refers to diaminopropinoic acid, Val refers to valine, Cit refers to citrulline, and PAB refers to para-aminobenzylcarbonyl.

∿ represents the point of attachment to an immune-stimulatory compound.

A method for bridging a pair of sulfhydryl groups derived from reduction of a native hinge disulfide bond has been disclosed and is depicted in the schematic below. An advantage of this methodology is the ability to synthesize homogenous DAR4 conjugates by full reduction of IgGs (to give 4 pairs of sulfhydryls from interchain disulfides) followed by reaction with 4 equivalents of the alkylating agent. Conjugates containing "bridged disulfides" are also claimed to have increased stability.

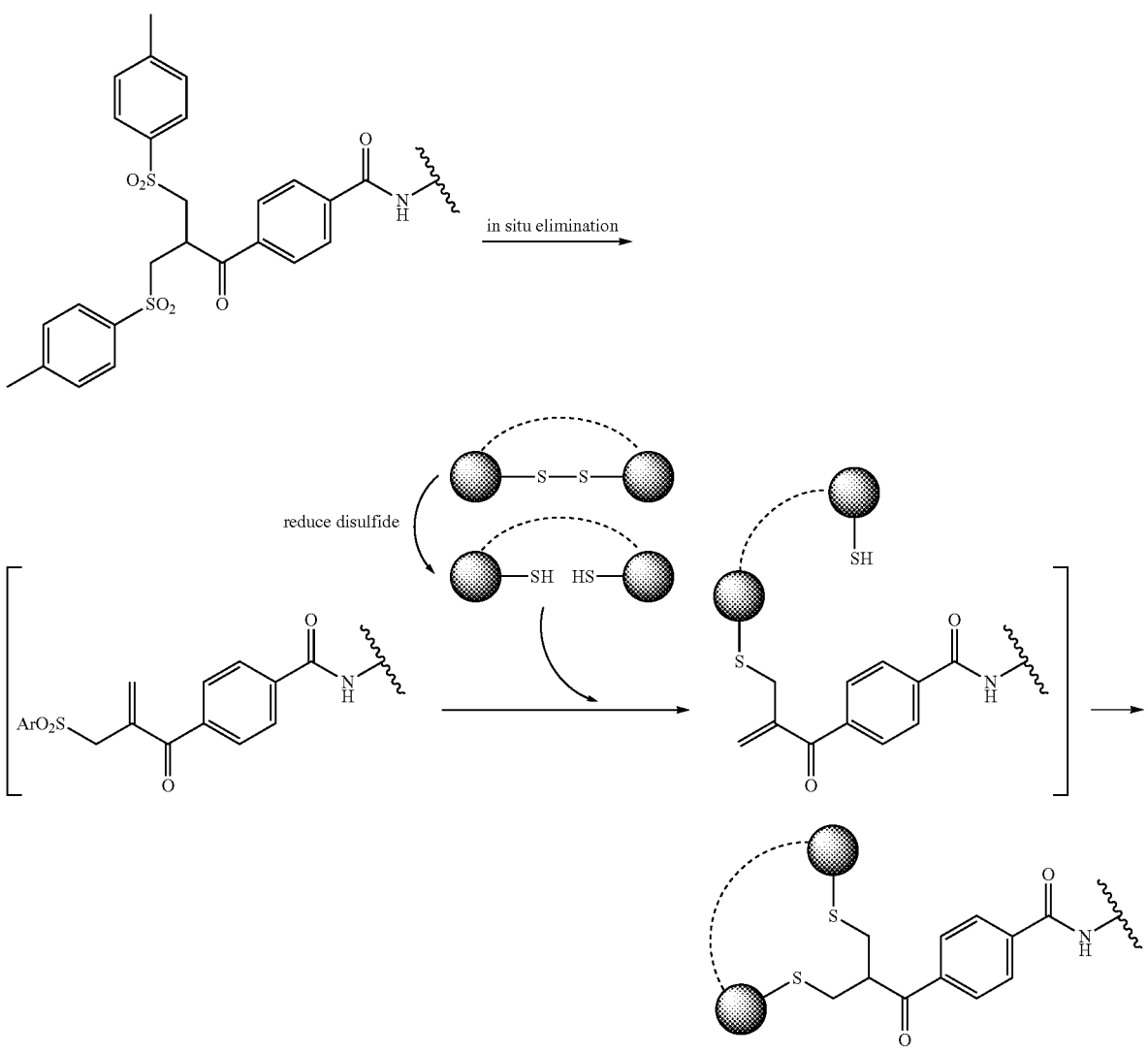

"bridged disulfide"

Similarly, as depicted below, a maleimide derivative that is capable of bridging a pair of sulfhydryl groups has been developed.

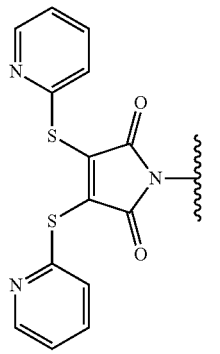

→

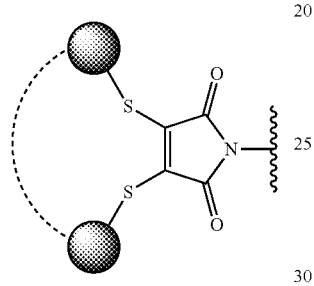

A linker can contain the following structural formulas (VIa), (VIb), or (VIc):

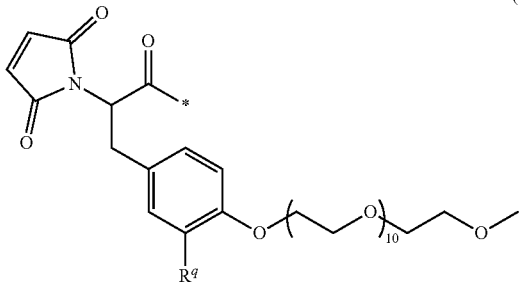
(VIa)

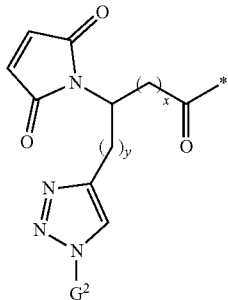
(VIb)

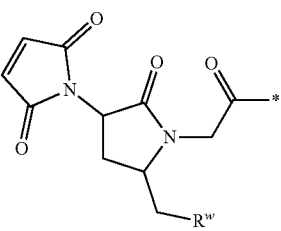
(VIc)

or salts thereof, wherein: $R^q$ is H or —O—(CH$_2$CH$_2$O)$_n$—CH$_3$; x is 0 or 1; y is 0 or 1; G$^2$ is —CH$_2$CH$_2$CH$_2$SO$_3$H or —CH$_2$CH$_2$O—(CH$_2$CH$_2$O)$_{11}$—CH$_3$; R$^w$ is -O—CH$_2$CH$_2$SO$_3$H or —NH(CO)—CH$_2$CH$_2$O—(CH$_2$CH$_2$O)$_{12}$—CH$_3$; and * represents the point of attachment to the remainder of the linker.

Exemplary embodiments of linkers according to structural formula (VIa) and (VIb) that can be included in the conjugates of the disclosure can include the linkers illustrated below (as illustrated, the linkers can include a group suitable for covalently linking the linker to an antibody or antigen-binding fragment thereof):

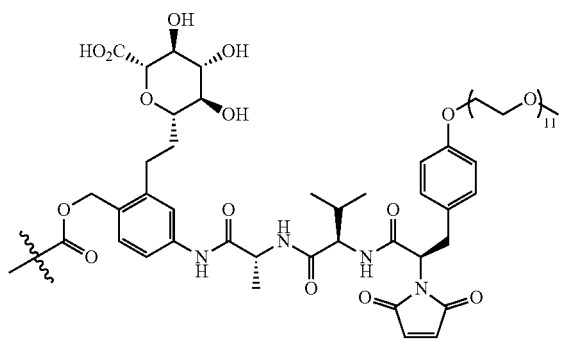
(VIa.1)

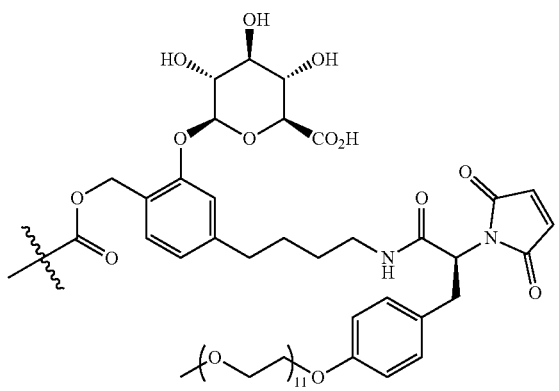
(VIa.2)

-continued
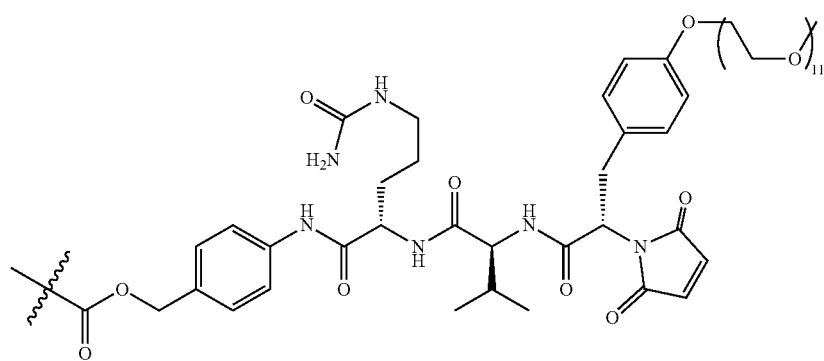
(VIa.3)
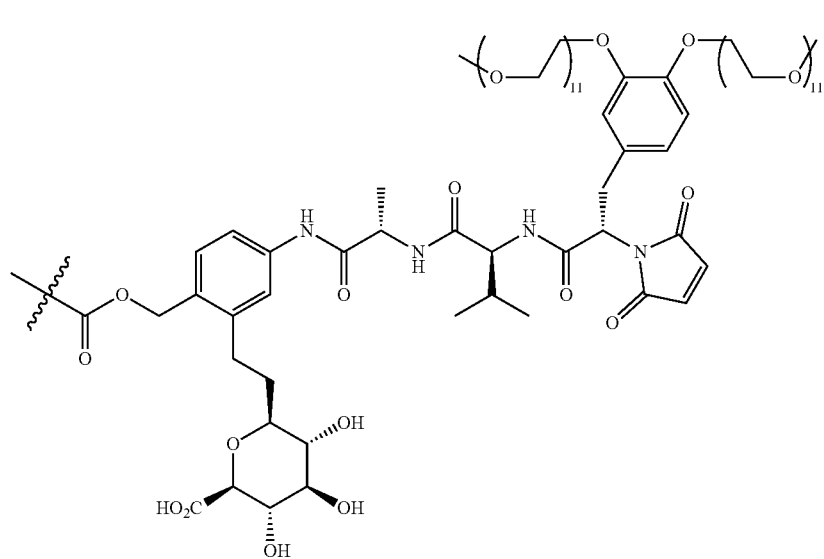
(VIa.4)
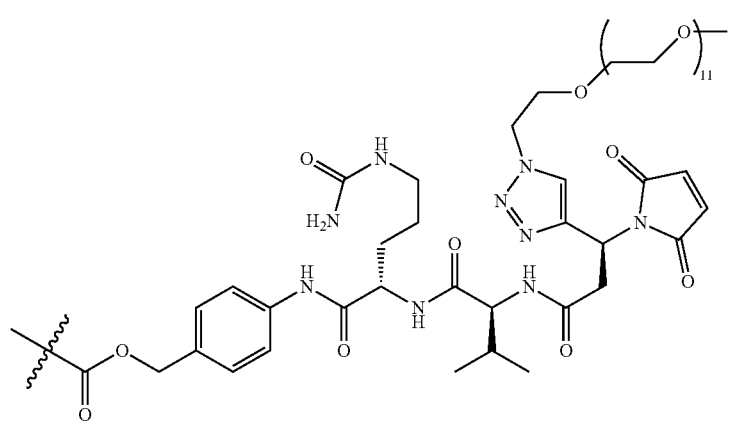
(VIb.1)

-continued
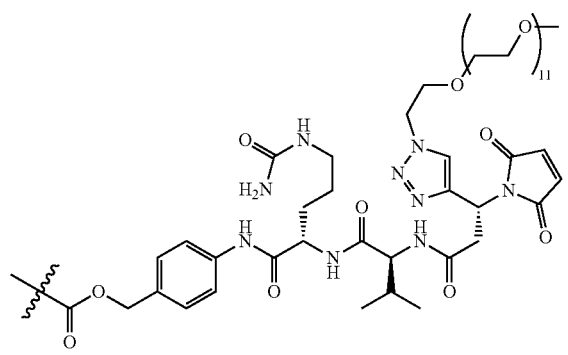
(VIb.2)
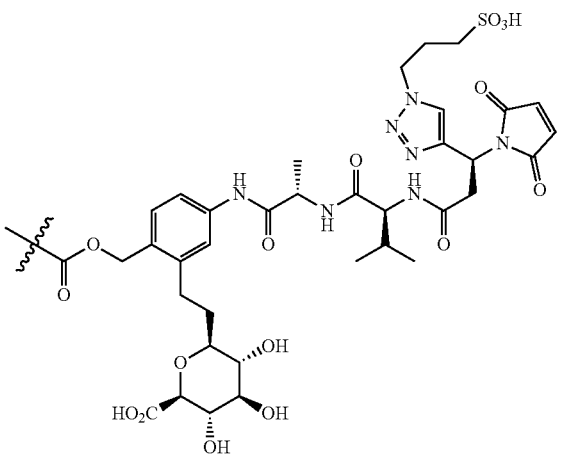
(VIb.3)
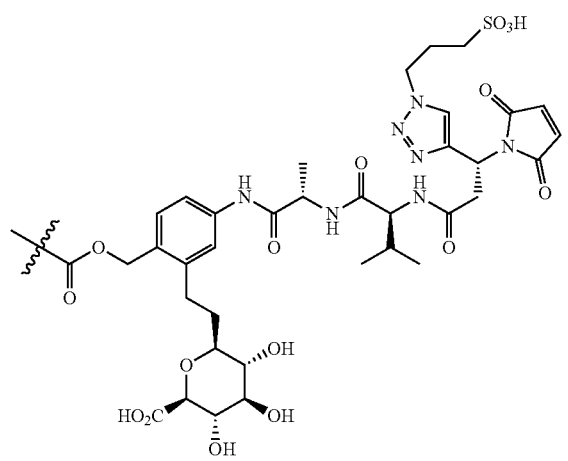
(VIb.4)
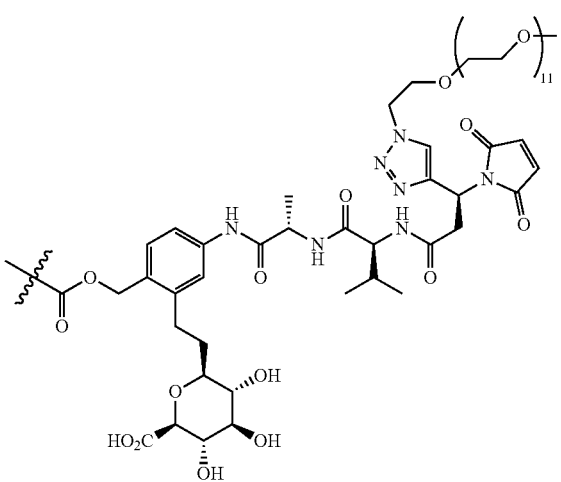
(VIb.6)
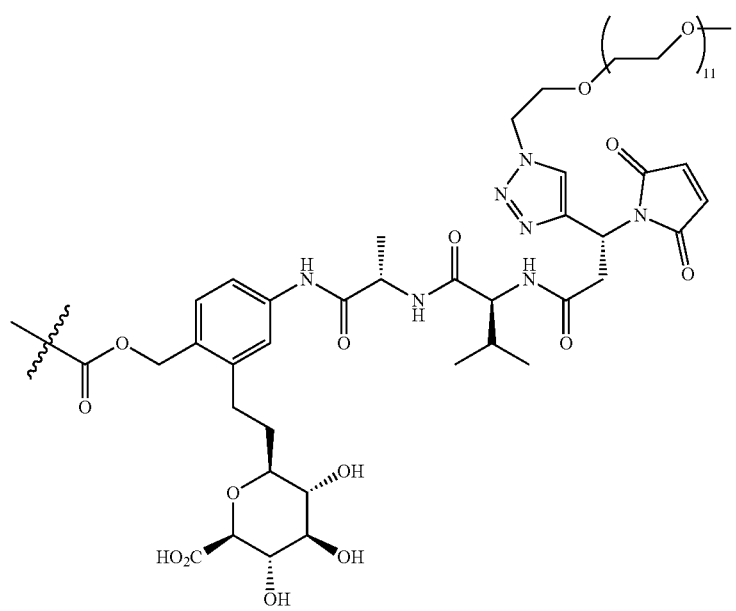
(VIb.7)

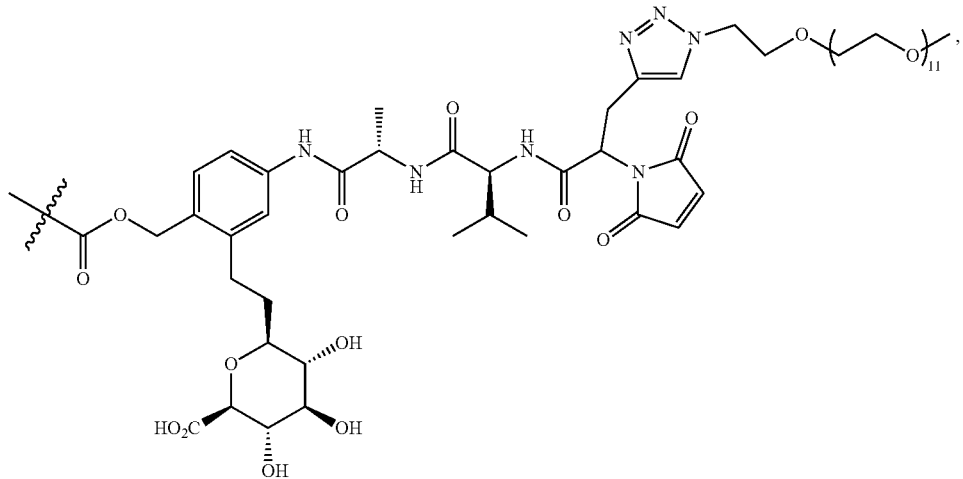
(VIIb.8)

wherein

represents the point of attachment of the linker to an immune-stimulatory compound.

Exemplary embodiments of linkers according to structural formula (VIc) that can be included in the immune-stimulatory conjugates of the disclosure can include the linkers illustrated below (as illustrated, the linkers can include a group suitable for covalently linking the linker to an antibody or antigen-binding fragment thereof):

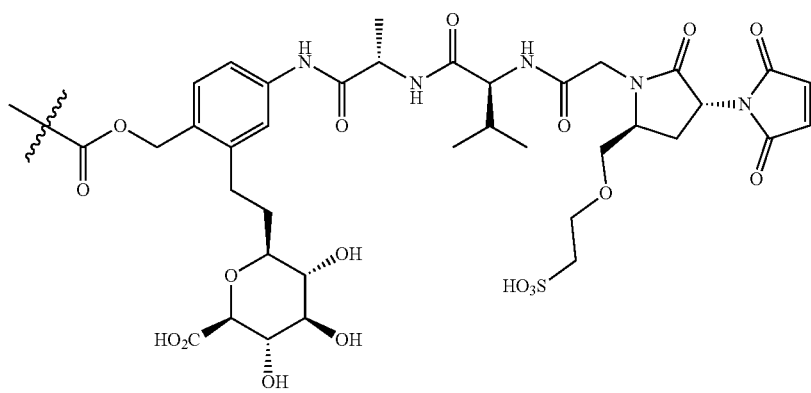
(VIc.1)

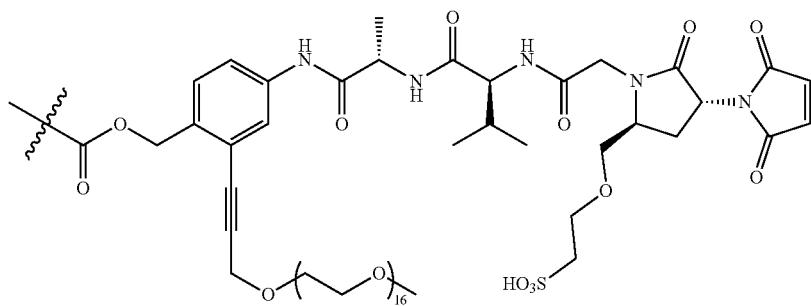
(VIc.2)

-continued
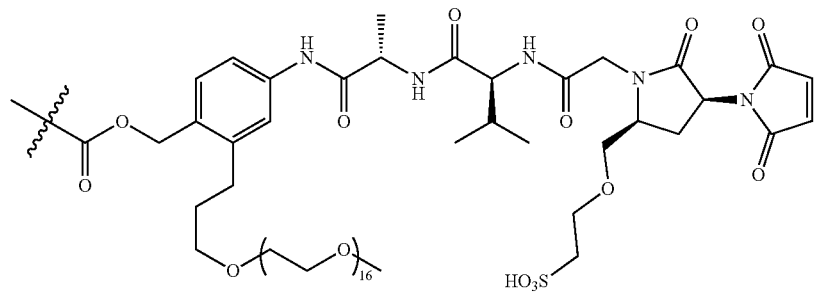
(VIc.3)
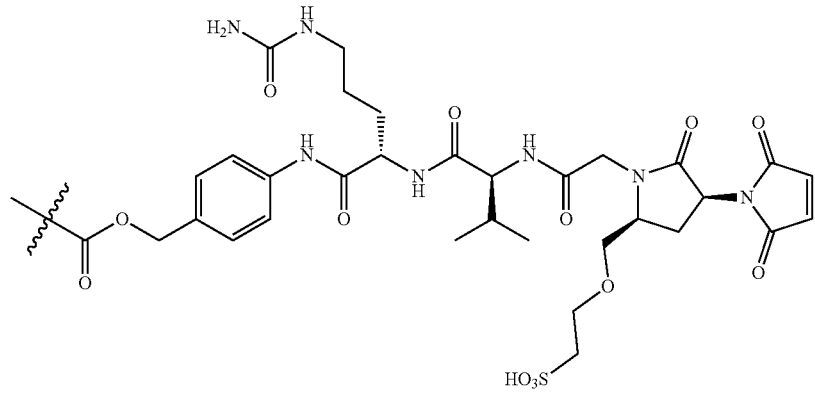
(VIc.4)
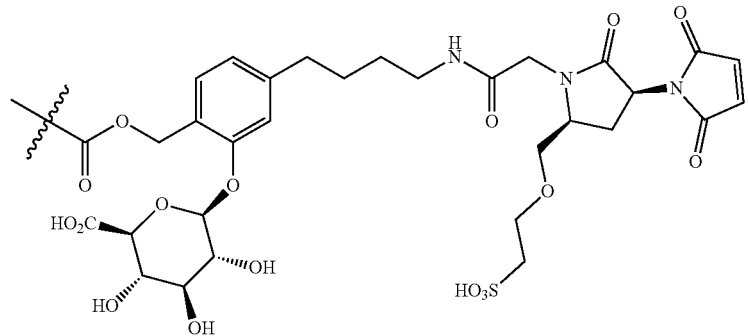
(VIc.5)
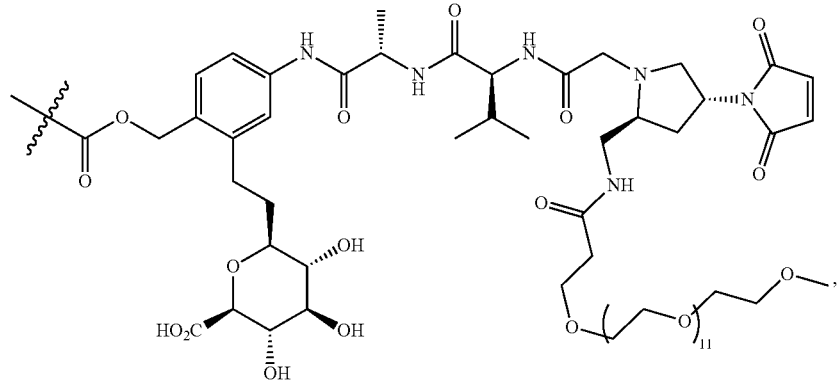
(VIc.6)

wherein

represents the point of attachment of the linker to an immune-stimulatory compound.

A linker can be attached to an antibody or antigen-binding fragment thereof at any suitable position. Factors to be considered in selecting an attachment site include whether the linker is cleavable or non-cleavable, the reactive group of the linker for attachment to the antibody or antigen-binding fragment thereof, the chemical nature of the immune-stimulatory compound and compatibility with reactive sites on the linker and the antibody or antigen-binding fragment thereof, and the effect of the attachment site on functional activities of the Fc domain. A linker may be attached to a terminus of an amino acid sequence of an antibody or antigen-binding fragment thereof or can be attached to a side chain of an amino acid of an antibody or antigen-binding fragment thereof, such as the side chain of a lysine, serine, threonine, cysteine, tyrosine, aspartic acid, glutamine, a non-natural amino acid residue, or glutamic acid residue. A linker may be bound to a terminus of an amino acid sequence of an Fc domain or Fc region of an antibody or antigen-binding fragment thereof, or may be bound to a side chain of an amino acid of an Fc domain of an antibody or antigen-binding fragment thereof, such as the side chain of a lysine, serine, threonine, cysteine, tyrosine, aspartic acid, glutamine, a non-natural amino acid residue, or glutamic acid residue.

In some embodiments, a linker is attached to a hinge cysteine of an antibody Fc domain. A linker can be attached to an antibody or antigen-binding fragment thereof at a light chain constant domain lysine. A linker can be attached to an antibody or antigen-binding fragment thereof at an engineered cysteine in the light chain. A linker can be attached to an antibody or antigen-binding fragment thereof at an engineered light chain glutamine. A linker can be attached to an antibody or antigen-binding fragment thereof at an unnatural amino acid engineered into the light chain. A linker can be attached to an antibody or antigen-binding fragment thereof at a heavy chain constant domain lysine. A linker can be attached to an antibody or antigen-binding fragment thereof at an engineered cysteine in the heavy chain. A linker can be attached to an antibody or antigen-binding fragment thereof at an engineered heavy chain glutamine. A linker can be attached to an antibody or antigen-binding fragment thereof at an unnatural amino acid engineered into the heavy chain. Amino acids can be engineered into an amino acid sequence of an antibody or antigen-binding fragment thereof as described in the disclosure or as known to the skilled artisan and can be connected to a linker of a conjugate. Engineered amino acids can be added to a sequence of existing amino acids. Engineered amino acids can be substituted for one or more existing amino acids of a sequence of amino acids.

A linker can be attached to an antibody or antigen-binding fragment thereof via a sulfhydryl group. A linker can be attached to an antibody or antigen-binding fragment thereof via a primary amine. A linker can be a link created between an unnatural amino acid on an antibody by reacting with oxime bond that was formed by modifying a ketone group with an alkoxyamine on an immune stimulatory compound.

As is known by skilled artisans, the linker selected for a particular conjugate may be influenced by a variety of factors, including but not limited to, the site of attachment to the antibody or antigen-binding fragment thereof (e.g., Lys, Cys or other amino acid residues), structural constraints of the drug pharmacophore and the lipophilicity of the drug. The specific linker selected for a conjugate should seek to balance these different factors for the specific antibody/drug combination.

For example, conjugates have been observed to effect killing of bystander antigen-negative cells present in the vicinity of the antigen-positive tumor cells. The mechanism of bystander cell killing by conjugates has indicated that metabolic products formed during intracellular processing of the conjugates may play a role. Neutral cytotoxic metabolites generated by metabolism of the conjugates in antigen-positive cells appear to play a role in bystander cell killing while charged metabolites may be prevented from diffusing across the membrane into the medium, or from the medium across the membrane, and therefore cannot affect bystander killing. In some embodiments, the linker is selected to attenuate the bystander effect caused by cellular metabolites of the conjugate. In some embodiments, the linker is selected to increase the bystander effect.

The properties of the linker, or linker-compound, may also impact aggregation of the conjugate under conditions of use and/or storage. Typically, conjugates reported in the literature contain no more than 3-4 drug molecules per antibody molecule. Attempts to obtain higher drug-to-antibody ratios ("DAR") often failed, particularly if both the drug and the linker were hydrophobic, due to aggregation of the conjugate. In many instances, DARs higher than 3-4 could be beneficial as a means of increasing potency. In instances where an immune-stimulatory compound is more hydrophobic in nature, it may be desirable to select linkers that are relatively hydrophilic as a means of reducing conjugate aggregation, especially in instances where DARs greater than 3-4 are desired. Thus, in some embodiments, a linker incorporates chemical moieties that reduce aggregation of the conjugates during storage and/or use. A linker may incorporate polar or hydrophilic groups such as charged groups or groups that become charged under physiological pH to reduce the aggregation of the conjugates. For example, a linker may incorporate charged groups such as salts or groups that deprotonate, e.g., carboxylates, or protonate, e.g., amines, at physiological pH.

In particular embodiments, the aggregation of the conjugates during storage or use is less than about 40% as determined by size-exclusion chromatography (SEC). In particular embodiments, the aggregation of the conjugates during storage or use is less than 35%, such as less than about 30%, such as less than about 25%, such as less than about 20%, such as less than about 15%, such as less than about 10%, such as less than about 5%, such as less than about 4%, or even less, as determined by size-exclusion chromatography (SEC).

The compounds and salts of the disclosure may be bound to a linker, e.g., a peptide linker. In some embodiments, the linker is also bound to an antibody, an antibody construct, or a targeting moiety, and may be referred to as an antibody conjugate, an antibody construct conjugate, or a targeting moiety conjugate, respectively, or may be referred to simply as a conjugate. Linkers of the conjugates may not affect the binding of active portions of a conjugate, e.g., the antigen binding domains, Fc region or domains, target binding domain, antibody, targeting moiety, or the like, to a target, which can be a cognate binding partner, such as an antigen. A conjugate can comprise multiple linkers, each having one or more compounds attached. The multiple linkers can be the same linker or different linkers contained on a single conjugate or on separate conjugates.

As will be appreciated by skilled artisans, a linker connects one or more immune-stimulatory compounds to an antibody or antigen-binding fragment thereof by forming a covalent linkage to the compound at one location and a covalent linkage to the antibody or antigen-binding fragment thereof at another location. The covalent linkages can be formed by reaction between functional groups on the linker and functional groups on the immune-stimulatory compound and on the antibody or antigen-binding fragment thereof. As used throughout the disclosure, the expression "linker" can include (i) unattached forms of the linker that can include a functional group capable of covalently attaching the linker to an immune-stimulatory compound and a functional group capable of covalently attached the linker to an antibody or antigen-binding fragment thereof; (ii) partially attached forms of the linker that can include a functional group capable of covalently attaching the linker to an antibody or antigen-binding fragment thereof and that can be covalently attached to an immune-stimulatory compound, or vice versa; and (iii) fully attached forms of the linker that can be covalently attached to both an immune-stimulatory compound and to an antibody or antigen-binding fragment thereof. In some specific embodiments, the functional groups on a linker and covalent linkages formed between the linker and an antibody or antigen-binding fragment thereof can be specifically illustrated as Rx and Rx', respectively.

A linker can be short, flexible, rigid, cleavable, non-cleavable, hydrophilic, or hydrophobic. A linker can contain segments that have different characteristics, such as segments of flexibility or segments of rigidity. The linker can be chemically stable to extracellular environments, for example, chemically stable in the blood stream, or may include linkages that are not stable or selectively stable. The linker can include linkages that are designed to cleave and/or immolate or otherwise breakdown specifically or non-specifically inside cells. A cleavable linker can be sensitive to enzymes. A cleavable linker can be cleaved by enzymes such as proteases.

A cleavable linker can include a valine-citrulline (Val-Cit) peptide, a valine-alanine (Val-Ala) peptide, a phenylalanine-lysine (Phe-Lys) or other peptide, such as a peptide that forms a protease recognition and cleavage site. Such a peptide-containing linker can contain a pentafluorophenyl group. A peptide-containing linker can include a succimide or a maleimide group. A peptide-containing linker can include a para aminobenzoic acid (PABA) group. A peptide-containing linker can include an aminobenzyloxycarbonyl (PABC) group. A peptide-containing linker can include a PABA or PABC group and a pentafluorophenyl group. A peptide-containing linker can include a PABA or PABC group and a succinimide group. A peptide-containing linker can include a PABA or PABC group and a maleimide group.

A non-cleavable linker is generally protease-insensitive and insensitive to intracellular processes. A non-cleavable linker can include a maleimide group. A non-cleavable linker can include a succinimide group. A non-cleavable linker can be maleimido-alkyl-C(O)— linker. A non-cleavable linker can be maleimidocaproyl linker. A maleimidocaproyl linker can be N-maleimidomethylcyclohexane-1-carboxylate. A maleimidocaproyl linker can include a succinimide group. A maleimidocaproyl linker can include pentafluorophenyl group.

A linker can be a combination of a maleimidocaproyl group and one or more polyethylene glycol molecules. A linker can be a maleimide-PEG4 linker. A linker can be a combination of a maleimidocaproyl linker containing a succinimide group and one or more polyethylene glycol molecules. A linker can be a combination of a maleimidocaproyl linker containing a pentafluorophenyl group and one or more polyethylene glycol molecules. A linker can contain a maleimide(s) linked to polyethylene glycol molecules in which the polyethylene glycol can allow for more linker flexibility or can be used lengthen the linker.

A linker can be a (maleimidocaproyl)-(valine-alanine)-(para-aminobenzyloxycarbonyl) linker. A linker can be a (maleimidocaproyl)-(valine-citrulline)-(para-aminobenzyloxycarbonyl) linker. A linker can be a (maleimidocaproyl)-(phenylalanine-lysine)-(para-aminobenzyloxycarbonyl) linker. A linker can be a linker suitable for attachment to an engineered cysteine (THIOMAB). A THIOMAB linker can be a (maleimidocaproyl)-(valine-citrulline)-(para-aminobenzyloxycarbonyl)-linker.

A linker can also contain segments of alkylene, alkenylene, alkynylene, polyether, polyester, polyamide, polyamino acids, peptides, polypeptides, cleavable peptides, and/or aminobenzyl-carbamates. A linker can contain a maleimide at one end and an N-hydroxysuccinimidyl ester at the other end. A linker can contain a lysine with an N-terminal amine acetylated, and a valine-citrulline, valine-alanine or phenylalanine-lysine cleavage site. A linker can be a link created by a microbial transglutaminase, wherein the link can be created between an amine-containing moiety and a moiety engineered to contain glutamine as a result of the enzyme catalyzing a bond formation between the acyl group of a glutamine side chain and the primary amine of a lysine chain. A linker can contain a reactive primary amine. A linker can be a Sortase A linker. A Sortase A linker can be created by a Sortase A enzyme fusing an LPXTG recognition motif (SEQ ID NO:237) to an N-terminal GGG motif to regenerate a native amide bond. The linker created can therefore link to a moiety attached to the LPXTG recognition motif (SEQ ID NO:237) with a moiety attached to the N-terminal GGG motif A linker can be a link created between an unnatural amino acid on one moiety reacting with oxime bond that was formed by modifying a ketone group with an alkoxyamine on another moiety. A moiety can be part of a conjugate. A moiety can be part of an antibody. A moiety can be part of an immune-stimulatory compound. A moiety can be part of a binding domain. A linker can be unsubstituted or substituted, for example, with a substituent. A substituent can include, for example, hydroxyl groups, amino groups, nitro groups, cyano groups, azido groups, carboxyl groups, carboxaldehyde groups, imine groups, alkyl groups, alkenyl groups, alkynyl groups, alkoxy groups, acyl groups, acyloxy groups, amide groups, and ester groups.

In the conjugates, a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) is linked to the antibody by way of a linker(s), also referred to in the disclosure as L. L, as used throughout the disclosure, may be selected from any of the linker moieties discussed in the disclosure. The linker linking the compound or salt to the antibody, antibody construct, or targeting moiety of a conjugate may be short, long, hydrophobic, hydrophilic, flexible or rigid, or may be composed of segments that each independently have one or more of the above-mentioned properties such that the linker may include segments having different properties. The linkers may be polyvalent such that they covalently link more than one compound or salt to a single site on the antibody, antibody construct, or targeting moiety, or monovalent such that covalently they link a single compound or salt to a single site on the antibody, antibody construct, or targeting moiety.

A linker can be polyvalent such that it covalently links more than one immune-stimulatory compound to a single site on the antibody or antigen-binding fragment thereof, or monovalent such that it covalently links a single immune-stimulatory compound to a single site on the antibody or antigen-binding fragment thereof.

In some embodiments for a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, the compound may further comprise a linker (L), which results a linker-payload. The linker may be covalently bound to any position, valence permitting, on a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or a pharmaceutically acceptable isomer, tautomer, racemate, hydrate, solvate, isotope, or salt thereof. For example, the linker may be bound to $R^7$ or $R^8$. In some embodiments, a linker is bound to $R^7$. In some embodiments, a linker is bound to a nitrogen atom, e.g., an amine, or oxygen atom, e.g., a hydroxyl, of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof. The linker may comprise a reactive moiety, e.g., an electrophile that can react to form a covalent bond with a reactive moiety of an antibody, an antibody construct, or a targeting moiety, e.g., a lysine, serine, threonine, cysteine, tyrosine, aspartic acid, glutamine, a non-natural amino acid residue, or glutamic acid residue. In some embodiments, a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, may be covalently bound through the linker to an antibody, an antibody construct, or a targeting moiety.

In the conjugates, a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, is linked to an antibody, an antibody construct, or a targeting moiety by way of a linker(s), also referred to throughout the disclosure as L. L, as used throughout the disclosure, may be selected from any of the linker moieties of the disclosure. The linker linking the compound or salt to an antibody, an antibody construct, or a targeting moiety of a conjugate may be short, long, hydrophobic, hydrophilic, flexible or rigid, or may be composed of segments that each independently have one or more of the above-mentioned properties, such that the linker may include segments having different properties. The linkers may be polyvalent such that they covalently link more than one compound or salt to a single site on an antibody, an antibody construct, or a targeting moiety, or monovalent, such that covalently they link a single compound or salt to a single site on an antibody construct, or a targeting moiety.

Linkers of the disclosure (L) may have from about 10 to about 500 atoms in a linker, such as from about 10 to about 400 atoms, such as about 10 to about 300 atoms in a linker. In some embodiments, linkers of the disclosure have from about 30 to about 400 atoms, such as from about 30 to about 300 atoms in the linker.

As will be appreciated by skilled artisans, the linkers may link a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) to an antibody, an the antibody construct, or a targeting moiety by a covalent linkages between the linker and the antibody, the antibody construct, or the targeting moiety, and the compound, to form a conjugate. As used throughout the disclosure, the expression "linker" is intended to include (i) unconjugated forms of the linker that include a functional group capable of covalently linking the linker to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, the disclosure and a functional group capable of covalently linking the linker to an antibody, an antibody construct, or a targeting moiety; (ii) partially conjugated forms of the linker that include a functional group capable of covalently linking the linker to the an antibody, the antibody construct, or the targeting moiety, and that is covalently linked to at least one compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope(s), or salt thereof(s) of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or vice versa; and (iii) fully conjugated forms of the linker that is covalently linked to both a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and an antibody, an antibody construct, or the targeting moiety. One embodiment pertains to a conjugate formed by contacting an antibody, an antibody construct, or a targeting moiety that binds a cell surface receptor or tumor-associated antigen expressed on a tumor cell with a linker-compound of the disclosure under conditions in which the linker-compound covalently links to the antibody, the antibody construct, or the targeting moiety. Further embodiments pertain to expression constructs. One embodiment pertains to a method of making a conjugate formed by contacting a linker-compound under conditions in which the linker-compound covalently links to an antibody, an antibody construct, or a targeting moiety.

In some embodiments, a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, Salts described in the section entitled "Compounds" is covalently bound to a linker (L) to form a linker-payload (L-P). The linker may be covalently bound to any position of the compound, valence permitting. The linker may comprise a reactive moiety, e.g., an electrophile that can react to form a covalent bond with a moiety of an antibody, an antibody construct, or a targeting moiety, such as, for example, a lysine, serine, threonine, cysteine, tyrosine, aspartic acid, glutamine, a non-natural amino acid residue, or glutamic acid residue. In some embodiments, a linker-payload, comprising a compound or salt of a compound in the section entitled "Compounds" of the disclosure and a linker, L, is covalently bound through L the linker to an antibody, an antibody construct, or a targeting moiety. In some embodiments, any one of the compounds or salts described in the section entitled "Compounds" is covalently bound to a linker (L). The linker may be covalently bound to any position, valence permitting. The linker may comprise a reactive moiety, e.g., an electrophile that can react to form a covalent bond with a moiety of an antibody, antibody construct, or targeting moiety, such as, for example, a lysine, serine, threonine, cysteine, tyrosine, aspartic acid, glutamine, a non-natural amino acid residue, or glutamic acid residue. In some embodiments, a compound or salt of a compound in the section entitled "Compounds" of the disclosure is covalently bound through the linker to an antibody, an antibody construct, or a targeting moiety.

In some embodiments, a linker-payload, comprising an immune-stimulatory compound or salt thereof of this disclosure and a linker, L, is covalently bound through L to an antibody. In some embodiments, a linker-payload, comprising an immune-stimulatory compound or salt thereof of this disclosure and a linker, L, is covalently bound through L to an antibody construct. In some embodiments, a linker-payload, comprising an immune-stimulatory compound or salt thereof of this disclosure and a linker, L, is covalently bound through L to a targeting moiety. In any of the aforementioned embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, L is a noncleavable linker. Alternatively, in any of the aforementioned embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, L is a cleavable linker, such as a linker cleavable by a lysosomal enzyme. In any of the aforementioned embodiments, the antibody, antibody construct, or targeting moiety may further comprise a second antigen or target binding domain.

In some embodiments, an immune-stimulatory compound of this disclosure is covalently attached to an antibody, an antibody construct, or a targeting moiety. In particular embodiments, an immune-stimulatory compound of this disclosure is covalently attached to an antibody. In some embodiments, an immune-stimulatory compound of this disclosure is covalently attached to an antibody construct. In some embodiments, the compound is covalently attached to a targeting moiety. In any of the aforementioned embodiments, the antibody, antibody construct, or targeting moiety may further comprise a second antigen or target binding domain.

Exemplary polyvalent linkers that may be used to link compounds of the disclosure to an antibody, an antibody construct, or a targeting moiety are provided in the disclosure. For example, Fleximer® linker technology has the potential to enable high-DAR conjugates with good physicochemical properties. As shown below, the Fleximer® linker technology is based on incorporating drug molecules into a solubilizing poly-acetal backbone via a sequence of ester bonds:

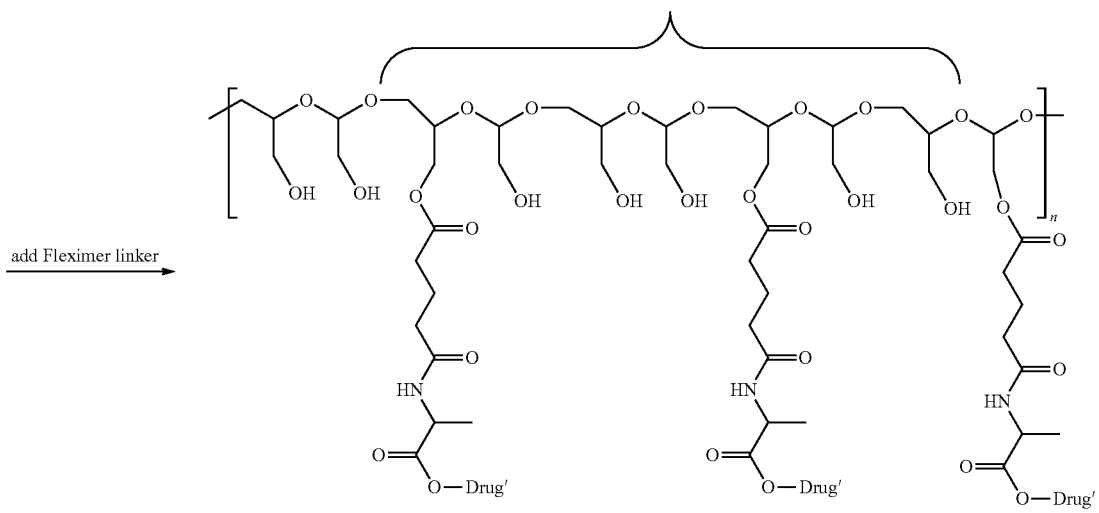

The methodology renders highly-loaded conjugates (DAR up to 20) whilst maintaining good physicochemical properties. This methodology can be utilized with an immune-stimulatory compound as shown in the scheme below, where Drug' refers to the immune-stimulatory compound.

To utilize the Fleximer® linker technology depicted in the scheme above, an aliphatic alcohol can be present or introduced into the immune-stimulatory compound. The alcohol moiety is then attached to an alanine moiety, which is then synthetically incorporated into the Fleximer® linker. Liposomal processing of the conjugate in vitro releases the parent alcohol-containing drug.

In some embodiments, a moiety, construct, or conjugate of the disclosure includes the symbol ⌇, which indicates the point of attachment, e.g., the point of attachment of a chemical or functional moiety to the compound, the point of attachment of a linker to a compound of the disclosure, or the point of attachment of a linker to an antibody, an antibody construct, or a targeting moiety.

By way of example and not limitation, some cleavable and noncleavable linkers that may be included in the conjugates are described below, in addition to any other of the disclosure.

Sulfamide linkers may be used to link many compounds of the disclosure to an antibody, an antibody construct, or a targeting moiety. Sulfamide linkers are of the present disclosure and e.g., U.S. Patent Publication Number 2019/0038765, the linkers of which are incorporated by reference herein.

Cleavable linkers can be cleavable in vitro, in vivo, or both. Cleavable linkers can include chemically or enzymatically unstable or degradable linkages. Cleavable linkers can rely on processes inside the cell to liberate a compound of Formula (I), such as reduction in the cytoplasm, exposure to acidic conditions in the lysosome, or cleavage by specific proteases or other enzymes within the cell. Cleavable linkers can incorporate one or more chemical bonds that are either chemically or enzymatically cleavable while the remainder of the linker can be non-cleavable.

In some embodiments, L is a linker comprising a reactive moiety. In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, -L is represented by the formula:

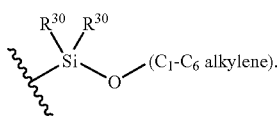

In some embodiments, -L is represented by the formula:

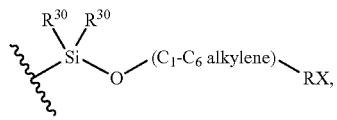

wherein each $R^{30}$ is independently selected from optionally substituted $C_1$-$C_6$ alkyl and optionally substituted phenyl, and RX is the reactive moiety. RX may comprise a leaving group. RX may be a maleimide. L may be further covalently bound to an antibody, an antibody construct, or a targeting moiety. In some embodiments, -L- is represented by the formula:

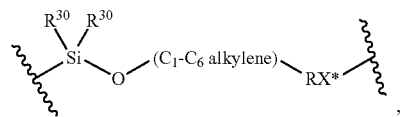

wherein RX* is a bond, a succinimide moiety, or a hydrolyzed succinimide moiety bound to a residue of an antibody, an antibody construct, or a targeting moiety, wherein

on RX* represents the point of attachment to a residue of the antibody, antibody construct, or targeting moiety; and each $R^{30}$ is independently selected from optionally substituted $C_1$-$C_6$ alkyl and optionally substituted phenyl.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and linker L; L comprises a methylene carbamate unit.

In some embodiments, for a linker-payload (L-P) comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and linker L-RX*; the L-P is part of a conjugate and RX* comprises a hydrolyzed succinamide moiety and is bound to a cysteine residue of an antibody, an antibody construct, or a targeting moiety. In any of the aforementioned embodiments, the antibody, antibody construct, or targeting moiety comprises an antigen binding domain that specifically binds to ASGR1.

By way of example and not limitation, some cleavable and noncleavable linkers that may be included in the conjugates are described below, in addition to any others of the disclosure.

A linker can contain a chemically labile group such as hydrazone and/or disulfide groups. Linkers comprising chemically labile groups can exploit differential properties between the plasma and some cytoplasmic compartments. The intracellular conditions that can facilitate release of a compound any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof for hydrazone containing linkers can be the acidic environment of endosomes and lysosomes, while the disulfide containing linkers can be reduced in the cytosol, which can contain high thiol concentrations, e.g., glutathione. The plasma stability of a linker containing a chemically labile group can be increased by introducing steric hindrance using substituents near the chemically labile group.

Acid-labile groups, such as hydrazone, can remain intact during systemic circulation in the blood's neutral pH environment (pH 7.3-7.5) and can undergo hydrolysis and can release a compound of the disclosure once the antibody conjugate is internalized into mildly acidic endosomal (pH 5.0-6.5) and lysosomal (pH 4.5-5.0) compartments of the cell. This pH dependent release mechanism can be associated with nonspecific release of the drug. To increase the stability of the hydrazone group of the linker, the linker can be varied by chemical modification, e.g., substitution, allowing tuning to achieve more efficient release in the lysosome with a minimized loss in circulation.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof; and a linker L, -L comprises a hydrazone moiety. For example, L may be selected from:

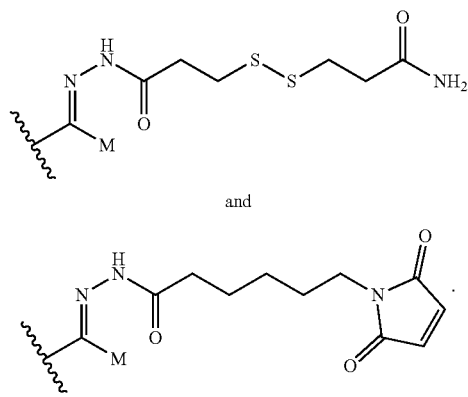

and wherein M is selected from $C_1$-$C_6$ alkyl, aryl, and —O—$C_1$-$C_6$ alkyl.

Hydrazone-containing linkers can contain additional cleavage sites, such as additional acid-labile cleavage sites and/or enzymatically labile cleavage sites. Conjugates including exemplary hydrazone-containing linkers can include, for example, the following structures:

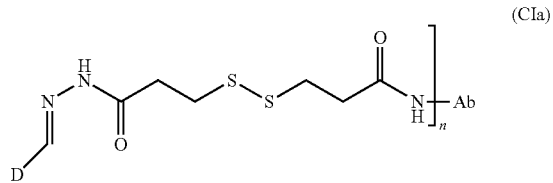
(CIa)

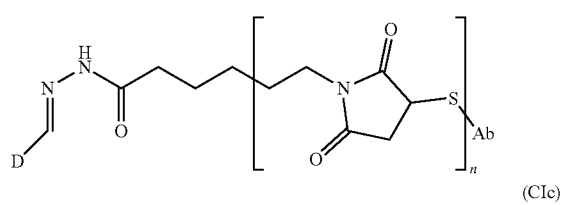
(CIb)

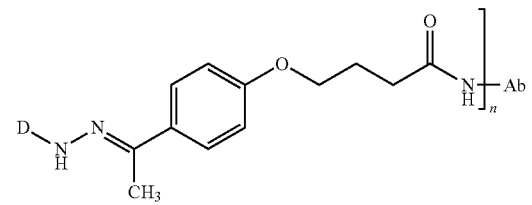
(CIc)

wherein D is a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) and Ab is an antibody, an antibody construct, or a targeting moiety, respectively, and n represents the number of compound-bound linkers (LP) bound to the antibody, antibody construct, or targeting moiety. In certain linkers, such as linker (Ia), the linker can comprise two cleavable groups, a disulfide and a hydrazone moiety. For such linkers, effective release of the unmodified free compound can require acidic pH or disulfide reduction and acidic pH. Linkers such as (Ib) and (Ic) can be effective with a single hydrazone cleavage site.

Other acid-labile groups that can be included in linkers include cis-aconityl-containing linkers. cis-Aconityl chemistry can use a carboxylic acid juxtaposed to an amide bond to accelerate amide hydrolysis under acidic conditions.

Cleavable linkers can also include a disulfide group. Disulfides can be thermodynamically stable at physiological pH and can be designed to release a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof; upon internalization inside cells, wherein the cytosol can provide a significantly more reducing environment compared to the extracellular environment. Scission of disulfide bonds can require the presence of a cytoplasmic thiol cofactor, such as (reduced) glutathione (GSH), such that disulfide-containing linkers can be reasonably stable in circulation, selectively releasing a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof; in the cytosol. The intracellular enzyme protein disulfide isomerase, or similar enzymes capable of cleaving disulfide bonds, can also contribute to the preferential cleavage of disulfide bonds inside cells. GSH can be present in cells in the concentration range of 0.5-10 mM compared with a significantly lower concentration of GSH or cysteine, the most abundant low-molecular weight thiol, in circulation at approximately 5 μM. Tumor cells, where irregular blood flow can lead to a hypoxic state, can result in enhanced activity of reductive enzymes and therefore even higher glutathione concentrations. The in vivo stability of a disulfide-containing linker can be enhanced by chemical modification of the linker, e.g., use of steric hindrance adjacent to the disulfide bond.

Conjugates comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and including exemplary disulfide-containing linkers can include the following structures:

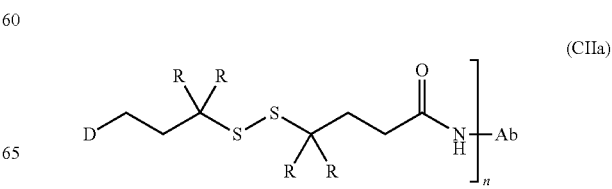
(CIIa)

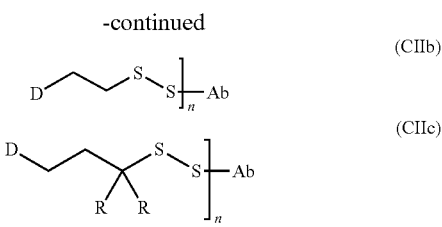
(CIIb)
(CIIc)

wherein D is a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and Ab is an anti-ASGR1 antibody, an anti-ASGR1 antibody construct, or a ASGR1 targeting moiety, n represents the number of compounds bound to linkers (L) bound to the antibody, antibody construct, or targeting moiety and R is independently selected at each occurrence from, for example, hydrogen or alkyl. Increasing steric hindrance adjacent to the disulfide bond can increase the stability of the linker. Structures such as (CIIa) and (CIIc) can show increased in vivo stability when one or more R groups is selected from a lower alkyl, such as methyl.

Another type of linker that can be used is a linker that is specifically cleaved by an enzyme. For example, the linker can be cleaved by a lysosomal enzyme. Such linkers can be peptide-based or can include peptidic regions that can act as substrates for enzymes. Peptide based linkers can be more stable in plasma and extracellular milieu than chemically labile linkers.

Peptide bonds can have good serum stability, as lysosomal proteolytic enzymes can have very low activity in blood due to endogenous inhibitors and the unfavorably high pH value of blood compared to lysosomes. Release of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, from an antibody, an antibody construct, or a targeting moiety conjugate can occur due to the action of lysosomal proteases, e.g., cathepsin B and plasmin. These proteases can be present at elevated levels in certain tumor tissues. The linker can be cleavable by a lysosomal enzyme. The lysosomal enzyme can be, for example, cathepsin B, β-glucuronidase, or β-galactosidase.

The cleavable peptide can be selected from tetrapeptides such as Gly-Phe-Leu-Gly (SEQ ID NO: 250), Ala-Leu-Ala-Leu (SEQ ID NO: 251) or dipeptides such as Val-Cit, Val-Ala, and Phe-Lys. Dipeptides can have lower hydrophobicity compared to longer peptides.

A variety of dipeptide-based cleavable linkers can be used with an antibody, an antibody construct, or a targeting moiety construct to form conjugates of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, of the disclosure.

Enzymatically cleavable linkers can include a self-immolative spacer to spatially separate a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, from the site of enzymatic cleavage. The direct attachment of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, to a peptide linker can result in proteolytic release of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, or of an amino acid adduct of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, thereby impairing its activity. The use of a self-immolative spacer can allow for the elimination of the fully active, chemically unmodified compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, upon amide bond hydrolysis.

One self-immolative spacer can be a bifunctional para-aminobenzyl alcohol (PABA) group, which can link to a peptide through an amino group, forming an amide bond, while an amine containing compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, can be attached through carbamate functionalities to the benzylic hydroxyl group of the linker (to give a p-amidobenzylcarbamate, PABC). The resulting pro-compound can be activated upon protease-mediated cleavage, leading to a 1,6-elimination reaction releasing the unmodified compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, carbon dioxide, and remnants of the linker group.

The following scheme depicts the fragmentation of p-amidobenzyl carbamate and release of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof:

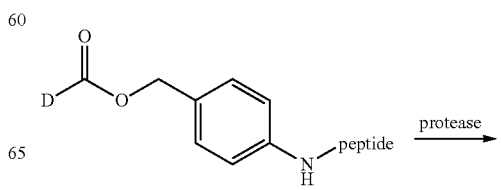

-continued

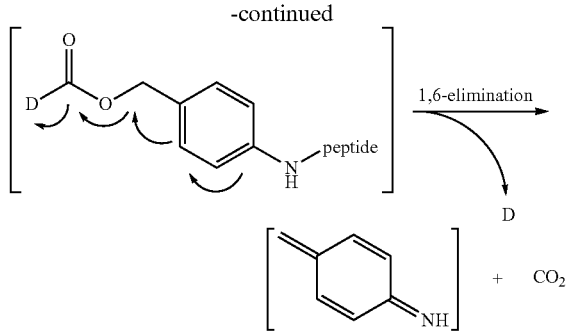

wherein D represents the unmodified drug or payload having the structure of a compound of Any one of Formulas (I)-(IX) or Table 1, or pharmaceutically acceptable isomer, tautomer, racemate, hydrate, solvate, isotope, or salt thereof.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, -L is represented by the formula:

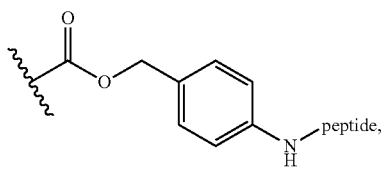

wherein peptide comprises from one to ten amino acids, and

represents the point of attachment to the compound (payload).

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, -L is represented by the formula:

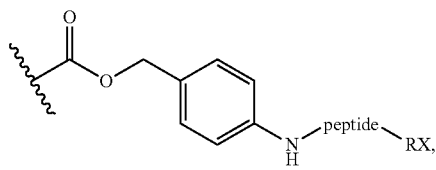

wherein peptide comprises from one to ten amino acids and RX is a reactive moiety, and

represents the point of attachment to the compound (payload).

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, -L is represented by the formula:

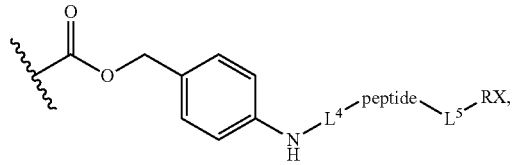

wherein peptide comprises from one to ten amino acids, $L^4$ is the C-terminus of the peptide and $L^5$ is selected from a bond, alkylene and heteroalkylene, wherein $L^5$ is optionally substituted with one or more groups independently selected from $R^{32}$, RX is a reactive moiety; and $R^{32}$ is independently selected at each occurrence from halogen, —OH, —CN, —O-alkyl, —SH, =O, =S, —S(O)$_2$OH, —NH$_2$, —NO$_2$; and $C_{1-10}$ alkyl, $C_{2-10}$ alkenyl, and $C_{2-10}$ alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$. The reactive moiety may be selected from an electrophile, e.g., an αβ-unsaturated carbonyl, such as a maleimide, and a leaving group. In some embodiments, RX comprises a leaving group. In some embodiments, RX is a maleimide.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, the L-P is part of a conjugate and -L is represented by the formula:

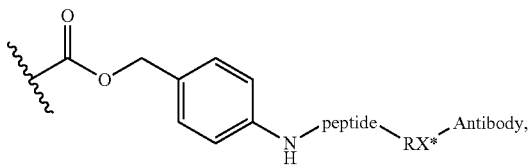

wherein Antibody is an anti-ASGR1 antibody, an RX* antibody construct, or a targeting moiety peptide comprises from one to 10 amino acids, RX* is a reactive moiety that has reacted with a moiety on the antibody, antibody construct, or targeting moiety to form a conjugate, and

represents the point of attachment to the compound (payload).

In some embodiments, L-P is part of a conjugate and -L- is represented by the formula:

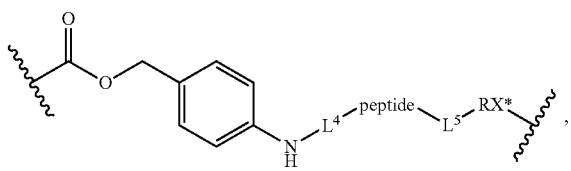

wherein peptide comprises from one to ten amino acids, $L^4$ is the C-terminus of the peptide and $L^5$ is selected from a bond, an alkylene and a heteroalkylene, each of which is optionally substituted with one or more groups independently selected from $R^{12}$;

on the left represents the point of attachment to the compound (payload), RX* is a bond, a succinimide moiety, or a hydrolyzed succinimide moiety attached at the

on the right to a residue of an antibody, an antibody construct, or a targeting moiety.

In some embodiments, L-P is part of a conjugate and -L- is represented by the formula:

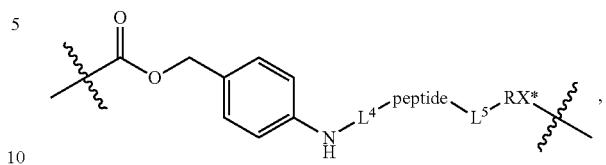

wherein peptide comprises from one to ten amino acids, $L^4$ represents the C-terminus of the peptide and $L^5$ is selected from a bond, alkylene and heteroalkylene, wherein $L^5$ is optionally substituted with one or more groups independently selected from $R^{32}$; RX* is a bond, a succinimide moiety, or a hydrolyzed succinimide moiety bound to a residue of an antibody, an antibody construct, or a targeting moiety, wherein

on RX* represents the point of attachment to the residue of the antibody, antibody construct, or targeting moiety; and $R^{32}$ is independently selected at each occurrence from halogen, —OH, —CN, —O-alkyl, —SH, =O, =S, —S(O)$_2$OH, —NH$_2$, —NO$_2$; and $C_{1-10}$ alkyl, $C_{2-10}$ alkenyl, and $C_{2-10}$ alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$. In some embodiments, the peptide of L comprises Val-Cit or Val-Ala.

In any of the aforementioned embodiments, -L is:

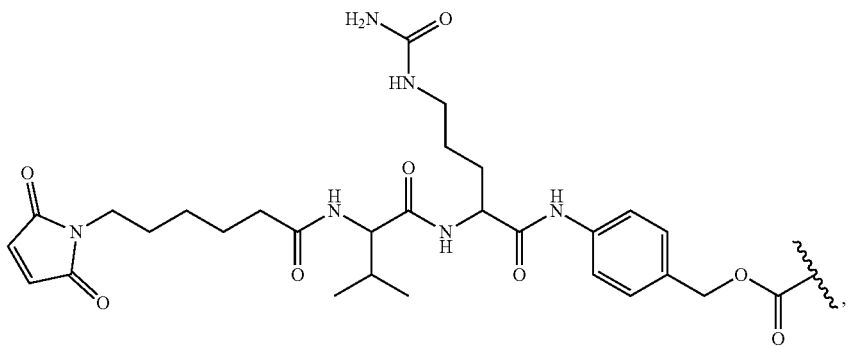

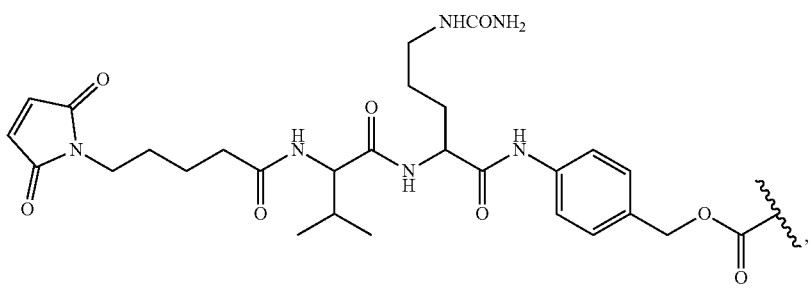

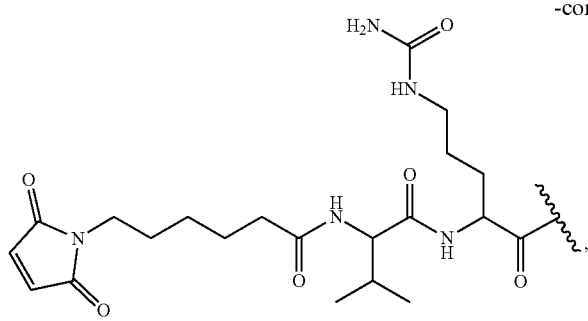 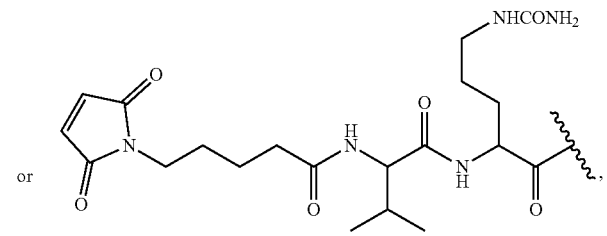

Heterocyclic variants of this self-immolative group may also be used.

The enzymatically cleavable linker can be a β-glucuronic acid-based linker. Facile release of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, can be realized through cleavage of the β-glucuronide glycosidic bond by the lysosomal enzyme β-glucuronidase. This enzyme can be abundantly present within lysosomes and can be overexpressed in some tumor types, while the enzyme activity outside cells can be low. β-Glucuronic acid-based linkers can be used to circumvent the tendency of an antibody, an antibody construct, or a targeting moiety conjugate of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, to undergo aggregation due to the hydrophilic nature of β-glucuronides. In some embodiments, β-glucuronic acid-based linkers can link an antibody, an antibody construct, or a targeting moiety to a hydrophobic compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

The following scheme depicts the release of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, (D) from a conjugate of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, containing a β-glucuronic acid-based linker:

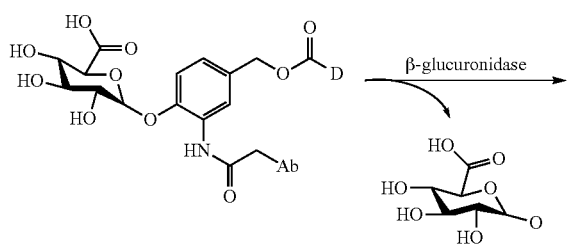

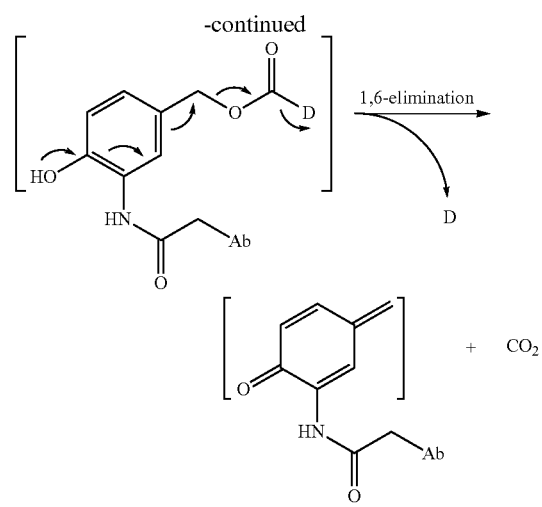

wherein Ab indicates an antibody, an antibody construct, or a targeting moiety.

A variety of cleavable β-glucuronic acid-based linkers useful for linking drugs such as auristatins, camptothecin analogues, doxorubicin analogues, CBI minor-groove binders, and psymberin to antibodies have been described. These β-glucuronic acid-based linkers may be used in the conjugates. In some embodiments, an enzymatically cleavable linker is a P-galactoside-based linker. P-Galactoside is present abundantly within lysosomes, while the enzyme activity outside cells is low.

Additionally, a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, containing a phenol group can be covalently bonded to a linker through the phenolic oxygen. One such linker relies on a methodology in which a diaminoethane "Space Link" is used in conjunction with traditional "PABO"-based self-immolative groups to deliver phenols.

Cleavable linkers can include non-cleavable portions or segments, and/or cleavable segments or portions can be included in an otherwise non-cleavable linker to render it cleavable. By way of example only, polyethylene glycol (PEG) and related polymers can include cleavable groups in the polymer backbone. For example, a polyethylene glycol or polymer linker can include one or more cleavable groups such as a disulfide, a hydrazone or a dipeptide.

Other degradable linkages that can be included in linkers can include ester linkages formed by the reaction of PEG carboxylic acids or activated PEG carboxylic acids with alcohol groups on a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, wherein such ester groups can hydrolyze under physiological conditions to release a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof. Hydrolytically degradable linkages can include carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including at the end of a polymer, and a 5' hydroxyl group of an oligonucleotide.

A linker can contain an enzymatically cleavable peptide, for example, a linker comprising structural formula (CIIIa), (CIIIb), (CIIIc), or (CIIId):

alkylene)-$G^1$]$_2$; $R^z$ is $C_{1-4}$ alkyl-(O)$_r$—($C_{1-4}$ alkylene)$_s$-$G^2$; $G^1$ is —$SO_3H$, —$CO_2H$, PEG 4-32, or a sugar moiety; $G^2$ is —$SO_3H$, —$CO_2H$, or a PEG 4-32 moiety; r is 0 or 1; s is 0 or 1; p is an integer ranging from 0 to 5; q is 0 or 1; x is 0 or 1; y is 0 or 1;

L represents the point of attachment of the linker to a compound of Any one of Formulas (I)-(IX) or Table 1, or pharmaceutically acceptable isomer, tautomer, racemate, hydrate, solvate, isotope, or salt thereof; and * represents the point of attachment to the remainder of the linker.

In some embodiments, a peptide can be selected to contain natural amino acids, unnatural amino acids, or any combination thereof. In some embodiments, a peptide can be a tripeptide or a dipeptide. In particular embodiments, a dipeptide comprises L-amino acids, such as Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-

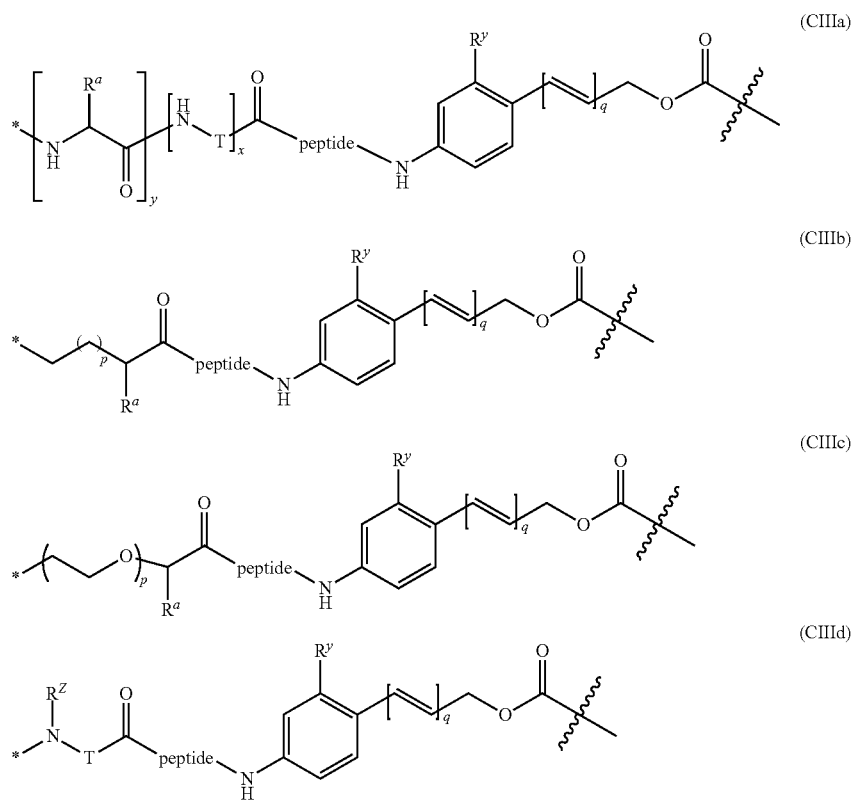

or a salt thereof, wherein: "peptide" represents a peptide (illustrated in N→C orientation, wherein peptide includes the amino and carboxy "termini") that is cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; $R^y$ is hydrogen or $C_{1-4}$ alkyl-(O)$_r$—($C_{1-4}$ alkylene)$_s$-$G^1$ or $C_{1-4}$ alkyl-(N)—[($C_{1-4}$ Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; and Trp-Cit, or salts thereof.

Exemplary embodiments of linkers according to structural formula (CIIIa) are illustrated below (as illustrated, the linkers include a reactive group suitable for covalently linking the linker to an antibody, an antibody construct, or a targeting moiety):

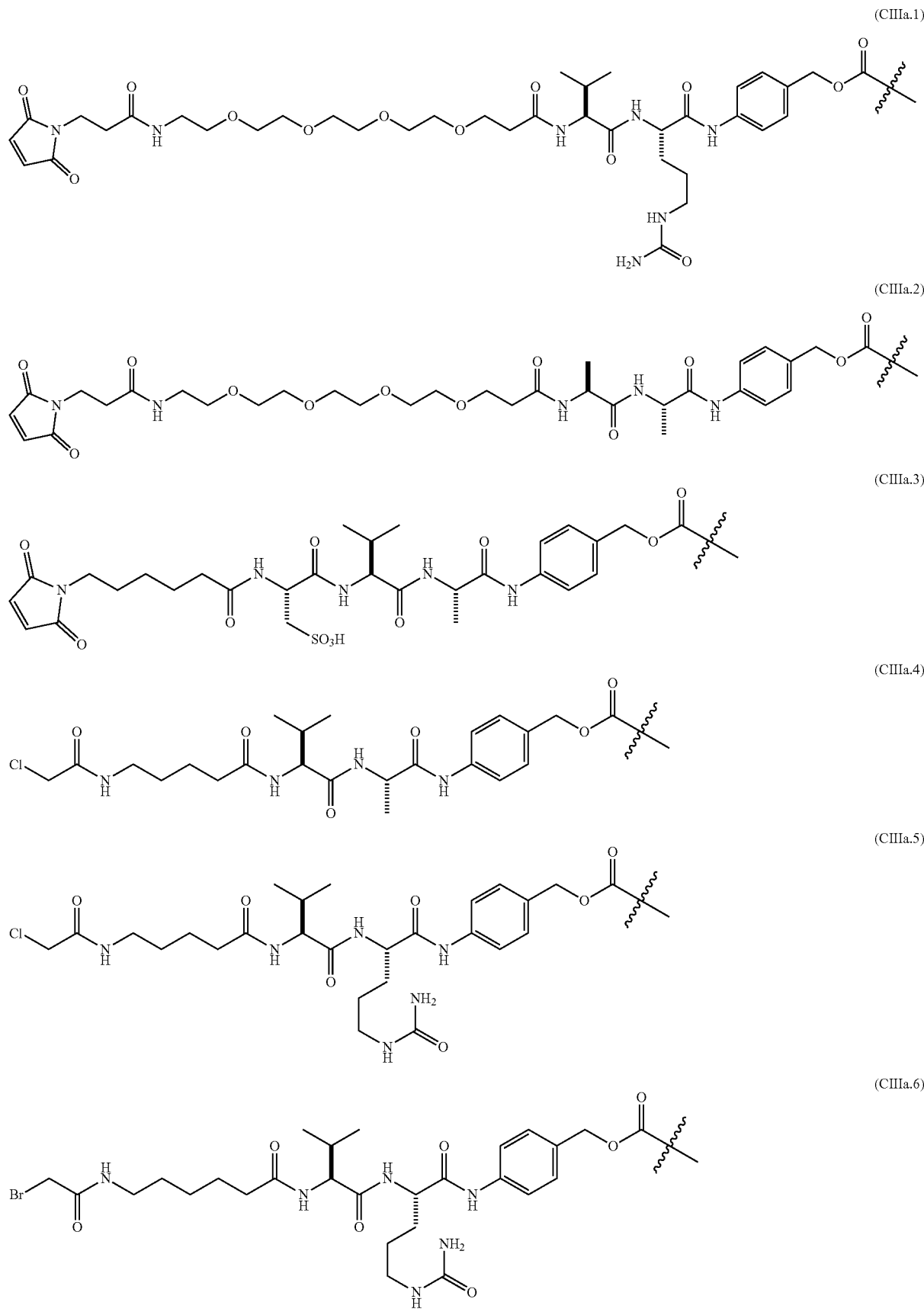

-continued (CIIIa.7)
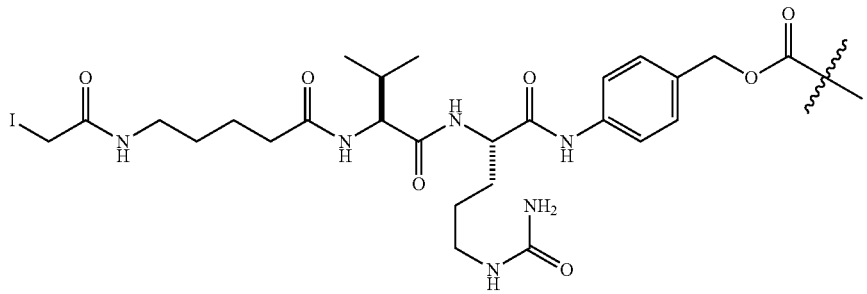

(CIIIa.8)
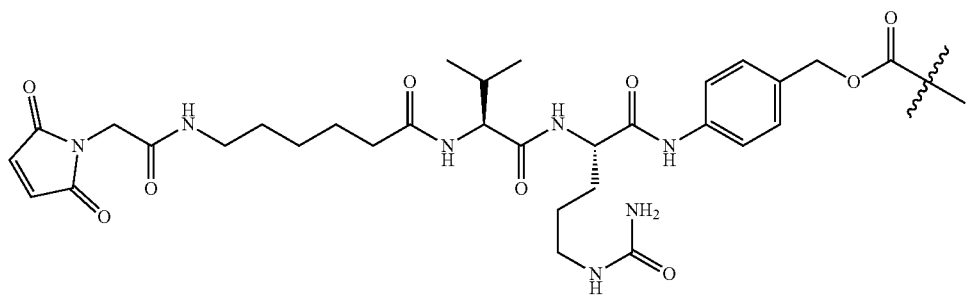

(CIIIa.9)
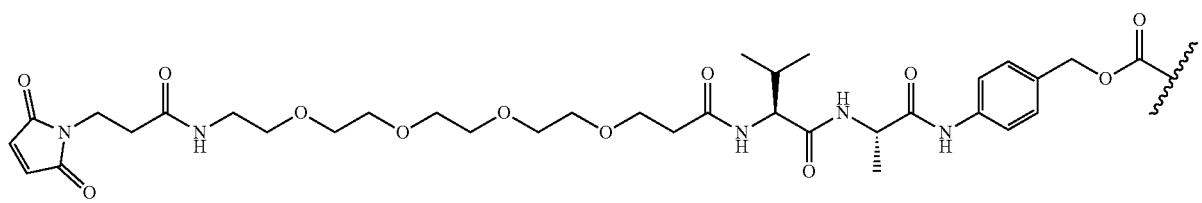

(CIIIa.10)
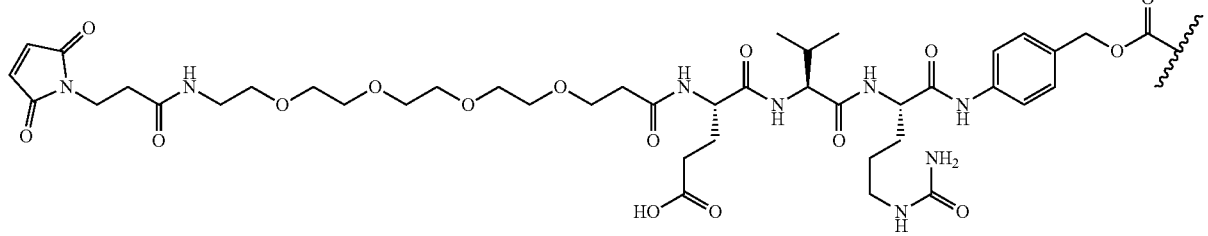

wherein

~~~ indicates an attachment site of a linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CIIIb), (CIIIc), or (CIIId) that can be included in the conjugates can include the linkers illustrated below (as illustrated, the linkers include a reactive group suitable for covalently linking the linker to an antibody, an antibody construct, or a targeting moiety):

(CIIIb.1)
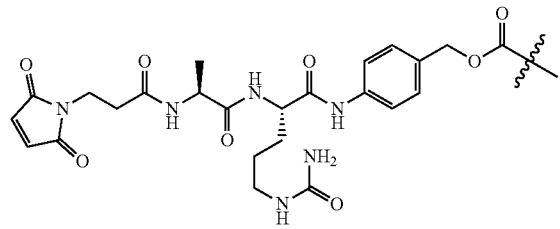
(CIIIb.2)
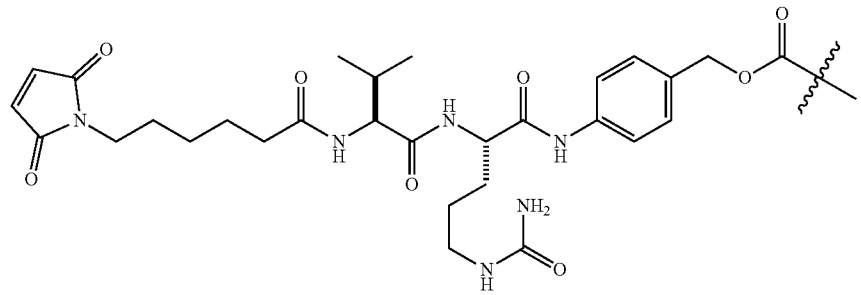
(CIIIb.3)
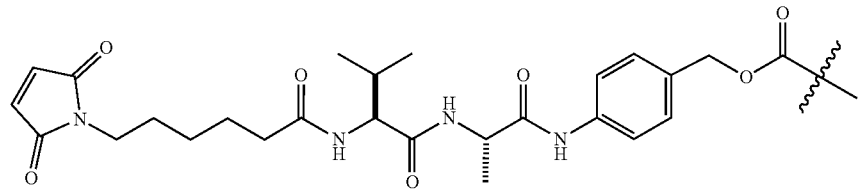
(CIIIb.4)
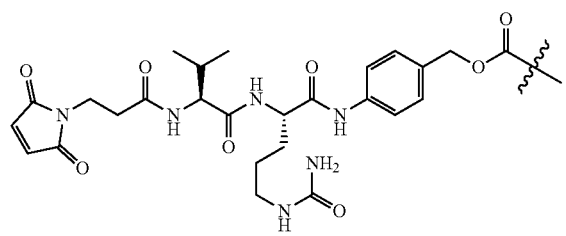
(CIIIb.5)
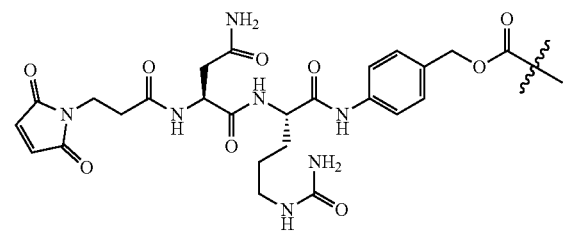
(CIIIb.6)
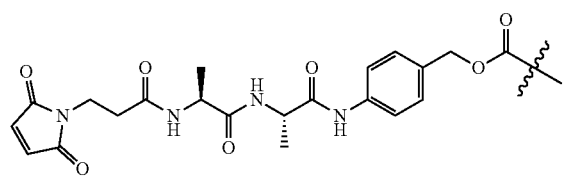
(CIIIb.7)
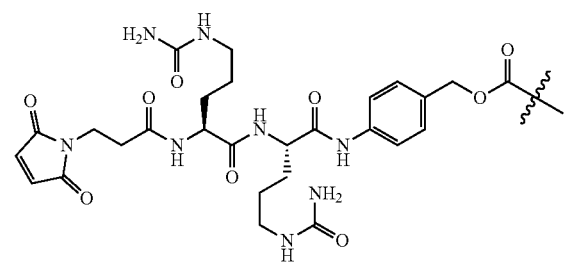
(CIIIb.8)
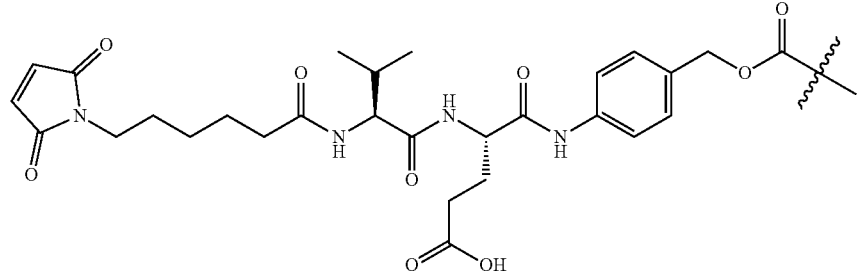

-continued
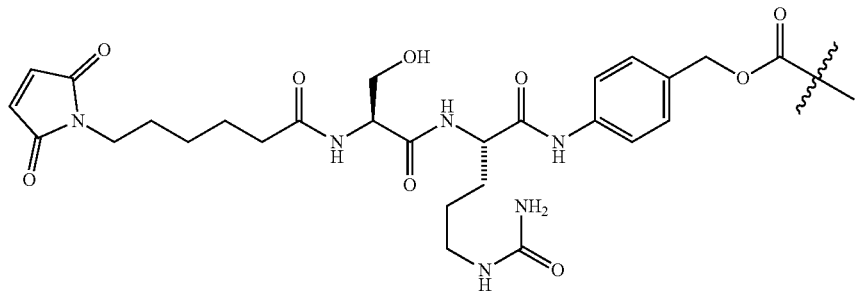
(CIIIb.9)
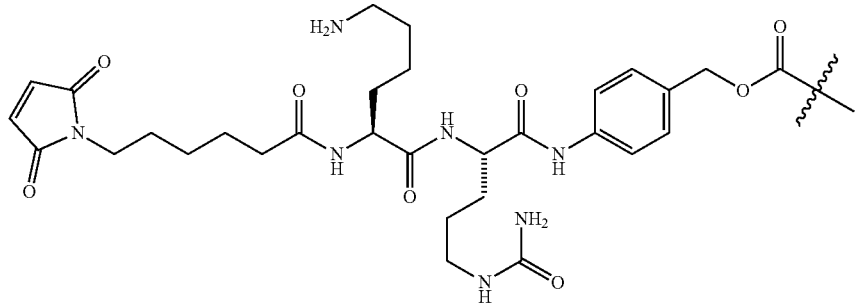
(CIIIb.10)
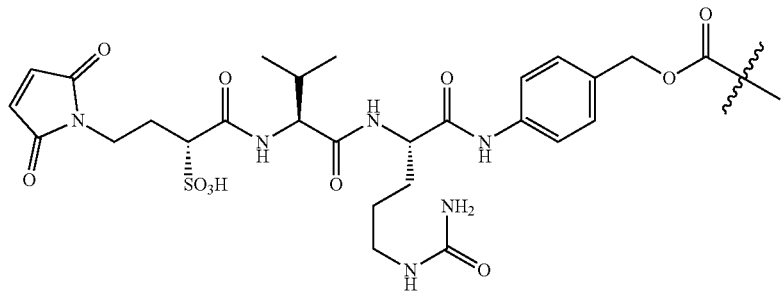
(CIIIb.11)
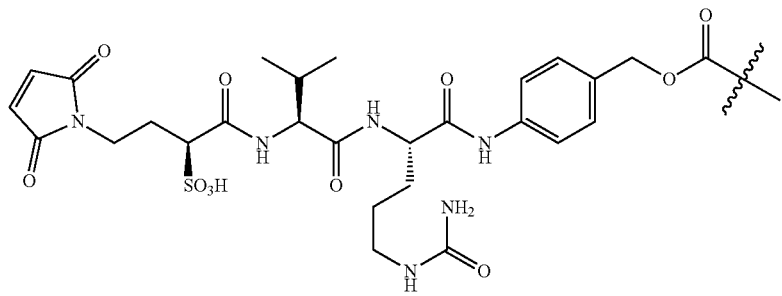
(CIIIb.12)
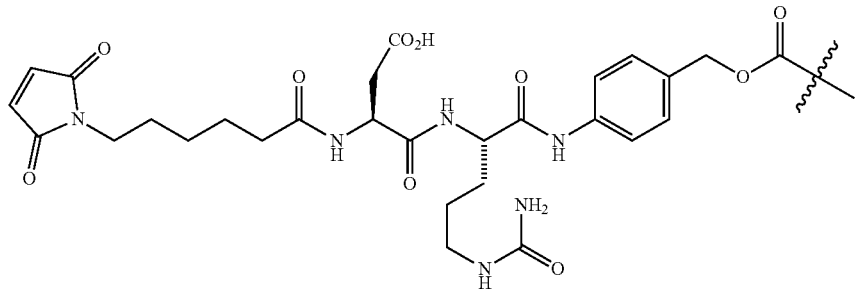
(CIIIb.13)

-continued
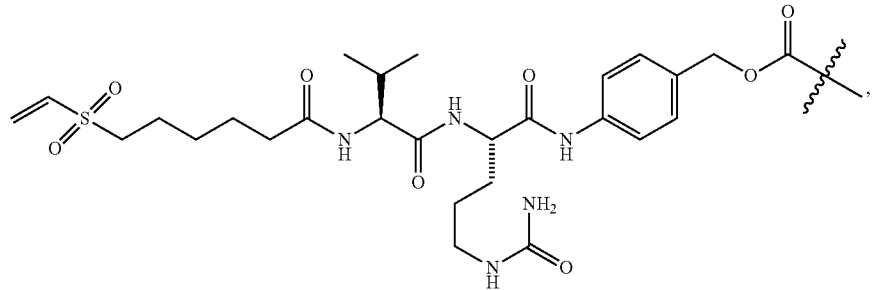
(CIIIb.14)
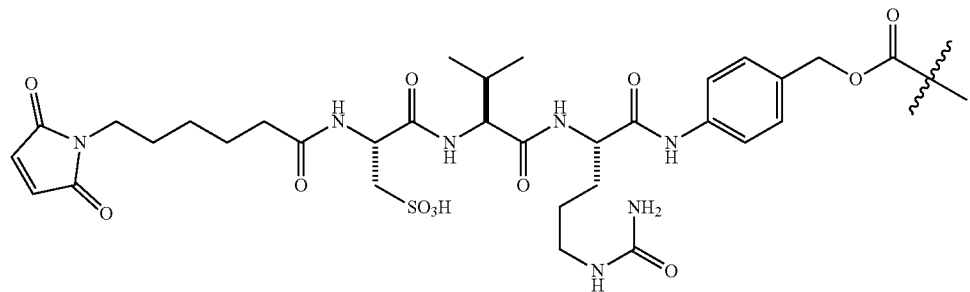
(CIIIb.15)
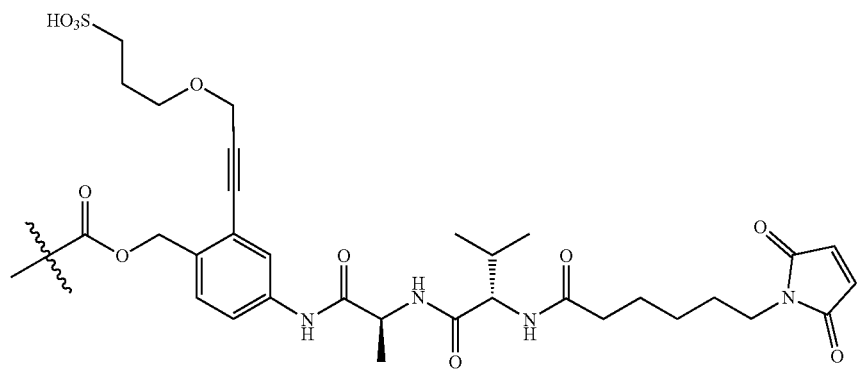
(CIIIb.16)
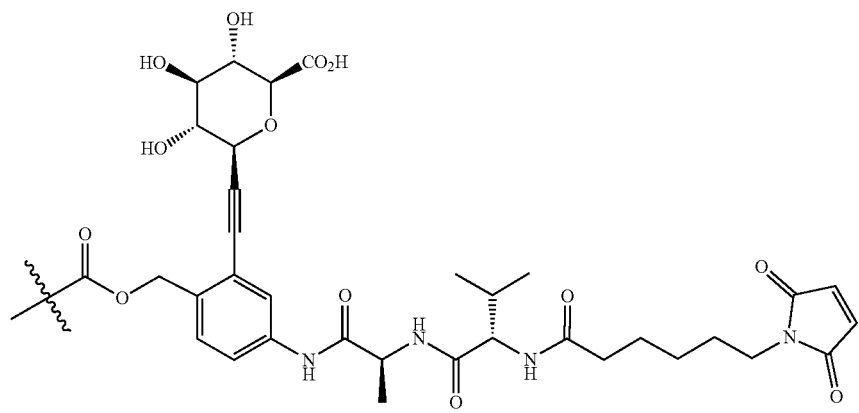
(CIIIb.17)

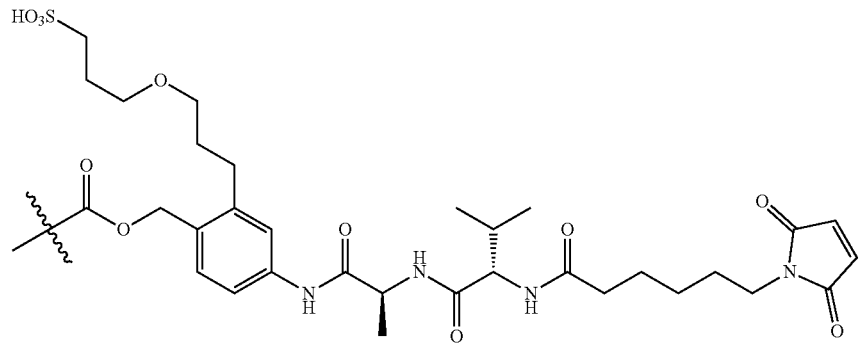
(CIIIb.18)
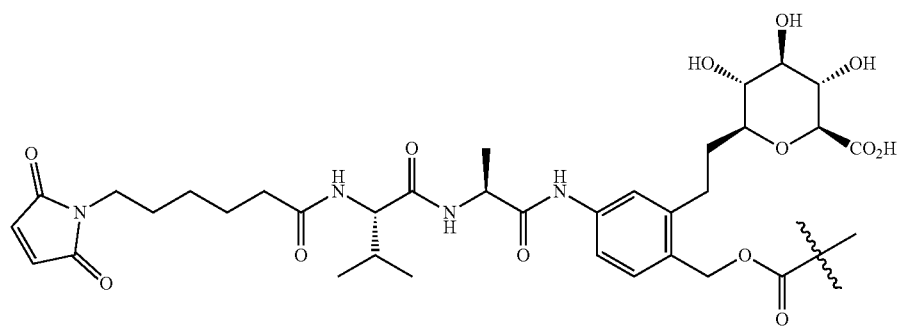
(CIIIb.19)
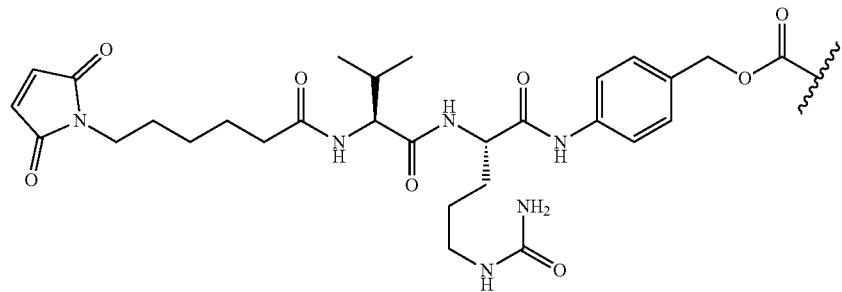
(CIIIb.20)
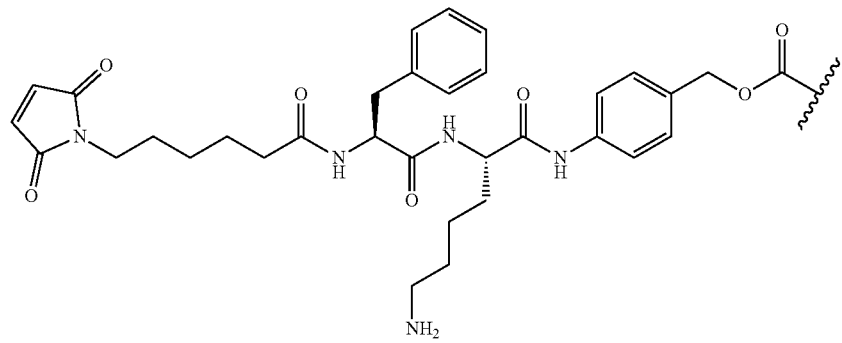
(CIIIb.21)
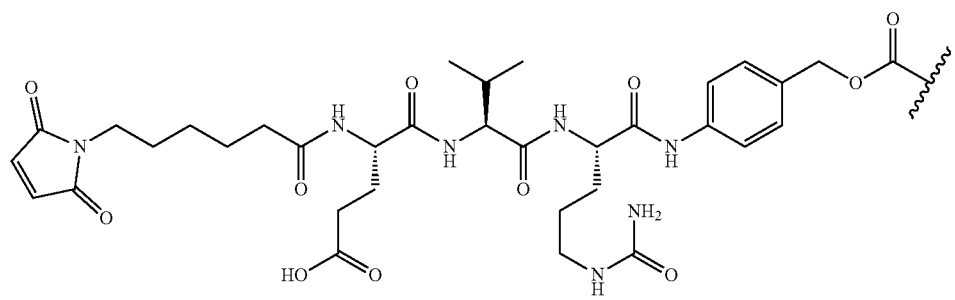
(CIIIb.22)

-continued
(CIIIc.1)
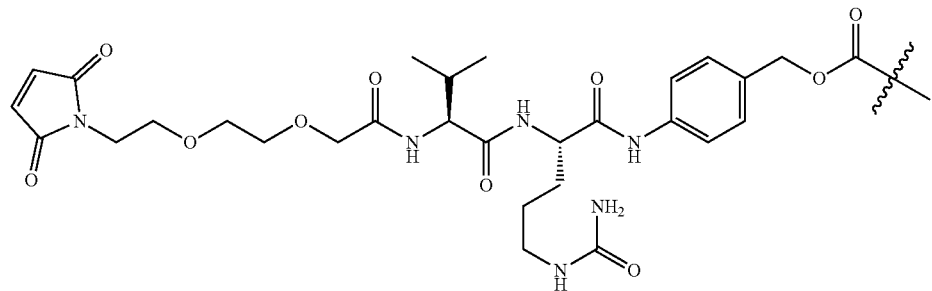
(CIIIc.2)
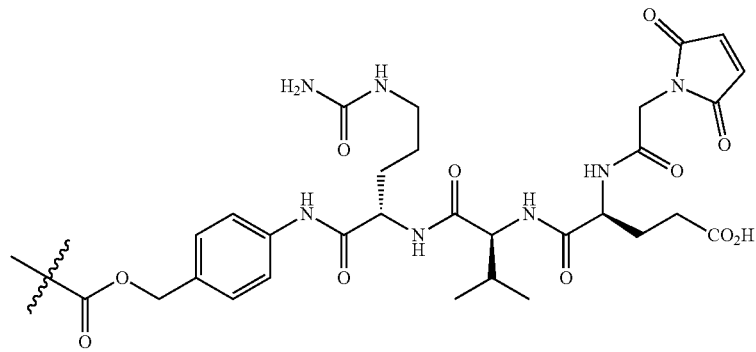
(CIIIc.3)
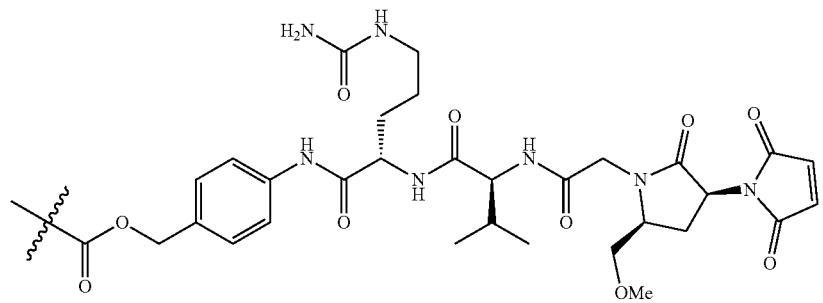
(CIIIc.4)
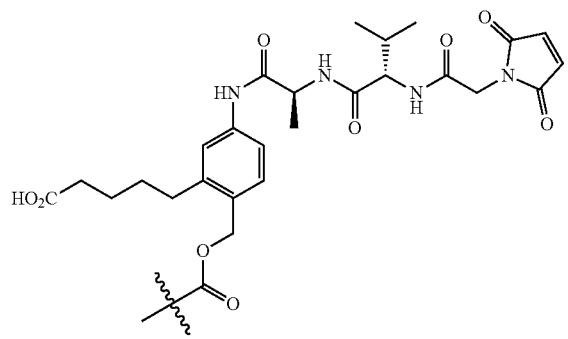
(CIIIc.5)
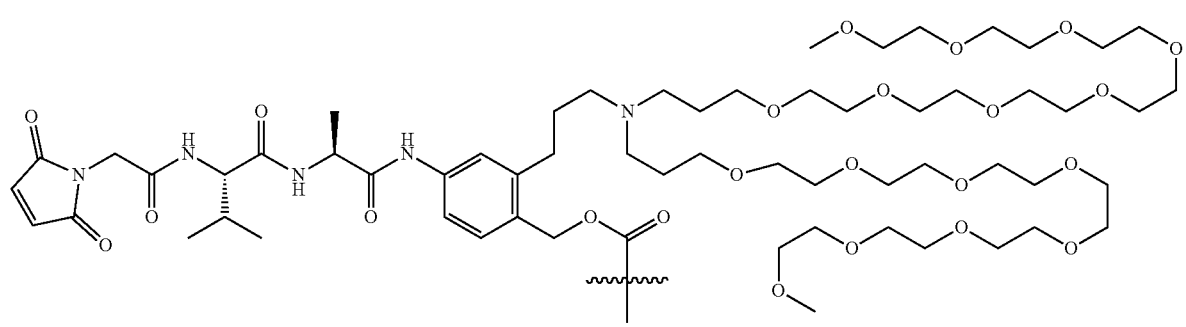

-continued
(CIIIc.6)
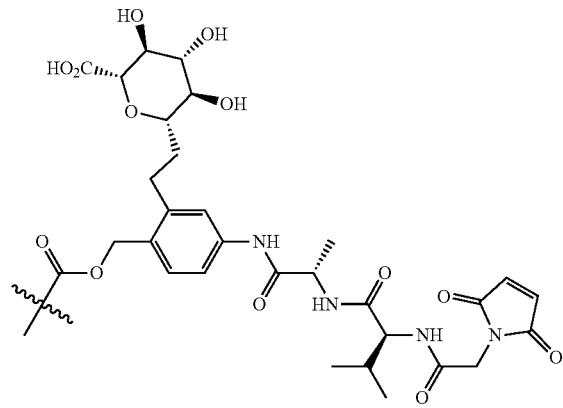
(CIIIc.7)
(CIIIc.8)
(CIIIc.9)
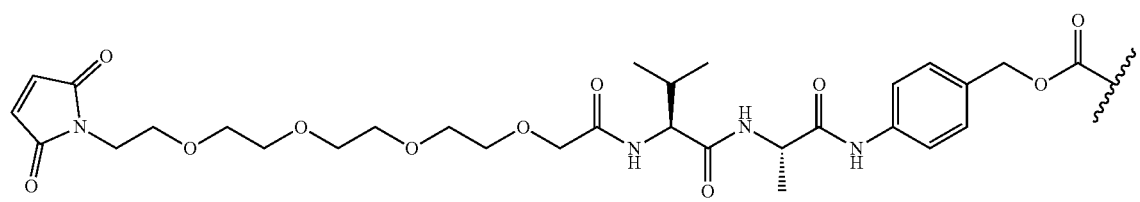
(CIIIc.10)
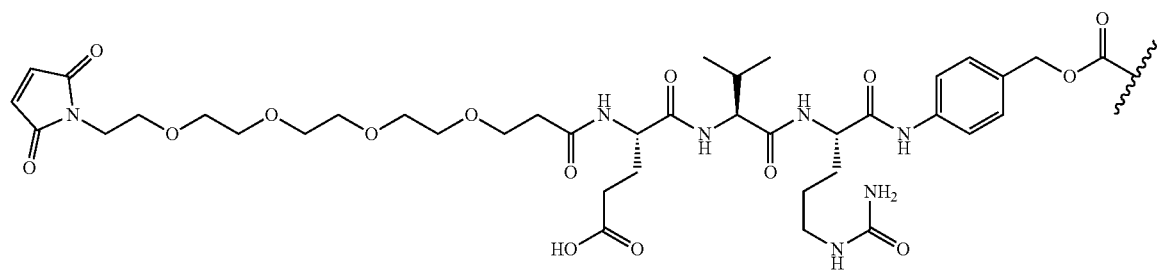
(CIIIc.11)
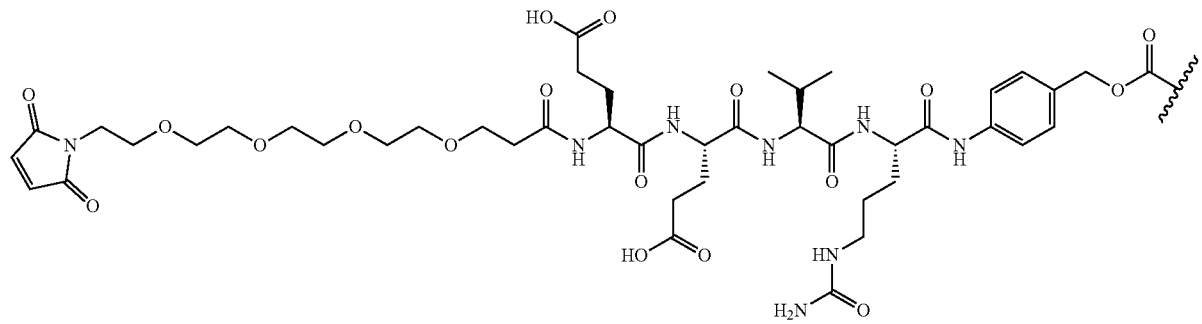

(CIIIc.12)
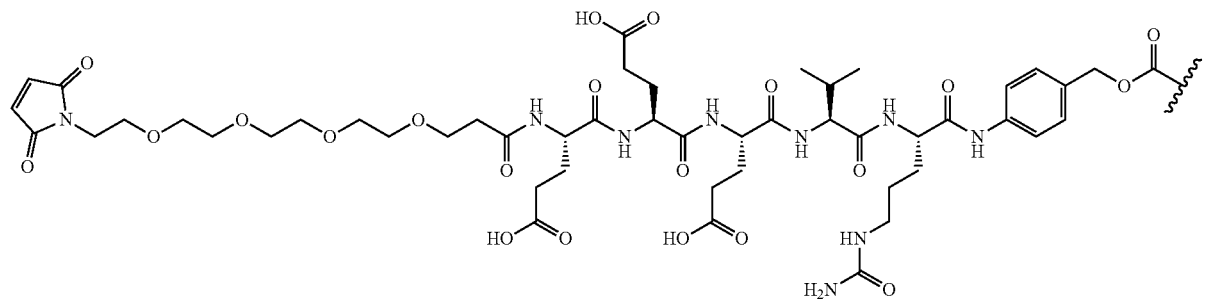
(CIIId.1)
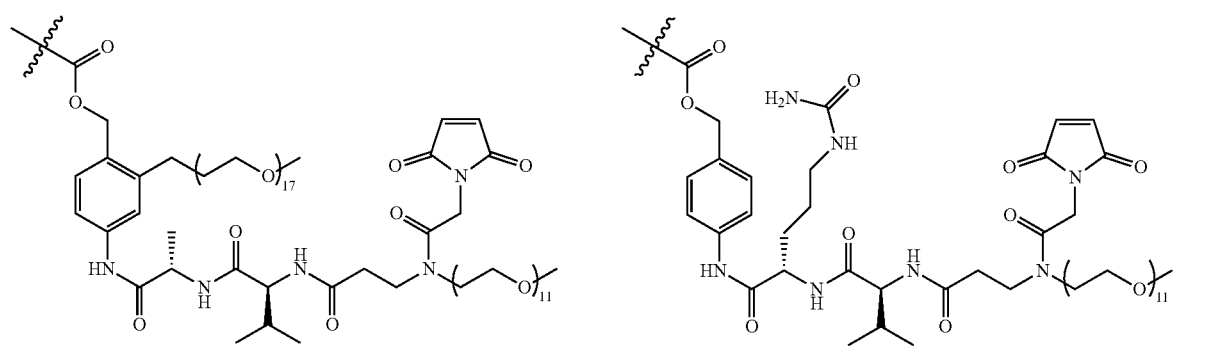
(CIIId.2)
(CIIId.3)
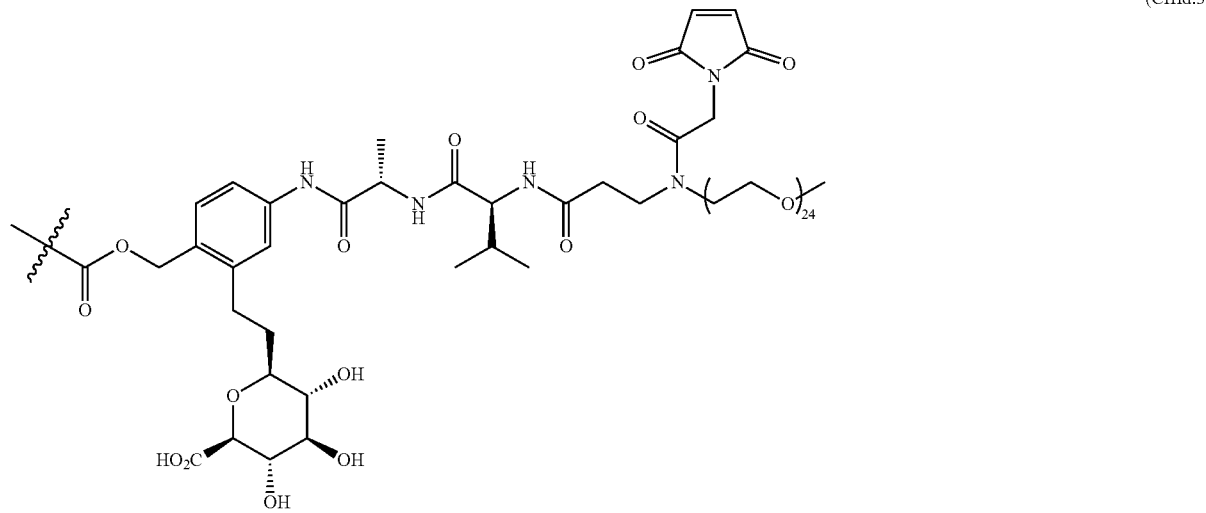
(CIIId.4)
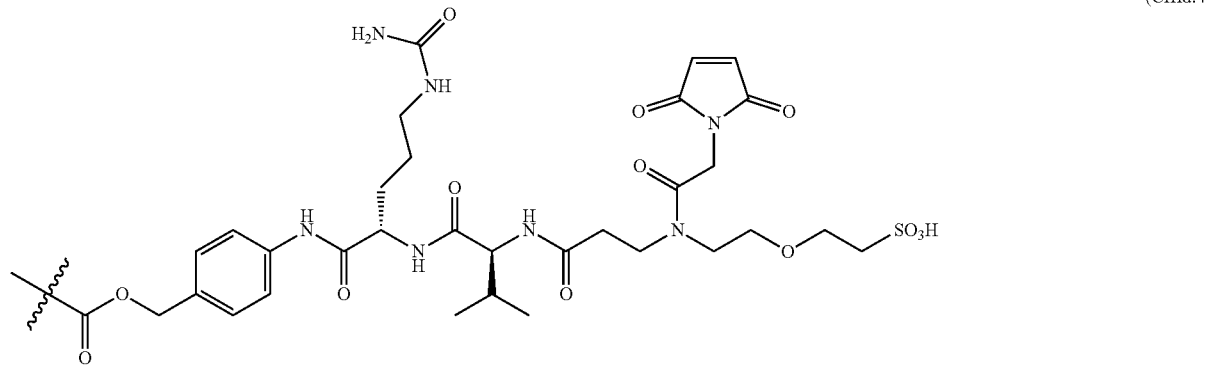

wherein

-continued indicates an attachment site to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

The linker can contain an enzymatically cleavable sugar moiety, for example, a linker comprising structural formula (CIVa), (CIVb), (CIVc), (CIVd), or (CIVe):

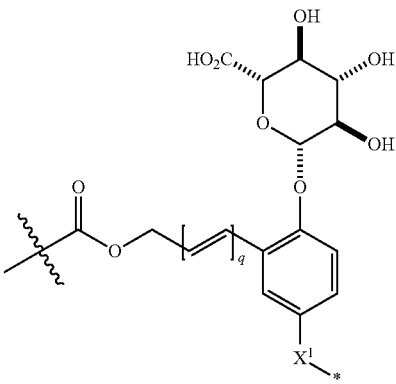

or a salt thereof, wherein: q is 0 or 1; r is 0 or 1; $X^1$ is $CH_2$, O or NH;

represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof; and * represents the point of attachment to the remainder of the linker.

Exemplary embodiments of linkers according to structural formula (CIVa) that may be included in the antibody, antibody construct, or targeting moiety conjugates of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, described throughout the disclosure can include the linkers illustrated below (as illustrated, the linkers include a group suitable for covalently linking the linker to an antibody, an antibody construct, or a targeting moiety):

(CIVa.1)
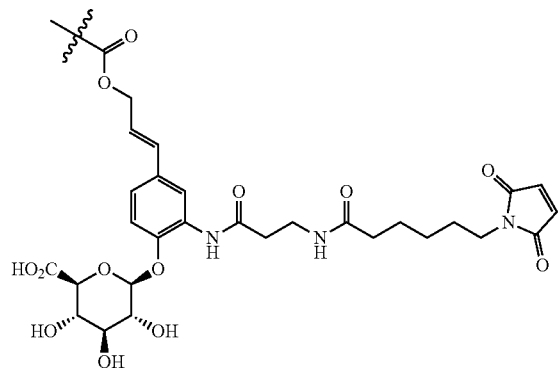
(CIVa.2)
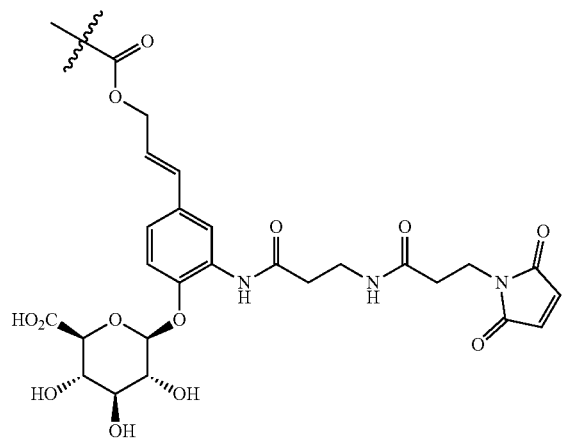
(CIVa.3)
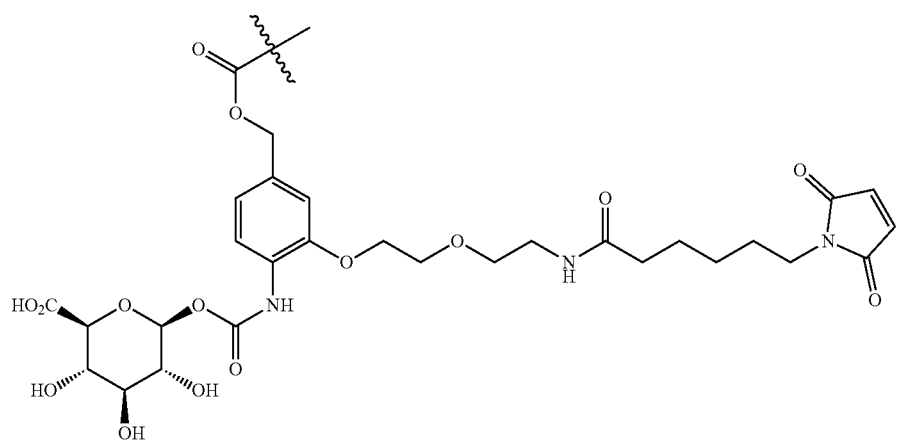
(CIVa.4)
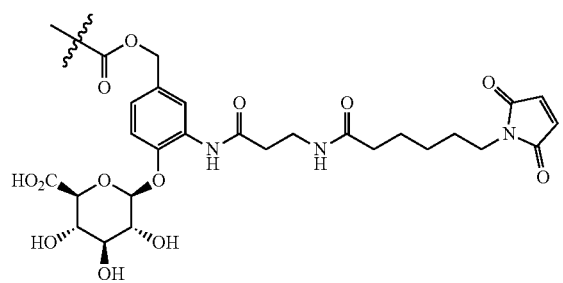
(CIVa.5)
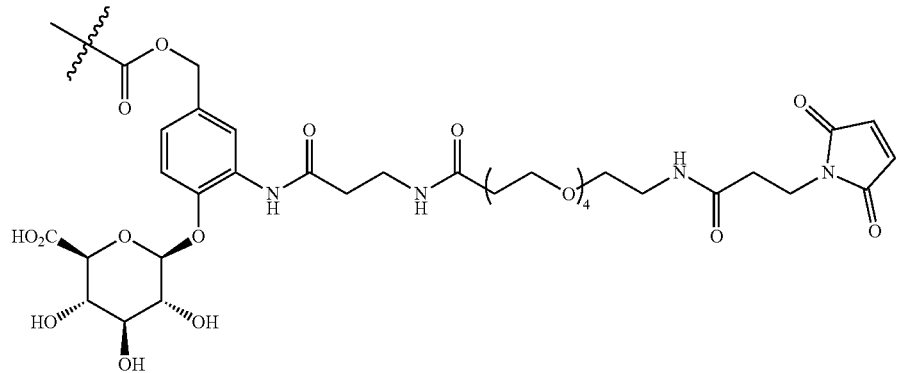

-continued
(CIVa.6)
(CIVa.7)
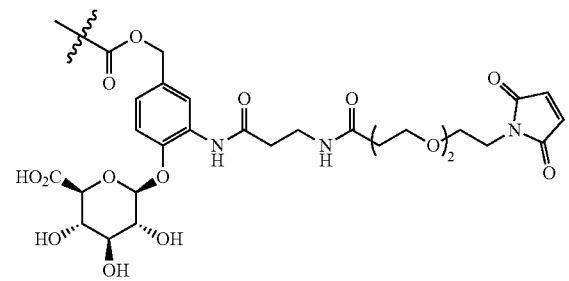
(CIVa.8)
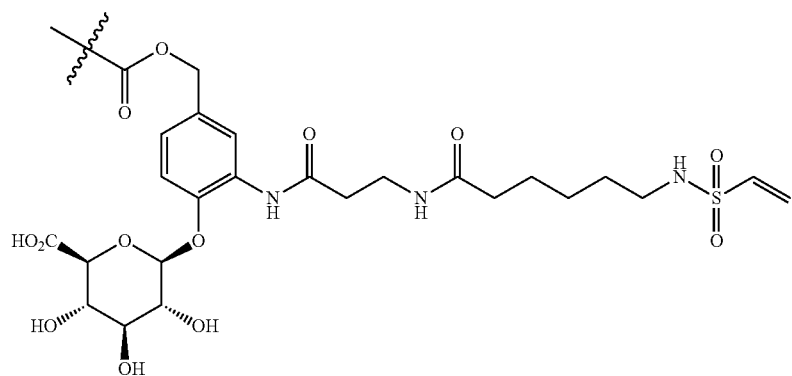
(CIVa.9)
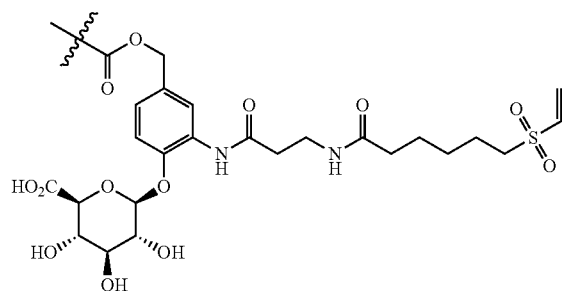
(CIVa.10)
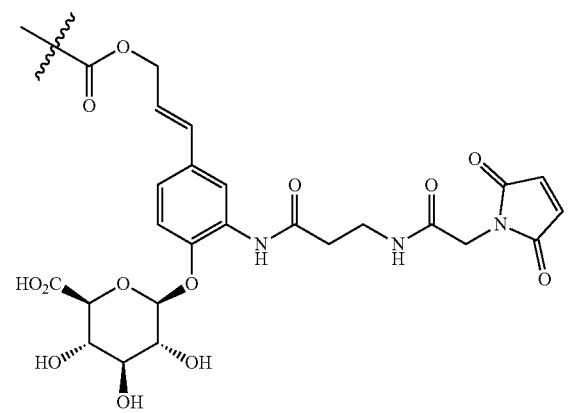
(CIVa.11)
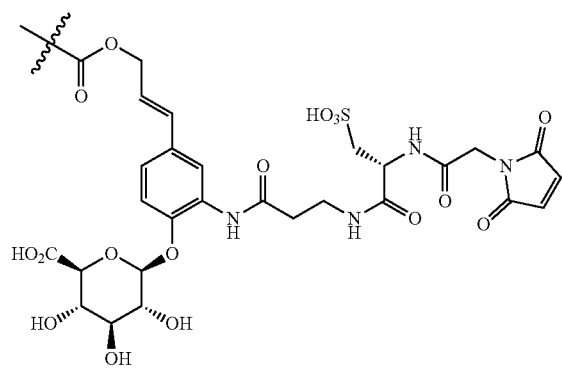
(CIVa.12)
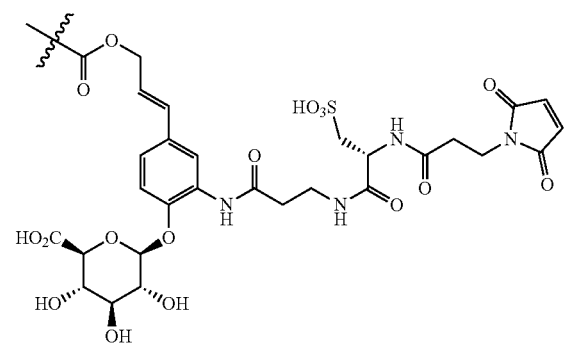

wherein

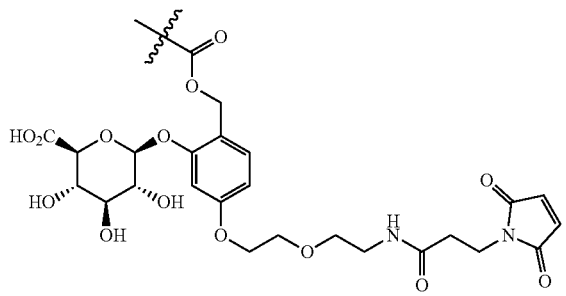

represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CIVb) that may be included in the conjugates include the linkers illustrated below (as illustrated, the linkers include a group suitable for covalently linking the linker to an antibody, an antibody construct, or a targeting moiety):

(CIVb.1)

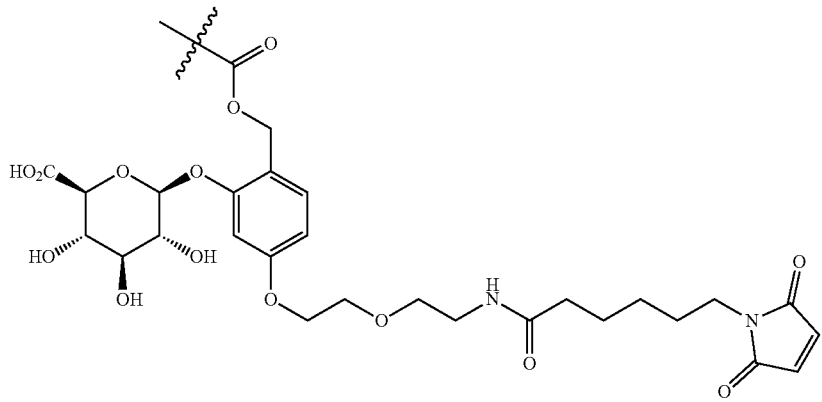

(CIVb.2)

(CIVb.3)

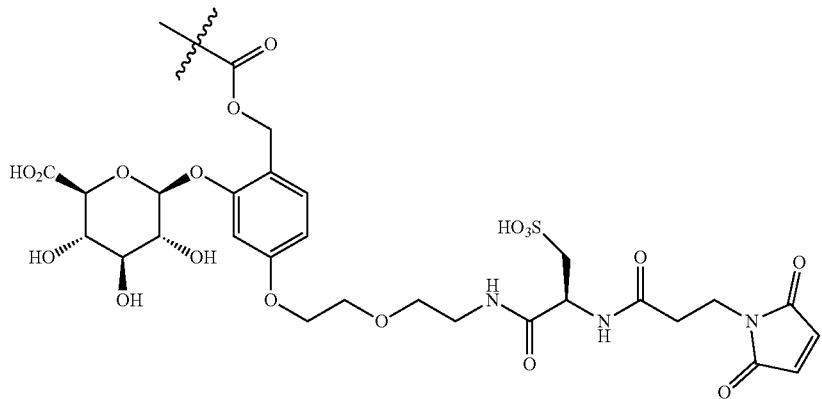

(CIVb.4)
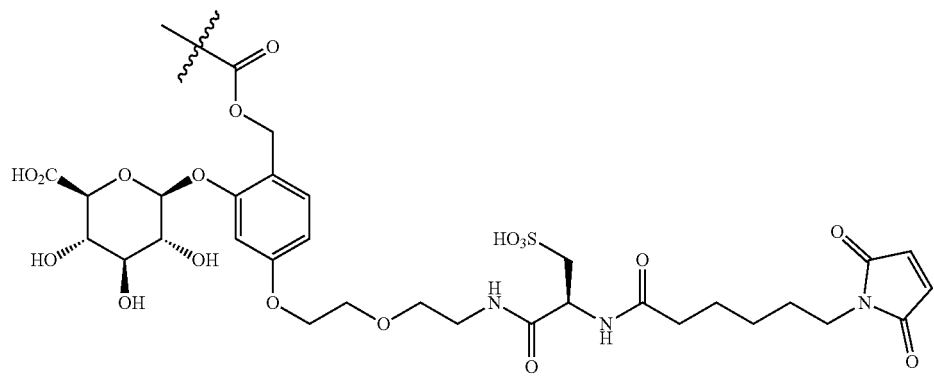
(CIVb.5)
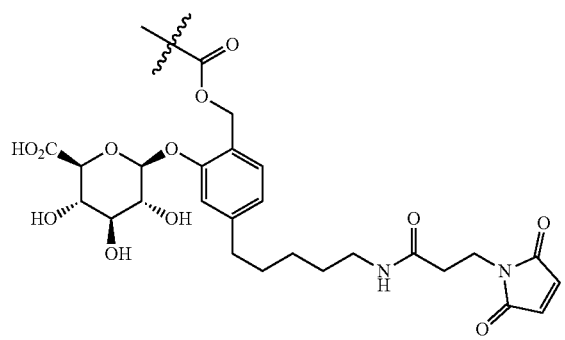
(CIVb.6)
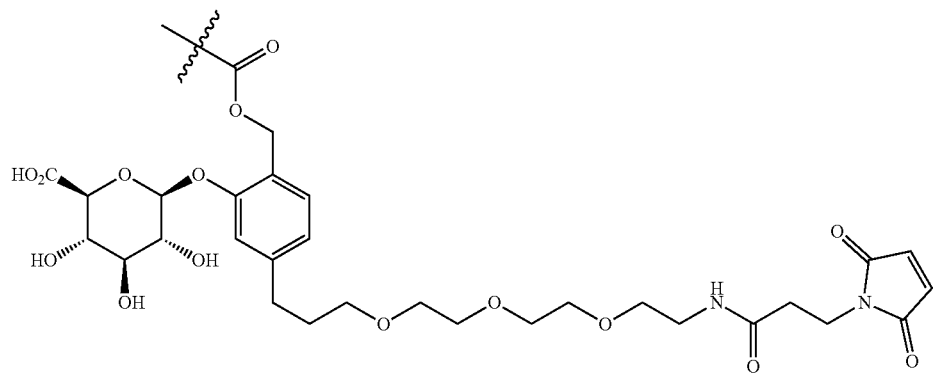
(CIVb.7)
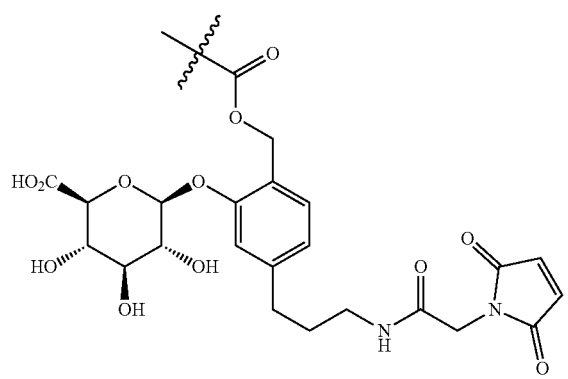
(CIVb.8)
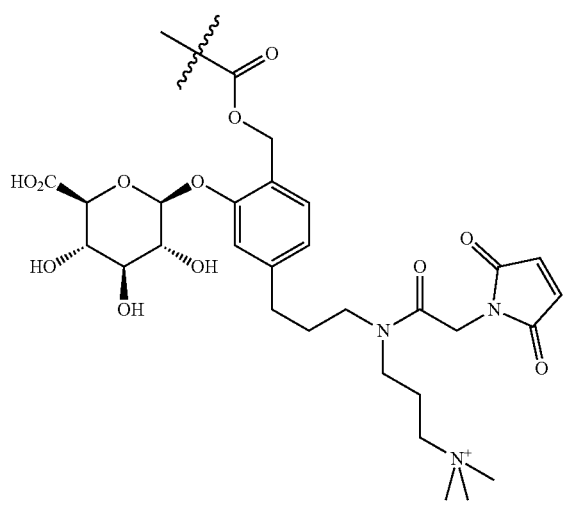

(CIVb.9)

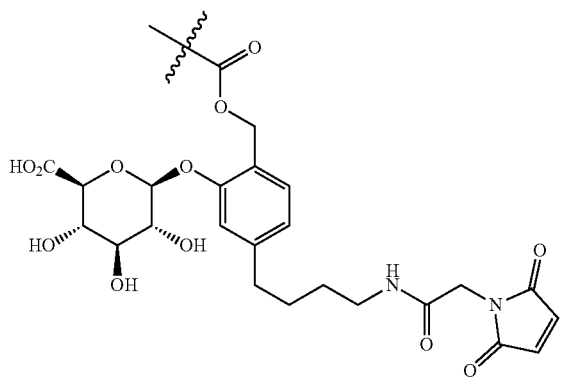

(CIVb.10)

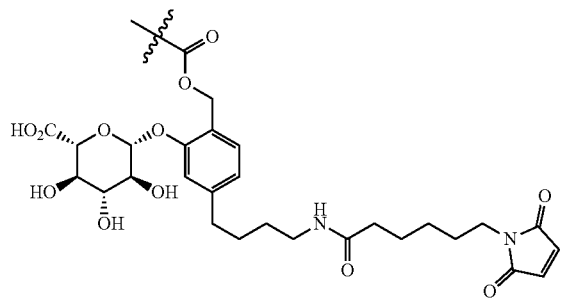

wherein

~~~ represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CIVc) that may be included in the conjugates include the linkers illustrated below (as illustrated, the linkers include a group suitable for covalently linking the linker to an antibody, an antibody construct, or a targeting moiety):

(CIVc.1)

(CIVc.2)

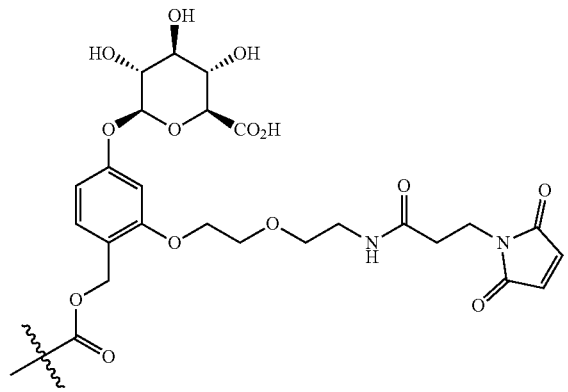

(CIVc.3)

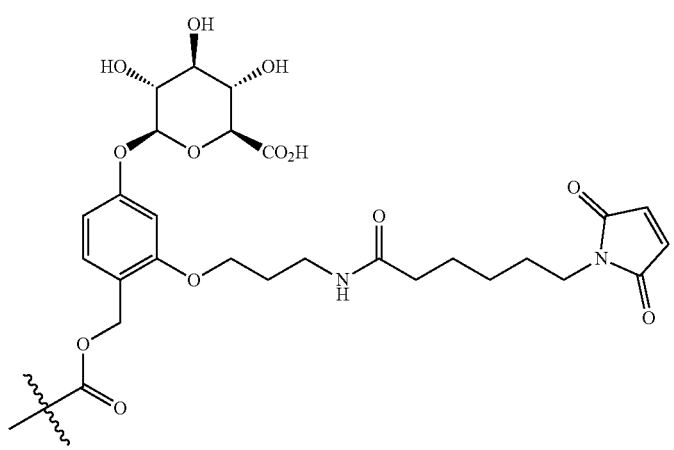

-continued
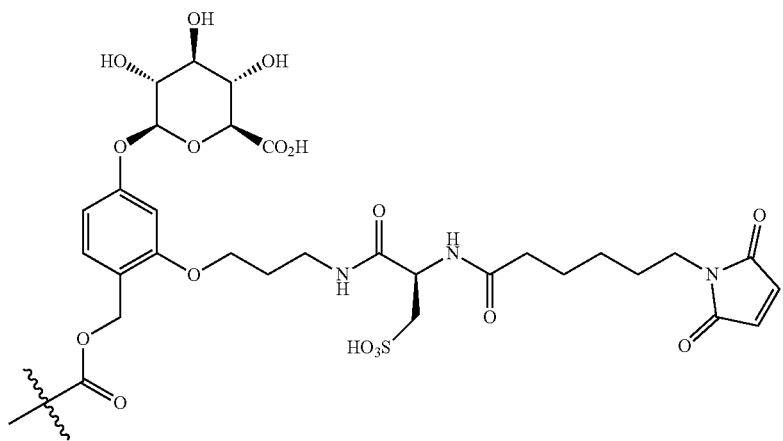
(CIVc.4)
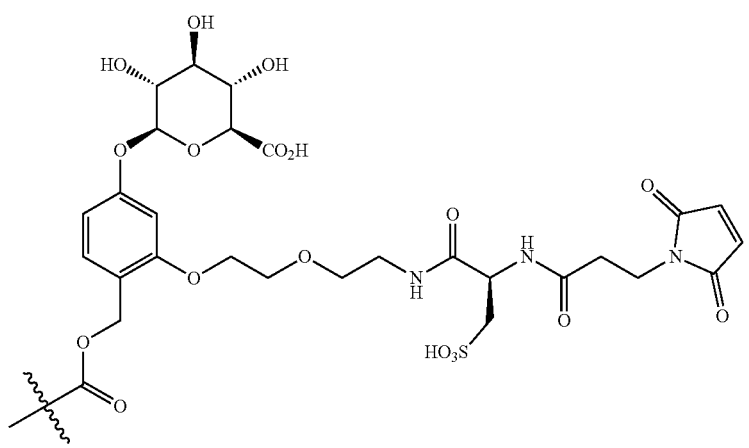
(CIVc.5)
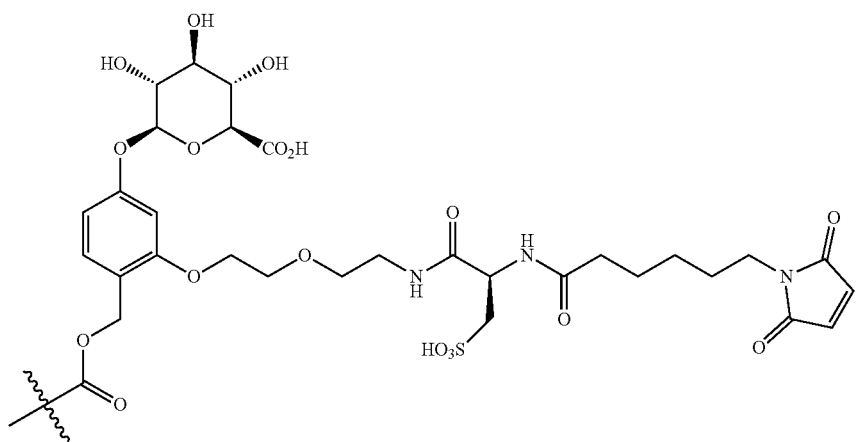
(CIVc.6)

 (CIVc.7)
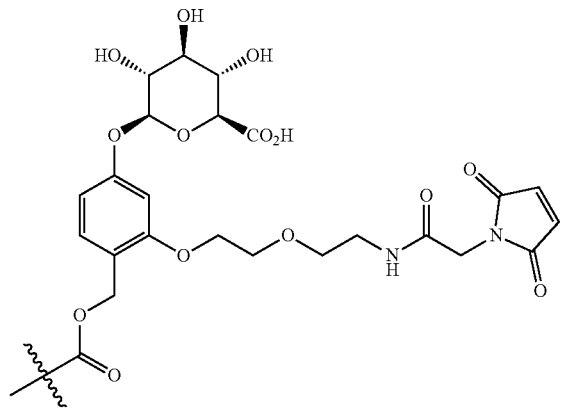 (CIVc.8)
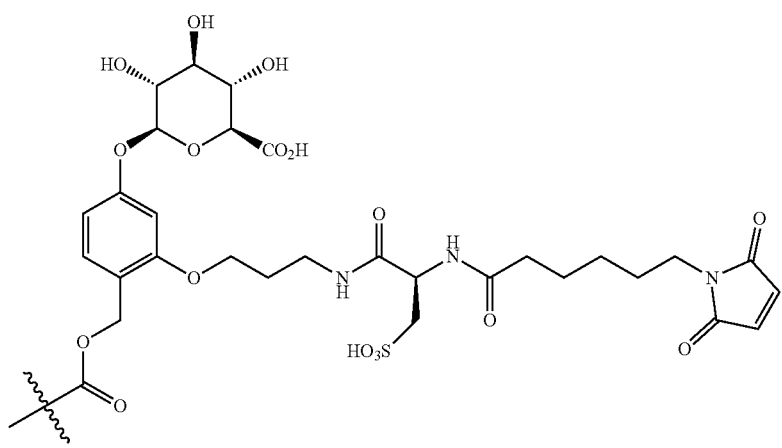 (CIVc.9)
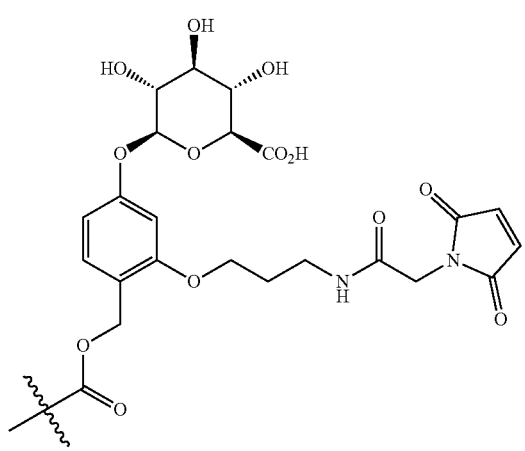 (CIVc.10)

-continued (CIV.11)

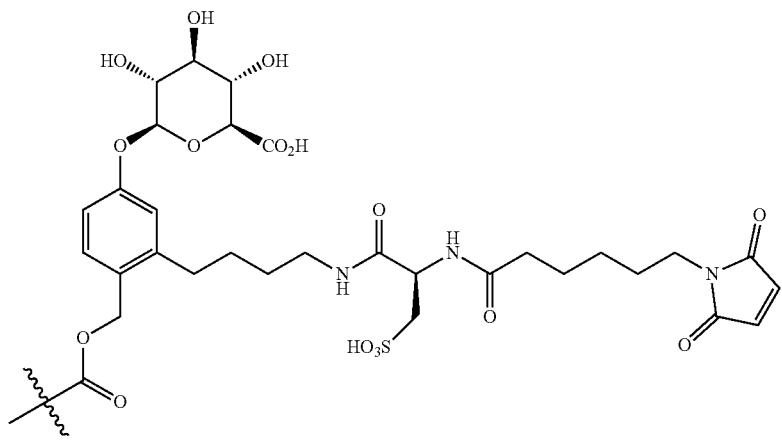

wherein

~~~ represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CIVd) that may be included in the conjugates include the linkers illustrated below (as illustrated, the linkers include a group suitable for covalently linking the linker to an antibody, an antibody construct, or a targeting moiety):

(CIVd.1)

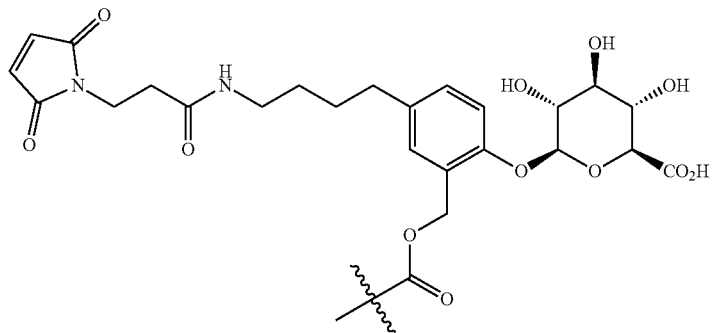

(CIVd.2)

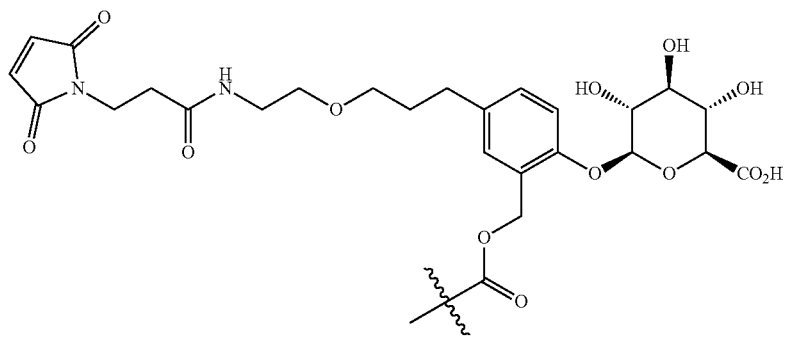

-continued (CIVd.3)
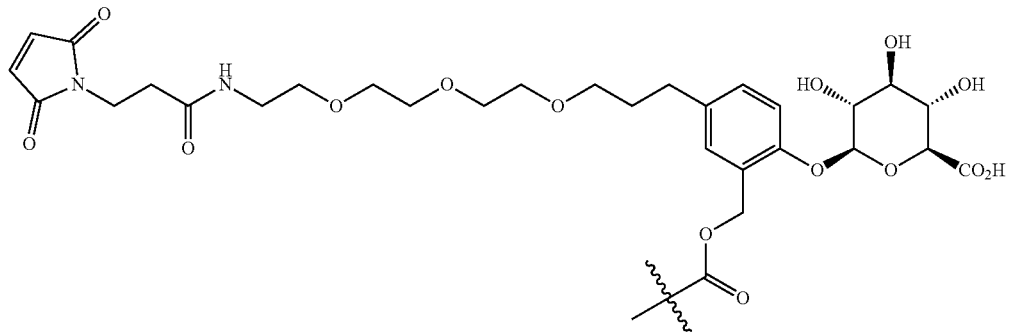

(CIVd.4)
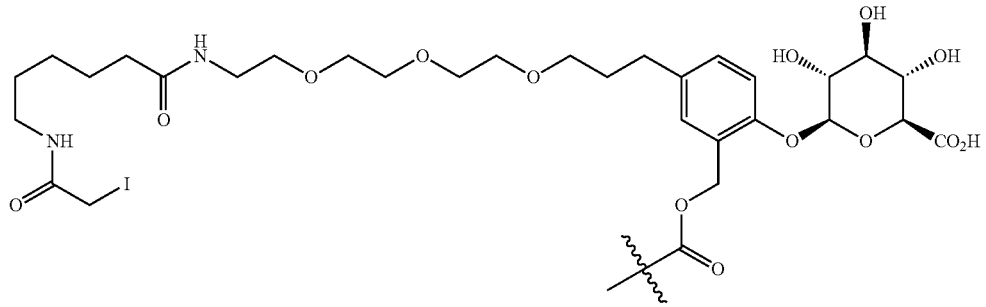

(CIVd.5)
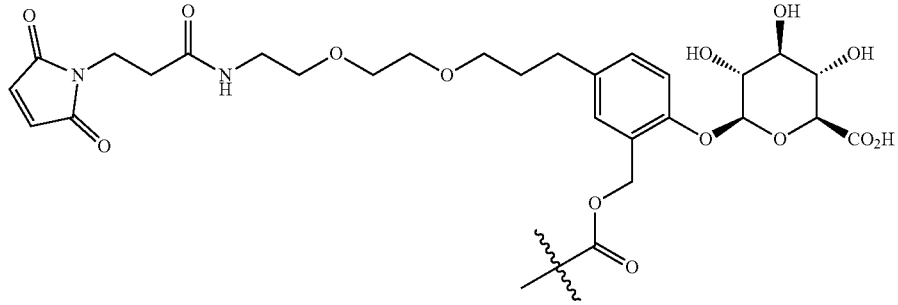

(CIVd.6)
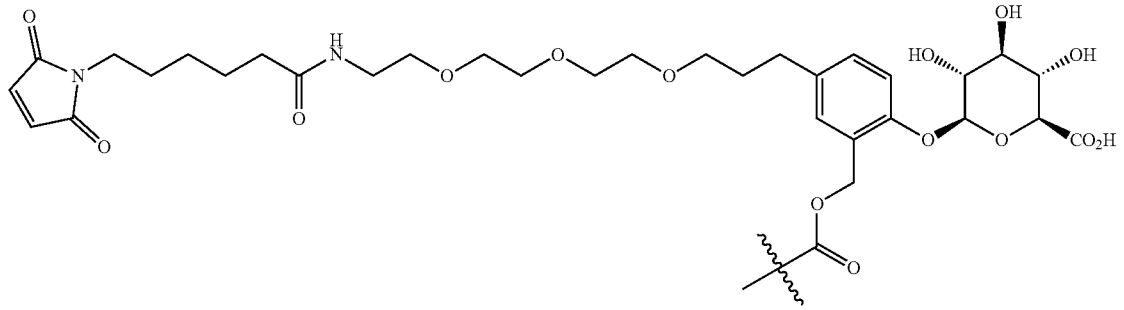

wherein

represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CIVe) that may be included in the conjugates include the linkers illustrated below (as illustrated, the linkers include a group suitable for covalently linking the linker to an antibody, an antibody construct, or a targeting moiety):

(CIVe.1)

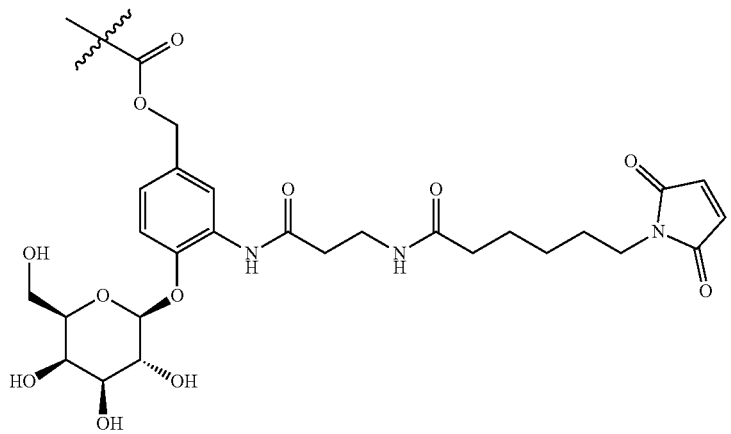

(CIVe.2)

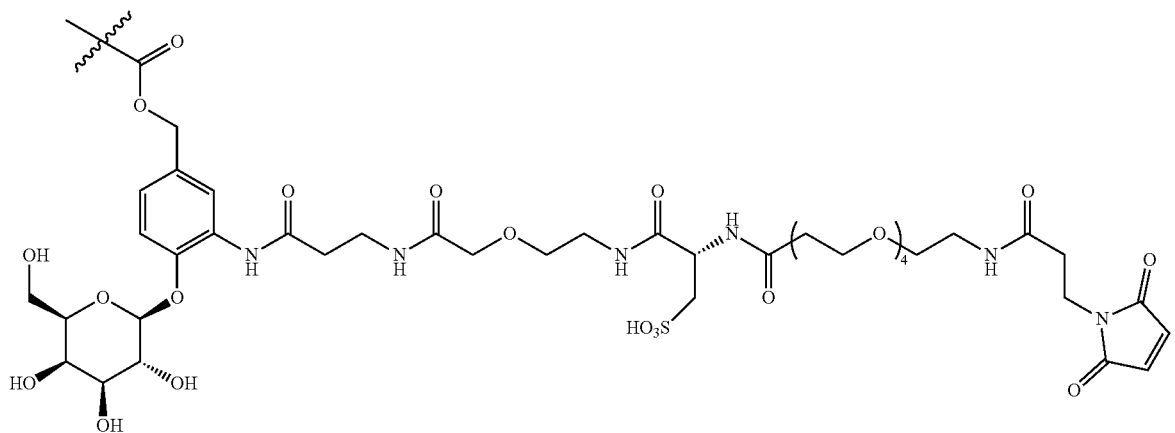

wherein

~~~ represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Although cleavable linkers can provide certain advantages, the linkers comprising the conjugate need not be cleavable. For non-cleavable linkers, the payload compound release may not depend on the differential properties between the plasma and some cytoplasmic compartments. The release of the payload compound can occur after internalization of the conjugate via antigen-mediated endocytosis and delivery to lysosomal compartment, where the antibody, antibody construct, or targeting moiety can be degraded to the level of amino acids through intracellular proteolytic degradation. This process can release a payload compound derivative (a metabolite of the conjugate containing a non-cleavable linker-heterocyclic compound), which is formed by the payload compound, the linker, and the amino acid residue or residues to which the linker was covalently attached. The payload compound derivative from conjugates with non-cleavable linkers can be more hydrophilic and less membrane permeable, which can lead to less bystander effects and less nonspecific toxicities compared to conjugates with a cleavable linker. Conjugates with non-cleavable linkers can have greater stability in circulation than conjugates with cleavable linkers. Non-cleavable linkers can include alkylene chains, or can be polymeric, such as, for example, based upon polyalkylene glycol polymers, amide polymers, or can include segments of alkylene chains, polyalkylene glycols and/or amide polymers. The linker can contain a polyethylene glycol segment having from 1 to 6 ethylene glycol units.

The linker can be non-cleavable in vivo, for example, a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and a linker L; -L is represented by the formulas below::

(CVa)

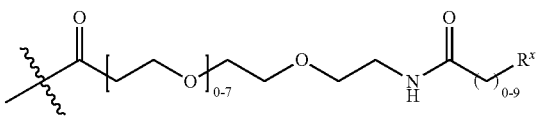

-continued (CVb)

(CVc)

(CVd)

(CVe)

or salts thereof, wherein: $R^a$ is selected from hydrogen, alkyl, sulfonate and methyl sulfonate; $R^x$ is a reactive moiety including a functional group capable of covalently linking the linker to an antibody, an antibody construct, or a targeting moiety; and represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and a linker L; -L is represented by the formula:

wherein n=0-9 and represents the point of attachment to the compound (payload).

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and a linker L; -L is represented by the formula:

wherein RX comprises a reactive moiety, e.g., a maleimide or a leaving group, n=0-9, and represents the point of attachment to the compound (payload).

In some embodiments, for a conjugate comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, a linker L, and an antibody, an antibody construct, or a targeting moiety; -L- is represented by the formula:

RX* is a bond, a succinimide moiety, or a hydrolyzed succinimide moiety attached at the on the right to a residue of the antibody, antibody construct, or targeting moiety, on the left represents the point of attachment to the compound (payload), and n=0-9.

Exemplary embodiments of linkers according to structural formula (CVa)-(Ve) that may be included in the conjugates include the linkers illustrated below (as illustrated, the linkers include a group suitable for covalently linking the linker to an antibody, an antibody construct, or a targeting moiety, and represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof:

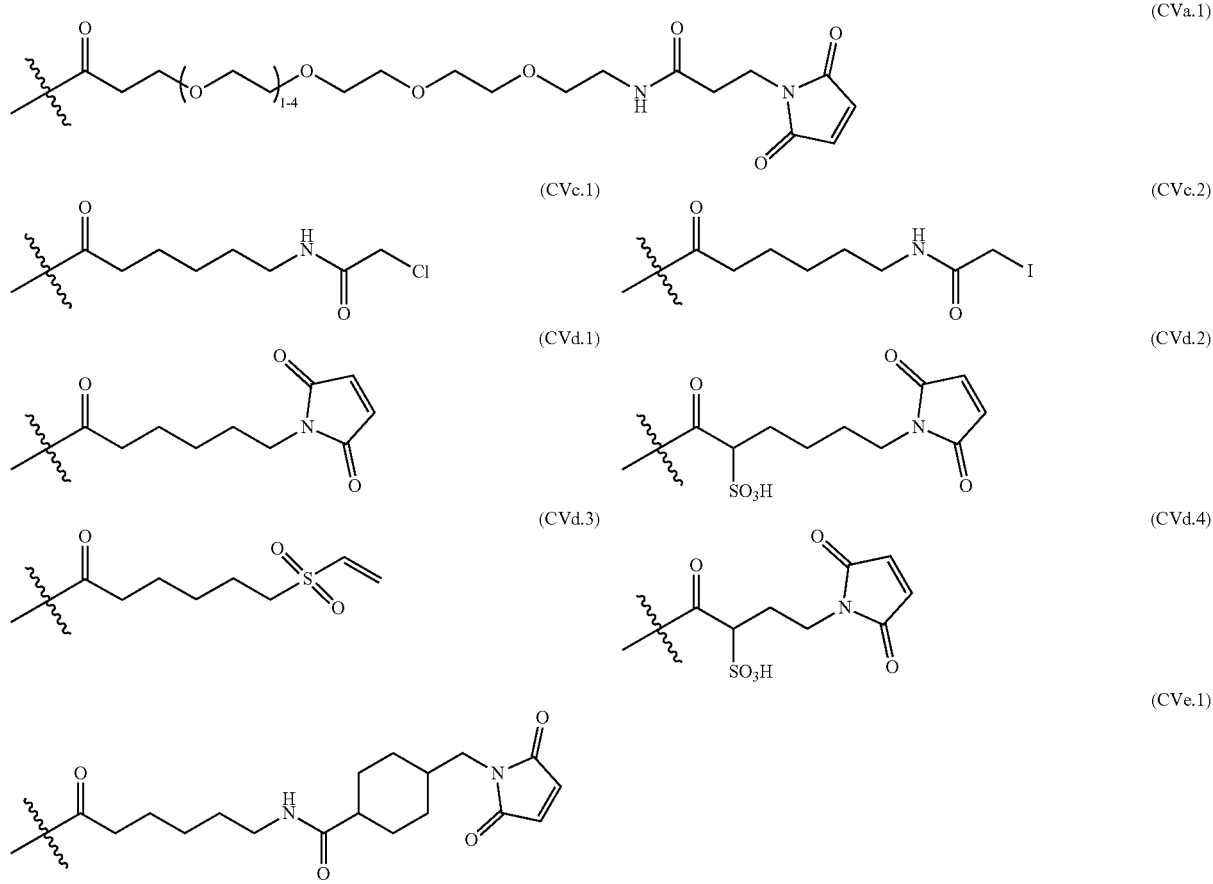

Attachment groups that are used to attach the linkers to an antibody, an antibody construct, or a targeting moiety can be electrophilic in nature and include, for example, maleimide groups, activated disulfides, active esters such as NHS esters and HOBt esters, haloformates, acid halides, alkyl, and benzyl halides such as haloacetamides. There are also emerging technologies related to "self-stabilizing" maleimides and "bridging disulfides" that can be used with immune-stimulatory compounds of this disclosure. Examples of cysteine based linkers are provided in PCT Patent Application Publication Number WO 2020/092385, the linkers of which are incorporated by reference herein.

Maleimide groups are frequently used in the preparation of conjugates because of their specificity for reacting with thiol groups of, for example, cysteine groups of an antibody, an antibody construct or a targeting moiety. The reaction between a thiol group of an antibody, an antibody construct or a targeting moiety and a drug with a linker (linker-payload) including a maleimide group proceeds according to the following scheme:

-continued

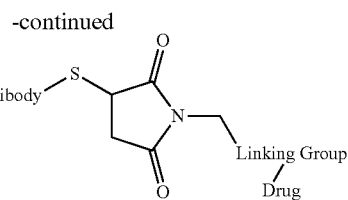

The reverse reaction leading to maleimide elimination from a thio-substituted succinimide may also take place. This reverse reaction is undesirable as the maleimide group may subsequently react with another available thiol group such as other proteins in the body having available cysteines. Accordingly, the reverse reaction can undermine the specificity of a conjugate. One method of preventing the reverse reaction is to incorporate a basic group into the linking group shown in the scheme above. Without wishing to be bound by theory, the presence of the basic group may increase the nucleophilicity of nearby water molecules to promote ring-opening hydrolysis of the succinimide group. The hydrolyzed form of the attachment group is resistant to deconjugation in the presence of plasma proteins. So-called "self-stabilizing" linkers provide conjugates with improved stability. A representative schematic is shown below:

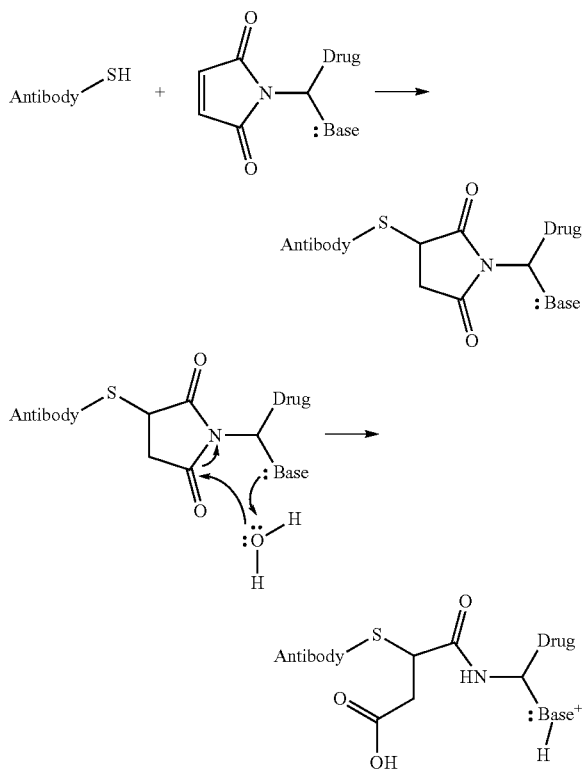

The hydrolysis reaction schematically represented above may occur at either carbonyl group of the succinimide group. Accordingly, two possible isomers may result, as shown below.

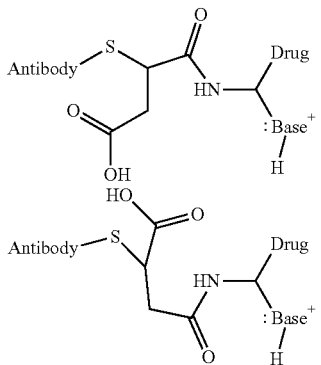

The identity of the base as well as the distance between the base and the maleimide group can be modified to tune the rate of hydrolysis of the thio-substituted succinimide group and optimize the delivery of a conjugate to a target by, for example, improving the specificity and stability of the conjugate.

Bases suitable for inclusion in a linker, e.g., any L with a maleimide group prior to conjugation to an antibody, an antibody construct, or a targeting moiety may facilitate hydrolysis of a nearby succinimide group formed after conjugation of the antibody, antibody construct, or targeting moiety to the linker. Bases may include, for example, amines (e.g., —N($R^{26}$)($R^{27}$), where $R^{26}$ and $R^{27}$ are independently selected from H and $C_{1-6}$ alkyl), nitrogen-containing heterocycles (e.g., a 3- to 12-membered heterocycle including one or more nitrogen atoms and optionally one or more double bonds), amidines, guanidines, and carbocycles or heterocycles substituted with one or more amine groups (e.g., a 3- to 12-membered aromatic or non-aromatic cycle optionally including a heteroatom such as a nitrogen atom and substituted with one or more amines of the type —N($R^{26}$)($R^{27}$), where $R^{26}$ and $R^{27}$ are independently selected from H or $C_{1-6}$ alkyl). A basic unit may be separated from a maleimide group by, for example, an alkylene chain of the form —$(CH_2)_m$—, where m is an integer from 0 to 10. An alkylene chain may be optionally substituted with other functional groups of the disclosure.

A linker (L) with a maleimide group may include an electron withdrawing groups, such as —C(O)R, =O, —CN, —$NO_2$, —$CX_3$, —X, —C(O)OR, —C(O)$NR_2$, —C(O)R, —C(O)X, —$SO_2$R, —$SO_2$OR, —$SO_2$NHR, —$SO_2NR_2$, —$PO_3R_2$, —P(O)($CH_3$)NHR, —NO, —$NR_3^+$, —CR=$CR_2$, and —C≡CR, where each R is independently selected from H and $C_{1-6}$ alkyl and each X is independently selected from F, Br, Cl, and I. Self-stabilizing linkers may also include aryl, e.g., phenyl, or heteroaryl, e.g., pyridine, groups optionally substituted with electron withdrawing groups, such as those of the disclosure.

Examples of self-stabilizing linkers are provided in, e.g., U.S. Patent Application Publication Number US 2013/0309256, the linkers of which are incorporated by reference herein. It will be understood that a self-stabilizing linker useful in conjunction with the compounds of the disclosure may be equivalently described as unsubstituted maleimide-including linkers, thio-substituted succinimide-including linkers, or hydrolyzed, ring-opened thio-substituted succinimide-including linkers.

In some embodiments, for a linker-payload comprising a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and a linker L; -L comprises a self-stabilizing moiety. For example, L may be selected from:

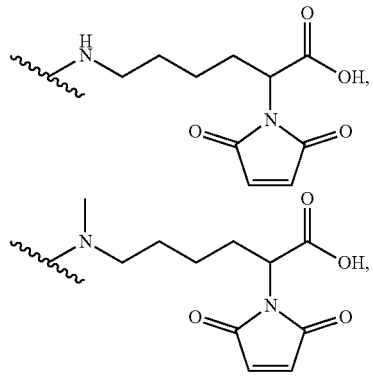

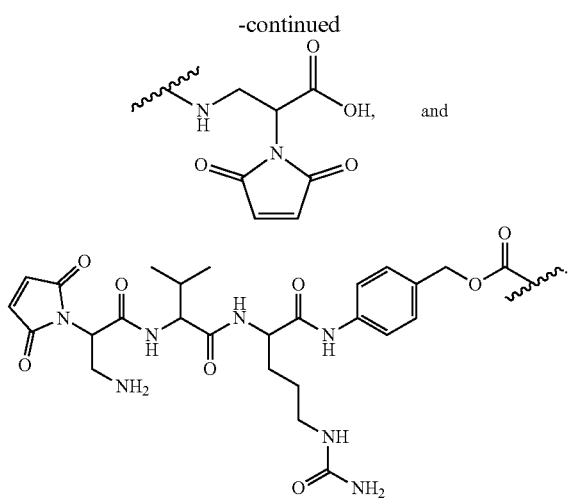

In the scheme provided above, the bottom structure may be referred to as (maleimido)-DPR-Val-Cit-PAB, where DPR refers to diaminopropinoic acid, Val refers to valine, Cit refers to citrulline, and PAB refers to para-aminobenzylcarbonyl.

represent the point of attachment to a compound of any one of Category A Formulas (IA), (IB), (IA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

A method for bridging a pair of sulfhydryl groups derived from reduction of a native hinge disulfide bond has been disclosed and is depicted in the schematic below. An advantage of this methodology is the ability to synthesize homogenous conjugates by full reduction of IgGs (to give 4 pairs of sulfhydryls from interchain disulfides, wherein the DAR can range from 1 to 8) followed by reaction with 4 equivalents of the alkylating agent. Conjugates containing "bridged disulfides" are also claimed to have increased stability.

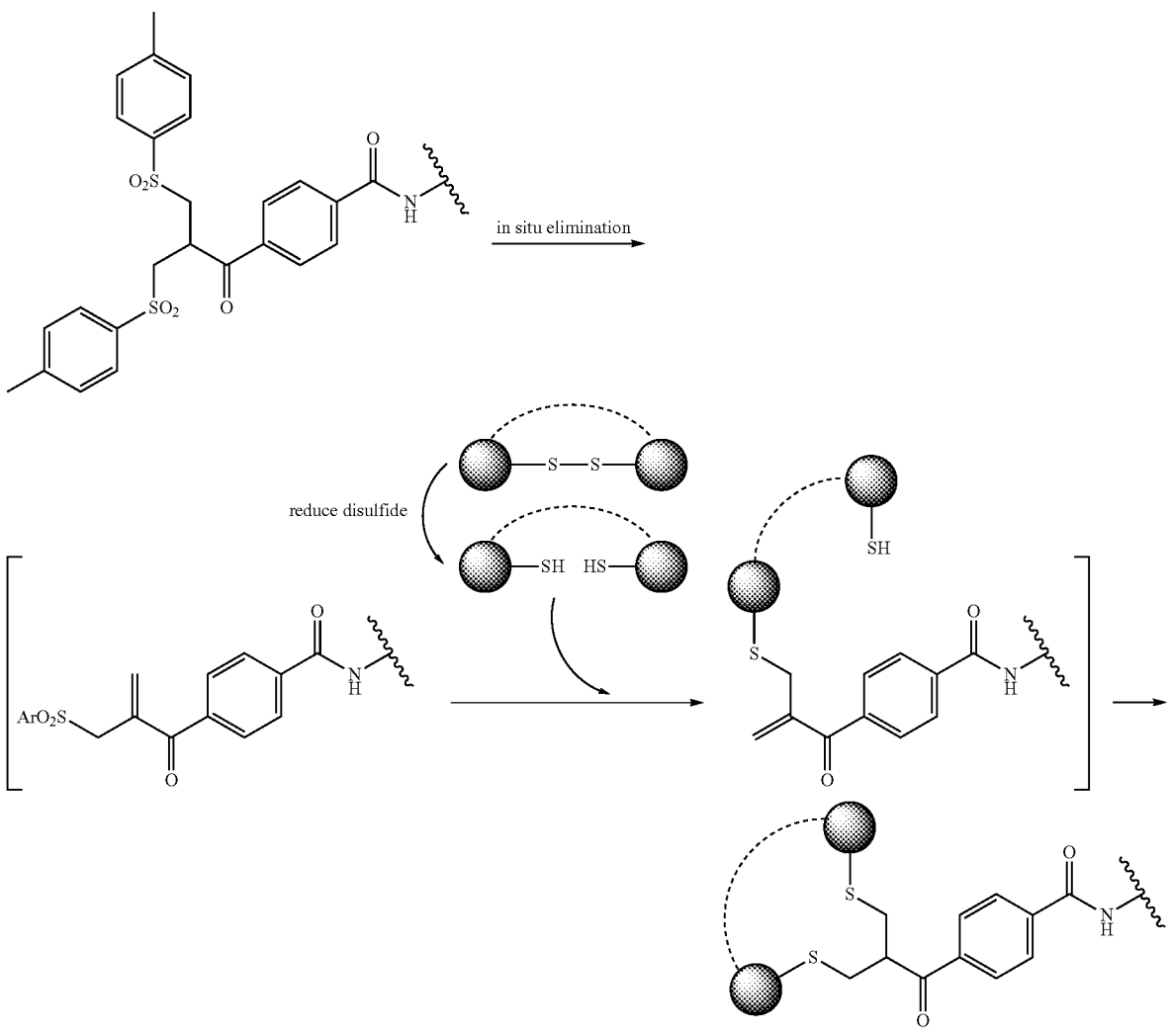

Similarly, as depicted below, a maleimide derivative that is capable of bridging a pair of sulfhydryl groups has been developed.

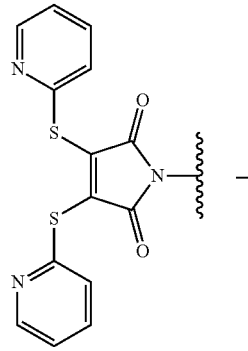

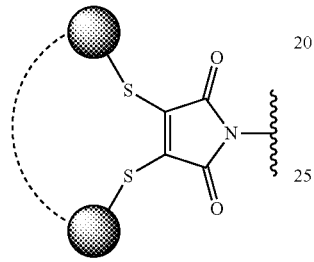

A linker of the disclosure, L, can contain the following structural formulas (CVIa), (CVIb), or (CVIc):

(CVIa)

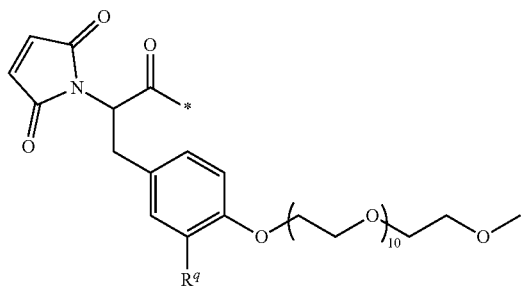

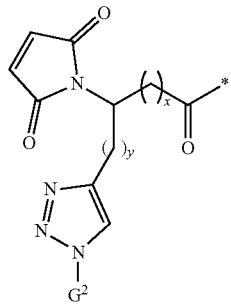
(CVIb)

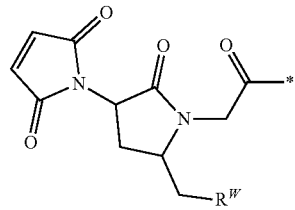
(CVIc)

or salts thereof, wherein: $R^q$ is H or —O—$(CH_2CH_2O)_{11}$—$CH_3$; x is 0 or 1; y is 0 or 1; $G^2$ is —$CH_2CH_2CH_2SO_3H$ or —$CH_2CH_2O$—$(CH_2CH_2O)_{11}$—$CH_3$; $R^w$ is —O—$CH_2CH_2SO_3H$ or —NH(CO)—$CH_2CH_2O$—$(CH_2CH_2O)_{12}$—$CH_3$; and * represents the point of attachment to the remainder of the linker.

Exemplary embodiments of linkers according to structural formula (CVIa) and (CVIb), which can be included in linker-payload and conjugate structures of this disclosure, include the linkers illustrated below (as illustrated, the linkers include a group suitable for covalently linking the linker to an antibody, an antibody construct, or a targeting moiety):

(CVIa.1)

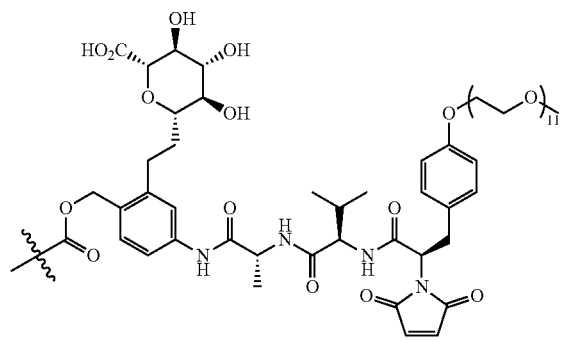

(CVIa.2)

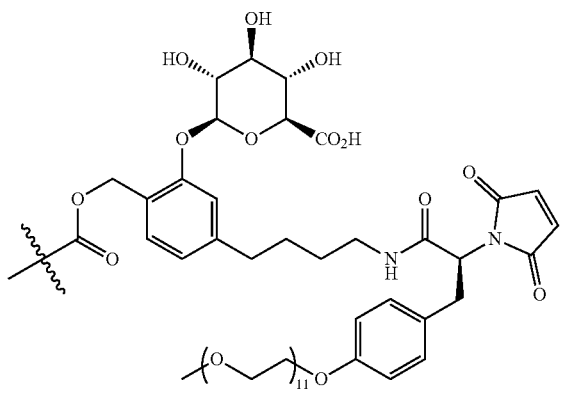

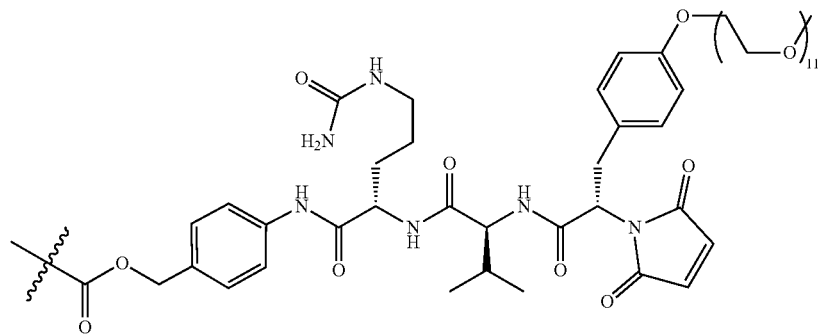
(CVIa.3)
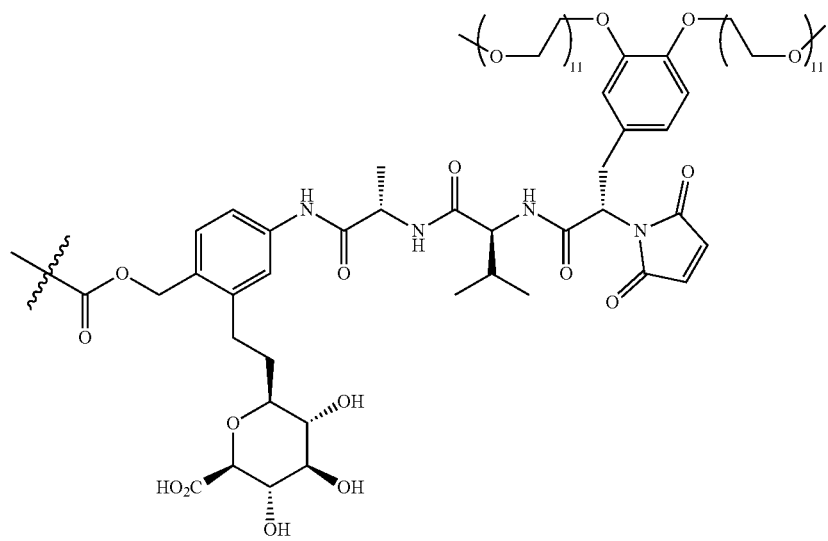
(CVIa.4)
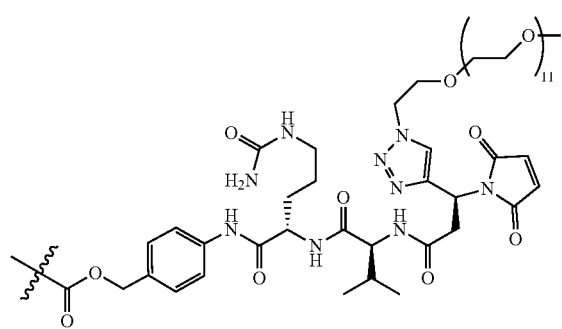
(CVIb.1)
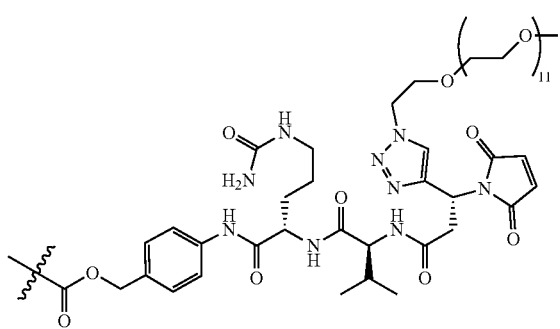
(CVIb.2)

-continued
(CVIb.3) 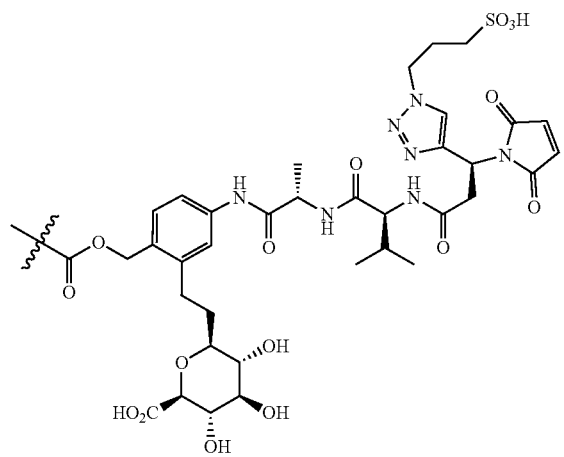
(CVIb.4) 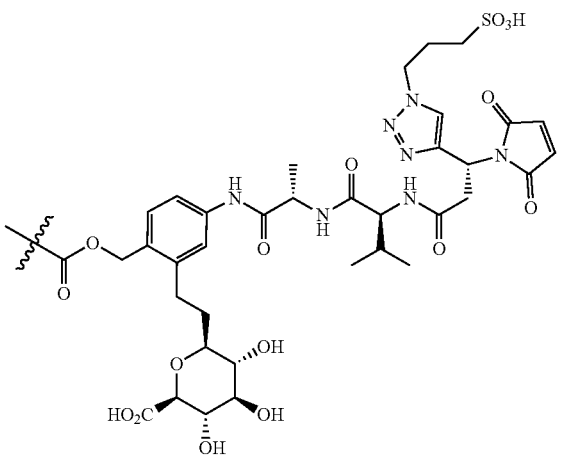
(CVIb.5) 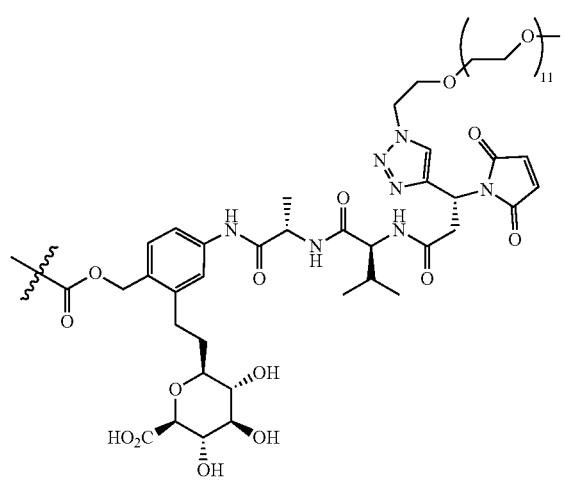
(CVIb.6)
(CVIb.7) 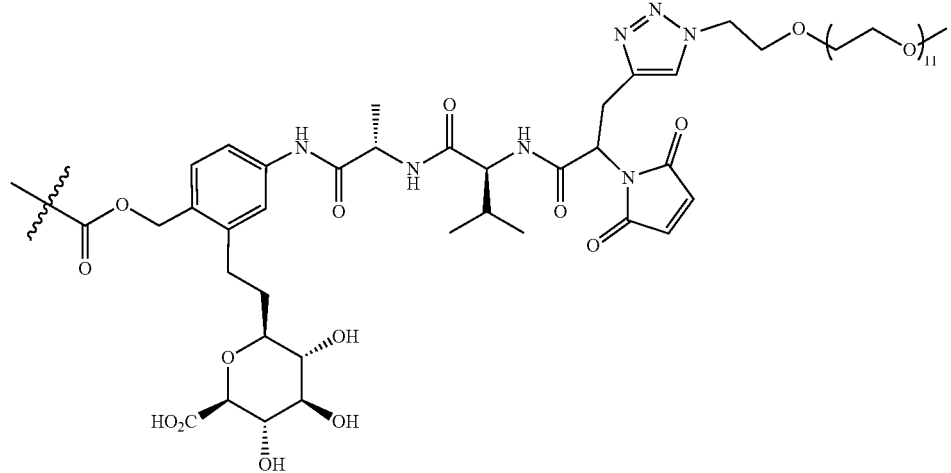
wherein
∿ represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Exemplary embodiments of linkers according to structural formula (CVIc), which can be included in linker-payload and conjugate structure of this disclosure, include the linkers illustrated below (as illustrated, the linkers include a group suitable for covalently linking the linker to an antibody, an antibody construct, or a targeting moiety):

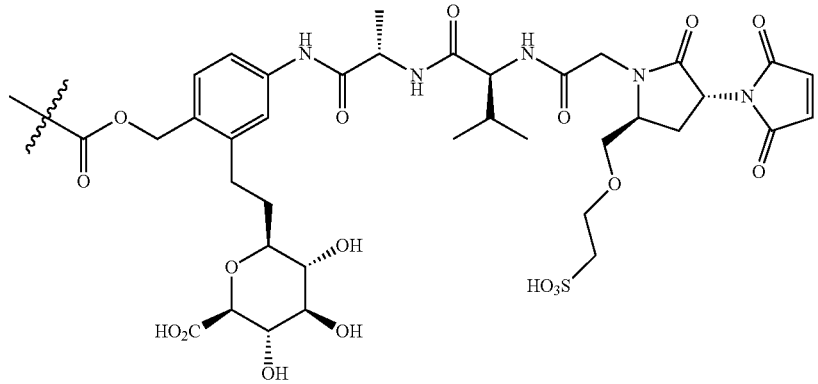
(CVIc.1)

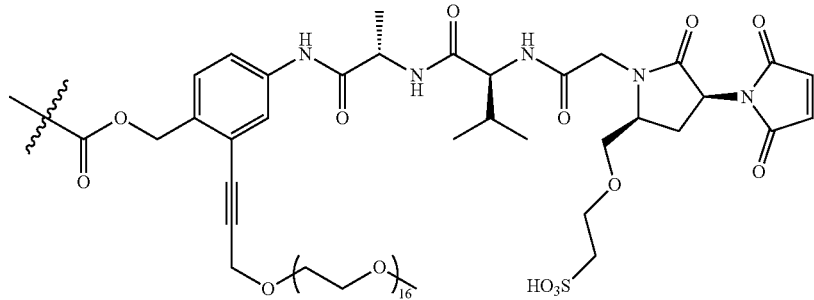
(CVIc.2)

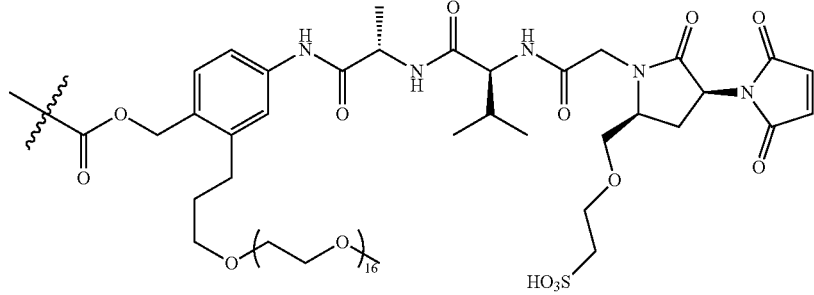
(CVIc.3)

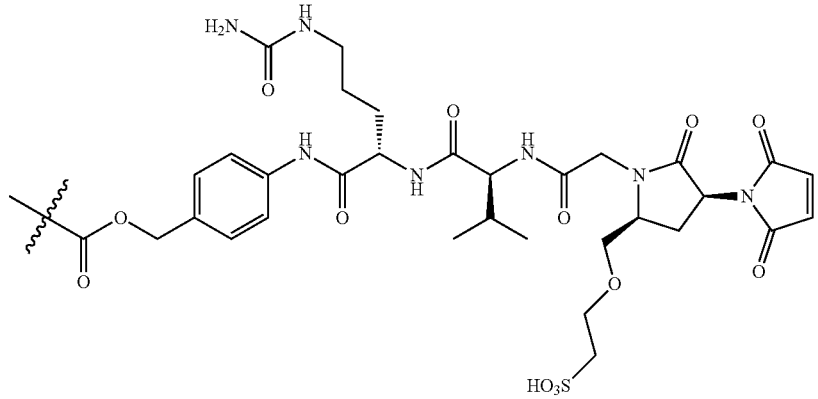
(CVIc.4)

-continued

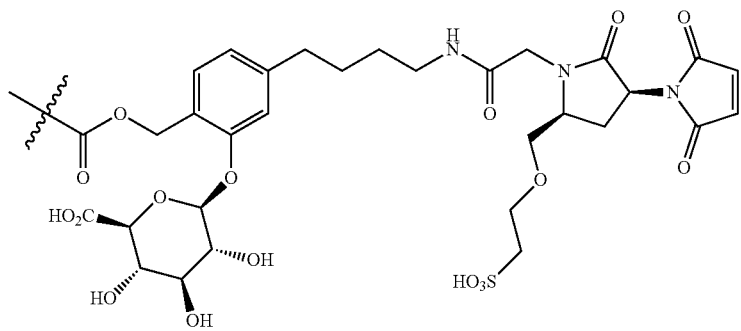

(CVIc.5)

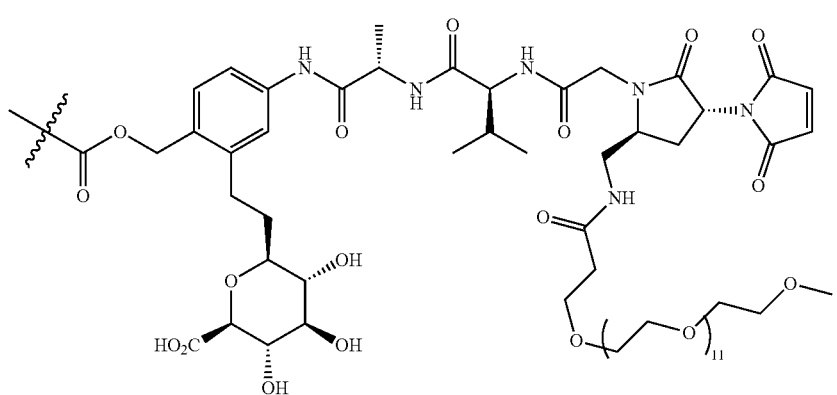

(CVIc.6)

wherein ⸹ represents the point of attachment of the linker (L) to a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

Some exemplary linkers (L) are described in the following paragraphs. In some embodiments for a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, wherein attachment of the linker is to a nitrogen of the compound and conjugation is to a cysteine residue of an antibody or targeting moiety, -L is represented by the formulas set forth in Table A1 below:

TABLE A1
| Cmpd Name | Structural Formula |
|---|---|
| L1 | 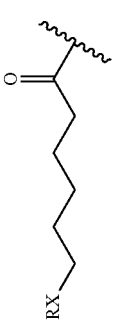 |
| L2 | 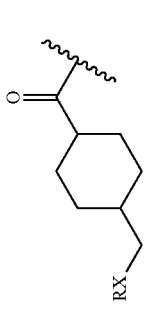 |
| L3 | 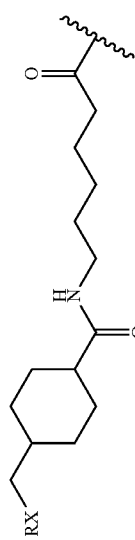 |
| L4 | 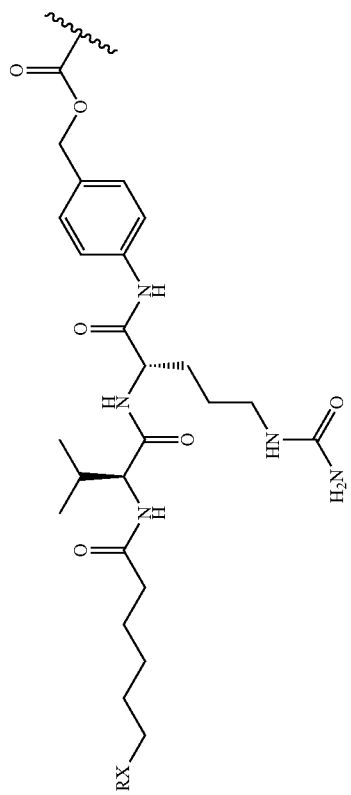 |

TABLE A1-continued

| Cmpd Name | Structural Formula |
|---|---|
| L5 | (structure) |
| L6 | (structure) |
| L7 | (structure) |
| L8 | (structure) |

TABLE A1-continued

| Cmpd Name | Structural Formula |
|---|---|
| L9 | |
| L10 | |
| L11 | | wherein

represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC); $L^4$ represents the C-terminus of the peptide and $L^5$ is selected from a bond, alkylene and heteroalkylene, wherein $L^5$ is optionally substituted with one or more groups independently selected from $R^{30}$, and $R^{30}$ is independently selected at each occurrence from halogen, —OH, —CN, —O-alkyl, —SH, =O, =S, —S(O)$_2$OH, —NH$_2$, —NO$_2$; and $C_1$-$C_{10}$alkyl, $C_2$-$C_{10}$alkenyl, and $C_2$-$C_{10}$alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$; and RX represents a reactive moiety. The reactive moiety may be selected, for example, from an electrophile, e.g., an α,β-unsaturated carbonyl, such as a maleimide, and a leaving group. For example, -L can be represented by the formulas set forth in Table A2 below:

TABLE A2

| Cmpd Name | Structural Formula |
|---|---|
| L12 | (6-maleimidocaproyl) |
| L13 | (4-(maleimidomethyl)cyclohexanecarbonyl) |
| L14 | (4-(maleimidomethyl)cyclohexanecarboxamido-hexanoyl) |
| L15 | (MC-Val-Cit-PAB) |

TABLE A2-continued

| Cmpd Name | Structural Formula |
|---|---|
| L16 | (structure) |
| L17 | (structure) |
| L18 | (structure) |
| L19 | (structure) |

TABLE A2-continued

| Cmpd Name | Structural Formula |
|---|---|
| L20 | |
| L21 | |

TABLE A2-continued

| Cmpd Name | Structural Formula |
|---|---|
| L22 | (structure) |
| L23 | (structure) |
| L24 | (structure) |

TABLE A2-continued
| Cmpd Name | Structural Formula |
|---|---|
| L25 | 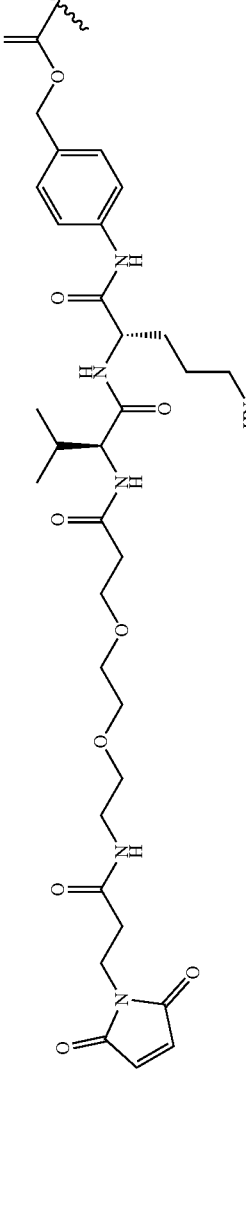 |
| L26 | 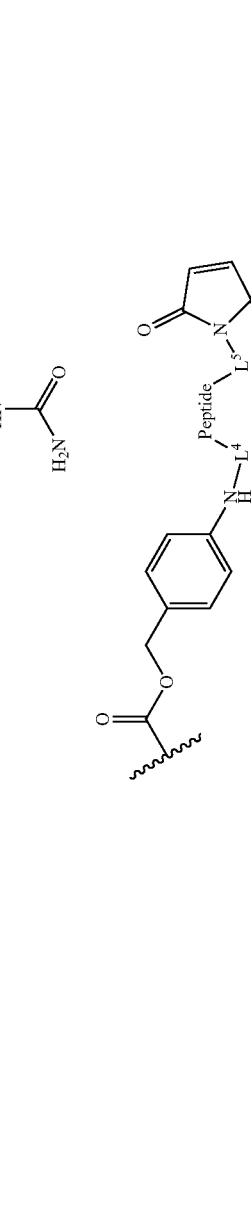 | wherein

 5 represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) and $L^4$ represents the C-terminus of the peptide and $L^5$ is selected from a bond, alkylene and heteroalkylene, wherein $L^5$ is optionally substituted with one or more groups independently selected from $R^{30}$, and $R^{30}$ is independently selected at each occurrence from halogen, —OH, —CN, —O-alkyl, —SH, =O, =S, —NH$_2$, —NO$_2$; and $C_1$-$C_{10}$alkyl, $C_2$-$C_{10}$alkenyl, and $C_2$-$C_{10}$alkynyl, each of which is independently optionally substituted at each occurrence with one or more substituents selected from halogen, —OH, —CN, —O-alkyl, —SH, =O, =S, —NH$_2$, and —NO$_2$.

When conjugated to the cysteine residue of the antibody or targeting moiety, such linkers can be, for example, represented by the Formulas set forth in Table A3 below:

TABLE A3
| Cmpd Name | Structural Formula |
|---|---|
| L27 |  |
| L28 |  |
| L29 |  |
| L30 |  |
| L31 |  |

TABLE A3-continued

| Cmpd Name | Structural Formula |
|---|---|
| L32 | |
| L33 | |
| L34 | |

TABLE A3-continued

| Cmpd Name | Structural Formula |
|---|---|
| L35 | |
| L36 | |
| L37 | | wherein RX* is a bond a succinimide moiety, or a hydrolyzed succinimide moiety bud to a cysteine residue of the antibody, antibody construct, or targeting moiety, wherein

on RX* represents the point of attachment to such residue; L⁴ when present represents the C-terminus of the peptide and L⁵ is selected from a bond, alkylene and heteroalkylene, wherein L⁵ is optionally substituted with one or more groups independently selected from R³⁰; and R³⁰ when present is independently selected at each occurrence from halogen, —OH, —CN, —O-alkyl, —SH, =O, =S, —S(O)₂OH, —NH₂, —NO₂; and C₁-C₁₀ alkyl, C₂-C₁₀ alkenyl, and C₂-C₁₀ alkynyl, each of which is independently optionally substituted at each occurrence with one or more substituents selected from halogen, —OH, —CN, —O-alkyl, —SH, =O, =S, —S(O)₂OH, —NH₂, and —NO₂. A particularly preferred peptide is Val-Ala or Val-Cit.

In some embodiments for a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, wherein attachment of the linker is to a nitrogen of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof, and conjugation is to a lysine residue of an antibody or other targeting moiety, -L is represented by the formulas set forth in Table A4 below:

TABLE A4
| Cmpd Name | Structural Formula |
|---|---|
| L38 | 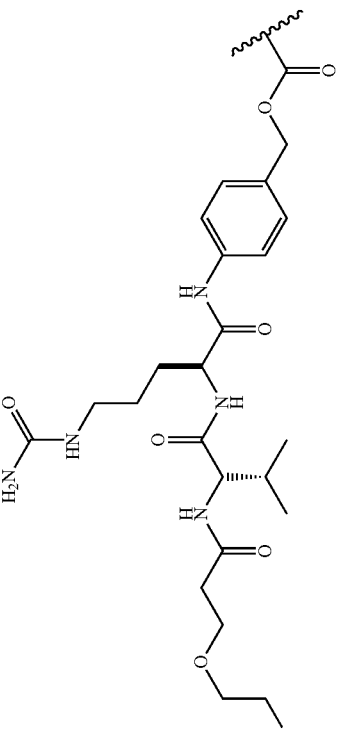 |

TABLE A4-continued
| Cmpd Name | Structural Formula |
|---|---|
| L39 | 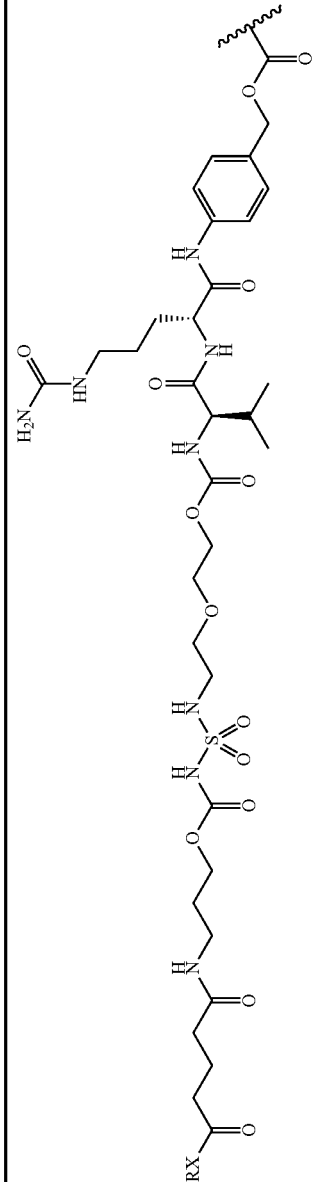 | wherein

represents attachment to a nitrogen of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (BB), and (IIC), or pharmaceutically acceptable isomer, tautomer, racemate, hydrate, solvate, isotope, or salt thereof, and RX represents a reactive moiety.

The reactive moiety may be selected from, for example, a leaving group. For example, -L can be represented by the formulas set forth in Table A5 below:

TABLE A5
| Cmpd Name | Structural Formula |
|---|---|
| L40 | 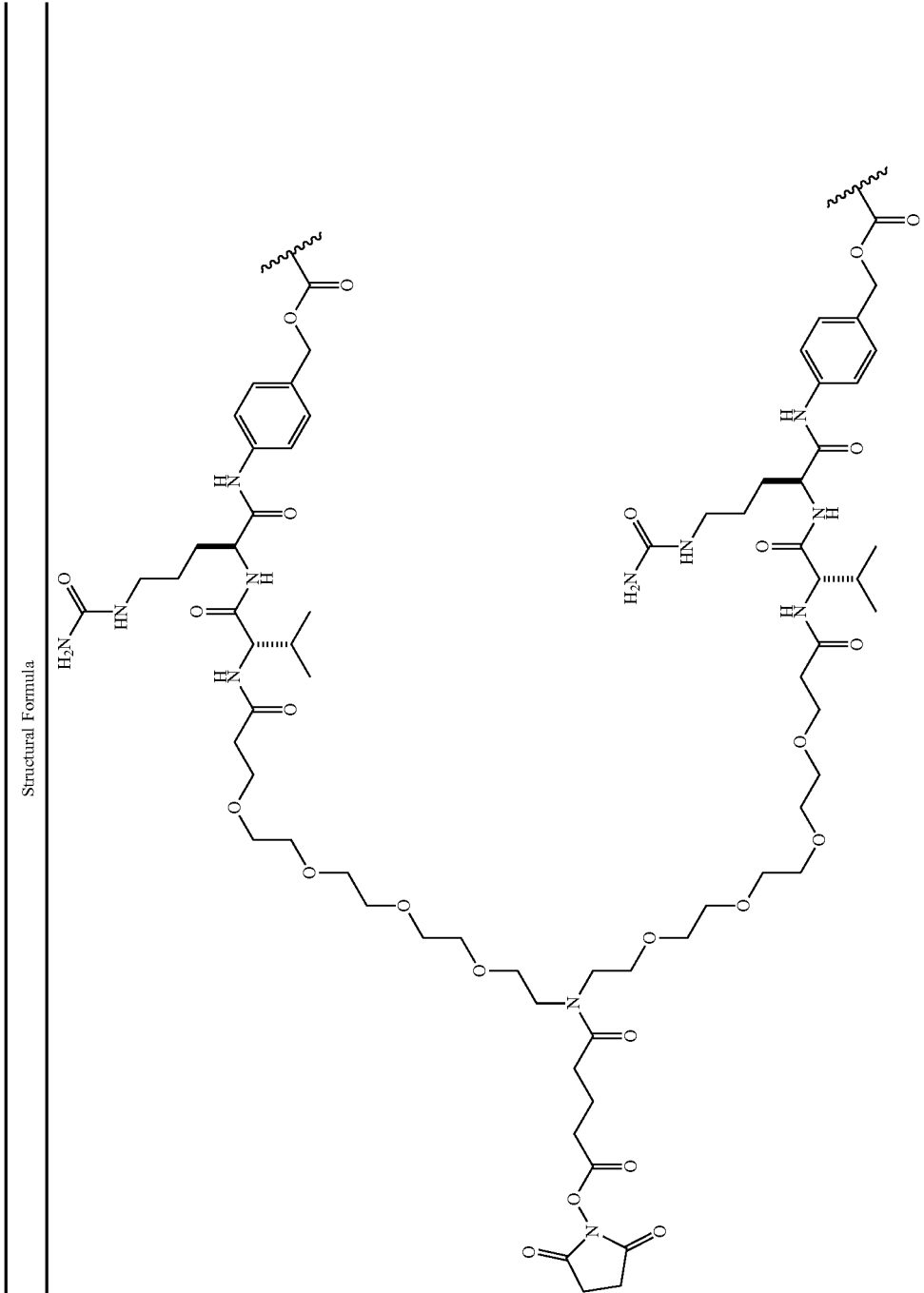 |

TABLE A5-continued

| Cmpd Name | Structural Formula |
|---|---|
| L41 | (structure) |

When conjugated to the lysine residue of an antibody or other targeting moiety, such linkers, can, for example, be represented by the Formulas set forth in Table A6 below wherein RX* is a bond to a nitrogen of the lysine residue of the antibody, antibody construct or targeting moiety, wherein
on RX* represents the point of attachment to such residue:

TABLE A6
| Cmpd Name | Structural Formula |
|---|---|
| L42 | 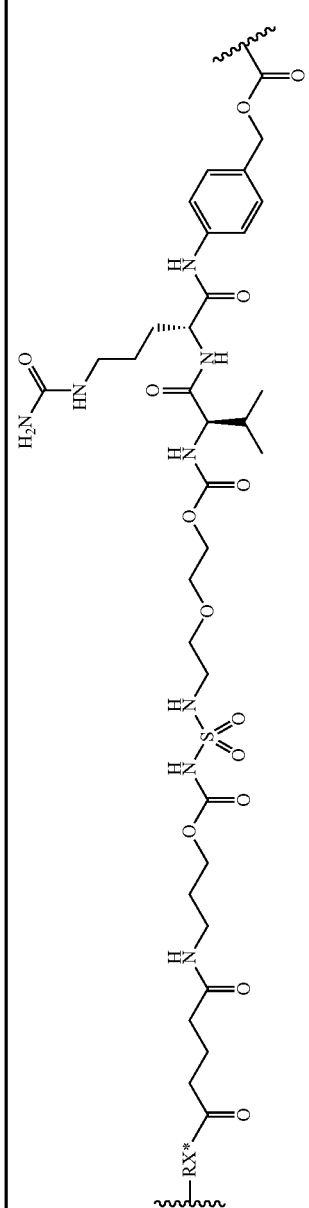 |

TABLE A6-continued
| Cmpd Name | Structural Formula |
|---|---|
| L43 | 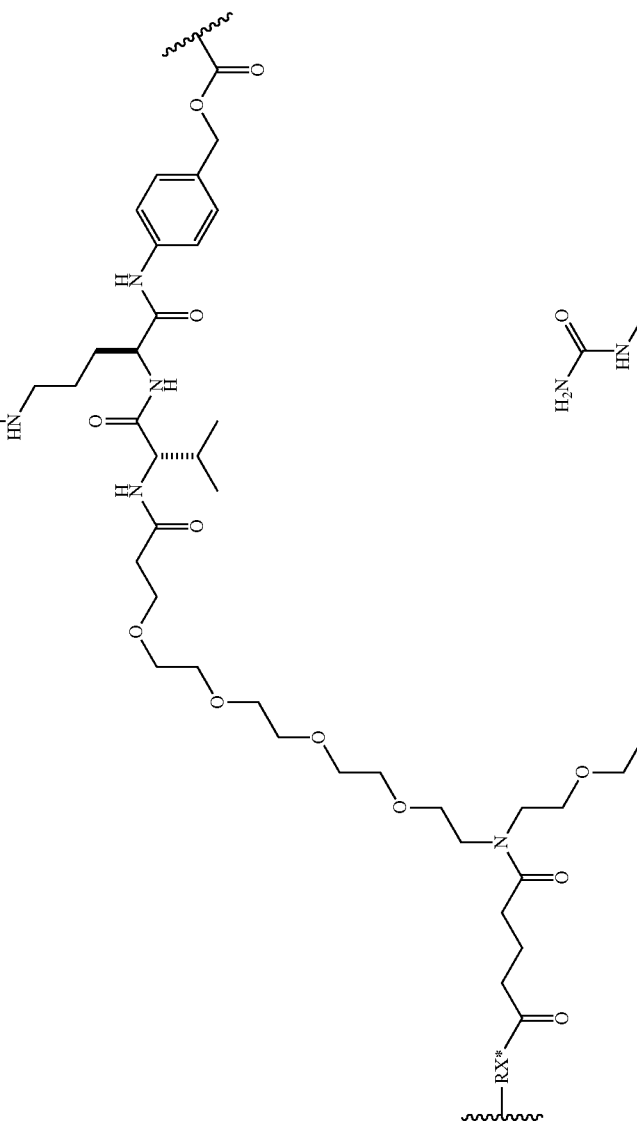 |

As noted,

represents attachment to a nitrogen of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC), or pharmaceutically acceptable isomer, tautomer, racemate, hydrate, solvate, isotope, or salt thereof.

As is known by skilled artisans, the linker selected for a particular conjugate may be influenced by a variety of factors, including the site of attachment to the antibody, antibody construct, or targeting moiety (e.g., lysine, cysteine, or other amino acid residues), structural constraints of the drug pharmacophore, and the lipophilicity of the drug. The specific linker selected for a conjugate should seek to balance these different factors for the specific antibody, antibody construct, or targeting moiety/drug combination.

For example, cytotoxic conjugates have been observed to effect killing of bystander antigen-negative cells present in the vicinity of the antigen-positive tumor cells. The mechanism of the bystander effect by cytotoxic conjugates has indicated that metabolic products formed during intracellular processing of the conjugates may play a role. Neutral cytotoxic metabolites generated by metabolism of the conjugates in antigen-positive cells appear to play a role in bystander cell killing while charged metabolites may be prevented from diffusing across the membrane into the medium, or from the medium across the membrane and, therefore, cannot effect cell killing via the bystander effect. In some embodiments, a linker is selected to attenuate the bystander effect caused by cellular metabolites of the conjugate. In some embodiments, a linker is selected to increase the bystander effect.

The properties of the linker, or linker-payload, may also impact aggregation of a conjugate under conditions of use and/or storage. Conjugates reported in the literature contain about 3-4 drug molecules per antibody molecule. Attempts to obtain higher drug-to-antibody ratios ("DAR") often failed, particularly if both the drug and the linker were hydrophobic, due to aggregation of the conjugate. In many instances, DARs higher than 3-4 could be beneficial as a means of increasing potency. In instances where the payload compound is more hydrophobic in nature, it may be desirable to select linkers that are relatively hydrophilic as a means of reducing conjugate aggregation, especially in instances where DARs greater than 3-4 are desired. Thus, in some embodiments, a linker incorporates chemical moieties that reduce aggregation of the conjugates during storage and/or use. A linker may incorporate polar or hydrophilic groups such as charged groups or groups that become charged under physiological pH to reduce the aggregation of the conjugates. For example, a linker may incorporate charged groups such as salts or groups that deprotonate, e.g., carboxylates, or protonate, e.g., amines, at physiological pH.

In preferred embodiments, aggregation of conjugates during storage or use is less than about 40% as determined by size-exclusion chromatography (SEC). In particular embodiments, the aggregation of the conjugates during storage or use is less than about 35%, such as less than about 30%, about 25%, about 20%, about 15%, about 10%, about 5%, about 4%, or even less, as determined by size-exclusion chromatography (SEC).

Some exemplary linkers (L) are described in the following paragraphs. In some embodiments for a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) wherein attachment of the linker is to a nitrogen of the compound and conjugation is to a cysteine residue of an antibody or targeting moiety, -L is represented by the formulas set forth in Table A7 below:

TABLE A7
| | |
|---|---|
| L44 | 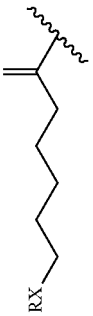 |
| L45 | 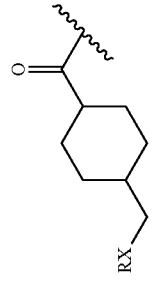 |
| L46 | 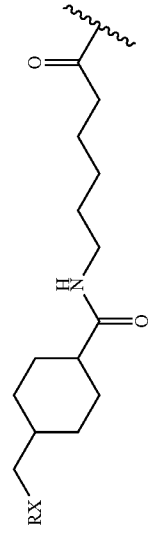 |
| L47 | 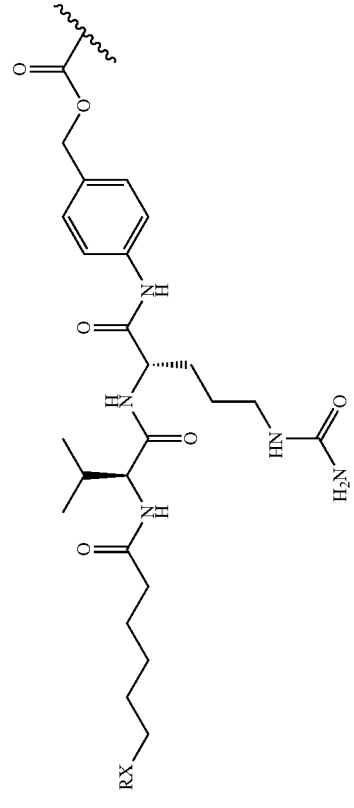 |

TABLE A7-continued
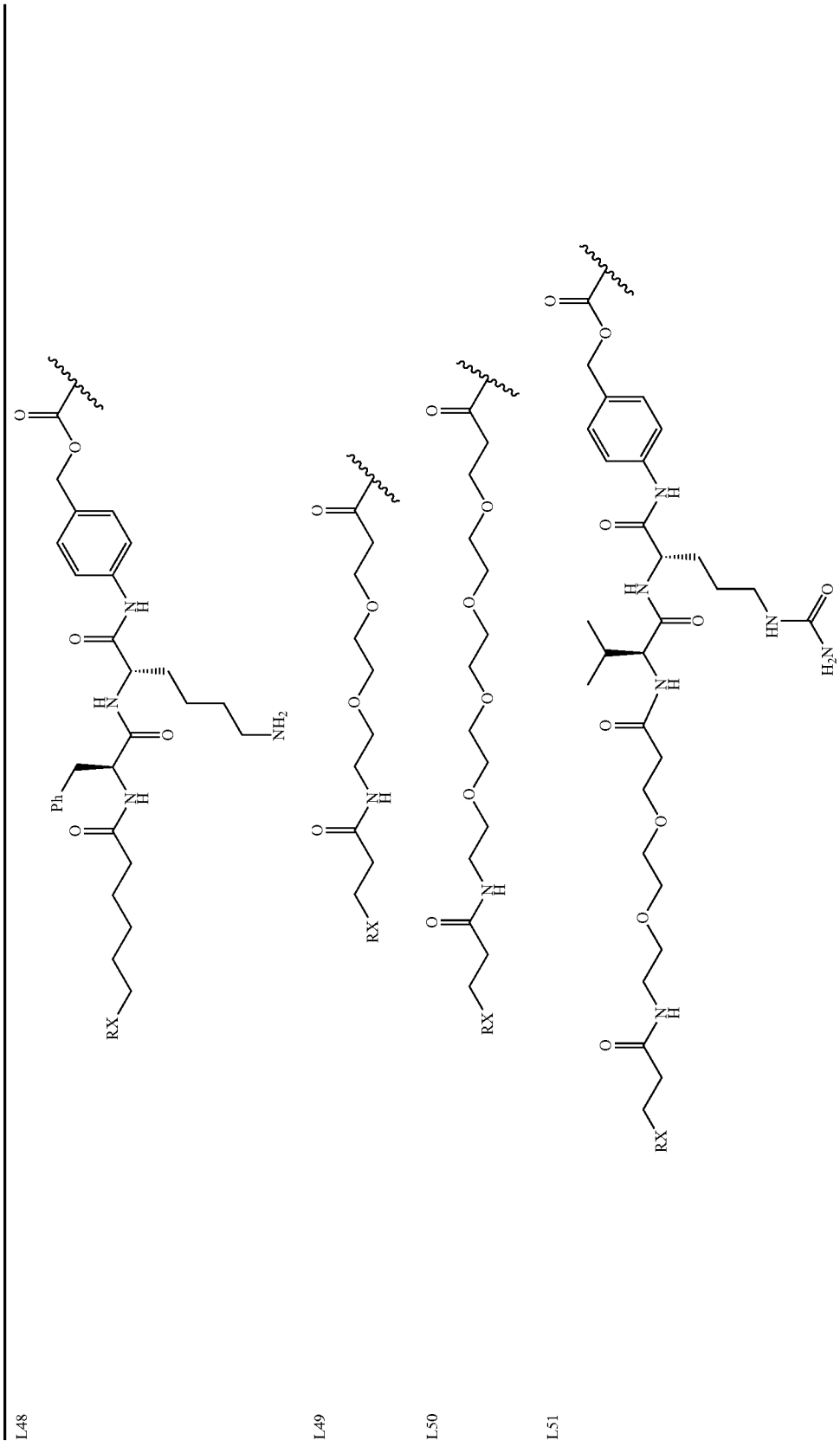
L48
L49
L50
L51

TABLE A7-continued
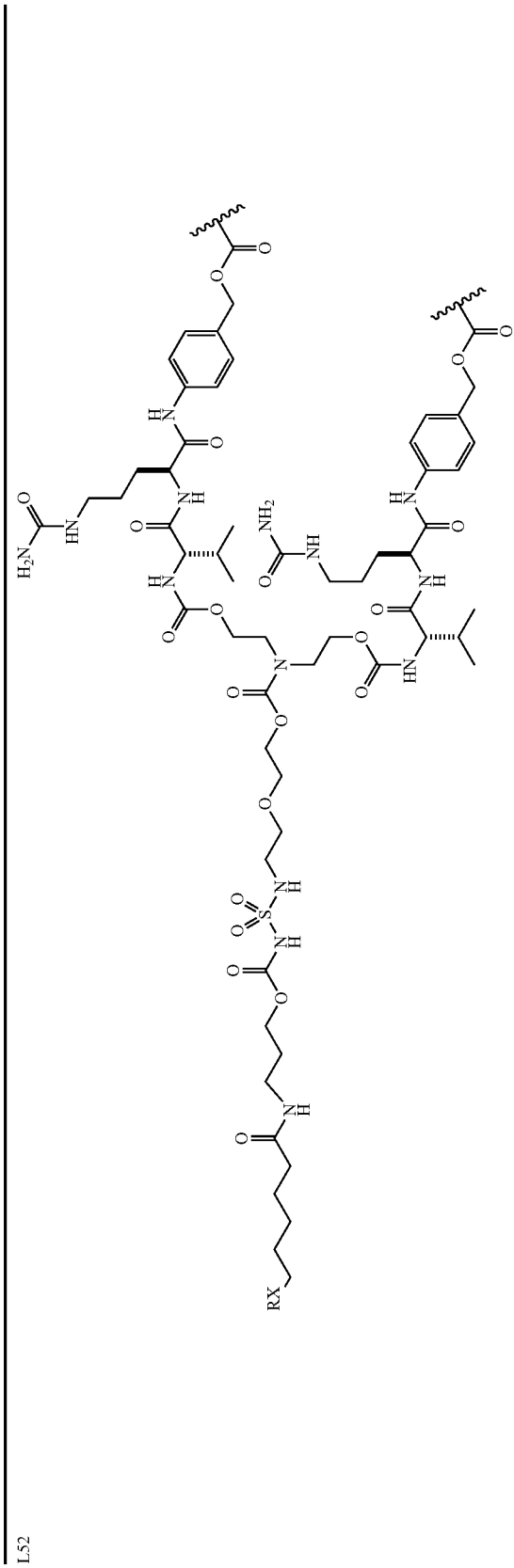
L52
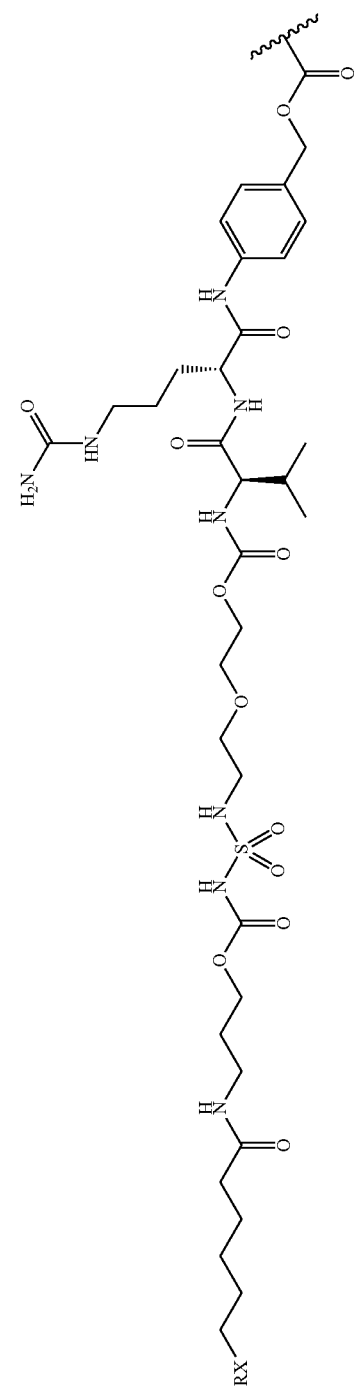
L53

TABLE A7-continued
L54 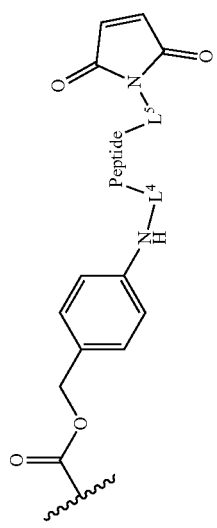

wherein

represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC); $L^4$ represents the C-terminus of the peptide and $L^5$ is selected from a bond, alkylene and heteroalkylene, wherein $L^5$ is optionally substituted with one or more groups independently selected from $R^{30}$, and $R^{30}$ is independently selected at each occurrence from halogen, —OH, —CN, —O-alkyl, —SH, =O, =S, —S(O)$_2$OH, —NH$_2$, —NO$_2$; and $C_1$-$C_{10}$ alkyl, $C_2$-$C_{10}$ alkenyl, and $C_2$-$C_{10}$ alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$; and RX represents a reactive moiety. The reactive moiety may be selected, for example, from an electrophile, e.g., an α,β-unsaturated carbonyl, such as a maleimide, and a leaving group. For example, -$L^3$ can be represented by the formulas set forth in Table A8 below:

TABLE A8
L55 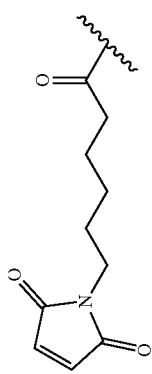
L56 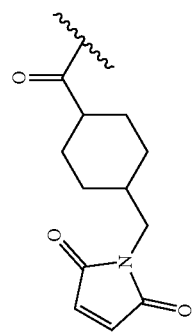
L57 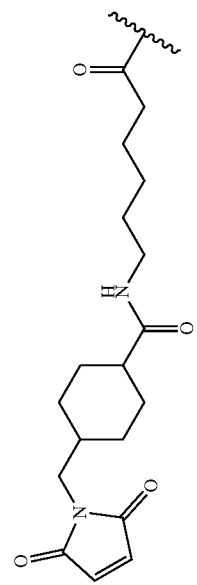
L58 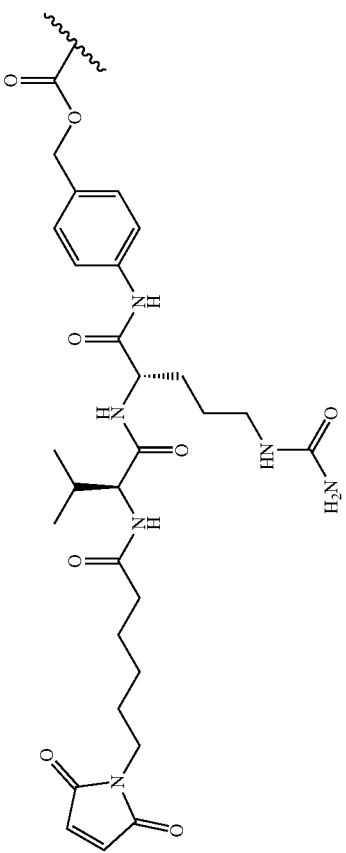

TABLE A8-continued
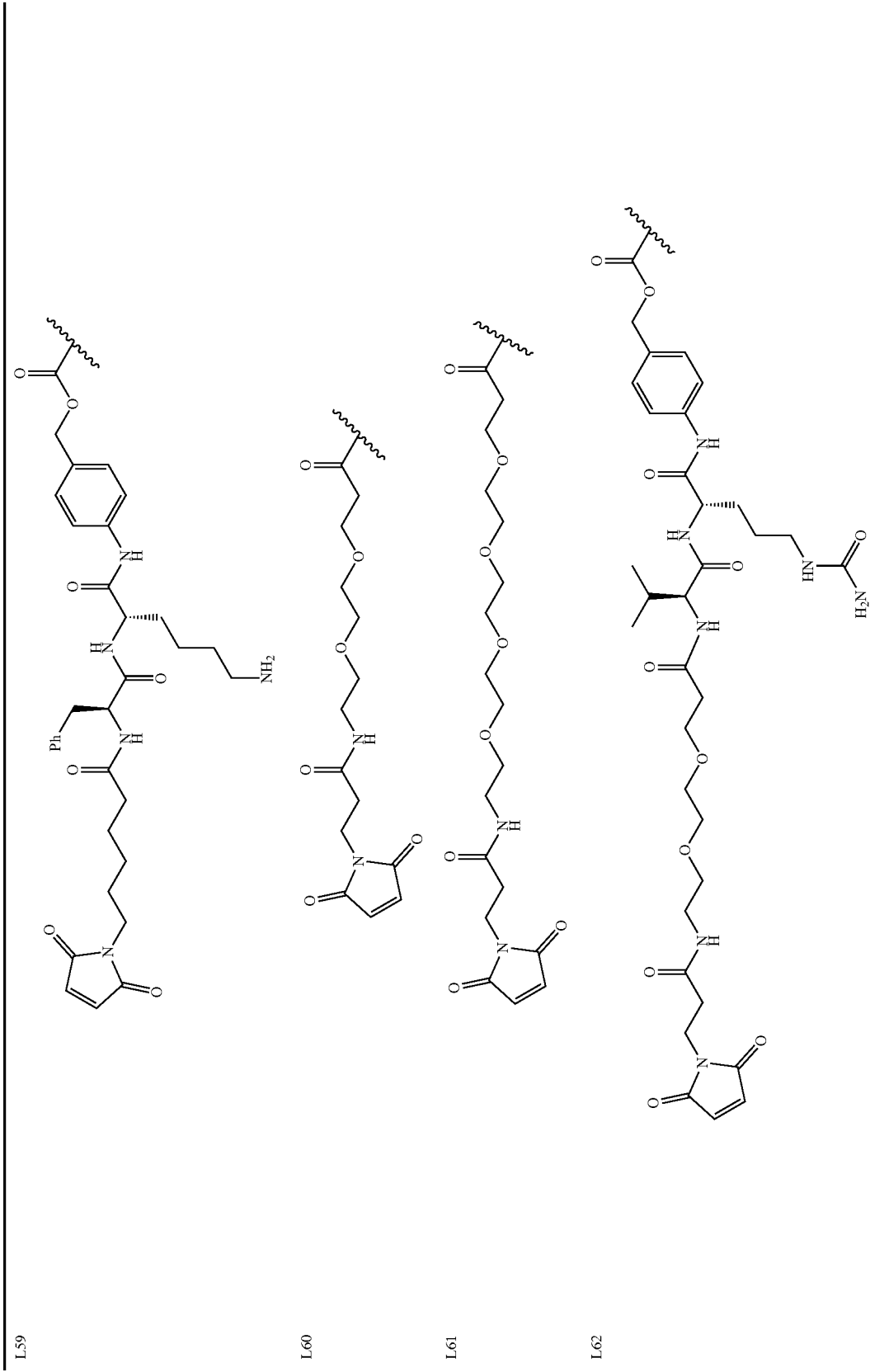
L59
L60
L61
L62

TABLE A8-continued
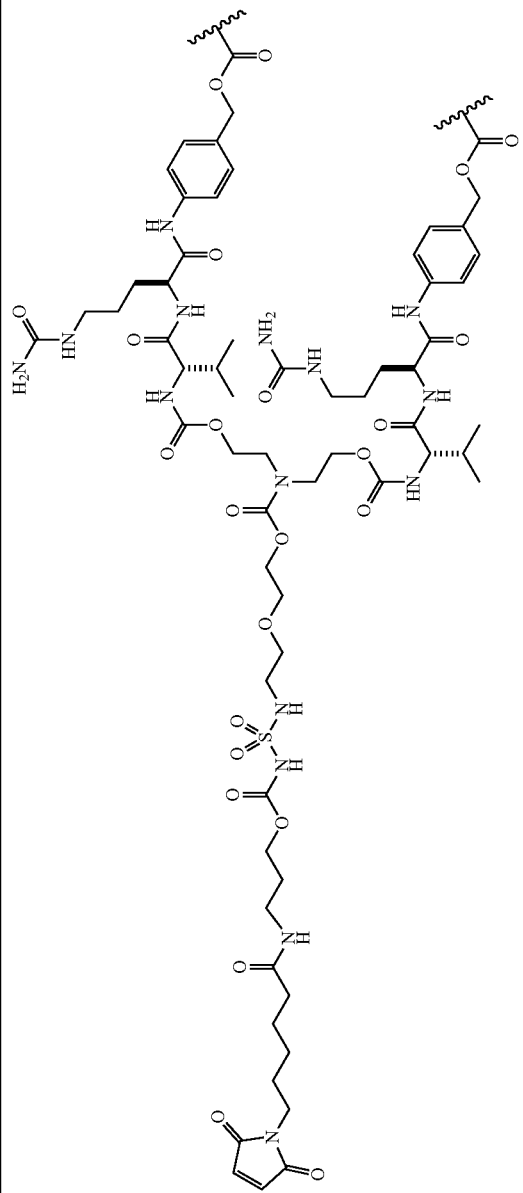
L63
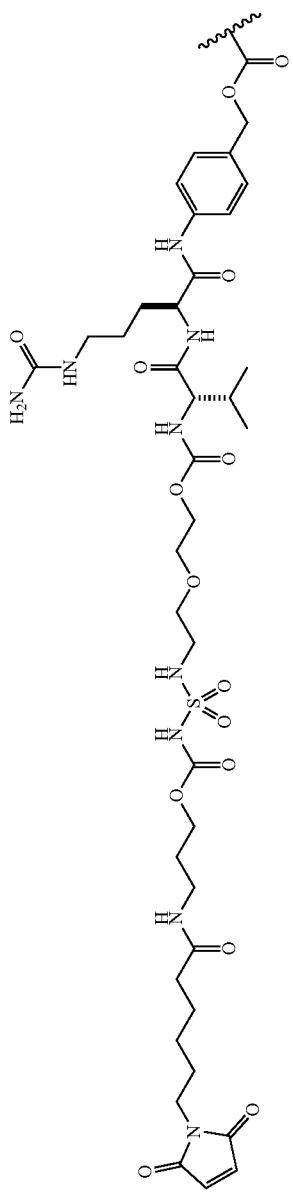
L64

TABLE A8-continued
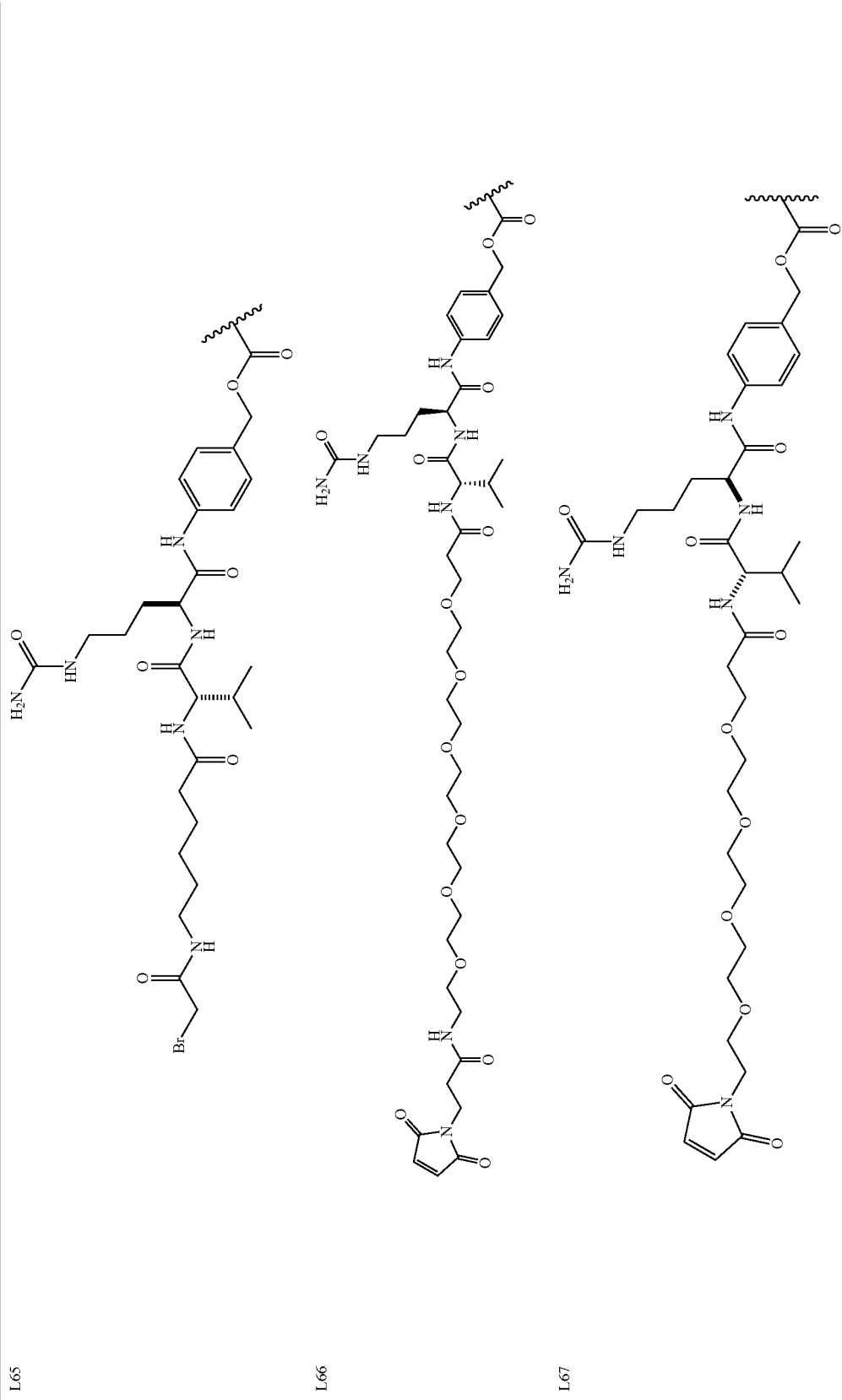
L65
L66
L67

TABLE A8-continued
| L68 | 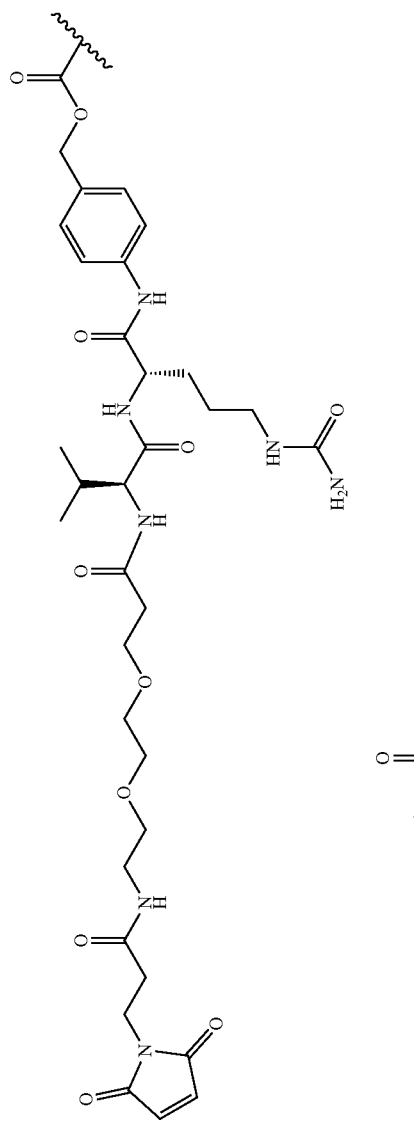 |
| L69 | 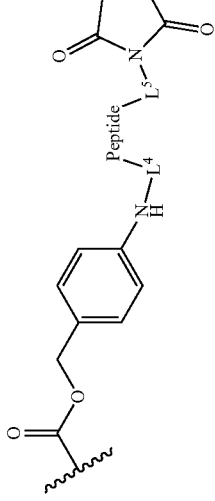 | wherein

represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) and $L^4$ represents the C-terminus of the peptide and $L^5$ is selected from a bond, alkylene and heteroalkylene, wherein $L^5$ is optionally substituted with one or more groups independently selected from $R^{30}$, and $R^{30}$ is independently selected at each occurrence from halogen, —OH, —CN, —O-alkyl, —SH, =O, =S, —S(O)$_2$OH, —NH$_2$, —NO$_2$; and $C_1$-$C_{10}$alkyl, $C_2$-$C_{10}$alkenyl, and $C_2$-$C_{10}$alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$.

When conjugated to the cysteine residue of the antibody or targeting moiety, such linkers can be, for example, represented by the Formulas set forth in Table A9 below:

TABLE A9

| Cmpd Name | Structural Formula |
|---|---|
| L70 | |
| L71 | |
| L72 | |
| L73 | |
| L74 | |

TABLE A9-continued

| Cmpd Name | Structural Formula |
|---|---|
| L75 | |
| L76 | |
| L77 | |

TABLE A9-continued
| Cmpd Name | Structural Formula |
|---|---|
| L78 | 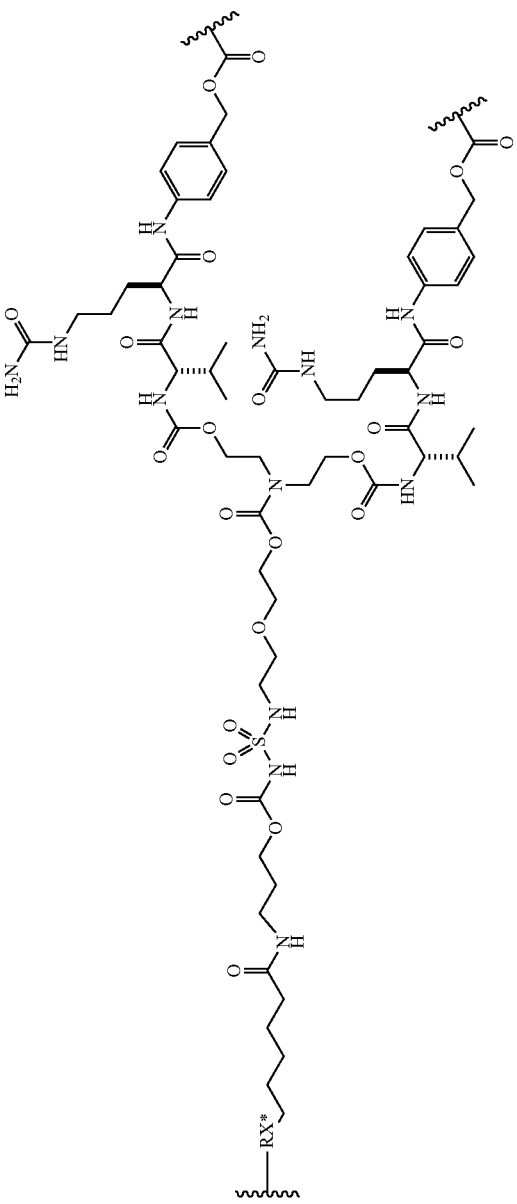 |
| L79 | |

TABLE A9-continued

| Cmpd Name | Structural Formula |
|---|---|
| L80 | |
| L81 | | wherein RX* is a bond, a succinimide moiety, or a hydrolyzed succinimide moiety bond to a cysteine residue of the antibody, antibody construct, or targeting moiety, wherein

on RX* represents the point of attachment to such residue; $L^4$ when present represents the C-terminus of the peptide and $L^5$ is selected from a bond, alkylene and heteroalkylene, wherein $L^5$ is optionally substituted with one or more groups independently selected from $R^{30}$; and $R^{30}$ when present is independently selected at each occurrence from halogen, —OH, —CN, —O-alkyl, —SH, =O, =S, —S(O)$_2$OH, —NH$_2$, —NO$_2$; and $C_1$-$C_{10}$ alkyl, $C_2$-$C_{10}$ alkenyl, and $C_2$-$C_{10}$ alkynyl, each of which is independently optionally substituted at each occurrence with one or more substituents selected from halogen, —OH, —CN, —O-alkyl, —SH, =O, =S, —S(O)$_2$OH, —NH$_2$, and —NO$_2$. A particularly preferred peptide is val-ala or val-cit.

In some embodiments for a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) wherein attachment of the linker is to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) and conjugation is to a lysine residue of an antibody or other targeting moiety, -$L^3$ is represented by the formulas set forth in Table A10 below:

TABLE A10
| Cmpd Name | Structural Formula |
|---|---|
| L82 | 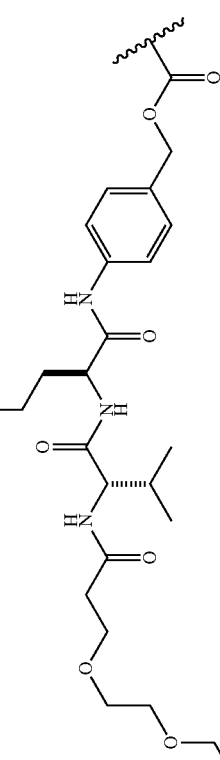 |

TABLE A10-continued
| Cmpd Name | Structural Formula |
|---|---|
| L83 |  | wherein

represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC) and RX represents a reactive moiety.

The reactive moiety may be selected from, for example, a leaving group. For example, -L$^3$ can be represented by the formulas set forth in Table A11 below:

TABLE A11
| Cmpd Name | Structural Formula |
|---|---|
| L84 | 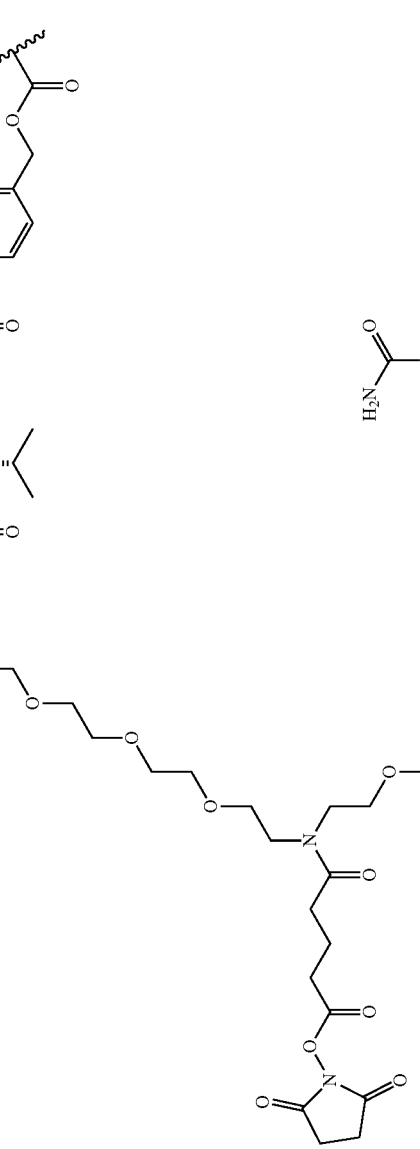 |

TABLE A11-continued

| Cmpd Name | Structural Formula |
|---|---|
| L85 | (structure) |

When conjugated to the lysine residue of an antibody or other targeting moiety, such linkers, can, for example, be represented by the Formulas set forth in Table A12 below wherein RX* is a bond to a nitrogen of the lysine residue of the antibody, antibody construct or targeting moiety, wherein
on RX* represents the point of attachment to such residue:

TABLE A12
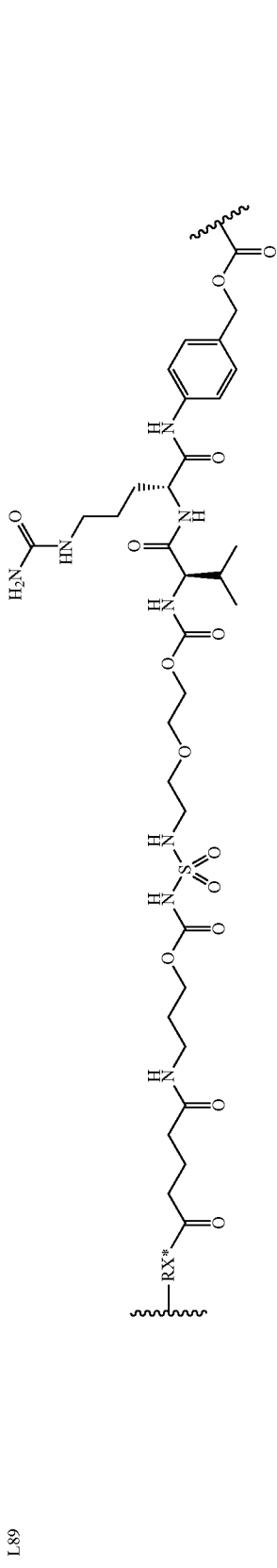
L89

TABLE A12-continued
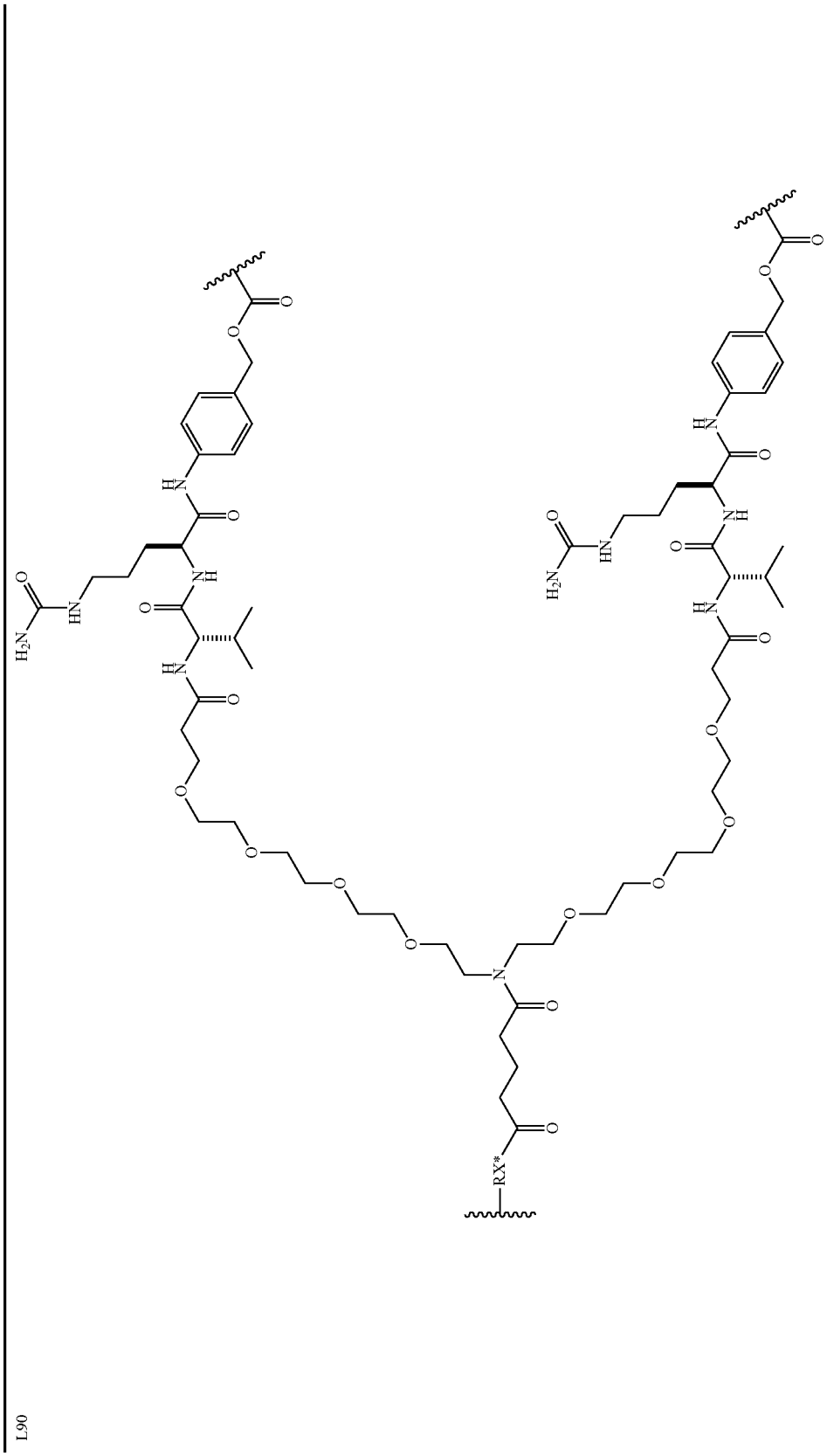
L90

As noted,

represents attachment to a nitrogen of a compound or salt of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC). In exemplary embodiments, the linkers of the disclosure, including those in the preceding paragraphs, are attached to a compound of the disclosure through the nitrogen of a secondary acyclic amine depicted in the structure of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC). In exemplary embodiments, the linkers of the disclosure, including those in the preceding paragraphs, are attached to a compound of the disclosure at a nitrogen atom.

As is known by skilled artisans, the linker selected for a particular conjugate may be influenced by a variety of factors, including but not limited to, the site of attachment to the antibody, antibody construct, or targeting moiety (e.g., lys, cys or other amino acid residues), structural constraints of the drug pharmacophore and the lipophilicity of the drug. The specific linker selected for a conjugate should seek to balance these different factors for the specific antibody, antibody construct, or targeting moiety/drug combination.

The properties of the linker, or linker-compound, may also impact aggregation of the conjugate under conditions of use and/or storage. Typically, conjugates reported in the literature contain no more than 3-4 drug molecules per antibody molecule. Attempts to obtain higher drug-to-antibody ratios ("DAR") often failed, particularly if both the drug and the linker were hydrophobic, due to aggregation of the conjugate. In many instances, DARs higher than 3-4 could be beneficial as a means of increasing potency. In instances where the payload compound is more hydrophobic in nature, it may be desirable to select linkers that are relatively hydrophilic as a means of reducing conjugate aggregation, especially in instances where DARs greater than 3-4 are desired. Thus, in some embodiments, the linker incorporates chemical moieties that reduce aggregation of the conjugates during storage and/or use. A linker may incorporate polar or hydrophilic groups such as charged groups or groups that become charged under physiological pH to reduce the aggregation of the conjugates. For example, a linker may incorporate charged groups such as salts or groups that deprotonate, e.g., carboxylates, or protonate, e.g., amines, at physiological pH.

In particular embodiments, the aggregation of the conjugates during storage or use is less than about 40% as determined by size-exclusion chromatography (SEC). In particular embodiments, the aggregation of the conjugates during storage or use is less than 35%, such as less than about 30%, such as less than about 25%, such as less than about 20%, such as less than about 15%, such as less than about 10%, such as less than about 5%, such as less than about 4%, or even less, as determined by size-exclusion chromatography (SEC).

Conjugates

A conjugate of the disclosure comprises an anti-ASGR1 antibody or an antigen-binding fragment thereof and at least one linker attached to at least one immune-stimulatory compound, such as a myeloid cell agonist or other agonist (e.g., TLR8 agonist, TLR7 agonist, other TLR agonist, STING agonist, RIG-I-Like receptor agonist, c-type lectin receptors agonist, or cytosolic DNA Sensors agonist). In some embodiments, the disclosure provides a conjugate represented by Formula I:

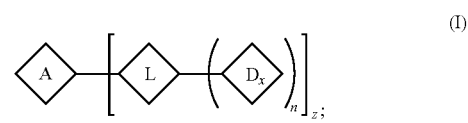

(I)

wherein: A is the anti-ASGR1 antibody or an antigen-binding fragment thereof, L is the linker; $D_x$ is the immune-stimulatory compound; n is selected from 1 to about 20 or from 2 to about 10 or from 3 to about 8; and z is selected from 1 to 20.

In further aspects, the disclosure provides an antibody conjugate represented by the formula:

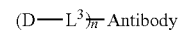

wherein:

n is selected from 1 to about 20 or from 2 to about 10 or from about 3 to about 8;

$L^3$ is a linker; and

D is selected from a compound or salt of a compound of any one of Category A Formulas (IA), (IB), (IIA), (IIB), (IIC), (IIIA), (IIIB), (IVA), (IVB), and (IVC), or any one of Category B Formulas (IA), (IB), (IC), (IIA), (IIB), and (IIC).

In some embodiments, the immune-stimulatory compound is a myeloid cell agonist. In some embodiments, the immune-stimulatory compound is a TLR8 agonist. In some embodiments, the immune-stimulatory compound is a TLR7 agonist. In some embodiments, the immune-stimulatory compound is a TLR3 agonist. In some embodiments, the immune-stimulatory compound is a TLR4 agonist. In some embodiments, the immune-stimulatory compound is a TLR5 agonist. In some embodiments, the immune-stimulatory compound is a TLR9 agonist. In some embodiments, the immune-stimulatory compound is a STING agonist. In some embodiments, the immune-stimulatory compound is a RIG-I-Like receptor agonist. In some embodiments, the immune-stimulatory compound is a c-type lectin receptors agonist. In some embodiments, the immune-stimulatory compound is a cytosolic DNA Sensors agonist.

The disclosure provides a conjugate comprising at least one immune-stimulatory compound (e.g., a compound or salt thereof), an anti-ASGR1 antibody or an antigen-binding fragment thereof, and at least one linker, wherein each immune-stimulatory compound is linked, i.e., covalently bound, to the anti-ASGR1 antibody or an antigen-binding fragment thereof through a linker. The linker can be selected from a cleavable or non-cleavable linker. In some embodiments, the linker is cleavable. In some embodiments, the linker is non-cleavable. Linkers are further described in the disclosure, any one of which can be used to connect an antibody or antigen-binding fragment thereof to an immune-stimulatory compound.

In some embodiments of a conjugate of the disclosure, the drug loading is represented by z, the number of immune-stimulatory compound-linker molecules per antibody, or the number of immune-stimulatory compounds per antibody, depending on the particular conjugate. Depending on the context, z can represent the average number of immune-stimulatory compound(-linker) molecules per antibody, also referred to the average drug loading. z can range from 1 to 20, from 1-50 or from 1-100. In some conjugates, z is preferably from 1 to 8. In some preferred embodiments, when z represents the average drug loading, z ranges from about 2 to about 5. In some embodiments, z is about 2, about 3, about 4, or about 5. The average number of immune-stimulatory compounds per antibody in a preparation of conjugate may be characterized by conventional means such as mass spectroscopy, liquid chromatography/mass spectrometry (LC/MS), HIC, ELISA assay, and HPLC.

A number of conjugates are consistent with the disclosure. The conjugates generally comprise an immune-stimulatory compound covalently bound to an anti-ASGR1 antibody or an antigen-binding fragment thereof that localizes the conjugate to a target tissue, cell population or cell. The anti-ASGR1 antibody or an antigen-binding fragment thereof is covalently attached to each immune-stimulatory compound, either directly or through a linker that tethers the immune-stimulatory compound to the anti-ASGR1 antibody or an antigen-binding fragment thereof. Anti-ASGR1 antibodies or an antigen-binding fragments thereof of the disclosure are consistent with the conjugates of the disclosure.

Some exemplary conjugates are as follows. A conjugate can comprise an anti-ASGR1 antibody or an antigen-binding fragment thereof, at least one immune-stimulatory compound, and optionally at least one linker. A conjugate can comprise an anti-ASGR1 antibody or an antigen-binding fragment thereof, at least one TLR7 agonist, and at least one linker. A conjugate can comprise an anti-ASGR1 antibody or an antigen-binding fragment thereof, at least one TLR8 agonist, and at least one linker. A conjugate can comprise an anti-ASGR1 antibody or an antigen-binding fragment thereof, at least one Compound A TLR8 agonist, and at least one linker. A conjugate can comprise an anti-ASGR1 antibody or an antigen-binding fragment thereof, at least one Compound B TLR7 agonist, and at least one linker. A conjugate can comprise an anti-ASGR1 antibody or an antigen-binding fragment thereof, at least one TLR3 agonist, and at least one linker. A conjugate can comprise an anti-ASGR1 antibody or an antigen-binding fragment thereof, at least one TLR4 agonist, and at least one linker. A conjugate can comprise an anti-ASGR1 antibody or an antigen-binding fragment thereof, at least one TLR5 agonist, and at least one linker. A conjugate can comprise an anti-ASGR1 antibody or an antigen-binding fragment thereof, at least one TLR9 agonist, and at least one linker. A conjugate can comprise an anti-ASGR1 antibody or an antigen-binding fragment thereof, at least one STING agonist, and at least one linker. A conjugate can comprise an anti-ASGR1 antibody or an antigen-binding fragment thereof, at least one RIG-I agonist, and at least one linker. A conjugate can comprise an anti-ASGR1 antibody or an antigen-binding fragment thereof, at least one c-type lectin receptor agonist, and at least one linker. A conjugate can comprise an anti-ASGR1 antibody or an antigen-binding fragment thereof, at least one cytosolic DNA Sensors agonist, and at least one linker.

Category A and Category B Conjugates

In some embodiments, the disclosure provides an immune-stimulatory conjugate (or conjugate) of an anti-ASGR1 antibody or an antigen-binding fragment thereof and at least one compound of any one of Category A Formulas (IA), (IB), (IIA), (IIB), (IIC), (IIIA), (IIIB), (IVA), (IVB), and (IVC), each compound optionally attached to the antibody or an antigen-binding fragment via a linker. In some embodiments, the disclosure provides an immune-stimulatory conjugate of an anti-ASGR1 antibody or an antigen-binding fragment thereof and at least one compound of any one of Category B Formulas (IA), (IB), (IC), (IIA), (IIB), and (IIC), each compound optionally attached to the antibody or an antigen-binding fragment via a linker. In some embodiments, the average Drug-to-Antibody Ratio (DAR) of the pharmaceutical composition is selected from 1 to about 8, 2 to about 6, about 3 to about 5, or about 4.

In some embodiments, the disclosure provides a pharmaceutical composition suitable for intravenous or subcutaneous administration, comprising an immune stimulatory conjugate of a compound of any one of Category A Formulas (IA), (IB), (IIA), (IIB), (IIC), (IIIA), (IIIB), (IVA), (IVB), and (IVC) and a pharmaceutically acceptable excipient. In some embodiments, the disclosure provides a pharmaceutical composition suitable for intravenous or subcutaneous administration, comprising an immune stimulatory conjugate of a compound of any one of Category B Formulas (IA), (IB), (IC), (IIA), (IIB), and (IIC), and a pharmaceutically acceptable excipient. In some embodiments, the average Drug-to-Antibody Ratio (DAR) of the pharmaceutical composition is selected from 1 to about 8, 2 to about 6, about 3 to about 5, or about 4.

In some embodiments, the disclosure provides a method for the treatment of a disease treatable by a TLR agonist (e.g., liver viral infections) comprising subcutaneously administering an effective amount of a conjugate of a compound of any one of Category A Formulas (IA), (IB), (IIA), (IIB), (IIC), (IIIA), (IIIB), (IVA), (IVB), and (IVC), or a pharmaceutical composition thereof suitable for intravenous or subcutaneous administration to a subject in need thereof. In some embodiments, the disclosure provides a method for the treatment of a liver viral infection (e.g., Hepatitis B or Hepatitis C infection), comprising intravenously or subcutaneously administering an effective amount of the conjugate of a compound of any one of Category B Formulas (IA), (IB), (IC), (IIA), (IIB), and (IIC), or a pharmaceutical composition thereof suitable for subcutaneous administration to a subject in need thereof. In some embodiments, the conjugate may be administered by slow infusion.

The disclosure provides a method of preparing an antibody conjugate of the formula:

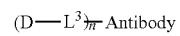

wherein:
n is selected from 1 to 20;
$L^3$ is a linker; and
D is selected from a compound or salt of a compound of any one of Category A Formulas (IA), (IB), (IIA), (IIB), (IIC), (IIIA), (IIIB), (IVA), (IVB), and (IVC), and Category B Formulas (IA), (IB), (IC), (IIA), (IIB), and (IIC),
comprising contacting D-$L^3$ with an anti-ASGR1 antibody or an antigen-binding fragment thereof.

The disclosure provides a method of preparing an anti-ASGR1 antibody or an antigen-binding fragment thereof conjugate of the formula:

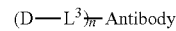

wherein: n is selected from 1 to 20; $L^3$ is a linker; and D is selected from a compound of any one of Category A Formulas (IA), (IB), (IIA), (IIB), (IIC), (IIIA), (IIIB), (IVA), (IVB), and (IVC), and Category B Formulas (IA), (IB), (IC), (IIA), (IIB), and (IIC), comprising contacting $L^3$ with the anti-ASGR1 antibody or an antigen-binding fragment thereof to form $L^3$-anti-ASGR1 antibody or antigen-binding fragment thereof and contacting $L^3$-anti-ASGR1 antibody or an antigen-binding fragment thereof with D to form the conjugate. In some embodiments, the disclosure provides a myeloid cell agonist conjugate or salt thereof represented by the formula:

$$(D-L^3)_{\overline{n}}\text{-Antibody,}$$

wherein Antibody is an anti-ASGR1 antibody comprising:

(a) a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33, or (b) a heavy chain variable region comprising the amino acid sequence of SEQ ID NO: 240 and a light chain variable region comprising the amino acid sequence of SEQ ID NO: 247;

n is from 2 to 8; and $L^3$-D is a linker-TLR8 agonist and has the structure:

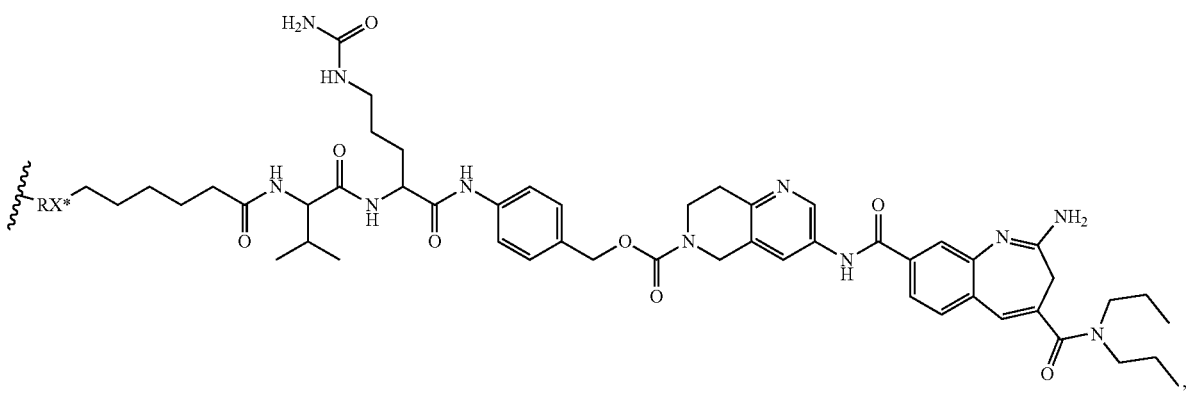

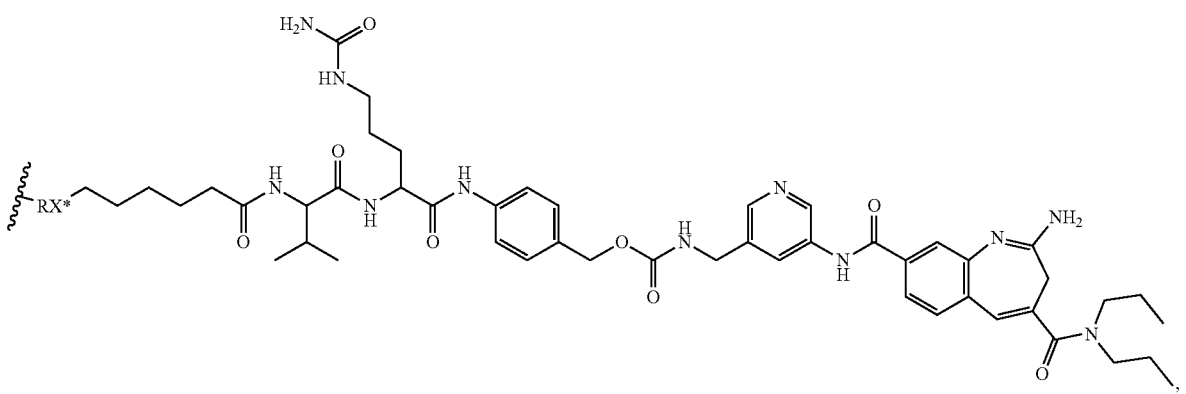

or

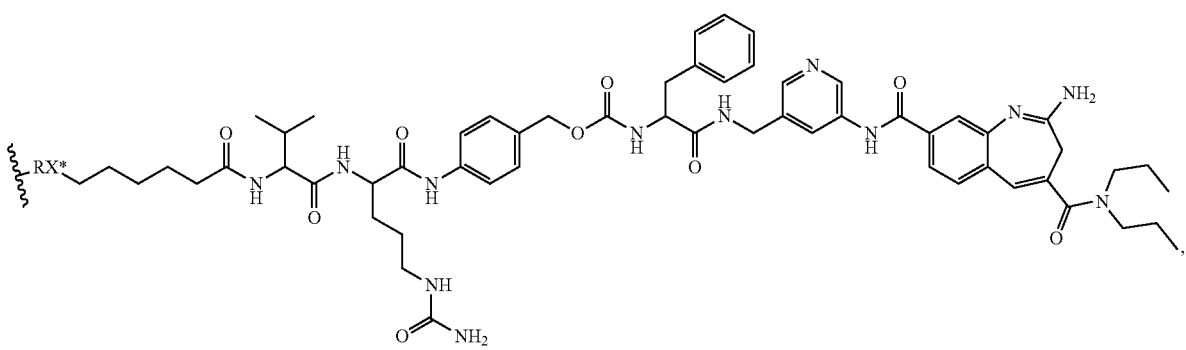

489 wherein RX* is a bond, a succinimide moiety, or a hydrolyzed succinimide moiety bound to a residue of the antibody, antibody construct, or targeting moiety, wherein

on RX* represents the point of attachment to a cysteine residue of the antibody, antibody construct, or targeting moiety.

In some embodiments, the disclosure provides a myeloid cell agonist conjugate or salt thereof represented by the formula:

$$(D—L^3)_{\overline{n}}\text{-Antibody},$$

490 wherein Antibody is an anti-ASGR1 antibody comprising:

(a) a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33, or (b) a heavy chain variable region comprising the amino acid sequence of SEQ ID NO: 239 and a light chain variable region comprising the amino acid sequence of SEQ ID NO: 247;

n is from 2 to 8; and $L^3$-D is a linker-TLR8 agonist and has the structure:

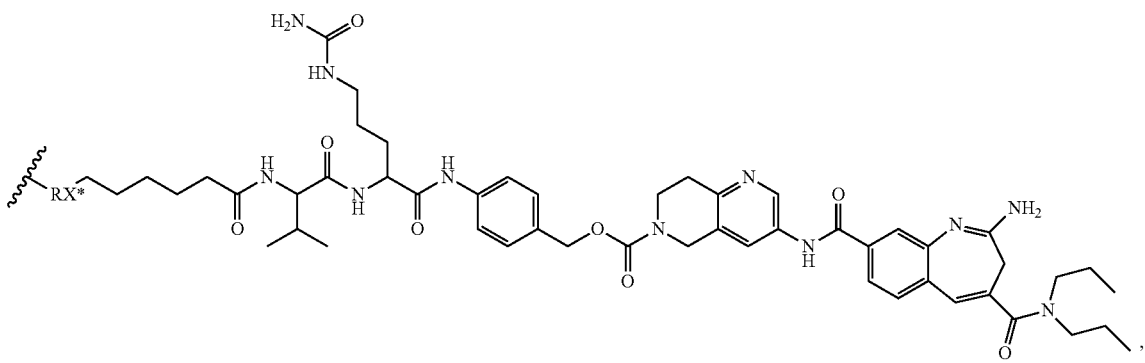

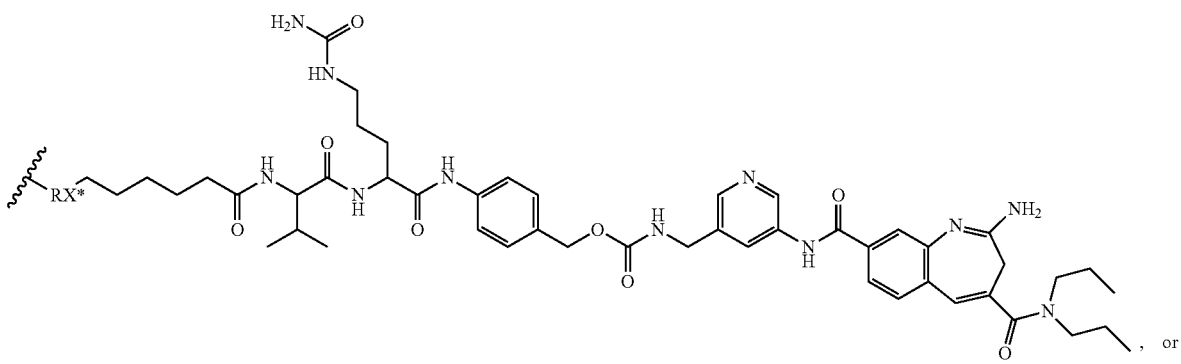

, or

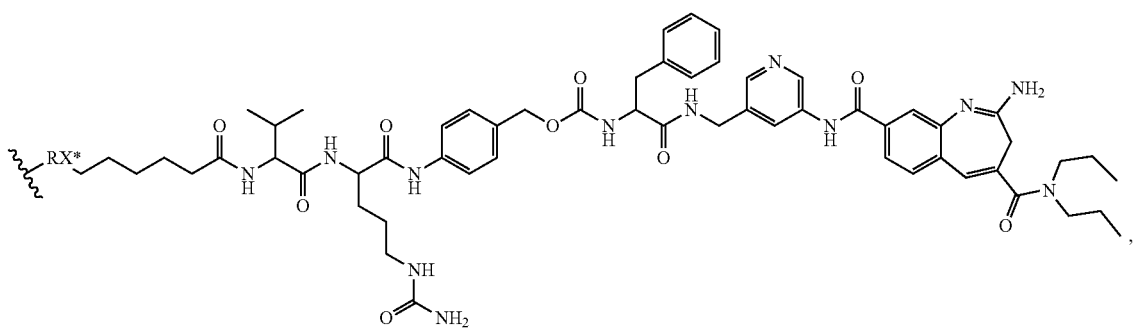

, wherein RX* is a bond, a succinimide moiety, or a hydrolyzed succinimide moiety bound to a residue of the antibody, antibody construct, or targeting moiety, wherein

on RX* represents the point of attachment to a cysteine residue of the antibody, antibody construct, or targeting moiety.

amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or (b) a heavy chain variable region comprising the amino acid sequence of SEQ ID NO: 89 and a light chain variable region comprising the amino acid sequence of SEQ ID NO: 134;

n is from 2 to 8; and

L³-D is a linker-TLR8 agonist and has the structure:

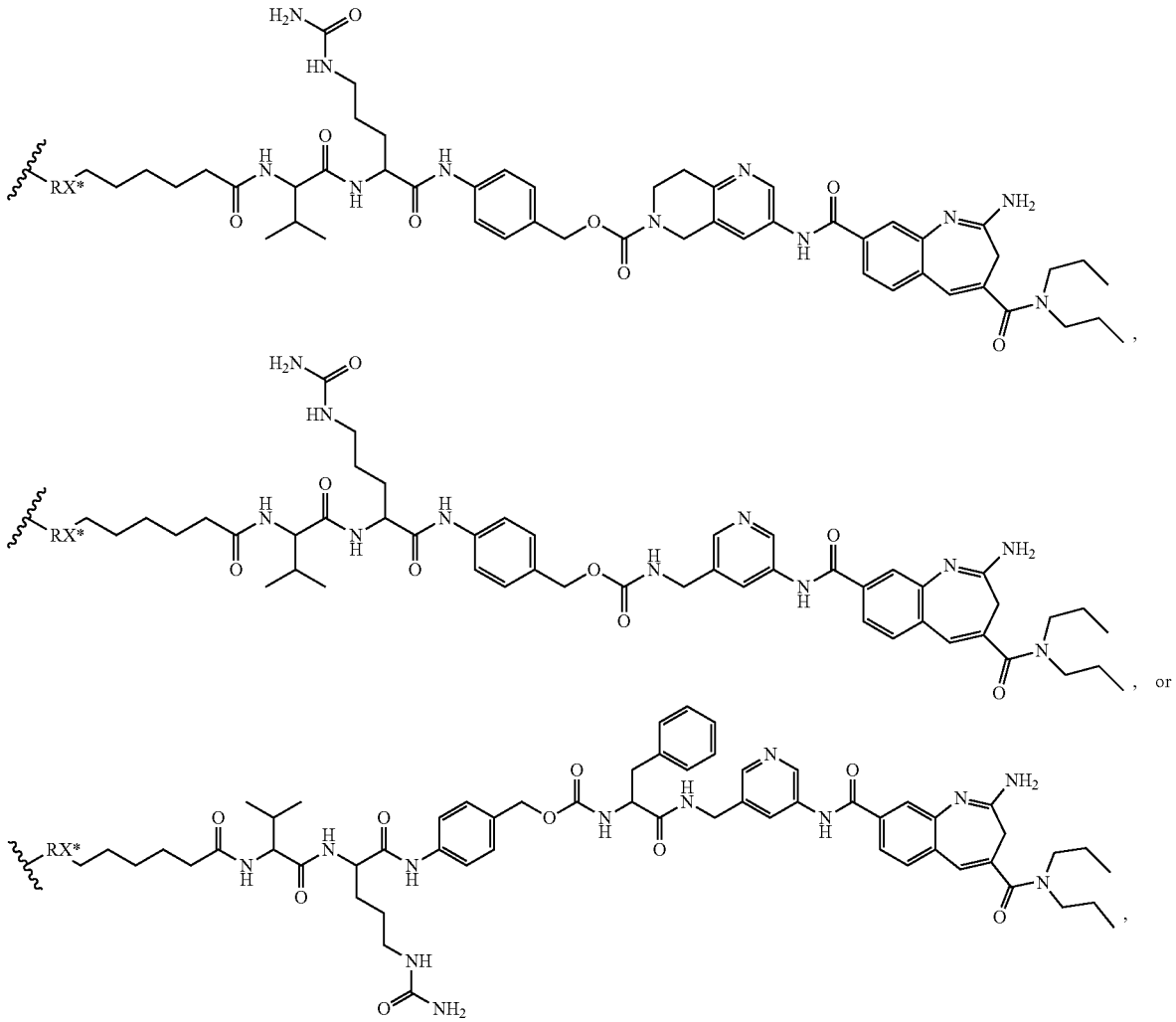

In some embodiments, the disclosure provides a myeloid cell agonist conjugate or salt thereof represented by the formula:

(D—L³)$_n$—Antibody, wherein Antibody is an anti-ASGR1 antibody comprising:

(a) a CDR1 (VH-CDR1) comprising the amino acid sequence of SEQ ID NO:2, a VH-CDR2 comprising the wherein RX* is a bond, a succinimide moiety, or a hydrolyzed succinimide moiety bound to a residue of the antibody, antibody construct, or targeting moiety, wherein

on RX* represents the point of attachment to a cysteine residue of the antibody, antibody construct, or targeting moiety.

In any of the aforementioned embodiments, $L^3$-D has the structure:

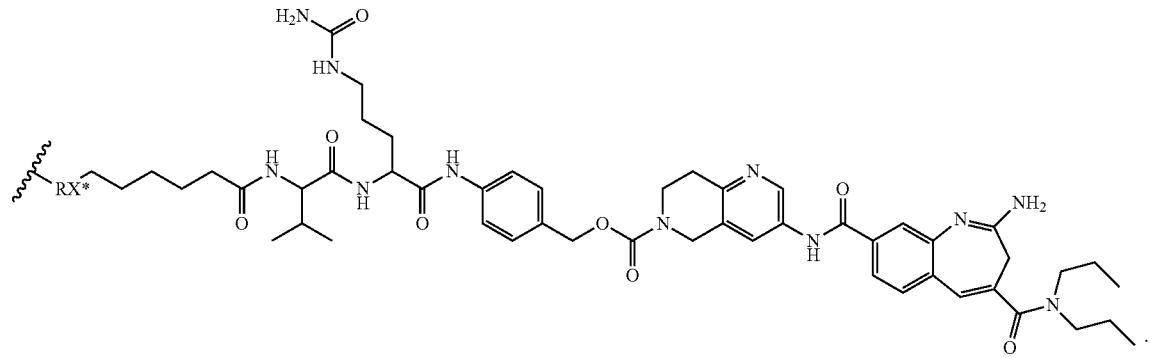

In any of the aforementioned embodiments, $L^3$-D has the structure:

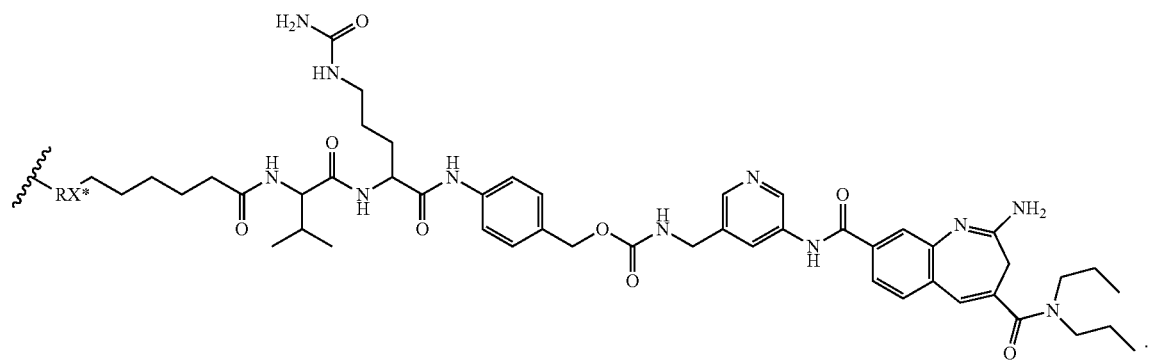

In any of the aforementioned embodiments, $L^3$-D has the structure:

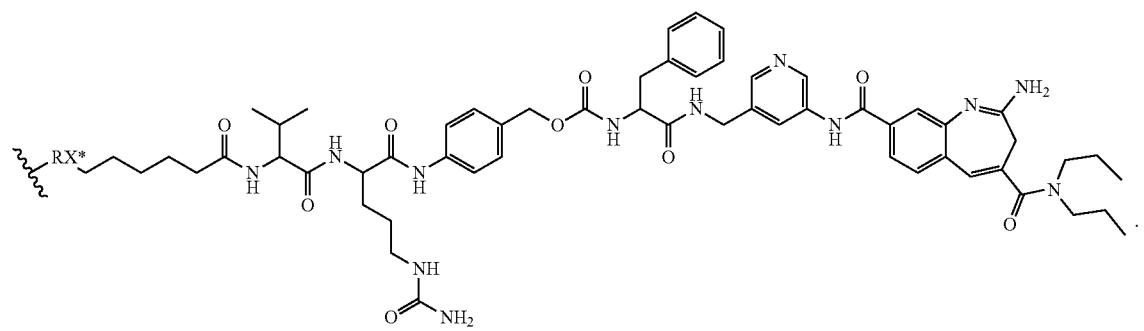

In certain such embodiments, RX* is a bond, a succinamide moiety, or a hydrolyzed succinamide moiety bound to a residue of the antibody, antibody construct, or targeting moiety, wherein

on RX* represents the point of attachment to a cysteine residue of the antibody, antibody construct, or targeting moiety.

The compounds of the disclosure, in some embodiments, are used in different enriched isotopic forms, e.g., enriched in the content of $^2$H, $^3$H, $^{11}$C, $^{13}$C and/or $^{14}$C. In particular embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted in the disclosure are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure optionally contain unnatural proportions of atomic isotopes at one or more atoms that constitute such compounds. For example, the compounds may be labeled with isotopes, such as for example, deuterium (2H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the disclosure, whether radioactive or not, are encompassed within the scope of the disclosure.

In some embodiments, the compounds of the disclosure have some or all of the 1H atoms replaced with 2H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr. Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods of the disclosure to provide for the synthesis of deuterium-containing compounds. Large numbers of deuterium-containing reagents and building blocks are available commercially from chemical vendors, such as Aldrich Chemical Co.

Compounds of the disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the disclosure are salts, particularly pharmaceutically acceptable salts, of the compounds of the disclosure. The compounds of the disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride.

The compounds of the disclosure may in some cases exist as diastereomers, enantiomers, or other stereoisomeric forms. The compounds provided in the disclosure include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley and Sons, Inc., 1981, herein incorporated by reference for this disclosure). Stereoisomers may also be obtained by stereoselective synthesis.

The methods and compositions of the disclosure include the use of amorphous forms as well as crystalline forms (also known as polymorphs). The compounds of the disclosure may be in the form of pharmaceutically acceptable salts. As well, active metabolites of these compounds having the same type of activity are included in the scope of the disclosure. In addition, the compounds of the disclosure can exist in unsolvated as well as solvated forms with pharmaceutically acceptable solvents such as water, ethanol, and the like. The solvated forms of the compounds presented in this disclosure are also considered to be disclosed in this disclosure.

In some embodiments, compounds or salts of the compounds of the disclosure may be prodrugs attached to anti-ASGR1 antibodies to form conjugates. The term "prodrug" is intended to encompass compounds which, under physiologic conditions, are converted into active compounds, e.g., TLR8 agonists, TLR7 agonists, other TLR agonists, STING agonist, RIG-I-Like receptor agonists, c-type lectin receptors agonists, or cytosolic DNA Sensors agonists. One method for making a prodrug is to include one or more selected moieties which are hydrolyzed or otherwise cleaved under physiologic conditions to reveal the desired molecule. In some embodiments, the prodrug is converted by an enzymatic activity of the host animal such as specific target cells in the host animal.

Prodrug forms of the compounds of the disclosure, wherein the prodrug is metabolized in vivo to produce a compound of the disclosure are included within the scope of the claims. In some cases, some of the compounds of the disclosure may be a prodrug for another derivative or active compound.

In some embodiments, an immune-stimulatory compound, such as a TLR8 agonist or TLR7 agonist, is modified as a prodrug with a masking group, such that the TLR8 agonist, TLR7 agonist or other agonist, has limited activity or is inactive until it reaches an environment where the masking group is removed to reveal the active compound. For example, a TLR8 agonist or TLR7 agonist can be covalently modified at an amine involved in binding to the active site of a TLR8 receptor such that the compound is unable to bind the active site of the receptor in its modified (prodrug) form. In such an example, the masking group is removed under physiological conditions, e.g., enzymatic or acidic conditions, specific to the site of delivery, e.g., intracellular or extracellular adjacent to target cells. Masking groups may be removed from the amine of the compound or salt of the disclosure due to the action of lysosomal proteases, e.g., cathepsin and plasmin. These proteases can be present at elevated levels in certain tumor tissues. The masking group may be removed by a lysosomal enzyme.

The lysosomal enzyme can be, for example, cathepsin B, cathepsin S, (3-glucuronidase, or P-galactosidase.

In some embodiments, an amine masking group inhibits binding of the amine group of the compound with residues of a TLR8 receptor. The amine masking group may be removable under physiological conditions within a cell but remains covalently bound to the amine outside of a cell. Masking groups that may be used to inhibit or attenuate binding of an amine group of a compound with residues of a TLR8 receptor include, for example, peptides and carbamates.

Synthetic chemistry transformations and methodologies useful in synthesizing the compounds of the disclosure are known in the art and include, for example, those described in R. Larock, Comprehensive Organic Transformations (1989); T. W. Greene and P. G. M. Wuts, Protective Groups in Organic Synthesis, 2d. Ed. (1991); L. Fieser and M. Fieser, Fieser and Fieser's Reagents for Organic Synthesis (1994); and L. Paquette, ed., Encyclopedia of Reagents for Organic Synthesis (1995).

Exemplary TLR8 and TLR7 agonists are provided in the disclosure. In some embodiments, a myeloid cell agonist-linker compound (Linker-Payload) is selected from any of Linker-Payloads provided in the disclosure. Examples of TLR8 agonist linker-compounds are provided in Table 2 and their stereoisomers. Examples of TLR7 agonist linker-compounds are provided in Table 4 and their stereoisomers. It is understood that for the compounds provided in Tables 2 and 4, salts of the compounds are also contemplated.

TABLE 2

TLR8 agonist Linker-Compounds 2.1-2.22

| Linker-Compound | Structure |
|---|---|
| 2.1 | 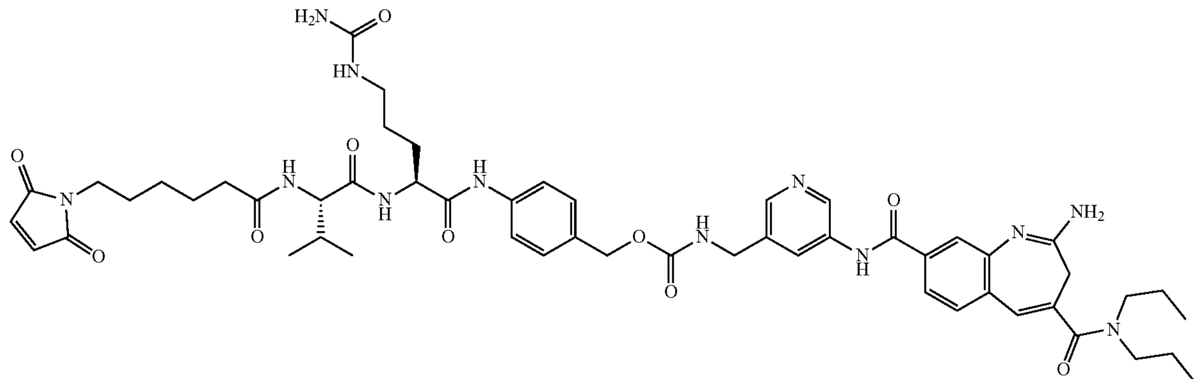 [SMILES: CCCN(CCC)C(=O)C1=Cc2ccc(C(=O)Nc3cncc(CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |
| 2.2 | 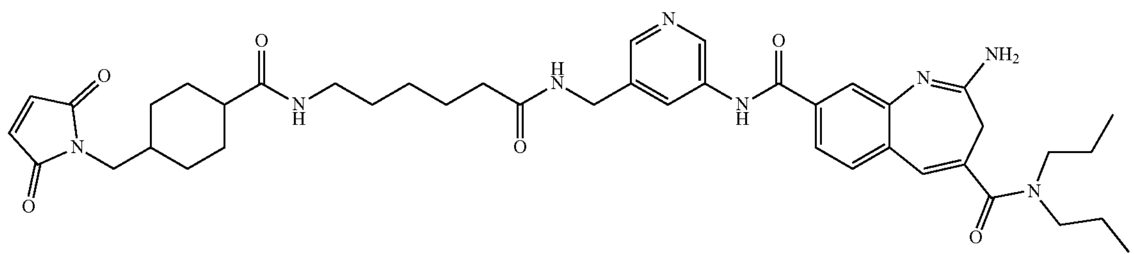 [SMILES: CCCN(CCC)C(=O)C1=Cc2ccc(C(=O)Nc3cncc(CNC(=O)CCCCCNC(=O)C4CCC(CN5C(=O)C=CC5=O)CC4)c3)cc2N=C(N)C1] |
| 2.3 | 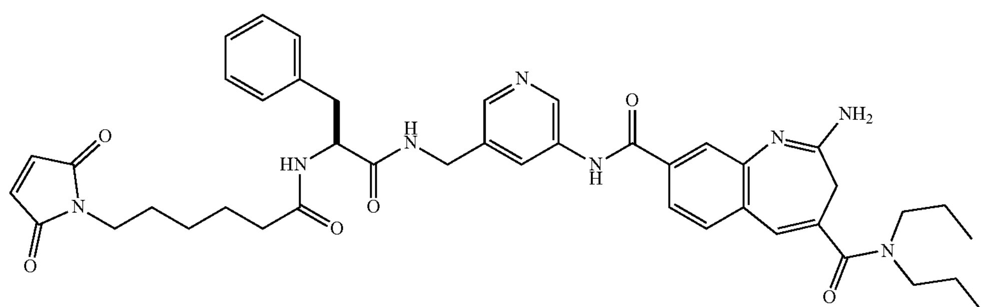 |

TABLE 2-continued

TLR8 agonist Linker-Compounds 2.1-2.22

| Linker-Compound | Structure |
|---|---|
| 2.4 | 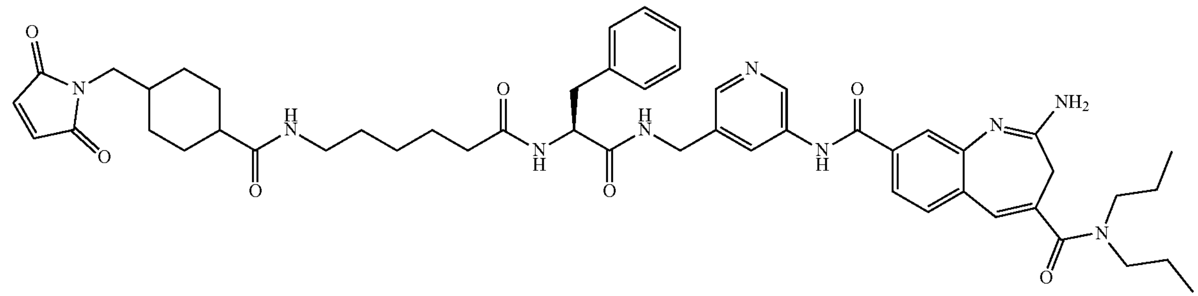 [SMILES: CCCN(CCC)C(=O)C1=Cc2ccc(C(=O)Nc3cncc(CNC(=O)[C@H](Cc4ccccc4)NC(=O)CCCCCNC(=O)C4CCC(CN5C(=O)C=CC5=O)CC4)c3)cc2N=C(N)C1] |
| 2.5 | 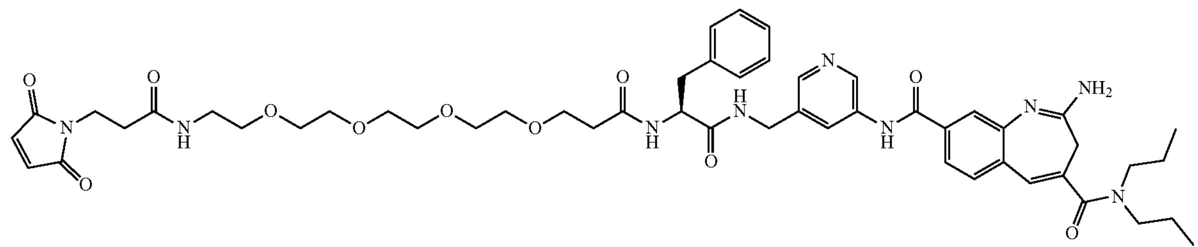 [SMILES: CCCN(CCC)C(=O)C1=Cc2ccc(C(=O)Nc3cncc(CNC(=O)[C@H](Cc4ccccc4)NC(=O)CCOCCOCCOCCOCCNC(=O)CCN4C(=O)C=CC4=O)c3)cc2N=C(N)C1] |
| 2.6 | 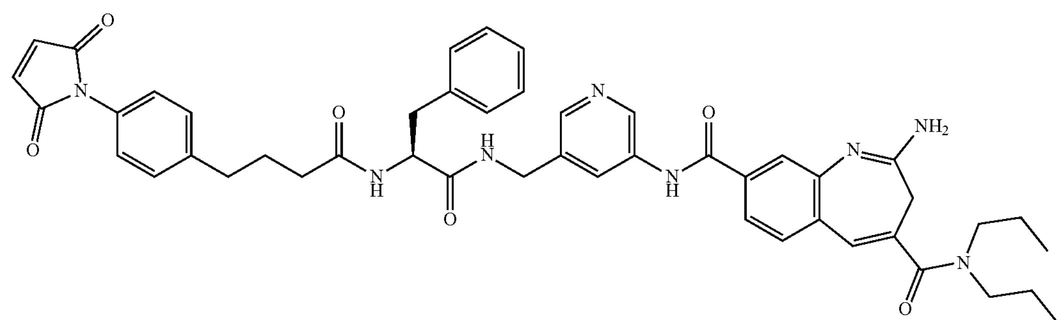 [SMILES: CCCN(CCC)C(=O)C1=Cc2ccc(C(=O)Nc3cncc(CNC(=O)[C@H](Cc4ccccc4)NC(=O)CCCc4ccc(N5C(=O)C=CC5=O)cc4)c3)cc2N=C(N)C1] |

TABLE 2-continued
TLR8 agonist Linker-Compounds 2.1-2.22
| Linker-Compound | Structure |
|---|---|
| 2.7 | 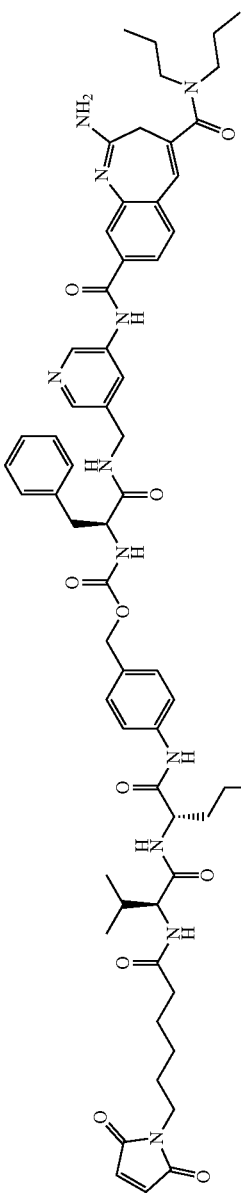 |
| 2.8 | 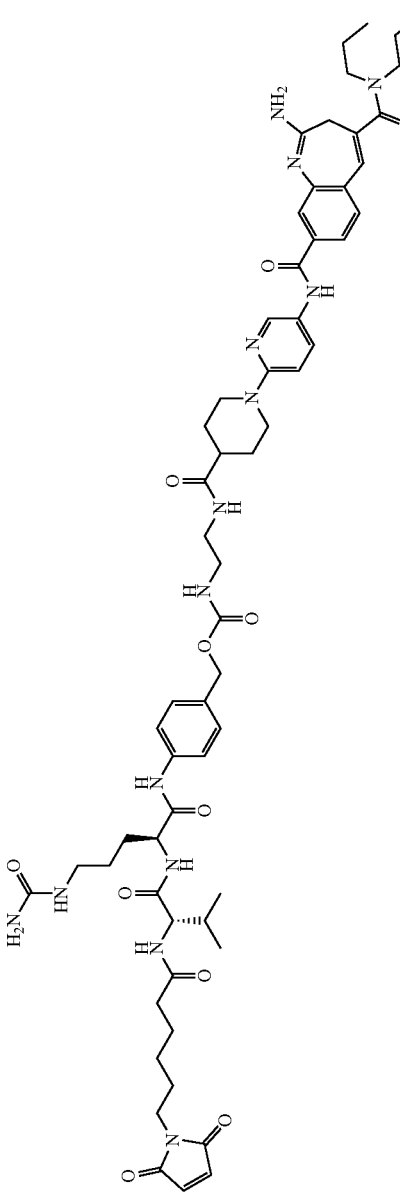 |

TABLE 2-continued
TLR8 agonist Linker-Compounds 2.1-2.22
| Linker-Compound | Structure |
|---|---|
| 2.9 | 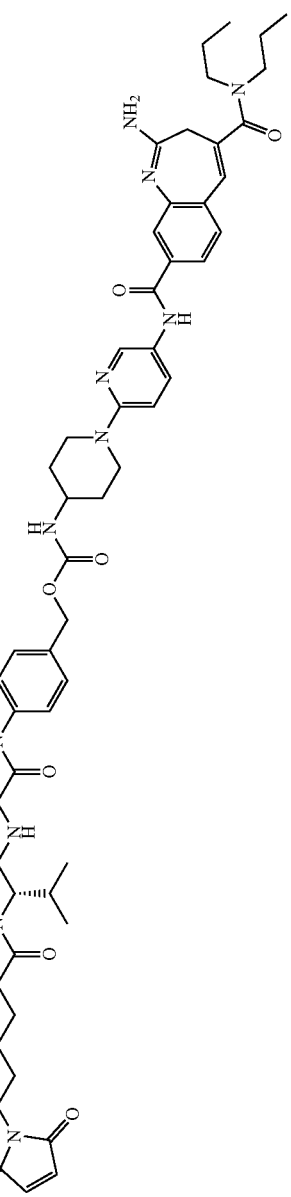 |
| 2.10 | 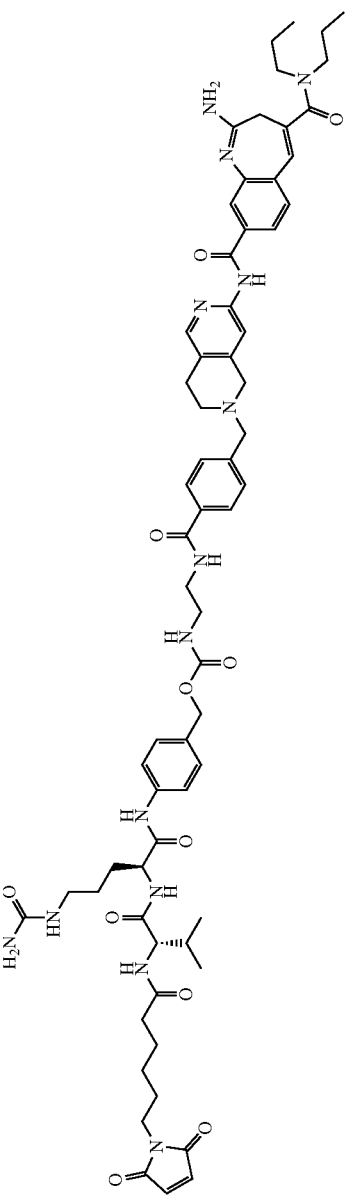 |

TABLE 2-continued
TLR8 agonist Linker-Compounds 2.1-2.22
| Linker-Compound | Structure |
|---|---|
| 2.11 | 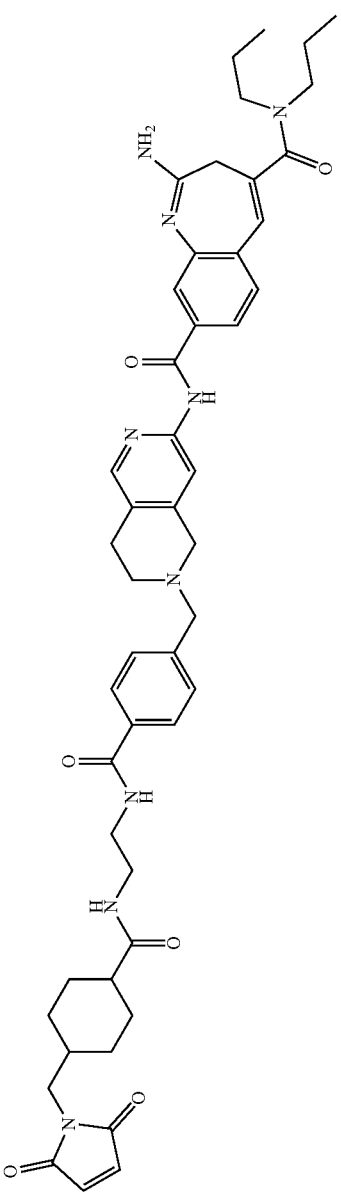 |
| 2.12 | 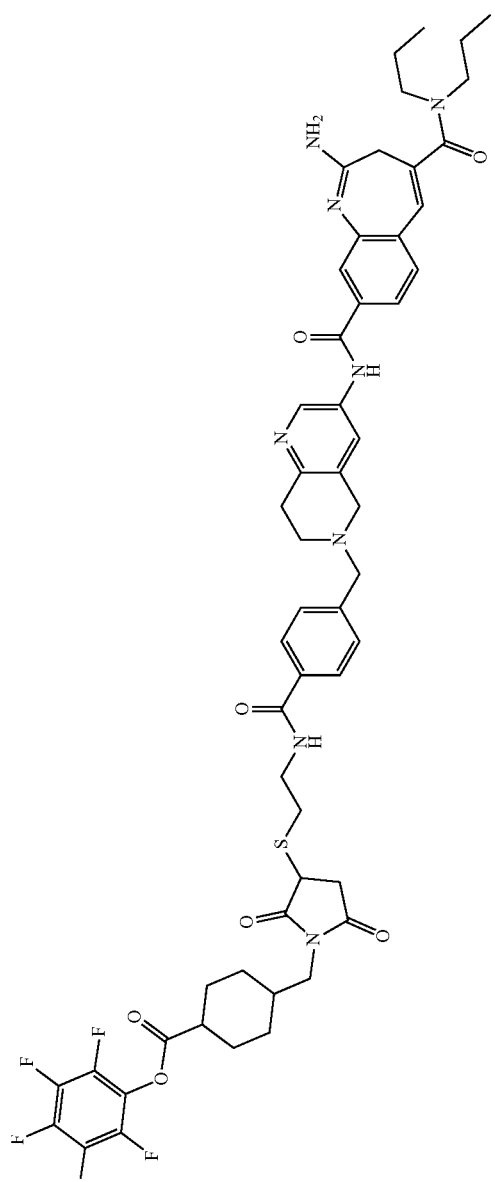 |

TABLE 2-continued
TLR8 agonist Linker-Compounds 2.1-2.22
| Linker-Compound | Structure |
|---|---|
| 2.14 | 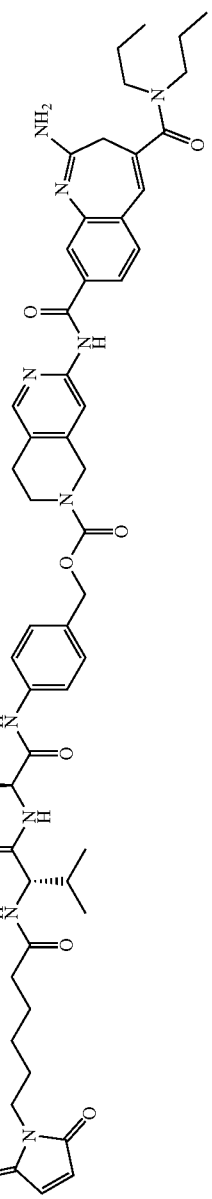 |
| 2.15 | 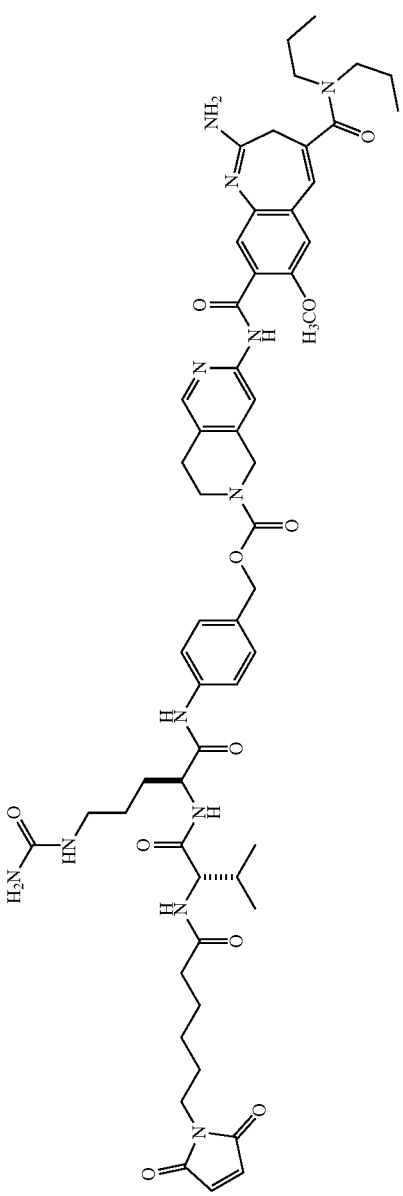 |

TABLE 2-continued

TLR8 agonist Linker-Compounds 2.1-2.22

| Linker-Compound | Structure |
|---|---|
| 2.16 | 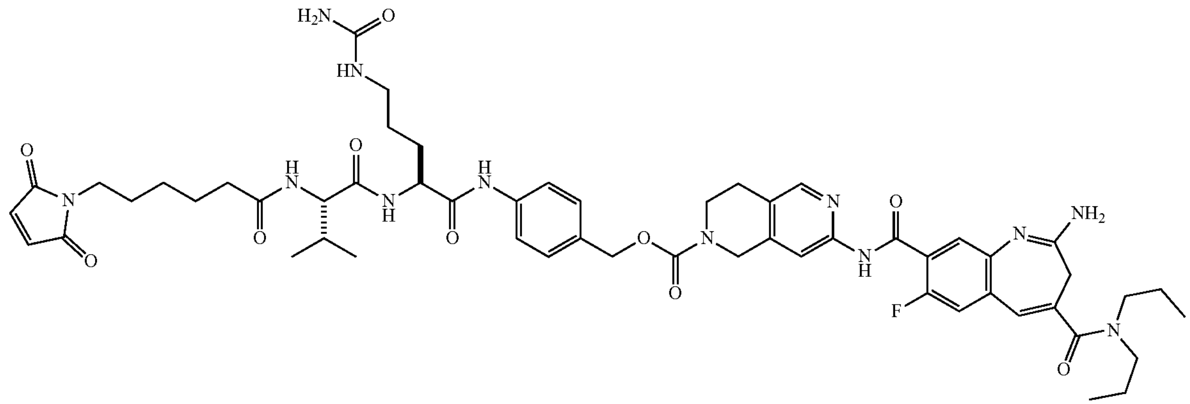 [SMILES: CCCN(CCC)C(=O)C1=Cc2cc(F)c(C(=O)Nc3cc4c(cn3)CCN(C(=O)OCc3ccc(NC(=O)[C@H](CCCNC(N)=O)NC(=O)[C@@H](NC(=O)CCCCCN5C(=O)C=CC5=O)C(C)C)cc3)C4)cc2N=C(N)C1] |
| 2.17 | 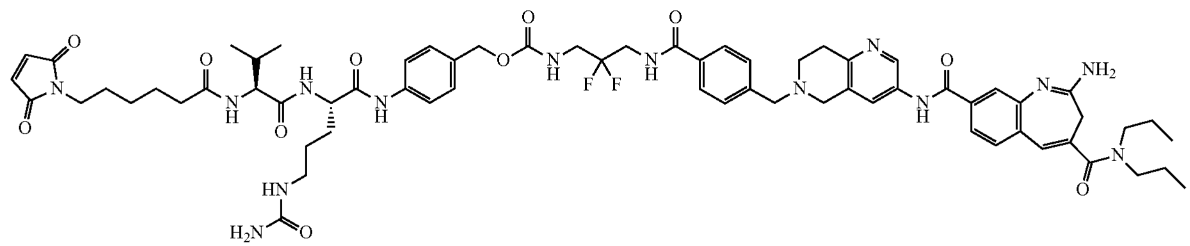 [SMILES: CCCN(CCC)C(=O)C1=Cc2ccc(C(=O)Nc3cnc4c(c3)CN(Cc3ccc(C(=O)NCC(F)(F)CNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1] |
| 2.20 | 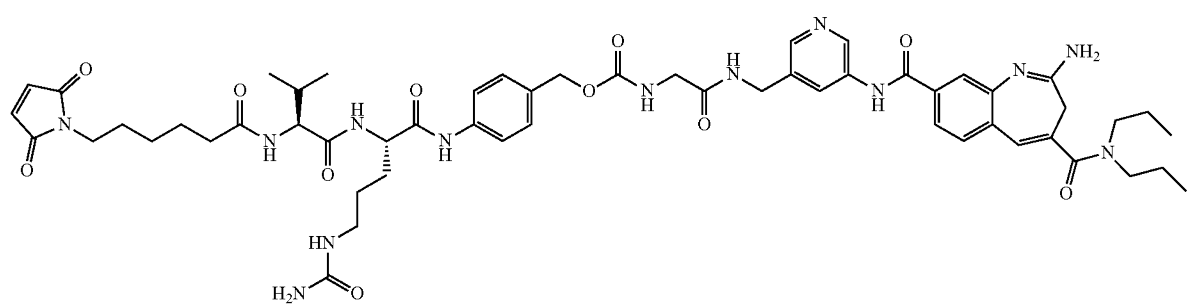 [SMILES: CCCN(CCC)C(=O)C1=Cc2ccc(C(=O)Nc3cncc(CNC(=O)CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |

TABLE 2-continued

TLR8 agonist Linker-Compounds 2.1-2.22

| Linker-Compound | Structure |
|---|---|
| 2.21 | 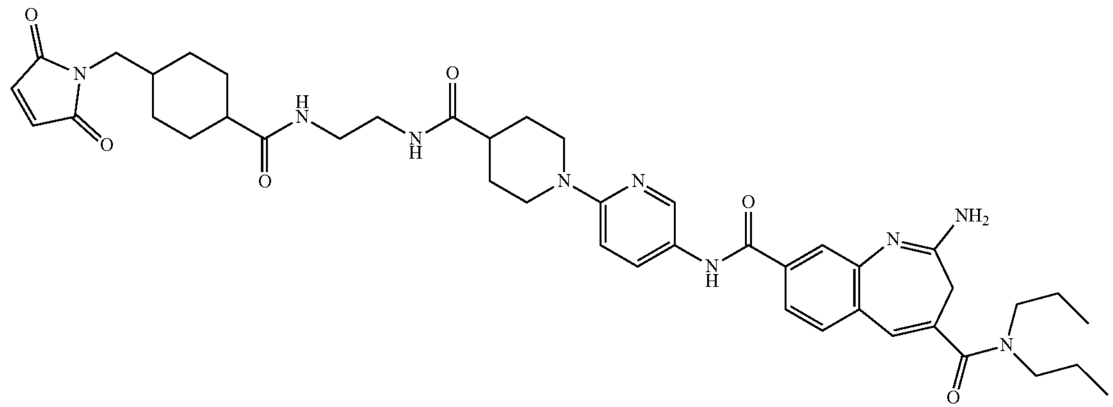 [SMILES: CCCN(CCC)C(=O)C1=Cc2ccc(C(=O)Nc3ccc(N4CCC(C(=O)NCCNC(=O)C5CCC(CN6C(=O)C=CC6=O)CC5)CC4)nc3)cc2N=C(N)C1] |
| 2.22 | 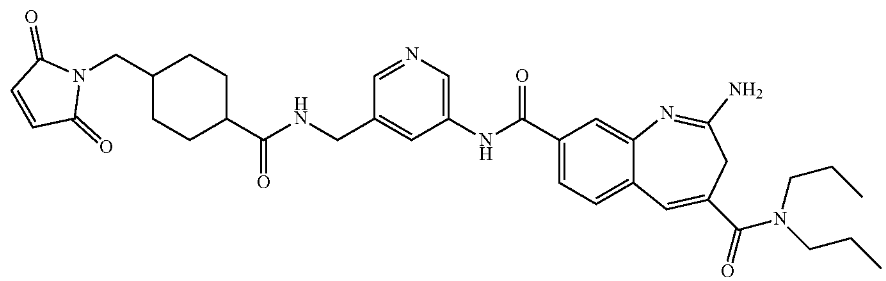 [SMILES: CCCN(CCC)C(=O)C1=Cc2ccc(C(=O)Nc3cncc(CNC(=O)C4CCC(CN5C(=O)C=CC5=O)CC4)c3)cc2N=C(N)C1] |

TABLE 4

TLR7 Agonist Linker-Compounds 4.1-4.20

| Linker-Compound | Structure |
|---|---|
| 4.1 | 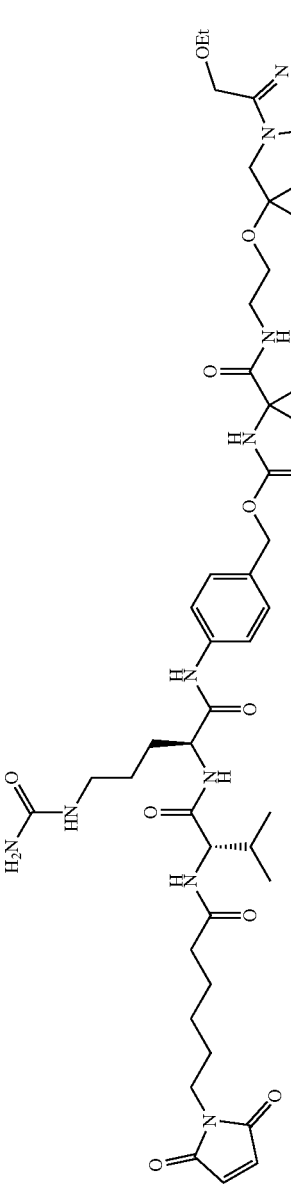 4-((S)-2-((S)-2-(6-(2,5-dioxo-2,5-dihydro-1H-pyrrol-1-yl)hexanamido)-5-ureidopentanamido)-3-methylbutanamido)benzyl (1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)carbamate |
| 4.2 | 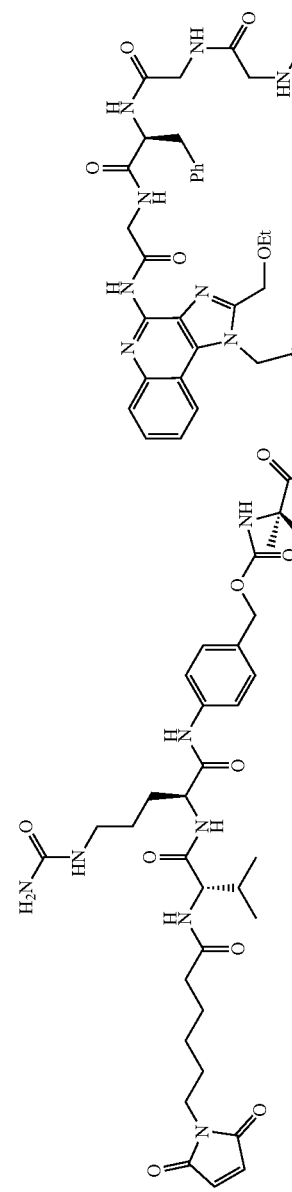 tert-butyl (2-((2-(((S)-1-((2-(((1-(4-((S)-2-((S)-2-(6-(2,5-dioxo-2,5-dihydro-1H-pyrrol-1-yl)hexanamido)-5-ureidopentanamido)phenyl)-5,5,11,11-tetramethyl-3,6-dioxo-2,10-dioxa-4,7-diazadodecan-12-yl)-2-(ethoxymethyl)-1H-imidazo[4,5-c]quinolin-4-yl)amino)-2-oxoethyl)amino)-1-oxo-3-phenylpropan-2-yl)amino)-2-oxoethyl)amino)-2-oxoethyl)carbamate |

TABLE 4-continued

TLR7 Agonist Linker-Compounds 4.1-4.20

| Linker-Compound | Structure |
| --- | --- |
| 4.3 | N-(1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)-6-(2,5-dioxo-2,5-dihydro-1H-pyrrol-1-yl)hexanamide |
| 4.4 | N-(2-((1-(4-amino-2-(ethoxymethyl)-1H-imidazo[4,5-c]quinolin-1-yl)-2-methylpropan-2-yoxy)ethyl)-2-(3-(2,5-dioxo-2,5-dihydro-1H-pyrrol-1-yl)propanamido)-2-methylpropanamide |

TABLE 4-continued
TLR7 Agonist Linker-Compounds 4.1-4.20
| Linker-Compound | Structure |
|---|---|
| 4.5 | 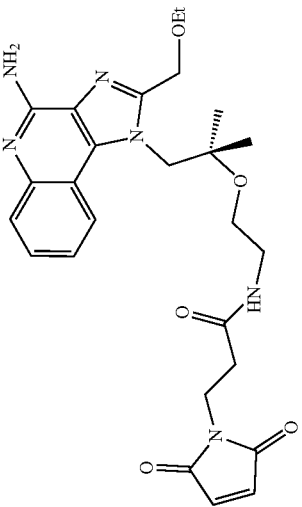 N-(2-((1-(4-amino-2-(ethoxymethyl)-1H-imidazo[4,5-c]quinolin-1-yl)-2-methylpropan-2-yl)oxy)ethyl)-3-(2,5-dioxo-2,5-dihydro-1H-pyrrol-1-yl)propanamide |
| 4.6 | 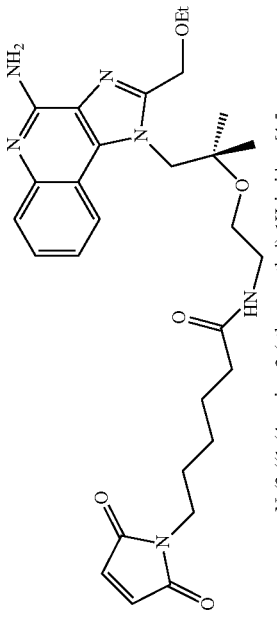 N-(2-((1-(4-amino-2-(ethoxymethyl)-1H-imidazo[4,5-c]quinolin-1-yl)-2-methylpropan-2-yl)oxy)ethyl)-6-(2,5-dioxo-2,5-dihydro-1H-pyrrol-1-yl)hexanamide |

TABLE 4-continued

TLR7 Agonist Linker-Compounds 4.1-4.20

| Linker-Compound | Structure |
|---|---|
| 4.7 | 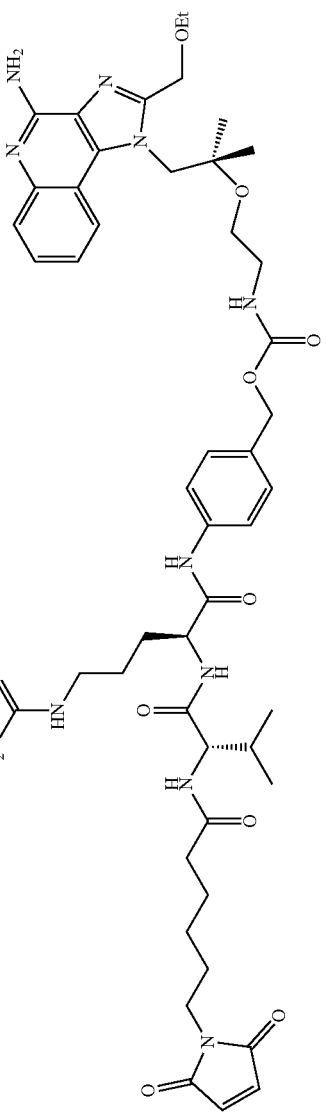 4-((S)-2-((S)-2-(6-(2,5-dioxo-2,5-dihydro-1H-pyrrol-1-yl)hexanamido)-3-methylbutanamido)-5-ureidopentanamido)benzyl (2-((1-(4-amino-2-(ethoxymethyl)-1H-imidazo[4,5-c]quinolin-1-yl)-2-methylpropan-2-yl)oxy)ethyl)carbamate |
| 4.8 | 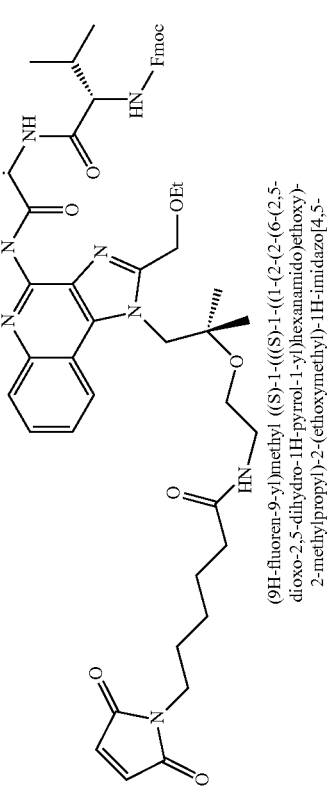 (9H-fluoren-9-yl)methyl ((S)-1-(((S)-1-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-1-oxo-5-ureidopentan-2-yl)amino)-3-methyl-1-oxobutan-2-yl)carbamate |

TABLE 4-continued

TLR7 Agonist Linker-Compounds 4.1-4.20

| Linker-Compound | Structure |
|---|---|
| 4.9 | 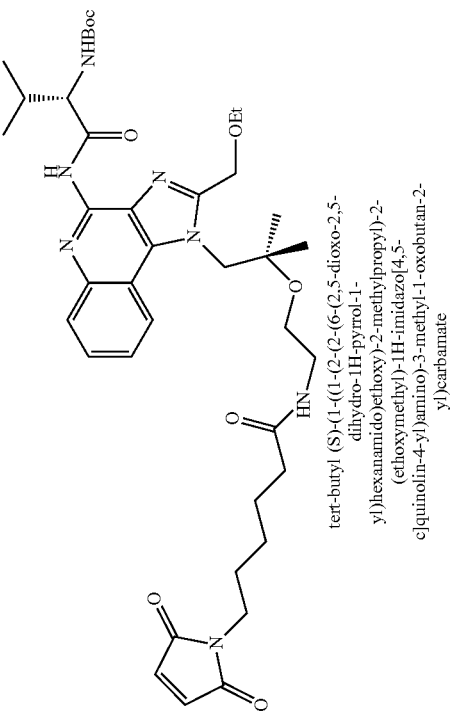 tert-butyl (S)-(1-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-3-methyl-1-oxobutan-2-yl)carbamate |
| 4.10 | 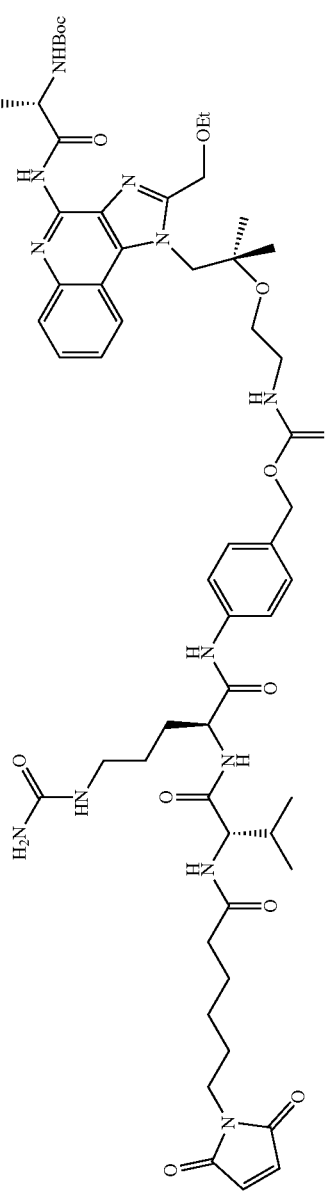 tert-butyl ((S)-1-((1-(2-(2-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)amino)-3-methyl-1-oxobutan-2-yl)carbamate |

TABLE 4-continued

TLR7 Agonist Linker-Compounds 4.1-4.20

| Linker-Compound | Structure |
|---|---|
| 4.11 | 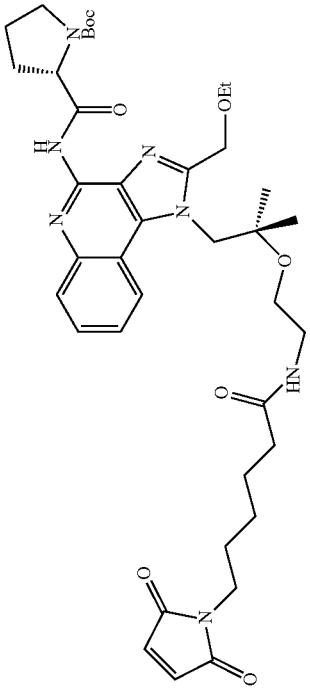 tert-butyl (S)-2-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)carbamoyl)pyrrolidine-1-carboxylate |
| 4.12 | 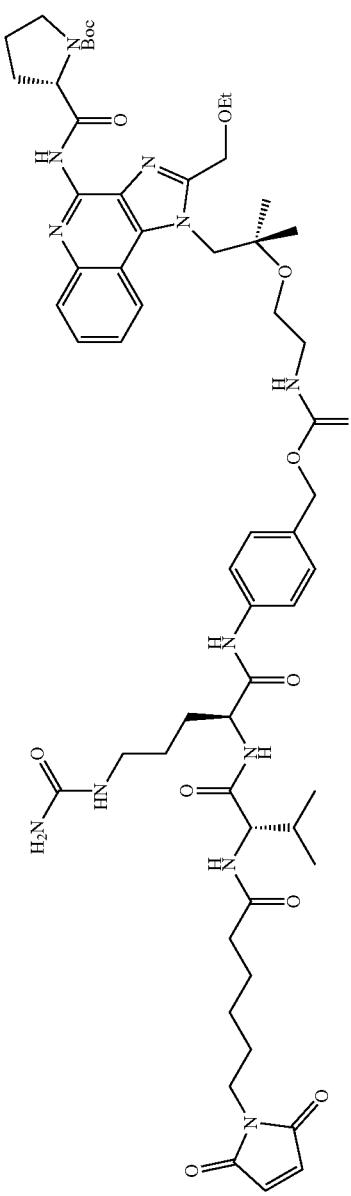 tert-butyl (S)-2-((1-(2-(2-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-1H-imidazo[4,5-c]quinolin-4-yl)carbamoyl)pyrrolidine-1-carboxylate |

TABLE 4-continued

TLR7 Agonist Linker-Compounds 4.1-4.20

| Linker-Compound | Structure |
|---|---|
| 4.13 | 4-((S)-2-((S)-2-((tert-butoxycarbonyl)amino)-3-methylbutanamido)propanamido)benzyl (1-(2-(2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methyl]propyl)-2-(ethoxymethyl)-1H-imidazo[4,5-c]quinolin-4-yl)carbamate |
| 4.14 | tert-butyl (S)-2-(2-((1-((2-((1-(2-(2-(6-(2,5-dioxo-2,5-dihydro-1H-pyrrol-1-yl)hexanamido)-2-methylpropanamido)ethoxy)-2-methylpropyl)-2-(ethoxymethyl)-1H-imidazo[4,5-c]quinolin-4-yl)amino)-2-oxoethyl)amino)-1-oxo-3-phenylpropan-2-yl)amino)-2-oxoethyl)amino-2-oxoethyl)carbamate |

TABLE 4-continued

TLR7 Agonist Linker-Compounds 4.1-4.20

| Linker-Compound | Structure |
|---|---|
| 4.15 | 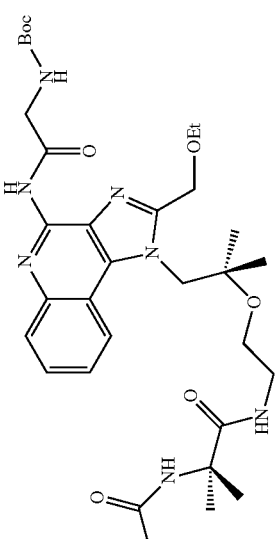 tert-butyl (2-((1-(2-(2-(2-(6-(2,5-dioxo-2,5-dihydro-1H-pyrrol-1-yl)hexanamido)-2-methylpropanamido)ethoxy)-2-methylpropyl)-2-(ethoxymethyl)-1H-imidazo[4,5-c]quinolin-4-yl)amino)-2-oxoethyl)carbamate |
| 4.16 | 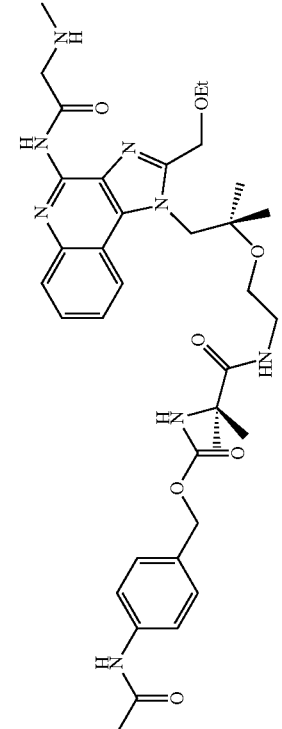 4-((S)-2-((S)-2-(6-(2,5-dioxo-2,5-dihydro-1H-pyrrol-1-yl)hexanamido)-3-methylbutanamido)-5-ureidopentanamido)benzyl (1-((2-((1-(4-(2-((tert-butoxycarbonyl)amino)acetamido)-2-(ethoxymethyl)-1H-imidazo[4,5-c]quinolin-1-yl)-2-methylpropan-2-yl)oxy)ethyl)amino)-2-methyl-1-oxopropan-2-yl)carbamate |

TABLE 4-continued

TLR7 Agonist Linker-Compounds 4.1-4.20

| Linker-Compound | Structure |
|---|---|
| 4.17 | 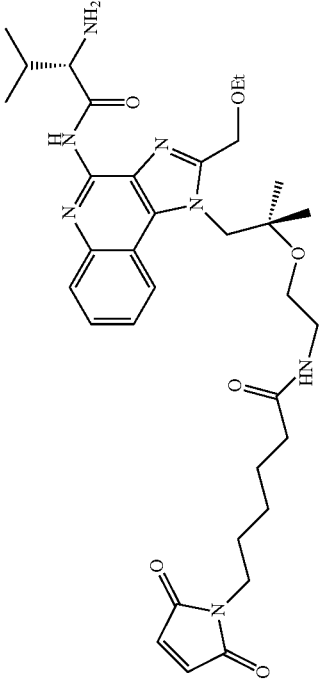 (S)-N-(2-((1-(4-(2-amino-3-methylbutanamido)-2-(ethoxymethyl)-1H-imidazo[4,5-c]quinolin-1-yl)-2-methylpropan-2-yl)oxy)ethyl)-6-(2,5-dioxo-2,5-dihydro-1H-pyrrol-1-yl)hexanamide |
| 4.18 | 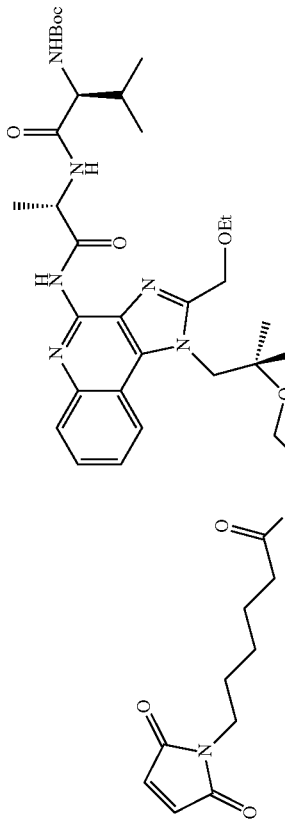 tert-butyl ((S)-1-(((S)-1-((1-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-1-oxopropan-2-yl)amino)-3-methyl-1-oxobutan-2-yl)carbamate |

TABLE 4-continued

TLR7 Agonist Linker-Compounds 4.1-4.20

| Linker-Compound | Structure |
|---|---|
| 4.19 | 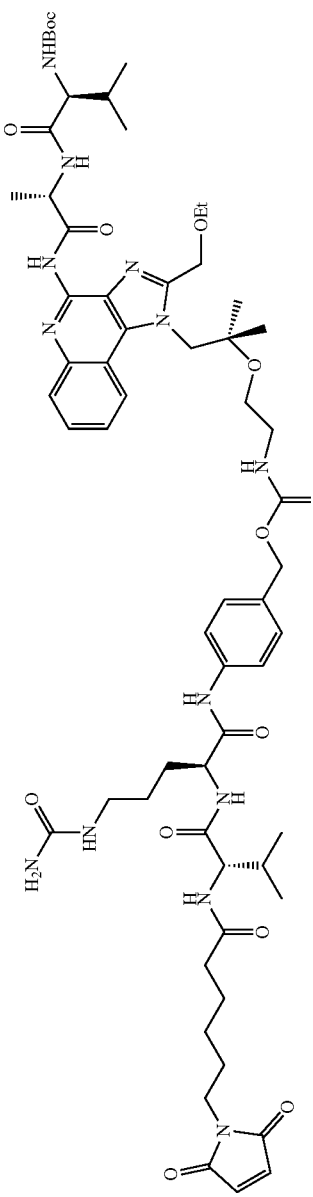 tert-butyl ((S)-1-(((S)-1-((2-(2-(((4-((S)-2-(((4-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)amino)-1-oxopropan-2-yl)amino)-3-methyl-1-oxobutan-2-yl)carbamate |
| 4.20 | 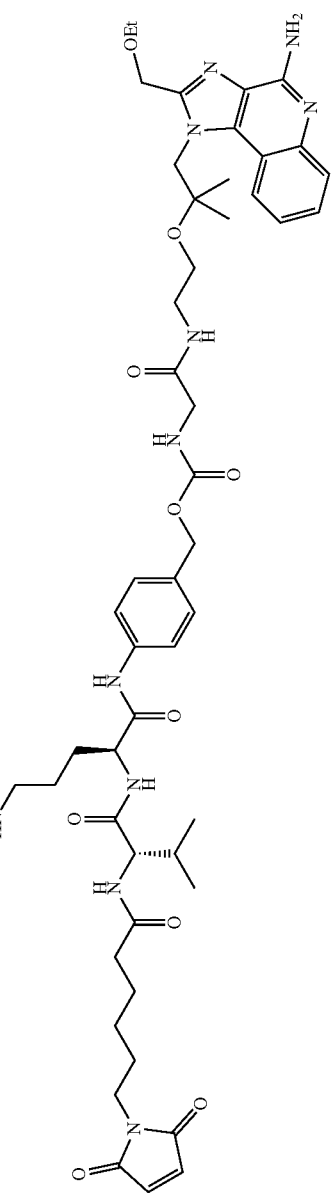 4-((S)-2-((S)-2-(6-(2,5-dioxo-2,5-dihydro-1H-pyrrol-1-yl)hexanamido)-3-methylbutanamido)-5-ureidopentanamido)benzyl (2-((2-((1-(4-amino-2-(ethoxymethyl)-1H-imidazo[4,5-c]quinolin-1-yl)-2-methylpropan-2-yl)oxy)ethyl)amino)-2-oxoethyl)carbamate |

In some embodiments, a myeloid cell agonist conjugate or salt thereof is represented by Formula (I):

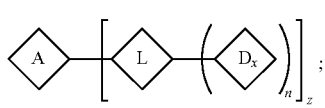

wherein:
n is selected from 1 to 20;
z is selected from 1 to 20;
L is the linker;
A is an anti-ASGR1 antibody or antigen-binding fragment thereof comprising:
(a) a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33, or
(b) a heavy chain variable region comprising the amino acid sequence of SEQ ID NO: 240 and a light chain variable region comprising the amino acid sequence of SEQ ID NO: 247; and
Dx is a myeloid cell agonist having the following structure:

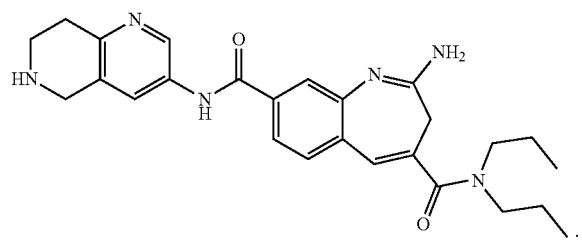 [SMILES: CCCN(CCC)C(=O)C1=Cc2ccc(C(=O)Nc3cnc4c(c3)CNCC4)cc2N=C(N)C1]

In some embodiments, a myeloid cell agonist conjugate or salt thereof is represented by Formula (I):

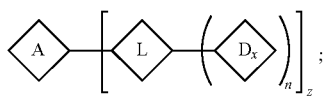

wherein:
n is selected from 1 to 20;
z is selected from 1 to 20;
L is the linker;
A is an anti-ASGR1 antibody or antigen-binding fragment thereof comprising:
(a) a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or
(b) a heavy chain variable region comprising the amino acid sequence of SEQ ID NO: 239 and a light chain variable region comprising the amino acid sequence of SEQ ID NO: 247; and
Dx is a myeloid cell agonist having the following structure:

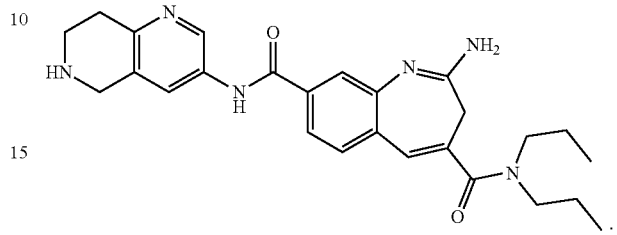

In some embodiments, a myeloid cell agonist conjugate or salt thereof is represented by Formula (I):

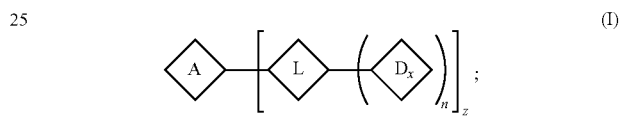

wherein:
n is selected from 1 to 20;
z is selected from 1 to 20;
L is the linker;
A is an anti-ASGR1 antibody or antigen-binding fragment thereof comprising:
(a) a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or
(b) a heavy chain variable region comprising the amino acid sequence of SEQ ID NO: 89 and a light chain variable region comprising the amino acid sequence of SEQ ID NO: 134; and
Dx is a myeloid cell agonist having the following structure:

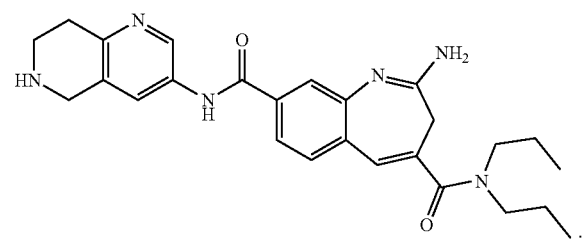 [SMILES: CCCN(CCC)C(=O)C1=Cc2ccc(C(=O)Nc3cnc4c(c3)CNCC4)cc2N=C(N)C1]

In some embodiments, a myeloid cell agonist conjugate compound is selected from:
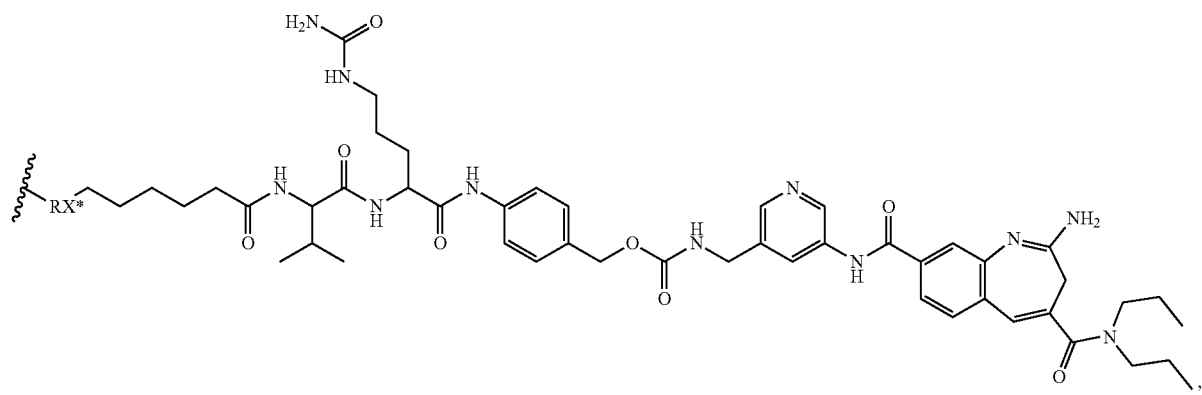
,
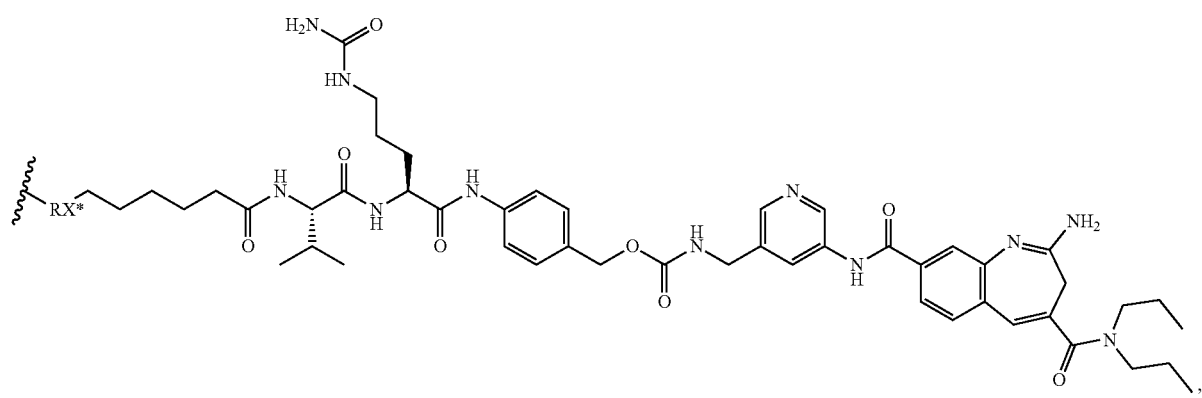
,
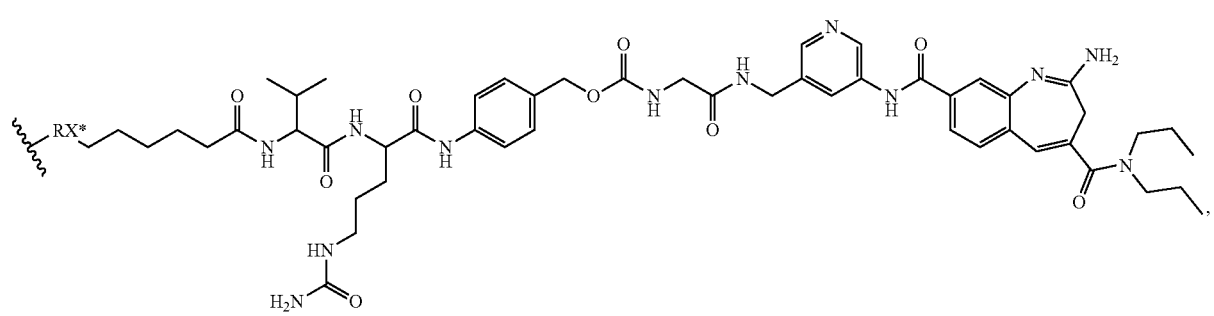
,
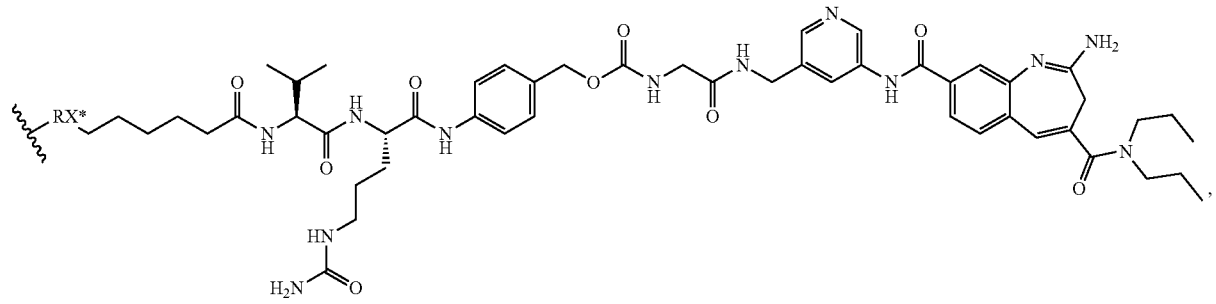
,

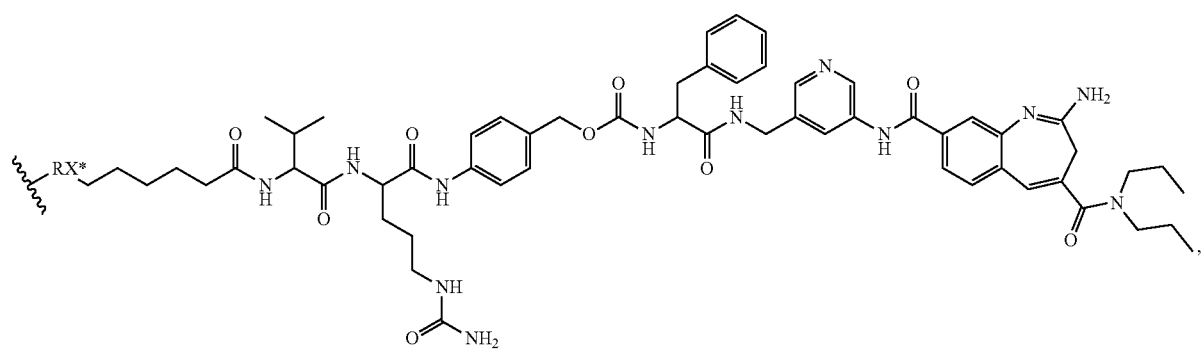
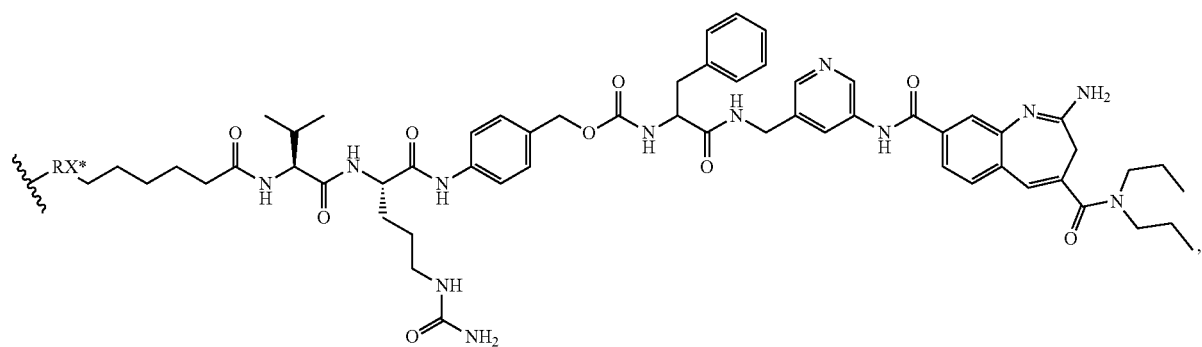
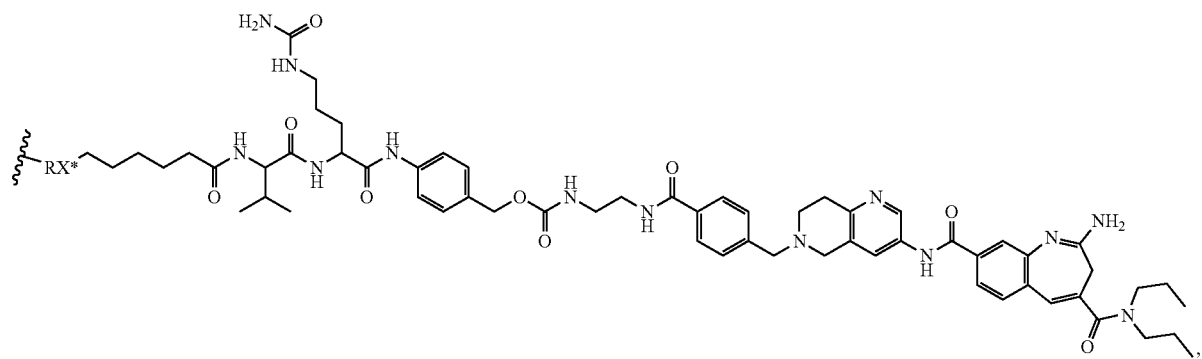
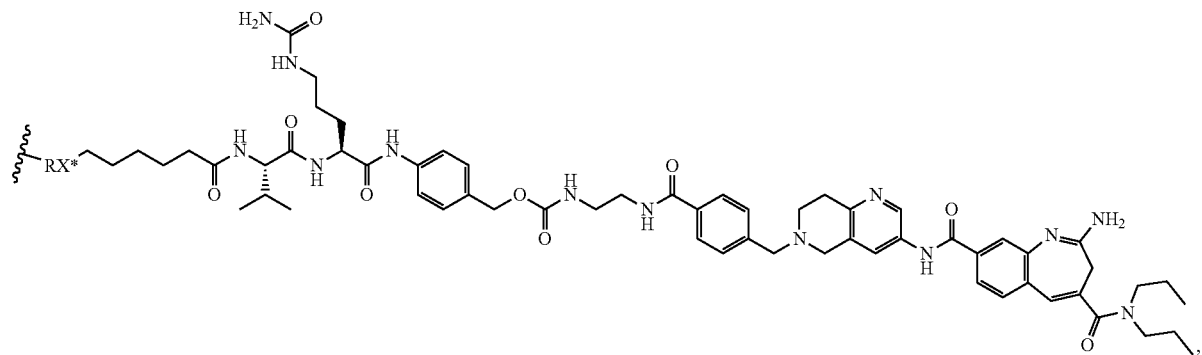

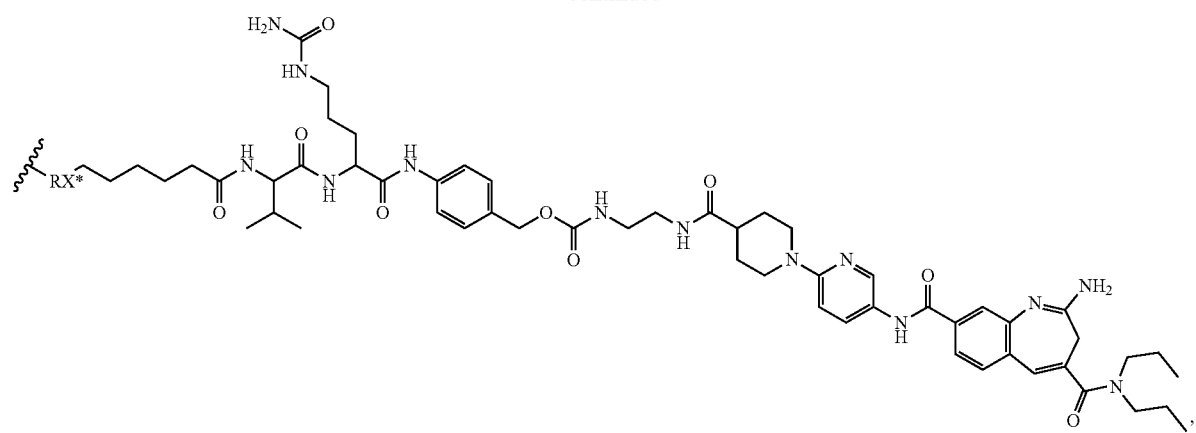
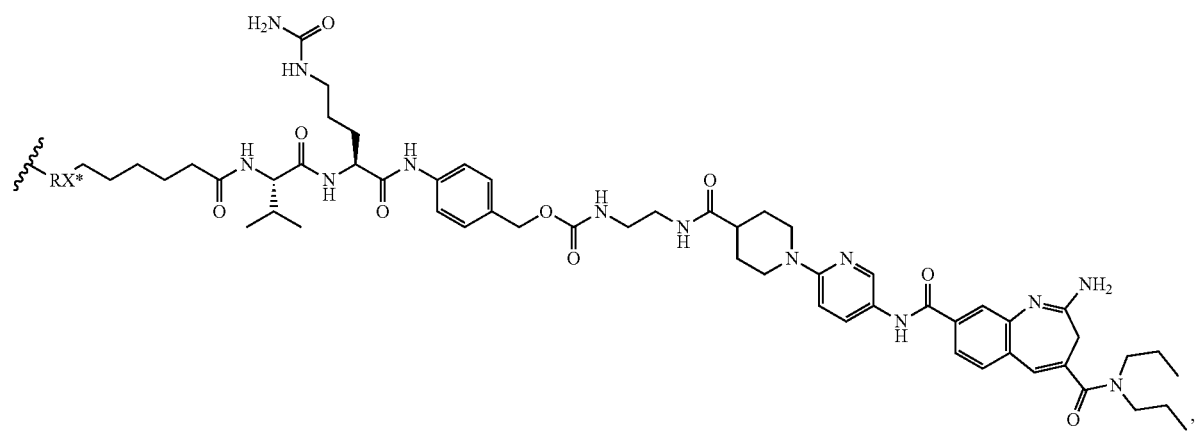
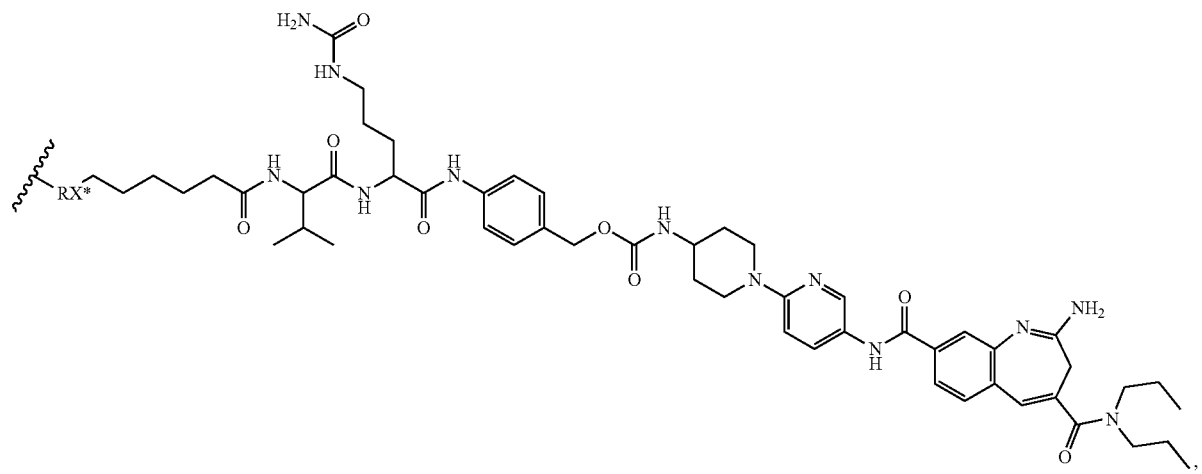

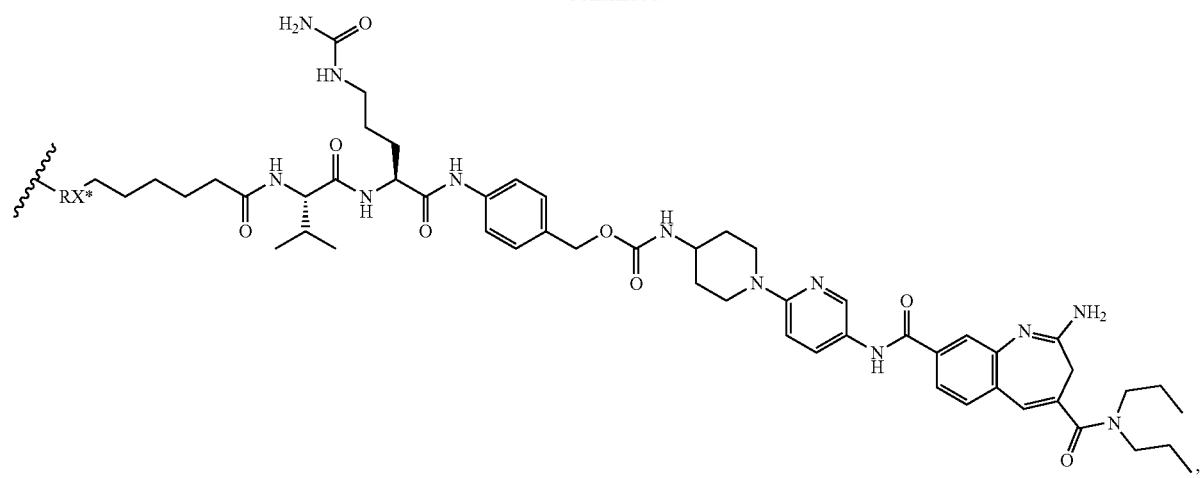
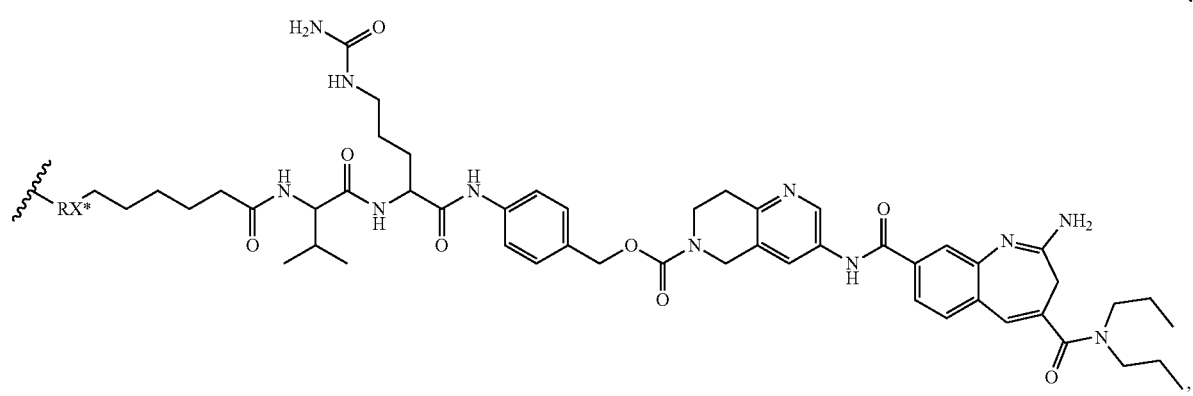
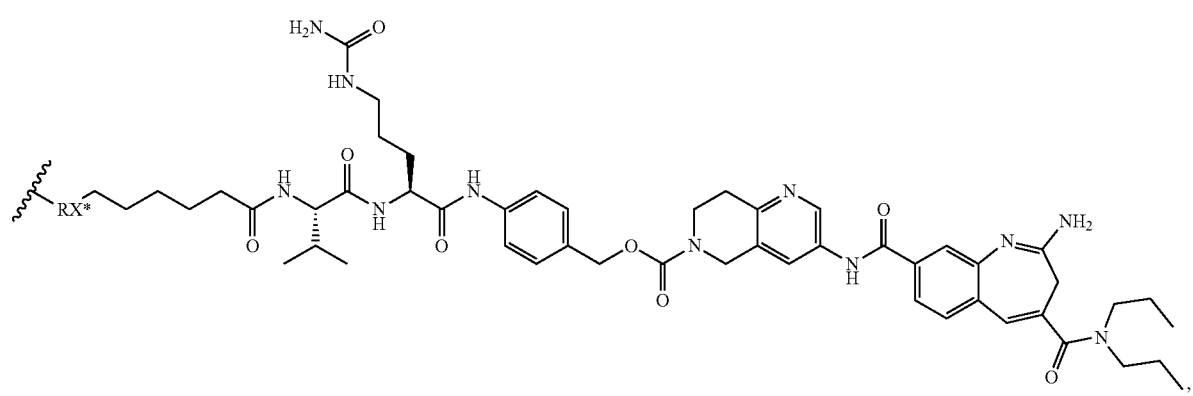
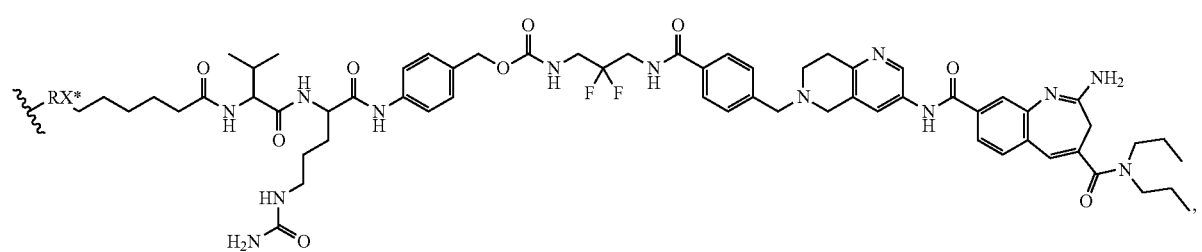

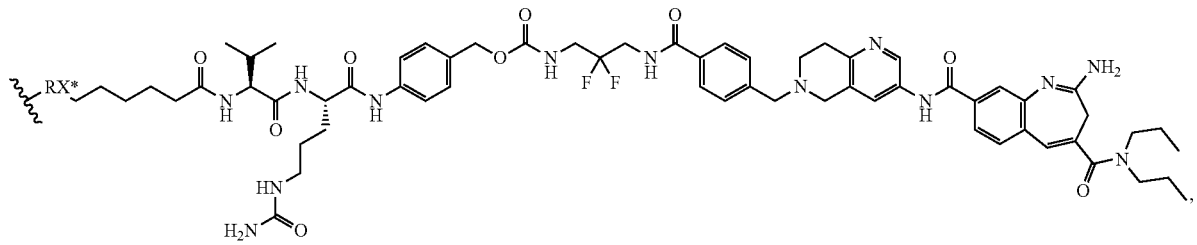

and a salt of any one thereof, wherein the RX* is a bond, a succinimide moiety, or a hydrolyzed succinimide moiety bound to a residue of an anti-ASGR1 antibody, antibody

construct, or targeting moiety, wherein on RX* represents the point of attachment to the residue of the anti-ASGR1 antibody, antibody construct, or targeting moiety.

In some embodiments, a myeloid cell agonist conjugate is represented by Formula (I):

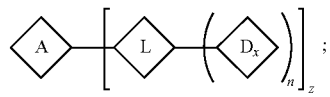 (I)

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

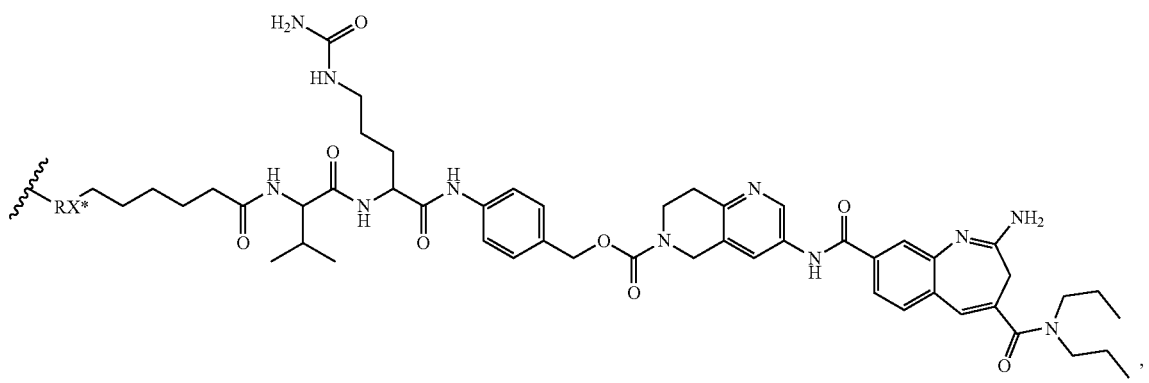

In some embodiments, a myeloid cell agonist conjugate is represented by Formula (I):

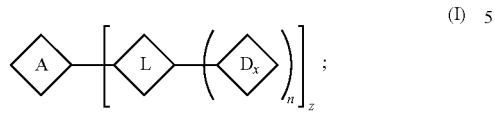

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

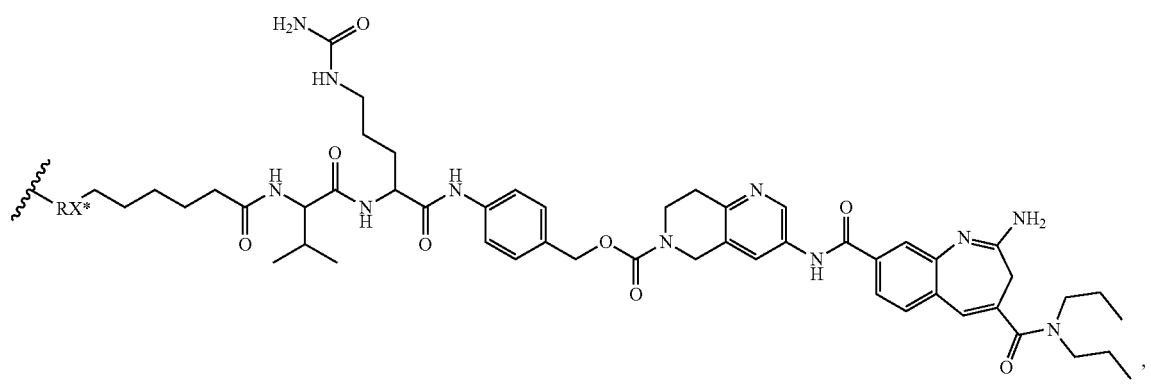

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

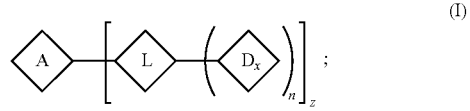

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and L and $D_x$ have a structure of:

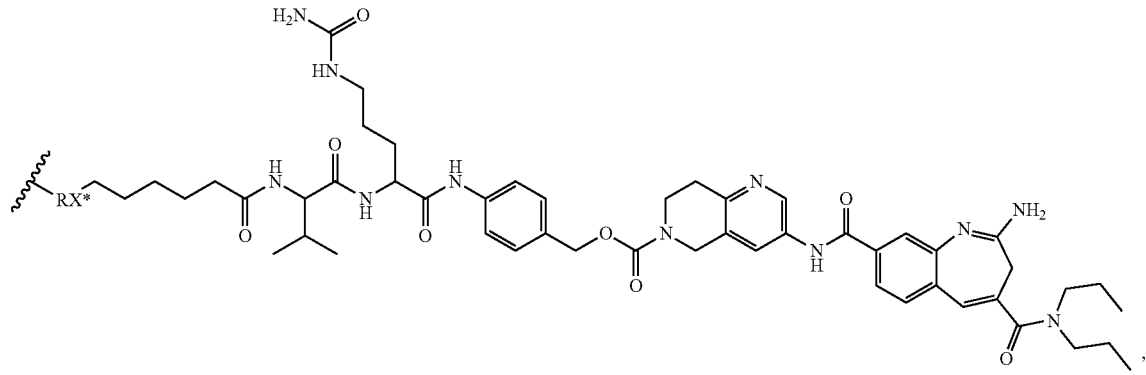

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1; wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

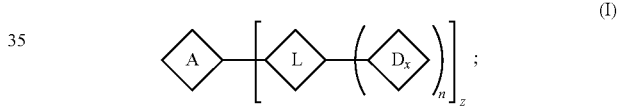

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

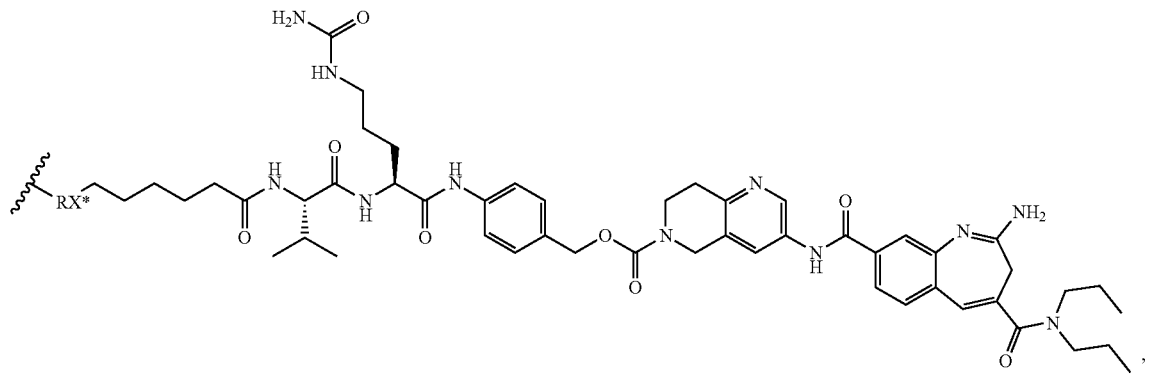

or a salt thereof, wherein the RX* is a bond a succinimide moiety, or a hydrolyzed succinimide moiety bound to a residue of an antibody, wherein

on RX* represents the point of attachment to the residue of the antibody, wherein the antibody binds to ASGR1; wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

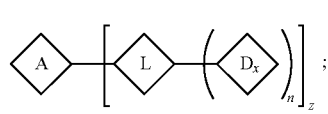

(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

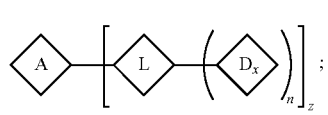

(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and

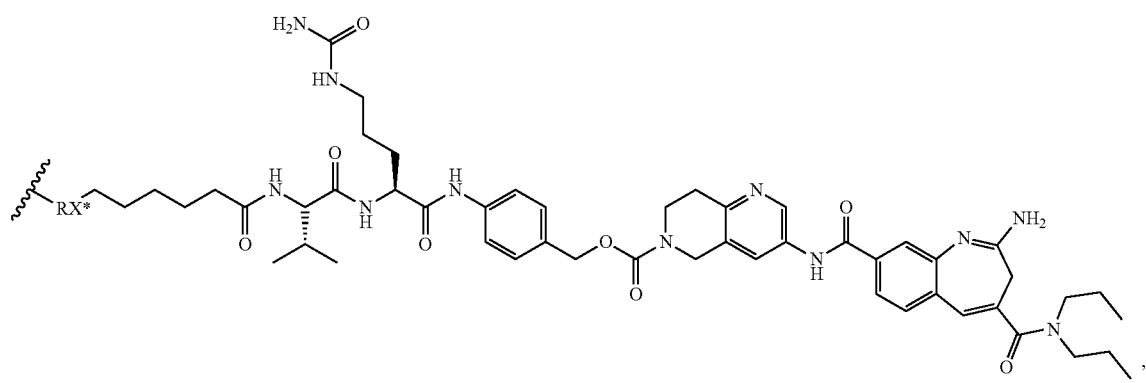

L and $D_x$ have a structure of:

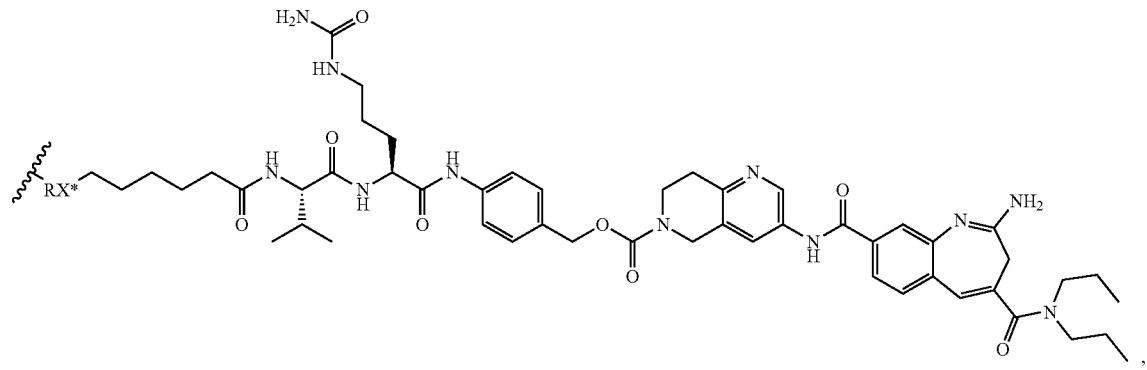

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

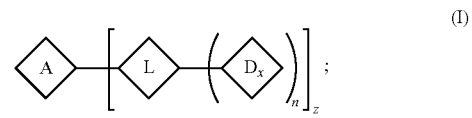

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

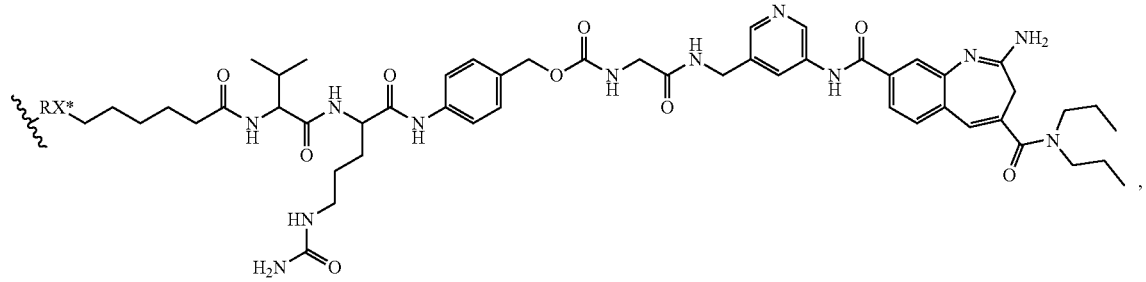

or a salt thereof, wherein the RX* is a bond, a succinimide moiety, or a hydrolyzed succinimide moiety bound to a residue of an antibody, wherein

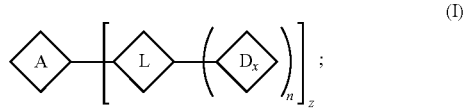

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

$$\langle A \rangle - \left[ \langle L \rangle - \left( \langle D_x \rangle \right)_n \right]_z ;$$ (I)

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

or a salt thereof, wherein the RX* is a bond, a succinimide moiety, or a hydrolyzed succinimide moiety bound to a residue of an antibody, wherein

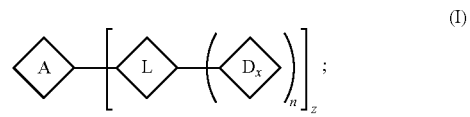

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

$$\langle A \rangle - \left[ \langle L \rangle - \left( \langle D_x \rangle \right)_n \right]_z ;$$ (I)

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and

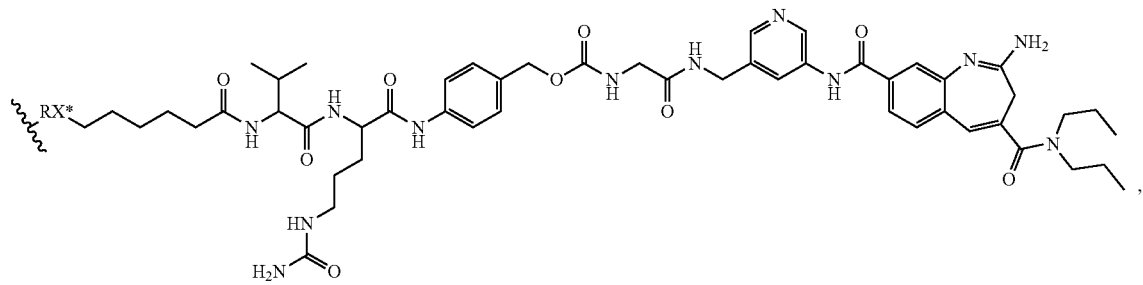

L and $D_x$ have a structure of:

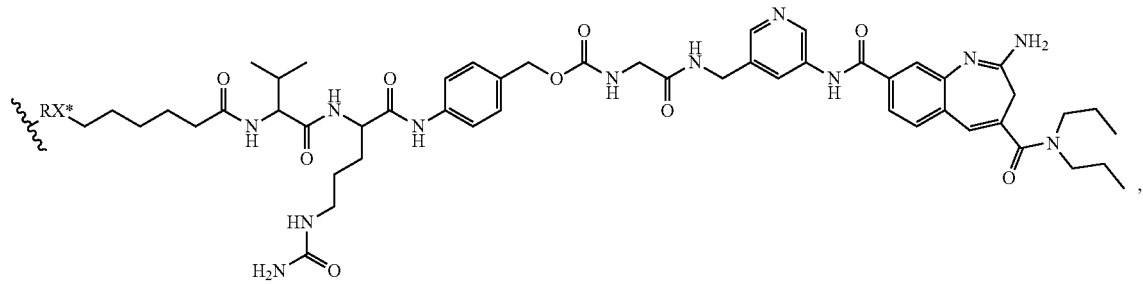

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

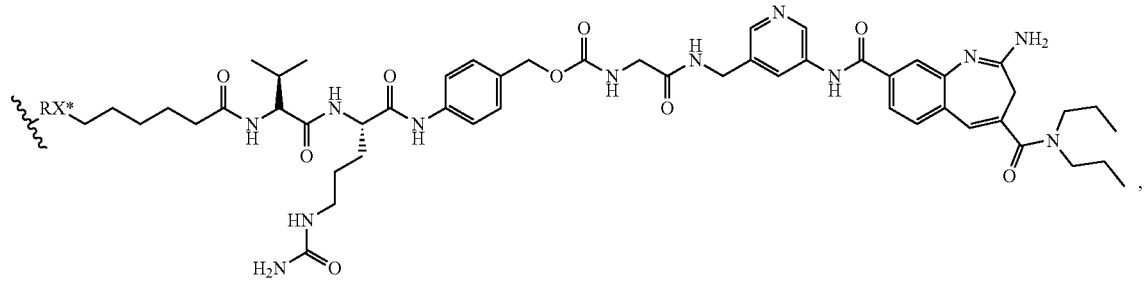

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

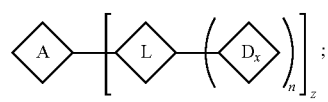

In some embodiments, a myeloid cell agonist conjugate is represented by Formula (I):

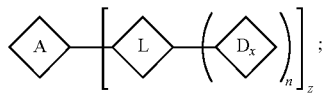

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

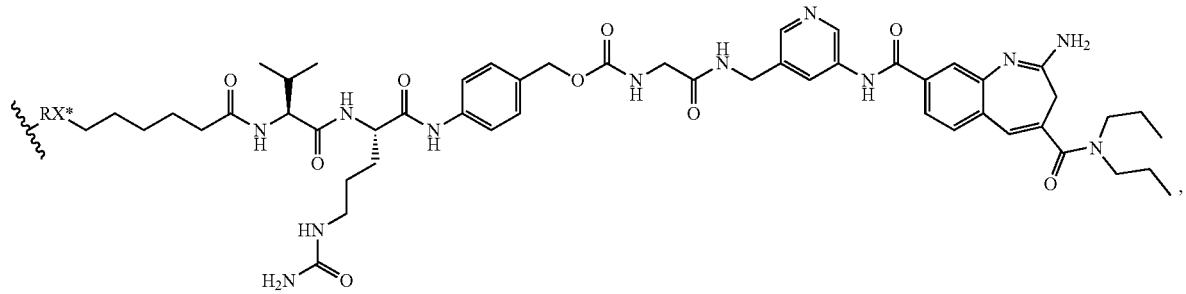

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

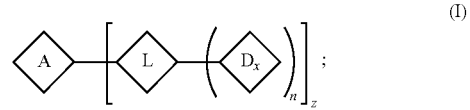

wherein:
A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

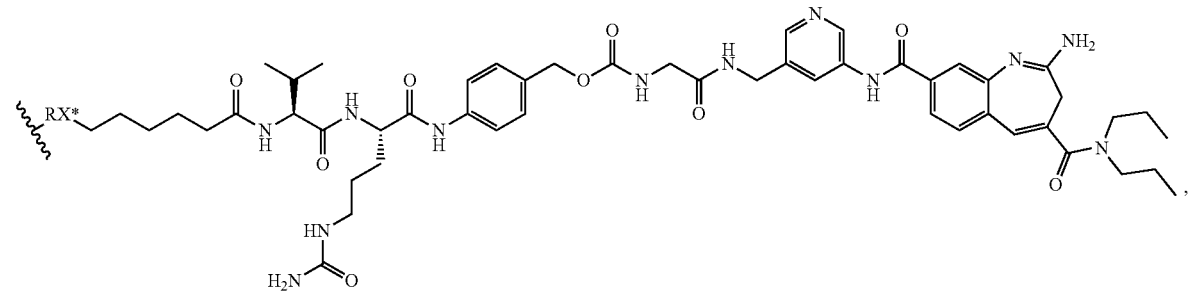

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

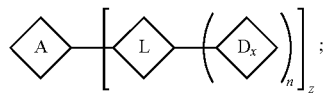

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

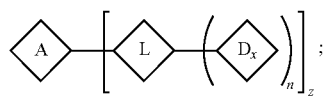

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and

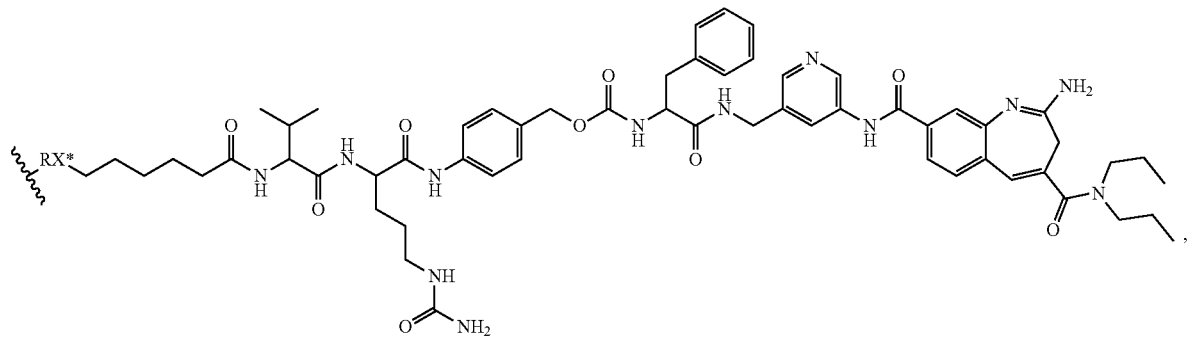

L and $D_x$ have a structure of:

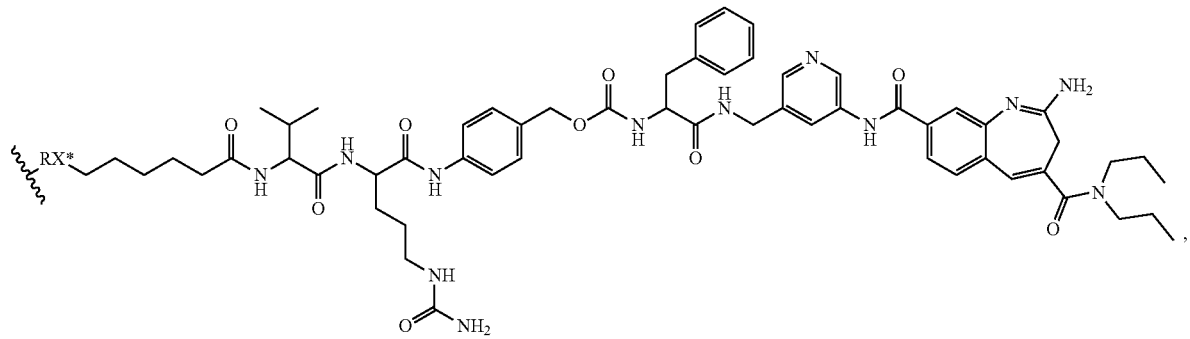

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

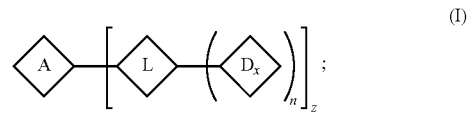

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

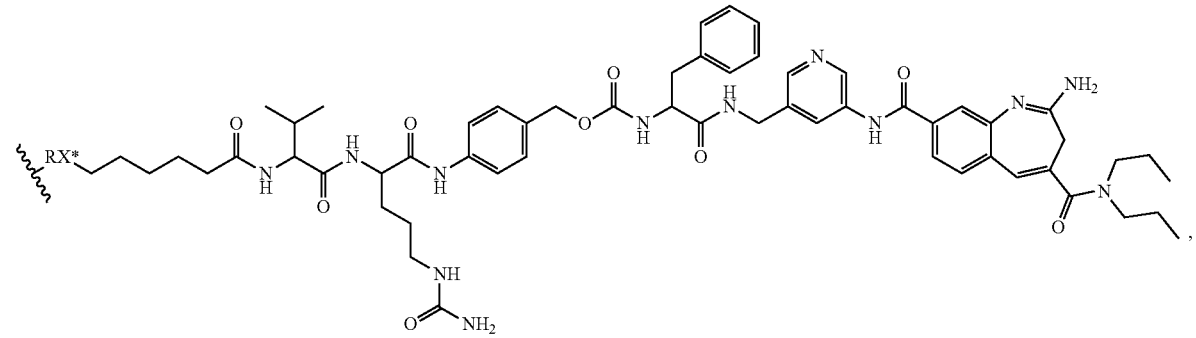

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

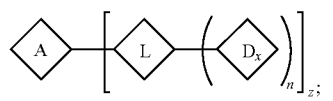
(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

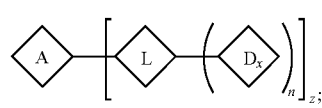
(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and

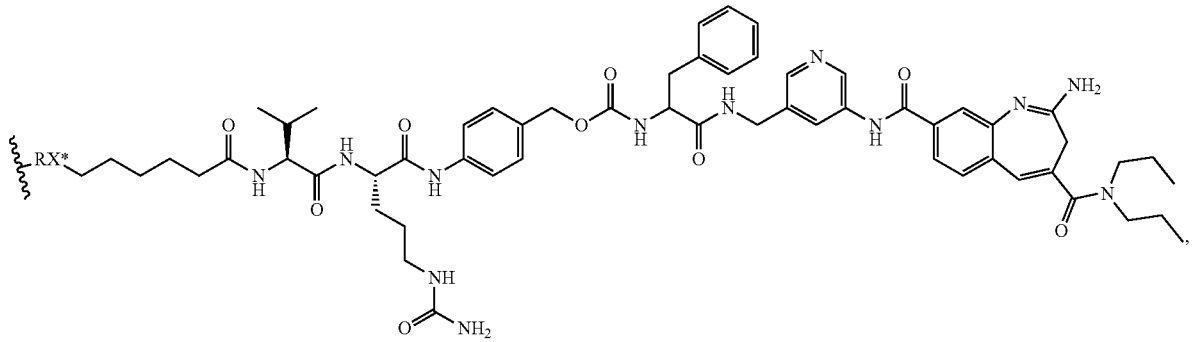

L and $D_x$ have a structure of:

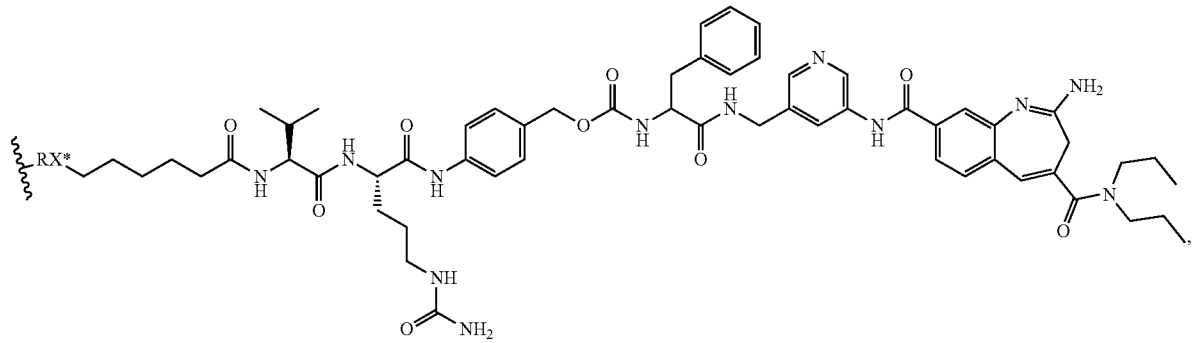

or a salt thereof, wherein the RX* is a bond, a succinimide moiety, or a hydrolyzed succinimide moiety bound to a residue of an antibody, wherein on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

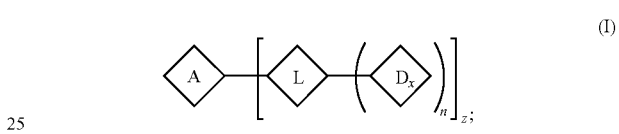

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

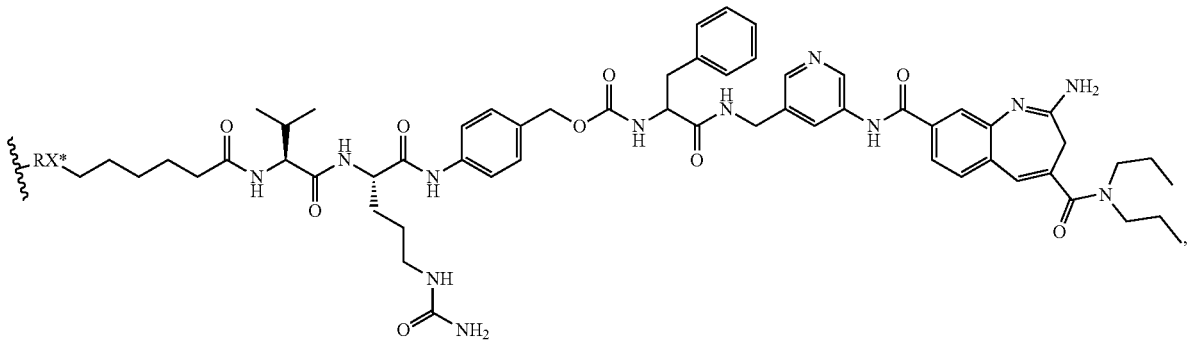

or a salt thereof, wherein the RX* is a bond, a succinimide moiety or a hydrolyzed succinimide moiety bound to a residue of an antibody, wherein on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

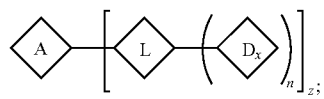

(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO: 1, a VH-CDR2 comprising the amino acid sequence of SEQ ID NO:8, a VH-CDR3 comprising the amino acid sequence of SEQ ID NO: 13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

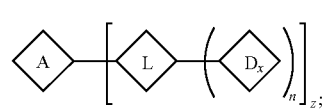

(I)

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and

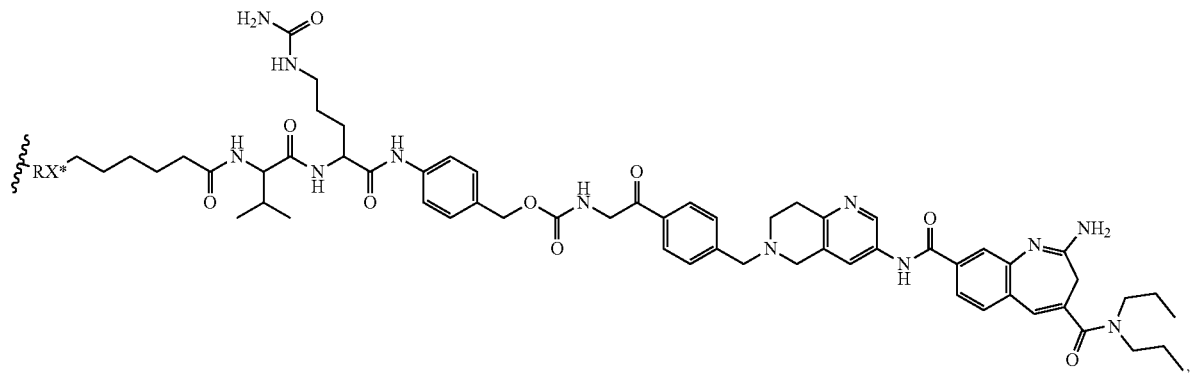

L and $D_x$ have a structure of:

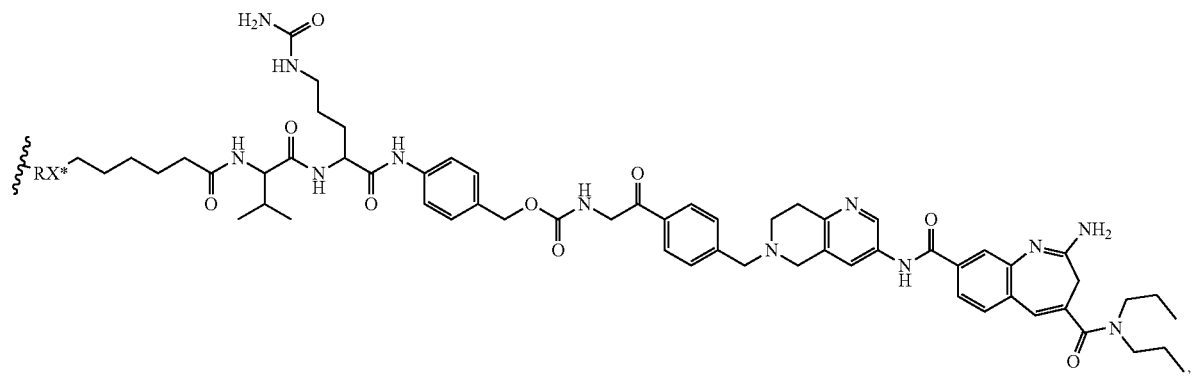

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

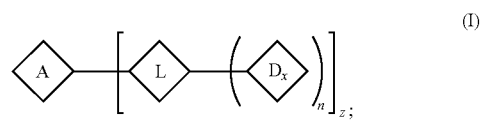

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

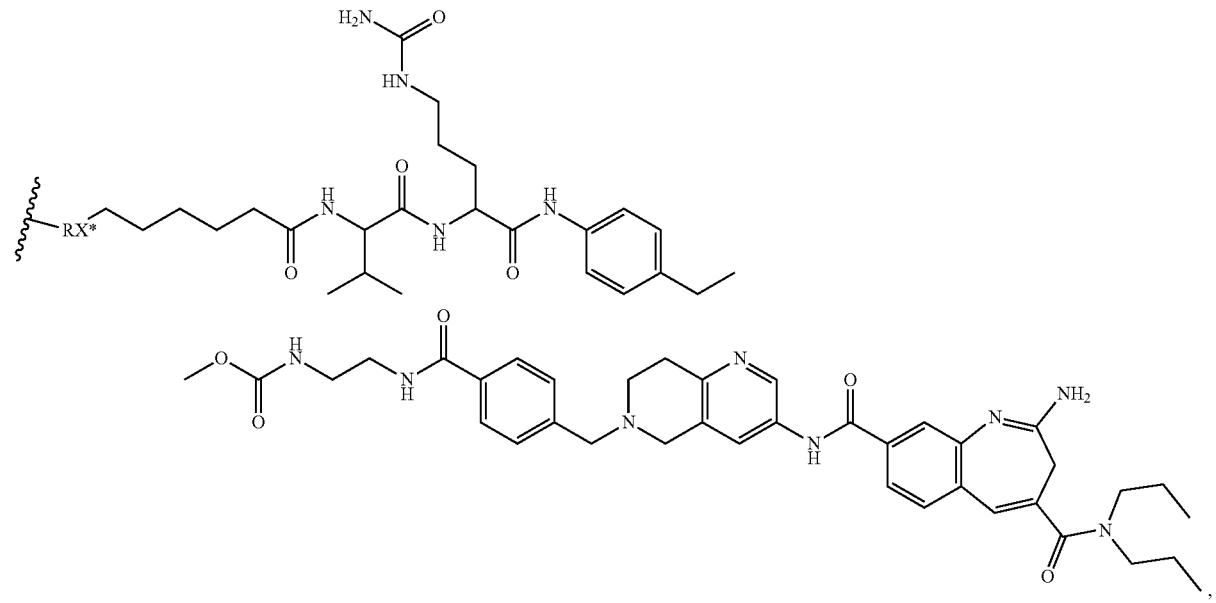

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein:

A is an anti-ASGR1 antibody or antigen-binding fragment thereof;

n is selected from 1 to 20;

z is selected from 1 to 20;

L is the linker; and

Dx is a myeloid cell agonist, wherein the myeloid cell agonist is a TLR8 agonist; and L and $D_x$ have a structure of:

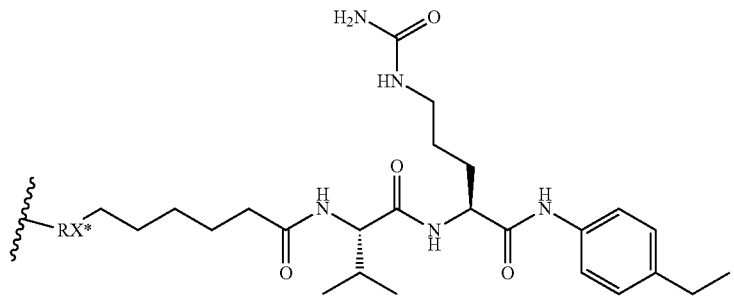

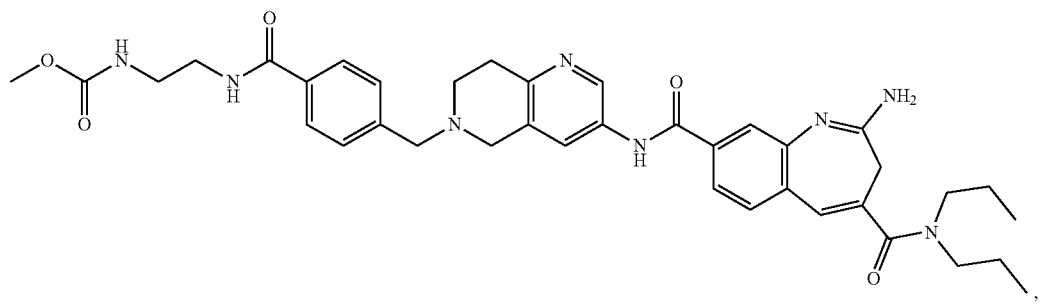

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

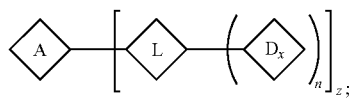

(I)

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

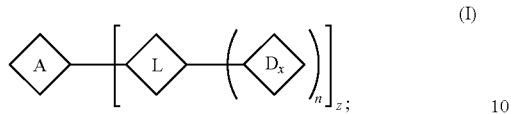

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

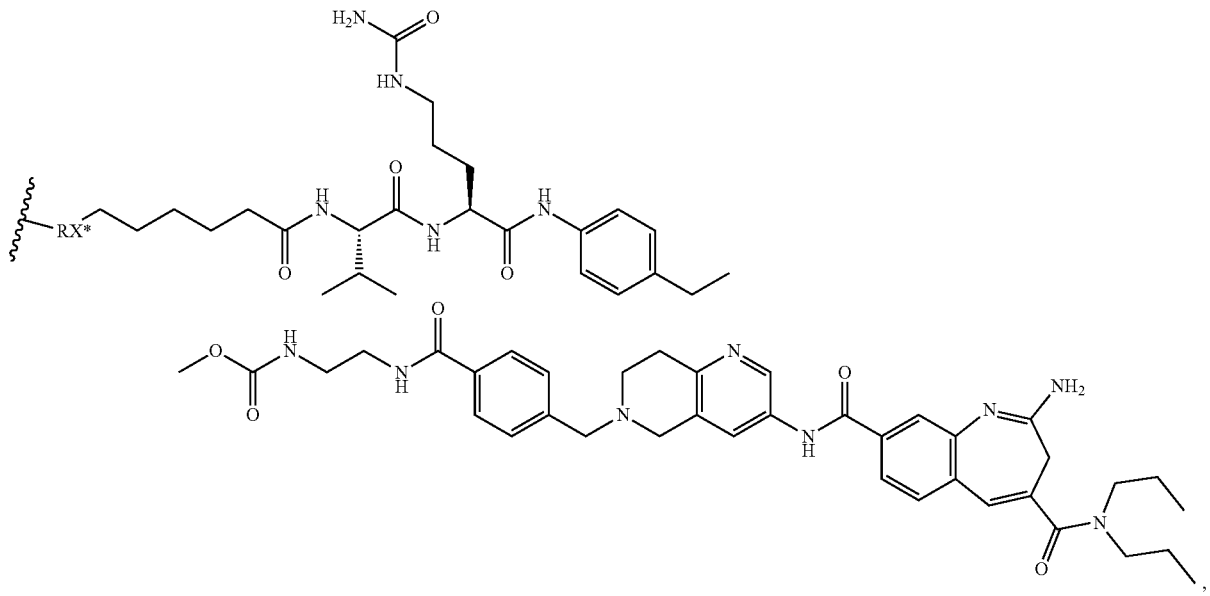

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

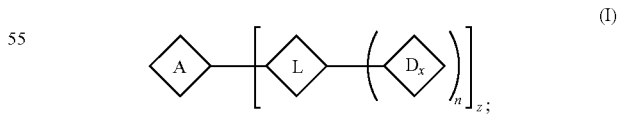

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and L and $D_x$ have a structure of:

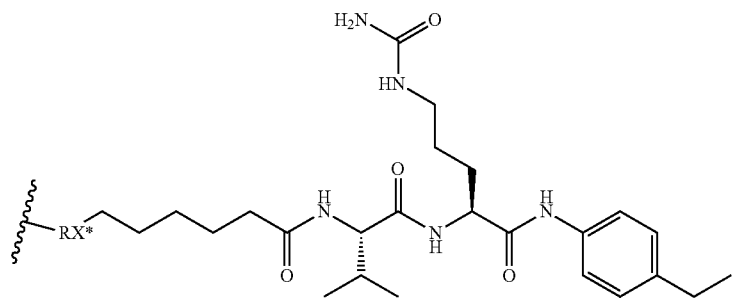

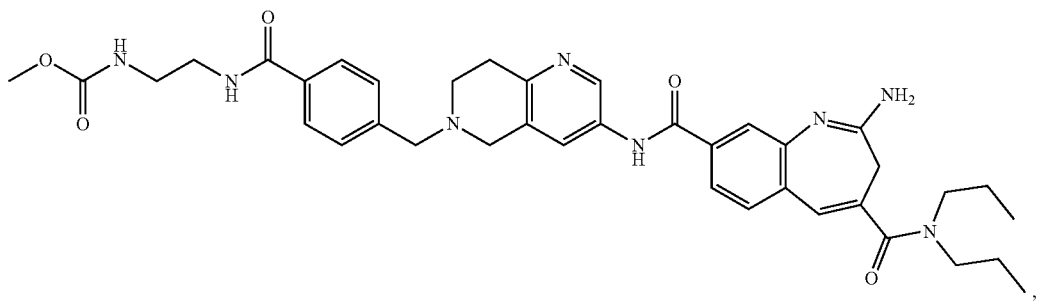

or a salt thereof, wherein the RX* is a bond, a succinimide moiety, or a hydrolyzed succinimide moiety bound to a residue of an antibody, wherein

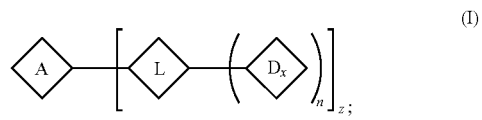

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

$$\text{A}-\left[\text{L}-\left(\text{D}_x\right)_n\right]_z; \quad (I)$$

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

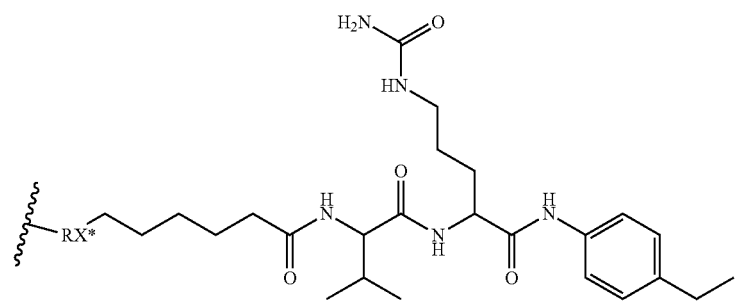

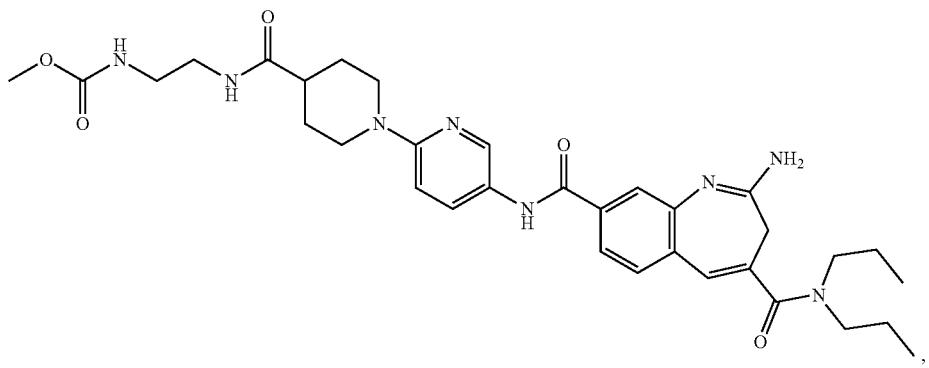

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

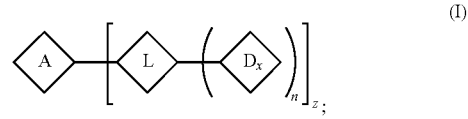

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

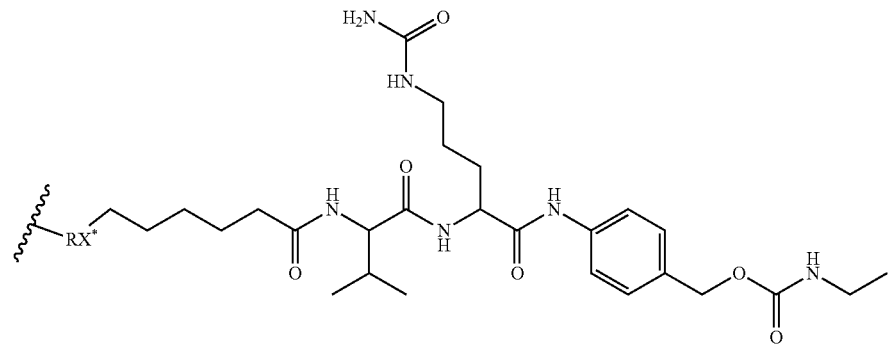

-continued

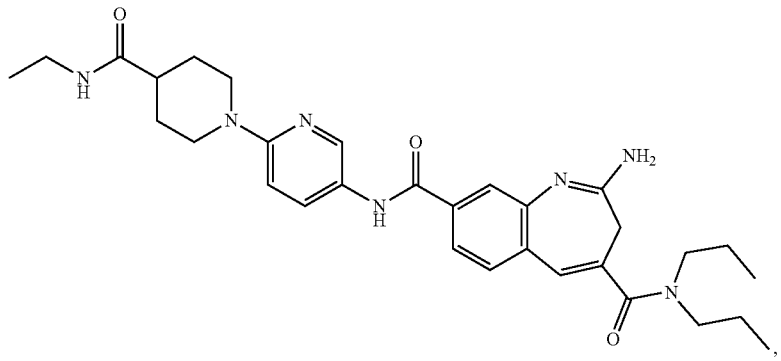

or a salt thereof, wherein the RX* is a bond, a succinimide moiety, or a hydrolyzed succinimide moiety bound to a residue of an antibody, wherein

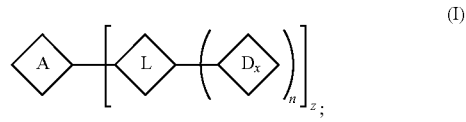

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

$$\boxed{A}-\left[\boxed{L}-\left(\boxed{D_x}\right)_n\right]_z;\qquad\qquad(I)$$

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

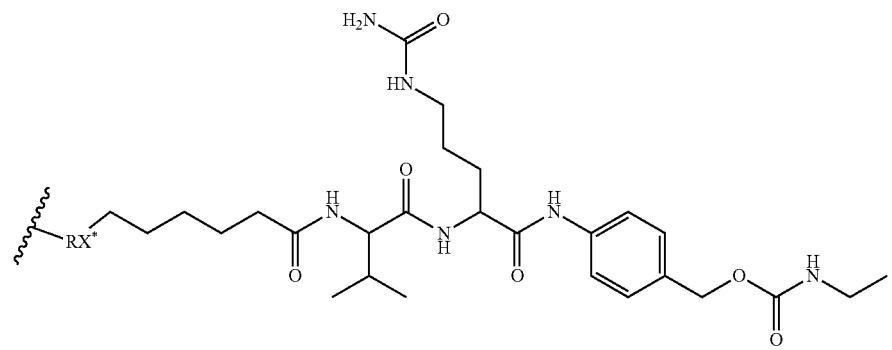

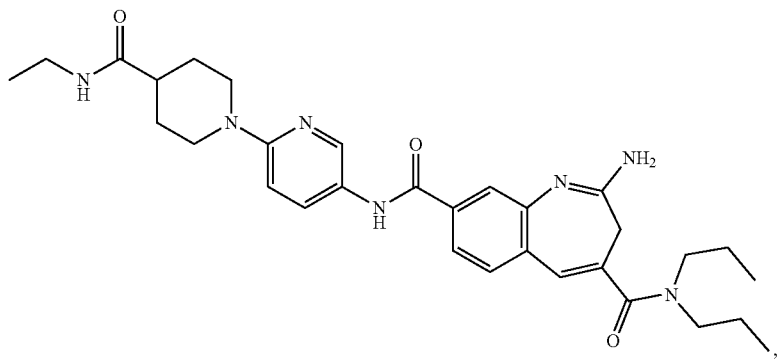

or a salt thereof, wherein the RX* is a bond, a succinimide moiety, or a hydrolyzed succinimide moiety bound to a residue of an antibody, wherein

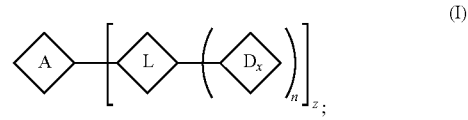

on RX* represents the point of attachment to the residue of the antibody, wherein the antibody binds to ASGR1; wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

$$A - \left[ L - \left( D_x \right)_n \right]_z \quad (I)$$

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

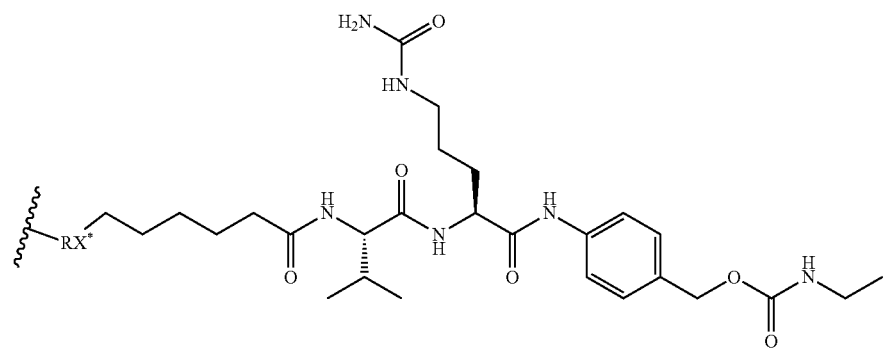

-continued

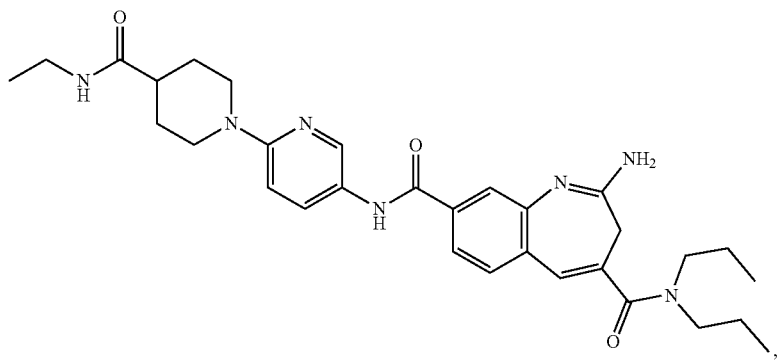

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1; wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

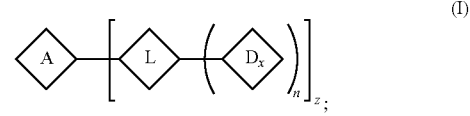

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

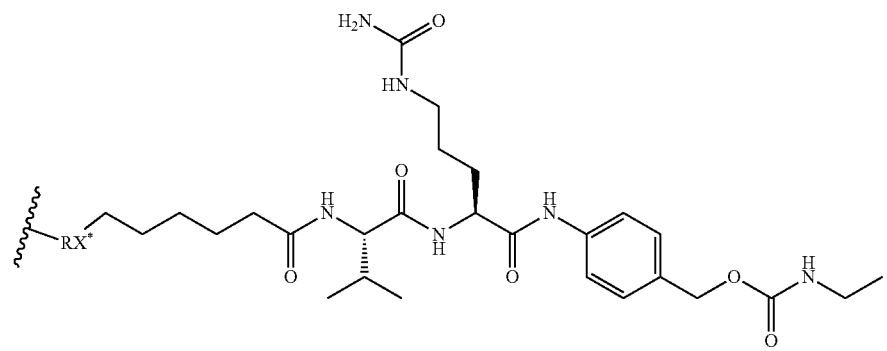

-continued

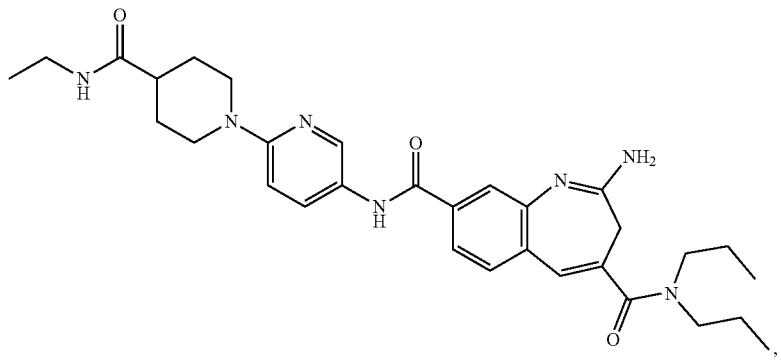

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

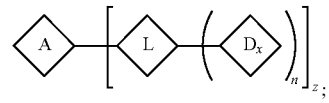

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

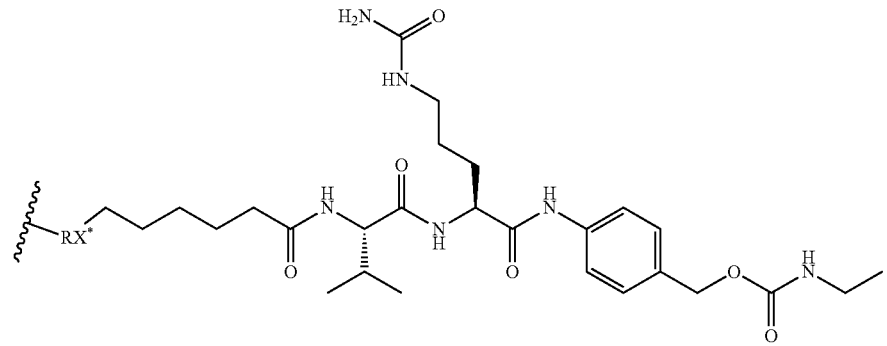

-continued

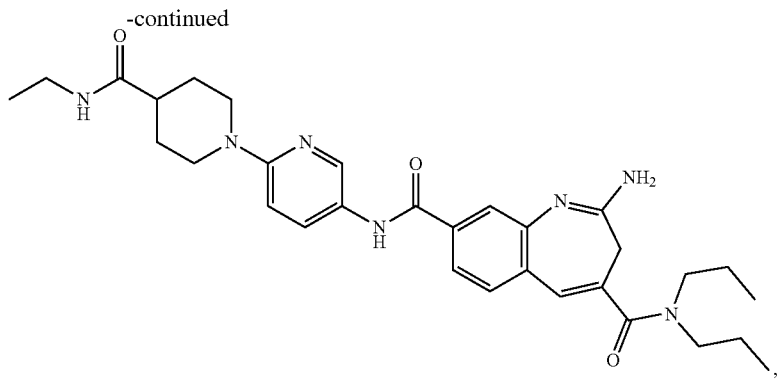

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

$$A \!-\!\!\left[ L \!-\!\!\left( D_x \right)_n \right]_z ; \tag{I}$$

wherein:
A is an anti-ASGR1 antibody or antigen-binding fragment thereof,
n is selected from 1 to 20;
z is selected from 1 to 20;
L is the linker; and
$D_x$ is a myeloid cell agonist, wherein the myeloid cell agonist is a TLR8 agonist; and
L and $D_x$ have a structure of:

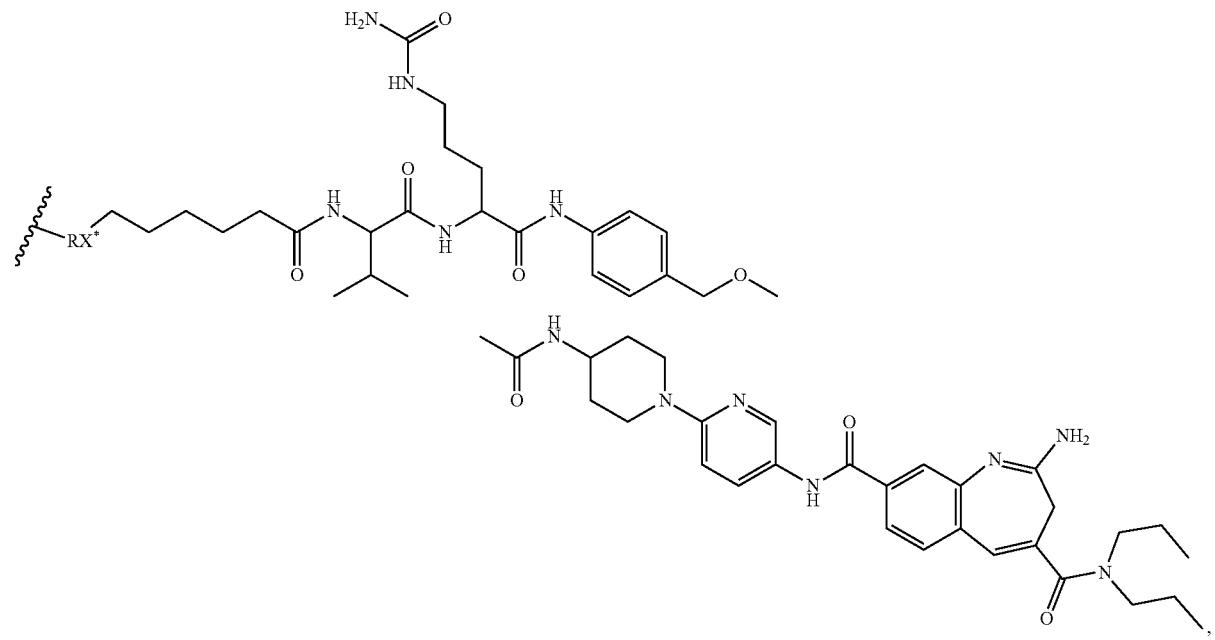

or a salt thereof, wherein the RX* is a bond, a succinimide moiety, or a hydrolyzed succinimide moiety bound to a residue of an antibody, wherein

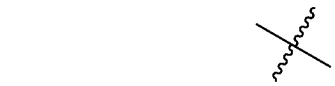

on RX* represents the point of attachment to the residue of the antibody, wherein the antibody binds to ASGR1;

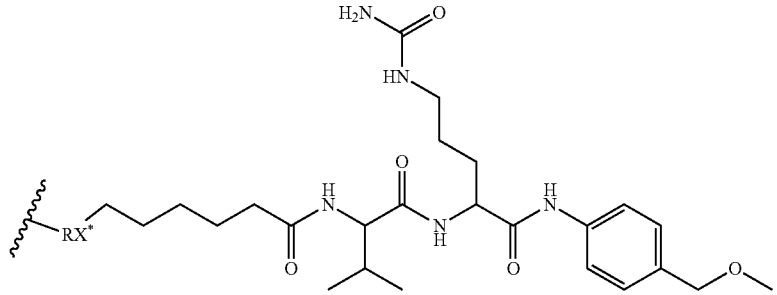

wherein:

A is an anti-ASGR1 antibody or antigen-binding fragment thereof;

n is selected from 1 to 20;

z is selected from 1 to 20;

L is the linker; and

Dx is a myeloid cell agonist, wherein the myeloid cell agonist is a TLR8 agonist; and L and $D_x$ have a structure of:

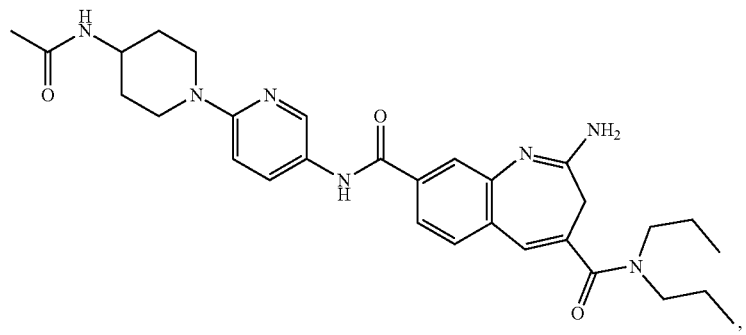

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

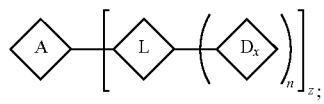

(I)

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

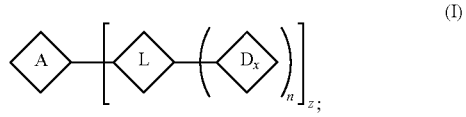

(I)

wherein

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

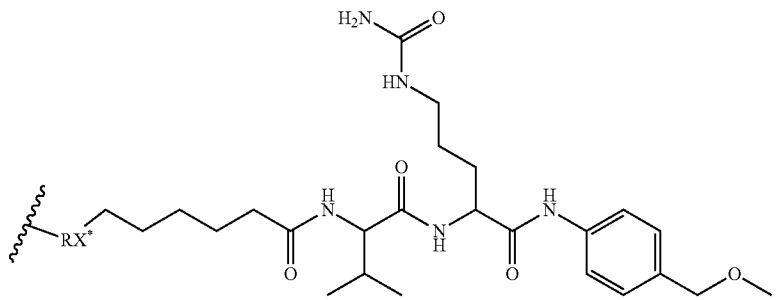

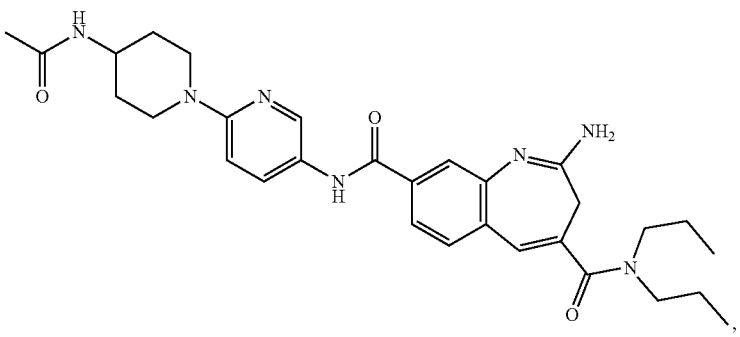

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

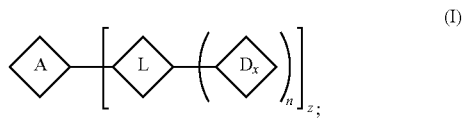

(I)

wherein:

A is an anti-ASGR1 antibody or antigen-binding fragment thereof;

n is selected from 1 to 20;

z is selected from 1 to 20;

L is the linker; and

Dx is a myeloid cell agonist, wherein the myeloid cell agonist is a TLR8 agonist; and L and D_x have a structure of:

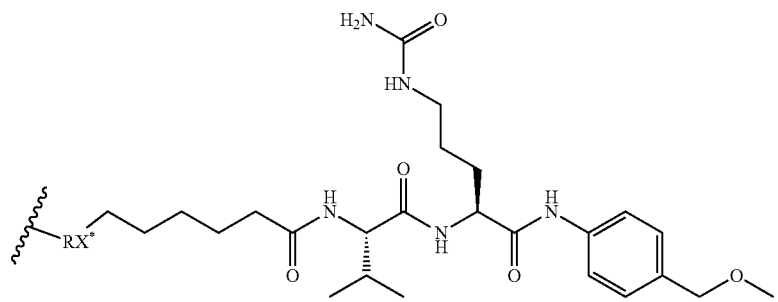

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

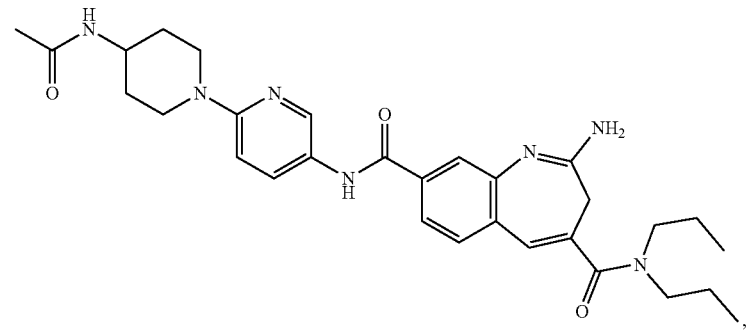

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and D_x have a structure of:

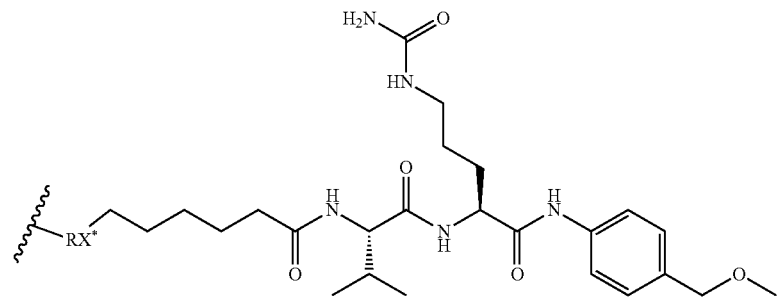

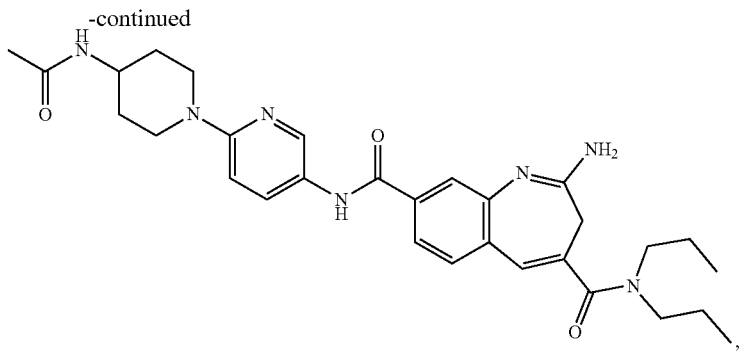

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

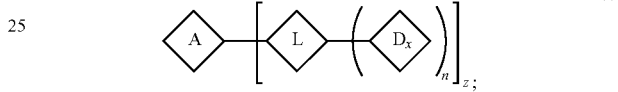

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

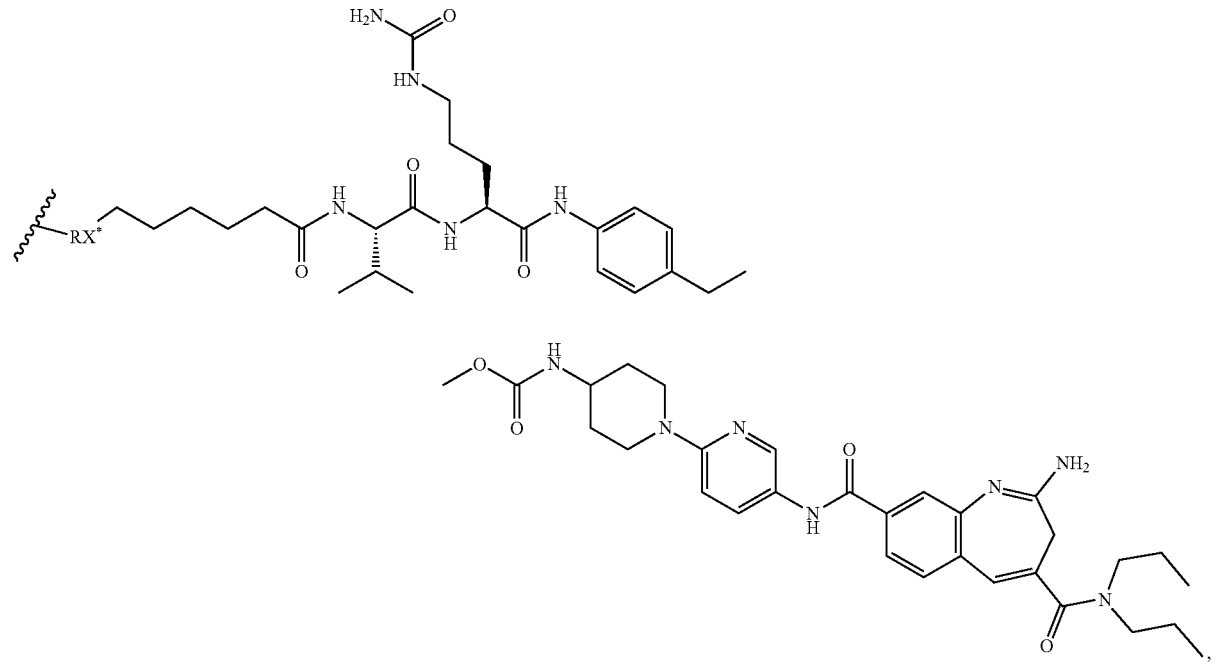

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

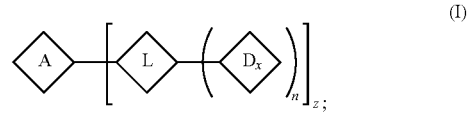

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

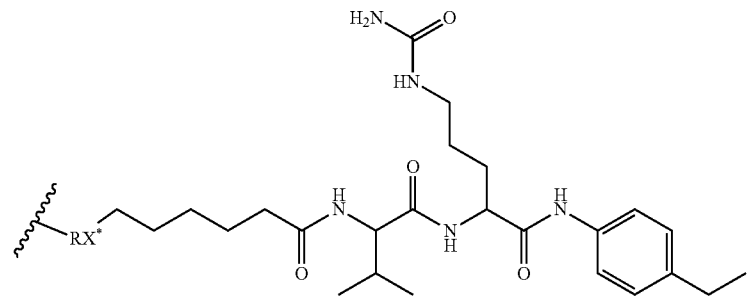

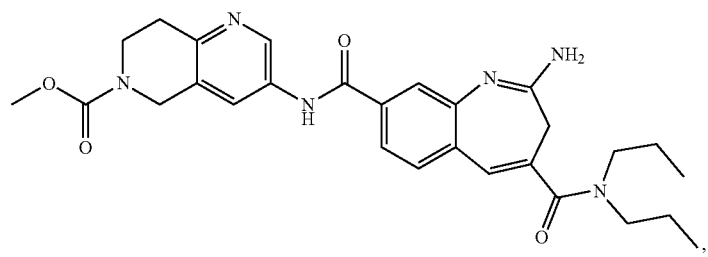

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein:

A is an anti-ASGR1 antibody or antigen-binding fragment thereof;

n is selected from 1 to 20;

z is selected from 1 to 20;

L is the linker; and

Dx is a myeloid cell agonist, wherein the myeloid cell agonist is a TLR8 agonist; and L and $D_x$ have a structure of:

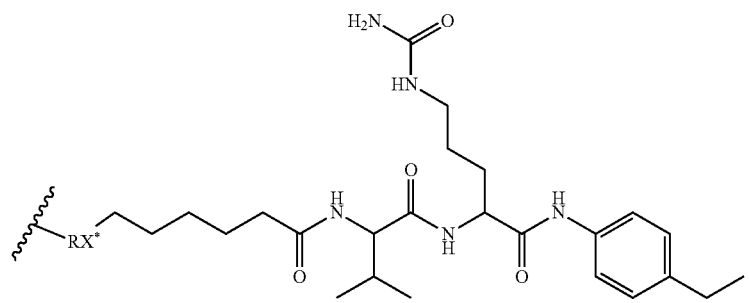

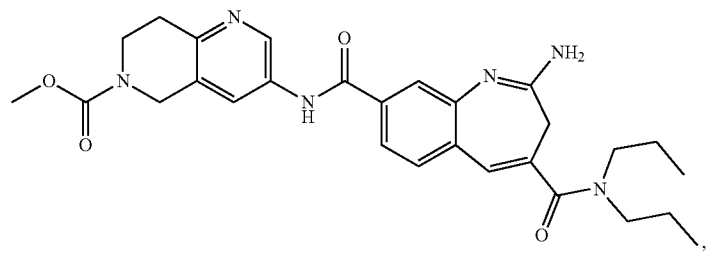

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

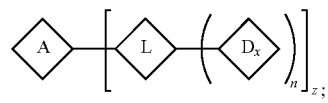

(I)

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

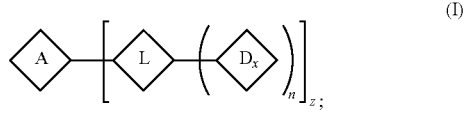

wherein:

A is an anti-ASGR1 antibody or antigen-binding fragment thereof;

n is selected from 1 to 20;

z is selected from 1 to 20;

L is the linker; and

Dx is a myeloid cell agonist, wherein the myeloid cell agonist is a TLR8 agonist; and L and $D_x$ have a structure of:

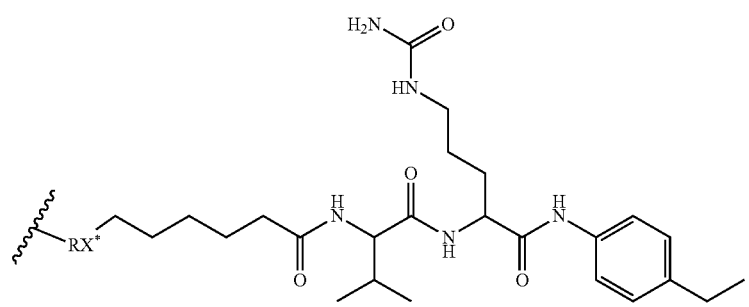

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

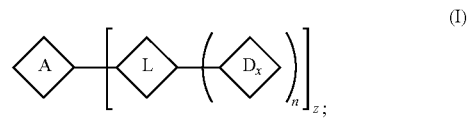

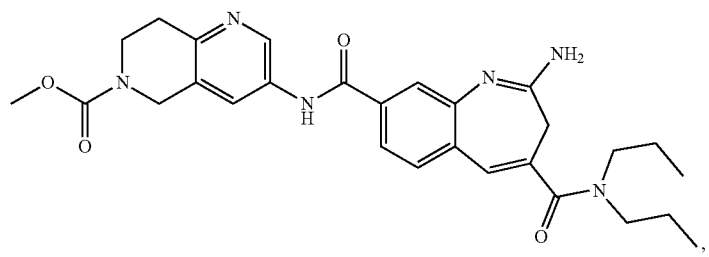

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

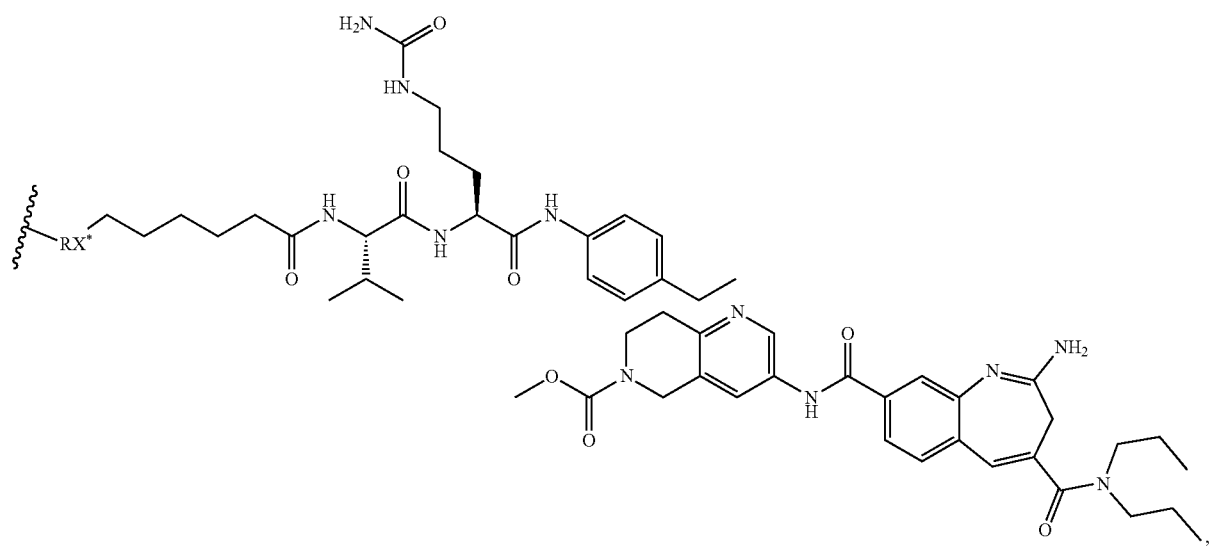

or a salt thereof, wherein the RX is a bond, a succinimide moiety, or a hydrolyzed succinimide moiety bound to a residue of an antibody, wherein

on RX* represents the point of attachment to the residue of the antibody, wherein the antibody binds to ASGR1; wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

$$A-\left[L-\left(D_x\right)_n\right]_z \quad (I)$$

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

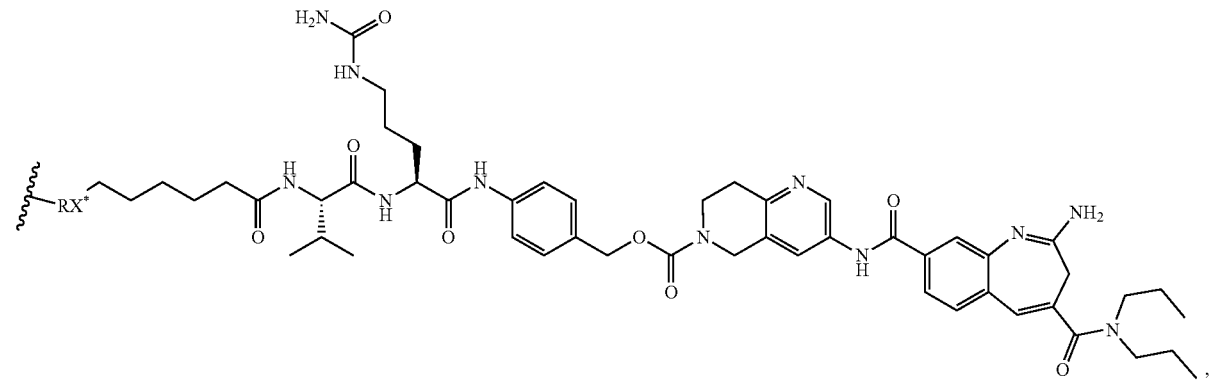

607 or a salt thereof, wherein the RX* is a bond, a succinimide moiety, or a hydrolyzed succinimide moiety bound to a residue of an antibody, wherein on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

$$\langle A \rangle - \left[ \langle L \rangle - \left( \langle D_x \rangle \right)_n \right]_z ;$$ (I)

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

608 or a salt thereof, wherein the RX* is a bond, a succinimide moiety, or a hydrolyzed succinimide moiety bound to a residue of an antibody, wherein on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO:134.

In some embodiments, a myeloid cell agonist conjugate is represented by Formula (I):

$$\langle A \rangle - \left[ \langle L \rangle - \left( \langle D_x \rangle \right)_n \right]_z ;$$ (I)

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

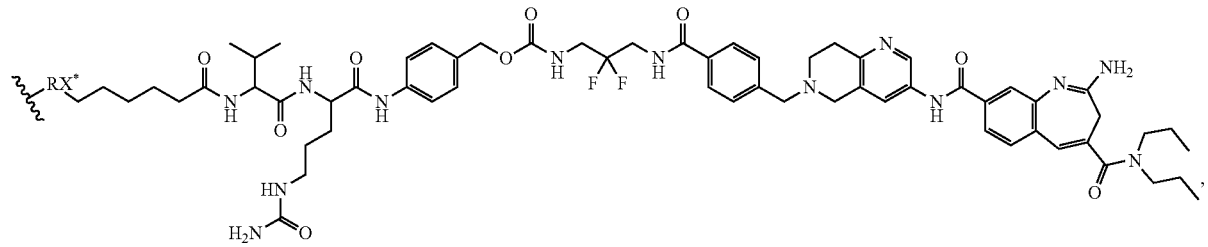

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

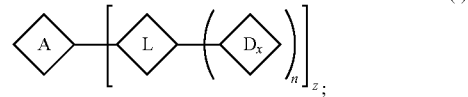

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

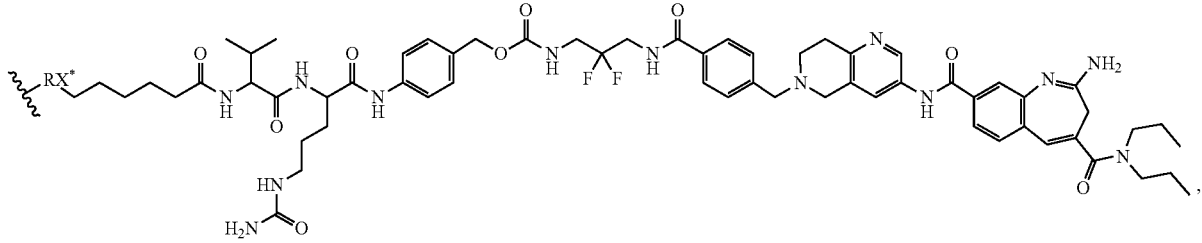

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

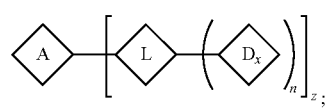

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

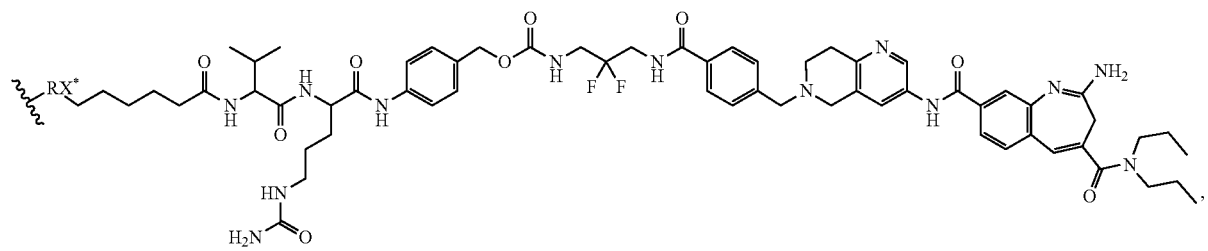

or a salt thereof, wherein the RX* is a bond, a succinimide moiety, or a hydrolyzed succinimide moiety bound to a residue of an antibody, wherein on RX* represents the point of attachment to the residue of the antibody, wherein the antibody binds to ASGR1;
wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

In some embodiments, a myeloid cell agonist conjugate is represented by Formula (I):

wherein:
A is an anti-ASGR1 antibody or antigen-binding fragment thereof;
n is selected from 1 to 20;
z is selected from 1 to 20;
L is the linker; and
Dx is a myeloid cell agonist, wherein the myeloid cell agonist is a TLR8 agonist; and L and $D_x$ have a structure of:

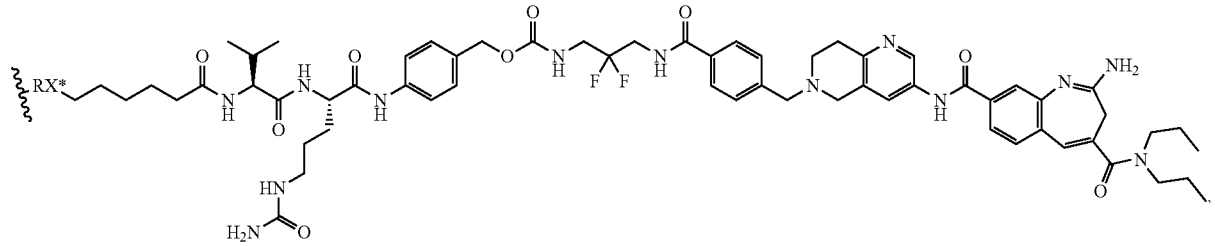

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 240 and a light chain variable region comprising the amino acid sequence of SEQ ID NO: 247.

In some embodiments, a myeloid cell agonist conjugate is represented by Formula (I):

$$A-\left[L-\left(D_x\right)_n\right]_z; \quad (I)$$

wherein:
A is an anti-ASGR1 antibody or antigen-binding fragment thereof,
n is selected from 1 to 20;
z is selected from 1 to 20;
L is the linker; and
Dx is a myeloid cell agonist, wherein the myeloid cell agonist is a TLR8 agonist; and
L and $D_x$ have a structure of:

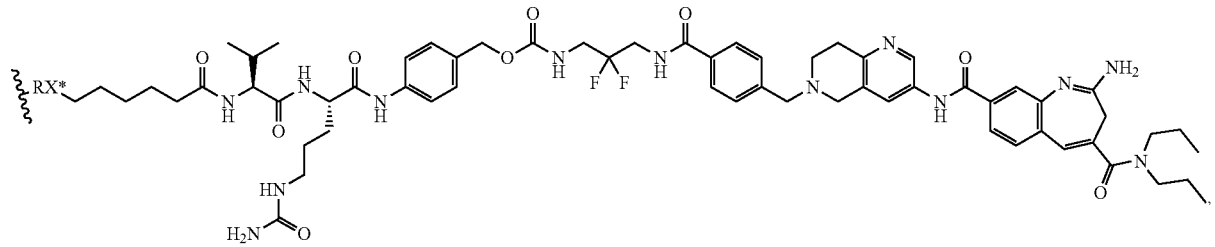

or a salt thereof, wherein the RX* is a bond, a succinimide moiety, or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or the antibody comprises a heavy chain variable region comprising the amino acid sequence of SEQ ID NO: 239 and a light chain variable region comprising the amino acid sequence of SEQ ID NO: 247.

In some embodiments, a myeloid cell agonist conjugate is represented by Formula (I):

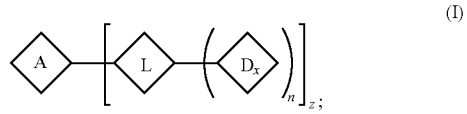

wherein:

A is an anti-ASGR1 antibody or antigen-binding fragment thereof, n is selected from 1 to 20;

z is selected from 1 to 20;

L is the linker; and

Dx is a myeloid cell agonist, wherein the myeloid cell agonist is a TLR8 agonist; and L and $D_x$ have a structure of:

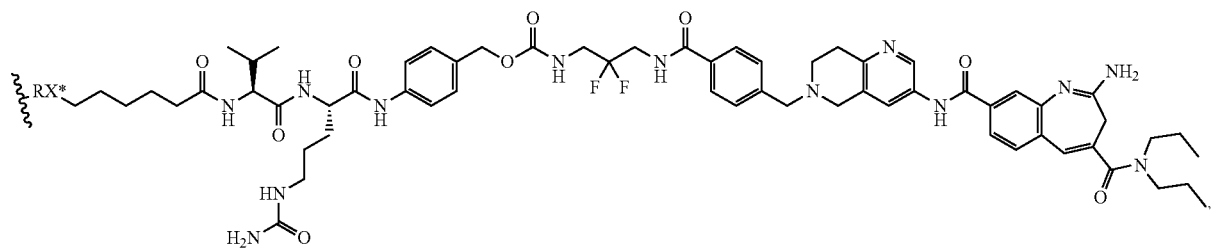

or a salt thereof, wherein the RX* is a bond, a succinimide moiety or a hydrolyzed succinimide moiety bound to a residue of an antibody, wherein

on RX* represents the point of attachment to the residue of the antibody, wherein the antibody binds to ASGR1;

wherein the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or the antibody comprises a heavy chain variable region comprising the amino acid sequence of SEQ ID NO: 89 and a light chain variable region comprising the amino acid sequence of SEQ ID NO: 134.

The activation, stimulation or augmentation of an immune response by an immune-stimulatory conjugate, such as a myeloid cell agonist, can be measured in vitro by co-culturing immune cells (e.g., myeloid cells) with cells targeted by the conjugate and measuring cytokine release, chemokine release, proliferation of immune cells, upregulation of immune cell activation markers, and/or ADCC. ADCC can be measured by determining the percentage of remaining target cells in the co-culture after administration of the conjugate with the target cells, myeloid cells, and other immune cells. In some embodiments, an immune-stimulatory conjugate can activate or stimulate immune cell activity, as determined by in vitro assay, such as a cytokine release assay, by detection of activation markers (e.g., MHC class II markers) or other assays known in the art. In some embodiments, an immune-stimulatory conjugate has an EC50 of 100 nM or less, as determine by cytokine release assay. In some embodiments, an immune-stimulatory conjugate has an EC50 of 50 nM or less, as determine by cytokine release assay. In some embodiments, an immune-stimulatory conjugate has an EC50 of 10 nM or less, as determine by cytokine release assay. In some embodiments, an immune-stimulatory conjugate has an EC50 of 1 mM or less.

In some embodiments, the disclosure provides a conjugate represented by the following structure:

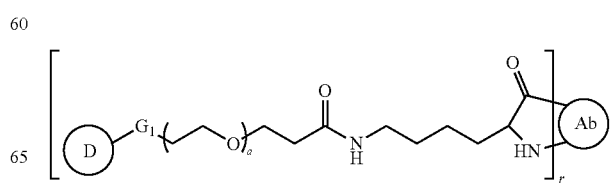

or a pharmaceutically acceptable salt thereof, wherein Ab comprises an anti-ASGR1 antibody or an antigen-binding fragment thereof of the disclosure, D is a compound or salt of a Category B compound of Formula (IID):

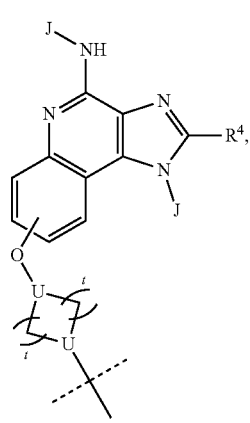

wherein R⁴ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10.

In some embodiments, D has the following structure:

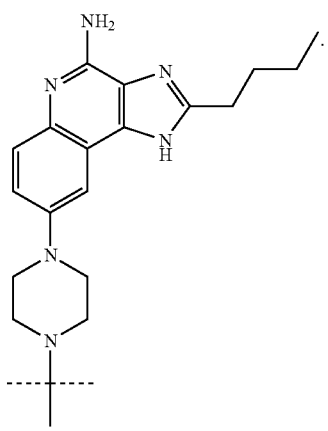

In some embodiments, the conjugate has the following structure:

In any of the aforementioned embodiments having a conjugate structure of:

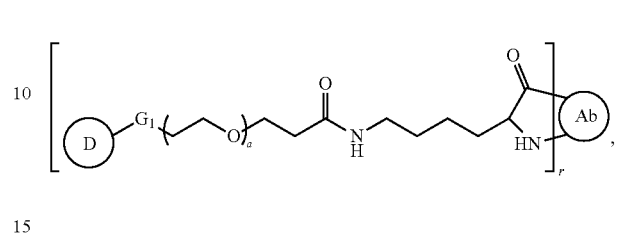

wherein D is a compound or salt of a Category B compound of a Formula (IID):

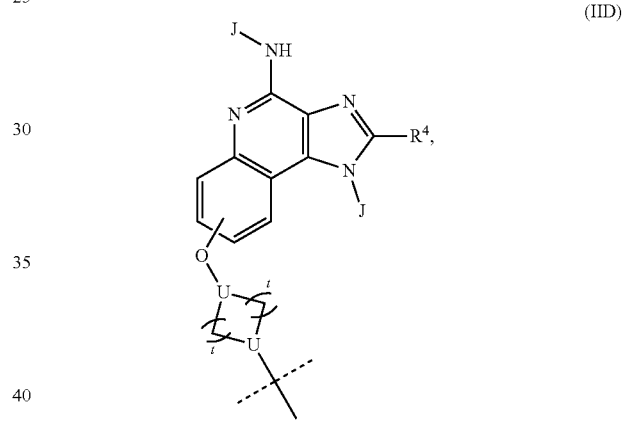

wherein R⁴ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10; or

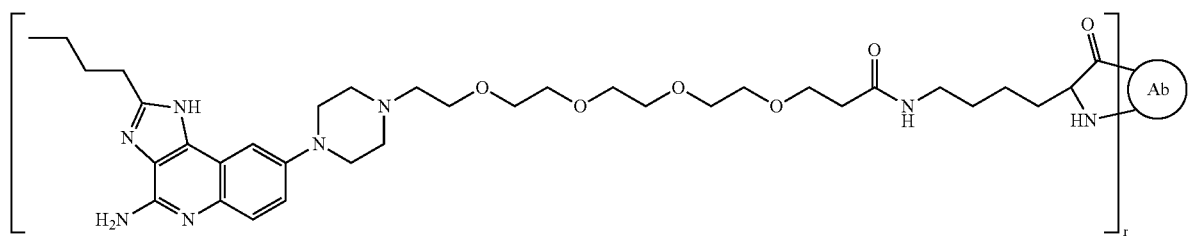

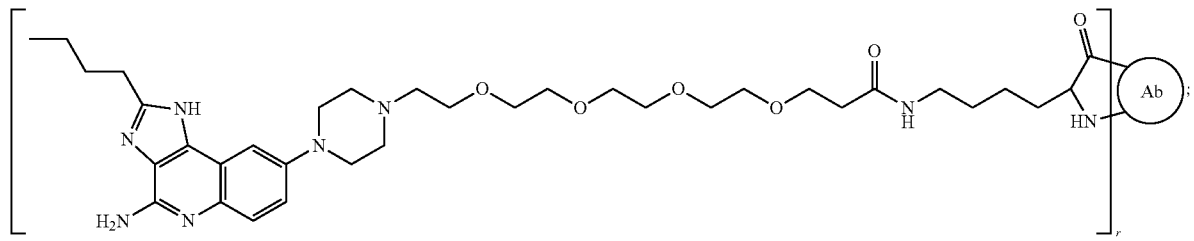

the antibody of the conjugate comprises a CDR1 (VH-CDR1) comprising the amino acid sequence of SEQ ID NO:1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or comprises a heavy chain variable region comprising the amino acid sequence of SEQ ID NO: 240 and a light chain variable region comprising the amino acid sequence of SEQ ID NO: 247.

In any of the aforementioned embodiments having a conjugate structure of:

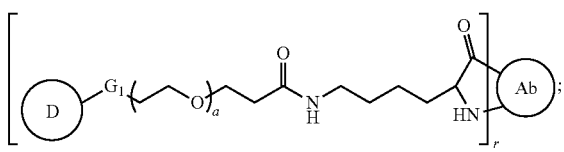

wherein D is a compound or salt of a Category B compound of Formula (IID):

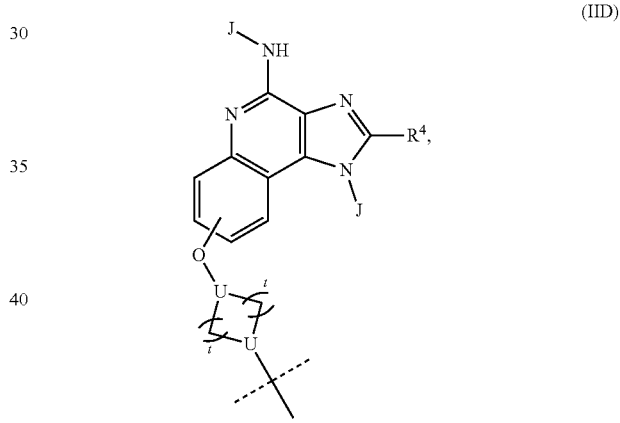

wherein $R^4$ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10; or

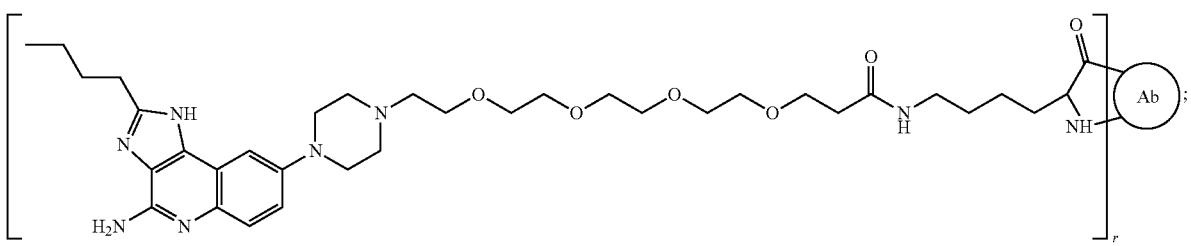

the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or comprises a heavy chain variable region comprising the amino acid sequence of SEQ ID NO: 239 and a light chain variable region comprising the amino acid sequence of SEQ ID NO: 247.

In any of the aforementioned embodiments having a conjugate structure of:

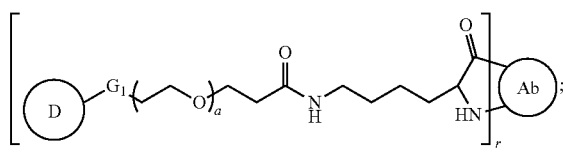

wherein D is a compound or salt of a Category B compound of Formula (IID):

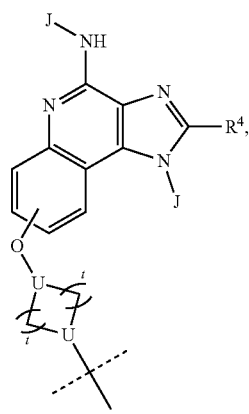

(IID)

wherein $R^4$ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10; or the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or comprises a heavy chain variable region comprising the amino acid sequence of SEQ ID NO: 89 and a light chain variable region comprising the amino acid sequence of SEQ ID NO:134.

In another aspect, the disclosure provides a conjugate represented by the following structure:

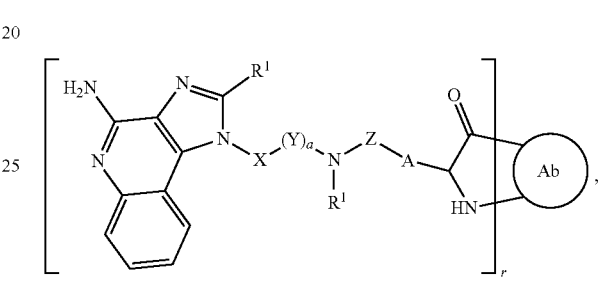

or a pharmaceutically acceptable salt thereof, wherein Ab comprises an anti-ASGR1 antibody or an antigen-binding fragment thereof of the disclosure; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$, $R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy; X is selected from O and $CH_2$; subscript n is an integer from 1 to 12; and subscript r is an integer from 1 to 10.

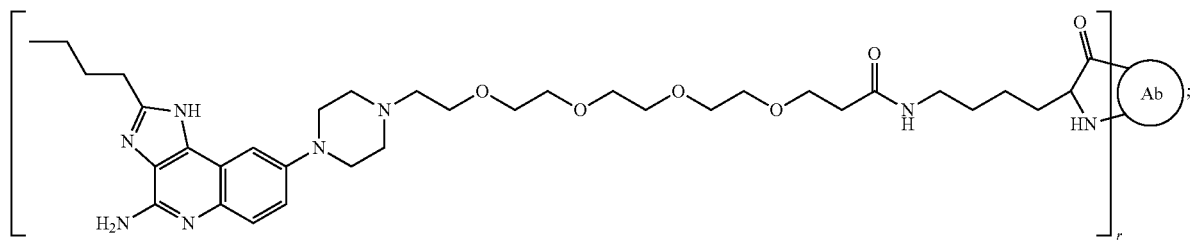

In some embodiments, the conjugate is represented by the following structure:

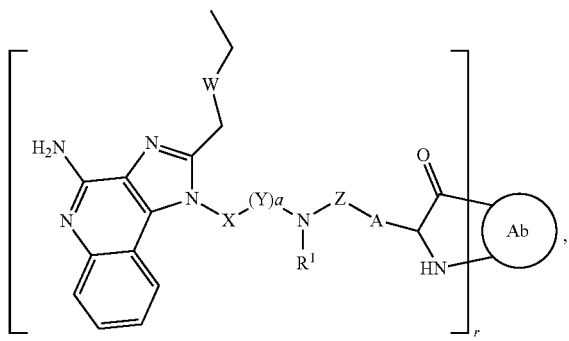

or a pharmaceutically acceptable salt thereof, wherein Ab comprises an anti-ASGR1 antibody or an antigen-binding fragment thereof of the disclosure; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$; X is selected from O and $CH_2$; subscript n is an integer from 1 to 12; and W is selected from the group consisting of O and $CH_2$.

In some embodiments, the conjugate is represented by the following structure:

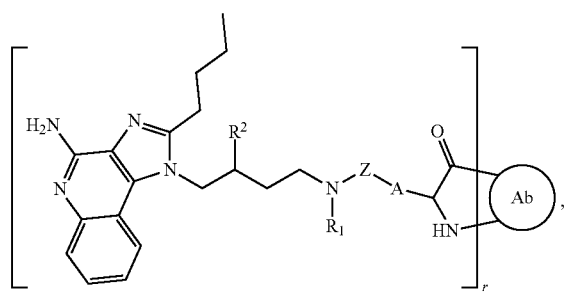

or a pharmaceutically acceptable salt thereof, wherein Ab comprises an anti-ASGR1 antibody or antigen-binding fragment thereof of the disclosure; subscript r is an integer from 1 to 10; A is an unmodified amino acid sidechain in the antibody or a modified amino acid sidechain in the antibody; Z is a linking moiety; and $R^1$ is selected from H and $C_{1-4}$ alkyl; or Z, $R^1$, and the nitrogen atom to which they are attached form a linking moiety comprising a 5- to 8-membered heterocycle; and $R^2$ is selected from H, OH, and $NH_2$.

In some embodiments, the conjugate is represented by the following structure:

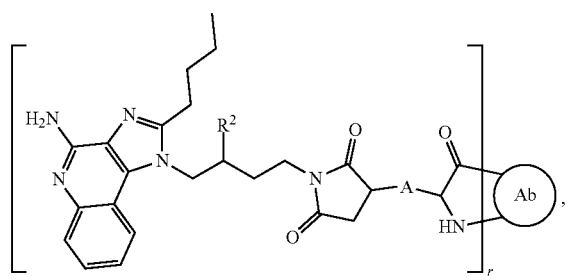

or a pharmaceutically acceptable salt thereof, wherein Ab comprises an anti-ASGR1 antibody or antigen-binding fragment thereof of the disclosure; A is an unmodified amino acid sidechain in the antibody or a modified amino acid sidechain in the antibody; $R^8$ is selected from H, OH, and $NH_2$; and subscript r is an integer from 1 to 10.

In embodiments having a conjugate structure of:

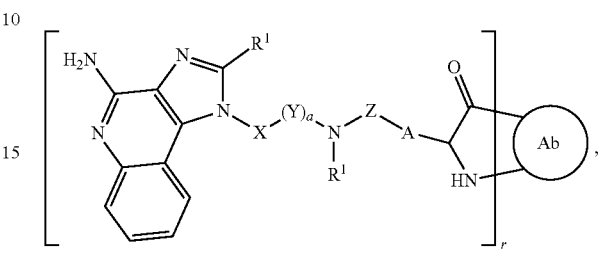

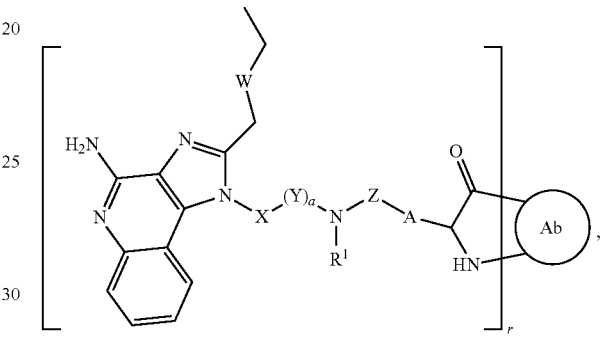

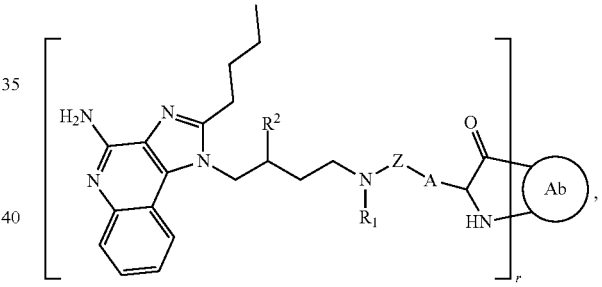

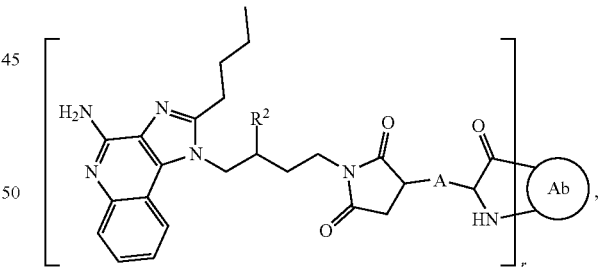

the antibody of the conjugate comprises a CDR1 (VH-CDR1) comprising the amino acid sequence of SEQ ID NO: 1, a VH-CDR2 comprising the amino acid sequence of SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or comprises a heavy chain variable region comprising the amino acid sequence of SEQ ID NO: 240 and a light chain variable region comprising the amino acid sequence of SEQ ID NO: 247.

625

In embodiments having a conjugate structure of:

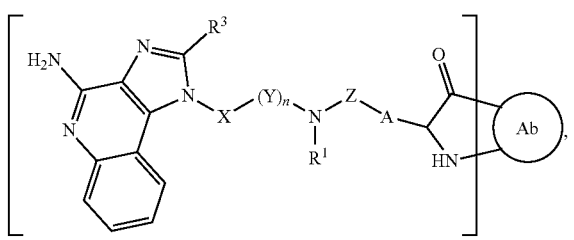

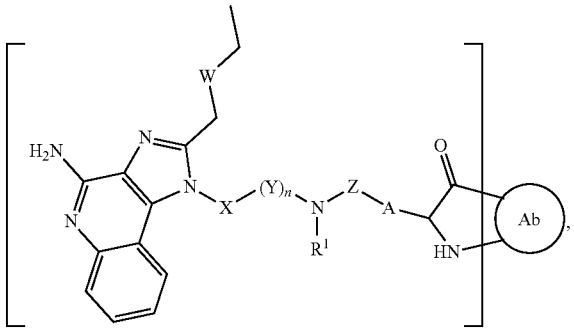

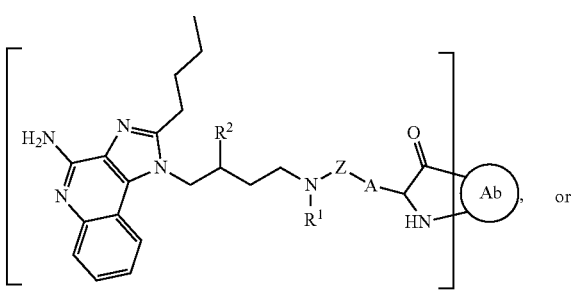

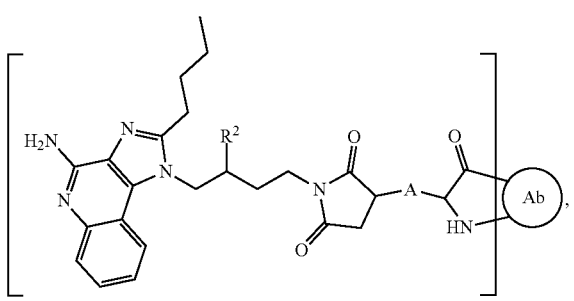

, or the antibody of the conjugate comprises a CDR1 (VH-CDR1) comprising the amino acid sequence of SEQ ID NO:1, a VH-CDR2 comprising the amino acid sequence of SEQ ID NO:6, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence of SEQ ID NO:23, and a VL-CDR3 comprising the amino acid sequence of SEQ ID NO:33; or comprises a heavy chain variable region comprising the amino acid sequence of SEQ ID NO: 239 and a light chain variable region comprising the amino acid sequence of SEQ ID NO: 247.

626

In embodiments having a conjugate structure of:

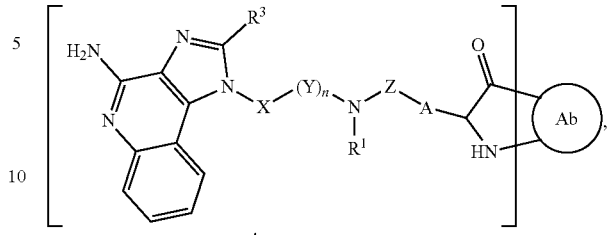

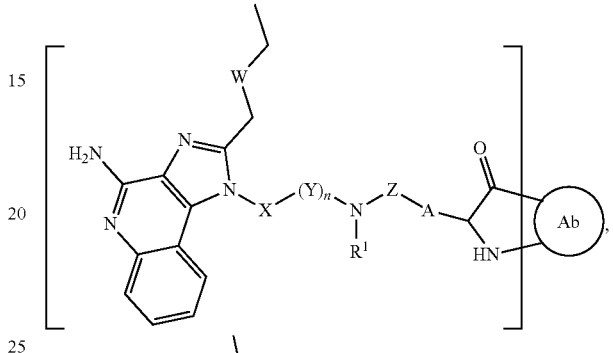

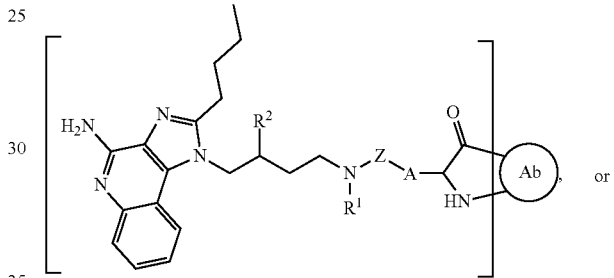

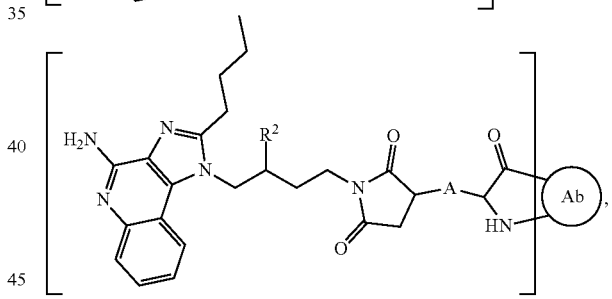

, or

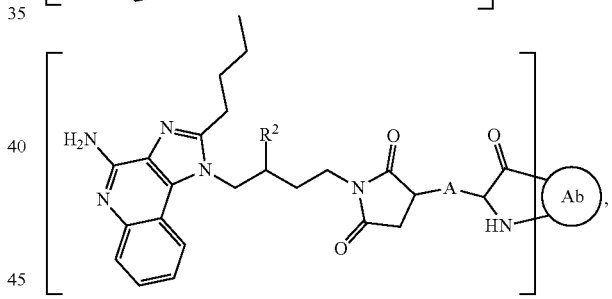

, the antibody of the conjugate comprises a CDR1 (VH-CDR1) comprising the amino acid sequence of SEQ ID NO:2, a VH-CDR2 comprising the amino acid sequence of SEQ ID NO:9, a VH-CDR3 comprising the amino acid sequence of SEQ ID NO:14; and the VL comprises a CDR1 (VL-CDR1) comprising the amino acid sequence of SEQ ID NO:19, a VL-CDR2 comprising the amino acid sequence of SEQ ID NO:26, and a VL-CDR3 comprising the amino acid sequence of SEQ ID NO:34; or comprises a heavy chain variable region comprising the amino acid sequence of SEQ ID NO: 89 and a light chain variable region comprising the amino acid sequence of SEQ ID NO:134.

Pharmaceutical Formulations

The conjugates of the disclosure are useful as pharmaceutical compositions for administration to a subject in need thereof. Pharmaceutical compositions can comprise the conjugates of the disclosure and one or more pharmaceutically acceptable excipients, suitable for administration by a selected route. A pharmaceutical composition can comprise any conjugate of the disclosure. A pharmaceutical composition can further comprise buffers, carbohydrates, and/or preservatives, as appropriate. Pharmaceutical compositions comprising a conjugate can be manufactured, for example, by lyophilizing the conjugate, mixing, dissolving, emulsifying, encapsulating or entrapping the conjugate. The pharmaceutical compositions can also include the conjugates of the disclosure in a free-base form or pharmaceutically-acceptable salt form.

Methods for formulation of the pharmaceutical compositions can include formulating any of the conjugates of the disclosure with one or more inert, pharmaceutically-acceptable excipients or carriers to form a solid, semi-solid, or liquid composition for intravenous or subcutaneous administration. Solid compositions can include, for example, powders, and in some embodiments, the solid compositions further contain nontoxic, auxiliary substances, for example wetting or emulsifying agents, pH buffering agents, and other pharmaceutically-acceptable additives. Alternatively, the compositions of the disclosure can be lyophilized or in powder form for re-constitution with a suitable vehicle, e.g., sterile pyrogen-free water, before use.

The pharmaceutical compositions and formulations can be sterilized. Sterilization can be accomplished by filtration through sterile filtration.

The pharmaceutical compositions of the disclosure can be formulated for administration as an injection, e.g., an intravenous or subcutaneous injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Alternatively, the pharmaceutical compositions of the disclosure can be lyophilized or in powder form for reconstitution with a suitable vehicle, e.g., sterile pyrogen-free water, before use.

The conjugates can be formulated for administration in a unit dosage form in association with a pharmaceutically acceptable vehicle. Such vehicles can be inherently non-toxic, and non-therapeutic. A vehicle can be water, saline, Ringer's solution, dextrose solution, and 5% human serum albumin. Nonaqueous vehicles such as fixed oils and ethyl oleate can also be used. The vehicle can contain minor amounts of additives such as substances that enhance isotonicity and chemical stability (e.g., buffers and preservatives).

In some embodiments, an aqueous formulation of a conjugate provided in the disclosure, such as for subcutaneous administration, has a pH from 4-5.2. The aqueous formulation may comprise one or more excipients, such as, for example, one or more buffering agents, one or more lyoprotectants, and the like. In some embodiments, the pH of the formulation is from 4-5.1, 4.1-5.1, 4.2-5.1, 4.3-5.1, 4.4-5.1, 4.5-5.1, 4-5, 4.1-5, 4.2-5, 4.3-5, 4.4-5, or 4.5-5. In some embodiments, the formulation comprises at least one buffer. In various embodiments, the buffer may be selected from histidine, citrate, aspartate, acetate, phosphate, lactate, tromethamine, gluconate, glutamate, tartrate, succinate, malic acid, fumarate, a-ketoglutarate, and combinations thereof. In some embodiments, the buffer is at least one buffer selected from histidine, citrate, aspartate, acetate, and combinations thereof. In some embodiments, the buffer is a combination of histidine and aspartate. In some embodiments, the total concentration of the buffer in the aqueous formulation is 10 mM to 40 mM, such as 15 mM-30 mM, 15 mM-25 mM, or 20 mM.

In some embodiments, the aqueous formulation comprises at least one lyoprotectant. In some embodiments, the at least one lyoprotectant is selected from sucrose, arginine, glycine, sorbitol, glycerol, trehalose, dextrose, alpha-cyclodextrin, hydroxypropyl beta-cyclodextrin, hydroxypropyl gamma-cyclodextrin, proline, methionine, albumin, mannitol, maltose, dextran, and combinations thereof. In some embodiments, the lyoprotectant is sucrose. In some embodiments, the total concentration of lyoprotectant in the aqueous formulation is 3-12%, such as 5-12%, 6-10%, 5-9%, 7-9%, or 8%.

In some embodiments, the aqueous formulation comprises at least one surfactant. Exemplary surfactants include polysorbate 80, polysorbate 20, poloxamer 88, and combinations thereof. In some embodiments, the aqueous formulation comprises polysorbate 80. In some embodiments, the total concentration of the at least one surfactant is 0.01%-0.1%, such as 0.01%-0.05%, 0.01%-0.08%, or 0.01%-0.06%, 0.01%-0.04%, 0.01%-0.03%, or 0.02%.

In some embodiments, the concentration of the conjugate in the aqueous formulation is 1 mg/mL-200 mg/mL, such as 10 mg/mL-160 mg/mL, 10 mg/mL-140 mg/mL, 10 mg/mL-120 mg/mL, 20 mg/mL-120 mg/mL, or 30 mg/mL-120 mg/mL, or 40 mg/mL-120 mg/mL, or 40 mg/mL-100 mg/mL. In some embodiments, the concentration of the conjugate in the aqueous formulation is 10 mg/mL-140 mg/mL or 40 mg/mL-140 mg/mL.

Therapeutic Applications

The conjugates, pharmaceutical compositions, and methods provided in the disclosure can be useful for the treatment of a plurality of diseases, conditions, preventing a disease or a condition in a subject or other therapeutic applications for subjects in need thereof. Often the conjugates, antibodies, antibody constructs, targeting moieties, pharmaceutical compositions, and methods provided in the disclosure can be useful for treatment of liver viral diseases, such as Hepatitis B infection and Hepatitis C infection.

The disclosure provides conjugates for use in a method of treatment of the human or animal body by therapy. Therapy may be by any mechanism of the disclosure, such as by modulation (e.g., stimulation) of the immune system. The disclosure provides conjugates for use in stimulation of the immune system or immunotherapy, including for example enhancing an immune response. The disclosure provides conjugates for prevention or treatment of any condition of the disclosure, for example viral infection. The disclosure also provides conjugates for obtaining any clinical outcome of the disclosure for any condition of the disclosure, such as reducing Hepatitis B virus or Hepatitis C virus infection in vivo. The disclosure also provides use of any conjugate of the disclosure in the manufacture of a medicament for preventing or treating any condition of the disclosure.

The antibodies or antigen-binding fragments thereof, conjugates and compositions (e.g., pharmaceutical compositions) of the disclosure can be useful for a plurality of different subjects including, but are not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof. In some embodiments, the subject is a human.

Anti-ASGR1 antibodies or antigen-binding fragments thereof, conjugates, and compositions thereof of this disclosure can be useful as a therapeutic, for example, a treatment that can be administered to a subject in need thereof. A therapeutic effect of the antibodies, conjugates and compositions thereof of the disclosure can be obtained in a subject by reduction, suppression, remission, or eradication of a disease state, including, but not limited to, a symptom thereof. A therapeutic effect in a subject having a disease or condition (e.g., a liver viral infection), or pre-disposed to have or is beginning to have the disease or condition, can be obtained by a reduction, a suppression, a prevention, a remission, or an eradication of the condition or disease, or pre-condition or pre-disease state.

A "subject in need thereof" refers to an individual at risk of, or suffering from, a disease, disorder or condition, such as a liver viral infection, that is amenable to treatment or amelioration with an anti-ASGR1 antibody or antigen-binding fragment thereof, a conjugate of an anti-ASGR1 antibody or antigen-binding fragment thereof with a myeloid cell agonist (e.g., TLR7 agonist, TLR8 agonist), or a composition thereof of the disclosure. In some embodiments, a subject in need thereof is administered an anti-ASGR1 antibody or antigen-binding fragment thereof, a conjugate of an anti-ASGR1 antibody or antigen-binding fragment thereof with a myeloid cell agonist (e.g., TLR8 agonist), or a composition thereof of the disclosure to treat a liver viral infection. In some embodiments, the subject does not have cancer.

"Treatment," "treat," and/or "treating" refer to an intervention that leads to any observable beneficial effect of the treatment or any indicia of statistically significant success in the treatment or amelioration of the disease or condition, such as ameliorating a sign, symptom, or progression of a disease or pathological condition. The beneficial effect can be evidenced by, for example, a reduction, delayed onset, or alleviation of the severity of clinical symptoms of the disease in a subject, a reduction in the frequency with which symptoms of a disease are experienced by a subject, a slower progression of the disease, a reduction in the number of relapses of the disease, an improvement in the overall health or well-being of the subject, or by other parameters that are specific to the particular disease.

A prophylactic treatment meant to "prevent" a disease or condition is a treatment administered to a subject who does not exhibit signs of a disease or exhibits only early signs, for the purpose of decreasing the risk of developing pathology or further advancement of the early disease. For example, if an individual at risk of having a liver viral infection is treated with the methods of the disclosure and does not later have the liver viral infection, then the disease has been prevented, at least over a period of time, in that individual. A prophylactic treatment can mean preventing recurrence of a disease or condition in a patient that has previously been treated for the disease or condition.

As used throughout the disclosure, the term "effective amount" or "effective dose" refers to a quantity of a specified antibody, conjugate, or composition thereof sufficient to achieve a desired (e.g., beneficial) effect in a subject being treated with that compound, conjugate, or composition thereof, such as an amount sufficient to result in amelioration of one or more symptoms of the disease being treated in a statistically significant manner, delaying worsening of a progressive disease in a statistically significant manner, or preventing onset of additional associated symptoms or diseases in a statistically significant manner, or any combination thereof. In some embodiments, an effective amount of an antibody, conjugate, or composition thereof is an amount sufficient to inhibit or treat the disease with minimal to no toxicity in the subject, excluding the presence of one or more adverse side effects. An effective amount or dose can be administered one or more times over a given period of time. An effective amount or dose can depend on the purpose of the treatment and can be ascertainable by one skilled in the art based on a subject's needs. When referring to an individual active ingredient, administered alone, an effective amount or dose refers to that ingredient alone. When referring to a combination, an effective amount or dose refers to combined amounts of the active ingredients that result in the therapeutic effect, whether administered serially or simultaneously.

Anti-ASGR1 antibodies or antigen-binding fragments thereof, conjugates, and pharmaceutical compositions of this disclosure that can be used in therapy can be formulated and dosages established in a fashion consistent with good medical practice taking into account the disease or condition to be treated, the condition of the individual patient, the site of delivery of the composition, the method of administration and other factors known to practitioners.

Administration to a subject of an effective amount or dose of an anti-ASGR1 antibody, conjugate, or composition thereof of this disclosure can be by one or more routes and can occur one or more times over a given period of time. One of ordinary skill in the art would understand that the amount, duration and frequency of administration of a compound, conjugate, or composition thereof of this disclosure to a subject in need thereof depends on several factors including, for example, the health of the subject, the specific disease or condition of the patient, the grade or level of a specific disease or condition of the patient, the additional treatments the subject is receiving or has received, or the like. Exemplary routes of administration include systemic, cutaneous, subcutaneous, intravenous, intra-arterial, subdural, intramuscular, intracranial, intrasternal, intratumoral, intraperitoneal. Additionally, a compound, conjugate, or composition thereof of this disclosure can be administered to a subject by other routes of administration, for example, by inhalation, or oral, dermal, intranasal or intrathecal administration. In some embodiments, a compound, conjugate, or composition thereof of the disclosure is administered at a site of the liver viral infection.

Anti-ASGR1 antibodies or antigen-binding fragments thereof, conjugates, and compositions thereof the disclosure can be administered to a subject in need thereof in a first administration, and subsequently in one or more additional administrations. The one or more additional administrations can be administered to the subject in need thereof minutes, hours, days, weeks or months following the first administration. Any one of the additional administrations can be administered to the subject in need thereof less than 21 days, or less than 14 days, less than 10 days, less than 7 days, less than 4 days or less than 1 day after the first administration. The one or more administrations can occur more than once per day, more than once per week or more than once per month. The administrations can be weekly, biweekly (every two weeks), every three weeks, monthly or bimonthly.

In some embodiments of practicing the methods of the disclosure, the conjugates are administered in an effective regimen of at least two or at least three cycles. Each cycle can optionally include a resting stage between cycles. Cycles of administration can be of any suitable length. In some embodiments, each cycle is a week (7 days), 10 days, every two weeks (14 days or biweekly), every three week (21 days) or every four weeks (28 days). In some embodiments, each cycle is a month. In some embodiments, at least two doses of the immune-stimulatory conjugate are administered more than 7 days apart, or more than 10 days apart. In some embodiments, at least one dose of the conjugate is administered more than 7 days, or more than 10 days, after the initial dose of the conjugate.

In some embodiments, the total dose of the conjugate within a cycle is from about 0.1 to about 10 mg/kg. In some embodiments, the total dose is from about 0.5 to about 7.5 mg/kg. In some embodiments, the total dose is from about 0.5 to about 5 mg/kg. In some embodiments, the total dose is from about 0.5 to about 4 mg/kg. In some embodiments, the total dose is from about 0.5 to about 3.5 mg/kg. In some embodiments, the total dose is from about 0.5 to about 2 mg/kg.

In some embodiments, using a conjugate of this disclosure can allow administration of the conjugate at greater levels of myeloid cell agonist in the form of the conjugate than the level of myeloid cell agonist alone. For example, the conjugate can be administered at a level higher than the maximum tolerated dose for that myeloid cell agonist administered in the absence of the being conjugated to the antibody, antibody construct, or targeting moiety in the conjugate. In some embodiments, administration of the conjugate can be associated with fewer side effects than when administered as the myeloid cell agonist alone.

In various embodiments, the method comprises administering an effective regimen that results in a Tmax of the conjugate of greater than 4 hours following each administration of the conjugate. In some embodiments, the effective regimen results in a Tmax greater than 6 hours, greater than 8 hours, greater than 10 hours, greater than 12 hours, or greater than 15 hours following each administration of the conjugate.

In some embodiments, the disclosure provides a method of treating a liver viral infection. In some embodiments, the disclosure provides a method of treating a liver viral infection comprising administering to a subject in need thereof an effective amount of: (a) an anti-ASGR1 antibody conjugate comprising a compound of Formula (X-1)-(X-9), Category A of Formula (IA), (IB), (IIA), (IIB), (IIC), (IIIA), (IIIB), (IVA), (IVB), or (IVC), or pharmaceutically acceptable isomer, racemate, hydrate, solvate, isotope, or salt thereof, or (b) a composition of (a).

In some embodiments, an antibody conjugate composition for use in the methods of treating disease (such as a liver viral infection) has an average DAR of the conjugate ranging from about 2 to about 8, about 1 to about 3, or about 3 to about 5. In some embodiments, an antibody conjugate in a composition will have an average DAR ranging from 1 to about 10, from 1 to about 9, from 1 to about 8, from 1 to about 6, from 1 to about 3, from about 2 to about 8, from about 2 to about 6, from about 2.5 to about 5.5, from about 2.5 to about 4.5, from about 2 to about 4, from about 3.5 to about 5.5, from about 3 to about 5, from about 3.5 to about 4.5, from about 3.5 to about 4, or from about 3 to about 4. In some embodiments, the average DAR for the conjugates of a composition used in the methods of treatment will be about 1.5, about 2, about 2.5, about 3, about 3.5, about 4, about 4.5, about 5, about 5.5, about 6, about 6.5, about 7, about 7.5, or about 8. In some embodiments, an anti-ASGR1 antibody conjugate of this disclosure comprises from 1-20 myeloid agonist compounds (e.g., TLR8 agonists) per antibody, preferably ranges from 1 to about 8, about 3 about 5, or 1 to about 3 myeloid agonist compounds (e.g., TLR8 agonists) per antibody.

In some embodiments, the methods of treating a liver viral infection further comprise administering an additional therapeutic agent to the subject, such as an anti-viral drug, an immunomodulator, a vaccine, or a combination thereof.

Anti-viral drugs include reverse transcriptase inhibitors (e.g., nucleoside analog reverse transcriptase inhibitors, nucleotide analog reverse transcriptase inhibitors, non-nucleoside reverse transcriptase inhibitors, and nucleoside reverse transcriptase translocation inhibitors), entry inhibitors (e.g., bulevirtide), capsid inhibitors (e.g., morphothiadin, JNJ 56136379, ABI-H0731, ABI-H2158, RG7907 (RO7049389), QL-007, EPD-514, AK0605, JNJ-6379 (JNJ-56136379), AB-506, ABI-H3733, ZM-H1505R, ALG-000184), siRNAs (e.g., VIR-2218, RG6346 (DCR HBVS), ARO-HBV, BB-103, Lunar-HBV, JNJ-3989, ALN-HBV02, RG6004, AB-729), antisense oligonucleotides (e.g., GSK 3228836 (ISIS-GSK3Rx or IONIS-HBVRx), GSK3389404 (IONIS-HBV-LRx), ALG-ASO), nucleic acid polymers, Hepatitis B surface antigen (HBsAg) inhibitors (e.g., REP 2139, REP2165, GC 1102, AK-074, AK0706, ALG-10133), apoptosis inhibitor (APG-1387), ciclofilin inhibitor (e.g., CRV 431), and gene editing therapy (e.g., EBT-106, EBT-107, HBV ARCUS).

Exemplary anti-viral nucleoside or nucleotide analogs that may be used with an anti-ASGR1 antibody-myeloid cell agonist conjugate of the disclosure include entecavir (Baraclude), tenofovir disoproxil fumarate (Viread), tenofovir alafenamide (Vemlidy), lamivudine (Epivir), adefovir dipivoxil (Hepsera), telbivudine (Tyzeka), Clevudine (Levovir), besifovir (Besivo).

In some embodiments, entecavir is used in combination with an anti-ASGR1 antibody-myeloid cell agonist conjugate of the disclosure. In some embodiments, the disclosure provides use of a combination of entecavir with a conjugate represented by Formula I:

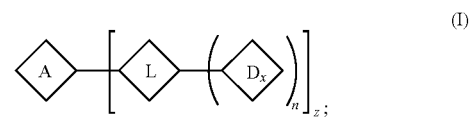

wherein: A is the anti-ASGR1 antibody or an antigen-binding fragment thereof, L is the linker; $D_x$ is the immune-stimulatory compound; n is selected from 1 to 20; and z is selected from 1 to 20, wherein the linker and the myeloid cell agonist together have a structure selected from any one of:

633 634
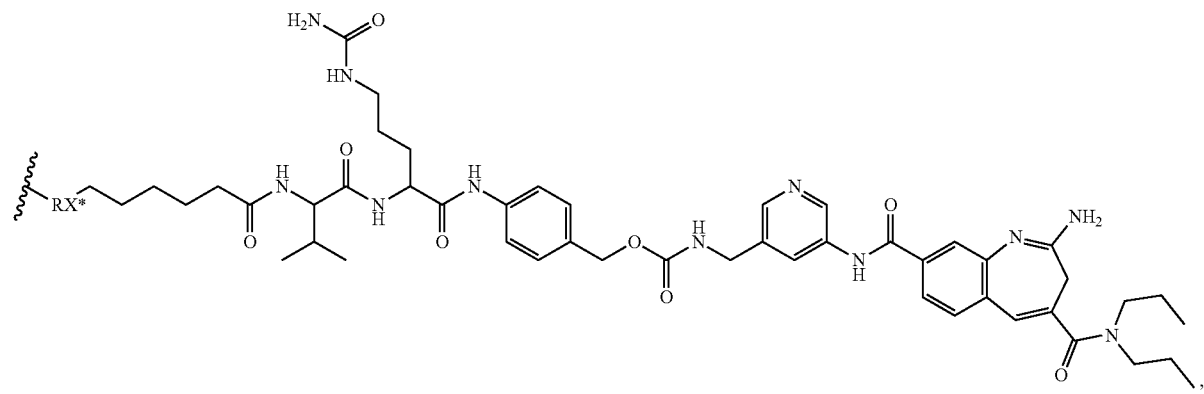
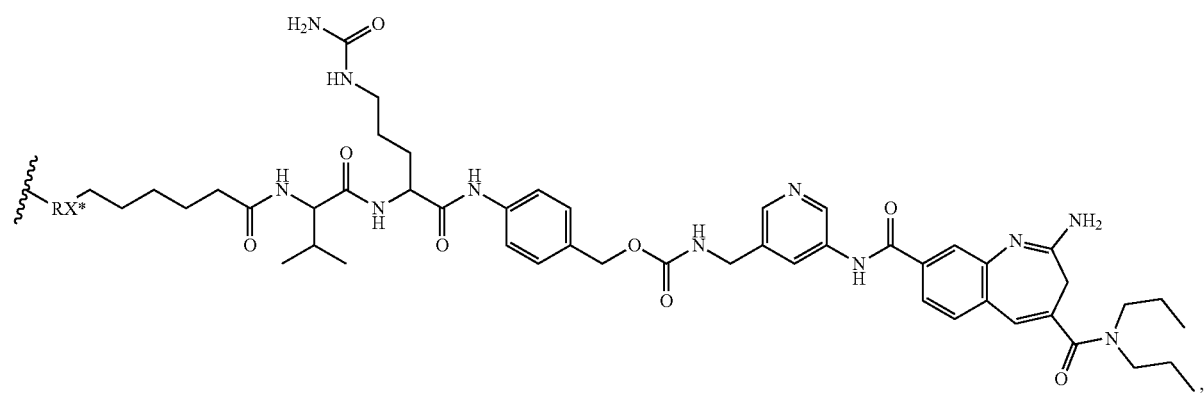
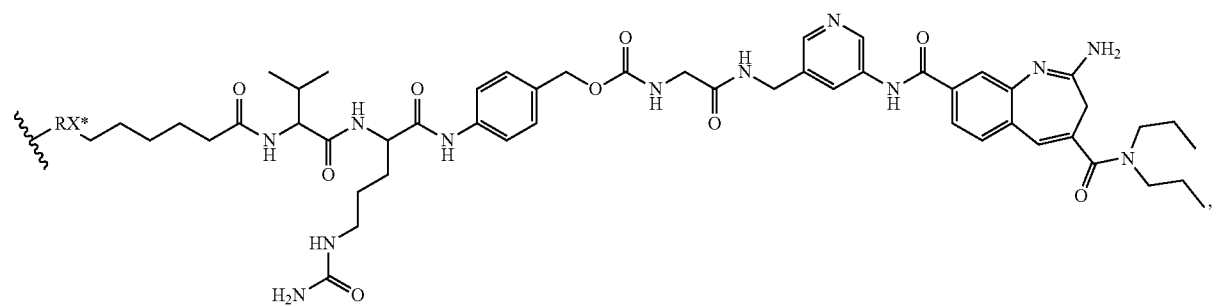
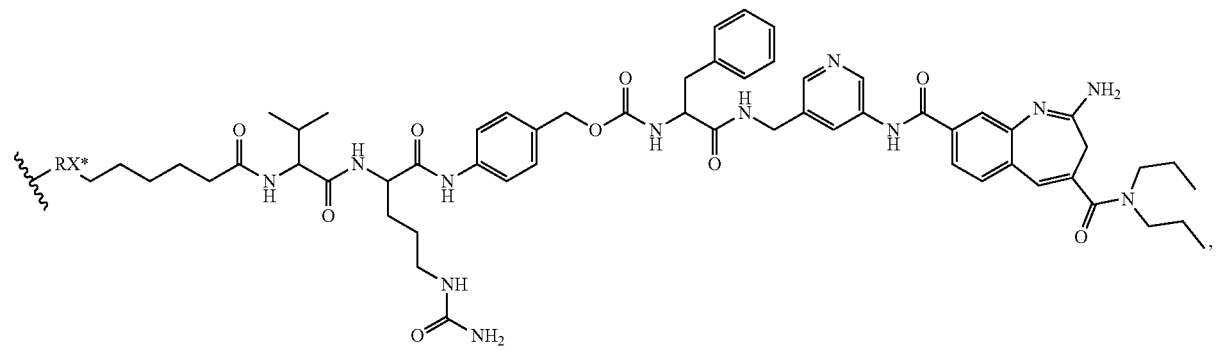

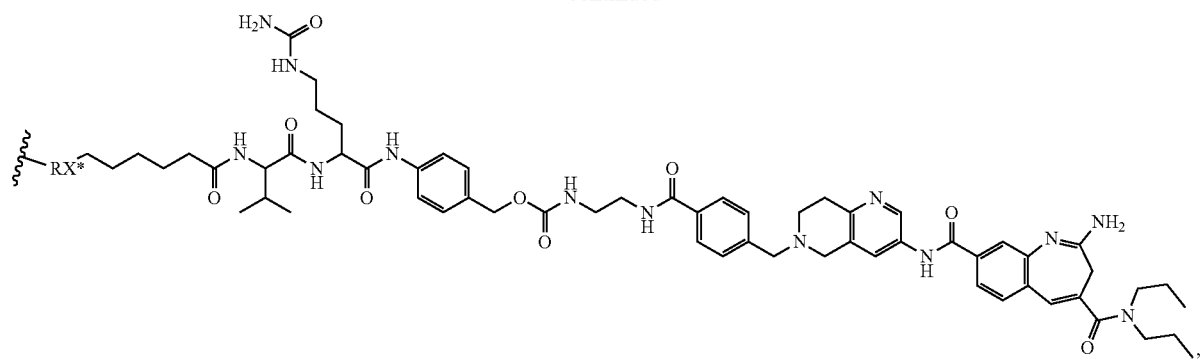
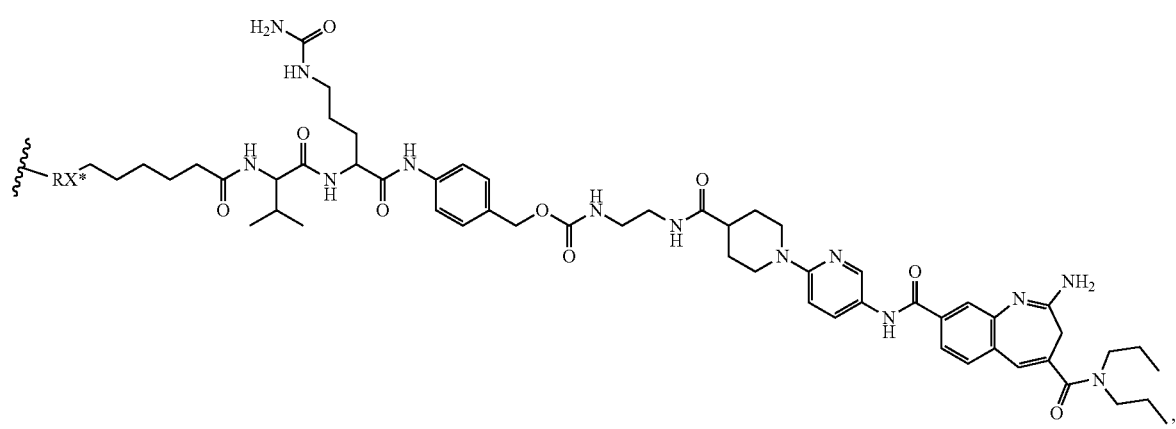
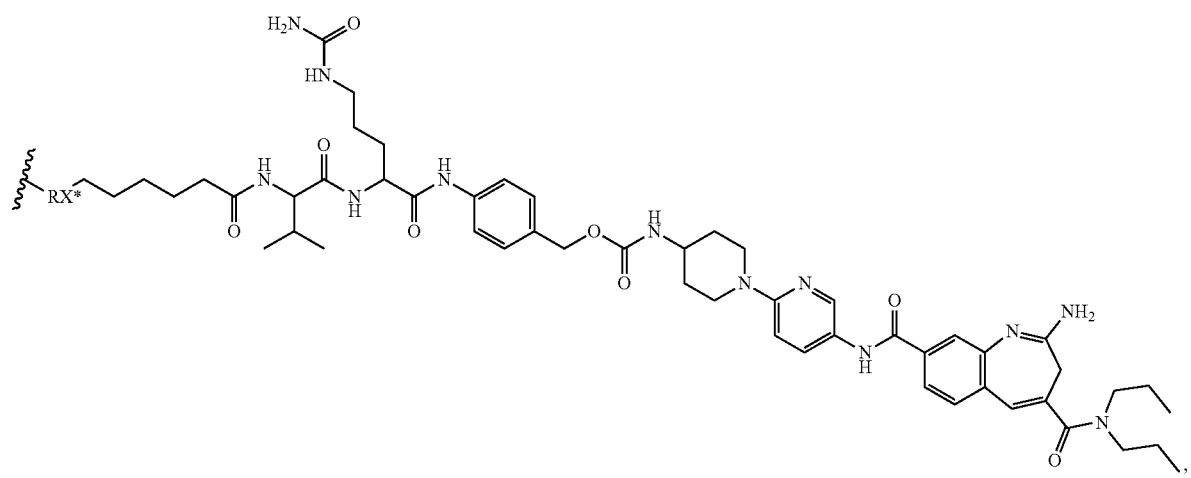
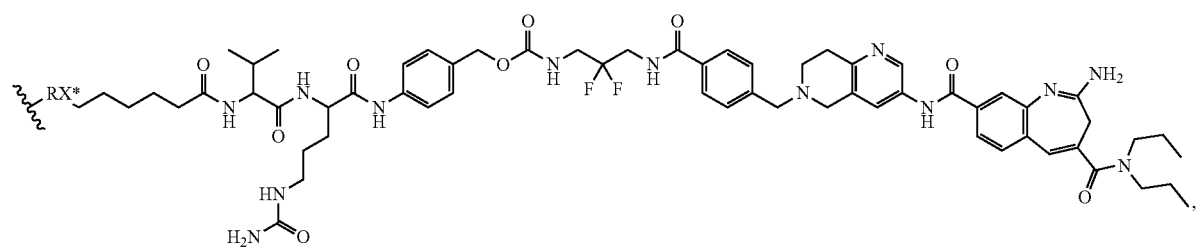

and a salt of any one thereof, wherein the RX is a bond, a succinimide moiety, or a hydrolyzed succinimide moiety bound to a residue of an antibody, antibody construct, or targeting moiety, and wherein

on RX* represents the point of attachment to the residue of the antibody, antibody construct, or targeting moiety.

Exemplary vaccines (e.g., hepatitis B vaccine) include AIC 649, INO-1800, HB-110, TG1050, HepTcell, JNJ 64300535, VBI-2601, Chimigen HBV, and CARG-201.

Exemplary immunomodulator drugs include TLR agonists (e.g., TLR2, TLR3, TLR4, TLR5, TLR6, TLR7, TLR7/TLR8, TLR8, TLR9, or TLR10 agonist), STING agonists (e.g., ADU-S100, MK-1454, MK-2118, BMS-986301, GSK3745417, SB-11285, IMSA-101), RIG-I agonists, interferon therapy, anti-PD1 therapy, anti-PD-L1 therapy, and PD-L1 inhibitors (e.g., aurigenei, BMSpep-57, BMS-103, BMS-142, BMS-1166, ASC22). Exemplary immunomodulators that may be used with an anti-ASGR1 antibody-myeloid cell agonist conjugate of the disclosure include but are not limited to Interferon a-2b (Intron A), peginterferon a-2a (Pegasys), thymalfasin (Zadaxin), Inarigivir, nivolumab, pembrolizumab, pidilizumab, toripalimab, cemiplimab, dostarlimab, spartalizumab, camrelizumab, sintilimab, tislelizumab, atezolizumab, GS-4224, RG6084 (R07191863), avelumab, durvalumab, vesatolimod, AZD8848, MEDI9197, ISA204, RG7854 (RO7020531), JNJ-4964 (AL-034), aurigenel, BMSpep-57, BMS-103, BMS-142, BMS-1166, ASC22, selgantolimod, motolimod, GS9688, RG7854, ADU-S100, MK-1454, MK-2118, BMS-986301, GSK3745417, SB-11285, IMSA-101, a TLR7 agonist of the disclosure, and a TLR8 agonist of the disclosure. In some embodiments, a TLR7 agonist is used in combination with an anti-ASGR1 antibody-TLR8 agonist conjugate of the disclosure. In some embodiments, the TLR7 agonist comprises a compound of Category B of the disclosure. In some embodiments, a TLR8 agonist is used in combination with an anti-ASGR1 antibody-TLR7 agonist conjugate of the disclosure. In some embodiments, the TLR8 agonist comprises a compound of Category A of the disclosure. The additional therapeutic agent may be administered simultaneously, prior to, or subsequent to the administration of an anti-ASGR1 antibody-myeloid cell agonist conjugate, and may be administered in the same manner as or a different route from the administration of an anti-ASGR1 antibody-myeloid cell agonist conjugate.

Application of immune-stimulatory conjugates of the disclosure shows substantial benefit in directing a subject's own immune response to cells of a particular site of disease or disorder, such as cells associated with the disease or disorder. Activating or stimulating an immune response directed to targeted cells facilitates the reduction, inhibition of proliferation, inhibition of growth, inhibition of progression, or otherwise inhibition up to and including in some cases clearance of the targeted cells. Thus, in some cases a targeted immune response activation or stimulation leads to inhibition of disease progression, or alleviation of at least one symptom of a manifest disease in a patient, up to and in some cases including complete elimination of from one symptom to an entire disease state in a subject.

In particular, the methods of the disclosure are well suited for use with immune stimulatory conjugates, such as immune stimulatory conjugates that direct an immune response in a subject to a particular disorder or disease location, cell type or cell. Accordingly, practice of some methods of the disclosure comprises selection of a suitable subject such as a subject to be subjected to or undergoing a treatment with a conjugate that directs a benzazepine or benzazepine-like compound of the conjugate to a particular disorder or disease site, cell type or cell. Often, the subject is selected for practice of the method due to having at least one symptom of a disease or disorder, or projected to develop at least one symptom of a disease or disorder (such as a subject in remission and at risk for relapse), suitable for treatment by a conjugate of the disclosure.

EXAMPLES

Example 1

Generation and Humanization of Anti-ASGR1 Monoclonal Antibodies

Hybridomas producing monoclonal antibodies (mAbs) specific for human ASGR1 were prepared from Balb/C mice immunized with ASGR1-AviHis at a service provider using their propriety protocol. Antibody heavy and light chain sequences were obtained, amplified, and cloned. Clone supernatants containing the expressed mAbs were screened for binding to a human ASGR1-IgG1Fc fusion protein, and those with a positive signal as measured by enzyme linked immunosorbent assay (ELISA) were screened for cell binding on HepG2 cells (which express ASGR1). Based on the initial selection criteria, sixteen (16) mAbs were expressed and isolated. The isolated mAbs were further analyzed for the additional characteristics including, for example, titer, low aggregate content following protein A purification, high titer, lack of cross-blocking of ligand GalNAc, calcium sensitivity, and cross-reactivity with rat ASGR1 protein. A total of five (5) clones (G2D, K2E, J4F, L4L and H8K) exhibiting strong signals in these assays were humanized and subjected to epitope binning (see Example 2) as compared to known anti-ASGR mAbs 4A2, 72G9 and 4F3 (see, e.g., PCT Publication Nos. WO 2017/058944 and WO 2014/023709), referred to in the disclosure as ASGR1 mAb-A, ASGR1 mAb-B, and ASGR1 mAb-C, respectively.

mAb G2D Humanization

For humanization of the G2D VH region (SEQ ID NO:38), the 3 CDR loops as defined by Kabat were grafted into the human germline sequence VH1-03 with JH6 to generate hzG2D VH (SEQ ID NO:43). In addition, several variants of hzG2D VH were constructed to contain one or more mouse back mutations in framework region 1 (FR1), in CDR2, at the junction of framework region 3 (FR3) with CDR2, in FR3, or any combination thereof (see SEQ ID NOS:44-51 and 82-88). Several of the humanized heavy chains were further changed by adding mutations in CDR2, namely N54Q or G55A, to remove a potential deamidation site (see SEQ ID NOS:52-81).

For humanization of the G2D VL region (SEQ ID NO:126) of clones 1-16, 19-21, 26-29, 31, and 33, the 3 CDR loops as defined by Kabat were grafted into the human germline sequence VKI-L1 with JK4 to generate hzG2D VL$_a$ (SEQ ID NO:131). In addition, mutations were introduced into humanized light chains at the CDR2/FR3 junction, namely D56S or D56E, to remove a potential isomerization site (see SEQ ID NOS:132-133).

For humanization of the G2D VL region (SEQ ID NO:126) of clones 22, 23, 30, 32, and 34-37, the 3 CDR loops as defined by Kabat were grafted into the human germline sequence VKI-O2 with JK4 to generate hzG2D VL$_b$ (SEQ ID NO:247). In addition, a mutation was introduced into humanized light chains at the CDR2/FR3 junction, namely D56S, to remove a potential isomerization site (see SEQ ID NO:248).

For humanization of the G2D VL region (SEQ ID NO:126) of clones 24 and 25, the 3 CDR loops as defined by Kabat were grafted into the human germline sequence VKI-A20 with JK4 to generate hzG2D VL$_c$ (SEQ ID NO:249).

Variable heavy region sequences were cloned into a vector containing a signal peptide sequence and human IgG1 constant region (SEQ ID NO:230), while variable light chain regions were cloned into a vector containing a signal peptide sequence and a human kappa light chain constant region (SEQ ID NO:232). A total of twenty two humanized heavy chains were paired with six humanized light chains to generate mAbs analyzed for the desirable characteristics noted above (see Table 5).

TABLE 5

Characterization of humanized G2D clones

| Name | VH (IgG1) | VL (kappa) | Titer mg/L | % POI | Guava HepG2 Screen | HepG2 EC$_{50}$ |
|---|---|---|---|---|---|---|
| G2D-C | G2D VH (SEQ ID NO:38) | G2D VL (SEQ ID NO:126) | 250 | 98 | 187/145 | 0.4 |
| hzG2D-1 | hzG2D VH V109L (SEQ ID NO:43) | hzG2D VL$_a$ (SEQ ID NO:131) | 9 | | 32/19 | |
| hzG2D-2 | hzG2.1D VH T28S, V109L (SEQ ID NO:44) | hzG2D VL$_a$ (SEQ ID NO:131) | 19 | | 38/20 | |
| hzG2D-3 | hzG2.45D VH A93T, R94S, V109L (SEQ ID NO:88) | hzG2D VL$_a$ (SEQ ID NO:131) | 59 | | 131/95 | |
| hzG2D-4 | hzG2.39D VH R66K, V67A, V109L (SEQ ID NO:82) | hzG2D VL$_a$ (SEQ ID NO:131) | 12 | | 55/22 | |
| hzG2D-5 | hzG2.8D VH T28S, A93T, R94S, V109L (SEQ ID NO:51) | hzG2D VL$_a$ (SEQ ID NO:131) | 75 | | 91/55 | |
| hzG2D-6 | hzG2.43D VH T68S, I69L, R71V, V109L (SEQ ID NO:86) | hzG2D VLa (SEQ ID NO:131) | 24 | | 39/23 | |
| hzG2D-7 | hzG2.2D VH T28S, R66K, V67A, V109L (SEQ ID NO:45) | hzG2D VLa (SEQ ID NO:131) | 12 | | 46/22 | |
| hzG2D-8 | hzG2.6D VH T28S, T68S, I69L, R71V, V109L (SEQ ID NO:49) | hzG2D VLa (SEQ ID NO:131) | 23 | | 31/21 | |
| hzG2D-9 | hzG2.40D VH R66K, V67A, A93T, R94S, V109L (SEQ ID NO:83) | hzG2D VL$_a$ (SEQ ID NO:131) | 23 | 81 | 155/117 | |
| hzG2D-10 | hzG2.44D VH T68S, I69L, R71V, A93T, R94S, V109L (SEQ ID NO:87) | hzG2D VL$_a$ (SEQ ID NO:131) | 102 | 30 | 149/63 | |
| hzG2D-11 | hzG2.41D VH R66K, V67A, T68S, I69L, R71V, V109L (SEQ ID NO:84) | hzG2D VL$_a$ (SEQ ID NO:131) | 10 | 68 | Very low | |
| hzG2D-12 | hzG2.3D VH T28S, R66K, V67A, A93T, R94S, V109L (SEQ ID NO:46) | hzG2D VL$_a$ (SEQ ID NO:131) | 19 | 67 | 158/113 | |
| hzG2D-13 | hzG2.7D VH T28S, T68S, I69L, R71V, A93T, R94S, V109L (SEQ ID NO:50) | hzG2D VL$_a$ (SEQ ID NO:131) | 54 | 46 | 140/83 | |
| hzG2D-14 | hzG2.4D VH T28S, R66K, V67A, T68S, I69L, R71V, V109L (SEQ ID NO:47) | hzG2D VL$_a$ (SEQ ID NO:131) | 10 | | 37/16 | |
| hzG2D-15 | hzG2.42D VH R66K, V67A, T68S, I69L, R71V, A93T, R94S, V109L (SEQ ID NO:85) | hzG2D VL$_a$ (SEQ ID NO:131) | 45 | 45 | 172/119 | |
| hzG2D-16 | hzG2.5D VH T28S, R66K, V67A, T68S, I69L, R71V, A93T, R94S, V109L (SEQ ID NO:48) | hzG2D VL$_a$ (SEQ ID NO:131) | 39 | 40 | 165/108 | |
| hzG2D-17 | hzG2.41D VH R66K, V67A, T68S, I69L, R71V, V109L (SEQ ID NO:84) | G2D VL (SEQ ID NO:126) | 80 | | Very low | |
| hzG2D-18 | hzG2.42D VH R66K, V67A, T68S, I69L, R71V, A93T, R94S, V109L (SEQ ID NO:85) | G2D VL (SEQ ID NO:126) | 206 | 76 | ND | |
| hzG2D-19 | G2D VH (SEQ ID NO:38) | hzG2D VLa (SEQ ID NO:131) | 33 | 90 | ND | |
| hzG2D-20 | hzG2.46D VH R66K, V67A, T68S, I69L, R71V (SEQ ID NO:238) | hzG2D VL$_a$ (SEQ ID NO:131) | 30 | | Very low | |

TABLE 5-continued

Characterization of humanized G2D clones

| Name | VH (IgG1) | VL (kappa) | Titer mg/L | % POI | Guava HepG2 Screen | HepG2 $EC_{50}$ |
|---|---|---|---|---|---|---|
| hzG2D-21 | hzG2.47D VH R66K, V67A, T68S, I69L, R71V, A93T, R94S (SEQ ID NO:239) | hzG2D $VL_a$ (SEQ ID NO:131) | 40 | | 199/127 | |
| hzG2D-22 | hzG2.46D VH R66K, V67A, T68S, I69L, R71V (SEQ ID NO:238) | hzG2D $VL_b$ (SEQ ID NO:247) | 115 | | None | |
| hzG2D-23 | hzG2.47D VH R66K, V67A, T68S, I69L, R71V, A93T, R94S (SEQ ID NO:239) | hzG2D $VL_b$ (SEQ ID NO:247) | 215 | 98 | 198/131 | 0.3 |
| hzG2D-24 | hzG2.46D VH R66K, V67A, T68S, I69L, R71V (SEQ ID NO:238) | hzG2D $VL_c$ (SEQ ID NO:249) | 3 | | None | |
| hzG2D-25 | hzG2.47D VH R66K, V67A, T68S, I69L, R71V, A93T, R94S (SEQ ID NO:239) | hzG2D $VL_c$ (SEQ ID NO:249) | 58 | | None | |
| hzG2D-26 | hzG2.47D VH R66K, V67A, T68S, I69L, R71V, A93T, R94S (SEQ ID NO:239) | hzG2.3D $VL_a$ K45E, S46T (SEQ ID NO:244) | 72 | 93 | 185/114 | |
| hzG2D-27 | hzG2D2.47D VH R66K, V67A, T68S, I69L, R71V, A93T, R94S (SEQ ID NO:239) | hzG2.4D $VL_a$ Q79E, P80Y (SEQ ID NO:245) | 165 | 98 | 191/116 | |
| hzG2D-28 | hzG2.47D VH R66K, V67A, T68S, I69L, R71V, A93T, R94S (SEQ ID NO:239) | hzG2.5D $VL_a$ F71Y, T72S (SEQ ID NO:246) | 72 | 66 | 145/92 | |
| hzG2D-29 | hzG2.49D VH R38K, R66K, V67A, T68S, I69L, R71V, A93T, R94S (SEQ ID NO:241) | hzG2D $VL_a$ (SEQ ID NO:131) | 57 | 72 | 189/108 | |
| hzG2D-30 | hzG2.49D VH R38K, R66K, V67A, T68S, I69L, R71V, A93T, R94S (SEQ ID NO:241) | hzG2D $VL_b$ (SEQ ID NO:247) | 189 | 96 | 198/115 | |
| hzG2D-31 | hzG2.50D VH R66K, V67A, T68S, I69L, R71V, L82F, S82aH, A93T, R94S (SEQ ID NO:242) | hzG2D $VL_a$ (SEQ ID NO:131) | 41 | 73 | 168/95 | |
| hzG2D-32 | hzG2.50D VH R66K, V67A, T68S, I69L, R71V, L82F, S82aH, A93T, R94S (SEQ ID NO:242) | hzG2D $VL_b$ (SEQ ID NO:247) | 153 | 94 | 167/103 | |
| hzG2D-33 | hzG2.51D VH R66K, V67A, T68S, I69L, R71V, R84T, A93T, R94S (SEQ ID NO:243) | hzG2D $VL_a$ (SEQ ID NO:131) | 60 | 61 | 164/85 | |
| hzG2D-34 | hzG2.51D VH R66K, V67A, T68S, I69L, R71V, R84T, A93T, R94S (SEQ ID NO:243) | hzG2D $VL_b$ (SEQ ID NO:247) | 198 | 86 | 194/109 | |
| hzG2D-35 | hzG2.47D VH R66K, V67A, T68S, I69L, R71V, A93T, R94S (SEQ ID NO:239) | hzG2.6D $VL_b$ D56S (SEQ ID NO:248) | 262 | 99 | ND | 0.3 |
| hzG2D-36 | hzG2.48D VH G55A, R66K, V67A, T68S, I69L, R71V, A93T, R94S (SEQ ID NO:240) | hzG2D $VL_b$ (SEQ ID NO:247) | 94 | 82 | ND | 0.3 |
| hzG2D-37 | hzG2.48D VH G55A, R66K, V67A, T68S, I69L, R71V, A93T, R94S (SEQ ID NO:240) | hzG2.6D $VL_b$ D56S (SEQ ID NO:248) | 403 | 98 | ND | 0.3 | mAb K2E Humanization

Germline VH1-46 with JH6 was used for CDR grafting the variable heavy chain (SEQ ID NO:39) and germline VKI-L1 with JK2 was used for CDR grafting the variable light chain (SEQ ID NO:127). CDR grafting was done using Kabat defined CDRs to generate hzK2E VH (SEQ ID NO:89) and hzK2E VL (SEQ ID NO:134). Several variants of hzK2E VH (SEQ ID NOS:90-93) and hzK2E VL (SEQ ID NO:135) containing mouse framework back mutations were generated, and the sequences determined using a 3D structural model for potential influence of residues on the CDR structure. In addition, mutations were introduced into humanized light chains at the CDR2/FR3 junction, namely D56E, to remove a potential isomerization site (see SEQ ID NOS:136-137). Variable heavy region sequences were cloned into a vector containing a signal peptide sequence and IgG1 constant region. Variable light regions were cloned into a vector containing a signal peptide sequence and kappa constant region.

Five humanized heavy chains were individually paired with each of four different humanized light chains to generate mAbs analyzed for the desirable characteristics noted above (see Table 6). The humanized sequences were further modified by adding an additional mutation in the light chain CDR2/FR3 junction, namely D56E, to remove a potential isomerization site.

TABLE 6

Characterization of humanized K2E clones

| Name | VH (IgG1) | VL (kappa) | Titer mg/L | % POI | HepG2 $EC_{50}$ |
|---|---|---|---|---|---|
| K2E-C | K2E VH (SEQ ID NO:39) | K2E VL (SEQ ID NO:127) | 512 | 99 | 0.50 |
| hzK2E-1 | hzK2E VH (SEQ ID NO:89) | hzK2E VL (SEQ ID NO:134) | 479 | 100 | 0.53 |
| hzK2E-2 | hzK2.1E VH R66K, V67T (SEQ ID NO:90) | hzK2E VL (SEQ ID NO:134) | 445 | 99 | 0.41 |
| hzK2E-3 | hzK2.4E VH M69L, R71A (SEQ ID NO:93) | hzK2E VL (SEQ ID NO:134) | 455 | 99 | 0.68 |
| hzK2E-4 | hzK2.2E VH R66K, V67T, M69L, R71A (SEQ ID NO:91) | hzK2E VL (SEQ ID NO:134) | 401 | 100 | 0.90 |
| hzK2E-5 | hzK2.3E VH R66K, V67T, M69L, R71A, T73K (SEQ ID NO:92) | hzK2E VL (SEQ ID NO:134) | 386 | 100 | 0.54 |
| hzK2E-6 | hzK2E VH (SEQ ID NO:89) | hzK2.1E VL S46T (SEQ ID NO:135) | 435 | 99 | |
| hzK2E-7 | hzK2.1E VH R66K, V67T (SEQ ID NO:90) | hzK2.1E VL S46T (SEQ ID NO:135) | 440 | 100 | |
| hzK2E-8 | hzK2.4E VH M69L, R71A (SEQ ID NO:93) | hzK2.1E VL S46T (SEQ ID NO:135) | 440 | 99 | |
| hzK2E-9 | hzK2.2E VH R66K, V67T, M69L, R71A (SEQ ID NO:91) | hzK2.1E VL S46T (SEQ ID NO:135) | 422 | 99 | |
| hzK2E-10 | hzK2.3E VH R66K, V67T, M69L, R71A, T73K (SEQ ID NO:92) | hzK2.1E VL S46T (SEQ ID NO:135) | 451 | 100 | 0.50 |
| hzK2E-11 | hzK2E VH (SEQ ID NO:89) | hzK2.2E VL D56E (SEQ ID NO:136) | 479 | 99 | 0.46 |
| hzK2E-12 | hzK2.1E VH R66K, V67T (SEQ ID NO:90) | hzK2.2E VL D56E (SEQ ID NO:136) | 393 | 393 | 0.45 |
| hzK2E-13 | hzK2.4E VH M69L, R71A (SEQ ID NO:93) | hzK2.2E VL D56E (SEQ ID NO:136) | 389 | 389 | 0.92 |
| hzK2E-14 | hzK2.2E VH R66K, V67T, M69L, R71A (SEQ ID NO:91) | hzK2.2E VL D56E (SEQ ID NO:136) | 411 | 411 | 0.77 |
| hzK2E-15 | hzK2.3E VH R66K, V67T, M69L, R71A, T73K (SEQ ID NO:92) | hzK2.2E VL D56E (SEQ ID NO:136) | 427 | 427 | |
| hzK2E-16 | hzK2E VH (SEQ ID NO:89) | hzK2.3E VL S46T D56E (SEQ ID NO:137) | 432 | 432 | |
| hzK2E-17 | hzK2.1E VH R66K, V67T (SEQ ID NO:90) | hzK2.3E VL S46T D56E (SEQ ID NO:137) | 384 | 384 | |
| hzK2E-18 | hzK2.4E VH M69L, R71A (SEQ ID NO:93) | hzK2.3E VL S46T D56E (SEQ ID NO:137) | 380 | 380 | |
| hzK2E-19 | hzK2.2E VH R66K, V67T, M69L, R71A (SEQ ID NO:91) | hzK2.3E VL S46T D56E (SEQ ID NO:137) | 361 | 361 | |
| hzK2E-20 | hzK2.3E VH R66K, V67T, M69L, R71A, T73K (SEQ ID NO:92) | hzK2.3E VL S46T D56E (SEQ ID NO:137) | 363 | 363 | | mAb L4L Humanization

Germline VH4-31 with JH6 was used for CDR grafting the variable heavy chain (SEQ ID NO:40) and germline VKI-O2 with JK4 were used for CDR grafting the variable light chain (SEQ ID NO:128). CDR grafting was done using Kabat defined CDRs to generate hzL4L VH (SEQ ID NO:94) and hzL4L VL (SEQ ID NO:138). Several variants of hzL4L VH (SEQ ID NOS:95-102) containing mouse framework back mutations were generated, and the sequences determined using a 3D structural model for potential influence of residues on the CDR structure. Variable heavy region sequences were cloned into a vector containing a signal peptide sequence and IgG1 constant region. Variable light regions were cloned into a vector containing a signal peptide sequence and kappa constant region.

Nine humanized heavy chains were individually co-transfected individually with four different humanized light chains (see Table 7) into the ExpiCHO™ expression system in a 30 mL culture, using the parental chimeric antibody, L4L, as a benchmark. The supernatant containing the antibody was purified and further characterized. Humanized sequences hzL4L-10 through hzL4L-14 were further modified by adding additional mutations in the light chain CDR2/FR3 junction, namely D56S (SEQ ID NO:139), D56E (SEQ ID NO:140) or G57A (SEQ ID NO:141), to remove a potential isomerization site. There was a reduction in percent purity, as measured by analytical size-exclusion chromatography (% protein of interest (POI)), seen with the chimeric and hzL4L-1, -2 and -6. Surprisingly, the G27Y mutation appears to help stabilize the structure, resulting in a more homogenous recovery (see Table 7).

TABLE 7

Characterization of Humanized L4L Clones

| Name | VH (IgG1) | VL (kappa) | Titer mg/L | % POI | Guava HepG2 Screen | Flow HepG2 EC$_{50}$ |
|---|---|---|---|---|---|---|
| L4L | L4L VH (SEQ ID NO:40) | L4L VL (SEQ ID NO:128) | 327 | 65 | Good | 1.9 |
| hzL4L-1 | hzL4L VH (SEQ ID NO:94) | hzL4L VL (SEQ ID NO:138) | 462 | 72 | Poor | |
| hzL4L-2 | hzL4L VH S30T, V67I, T68S, S70T, V71R hzL4.1L (SEQ ID NO:95) | hzL4L VL (SEQ ID NO:138) | 495 | 71 | Good | |
| hzL4L-3 | hzL4L VH G27Y, S30T, V67I, T68S, S70T, V71R hzL4.2L VH (SEQ ID NO:96) | hzL4L VL (SEQ ID NO:138) | 289 | 98 | Good | 1.5 |
| hzL4L-4 | hzL4L VH G27Y, S30T hzL4.3L VH (SEQ ID NO:97) | hzL4L VL (SEQ ID NO:138) | 337 | 91 | Poor | 1.8 |
| hzL4L-5 | hzL4L VH G27Y, V67I, T68S, S70T, V71R hzL4.4L VH (SEQ ID NO:98) | hzL4L VL (SEQ ID NO:138) | 237 | 99 | Good | |
| hzL4L-6 | hzL4L VH G27Y, S30T, S70T, V71R hzL4.5L VH (SEQ ID NO:99) | hzL4L VL (SEQ ID NO:138) | 620 | 82 | Good | |
| hzL4L-7 | hzL4L VH G27Y, S70T, V71R hzL4.6L VH (SEQ ID NO:100) | hzL4L VL (SEQ ID NO:138) | 407 | 97 | Good | 2.1 |
| hzL4L-8 | hzL4L VH G27Y, S30T, V67I, T68S hzL4.7L VH (SEQ ID NO:101) | hzL4L VL (SEQ ID NO:138) | 316 | 99 | Poor | |
| hzL4L-9 | hzL4L VH G27Y, V67I, T68S hzL4.8L VH (SEQ ID NO:102) | hzL4L VL (SEQ ID NO:138) | 291 | 98 | Poor | |
| hzL4L-10 | hzL4L VH G27Y, S30T, V67I, T68S, S70T, V71R hzL4.2L VH (SEQ ID NO:96) | hzL4L VL D56S hzL4.1L VL (SEQ ID NO:139) | 158 | 91 | Good | |
| hzL4L-11 | hzL4L VH G27Y, S30T, V67I, T68S, S70T, V71R hzL4.2L VH (SEQ ID NO:96) | hzL4L VL D56E hzL4.2L VL (SEQ ID NO:140) | 282 | 96 | Good | 2.0 |
| hzL4L-12 | hzL4L VH G27Y, S30T, V67I, T68S, S70T, V71R hzL4.2L VH (SEQ ID NO:96) | hzL4L VL G57A hzL4.3L VL (SEQ ID NO:141) | ND | ND | ND | ND |
| hzL4L-13 | hzL4L VH G27Y, V67I, T68S, S70T, V71R hzL4.4L VH (SEQ ID NO:98) | hzL4L VL D56E hzL4.2L VL (SEQ ID NO:140) | 429 | 99 | ND | 1.3 |
| hzL4L-14 | hzL4L VH G27Y, S70T, V71R hzL4.6L VH (SEQ ID NO:100) | hzL4L VL D56E hzL4.2L VL (SEQ ID NO:140) | 659 | 97 | ND | 1.4 | mAb H8K Humanization

Germline VH with JH6 was used for CDR grafting the variable heavy chain (SEQ TD NO:41) and germlines VL with JK4 were used for CDR grafting the variable light chain (SEQ ID NO: 129). CDR grafting was done using Kabat defined CDRs to generate hzH8K VH (SEQ ID NO: 103) and hzH8K VL (SEQ ID NO: 142). Several variants containing mouse framework back mutations were generated (SEQ ID NOS:104-112), and the sequences determined using a 3D structural model for potential influence of residues on the CDR structure. Variable heavy region sequences were cloned into a vector containing a signal peptide sequence and IgG1 constant region. Variable light regions were cloned into a vector containing a signal peptide sequence and kappa constant region.

Ten humanized heavy chain were individually co-transfected with one humanized light chain into the ExpiCHO™ expression system in a 30 mL culture, using the parental chimeric antibody, H8K, as a benchmark. The supernatant was purified and further characterized as shown in Table 8.

TABLE 8

Humanized H8K Clones

| Name | VH (IgG1) | VL (kappa) | Titer mg/L | % POI | HepG2 EC$_{50}$ |
|---|---|---|---|---|---|
| H8K-C | H8K VH (SEQ ID NO:41) | H8K VL (SEQ ID NO:129) | 364 | 99 | 3.1 |
| hzH8K-1 | hzH8K VH (SEQ ID NO:103) | hzH8K VL (SEQ ID NO:142) | 435 | 99 | 3.4 |
| hzH8K-2 | hzH8K VH S30T hzH8.1KVH (SEQ ID NO:104) | hzH8K VL (SEQ ID NO:142) | 438 | 99 | 2.5 |
| hzH8K-3 | hzH8K VH G27F, S30T hzH8.2KVH (SEQ ID NO:105) | hzH8K VL (SEQ ID NO:142) | 442 | 99 | 3.2 |
| hzH8K-4 | hzH8K VH V67I, T68S, S70T, V71R hzH8.3KVH (SEQ ID NO:106) | hzH8K VL (SEQ ID NO:142) | 373 | 96 | 2.2 |

TABLE 8-continued

Humanized H8K Clones

| Name | VH (IgG1) | VL (kappa) | Titer mg/L | % POI | HepG2 $EC_{50}$ |
|---|---|---|---|---|---|
| hzH8K-5 | hzH8K VH S3OT, V67I, T68S, S70T, V71R<br>hzH8.4K (SEQ ID NO:107) | hzH8K VL (SEQ ID NO:142) | 421 | 94 | 3.6 |
| hzH8K-6 | hzH8K VH G27F, S30T, V67I, T68S, S70T, V71R<br>hzH8.5K (SEQ ID NO:108) | hzH8K VL (SEQ ID NO:142) | 318 | 94 | 4.9 |
| hzH8K-7 | hzH8K VH S30T, V67I, T68S<br>hzH8.6K (SEQ ID NO:109) | hzH8K VL (SEQ ID NO:142) | 617 | 98 | 3.1 |
| hzH8K-8 | hzH8K VH S30T, S70T, V71R<br>hzH8.7K (SEQ ID NO:110) | hzH8K VL (SEQ ID NO:142) | 587 | 92 | 3.5 |
| hzH8K-9 | hzH8K VH V67I, T68S<br>hzH8.8K (SEQ ID NO:111) | hzH8K VL (SEQ ID NO:142) | 440 | 97 | 2.1 |
| hzH8K-10 | hzH8K VH S70T, V71R<br>hzH8.9K (SEQ ID NO:112) | hzH8K VL (SEQ ID NO:142) | 744 | 96 | 2.2 |

J4F Humanization

Germline VH1-46 with JH6 was used for CDR grafting the variable heavy chain (SEQ ID NO:42) and germline VL with JK4 was used for CDR grafting the variable light chain (SEQ ID NO:130). CDR grafting was done using Kabat defined CDRs to generate hzJ4F VH (SEQ ID NO:113) and hzJ4F VL (SEQ ID NO:143). Several variants containing mouse framework back mutations were generated (SEQ ID NOS:114-125 for VH and SEQ ID NOS:144-149 for VL), and the sequences determined using a 3D structural model for potential influence of residues on the CDR structure. Variable heavy region sequences were cloned into a vector containing a signal peptide sequence and IgG1 constant region. Variable light regions were cloned into a vector containing a signal peptide sequence and kappa constant region.

Thirteen humanized heavy chains were each individually co-transfected with each of seven different humanized light chains into the ExpiCHO™ expression system in a 30 mL culture, using the parental chimeric antibody, J4F, as a benchmark. Humanized variants hzJ4F-1 through hzJ4F-20 showed reduced binding compared to the parent chimeric mAb J4F (see Table 9). Therefore, additional humanized variable region sequences were designed to screen for hzJ4F heavy chain and light chain combinations (hzJ4F-21-hzJ4F-58) with binding similar to or better than the chimeric parent mAb J4F.

TABLE 9

Humanized J4F Clones

| Name | VH (IgG1) | VL (kappa) | Binding |
|---|---|---|---|
| J4F | J4F VH (SEQ ID NO:42) | J4F VL (SEQ ID NO:130) | ++++ |
| hzJ4F-1 | hzJ4F VH (SEQ ID NO:113) | hzJ4F VL (SEQ ID NO:143) | ++++ |
| hzJ4F-2 | hzJ4F VH R66K, V67A, M69L, R71V<br>hzJ4.8FVH (SEQ ID NO:121) | hzJ4F VL (SEQ ID NO:143) | ++ |
| hzJ4F-3 | hzJ4F VH R66K, V67A<br>hzJ4.5FVH (SEQ ID NO:118) | hzJ4F VL (SEQ ID NO:143) | ++ |
| hzJ4F-4 | hzJ4F VH M69L, R71V<br>hzJ4.9FVH (SEQ ID NO:122) | hzJ4F VL (SEQ ID NO:143) | + |
| hzJ4F-5 | hzJ4F VH R71V<br>hzJ4.10FVH (SEQ ID NO:123) | hzJ4F VL (SEQ ID NO:143) | -/+ |
| hzJ4F-6 | hzJ4F VH (SEQ ID NO:113) | hzJ4F VL Q3V<br>hzJ4.1FVL (SEQ ID NO:144) | ++ |
| hzJ4F-7 | hzJ4F VH R66K, V67A, M69L, R71V<br>hzJ4.8FVH (SEQ ID NO:121) | hzJ4F VL Q3V<br>hzJ4.1FVL (SEQ ID NO:144) | ++ |
| hzJ4F-8 | hzJ4F VH R66K, V67A<br>hzJ4.5FVH (SEQ ID NO:118) | hzJ4F VL Q3V<br>hzJ4.1FVL (SEQ ID NO:144) | ++ |
| hzJ4F-9 | hzJ4F VH M69L, R71V<br>hzJ4.9FVH (SEQ ID NO:122) | hzJ4F VL Q3V<br>hzJ4.1FVL (SEQ ID NO:144) | + |
| hzJ4F-10 | hzJ4F VH R71V<br>hzJ4.10FVH (SEQ ID NO:123) | hzJ4F VL Q3V<br>hzJ4.1FVL (SEQ ID NO:144) | ++ |
| hzJ4F-11 | hzJ4F VH (SEQ ID NO:113) | hzJ4F VL L46A<br>hzJ4.3FVL (SEQ ID NO:146) | ++ |
| hzJ4F-12 | hzJ4F VH R66K, V67A, M69L, R71V<br>hzJ4.8FVH (SEQ ID NO:121) | hzJ4F VL L46A<br>hzJ4.3FVL (SEQ ID NO:146) | ++ |
| hzJ4F-13 | hzJ4F VH R66K, V67A<br>hzJ4.5FVH (SEQ ID NO:118) | hzJ4F VL L46A<br>hzJ4.3FVL (SEQ ID NO:146) | ++ |
| hzJ4F-14 | hzJ4F VH M69L, R71V<br>hzJ4.9FVH (SEQ ID NO:122) | hzJ4F VL L46A<br>hzJ4.3FVL (SEQ ID NO:146) | ++ |

TABLE 9-continued

| | Humanized J4F Clones | | |
|---|---|---|---|
| Name | VH (IgG1) | VL (kappa) | Binding |
| hzJ4F-15 | hzJ4F VH R71V<br>hzJ4.10FVH (SEQ ID NO:123) | hzJ4F VKL L46A<br>hzJ4.3FVL (SEQ ID NO:146) | ++ |
| hzJ4F-16 | hzJ4F VH<br>(SEQ ID NO:113) | hzJ4F VL Q3V L46A<br>hzJ4.2FVL (SEQ ID NO:145) | ++ |
| hzJ4F-17 | hzJ4F VH R66K, V67A, M69L, R71V<br>hzJ4.8FVH (SEQ ID NO:121) | hzJ4F VL Q3V L46A<br>hzJ4.2FVL (SEQ ID NO:145) | ++ |
| hzJ4F-18 | hzJ4F VH R66K, V67A<br>hzJ4.5FVH (SEQ ID NO:118) | hzJ4F VL Q3V L46A<br>hzJ4.2FVL (SEQ ID NO:145) | ++ |
| hzJ4F-19 | hzJ4F VH M69L, R71V<br>hzJ4.9FVH (SEQ ID NO:122) | hzJ4F VL Q3V L46A<br>hzJ4.2FVL (SEQ ID NO:145) | ++ |
| hzJ4F-20 | hzJ4F VH R71V<br>hzJ4.10FVH (SEQ ID NO:123) | hzJ4F VL Q3V L46A<br>hzJ4.2FVL (SEQ ID NO:145) | |
| hzJ4F-21 | hzJ4F VH V37I<br>hzJ4.1FVH (SEQ ID NO:114) | hzJ4F VL L46A<br>hzJ4.3FVL (SEQ ID NO:146) | |
| hzJ4F-22 | hzJF4 VH V37I, R38K, M48I<br>hzJ4.2FVH (SEQ ID NO:115) | hzJ4F VL L46A<br>hzJ4.3FVL (SEQ ID NO:146) | |
| hzJ4F-23 | hzJ4F VH V37I, R66K, V67A<br>hzJ4.3FVH (SEQ ID NO:116) | hzJ4F VL L46A<br>hzJ4.3FVL (SEQ ID NO:146) | |
| hzJ4F-24 | hzJ4F VH V37I, R38K, M48I, R66K, V67A<br>hzJ4.4FVH (SEQ ID NO:117) | hzJ4F VL L46A<br>hzJ4.3FVL (SEQ ID NO:146) | |
| hzJ4F-25 | hzJ4F VH V78A<br>hzJ4.11FVH (SEQ ID NO:124) | hzJ4F VL L46A<br>hzJ4.3FVL (SEQ ID NO:146) | |
| hzJ4F-26 | hzJ4F VH V78A, M80I, E81Q<br>hzJ4.12FVH (SEQ ID NO:125) | hzJ4F VL L46A<br>hzJ4.3FVL (SEQ ID NO:146) | |
| hzJ4F-27 | hzJ4F VH R66K, V67A, V78A<br>hzJ4.6FVH (SEQ ID NO:119) | hzJ4F VL L46A<br>hzJ4.3FVL (SEQ ID NO:146) | |
| hzJ4F-28 | hzJ4F VH R66K, V67A, V78A, M80I, E81Q<br>hzJ4.7FVH (SEQ ID NO:120) | hzJ4F VL L46A<br>hzJ4.3FVL (SEQ ID NO:146) | |
| hzJ4F-29 | hzJ4F VH<br>(SEQ ID NO:113) | hzJ4F VL L46A, L47V<br>hzJ4.4FVL (SEQ ID NO:147) | |
| hzJ4F-30 | hz9C5.1 VH R66K, V67A<br>hzJ4.5FVH (SEQ ID NO:118) | hzJ4F VL L46A, L47V<br>hzJ4.4FVL (SEQ ID NO:147) | |
| hzJ4F-31 | hzJ4F VH V37I<br>hzJ4.1FVH (SEQ ID NO:114) | hzJ4F VL L46A, L47V<br>hzJ4.4FVL (SEQ ID NO:147) | |
| hzJ4F-32 | hzJF4 VH V37I, R38K, M48I<br>hzJ4.2FVH (SEQ ID NO:115) | hzJ4F VL L46A, L47V<br>hzJ4.4FVL (SEQ ID NO:147) | |
| hzJ4F-33 | hzJ4F VH V37I, R66K, V67A<br>hzJ4.3FVH (SEQ ID NO:116) | hzJ4F VL L46A, L47V<br>hzJ4.4FVL (SEQ ID NO:147) | |
| hzJ4F-34 | hzJ4F VH V37I, R38K, M48I, R66K, V67A<br>hzJ4.4FVH (SEQ ID NO:117) | hzJ4F VL L46A, L47V<br>hzJ4.4FVL (SEQ ID NO:147) | |
| hzJ4F-35 | hzJ4F VH V78A<br>hzJ4.11FVH (SEQ ID NO:124) | hzJ4F VL L46A, L47V<br>hzJ4.4FVL (SEQ ID NO:147) | |
| hzJ4F-36 | hzJ4F VH V78A, M80I, E81Q<br>hzJ4.12FVH (SEQ ID NO:125) | hzJ4F VL L46A, L47V<br>hzJ4.4FVL (SEQ ID NO:147) | |
| hzJ4F-37 | hzJ4F VH R66K, V67A, V78A<br>hzJ4.6FVH (SEQ ID NO:119) | hzJ4F VL L46A, L47V<br>hzJ4.4FVL (SEQ ID NO:147) | |
| hzJ4F-38 | hzJ4F VH R66K, V67A, V78A, M80I, E81Q<br>hzJ4.7FVH (SEQ ID NO:120) | hzJ4F VL L46A, L47V<br>hzJ4.4FVL (SEQ ID NO:147) | |
| hzJ4F-39 | hzJ4F VH<br>(SEQ ID NO:113) | hzJ4F VL L46A, L47V, F62L<br>hzJ4.5FVL (SEQ ID NO:148) | |
| hzJ4F-40 | hz9C5.1 VH R66K, V67A<br>hzJ4.5FVH (SEQ ID NO:118) | hzJ4F VL L46A, L47V, F62L<br>hzJ4.5FVL (SEQ ID NO:148) | |
| hzJ4F-41 | hzJ4F VH V37I<br>hzJ4.1FVH (SEQ ID NO:114) | hzJ4F VL L46A, L47V, F62L<br>hzJ4.5FVL (SEQ ID NO:148) | |
| hzJ4F-42 | hzJF4 VH V37I, R38K, M48I<br>hzJ4.2FVH (SEQ ID NO:115) | hzJ4F VL L46A, L47V, F62L<br>hzJ4.5FVL (SEQ ID NO:148) | |
| hzJ4F-43 | hzJ4F VH V37I, R66K, V67A<br>hzJ4.3FVH (SEQ ID NO:116) | hzJ4F VL L46A, L47V, F62L<br>hzJ4.5FVL (SEQ ID NO:148) | |
| hzJ4F-44 | hzJ4F VH V37I, R38K, M48I, R66K, V67A<br>hzJ4.4FVH (SEQ ID NO:117) | hzJ4F VL L46A, L47V, F62L<br>hzJ4.5FVL (SEQ ID NO:148) | |
| hzJ4F-45 | hzJ4F VH V78A<br>hzJ4.11FVH (SEQ ID NO:124) | hzJ4F VL L46A, L47V, F62L<br>hzJ4.5FVL (SEQ ID NO:148) | |
| hzJ4F-46 | hzJ4F VH V78A, M80I, E81Q<br>hzJ4.12FVH (SEQ ID NO:125) | hzJ4F VL L46A, L47V, F62L<br>hzJ4.5FVL (SEQ ID NO:148) | |
| hzJ4F-47 | hzJ4F VH R66K, V67A, V78A<br>hzJ4.6FVH (SEQ ID NO:119) | hzJ4F VL L46A, L47V, F62L<br>hzJ4.5FVL (SEQ ID NO:148) | |
| hzJ4F-48 | hzJ4F VH R66K, V67A, V78A, M80I, E81Q<br>hzJ4.7FVH (SEQ ID NO:120) | hzJ4F VL L46A, L47V, F62L<br>hzJ4.5FVL (SEQ ID NO:148) | |

TABLE 9-continued

Humanized J4F Clones

| Name | VH (IgG1) | VL (kappa) | Binding |
|---|---|---|---|
| hzJ4F-49 | hzJ4F VH (SEQ ID NO:113) | hzJ4F VL L46A, L47V, S60D, F62L, S63T hzJ4.6FVL (SEQ ID NO:149) | |
| hzJ4F-50 | hzJ4F VH R66K, V67A hzJ4.5FVH (SEQ ID NO:118) | hzJ4F VL L46A, L47V, S60D, F62L, S63T hzJ4.6FVL (SEQ ID NO:149) | |
| hzJ4F-51 | hzJ4F VH V37I hzJ4.1FVH (SEQ ID NO:114) | hzJ4F VL L46A, L47V, S60D, F62L, S63T hzJ4.6FVL (SEQ ID NO:149) | |
| hzJ4F-52 | hzJF4 VH V37I, R38K, M48I hzJ4.2FVH (SEQ ID NO:115) | hzJ4F VL L46A, L47V, S60D, F62L, S63T hzJ4.6FVL (SEQ ID NO:149) | |
| hzJ4F-53 | hzJ4F VH V37I, R66K, V67A hzJ4.3FVH (SEQ ID NO:116) | hzJ4F VL L46A, L47V, S60D, F62L, S63T hzJ4.6FVL (SEQ ID NO:149) | |
| hzJ4F-54 | hzJ4F VH V37I, R38K, M48I, R66K, V67A hzJ4.4FVH (SEQ ID NO:117) | hzJ4F VL L46A, L47V, S60D, F62L, S63T hzJ4.6FVL (SEQ ID NO:149) | |
| hzJ4F-55 | hzJ4F VH V78A hzJ4.11FVH (SEQ ID NO:124) | hzJ4F VL L46A, L47V, S60D, F62L, S63T hzJ4.6FVL (SEQ ID NO:149) | |
| hzJ4F-56 | hzJ4F VH V78A, M80I, E81Q hzJ4.12FVH (SEQ ID NO:125) | hzJ4F VL L46A, L47V, S60D, F62L, S63T hzJ4.6FVL (SEQ ID NO:149) | |
| hzJ4F-57 | hzJ4F VH R66K, V67A, V78A hzJ4.6FVH (SEQ ID NO:119) | hzJ4F VL L46A, L47V, S60D, F62L, S63T hzJ4.6FVL (SEQ ID NO:149) | |
| hzJ4F-58 | hzJ4F VH R66K, V67A, V78A, M80I, E81Q hzJ4.7FVH (SEQ ID NO:120) | hzJ4F VL L46A, L47V, S60D, F62L, S63T hzJ4.6FVL (SEQ ID NO:149) | |

Example 2

Epitope Binning of Anti-ASGR1 Antibodies to Human ASGR1 Extracellular Domain This example shows that antibodies of this disclosure raised against human ASGR1 extracellular domain (ECD) bind to several different epitopes as tested by simultaneous binding with control anti-ASGR1 antibodies ASGR1 mAb-A, ASGR1 mAb-B, and ASGR1 mAb-C. Chimeric antibodies were chG2D (heavy chain SEQ ID NO:150; light chain SEQ ID NO:206), chH8K (heavy chain SEQ ID NO:153; light chain SEQ ID NO:209), chJ4F (heavy chain SEQ ID NO:154; light chain SEQ ID NO:210), chK2E (heavy chain SEQ ID NO:151; light chain SEQ ID NO:207), chL4L (heavy chain SEQ ID NO:152; light chain SEQ ID NO:208), and their corresponding parental antibodies were G2D, H8K, J4F, K2E, and L4L, were analyzed.

Antibody epitope binning experiment utilizing OCTET® (ForteBio, Inc.) kinetic analysis (observing competitive versus simultaneous binding to human ASGR1 ECD) revealed a competitive blocking profile of four (4) different epitope bins, referred to as bins A, B, C, and D (see Table 10). Briefly, human Fc-fused ASGR1 ECD was immobilized on anti-human IgG Fc Capture (AHC) biosensors and incubated with mouse IgG2a isotype control antibodies ASGR1 mAb-A, ASGR1 mAb-B, and ASGR1 mAb-C until saturation was reached in kinetics buffer (PBS+1% BSA+0.2% Tween20+ 0.9 mM CaCl$_2$) at pH 7.4), followed by binding of anti-ASGR1 antibodies G2D, H8K, J4F, K2E, and L4L of this disclosure. Recombinant chG2D, chH8K, chJ4F, chK2E, and chL4L antibodies were tested using mouse Fc-fused ASGR1 ECD immobilized on anti-mouse IgG Fc Capture (AMC) biosensors and incubated with control human IgG1 isotype antibodies ASGR1 mAb-A, ASGR1 mAb-C, and ASGR1 mAb-C. The interactions of the anti-ASGR1 antibodies of this disclosure and control mAbs with human ASGR1 ECD were analyzed using the OCTET® Data Analysis Software 9.0 (ForteBio).

Unexpectedly, anti-ASGR1 antibodies H8K and L4L of this disclosure were observed to bind in the presence of all 3 control mAbs and, therefore, were determined to belong to a unique epitope bin. Antibodies H8K and L4L belong to the same bin because they were found to block binding of each other, denoted bin D in Table 10 below. The other three antibodies of this disclosure (G2D, J4F, and K2E) binned with control antibody ASGR1 mAb-B.

TABLE 1

Epitope Bins of Anti-ASGR1 Antibodies to Human ASGR1 ECD*

| Antibody | mAb-A | mAb-B | mAb-C | L4L | Bin |
|---|---|---|---|---|---|
| ASGR1 mAb-A | − | + | + | + | A |
| ASGR1 mAb-B | + | − | + | + | B |
| G2D | + | − | + | + | B |
| K2E | + | − | + | + | B |
| J4F | + | − | + | + | B |
| ASGR1 mAb-C | + | + | − | + | C |
| H8K | + | + | + | − | D |
| L4L | + | + | + | − | D |

*If binding of antibody was blocked by control antibody, test antibody is assigned (−). If test antibody bound in presence of control antibody, test antibody is assigned (+).

Additional epitope binning was performed using chimeric antibodies chG2D, chJ4F, and chL4L. The procedure outlined above was essentially repeated with the following exceptions: OCTET® biosensor was AMC, antigen reagent used was mouse Fc-fused human ASGR1 and control antibodies contained human IgG1 backbone. Data was in consistent with the data in Table 10 above.

Example 3

Binding of Anti-ASGR1 Antibodies to an ASGR1-Expressing Tumor Cell Line

Figure 1B:
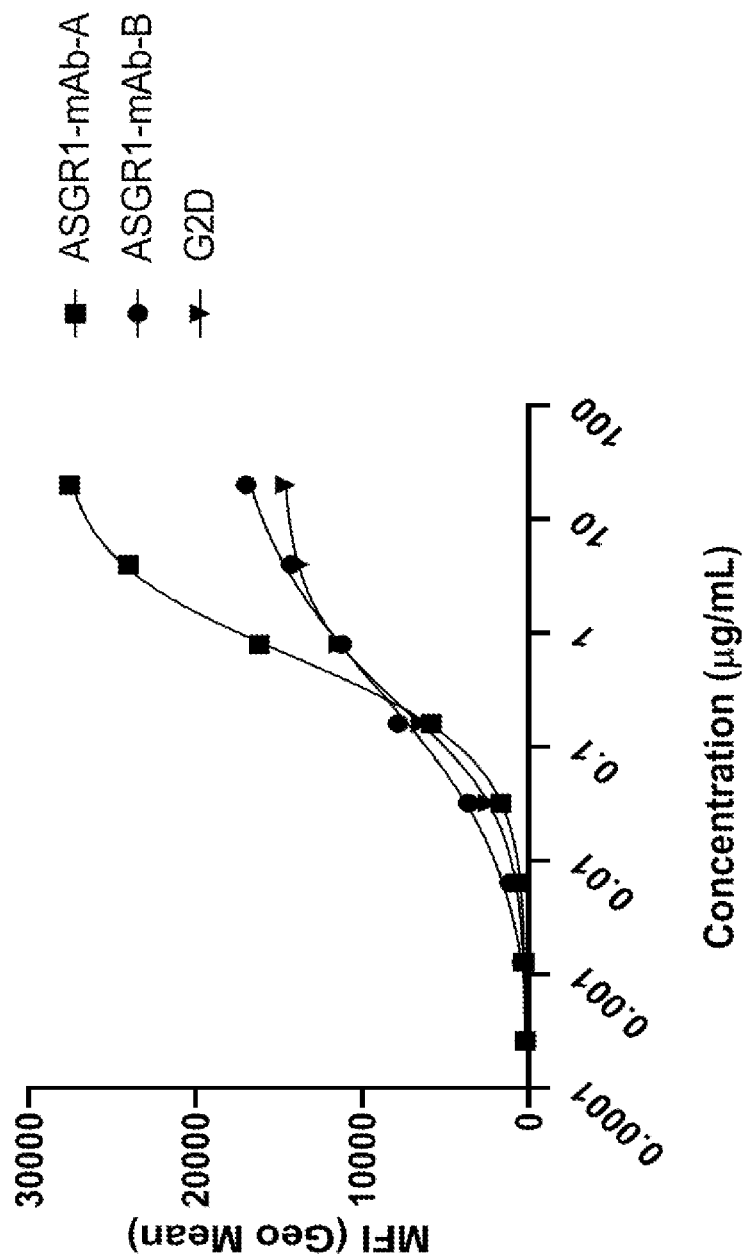
Figure 1C:
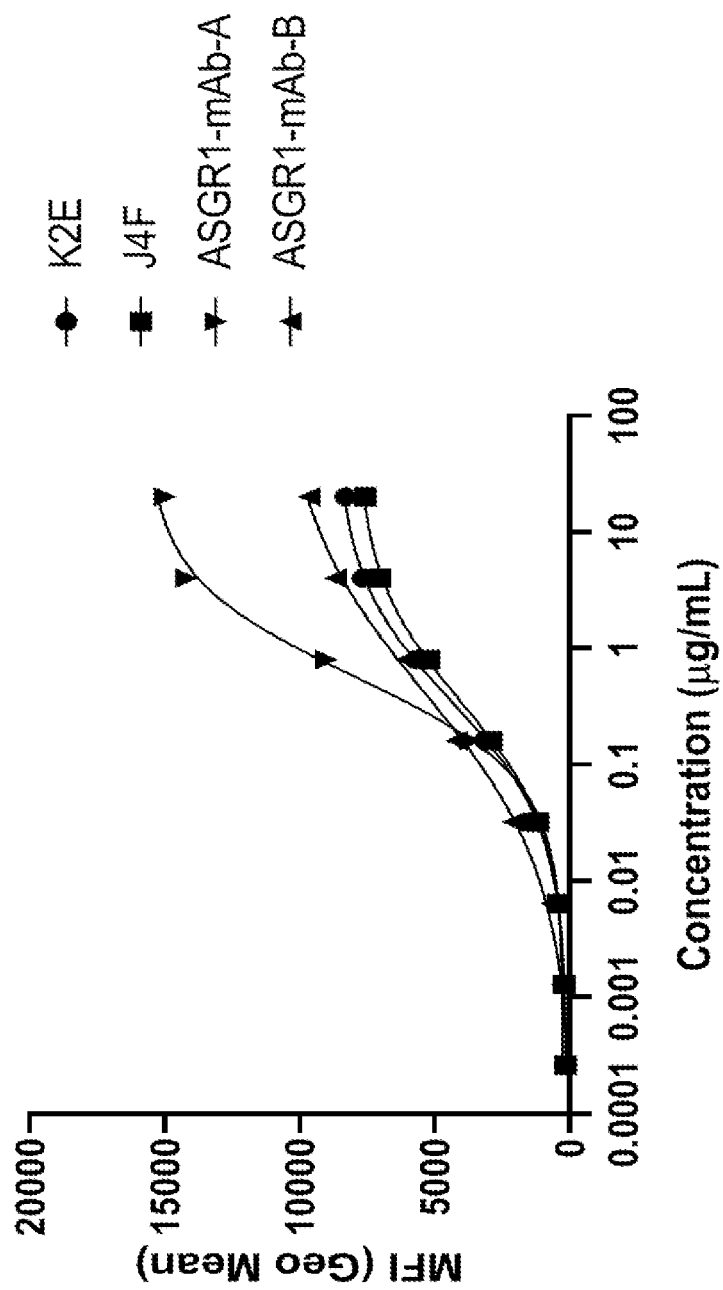
Figure 1D:
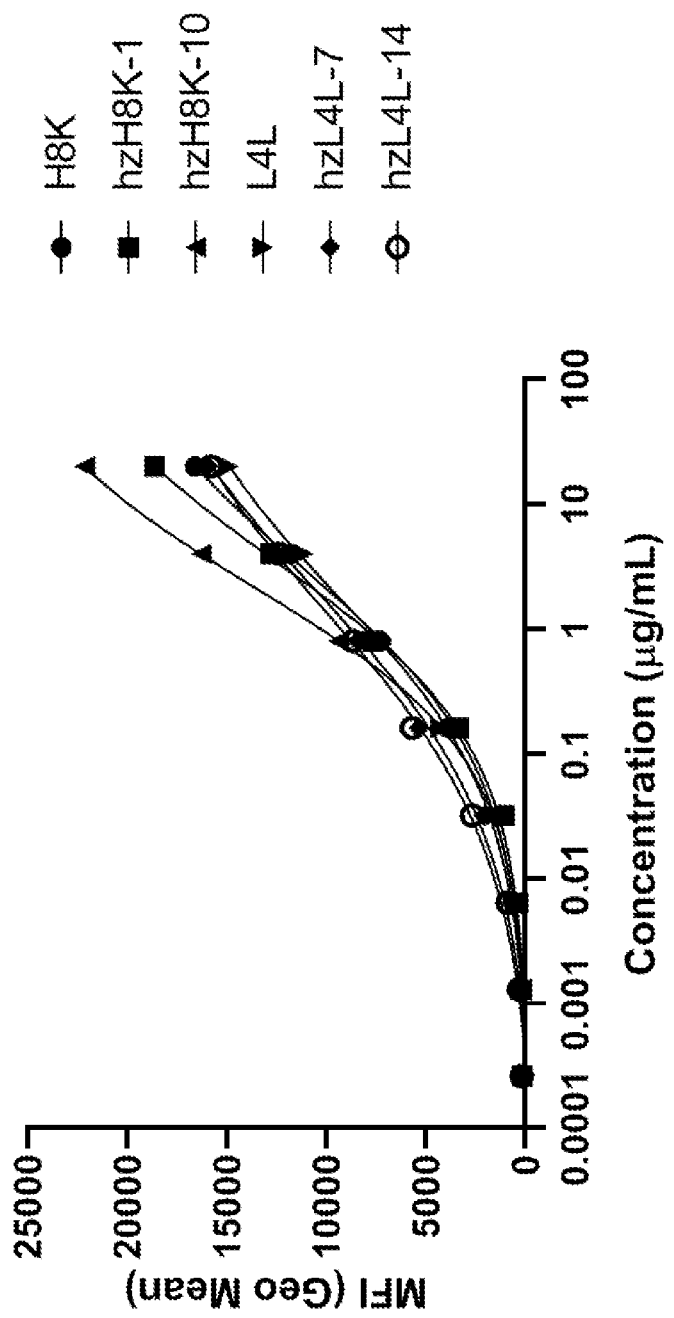

FIGS. 1A-1D show binding of various anti-ASGR1 antibodies to ASGR1-expressing cell line HepG2. Briefly, $5\times10^4$ HepG2 cells/well were contacted with titrating concentrations of anti-ASGR1 antibodies in FACS Buffer (FB: PBS+ 2% FBS+1 mM $CaCl_2$)) for 30 minutes at 4° C. Cells were washed twice in FB, then incubated in anti-human IgG PE secondary for 30 minutes at 4° C. Cells were washed twice in FB, then analyzed by flow cytometry. FIGS. 1A-1C show the binding of mouse anti-ASGR1 antibodies L4L, H8K, J4F, K2E, or G2D and examined for binding as compared to control antibodies ASGR1-mAb-A, ASGR1-mAb-B, and ASGR1-mAb-C (FIG. 1A), or ASGR1-mAb-A and ASGR1-mAb-B (FIGS. 1B and 1C). Each of the test mouse anti-ASGR1 antibodies bound at a level similar to the control anti-ASGR1 antibodies. FIG. 1D shows binding of humanized anti-ASGR1 antibodies hzL4L-7 and hzL4L-14 as compared to parent mouse anti-ASGR1 antibody L4L, and binding of humanized anti-ASGR1 antibodies hzH8K-1 and hzH8K-10 as compared to parent mouse anti-ASGR1 antibody H8K. Each of the humanized anti-ASGR1 antibodies bound to the ASGR1-expressing cell line HepG2 as well as or better than the parent mouse antibodies. No binding was detected in ASGR1 negative cell line HEK293 (data not shown).

Example 4

Cross-Reactivity of Anti-Human ASGR1 MAbs to *Cynomolgus Macaque* and Rat ASGR1

Figure 2A:
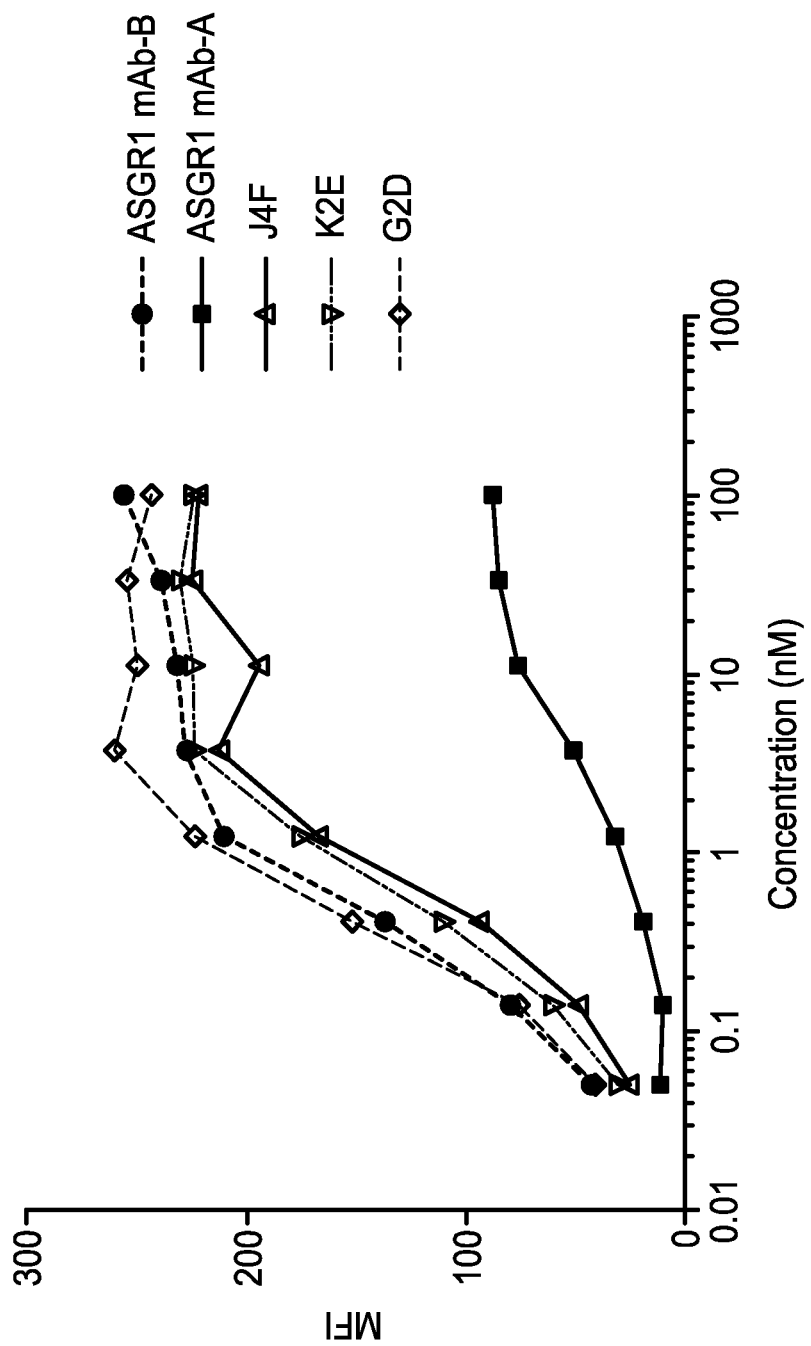
FIGS. 2A-2B are a series of graphs showing binding of anti-human ASGR1 mAbs to (A) rat ASGR1 or (B) Cynomologous ASGR1, when transiently expressed by CHO-S cells.
Figure 2B:
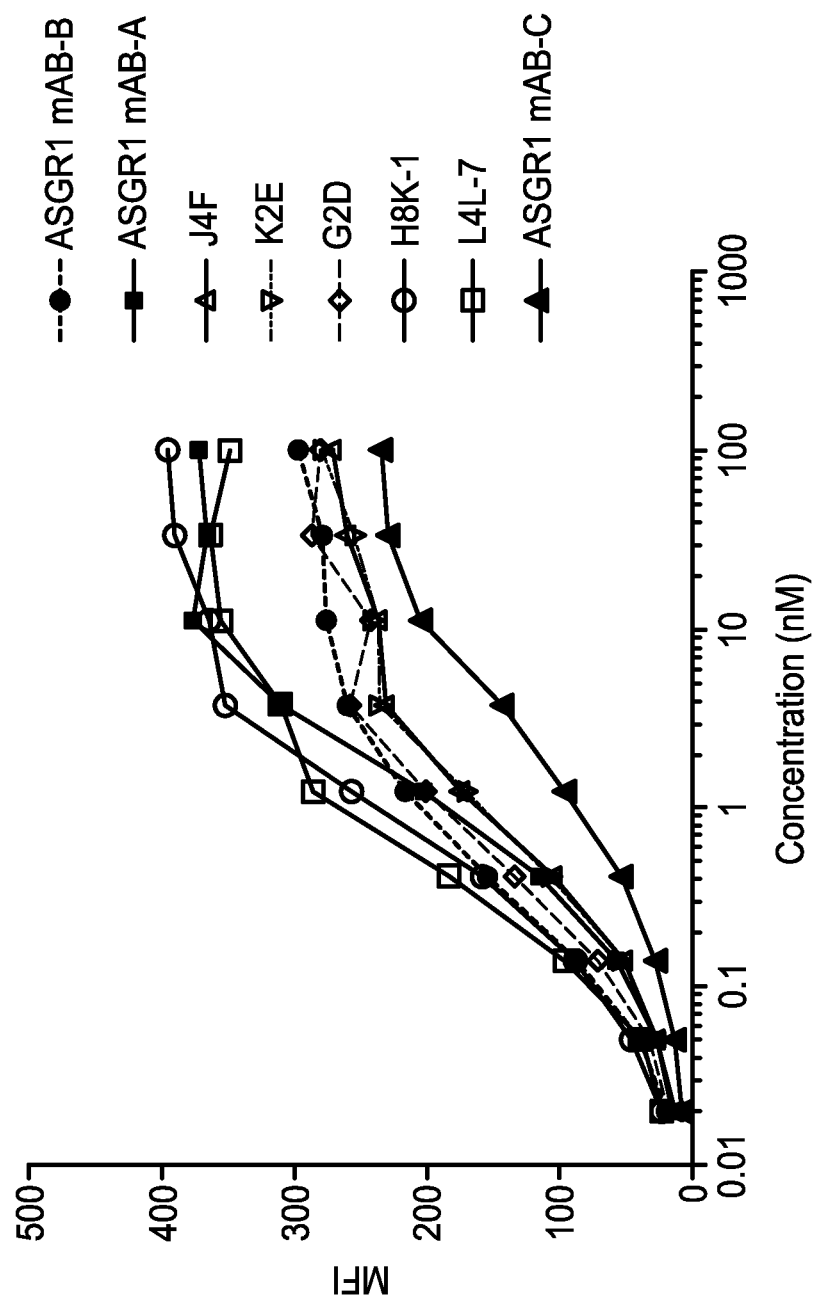

Anti-human ASGR1 antibodies of this disclosure were examined for cross-reactivity with *Cynomolgus macaque* and rat ASGR1. Briefly, sequence encoding *Cynomolgus macaque* or rat ASGR1 was transiently transfected into CHO-S cells. Transfected cells were before performing cell binding assay. A total of about $1.5\times10^4$ transfected cells/well were added to 96-well V-bottom assay plate, incubated at 37° C., 5% $CO_2$ for 48-72 hours, and then washed with culture medium before adding 100 µl of each ASGR1 antibody at different concentrations starting from 100 nM and 3-fold dilutions to a total of eight wells. The cells with antibody were incubated for 40 minutes at 4° C., then washed three times with 200 µl of fresh culture medium. To each well was added 50 µl PE conjugated goat anti-human Fc (SouthernBiotech) at 1:200 dilution in culture medium and then incubated at 4° C. for 20 minutes. After washing the plate once, the treated cells were resuspended in 200 µl culture medium and then the stained cells were analyzed on GUAVA® using Incyte software. Table 11 (see also FIG. 2B) shows that all of the anti-ASGR1 antibodies of this disclosure cross-react with *Cynomolgus macaque* ASGR1, whereas Table 12 (see also FIG. 2A) shows that only antibodies G2D, K2E, and J4F were capable of binding rat ASGR1 (mAbs H8K-1 and L4L-7 were not rat cross-reactive (data not shown)).

TABLE 11

Binding Cell Surface Expressed Cynomologous ASGR1

| Sample ID | $EC_{50}$ (nM) |
|---|---|
| ASGR1 mAb-A | 1.07 |
| ASGR1 mAb-B | 0.36 |
| G2D | 0.47 |
| K2E | 0.68 |
| J4F | 0.67 |
| ASGR1 mAb-C | 2.35 |
| H8K-1 | 0.66 |
| L4L-7 | 0.39 |

TABLE 12

Binding Cell Surface Expressed Rat ASGR1

| Anti-ASGR1 mAb | $EC_{50}$ (nM) |
|---|---|
| Control mAb-A | 3.22 |
| Control mAb-B | 0.38 |
| G2D | 0.37 |
| K2E | 0.52 |
| J4F | 0.62 |

Example 5

Cross-Reactivity of Anti-ASGR1 Antibodies to Rat CLEC10A

Anti-human ASGR1 antibodies of this disclosure were examined for off-target binding to rat C-type lectin domain family 10 member A (CLEC10A). ASGR1 mAb-B (72G9) has been reported to bind to rat CLEC10A (see, e.g., PCT Publication No. WO 2017/058944) and was used as a positive control in these experiments. The chimeric antibodies of this disclosure being tested include chG2D, chH8K, chJ4F, chK2E, and chL4L. In addition, humanized antibodies tested were hzH8K-1 and hzL4L-7. Finally, the control antibodies included ASGR1 mAb-A (4A2), ASGR1 mAb-B (72G9), and ASGR1 mAb-C (4F3).

Analysis of binding to the rat CLEC10A ECD was performed using the OCTET® Red 96 instrument (ForteBio). His-tagged rat CLEC10A ECD (R&D Systems) was immobilized to OCTET® Penta-His biosensors and subjected to avidity binding of test antibodies in kinetics buffer (PBS+1% BSA+0.2% Tween20+0.9 mM $CaCl_2$) at pH 7.4) in the following steps: (1) hydration of Penta-His biosensors in kinetics buffer (10 min); (2) regeneration and neutralization of Penta-His biosensor in 10 mM glycine-HCl (pH 1.5) and kinetics buffer, respectively in triplicate; (3) baseline acquisition (30 s); (4) immobilization of rat CLEC10A ECD to Penta-His biosensors at a concentration of 10 µg/mL (180 s); (5) second baseline acquisition (60 s); (6) association of test antibody at 25 µg/mL (60 s); (7) dissociation in kinetics buffer (60 s).

The interactions of test mAbs with rat CLEC10A ECD was analyzed using the OCTET® Data Analysis Software 9.0 (ForteBio). No observable binding signal was reached with chG2D, chH8K, chJ4F, chL4L, hzL4L-7, ASGR1 mAb-A, and ASGR1 mAb-C (see Table 13). As expected, ASGR1 mAb-B gave the strongest signal to rat CLEC10A ECD as shown in Table 13. A minor signal above background was observed with chK2E, with even less above background binding observed for hzH8K-1 (see Table 13).

TABLE 13

Binding of anti-ASGR1 antibodies to rat CLEC10A ECD

| Antibody | Response (nm) |
|---|---|
| chG2D | —* |
| chH8K | — |
| hzH8K-1 | 0.0495 |
| chJ4F | — |
| chK2E | 0.0984 |
| chL4L | — |
| hzL4L-7 | — |
| ASGR1 mAb-A | — |
| ASGR1 mAb-B | 0.5979 |
| ASGR1 mAb-C | — |

*Antibodies tested with response of <0.02 nm were below the limit of detection (—)

Further analysis of chK2E and ASGR1 mAb-B were investigated to determine equilibrium dissociation constants to rat CLEC10A ECD by OCTET® Red 96 instrument (ForteBio). Antibodies chK2E and ASGR1 mAb-B were minimally biotinylated prior to capture to streptavidin (SA) biosensors using EZ-LINK™ NHS-PEG4-Biotin, NO-WEIGH™ Format (Thermo Scientific) at a calculated ratio of three biotins to one mAb. Biotinylated proteins were purified by ZEBA™ spin desalting columns (Thermo Scientific) to remove free biotin. The interacting monomeric rat CLEC10 ECD (R&D Systems) was used at 5-6 concentrations of a 3-fold concentration series to determine equilibrium constants in kinetics buffer using the following steps: (1) hydration of SA biosensors in kinetics buffer (10 min); (2) baseline acquisition (30 s); (3) immobilization biotinylated chK2E or ASGR1 mAb-B at concentration of 5 g/mL (180 s or until all sensors reached a 1 nm shift); (4) second baseline acquisition (60 s); (5) association of rat CLEC10A ECD starting at 200 nM with 3× dilutions (300 s); (7) dissociation in kinetics buffer (600 s).

The data were analyzed using OCTET® Data Analysis Software 9.0 (ForteBio) and fit to the bivalent binding model. The equilibrium dissociation constants ($K_D$) were calculated by the ratio of $k_{off}$ to $k_{on}$. ASGR1 mAb-B was determined to have a $K_D$ of 28.1 nM, while chK2E was not observed to bind rat CLEC10A ECD in this assay's orientation. This confirms that antibodies G2D and K2E of this disclosure unexpectedly differ from the antibody with which they epitope binned, ASGR1 mAb-B, in that G2D and K2E do not exhibit off-target binding to CLEC10A as ASGR1 mAb-B does.

Example 6

Certain Anti-Human ASGR1 Antibodies Compete with ASGR1 Ligand (GalNAc) Binding

The F(ab')$_2$ fragments of ASGR1 antibodies were tested for GalNAc ligand blocking using competition cell binding with human ASGR1 full length DNA transiently transfected CHO-S cells. GalNAc ligand was linked to a human IgG1 Fc tail (referred to throughout the disclosure as GalNAc-hFc). Competitive cell binding method was carried out as follows: (1) transfer 200 µl human ASGR1 expressing CHO-S cells (100 k/well) into a V-bottom 96-well assay plate and the cells were washed once, harvested, and resuspended in cell culture medium; (2) resuspended cells were incubated with 100 µl GalNAc-hFc starting with 900 nM, diluted 1:2 for a total of 8 concentrations in medium containing 200 nM F(ab')$_2$ fragments of ASGR1 antibodies, and incubated for 40 minutes at 4° C.; (3) the treated cells were washed three times, resuspended with 50 µl of medium containing commercial PE conjugated anti-human Fc (SouthernBiotech) as secondary antibody (1:200 dilution), and incubates for 20 minutes at 4° C.; and (4) finally the plates were washed twice and the samples were analyzed on a GUAVA® EASYCYTE™ 8HT flow cytometer. The percent of GalNAc-hFc (at a 33 nM concentration) blocked from binding ASGR1 due to the presence of anti-ASGR1 antibody was measured.

Table 14 (below) shows that even though antibodies G2D and K2E epitope binned with control ASGR1 mAb-B (having CDRs from anti-ASGR1 antibody 72G9), they differ from ASGR1 mAb-B because G2D does not compete with ASGR1 ligand (GalNAc) binding and K2E only minimally blocks GalNAc binding. In this regard, G2D and K2E are more like control ASGR1 mAb-C (having CDRs from anti-ASGR1 antibody 4F3). In contrast, the antibodies showing a unique epitope bin, H8K and L4L, strongly block GalNAc binding to ASGR1.

TABLE 14

Anti-ASGR1 mAb Competition with ASGR1 Ligand (GalNAc) Binding

| Antibody | % Blocking GalNAc Binding |
|---|---|
| ASGR1 mAb-A | 97.6 |
| ASGR1 mAb-B | 42.8 |
| G2D | −0.3 |
| K2E | 10.0 |
| J4F | −32.1 |
| ASGR1 mAb-C | −5.4 |
| hzH8K-1 | 81.3 |
| hzL4L-14 | 90.7 |

Example 7

Effect of Calcium on Anti-ASGR1 Binding to ASGR1

The ability of anti-human ASGR1 antibodies of this disclosure to bind to human ASGR1 in the presence or absence of calcium in binding buffer was examined. Briefly, ASGR1 antibodies were bound to immobilized human ASGR1 extracellular domain (ECD) at saturating levels and subsequently dissociated under three different conditions as follows: (a) binding and dissociation with buffer containing calcium (PBS+1% BSA+0.2% Tween20+0.9 mM CaCl$_2$), pH 7.4); (b) binding with buffer containing calcium and dissociation with buffer lacking calcium; and (c) binding and dissociation with buffer lacking calcium. Analysis of ASGR1 antibody binding to human ASGR1 ECD was performed using the OCTET® Red 96 instrument and analyzed using the OCTET®Data Analysis Software 9.0 (ForteBio). His-tagged human ASGR1 ECD was immobilized to OCTET® Penta-His biosensors and ASGR1 antibodies were subjected to avidity binding under the conditions described above. Association with the ASGR1 ECD was measured by the rate of and increase in magnitude of signal response at a given antibody concentration. Dissociation from the ASGR1 ECD was measured as the rate of loss in signal upon removal of the antibody and further incubation with or without $Ca^{2+}$. Tested in these assays were chimeric anti-ASGR1 antibodies chG2D, chJ4F, chK2E, and chL4L of this disclosure (each comprising the variable regions of anti-ASGR1 antibodies G2D, J4F, K2E, and L4L, respectively, of this disclosure fused to human IgG1 Fc domain). Also tested were humanized antibodies hzH8K-1 and hzL4L-7. Control antibodies were ASGR1 mAb-A, ASGR1 mAb-B, and ASGR1 mAb-C.

Tested mAbs were considered sensitive to calcium when saturation binding of ASGR1 mAb to human ASGR1 ECD in the presence of calcium showed a difference in binding signal after dissociation in the presence of calcium that was >±10% as compared to the binding signal after dissociation in the absence of calcium (i.e., calcium sensitivity refers to antibodies that appear to require $Ca^{2+}$ to remain bound to ASGR1 ECD). Antibodies lacking sensitivity to calcium included chG2D, chH8K, chK2E, hzL4L-7, and control antibodies ASGR1 mAb-A and ASGR1 mAb-B. In contrast, chJ4F showed calcium sensitivity since this antibody exhibited a binding signal decrease of 67% from saturation when dissociation was carried out in the absence of calcium, whereas only 10% of binding signal loss was observed when the dissociation step was carried out in the presence of calcium. Control antibody ASGR1 mAb-C shows a dramatic loss in binding signal when dissociation is carried out in the presence (73% loss) or absence (93% loss) of calcium during the dissociation step. The binding dissociation by control antibody ASGR1 mAb-C appears to be affected by calcium, but its binding profile has a unique response to calcium since its association to ligand is not affected by calcium.

Further analysis of the antibodies of this disclosure was to determine whether the presence of calcium was needed for binding (i.e., during association) of the antibodies to human ASGR1 ECD. Under these conditions, several antibodies displayed the complete inability to bind to human ASGR1 ECD (i.e., calcium dependent binding). Table 15 provides a summary of the calcium sensitivity results.

TABLE 15

Calcium Sensitivity of ASGR1 Antibodies

| mAb | $Ca^{2+}$ Sensitivity during: | | $Ca^{2+}$ Sensitivity |
|---|---|---|---|
| | Association | Dissociation | |
| ASGR1 mAb-A | N | N | N |
| ASGR1 mAb-B | Y | N | Y |
| chG2D | Y | N | Y |
| chK2E | Y | N | Y |
| chJ4F | Y | Y | Y |
| ASGR1 mAb-C | N | Y | N |
| hzH8K-1 | N | N | N |
| hzL4L-7 | N | N | N |

N = No; Y = Yes

Example 8

TNF-α Production by Tumor Cells Contacted with Anti-ASGR1-TLR8 Agonist Conjugates The effect on TNF-α production by human PBMCs co-cultured with ASGR1 expressing HepG2 tumor cells and in the presence of anti-ASGR1-TLR8 agonist conjugates was examined. An increase in TNF-α production by human PBMCs would indicate that myeloid cells are being activated. Briefly, peripheral blood mononuclear cells (PBMC) were isolated from normal human donor blood using SEPMATE™-50 PBMC Isolation Tubes (STEMCELL Technologies) according to manufacturer's instructions. Isolated PBMC were cultured with the ASGR1-expressing tumor cell line HepG2 or the ASGR1-negative cell line HEK 293 at a 5:1 ratio in the presence of titrated concentrations of anti-ASGR1-TLR8 agonist conjugates (G2D-Compound 2.14, J4F-Compound 2.14, K2E-Compound 2.14, L4L-Compound 2.14, hzL4L-7-Compound 2.14, hzL4L-14-Compound 2.14, H8K-Compound 2.14, hzH8K-1-Compound 2.14, and hzH8K-10-Compound 2.14, as well as control conjugates comprised of ASGR1-mAb-A-Compound 2.14, ASGR1-mAb-B-Compound 2.14, ASGR1-mAb-C-Compound 2.14, anti-digoxin mAb-Compound 2.14, and unconjugated antibody controls). After 24 hours, cell-free supernatants were collected and stored at −80° C. prior to analysis. TNF-α levels in the cell-free supernatants were quantified using the TNF-α (human) AlphaLISA® Detection Kit (Perkin Elmer) according to manufacturer's instructions.

Figure 3A:
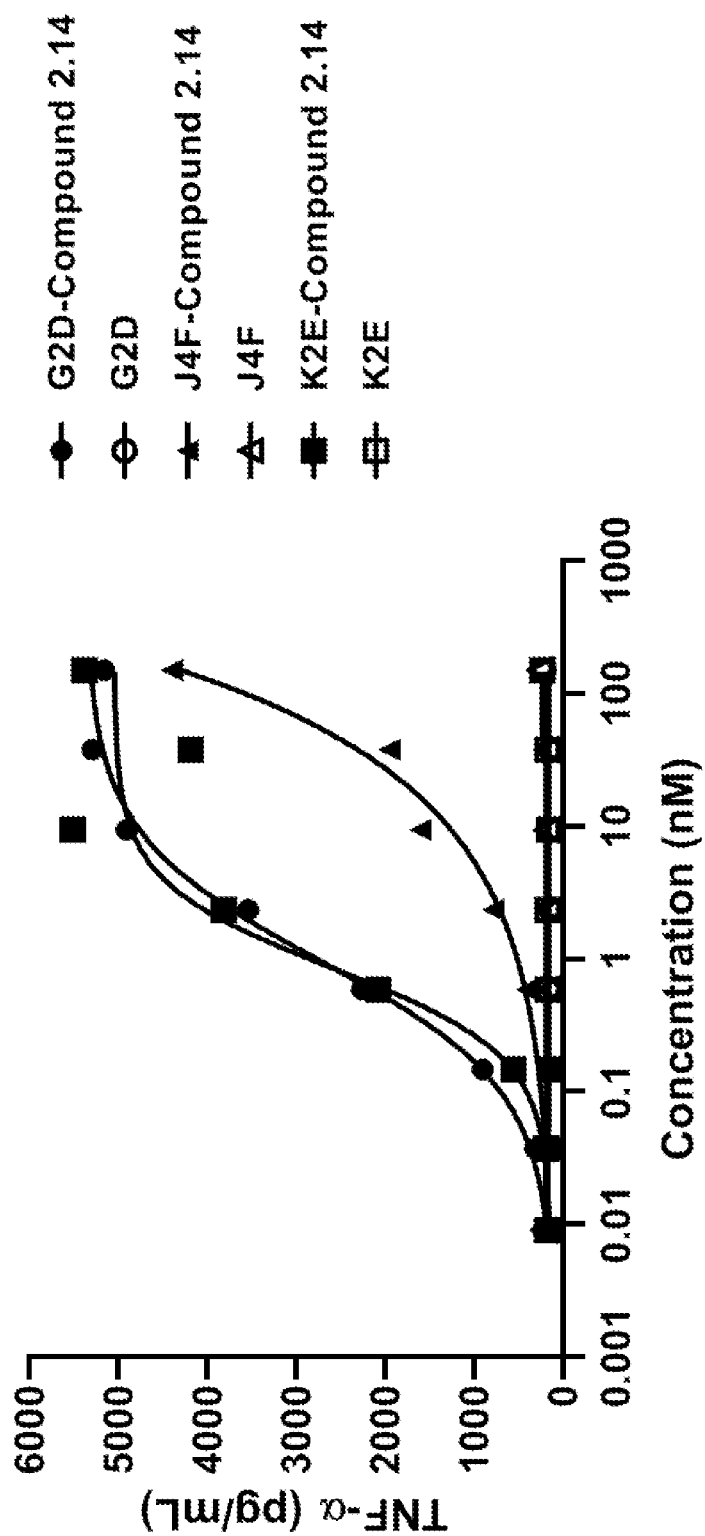
FIGS. 3A-3C are a series of graphs showing TNF-α induction in human PBMCs from 3 separate donors (A, B, C) when cultured for 24 hours with ASGR1-expressing cell line HepG2 in the presence of an anti-ASGR1-Compound 2.14 conjugate, matched unconjugated mAb controls or control mAb-Compound 2.14 conjugate.
Figure 3B:
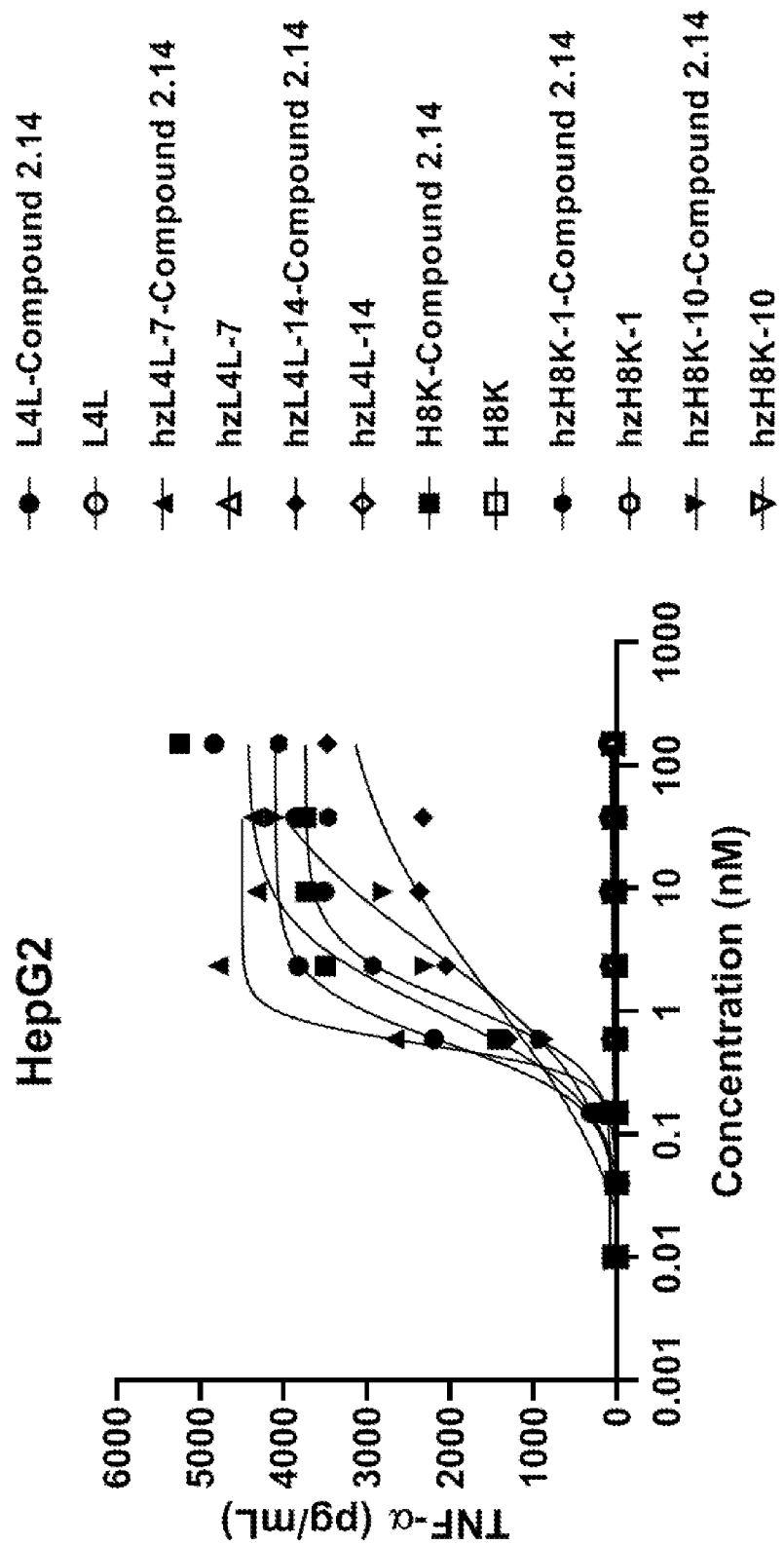
Figure 3C:
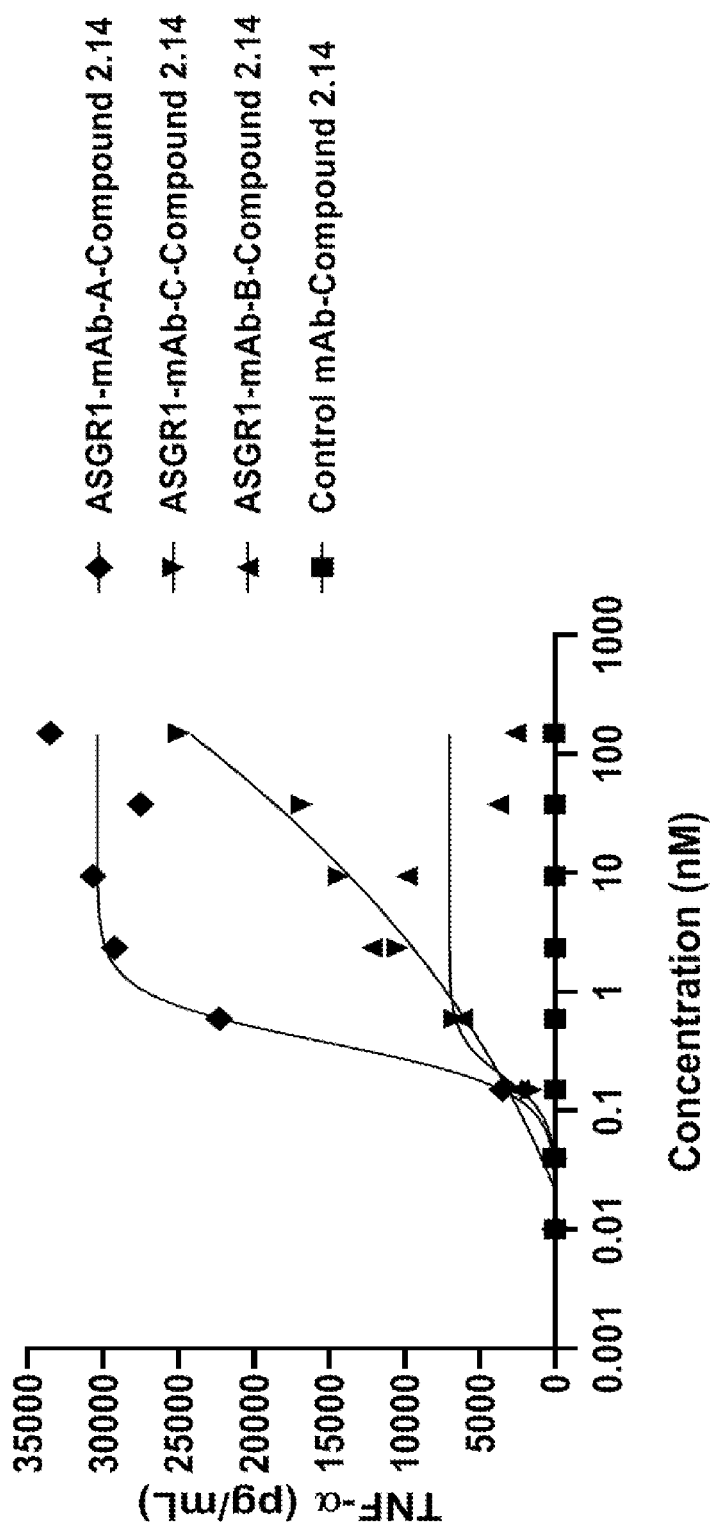

As shown in FIGS. 3A-3C, anti-ASGR1-Compound 2.14 conjugates induced TNF-α production in a dose-dependent manner from human PBMCs in the presence of the ASGR1-expressing HepG2 tumor cell line, but not in the presence of ASGR1-negative cells HEK 293 (data not shown). FIG. 3B shows that some of the humanized anti-ASGR1 conjugates (such as hzL4L-7 and hzH8K-1) were more efficient at inducing TNF-α production as compared to the parent antibody conjugates. TNF-α production by PBMC was not induced in the presence of the ASGR1 expressing tumor cell line with unconjugated antibodies or the anti-digoxin conjugate control (Control-mAb-Compound 2.14), which indicated that the combination of ASGR1 binding and Compound 2.14 TLR8 agonism promote TNF-α release. Furthermore, none of the conjugated or unconjugated antibodies stimulated TNF-α production from PBMCs in the absence of ASGR1-expressing tumor cells (data not shown), indicating that the activity is dependent upon ASGR1 expression.

Example 9

Figure 7:
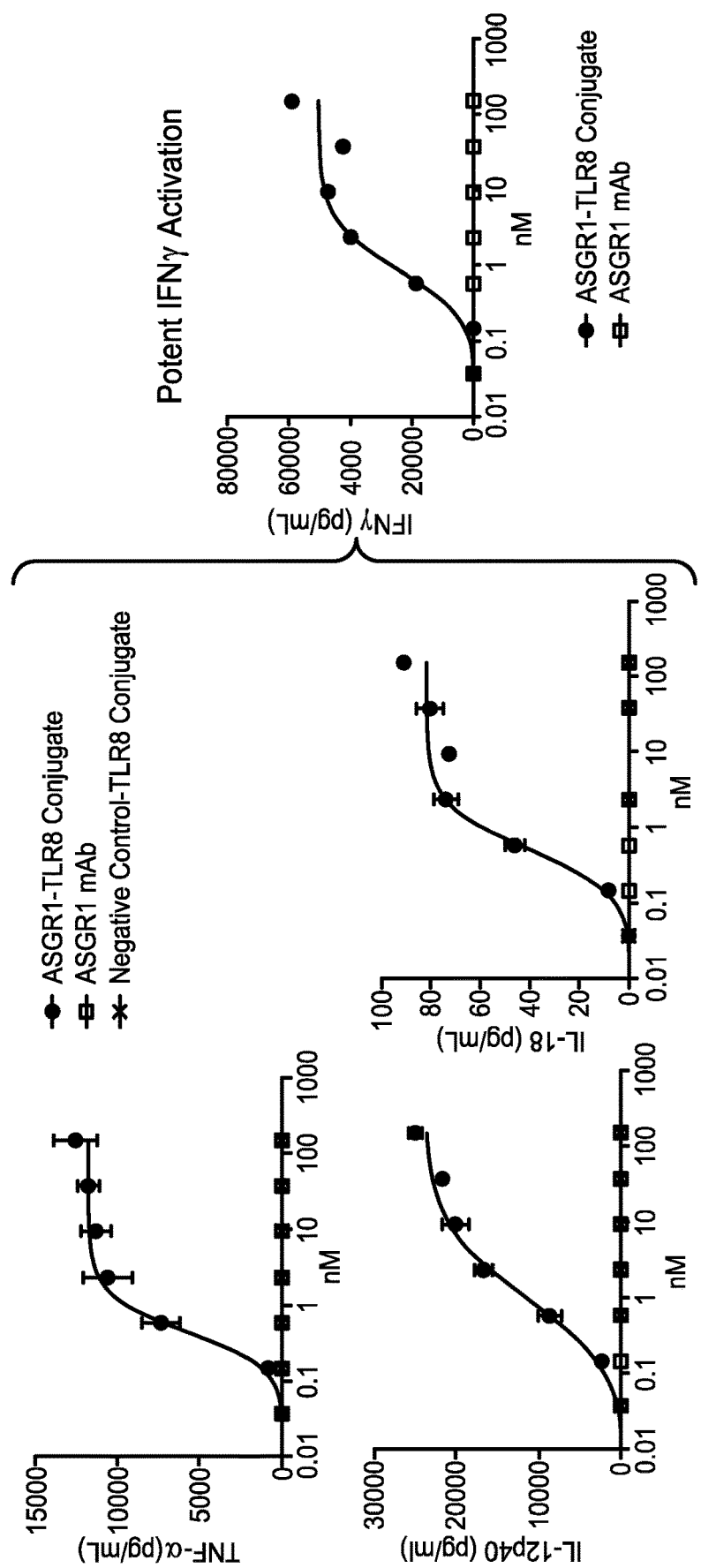
FIG. 7 are a series of graphs showing that ASGR1-TLR8 conjugate potently activates human myeloid cells to elicit cytokine production that promote an anti-viral response directly, or indirectly through other immune cells. PBMCs were co-cultured with ASGR1$^{pos}$ cells in the presence of indicated conjugates or control antibody for 24 hours. Supernatants were tested for cytokine levels by MSD assay or ELISA.

Anti-ASGR-TLR8 Agonist Conjugate Activate Myeloid Cells Eliciting Cytokines that Promote an Anti-Viral Response Directly or Indirectly Through Other Immune Cells An anti-ASGR1-TLR8 conjugated to the mouse A6A2 binding domain fused to human IgG1 Fc region was used to demonstrate anti-viral cytokines produced by anti-ASGR1-TLR8 agonism in human PBMC and ASGR1$^{pos}$ cell co-cultures as follows. PBMCs were isolated from blood of normal human donors by density gradient centrifugation, resuspended in complete RPMI, and plated in 96-well flat bottom microtiter plates (125,000/well). ASGR1$^{pos}$ cells (HepG2 cells transfected with ASGR1 gene to increase ASGR1 expression to more physiological levels) were then added (25,000/well) along with various concentrations of anti-ASGR1-TLR8 agonist conjugate, unconjugated anti-ASGR1 antibody, or anti-digoxigenin-TLR8 agonist conjugate as a non-ASGR1-TLR8 conjugate control. After 24 hours of incubation at 37° C. in a 5% $CO_2$ tissue culture incubator, supernatants were removed from wells and a multiplex electrochemiluminescence assay (Meso Scale Discovery Inc.) was performed to determine TNF-α, IL-12p40, IL-18, and IFNγ levels. As seen in FIG. 7, anti-AGSR1-TLR8 conjugate induced a large increase in anti-viral cytokines while controls did not.

Example 10

Anti-ASGR1-TLR8 Agonist Conjugate Treatment in Mouse AAV-HBV Model for Chronic HBV An in vivo mouse model for chronic HBV to examine the therapeutic effect of ASGR1-TLR8 agonists of the instant disclosure. However, rodents do not express a functional homolog of TLR8 and attempts by multiple groups to generate relevant human TLR8 transgenic mice have been unsuccessful (Wang, *J. Biol. Chem.* 281:37427, 2006; Guiducci, *J. Exp. Med.* 210:2903, 2013). Like TLR8 in humans, and in contrast to TLR7 in humans, TLR7 in mice is expressed in myeloid cells, like macrophages. Thus, for in vivo murine experiments, an anti-ASGR1-TLR7 agonist conjugate was generated as a surrogate for human anti-ASGR1-TLR8 agonist conjugates. In addition, the anti-human ASGR1 antibody 4F3 was "murinized" so as to bind to mouse ASGR1. The surrogate (i.e., murinized ASGR1 mAb-C (having 4F3 CDRs)-IgG2a conjugated to a TLR7 agonist Compound 4.1) is referred to throughout the disclosure as "ASGR1-TLR8-S." The heavy chain and light chain sequences of mzASGR1 mAb-C are set forth in SEQ ID NOS:228 and 229, respectively.

HBV DNA and HBsAg Antigen

Figure 4A:
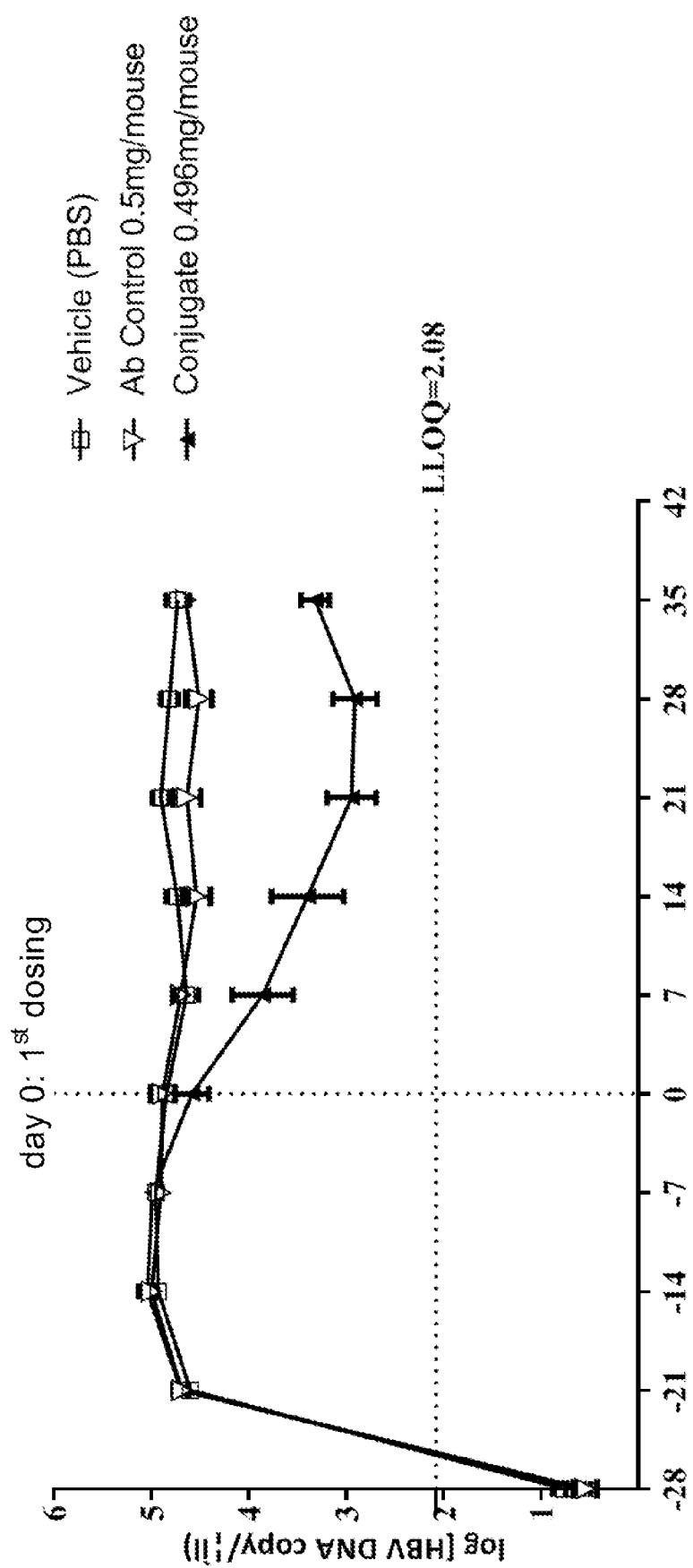
FIGS. 4A-4C are a series of graphs showing serum levels of (A) viral DNA, (B) HBsAg titer, and (C) anti-HBsAg antibody titer (seroconversion) in an in vivo AAV-HBV mouse model for chronic HBV infection when treated with a surrogate of the ASGR1-TLR8 agonist conjugates of this disclosure.
Figure 4B:
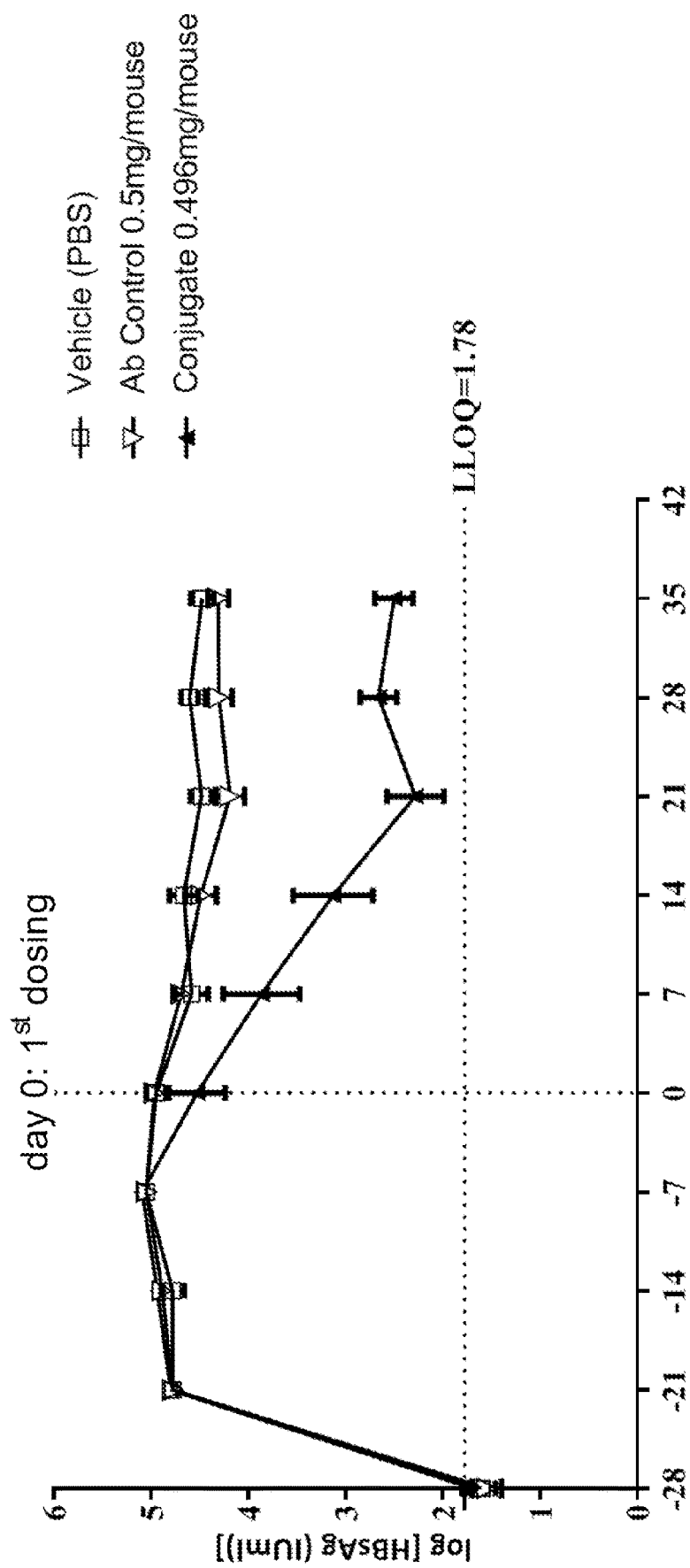

Male C57BL/6 mice were injected intravenously with AAV-HBV1.8 DNA on day −28 and were monitored weekly for levels of viral DNA and the viral antigens HBsAg and HBsAg to demonstrate chronic viral expression. On day 0 animals were sorted into viral load-balanced treatment groups of 10. Animals were treated with a subcutaneous dose once a week for 5 weeks of 0.5 mg ASGR1-TLR8-S, 0.5 mg unconjugated anti-mASGR1 monoclonal antibody, or vehicle alone. The experiment was ended on day 35. Weekly plasma samples were assessed for viral DNA and antigens, including samples from post-transduction (i.e., infection) but pre-treatment. HBV DNA in mouse plasma was isolated with QIAAMP® 96 DNA Blood Kit following the manual and quantified by qPCR. The standard curve DNA of $10^7$ copies/μL was prepared by 60-fold dilution of 5 ng/μL pAAV2-HBV1.3 plasmid DNA, then serially diluted 10-fold with AE buffer from $10^7$ to 10 copies/μL. A 2 μl volume from samples was added to standard qPCR assay mixtuRes. The PCR mixture and samples or plasmid DNA standard were added to 384-well optical reaction plates. PCR was run at 95° C. for 10 min for 1 cycle, at 95° C. for 15 sec, 60° C. for 1 min for 40 cycles. HBsAg plasma levels were determined by ELISA assay using HBsAg ELISA kit (Autobio) according to the manual. As is evident in FIGS. 4A and 4B, treatment with ASGR1-TLR8-S significantly lowered both viral DNA and HBsAg antigen, respectively, as determined by the Mann-Whitney test using GraphPad Prism software.

Treatment Effect on Animals

Throughout the course of this experiment, weekly body weights were obtained for each animal. In addition, the animals were monitored for an increase in ALT enzyme activity as a sign of liver damage. Plasma samples from d0, d7, d21, and d35 were assayed for levels of ALT with ALT Activity Assay Kit (Sigma Chemical Co., MAK052).

Figure 6A:
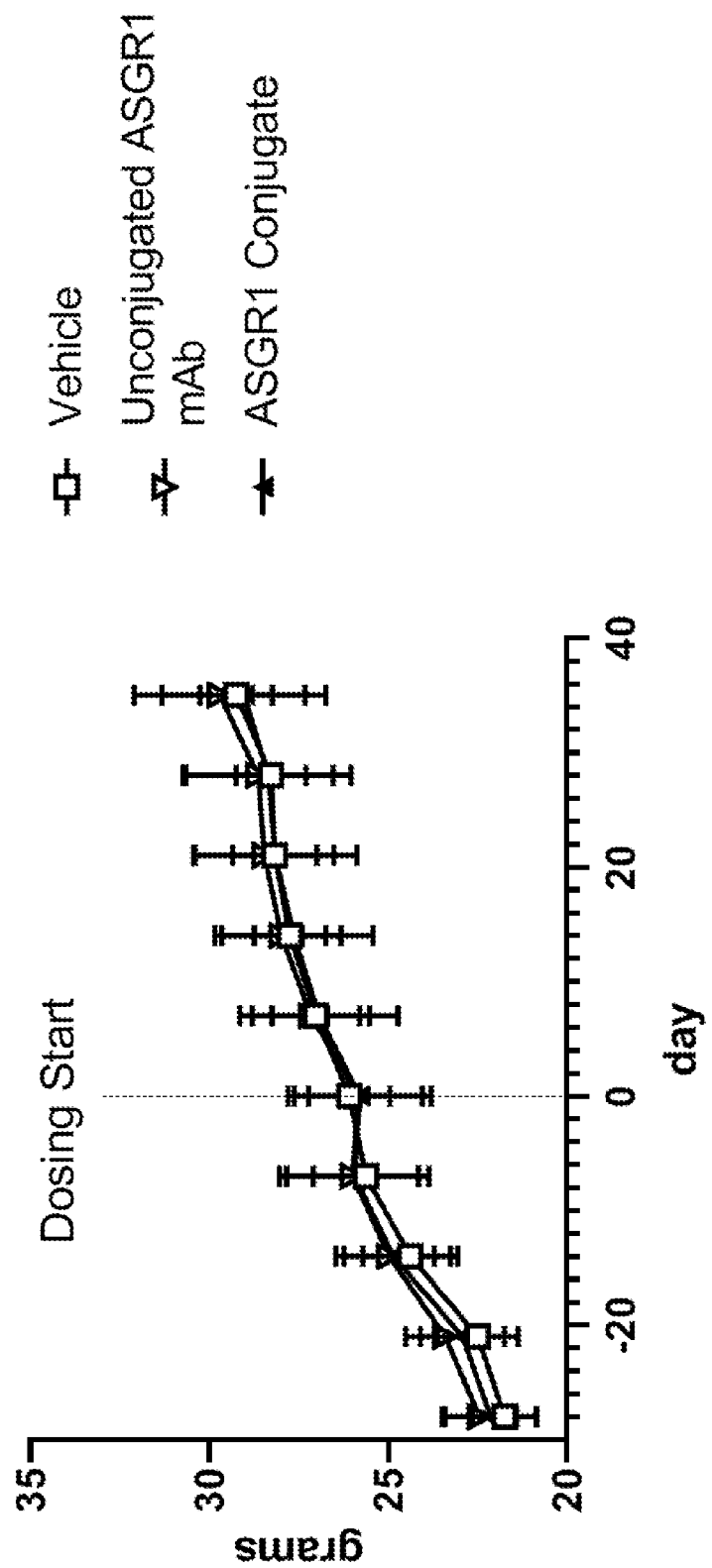
FIGS. 6A-6B are a series of graphs showing the (A) body weight and (B) ALT enzyme levels in an in vivo AAV-HBV mouse model for chronic HBV infection when treated with a surrogate of the ASGR1-TLR8 agonist conjugates of this disclosure.
Figure 6B:
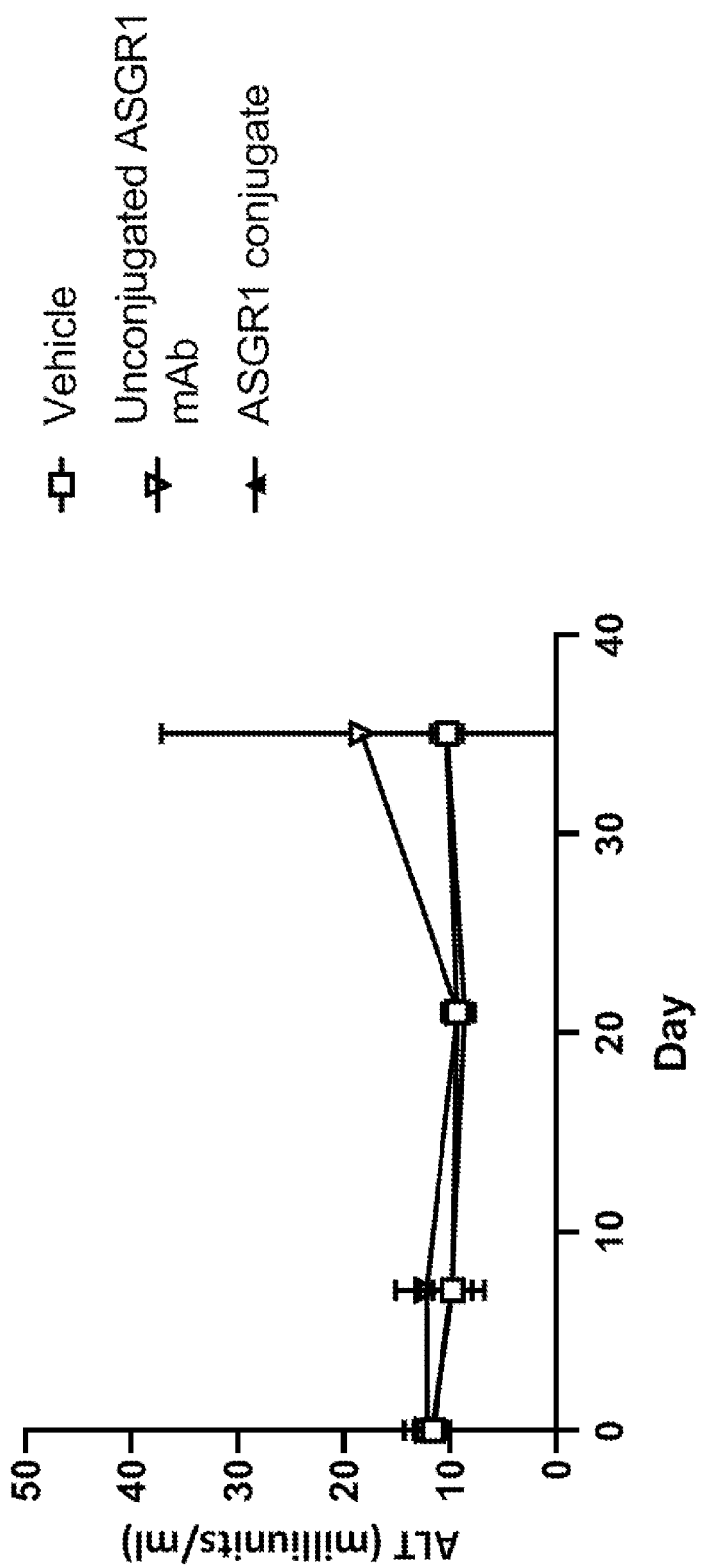

FIG. 6A shows the average body weight for each group and there was no differences in average weight for the duration of the experiment. The ASGR1-TLR8-S conjugate treated animals gained weight like control animals. Similarly, no increase in ALT enzyme activity (FIG. 6B) was observed in any animal treated with the ASGR1-TLR8-S conjugate compared to control animals. In sum, these data indicate that there was no deleterious effects on the overall health and a lack of any significant liver damage as result of ASGR1-TLR8-S conjugate treatment.

FIG. 13 is a table demonstrating liver PK following ASGR1-Surrogate (ASGR1-S) treatment in the AAV-HBV mouse model can be used to define target exposures in non-human primates (NHPs). SC doses assessed are similar to those in FIGS. 6A and 6B. Liver payload PK was used as measure of conjugate uptake. Results provided in this table defined a target payload liver concentration of approximately 100 ng/g. Seroconversion in the AAV-HBV model was observed in some animals at 5 mg/kg and 10 mg/kg.

Anti-HBV T and B Cells

At the conclusion of the study (day 35), spleens were harvested from animals and single cell suspensions of splenocytes isolated using sterile technique by maceration in RPMI media. Briefly, $2\times10^5$ splenocytes were plated onto the membranes and incubated for 22 hours in the presence of 2 μg/ml of either a HBsAg or HBcAg peptide mixture or media alone as a control. IFNγ-secreted by T cells was identified with a biotin-labeled anti-IFNγ antibody and a streptavidin-HRP secondary reagent and incubated with the HRP substrate BCIP/NBT. The specific IFNγ-secreting cells were counted using the AID iSpot reader (Autoimmun Diagnostika). For detection of B cells secreting anti-HBsAg antibody without stimulation, $2\times10^5$ splenocytes were plated on membranes impregnated with an anti-mouse IgG capture antibody, incubated for 18 hours, and spot-forming cells were visualized with anti-HBsAg with an HBsAg-peroxidase conjugate and application of peroxidase substrate. The unstimulated HBsAg specific B cells were counted using the AID iSpot reader (Autoimmun Diagnostika). For anti-HBsAg B cells after stimulation splenocytes were cultured in the presence of R848 and IL-2 in 6 wells plate for 4 days and then viral specific B cells were enumerated by the ELISpot procedure described for unstimulated splenocytes. IFNγ+ T cells and anti-HBsAg antibody B cells were quantified by using Mouse IFN-γ ELISpot PRO (ALP) strips and Mouse IgG ELISpot BASIC (ALP) (MabTech Inc.), respectively. Statistical significance was determined using Mann-Whitney test and Prism 8.4.2 software (Graphpad Inc.).

Figure 5A:
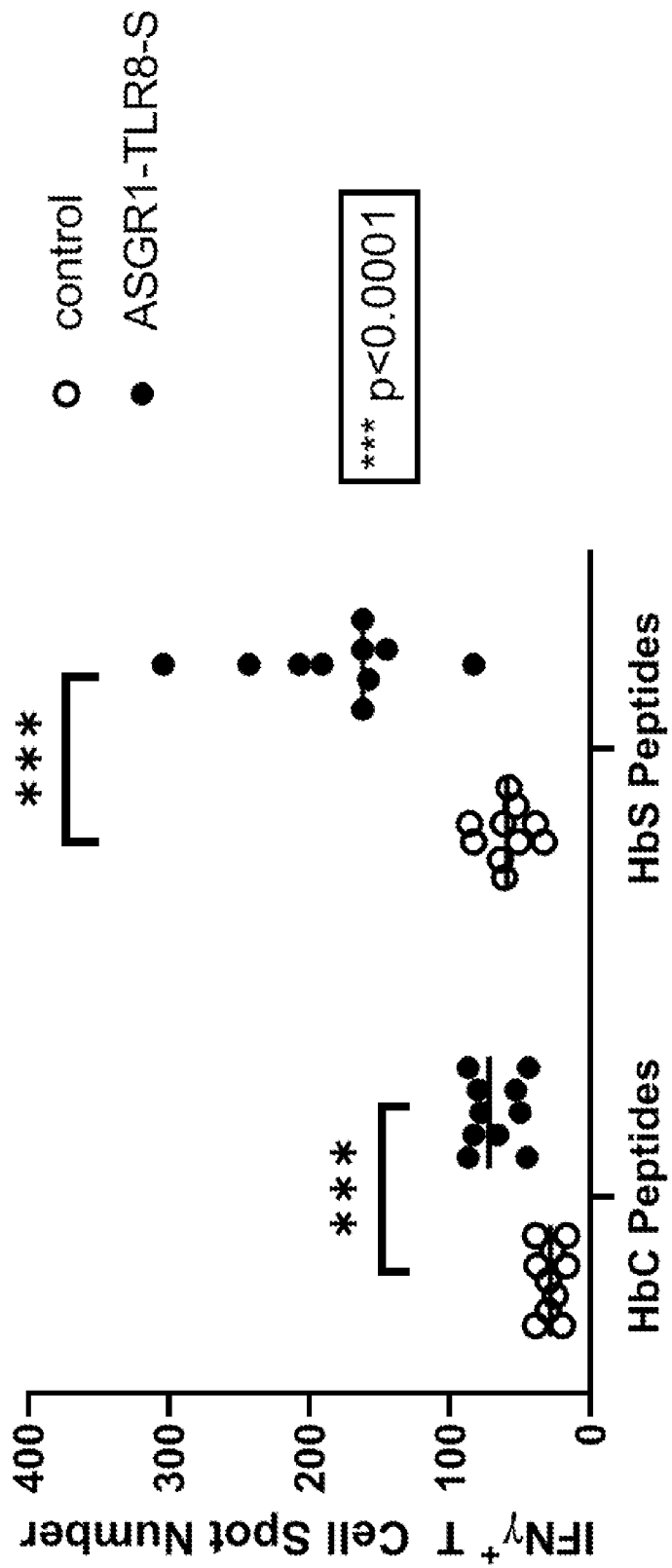
FIGS. 5A-5B are a series of graphs showing (A) IFNγ+ T cells and (B) anti-HBsAg antibody B cells produced by animals in an in vivo AAV-HBV mouse model for chronic HBV infection when treated with a surrogate of the ASGR1-TLR8 agonist conjugates of this disclosure.
Figure 5B:
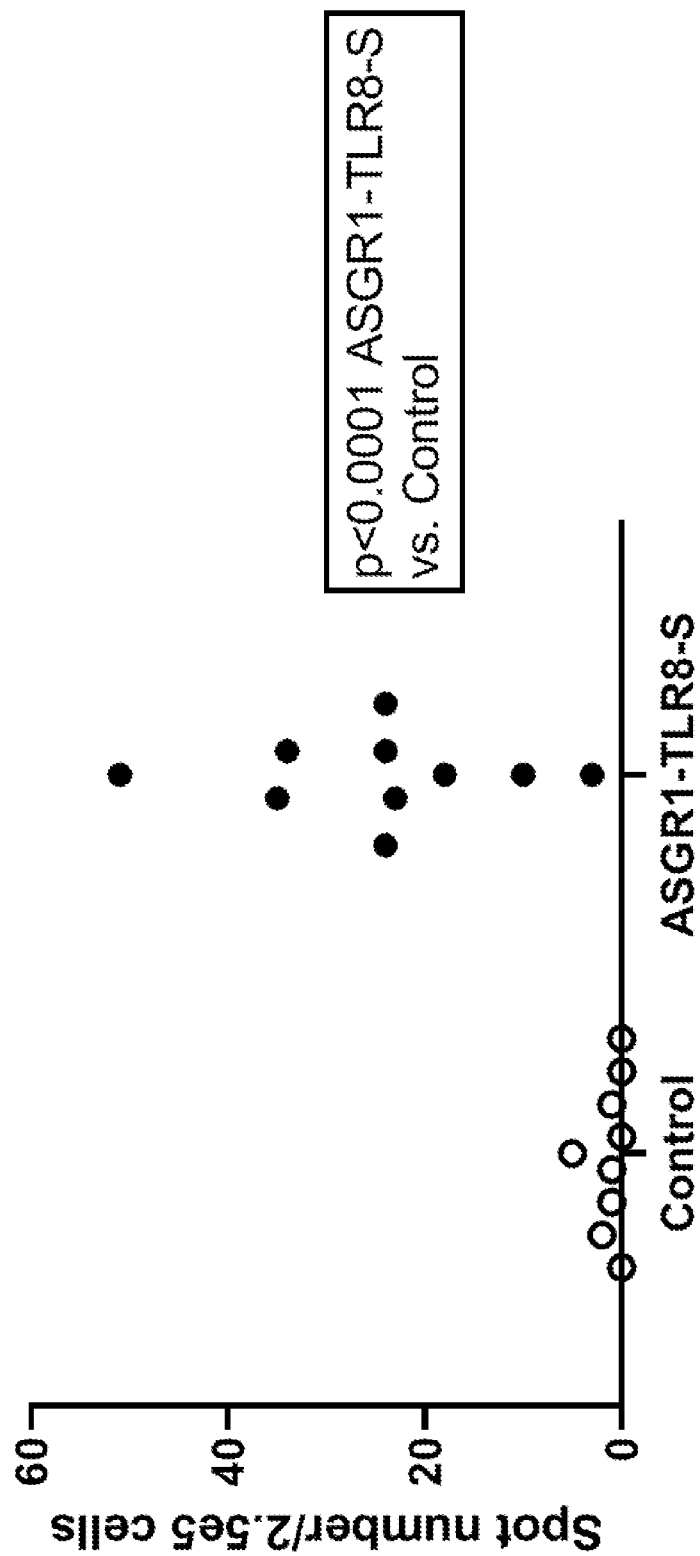

FIGS. 5A and 5B show that treatment with the ASGR1-TLR8-S conjugate generated a significant increase in IFNγ T cells and B cells anti-viral antigen responses in the AAV-HBV transduced mice.

Anti-HBV Antibody Titer (Seroconversion)

Figure 4C:
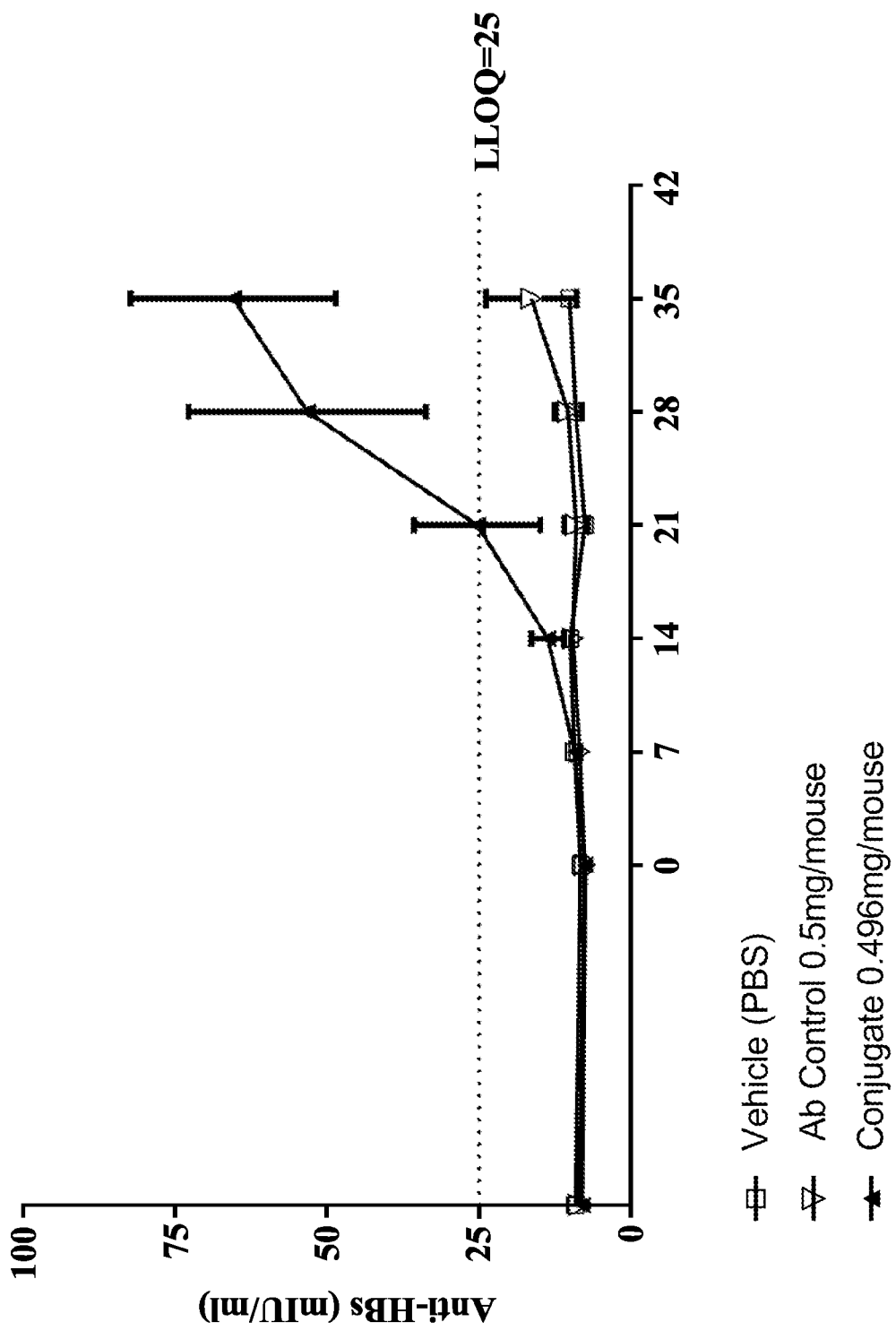

To assess the effect of ASGR1-TLR8-S treatment on anti-HBsAg antibody titers, blood samples were taken from AAV-HBV1.8 transduced animals weekly beginning on day −14 until the end of the experiment. Plasma was assayed for antibody titers using an HBsAg antigen capture ELISA format. Anti-HBs was detected using the Anti-HBs ELISA kit (Autobio) according to the manual. Beginning on day 21, the animals treated with the ASGR1-TLR8-S conjugate surprisingly achieved seroconversion (FIG. 4C) unlike animals in the control groups. This was judged highly significant by Mann-Whitney test using GraphPad Prism software. Generally, seroconversion is rare in this HBV model, and TLR7 agonists have been shown to have a modest effect on viral and not result in seroconversion (see, e.g., Zhu et al., Roche Innovations, HBV Cure Workshop, 2018 Toronto, Canada). These results demonstrate that treatment with ASGR1-TLR8-S conjugate led to anti-HBsAg seroconversion in AAV-HBV transduced mice expressing high levels of HBsAg antigen at start of treatment.

Testing of anti-ASGR1-TLR8-S conjugate treatment in mouse AAV-HBV model was replicated as described above. Similar to previous experiment, there were no deleterious effects on the overall health and a lack of any significant liver damage as result of ASGR1-TLR8-S conjugate treatment (data not shown). Treatment with the ASGR1-TLR8-S conjugate generated a significant increase in IFNγ⁺ T cells and B cells anti-viral antigen responses in the AAV-HBV transduced mice, which parallels what was observed in the first experiment (data not shown).

Figure 8A:
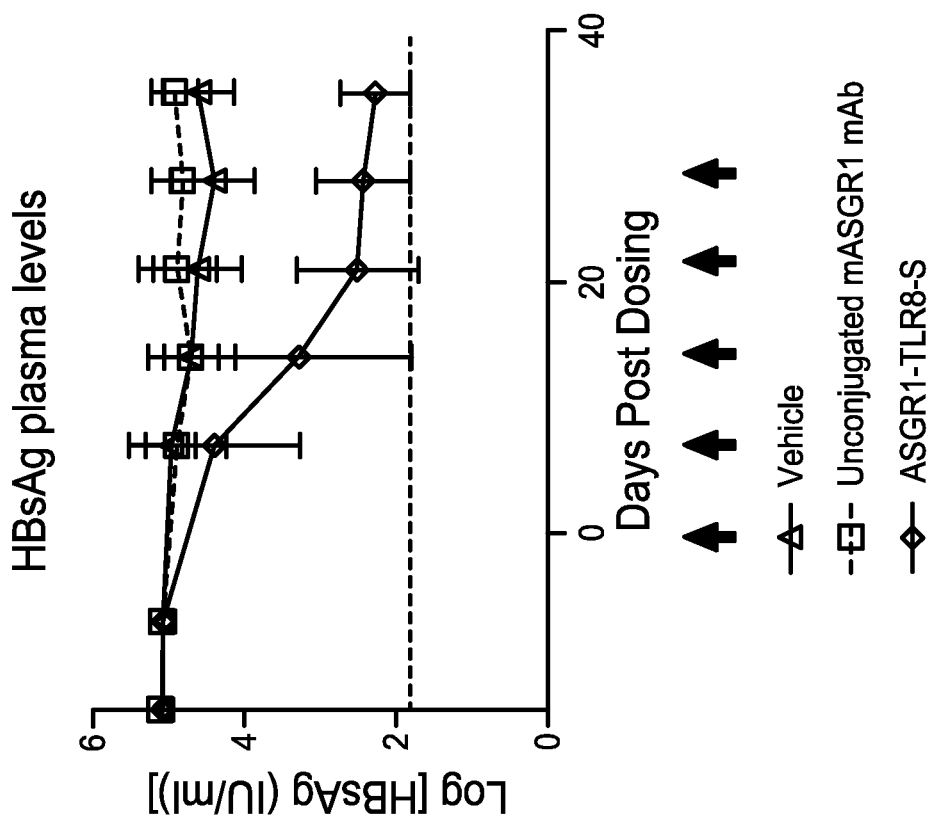
FIGS. 8A-8B are a pair of graphs showing that ASGR1-TLR8-S reduces HBsAg and drives seroconversion in AAV-HBV mouse model. C57BL/6 mice were transduced with AAV8-HBV1.2 vector and sorted into treatment groups (n=10). Animals received 0.5 mg/dose of ASGR1-TLR8-S, 0.5 mg of unconjugated mASGR1 mAb or vehicle, sc QWx5 beginning d0 (black arrows).

Treatment with ASGR1-TLR8-S significantly lowered both viral DNA (data not shown) and HBsAg antigen (FIG. 8A).

Figure 8B:
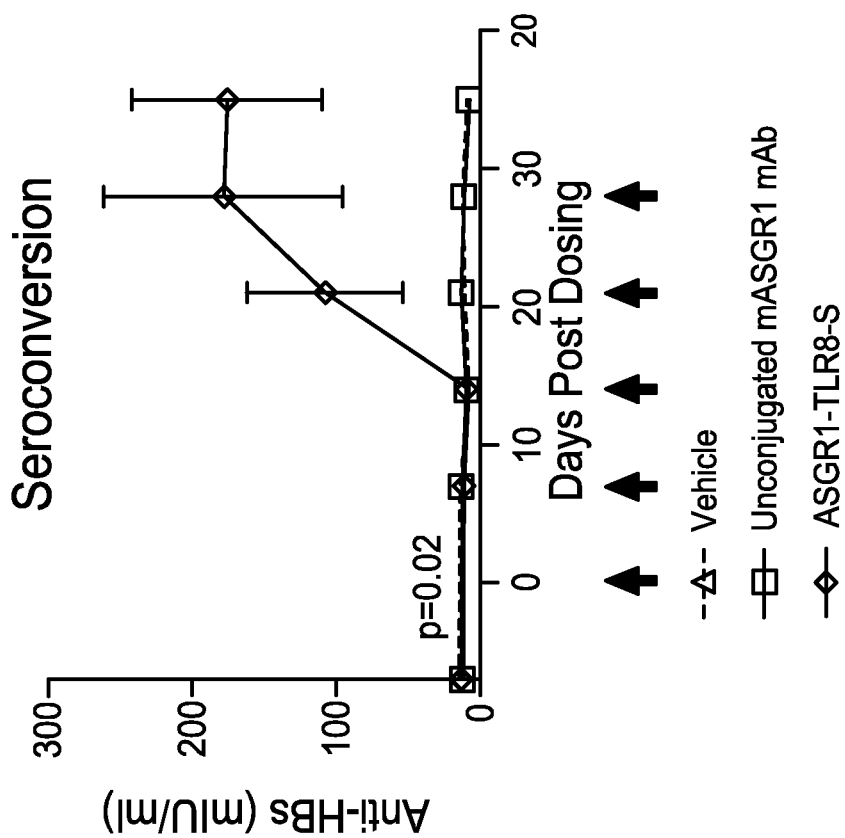

As shown in FIG. 8B, similar to the previous experiment, treatment with ASGR1-TLR8-S conjugate led to anti-HBsAg seroconversion in AAV-HBV transduced mice expressing high levels of HBsAg antigen at the start of treatment.

Example 11

Anti-ASGR1-TLR8 Agonist Conjugate Myeloid Activation Leads to CD86 Cell Surface Increase on B Cells in Human PBMC and ASGR1$^{Pos}$ Target Cell Co-Culture, a Sign of Increased Igg Secretion and Antigen Presentation Capacity Normal human donor PBMCs were co-cultured with cell lines expressing ASGR1 (ASGR1$^{pos}$) or not (ASGR1$^{neg}$) in the presence of 10 nM of either anti-ASGR1-TLR8 conjugate, the unconjugated antibody, an anti-digoxigenin-TLR8 conjugate or no treatment. After 24 or 48 hours of incubation, cells were harvested and processed for FACS analysis (BD FACSCelesta™ Flow Cytometer) by standard procedures for washing and incubation with immune cell lineage antibodies, that included anti-CD19 antibody to identify B cells, and antibodies to detect levels of cell activation molecules, including anti-CD86 antibody.

Figure 9:
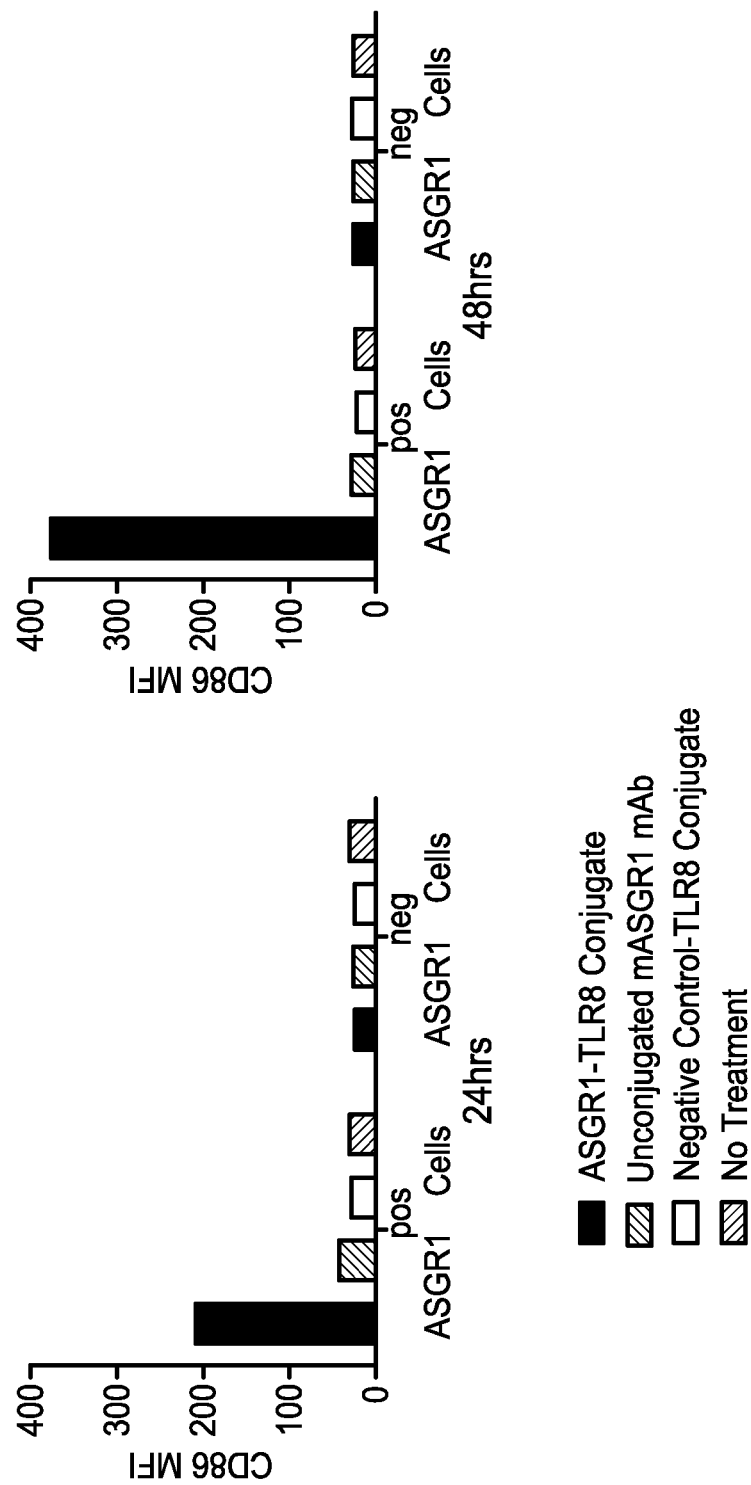
FIG. 9 is a pair of graphs showing that ASGR1-TLR8 increases B cell expression of CD86, an activation marker indicative of increased antigen presentation and IgG secretion. CD86 levels on CD19$^{pos}$ B cells were determined by flow cytometry after co-culture of PBMC with ASGR1$^{pos}$ or ASGR1$^{neg}$ cells in presence of test articles at 10 nM at 24 hours (left) and 48 hours (right). This ASGR1-TLR8 contains a mouse-human chimeric anti-ASGR1 antibody.
Figure 11:
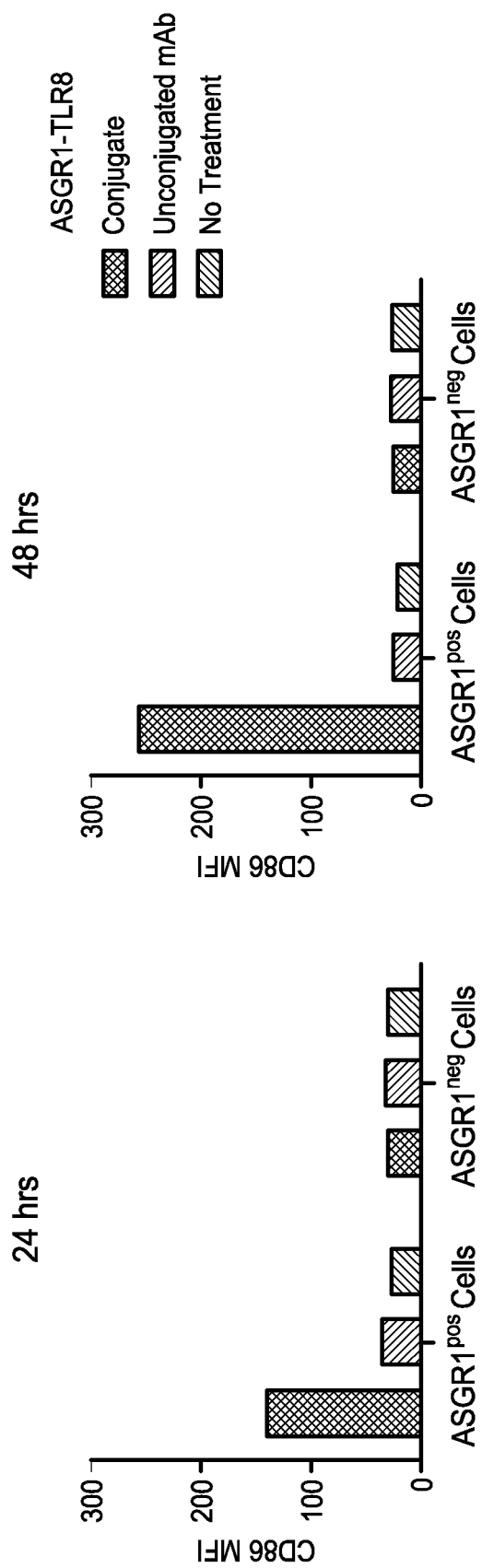
FIG. 11 is a pair of graphs demonstrating that ASGR1-TLR8 conjugate dependent myeloid activation promotes B cell activation. ASGR1-TLR8 conjugate activation increases B-cell expression of CD86, an activation marker indicating increased antigen presentation and IgG secretion. Abbreviations: monoclonal antibody (mAb), positive (pos), negative (neg), mean fluorescence intensity (MFI), hours (hrs). This ASGR1-TLR8 conjugate contains a humanized anti-ASGR1 antibody and has a DAR4.
Figure 12:
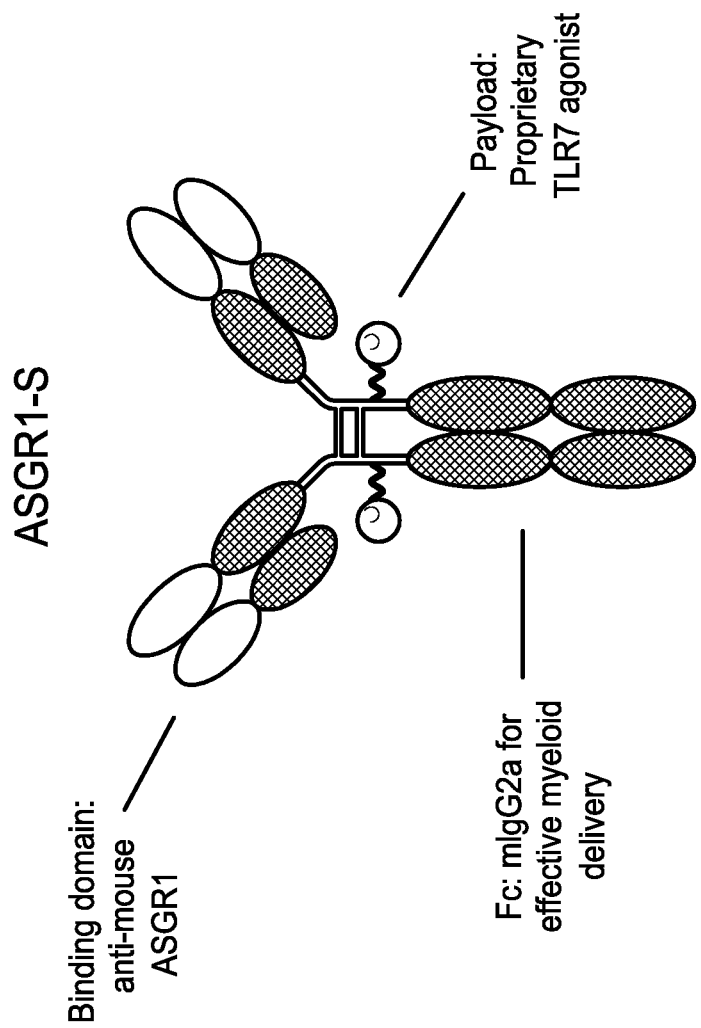
FIG. 12 is a schematic diagram depicting "ASGR1-Surrogate (ASGR1-S)," a mouse conjugate surrogate for an ASGR1-TLR8 conjugate intended for therapeutic use in a human. ASGR1-S may also be referred to as "ASGR1-TLR8-S" or "ASGR1-TLR8 Conjugate Surrogate."

Shown as MFI are the levels of CD86 found on CD19$^{pos}$ cells that demonstrate B cells were activated in the co-culture experiments by ASGR1-TLR8 agonism (FIG. 9 and FIG. 11).

Example 12

Anti-ASGR1-TLR8 Agonist Conjugate Myeloid Activation Leads to NK Cell and T Cell IFNγ Responses in Human PBMC and ASGR1$^{Pos}$ Target Cell Co-Culture Normal human donor PBMCs were co-cultured with cell lines expressing ASGR1 (ASGR1$^{pos}$) or not (ASGR1$^{neg}$) in the presence of 10 nM of either anti-ASGR1-TLR8 conjugate, the unconjugated antibody, an anti-digoxigenin-TLR8 conjugate or no treatment. After 24 or 48 hours of incubation, cells were harvested and processed for FACS analysis (BD FACSCelesta™ Flow Cytometer) by standard procedures for washing and incubation with immune cell lineage antibodies, that included antibodies to detect levels of cell activation molecules, including anti-IFNγ antibody.

Figure 10:
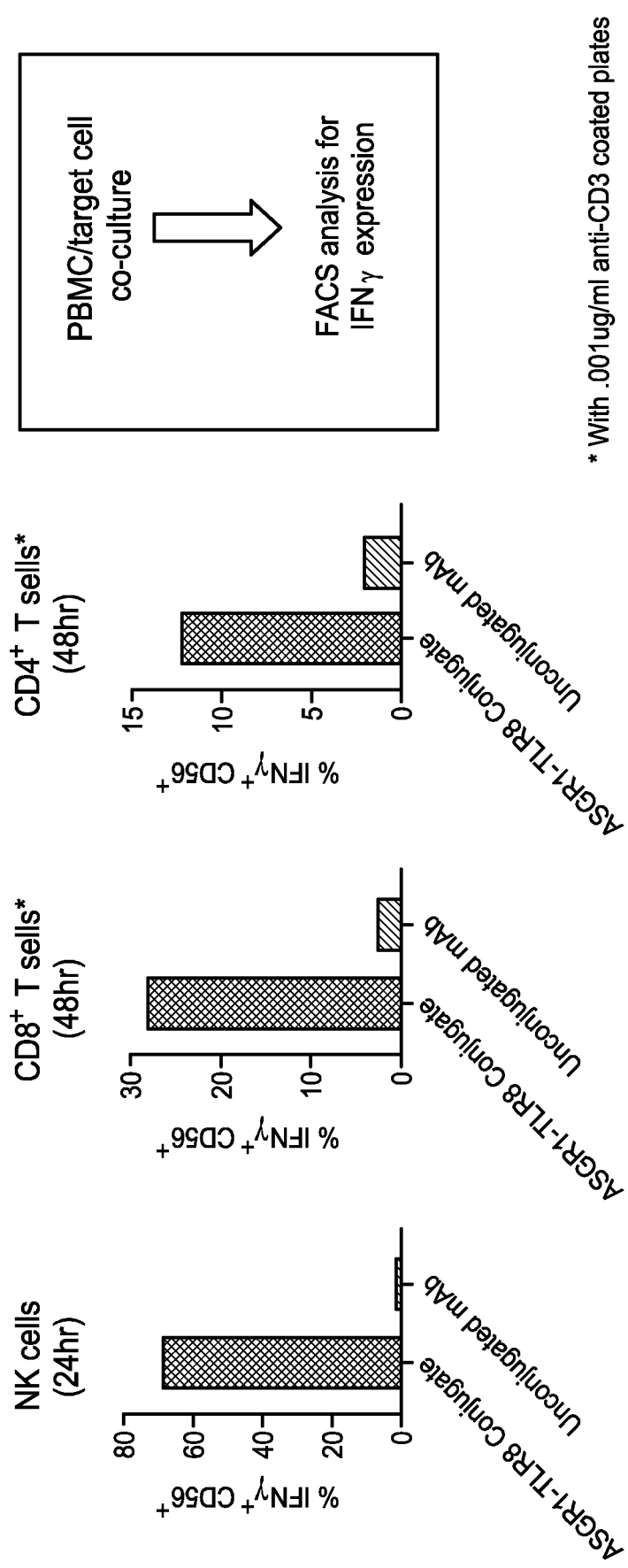
FIG. 10 is a series of graphs demonstrating that ASGR1-TLR8 conjugate dependent myeloid activation promotes NK cell (left) and T cell (CD8$^+$, center and CD4$^+$, right) interferon gamma (IFNγ) responses in vitro. A schematic diagram at the far right is depicting the experimental paradigm for myeloid activation by which the ASGR1-TLR8 conjugate is introduced into a PBMC and target cell co-culture. Following a period of myeloid cell differentiation, FACS analysis is performed on the resultant NK cells, CD8$^+$ T cells and CD4$^+$ T cells. This ASGR1-TLR8 conjugate contains a humanized anti-ASGR1 antibody and has a DAR4.

Shown as MFI are the levels of IFNγ found on NK cells, CD8$^+$ T cells, and CD4$^+$ T cells, demonstrating that in the co-culture experiments, ASGR1-TLR8 agonism drives an IFNγ response in vitro (see FIG. 10).

Example 13

Safety Studies in Non-Human Primates (NHPS) Indicate Favorable Tolerability and Effective Liver Targeting for ASGR1-TLR8

Figure 14:
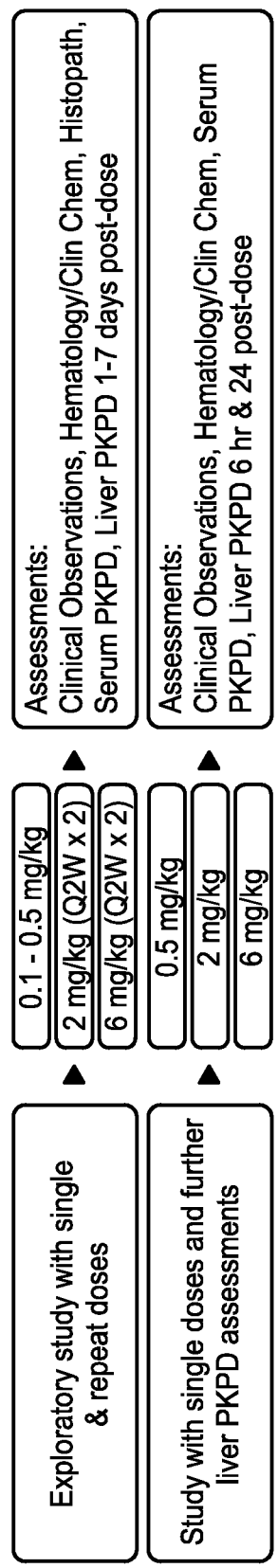
FIG. 14 is a schematic diagram depicting two exploratory safety studies in non-human primates (NHPs; *Cynomolgus macaque (Macaca fascicularis)*), that indicate favorable tolerability and effective liver targeting for ASGR1-TLR8 Conjugate. In some embodiments, a favorable tolerability profile includes no adverse events at any dose across studies indicating no-observed-adverse-effect-level (NOAEL) >6 mg/kg (potentially ≥12 mg/kg); no clinical signs or notable histopathology findings in liver or other tissues; and/or transient, mild clinical pathology changes, but no increases in alanine transaminase (ALT)/aspartate transaminase (AST) at any dose level. In some embodiments, effective liver targeting includes dose-related increases in cytokine/chemokine serum levels and mRNA in liver at ≥0.5 mg/kg and/or liver payload concentrations at 2 mg/kg ASGR1-TLR8 Conjugate exceed those for surrogate at efficacious AAV-HBV doses.
Figure 15:
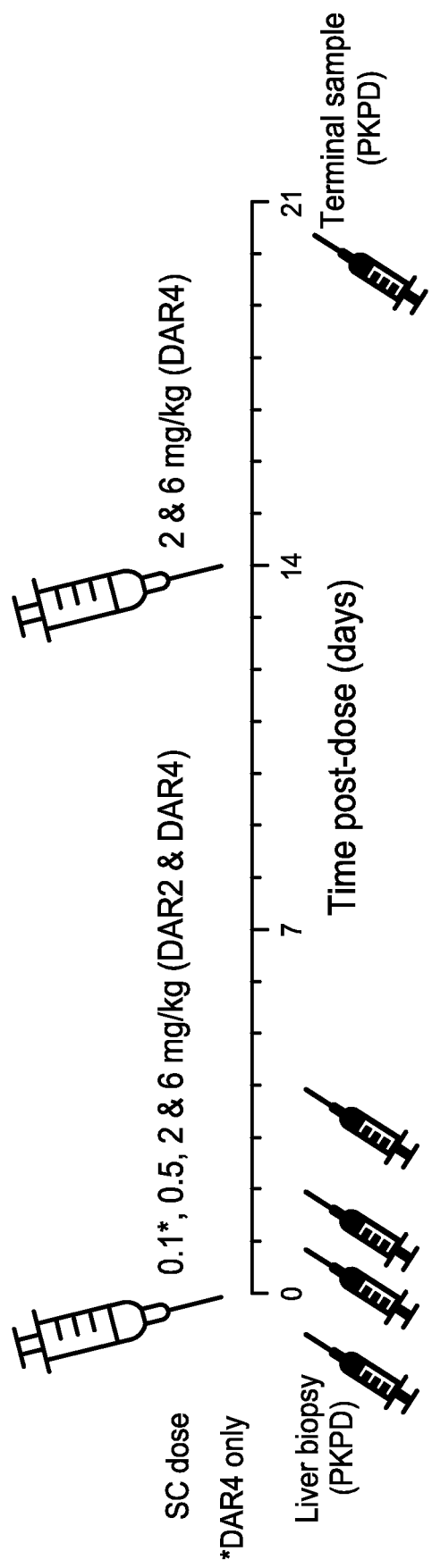
FIG. 15 is a schematic diagram depicting the schedule of doses and biopsies for the studies described in FIG. 14. Liver biopsies were obtained and evaluated for systemic and liver pharmacokinetic (PK)/pharmacodynamic (PD) modeling. Results for serum PK indicated very low conjugate levels (similar for DAR2 versus DAR4) and short half-lives, consistent with effective liver targeting. Results for serum PD indicated similar cytokine and chemokine increases for DAR2 versus DAR4 at low doses (0.5 mg/kg), demonstrating that the 0.5 mg/kg dose is active in the liver. For repeat dosing at 2 mg/kg and 6 mg/kg doses (DAR4), anti-drug antibody (ADA) formation prior to dose 2 led to reduced or non-quantifiable drug levels in serum, but liver uptake and serum PD profiles were maintained. This ASGR1-TLR8 conjugate contains a humanized anti-ASGR1 antibody.

Two exploratory safety studies in non-human primates (NHPs) were performed to determine the safety and tolerability of anti-ASGR-TLR8 (see FIGS. 14 and 15). Briefly, an anti-ASGR1-TLR8 conjugate, having a drug-to-antibody ratio of either 2 (DAR2) or 4 (DAR4), were administered to NHP subjects (Cynomolgus macaque (Macaca fascicularis)) by a subcutaneous route at day 0 and/or day 14. Liver Biopsies were obtained for PKPD analyses prior to the initial administration, and then at days 1, 2, and 4 post-administration. A final biopsy was obtained at the end of the 21-day study (the terminal sample).

Results for serum PK indicated very low conjugate levels (similar for DAR2 versus DAR4) and short half-lives, consistent with effective liver targeting. Results for serum PD indicated similar cytokine and chemokine increases for DAR2 versus DAR4 at low doses (0.5 mg/kg), demonstrating that the 0.5 mg/kg dose is active in the liver. For repeat dosing at 2 mg/kg and 6 mg/kg doses (DAR4), anti-drug antibody (ADA) formation prior to dose 2 led to reduced or non-quantifiable drug levels in serum, but liver uptake and serum PD profiles were maintained.

FIG. 16 provides liver payload exposure data after subcutaneous (SC) doses of DAR2 and DAR4 ASGR1-TLR8 conjugates. Efficiency of liver update is similar for DAR2 versus DAR4 ASGR1-TLR8 conjugates. For both DAR2 and DAR4, liver exposures increased with dose and the estimated % dose in liver was generally between about 30% and about 70%. For example, 2 mg/kg DAR2 results in similar or approximately 2-fold greater payload levels compared to target exposure.

Figure 17:
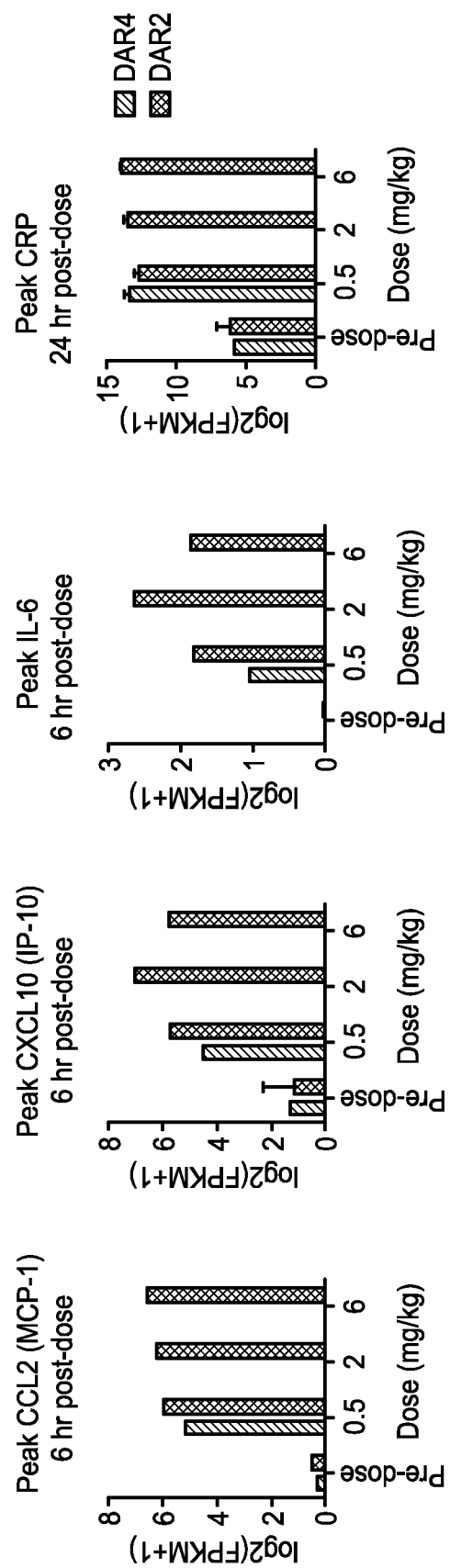
FIG. 17 is a series of graphs demonstrating ASGR1-TLR8 conjugate-mediated myeloid cell activation at a low dose (0.5 mg/kg) and comparable effects for DAR2 versus DAR4. The low dose of 0.5 mg/kg DAR2 versus DAR4 resulted in comparable increases across multiple markers using Liver RNAseq (from left to right: CCL2 (MCP-1), CXCL10 (IP-10), IL-6, and CRP), demonstrating that the 0.5 mg/kg dose level activates myeloid cells in liver. Liver PD responses across a range of dose levels from 0.5 mg/kg to 6 mg/kg DAR2 were comparable, indicating that lower dose levels are active. The data support 0.5 mg/kg to 2 mg/kg DAR2 as biologically effective doses (BEDs). IFNγ increases were not observed. Biomarker expression levels were transformed to logarithmic space by using log 2(FPKM+1). This ASGR1-TLR8 conjugate contains a humanized anti-ASGR1 antibody.

Liver RNAseq was performed on the biopsy samples to assess the expression of a series of biomarkers of myeloid cell activation, including CCL2 (MCP-1), CXCL10 (IP-10), IL-6, and CRP. The data show that the low dose of 0.5 mg/kg DAR2 versus DAR4 resulted in comparable increases across multiple markers, demonstrating that the 0.5 mg/kg dose level activates myeloid cells in liver. Liver PD responses across a range of dose levels from 0.5 mg/kg to 6 mg/kg DAR2 were comparable, indicating that lower dose levels are active (see, FIG. 17). The data support 0.5 mg/kg to 2 mg/kg DAR2 as biologically effective doses (BEDs). IFNγ increases were not observed (data not shown).

Figure 18:
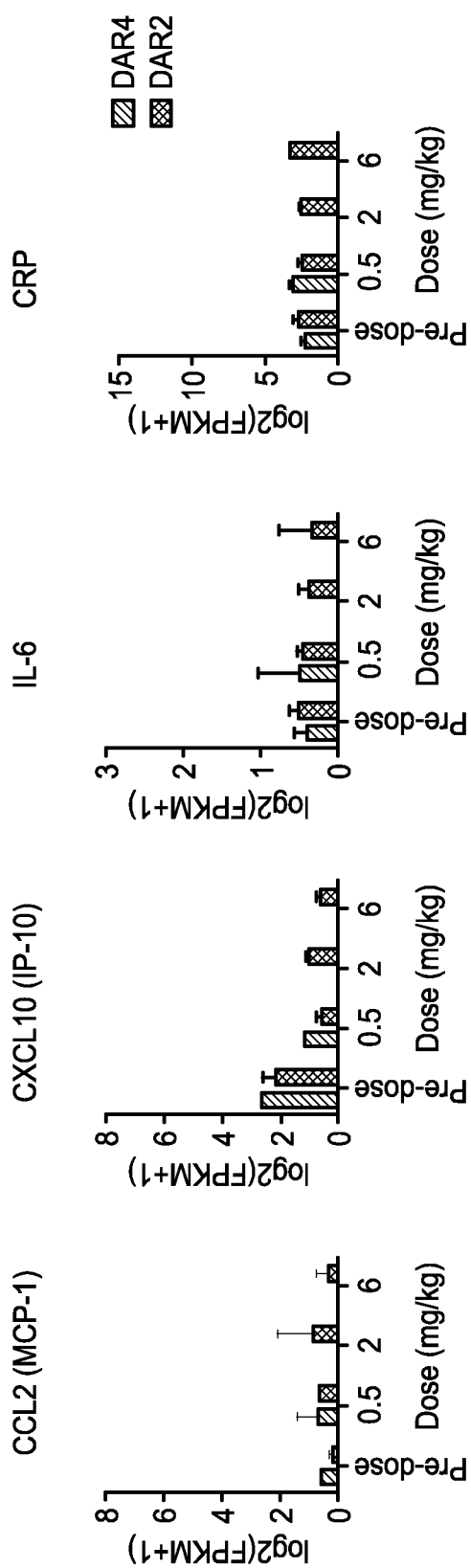
FIG. 18 is a series of graphs demonstrating that, following ASGR1-TLR8 conjugate-mediated myeloid cell activation, serum cytokine increases are not derived from blood cells. Blood RNAseq and serum data evaluating expression levels of, from left to right, CCL2 (MCP-1), CXCL10 (IP-10), IL-6, and CRP, demonstrate a lack of increase in RNA for MCP-1, IP-10 and IL-6 in blood at any dose. This result contrasts with data showing robust increases of MCP-1, IP-10 and IL-6 in liver following ASGR1-TLR8 conjugate-mediated myeloid cell activation (see FIG. 17). The data demonstrating increased levels of MCP-1, IP-10 and IL-6 in serum indicate that these chemokines and cytokines are likely derived from liver and/or lymph node-resident myeloid cells after SC administration of an ASGR1-TLR8 conjugate. The lack of change in blood was consistent with the fact that CRP is produced predominantly by hepatocytes. This ASGR1-TLR8 conjugate contains a humanized anti-ASGR1 antibody.

To confirm the location of the activated myeloid cells, Blood RNAseq was performed to assess the abundance of this series of biomarkers of myeloid cell activation, including CCL2 (MCP-1), CXCL10 (IP-10), IL-6, and CRP, in the serum obtained from NHPs in this study. The data demonstrate a lack of increase in RNA for MCP-1, IP-10 and IL-6 in blood at any dose (FIG. 18). This result contrasts with data showing robust increases of MCP-1, IP-10 and IL-6 in liver following ASGR1-TLR8 conjugate-mediated myeloid cell activation (see FIG. 17). The data demonstrating increased levels of MCP-1, IP-10 and IL-6 in serum indicate that these chemokines and cytokines are likely derived from liver and/or lymph node-resident myeloid cells after SC administration of an ASGR1-TLR8 conjugate. The lack of change in blood was consistent with the fact that CRP is produced predominantly by hepatocytes.

Taken together, the safety and PD profiles of an ASGR1-TLR8 conjugate in NHP indicated favorable safety margin and therapeutic index for DAR2 in humans (see FIG. 19). Mouse liver PK data (see FIG. 13) provided a bridge from efficacious doses in AAV-HBV model to NHP.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application No. 63/047,221, filed on Jul. 1, 2020, U.S. Patent Application No. 63/090,158, filed on Oct. 9, 2020, U.S. Patent Application No. 63/151,561, filed on Feb. 19, 2021, and U.S. Patent Application No. 63/213,155, filed on Jun. 21, 2021, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A myeloid cell agonist conjugate or a salt thereof, wherein the conjugate is represented by Formula (I):

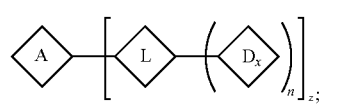

(I)

wherein:

A is an anti-ASGR1 antibody or antigen-binding fragment thereof, comprising a heavy chain variable region (VH) and a light chain variable region (VL), wherein:
the VH comprises a CDR1 (VH-CDR1) comprising the amino acid sequence of SEQ ID NO:1, a VH-CDR2 comprising the amino acid sequence SEQ ID NO:6 or SEQ ID NO:8, a VH-CDR3 comprising the amino acid sequence of SEQ ID NO:13; and the VL comprises a CDR1 (VL-CDR1) comprising the amino acid sequence of SEQ ID NO:18, a VL-CDR2 comprising the amino acid sequence SEQ ID NO:23 or SEQ ID NO:24, and a VL-CDR3 comprising the amino acid sequence of SEQ ID NO:33;

L is a linker;

$D_x$ comprises a TLR8 agonist;

n is selected from 1 to 20; and z is selected from 1 to 20.

2. The myeloid cell agonist conjugate of claim 1, wherein the anti-ASGR1 antibody or antigen-binding fragment thereof comprises:

(a) a VH comprising the amino acid sequence that has at least 90% identity with the amino acid sequence of SEQ ID NO:240, and a VL comprising the amino acid sequence that has at least 90% identity with the amino acid sequence of SEQ ID NO:247, provided that the amino acid sequences of the VH-CDRs and VL-CDRs are unchanged;

(b) a VH comprising the amino acid sequence that has at least 90% identity with the amino acid sequence of SEQ ID NO:239, and a VL comprising the amino acid sequence that has at least 90% identity with the amino acid sequence of SEQ ID NO:247, provided that the amino acid sequences of the VH-CDRs and VL-CDRs are unchanged;
(c) a VH comprising the amino acid sequence that has at least 90% identity with the amino acid sequence of SEQ ID NO:239, and a VL comprising the amino acid sequence that has at least 90% identity with the amino acid sequence of SEQ ID NO:248, provided that the amino acid sequences of the VH-CDRs and VL-CDRs are unchanged; or
(d) a VH comprising the amino acid sequence that has at least 90% identity with the amino acid sequence of SEQ ID NO:240, and a VL comprising the amino acid sequence that has at least 90% identity with the amino acid sequence of SEQ ID NO:248, provided that the amino acid sequences of the VH-CDRs and VL-CDRs are unchanged; or
(e) a VH comprising the amino acid sequence that has at least 90% identity with the amino acid sequence of SEQ ID NO:43, and a VL comprising the amino acid sequence that has at least 90% identity with the amino acid sequence of SEQ ID NO:131, provided that the amino acid sequences of the VH-CDRs and VL-CDRs are unchanged; or
(f) a VH comprising the amino acid sequence of SEQ ID NO:43, and a VL comprising the amino acid sequence of SEQ ID NO:131; or
(g) a VH comprising the amino acid sequence of SEQ ID NO:240, and a VL comprising the amino acid sequence of SEQ ID NO:247; or
(h) a VH comprising the amino acid sequence of SEQ ID NO:239, and a VL comprising the amino acid sequence of SEQ ID NO:247; or
(i) a VH comprising the amino acid sequence of SEQ ID NO:239, and a VL comprising the amino acid sequence of SEQ ID NO:248; or
(j) a VH comprising the amino acid sequence of SEQ ID NO:240, and a VL comprising the amino acid sequence of SEQ ID NO:248.

3. The myeloid cell agonist conjugate of claim 1, wherein A is an anti-ASGR1 antibody and the antibody comprises:
(a) a heavy chain comprising a VH comprising the amino acid sequence that has at least 90% identity with the amino acid sequence of SEQ ID NO:240 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:247 and a human kappa constant region comprising the amino acid sequence that has at least 90% identity with the amino acid sequence of SEQ ID NO:232, provided that the amino acid sequences of the VH-CDRs and VL-CDRs are unchanged; or
(b) a heavy chain comprising a VH comprising the amino acid sequence that has at least 90% identity with the amino acid sequence of SEQ ID NO:239 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:247 and a human kappa constant region comprising the amino acid sequence that has at least 90% identity with the amino acid sequence of SEQ ID NO:232, provided that the amino acid sequences of the VH-CDRs and VL-CDRs are unchanged; or
(c) a heavy chain comprising a VH comprising the amino acid sequence that has at least 90% identity with the amino acid sequence of SEQ ID NO:239 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:248 and a human kappa constant region comprising the amino acid sequence that has at least 90% identity with the amino acid sequence of SEQ ID NO:232, provided that the amino acid sequences of the VH-CDRs and VL-CDRs are unchanged; or
(d) a heavy chain comprising a VH comprising the amino acid sequence that has at least 90% identity with the amino acid sequence of SEQ ID NO:240 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:248 and a human kappa constant region comprising the amino acid sequence that has at least 90% identity with the amino acid sequence of SEQ ID NO:232, provided that the amino acid sequences of the VH-CDRs and VL-CDRs are unchanged; or
(e) a heavy chain comprising a VH comprising the amino acid sequence that has at least 90% identity with the amino acid sequence of SEQ ID NO:43 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:131 and a human kappa constant region comprising the amino acid sequence that has at least 90% identity with the amino acid sequence of SEQ ID NO:232, provided that the amino acid sequences of the VH-CDRs and VL-CDRs are unchanged; or
(f) a heavy chain comprising a VH comprising the amino acid sequence of SEQ ID NO:43 and a human IgG1 constant region comprising the amino acid sequence of SEQ ID NO:230, and a light chain comprising a VL comprising the amino acid sequence of SEQ ID NO:131 and a human kappa constant region comprising the amino acid sequence of SEQ ID NO:232; or
(g) a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232;
(h) a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232; or (i) a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232; or (j) a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232.

4. The myeloid cell agonist conjugate of claim 1, wherein the antibody comprises a human IgG1 constant region.

5. The myeloid cell agonist conjugate of claim 1, wherein the TLR8 agonist is selected from compounds 1.1-1.69 or a salt thereof.

6. The myeloid cell agonist conjugate of claim 1, wherein the TLR8 agonist is compound 1.36, 1.50, 1.57, 1.60, or 1.64 or a salt thereof.

7. The myeloid cell agonist conjugate of claim 1, wherein the TLR8 agonist is

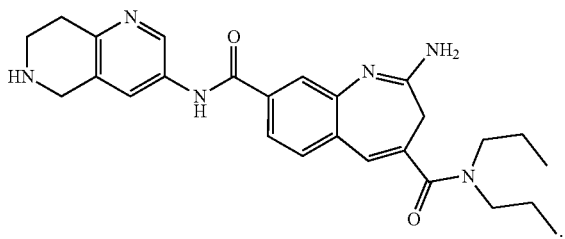 [SMILES: CCCN(CCC)C(=O)C1=Cc2ccc(C(=O)Nc3cnc4c(c3)CNCC4)cc2N=C(N)C1]

8. The myeloid cell agonist conjugate of claim 1, wherein the linker is a cleavable linker.

9. The myeloid cell agonist conjugate of claim 8, wherein the peptide of the linker is Val-Cit or Val-Ala.

10. The myeloid cell agonist conjugate of claim 1, wherein the linker is represented by formula (V):

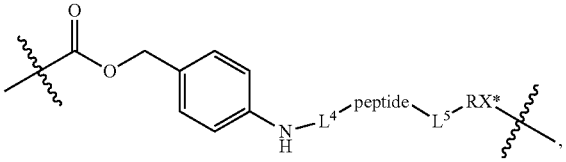

wherein $L^4$ represents the C-terminal of the peptide and $L^5$ is selected from a bond, alkylene and heteroalkylene, wherein $L^5$ is optionally substituted with one or more groups independently selected from $R^{32}$; RX* comprises a bond, a succinimide moiety or a hydrolyzed succinimide moiety bound to a residue of the antibody, wherein

on RX* represents the point of attachment to the residue of the antibody and the other

represents the point of attachment to the TLR8 agonist; and $R^{32}$ is independently selected at each occurrence from halogen, —OH, —CN, —O—$C_{1-10}$ alkyl, —SH, =O, =S, —NH$_2$, —NO$_2$; $C_{1-10}$ alkyl, $C_{2-10}$ alkenyl, and $C_{2-10}$ alkynyl, each of which is optionally substituted with one or more substituents independently selected from halogen, —OH, —CN, —O—$C_{1-10}$ alkyl, —SH, =O, =S, —NH$_2$, and —NO$_2$.

11. The myeloid cell agonist conjugate of claim 1, wherein L-D$_x$ has a structure selected from any one of:

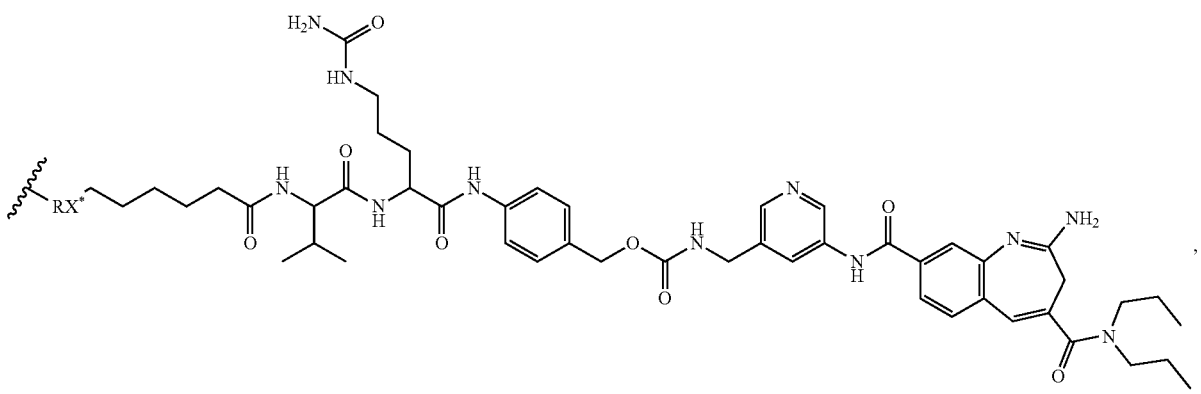

-continued
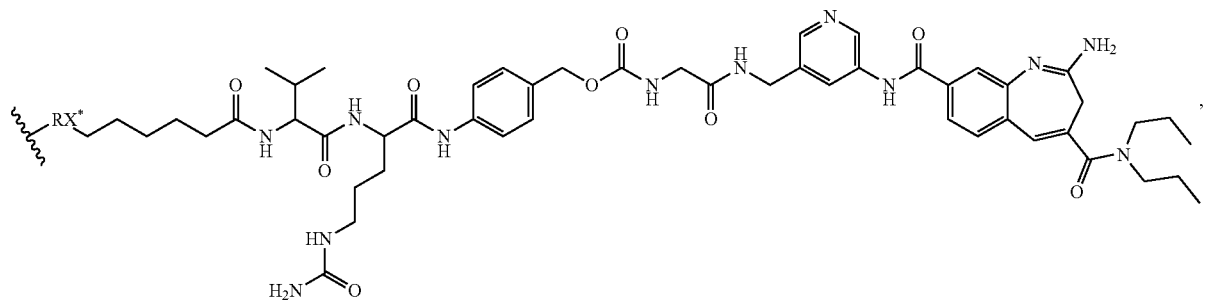
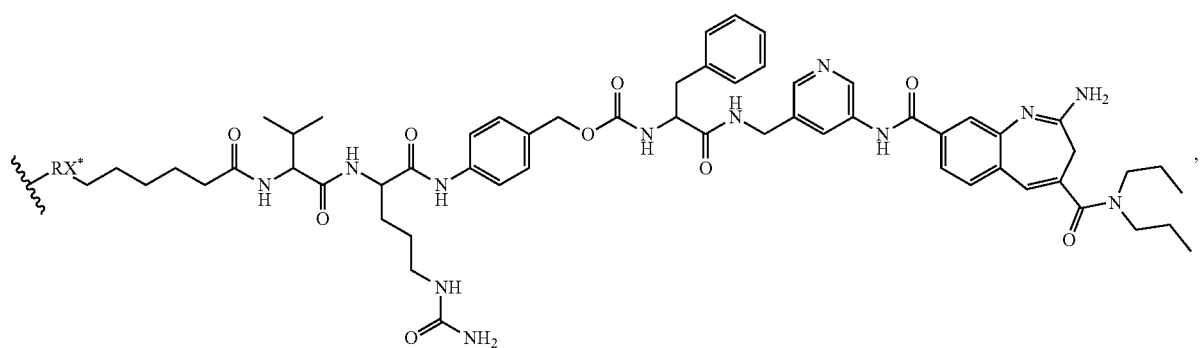
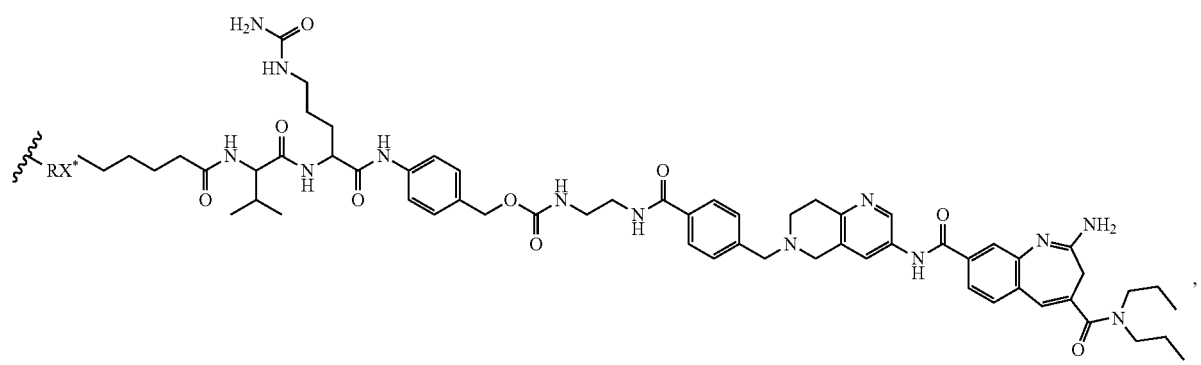
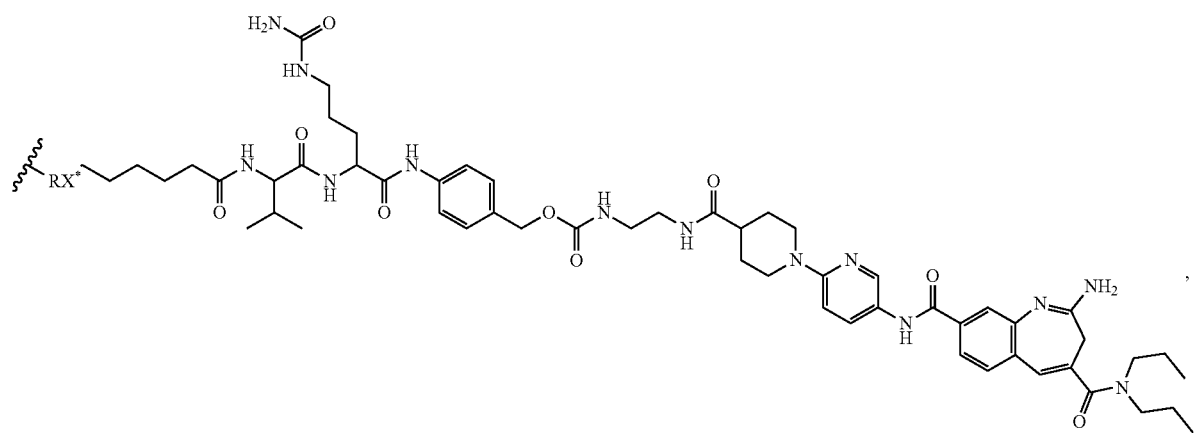

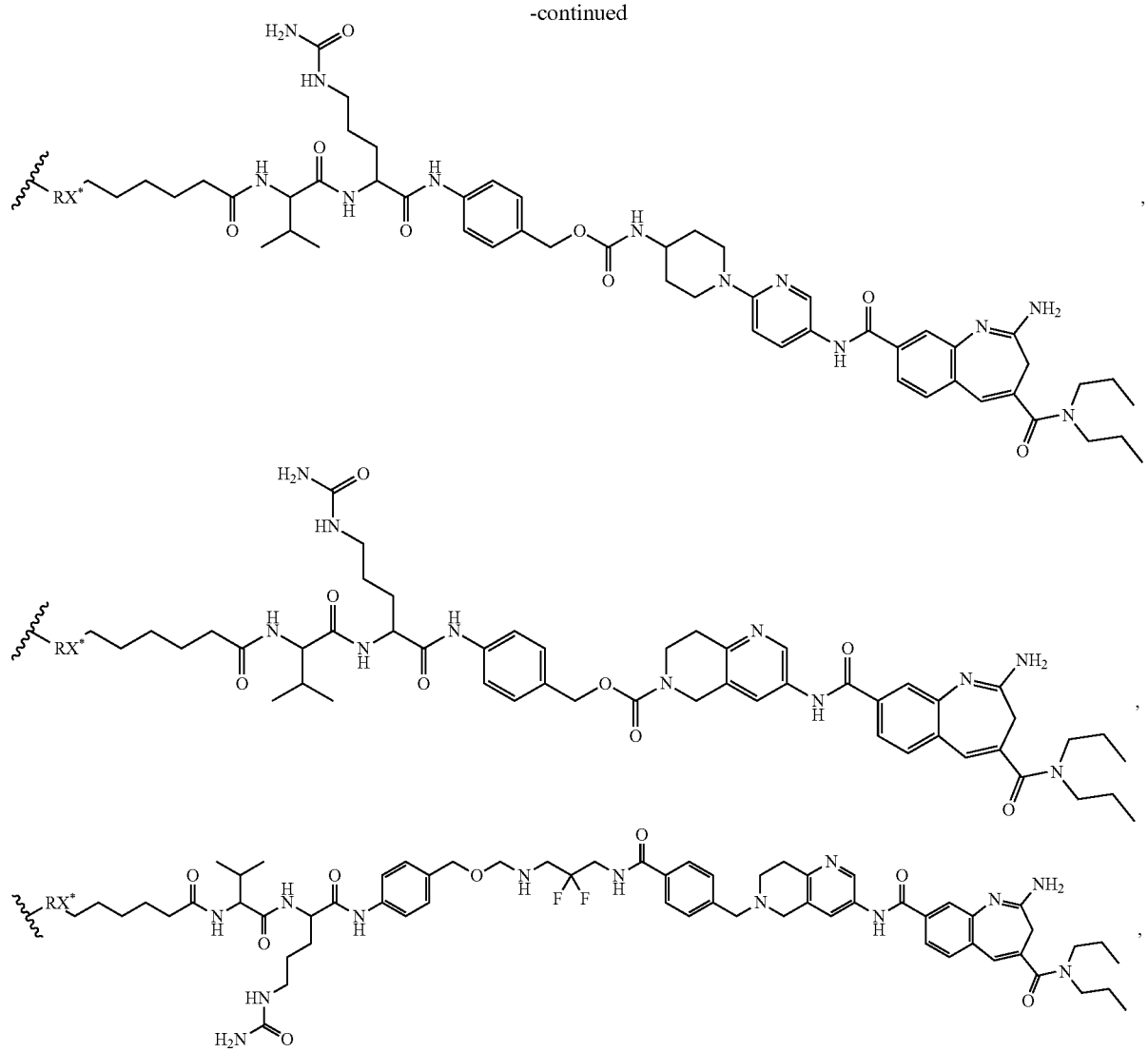

and a salt of any one thereof,
wherein the RX* is a bond, a succinimide moiety, or a hydrolyzed succinimide moiety bound to a residue of the antibody, and
wherein

on RX* represents the point of attachment to the residue of the antibody.

12. The myeloid cell agonist conjugate of claim 11, wherein
(a) n is an integer from 1 to about 10, or from 1 to about 5, or is 1 or 2, or is 1; and
(b) z ranges from 1 to about 10, or from 1 to about 9, or from 1 to about 8, or from 2 to about 6, or from 3 to about 5, or is about 4.

13. A pharmaceutical composition comprising the myeloid cell agonist conjugate of claim 1 and a pharmaceutically acceptable excipient.

14. The pharmaceutical composition of claim 13, wherein the average TLR8 agonist-to-antibody ratio of the conjugate ranges from about 2 to about 8, from about 3 to about 8, from about 3 to about 7, or from about 3 to about 5.

15. The pharmaceutical composition of claim 13, wherein the average TLR8 agonist-to-antibody ratio of the conjugate is from 2 to 4.

16. The myeloid cell agonist conjugate or a salt thereof of claim 1, wherein:
A is an anti-ASGR1 antibody comprising:
(a) a heavy chain comprising a VH comprising the amino acid sequence that has at least 90% identity with the amino acid sequence of SEQ ID NO:240 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:247 and a human kappa constant region comprising the amino acid sequence that has at least 90% identity with the amino acid sequence of SEQ ID NO:232, provided that the amino acid sequences of the VH-CDRs and VL-CDRs are unchanged; or (b) a heavy chain comprising a VH comprising the amino acid sequence that has at least 90% identity with the amino acid sequence of SEQ ID NO:239 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:247 and a human kappa constant region comprising the amino acid sequence that has at least 90% identity with the amino acid sequence of SEQ ID NO:232, provided that the amino acid sequences of the VH-CDRs and VL-CDRs are unchanged; or (c) a heavy chain comprising a VH comprising the amino acid sequence that has at least 90% identity with the amino acid sequence of SEQ ID NO:239 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:248 and a human kappa constant region comprising the amino acid sequence that has at least 90% identity with the amino acid sequence of SEQ ID NO:232, provided that the amino acid sequences of the VH-CDRs and VL-CDRs are unchanged; or (d) a heavy chain comprising a VH comprising the amino acid sequence that has at least 90% identity with the amino acid sequence of SEQ ID NO:240 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:248 and a human kappa constant region comprising the amino acid sequence that has at least 90% identity with the amino acid sequence of SEQ ID NO:232, provided that the amino acid sequences of the VH-CDRs and VL-CDRs are unchanged; or (e) a heavy chain comprising a VH comprising the amino acid sequence that has at least 90% identity with the amino acid sequence of SEQ ID NO:43 and a human IgG1 constant region comprising the amino acid sequence that has at least 90% identity with the amino acid sequence of SEQ ID NO:230, and a light chain comprising a VL comprising the amino acid sequence that has at least 90% identity with the amino acid sequence of SEQ ID NO:131 and a human kappa constant region comprising the amino acid sequence that has at least 90% identity with the amino acid sequence of SEQ ID NO:232, provided that the amino acid sequences of the VH-CDRs and VL-CDRs are unchanged;

$L$-$D_x$ has a structure selected from any one of:

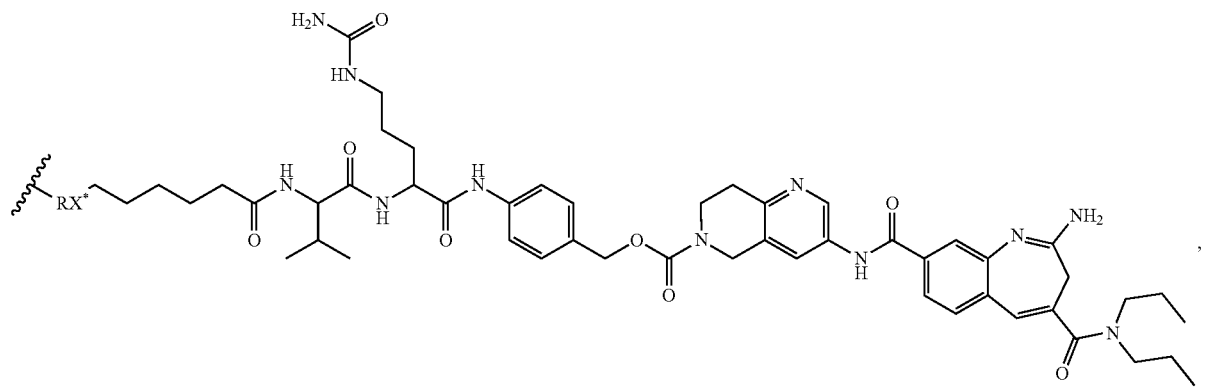

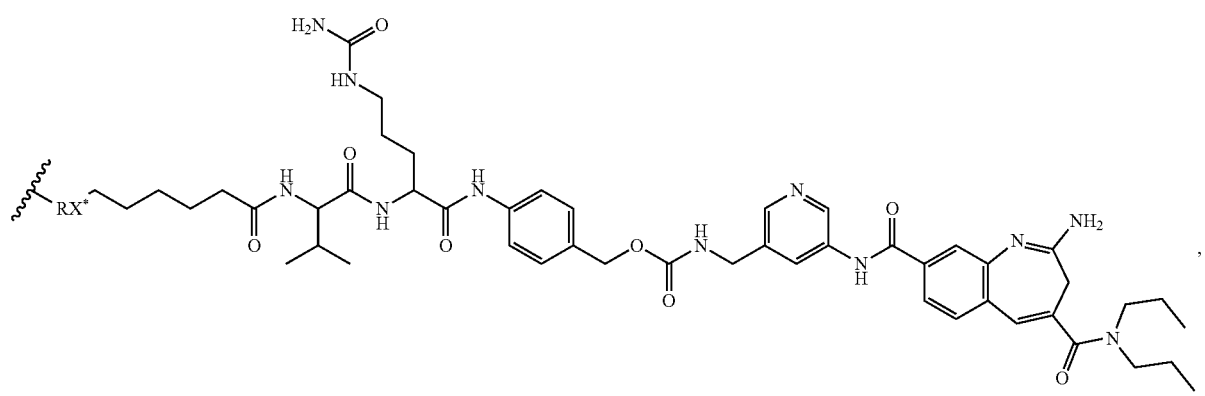

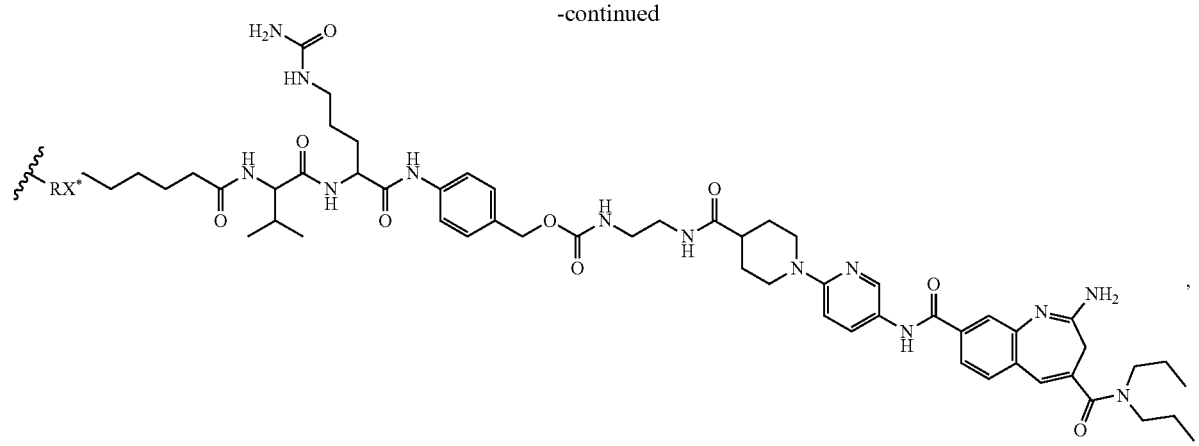

and

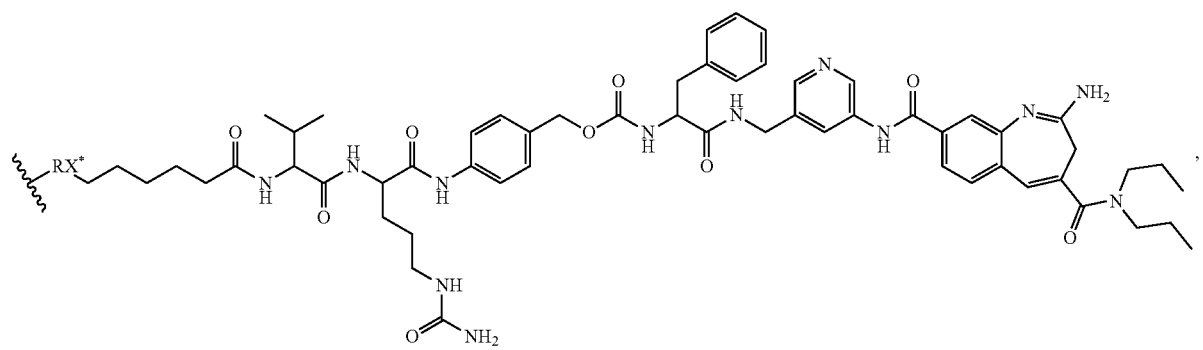

wherein RX* is a bond, a succinimide moiety, or a hydrolyzed succinimide moiety bound to a residue of the antibody, wherein

on RX* represents the point of attachment to a cysteine residue of the antibody;

n is 1; and z ranges from 2 to about 6.

17. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-$D_x$ has a structure of:

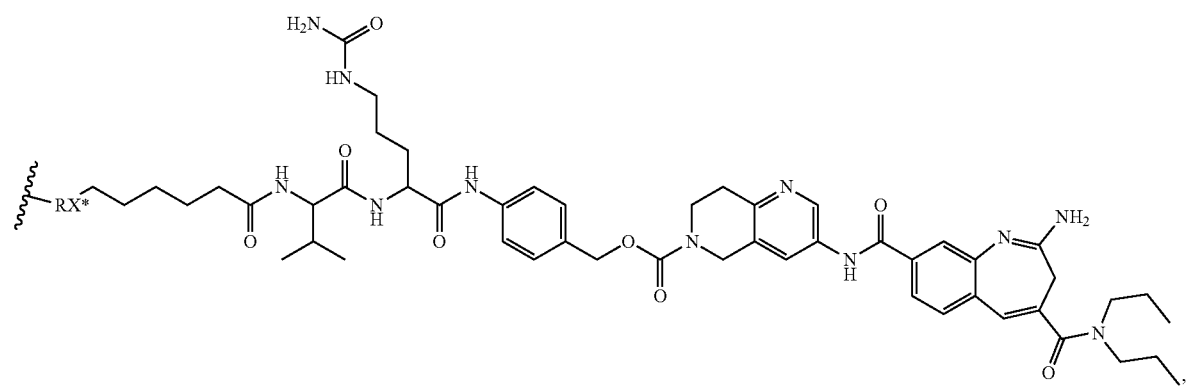

18. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

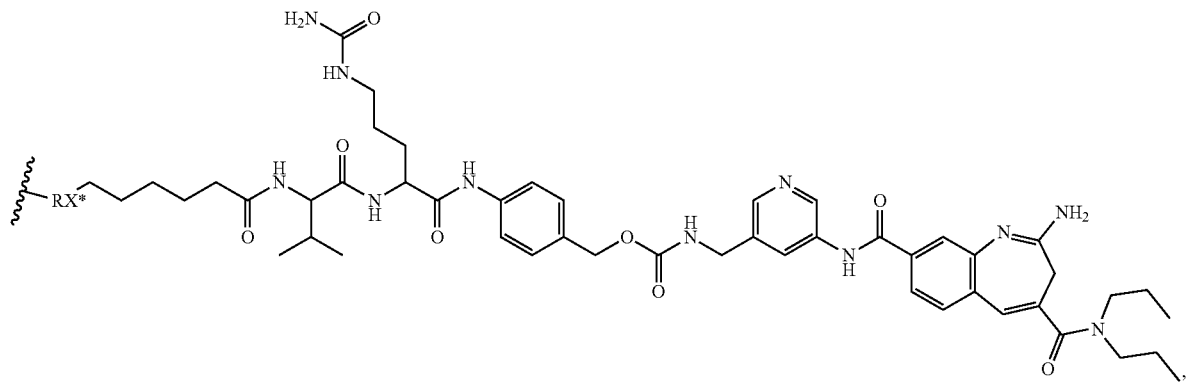

19. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

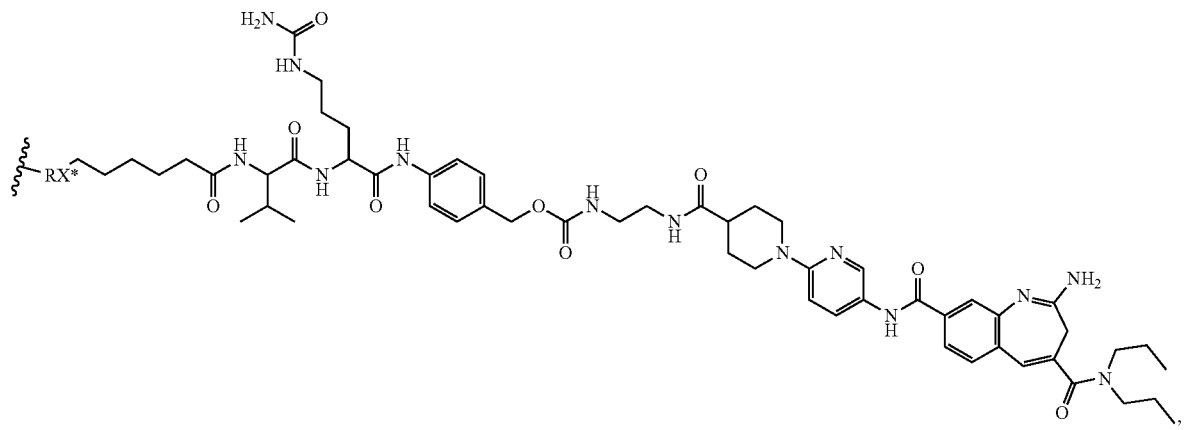

20. The myeloid cell agonist conjugate or a salt thereof of claim 16, wherein A is an anti-ASGR1 antibody comprising comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

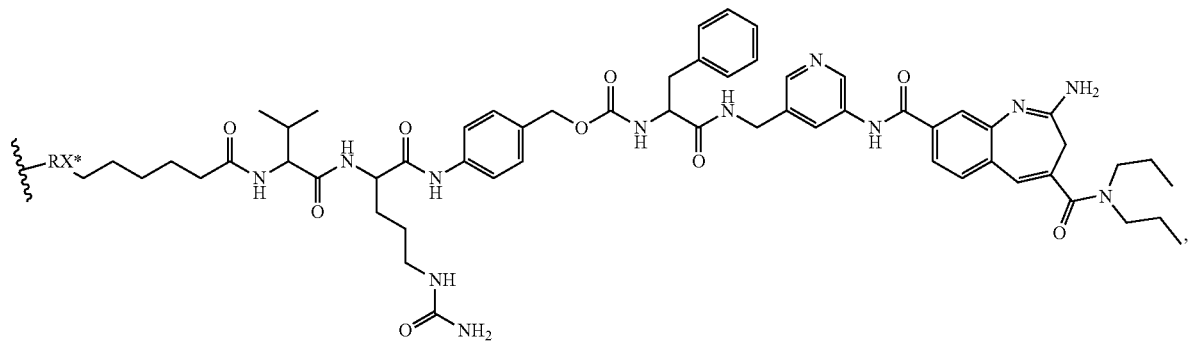

21. The myeloid cell agonist conjugate or a salt thereof of claim 16, wherein A is an anti-ASGR1 antibody comprising a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

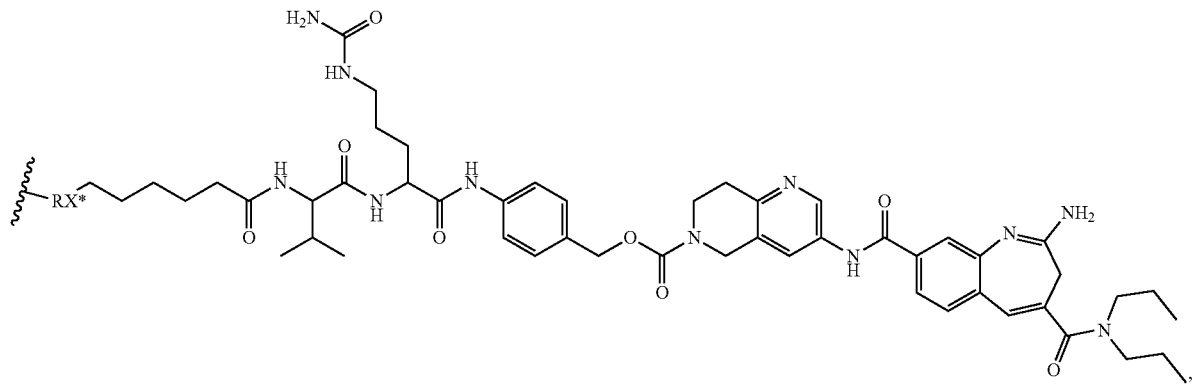

22. The myeloid cell agonist conjugate or a salt thereof of claim 16, wherein A is an anti-ASGR1 antibody comprising a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

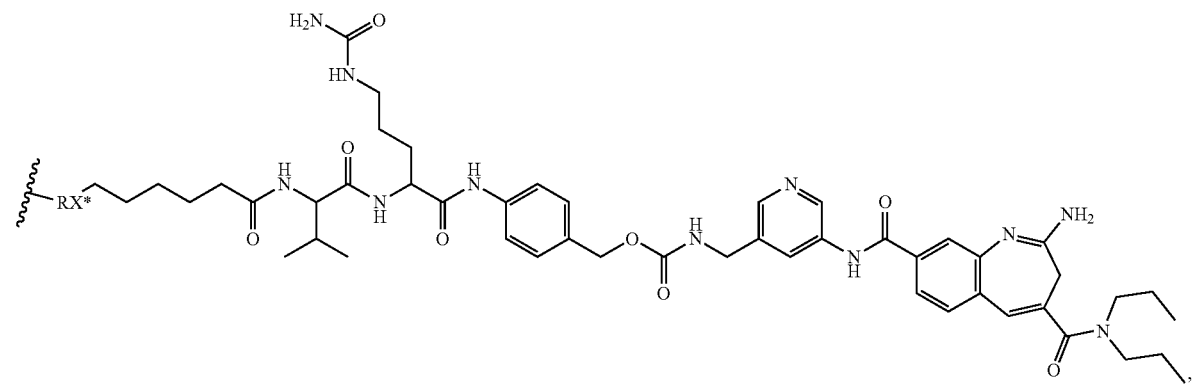

23. The myeloid cell agonist conjugate or a salt thereof of claim 16, wherein A is an anti-ASGR1 antibody comprising a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

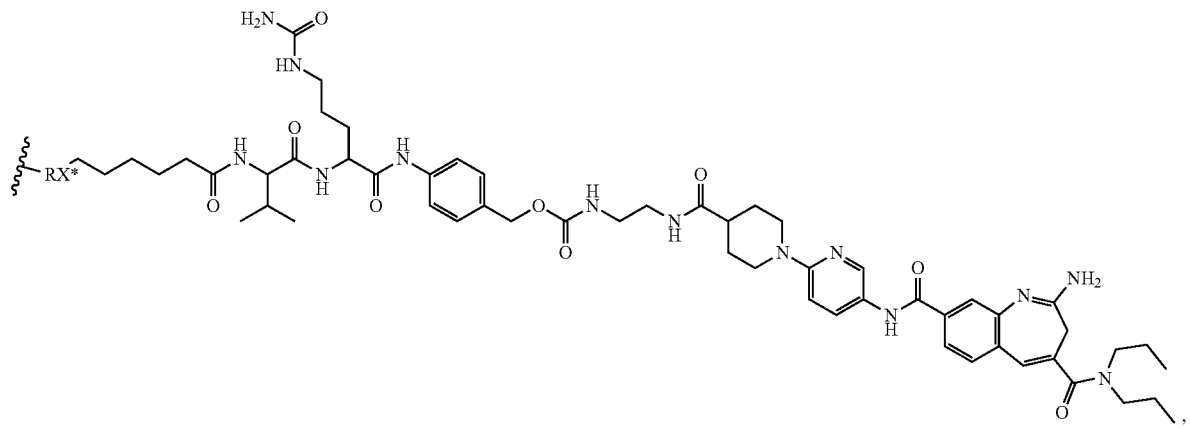

24. The myeloid cell agonist conjugate or a salt thereof of claim 16, wherein A is an anti-ASGR1 antibody comprising comprising a heavy chain comprising a VH comprising the amino acid sequence of SEQ ID NO:240 and a human IgG1 constant region comprising the amino acid sequence of SEQ ID NO:230, and a light chain comprising a VL comprising the amino acid sequence of SEQ ID NO:247 and a human kappa constant region comprising the amino acid sequence of SEQ ID NO:232, and L-D$_x$ has a structure of:

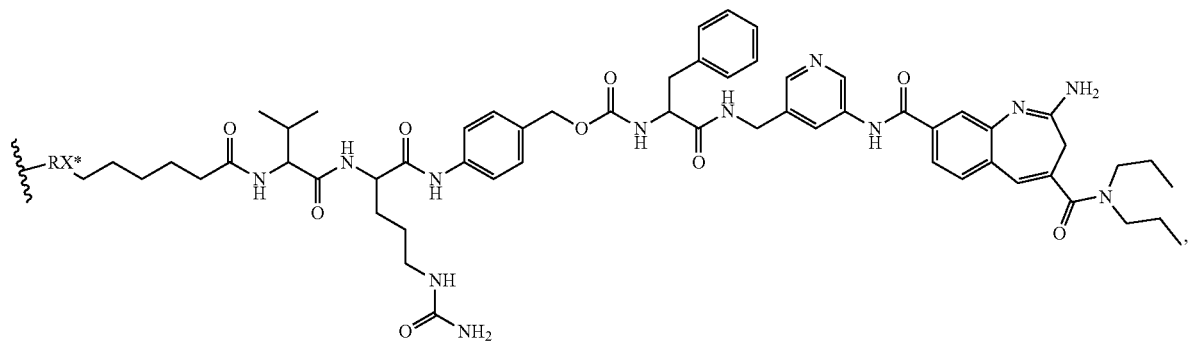

25. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232, and L-D$_x$ has a structure of:

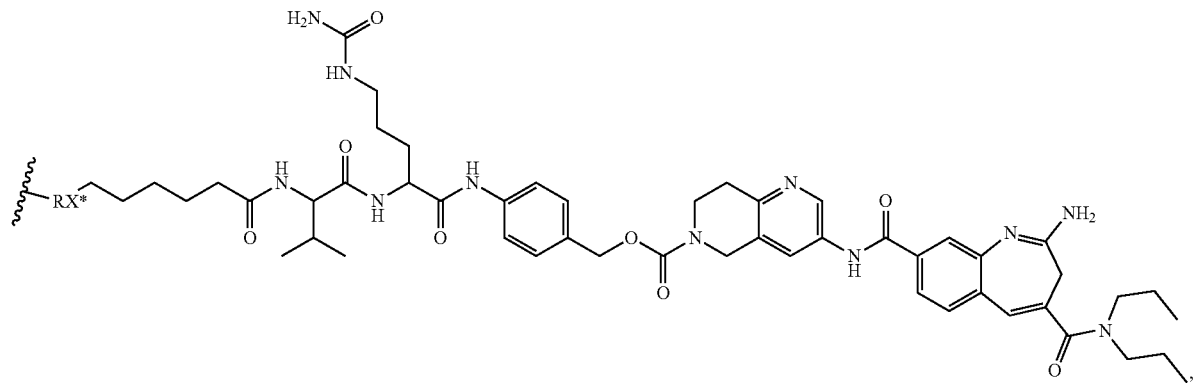

26. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232, and L-$D_x$ has a structure of:

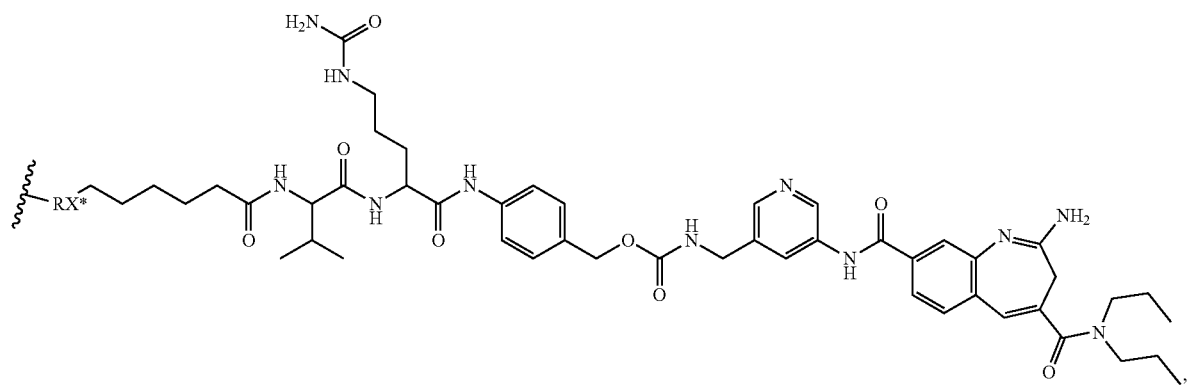

27. The myeloid cell agonist conjugate or a salt thereof of claim 16, wherein A is an anti-ASGR1 antibody comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232, and L-$D_x$ has a structure of:

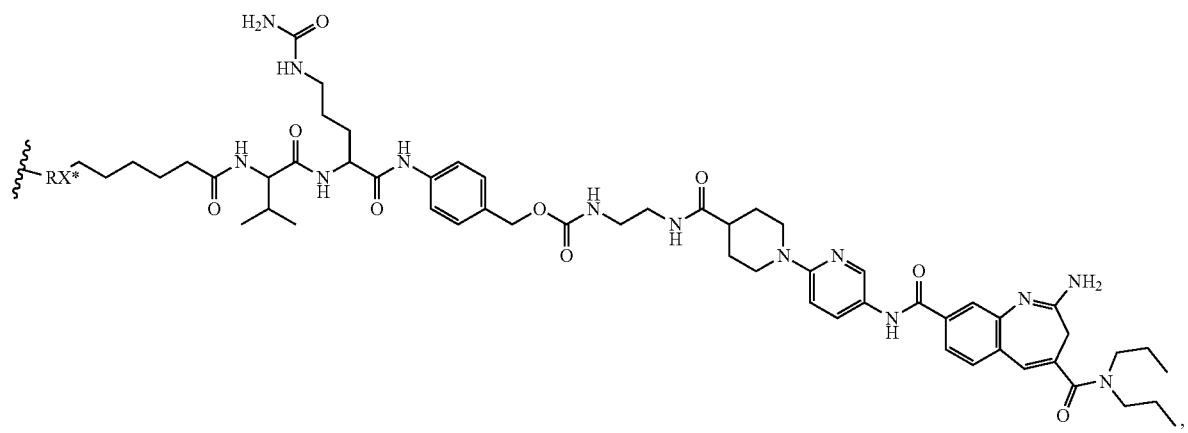

28. The myeloid cell agonist conjugate or a salt thereof of claim 16, wherein A is an anti-ASGR1 antibody comprising comprising a heavy chain comprising a VH comprising the amino acid sequence of SEQ ID NO:239 and a human IgG1 constant region comprising the amino acid sequence of SEQ ID NO:230, and a light chain comprising a VL comprising the amino acid sequence of SEQ ID NO:248 and a human kappa constant region comprising the amino acid sequence of SEQ ID NO:232, and L-D$_x$ has a structure of:

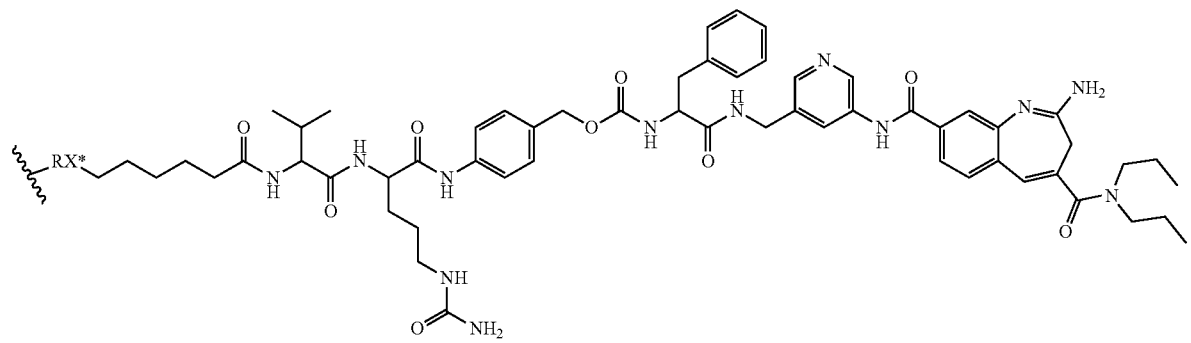

29. A pharmaceutical composition comprising the myeloid cell agonist conjugate of claim 16 and a pharmaceutically acceptable excipient.

30. The pharmaceutical composition of claim 29, wherein the average TLR8 agonist-to-antibody ratio of the conjugate ranges from about 2 to about 8, about 3 to about 8, about 3 to about 7, or about 3 to about 5.

* * * * *

SEQUENCE LISTING

```
<160> NUMBER OF SEQ ID NOS: 316

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence G2D VH CDR1

<400> SEQUENCE: 1

Gly Tyr Tyr Met His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic sequence K2E VH CDR1

<400> SEQUENCE: 2

Ser Tyr Thr Met His
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic sequence L4L VH CDR1

<400> SEQUENCE: 3

Ser Asp Tyr Ala Trp Asn
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic sequence H8K VH CDR1

<400> SEQUENCE: 4

Ser Asp Tyr Ala Trp Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic sequence J4F VH CDR1

<400> SEQUENCE: 5
```

Ser Tyr Trp Ile Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic sequence G2D VH CDR2

<400> SEQUENCE: 6

Arg Ile Asn Pro Asn Asn Gly Ala Thr Asn Tyr Asn Gln Asn Phe Lys
1               5                   10                  15
Asp

<210> SEQ ID NO 7
<211> LENGTH: 17
<212> TYPE: PRT
<213> ORGANISM: Artificial Sequence
<220> FEATURE:
<223> OTHER INFORMATION: Synthetic sequence G2.1D VH CDR2

<400> SEQUENCE: 7

Arg Ile Asn Pro Asn Gln Gly Ala Thr Asn Tyr Asn Gln Asn Phe Lys
1               5                   10                  15
Asp

<210> SEQ ID NO 8
<211> LENGTH: 17
<212> TYPE: PRT
<213> ORGANISM: Artificial Sequence
<220> FEATURE:
<223> OTHER INFORMATION: Synthetic sequence G2.2D VH CDR2

<400> SEQUENCE: 8

Arg Ile Asn Pro Asn Asn Ala Ala Thr Asn Tyr Asn Gln Asn Phe Lys
1               5                   10                  15
Asp

<210> SEQ ID NO 9
<211> LENGTH: 17
<212> TYPE: PRT
<213> ORGANISM: Artificial Sequence
<220> FEATURE:
<223> OTHER INFORMATION: Synthetic sequence K2E VH CDR2

<400> SEQUENCE: 9

Tyr Ile Ser Pro Ser Ser Gly Tyr Thr Glu Tyr Asn Gln Lys Phe Lys
1               5                   10                  15
Asp

<210> SEQ ID NO 10
<211> LENGTH: 16
<212> TYPE: PRT
<213> ORGANISM: Artificial Sequence
<220> FEATURE:
<223> OTHER INFORMATION: Synthetic sequence L4L VH CDR2

<400> SEQUENCE: 10

Tyr Ile Ser Tyr Ser Gly Ser Thr Arg Tyr Asn Pro Ser Leu Lys Ser
1               5                   10                  15

<210> SEQ ID NO 11
<211> LENGTH: 16

```
<212> TYPE: PRT
<213> ORGANISM: Artificial Sequence
<220> FEATURE:
<223> OTHER INFORMATION: Synthetic sequence H8K VH CDR2

<400> SEQUENCE: 11

Tyr Arg Ser Tyr Arg Gly Ser Thr Ser Tyr Asn Pro Ser Leu Lys Ser
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic sequence J4F VH CDR2

<400> SEQUENCE: 12

Arg Ile Val Pro Gly Ser Gly Ser Thr Tyr Tyr Asn Glu Met Phe Lys
1               5                   10                  15

Asp

<210> SEQ ID NO 13
<211> LENGTH: 5
<212> TYPE: PRT
<213> ORGANISM: Artificial Sequence
<220> FEATURE:
<223> OTHER INFORMATION: Synthetic sequence G2D VH CDR3

<400> SEQUENCE: 13

Val Asn Phe Tyr Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic sequence K2E VH CDR3

<400> SEQUENCE: 14

Lys Phe Asp Tyr
1

<210> SEQ ID NO 15
<211> LENGTH: 12
<212> TYPE: PRT
<213> ORGANISM: Artificial Sequence
<220> FEATURE:
<223> OTHER INFORMATION: Synthetic sequence L4L VH CDR3

<400> SEQUENCE: 15

Arg Tyr Arg Tyr Asp Glu Gly Tyr Gly Met Asp Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic sequence H8K VH CDR3

<400> SEQUENCE: 16

Arg Gly Tyr Tyr Gly Ser Ser Ser His Trp Tyr Phe Asp Val
1               5                   10

<210> SEQ ID NO 17
```

```
<211> LENGTH: 6
<212> TYPE: PRT
<213> ORGANISM: Artificial Sequence
<220> FEATURE:
<223> OTHER INFORMATION: Synthetic sequence J4F VH CDR3

<400> SEQUENCE: 17

Lys Pro Asn Phe Asp Val
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic sequence G2D VL CDR1

<400> SEQUENCE: 18

Lys Ala Ser Gln Val Ile Asn Ser Tyr Leu Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic sequence K2E VL CDR1

<400> SEQUENCE: 19

Lys Ala Ser Gln Asp Ile Asn Ser Tyr Leu Ser
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic sequence L4L VL CDR1

<400> SEQUENCE: 20

Arg Ala Ser Glu Asn Ile Tyr Ser Asn Leu Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic sequence H8K VL CDR1

<400> SEQUENCE: 21

Arg Ala Ser Glu Asn Ile Tyr Ser Tyr Leu Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic sequence J4F VL CDR1

<400> SEQUENCE: 22

Lys Ala Ser Gln Asn Val Gly Thr Asn Val Ala
1               5                   10

<210> SEQ ID NO 23
<211> LENGTH: 7
```

```
<212> TYPE: PRT
<213> ORGANISM: Artificial Sequence
<220> FEATURE:
<223> OTHER INFORMATION: Synthetic sequence G2D VL CDR2

<400> SEQUENCE: 23

Arg Ala Asn Thr Leu Val Asp
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic sequence G2.1D VL CDR2

<400> SEQUENCE: 24

Arg Ala Asn Thr Leu Val Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic sequence G2.2D VL CDR2

<400> SEQUENCE: 25

Arg Ala Asn Thr Leu Val Glu
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic sequence K2E VL CDR2

<400> SEQUENCE: 26

Arg Ala Asn Arg Leu Val Asp
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic sequence K2.1E VL CDR2

<400> SEQUENCE: 27

Arg Ala Asn Arg Leu Val Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic sequence L4L VL CDR2

<400> SEQUENCE: 28

Ala Ala Thr Asn Leu Ala Asp
1               5

<210> SEQ ID NO 29
<211> LENGTH: 7
<212> TYPE: PRT
```

```
<213> ORGANISM: Artificial Sequence
<220> FEATURE:
<223> OTHER INFORMATION: Synthetic sequence L4.1L VL CDR2

<400> SEQUENCE: 29

Ala Ala Thr Asn Leu Ala Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic sequence L4.2L VL CDR2

<400> SEQUENCE: 30

Ala Ala Thr Asn Leu Ala Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic sequence H8K VL CDR2

<400> SEQUENCE: 31

Asn Ala Lys Thr Leu Ala Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic sequence J4F VL CDR2

<400> SEQUENCE: 32

Ser Ala Ser Tyr Arg Phe Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic sequence G2D VL CDR3

<400> SEQUENCE: 33

Leu Gln Tyr Ala Glu Phe Pro Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic sequence K2E VL CDR3

<400> SEQUENCE: 34

Leu Gln Tyr Asp Glu Phe Pro Phe Thr
1               5

<210> SEQ ID NO 35
<211> LENGTH: 10
<212> TYPE: PRT
<213> ORGANISM: Artificial Sequence
```

-continued

```
<220> FEATURE:
<223> OTHER INFORMATION: Synthetic sequence L4L VL CDR3

<400> SEQUENCE: 35

Gln His Phe Trp Gly Thr Pro Pro Trp Thr
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Synthetic sequence H8K VL CDR3

<400> SEQUENCE: 36

Gln His His Tyr Gly Thr Pro Leu Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic sequence J4F VL CDR3

<400> SEQUENCE: 37

Gln Gln Tyr Asn Ser Tyr Pro Leu Thr
1               5

<210> SEQ ID NO 38
<211> LENGTH: 114
<212> TYPE: PRT
<213> ORGANISM: Artificial Sequence
<220> FEATURE:
<223> OTHER INFORMATION: Synthetic sequence G2D VH

<400> SEQUENCE: 38

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Val Lys Ser Leu Glu Trp Ile
            35                  40                  45

Gly Arg Ile Asn Pro Asn Asn Gly Ala Thr Asn Tyr Asn Gln Asn Phe
        50                  55                  60

Lys Asp Lys Ala Ser Leu Thr Val Asp Lys Ser Ser Thr Ala Tyr
65                  70                  75                  80

Met Glu Phe His Ser Leu Thr Ser Glu Asp Ser Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 39
<211> LENGTH: 113
<212> TYPE: PRT
<213> ORGANISM: Artificial Sequence
<220> FEATURE:
<223> OTHER INFORMATION: Synthetic sequence K2E VH

<400> SEQUENCE: 39

Gln Val Gln Leu Gln Gln Ser Ala Ala Glu Leu Ala Arg Pro Gly Ala
1               5                   10                  15
```

```
Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Ser Pro Ser Ser Gly Tyr Thr Glu Tyr Asn Gln Lys Phe
50                          55                  60

Lys Asp Lys Thr Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Lys Phe Asp Tyr Trp Gly Gln Gly Thr Thr Leu Thr Val Ser
            100                 105                 110

Ser
```

```
<210> SEQ ID NO 40
<211> LENGTH: 121
<212> TYPE: PRT
<213> ORGANISM: Artificial Sequence
<220> FEATURE:
<223> OTHER INFORMATION: Synthetic sequence L4L VH

<400> SEQUENCE: 40

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Arg Tyr Asn Pro Ser Leu
50                          55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Ser Val Thr Val Ser Ser
        115                 120
```

```
<210> SEQ ID NO 41
<211> LENGTH: 123
<212> TYPE: PRT
<213> ORGANISM: Artificial Sequence
<220> FEATURE:
<223> OTHER INFORMATION: Synthetic sequence H8K VH

<400> SEQUENCE: 41

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
            20                  25                  30

Tyr Ala Trp Asn Trp Ile Arg Gln Phe Pro Gly Asn Gln Leu Glu Trp
            35                  40                  45

Met Gly Tyr Arg Ser Tyr Arg Gly Ser Thr Ser Tyr Asn Pro Ser Leu
50                          55                  60

Lys Ser Arg Ile Ser Ile Thr Arg Asp Thr Ser Lys Asn Gln Phe Phe
65                  70                  75                  80
```

Leu Gln Leu Asn Ser Val Thr Glu Asp Thr Ala Thr Tyr Tyr Cys
                85                  90                  95

Ala Arg Arg Gly Tyr Tyr Gly Ser Ser Ser His Trp Tyr Phe Asp Val
            100                 105                 110

Trp Gly Ala Gly Thr Thr Val Thr Val Ser Ser
        115                 120

<210> SEQ ID NO 42
<211> LENGTH: 115
<212> TYPE: PRT
<213> ORGANISM: Artificial Sequence
<220> FEATURE:
<223> OTHER INFORMATION: Synthetic sequence J4F VH

<400> SEQUENCE: 42

Gln Val Gln Leu Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly Arg Ile Val Pro Gly Ser Gly Ser Thr Tyr Tyr Asn Glu Met Phe
    50                  55                  60

Lys Asp Lys Ala Thr Leu Thr Val Asp Thr Ser Ser Ser Thr Ala Tyr
65                  70                  75                  80

Ile Gln Leu Ser Ser Leu Ser Ser Glu Asp Ser Ala Val Tyr Phe Cys
                85                  90                  95

Ala Arg Lys Pro Asn Phe Asp Val Trp Gly Ala Gly Thr Thr Val Thr
            100                 105                 110

Val Ser Ser
        115

<210> SEQ ID NO 43
<211> LENGTH: 114
<212> TYPE: PRT
<213> ORGANISM: Artificial Sequence
<220> FEATURE:
<223> OTHER INFORMATION: Synthetic sequence hzG2D VH V109L

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 44

```
<211> LENGTH: 114
<212> TYPE: PRT
<213> ORGANISM: Artificial Sequence
<220> FEATURE:
<223> OTHER INFORMATION: Synthetic sequence hzG2.1D VH T28S, V109L

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 45
<211> LENGTH: 114
<212> TYPE: PRT
<213> ORGANISM: Artificial Sequence
<220> FEATURE:
<223> OTHER INFORMATION: Synthetic sequence hzG2.2D VH T28S, R66K, V67A,
      V109L

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 46
<211> LENGTH: 114
<212> TYPE: PRT
<213> ORGANISM: Artificial Sequence
<220> FEATURE:
<223> OTHER INFORMATION: Synthetic sequence hzG2.3D VH T28S, R66K, V67A,
      A93T, R94S, V109L

<400> SEQUENCE: 46

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 47
<211> LENGTH: 114
<212> TYPE: PRT
<213> ORGANISM: Artificial Sequence
<220> FEATURE:
<223> OTHER INFORMATION: Synthetic sequence hzG2.4D VH T28S, R66K, V67A,
      T68S, I69L, R71V, V109L

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 48
<211> LENGTH: 114
<212> TYPE: PRT
<213> ORGANISM: Artificial Sequence
<220> FEATURE:
<223> OTHER INFORMATION: Synthetic sequence hzG2.5D VH T28S, R66K, V67A,
      T68S, I69L, R71V, A93T, R94S, V109L

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 49
<211> LENGTH: 114
<212> TYPE: PRT
<213> ORGANISM: Artificial Sequence
<220> FEATURE:
<223> OTHER INFORMATION: Synthetic sequence hzG2.6D VH T28S, T68S, I69L,
      R71V, V109L

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 50
<211> LENGTH: 114
<212> TYPE: PRT
<213> ORGANISM: Artificial Sequence
<220> FEATURE:
<223> OTHER INFORMATION: Synthetic sequence hzG2.7D VH T28S, T68S, I69L,
      R71V, A93T, R94S, V109L

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 51
```

```
<211> LENGTH: 114
<212> TYPE: PRT
<213> ORGANISM: Artificial Sequence
<220> FEATURE:
<223> OTHER INFORMATION: Synthetic sequence hzG2.8D VH T28S, A93T, R94S,
      V109L

<400> SEQUENCE: 51
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

```
<210> SEQ ID NO 52
<211> LENGTH: 114
<212> TYPE: PRT
<213> ORGANISM: Artificial Sequence
<220> FEATURE:
<223> OTHER INFORMATION: Synthetic sequence hzG2.9D VH T28S, N54Q

<400> SEQUENCE: 52
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

```
<210> SEQ ID NO 53
<211> LENGTH: 114
<212> TYPE: PRT
<213> ORGANISM: Artificial Sequence
<220> FEATURE:
<223> OTHER INFORMATION: Synthetic sequence hzG2.10D VH T28S, N54Q,
      R66K, V67A

<400> SEQUENCE: 53
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 54
<211> LENGTH: 114
<212> TYPE: PRT
<213> ORGANISM: Artificial Sequence
<220> FEATURE:
<223> OTHER INFORMATION: Synthetic sequence hzG2.11D VH T28S, N54Q,
      R66K, V67A, A93T, R94S

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 55
<211> LENGTH: 114
<212> TYPE: PRT
<213> ORGANISM: Artificial Sequence
<220> FEATURE:
<223> OTHER INFORMATION: Synthetic sequence hzG2.12D VH T28S, N54Q,
      R66K, V67A, T68S, I69L, R71V

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 56
<211> LENGTH: 114
<212> TYPE: PRT
<213> ORGANISM: Artificial Sequence
<220> FEATURE:
<223> OTHER INFORMATION: Synthetic sequence hzG2.13D VH T28S, N54Q,
      R66K, V67A, T68S, I69L, R71V, A93T, R94S

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 57
<211> LENGTH: 114
<212> TYPE: PRT
<213> ORGANISM: Artificial Sequence
<220> FEATURE:
<223> OTHER INFORMATION: Synthetic sequence hzG2.14D VH T28S, N54Q,
      T68S, I69L, R71V

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 58

```
<211> LENGTH: 114
<212> TYPE: PRT
<213> ORGANISM: Artificial Sequence
<220> FEATURE:
<223> OTHER INFORMATION: Synthetic sequence hzG2.15D VH T28S, N54Q,
      T68S, I69L, R71V, A93T, R94S

<400> SEQUENCE: 58
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
        50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser

```
<210> SEQ ID NO 59
<211> LENGTH: 114
<212> TYPE: PRT
<213> ORGANISM: Artificial Sequence
<220> FEATURE:
<223> OTHER INFORMATION: Synthetic sequence hzG2.16D VH T28S, N54Q,
      A93T, R94S

<400> SEQUENCE: 59
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser

```
<210> SEQ ID NO 60
<211> LENGTH: 114
<212> TYPE: PRT
<213> ORGANISM: Artificial Sequence
<220> FEATURE:
<223> OTHER INFORMATION: Synthetic sequence hzG2.17D VH T28S, G55A

<400> SEQUENCE: 60
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 61
<211> LENGTH: 114
<212> TYPE: PRT
<213> ORGANISM: Artificial Sequence
<220> FEATURE:
<223> OTHER INFORMATION: Synthetic sequence hzG2.18D VH T28S, G55A,
      R66K, V67A

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 62
<211> LENGTH: 114
<212> TYPE: PRT
<213> ORGANISM: Artificial Sequence
<220> FEATURE:
<223> OTHER INFORMATION: Synthetic sequence hzG2.19D VH T28S, G55A,
      R66K, V67A, A93T, R94S

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 63
<211> LENGTH: 114
<212> TYPE: PRT
<213> ORGANISM: Artificial Sequence
<220> FEATURE:
<223> OTHER INFORMATION: Synthetic sequence hzG2.20D VH T28S, G55A,
      R66K, V67A, T68S, I69L, R71V

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 64
<211> LENGTH: 114
<212> TYPE: PRT
<213> ORGANISM: Artificial Sequence
<220> FEATURE:
<223> OTHER INFORMATION: Synthetic sequence hzG2.21D VH T28S, G55A,
      R66K, V67A, T68S, I69L, R71V, A93T, R94S

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 65

```
<211> LENGTH: 114
<212> TYPE: PRT
<213> ORGANISM: Artificial Sequence
<220> FEATURE:
<223> OTHER INFORMATION: Synthetic sequence hzG2.22D VH T28S, G55A,
      T68S, I69L, R71V

<400> SEQUENCE: 65
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

```
<210> SEQ ID NO 66
<211> LENGTH: 114
<212> TYPE: PRT
<213> ORGANISM: Artificial Sequence
<220> FEATURE:
<223> OTHER INFORMATION: Synthetic sequence hzG2.23D VH T28S, G55A,
      T68S, I69L, R71V, A93T, R94S

<400> SEQUENCE: 66
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

```
<210> SEQ ID NO 67
<211> LENGTH: 114
<212> TYPE: PRT
<213> ORGANISM: Artificial Sequence
<220> FEATURE:
<223> OTHER INFORMATION: Synthetic sequence hzG2.24D VH T28S, G55A,
      A93T, R94S

<400> SEQUENCE: 67
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
            35                  40                  45

Gly Arg Ile Asn Pro Asn Asn Ala Ala Thr Asn Tyr Asn Gln Asn Phe
 50                  55                  60

Lys Asp Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Ser Val Asn Phe Tyr Tyr Trp Gly Gln Gly Thr Thr Leu Thr Val
            100                 105                 110

Ser Ser

<210> SEQ ID NO 68
<211> LENGTH: 114
<212> TYPE: PRT
<213> ORGANISM: Artificial Sequence
<220> FEATURE:
<223> OTHER INFORMATION: Synthetic sequence hzG2.25D VH N54Q, R66K, V67A

<400> SEQUENCE: 68

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
 50                  55                  60

Lys Asp Lys Ala Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Asn Phe Tyr Tyr Trp Gly Gln Gly Thr Thr Leu Thr Val
            100                 105                 110

Ser Ser

<210> SEQ ID NO 69
<211> LENGTH: 114
<212> TYPE: PRT
<213> ORGANISM: Artificial Sequence
<220> FEATURE:
<223> OTHER INFORMATION: Synthetic sequence hzG2.26D VH N54Q, R66K,
      V67A, A93T, R94S

<400> SEQUENCE: 69

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
 50                  55                  60

Lys Asp Lys Ala Thr Ile Thr Arg Asp Thr Ser Ala Ser Thr Ala Tyr
 65                  70                  75                  80
```

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 70
<211> LENGTH: 114
<212> TYPE: PRT
<213> ORGANISM: Artificial Sequence
<220> FEATURE:
<223> OTHER INFORMATION: Synthetic sequence hzG2.27D VH N54Q, R66K,
      V67A, T68S, I69L, R71V

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 71
<211> LENGTH: 114
<212> TYPE: PRT
<213> ORGANISM: Artificial Sequence
<220> FEATURE:
<223> OTHER INFORMATION: Synthetic sequence hzG2.28D VH N54Q, R66K,
      V67A, T68S, I69L, R71V, A93T, R94S

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 72

```
<211> LENGTH: 114
<212> TYPE: PRT
<213> ORGANISM: Artificial Sequence
<220> FEATURE:
<223> OTHER INFORMATION: Synthetic sequence hzG2.29D VH N54Q, T68S,
      I69L, R71V

<400> SEQUENCE: 72
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

```
<210> SEQ ID NO 73
<211> LENGTH: 114
<212> TYPE: PRT
<213> ORGANISM: Artificial Sequence
<220> FEATURE:
<223> OTHER INFORMATION: Synthetic sequence hzG2.30D VH N54Q, T68S,
      I69L, R71V, A93T, R94S

<400> SEQUENCE: 73
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

```
<210> SEQ ID NO 74
<211> LENGTH: 114
<212> TYPE: PRT
<213> ORGANISM: Artificial Sequence
<220> FEATURE:
<223> OTHER INFORMATION: Synthetic sequence hzG2.31D VH N54Q, A93T, R94S

<400> SEQUENCE: 74
```

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
50                      55                  60

Lys Asp Arg Val Thr Ile Thr Arg Asp Thr Ser Ala Ser Thr Ala Tyr
65              70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 75
<211> LENGTH: 114
<212> TYPE: PRT
<213> ORGANISM: Artificial Sequence
<220> FEATURE:
<223> OTHER INFORMATION: Synthetic sequence hzG2.32D VH G55A, R66K, V67A

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
50                      55                  60

Lys Asp Lys Ala Thr Ile Thr Arg Asp Thr Ser Ala Ser Thr Ala Tyr
65              70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: Synthetic sequence hzG2.33D VH G55A, R66K,
      V67A, A93T, R94S

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
50                      55                  60

Lys Asp Lys Ala Thr Ile Thr Arg Asp Thr Ser Ala Ser Thr Ala Tyr
65              70                  75                  80

```
Met Glu Leu Ser Ser Leu Arg Ser Glu Asp Thr Ala Val Tyr Tyr Cys
            85                  90                  95

Thr Ser Val Asn Phe Tyr Tyr Trp Gly Gln Gly Thr Thr Leu Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: Synthetic sequence hzG2.34D VH G55A, R66K,
      V67A, T68S, I69L, R71V

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Phe Tyr Tyr Trp Gly Gln Gly Thr Thr Leu Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: Synthetic sequence hzG2.35D VH G55A, R66K,
      V67A, T68S, I69L, R71V, A93T, R94S

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Thr Ser Val Asn Phe Tyr Tyr Trp Gly Gln Gly Thr Thr Leu Thr Val
            100                 105                 110

Ser Ser

<210> SEQ ID NO 79
<211> LENGTH: 114
```

```
<212> TYPE: PRT
<213> ORGANISM: Artificial Sequence
<220> FEATURE:
<223> OTHER INFORMATION: Synthetic sequence hzG2.36D VH G55A, T68S,
      I69L, R71V

<400> SEQUENCE: 79
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

```
<210> SEQ ID NO 80
<211> LENGTH: 114
<212> TYPE: PRT
<213> ORGANISM: Artificial Sequence
<220> FEATURE:
<223> OTHER INFORMATION: Synthetic sequence hzG2.37D VH G55A, T68S,
      I69L, R71V, A93T, R94S

<400> SEQUENCE: 80
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

```
<210> SEQ ID NO 81
<211> LENGTH: 114
<212> TYPE: PRT
<213> ORGANISM: Artificial Sequence
<220> FEATURE:
<223> OTHER INFORMATION: Synthetic sequence hzG2.38D VH G55A, A93T, R94S

<400> SEQUENCE: 81
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr

-continued

```
                20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 82
<211> LENGTH: 114
<212> TYPE: PRT
<213> ORGANISM: Artificial Sequence
<220> FEATURE:
<223> OTHER INFORMATION: Synthetic sequence hzG2.39D VH R66K, V67A,
      V109L

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 83
<211> LENGTH: 114
<212> TYPE: PRT
<213> ORGANISM: Artificial Sequence
<220> FEATURE:
<223> OTHER INFORMATION: Synthetic sequence hzG2.40D VH R66K, V67A,
      A93T, R94S, V109L

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
                    85                  90                  95

Thr Ser Val Asn Phe Tyr Tyr Trp Gly Gln Gly Thr Thr Leu Thr Val
            100                 105                 110

Ser Ser

<210> SEQ ID NO 84
<211> LENGTH: 114
<212> TYPE: PRT
<213> ORGANISM: Artificial Sequence
<220> FEATURE:
<223> OTHER INFORMATION: Synthetic sequence hzG2.41D VH R66K, V67A,
      T68S, I69L, R71V, V109L

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
        50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Val Asn Phe Tyr Tyr Trp Gly Gln Gly Thr Thr Leu Thr Val
            100                 105                 110

Ser Ser

<210> SEQ ID NO 85
<211> LENGTH: 114
<212> TYPE: PRT
<213> ORGANISM: Artificial Sequence
<220> FEATURE:
<223> OTHER INFORMATION: Synthetic sequence hzG2.42D VH R66K, V67A,
      T68S, I69L, R71V, A93T, R94S, V109L

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
        50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Thr Ser Val Asn Phe Tyr Tyr Trp Gly Gln Gly Thr Thr Leu Thr Val
            100                 105                 110

Ser Ser

<210> SEQ ID NO 86
<211> LENGTH: 114

```
<212> TYPE: PRT
<213> ORGANISM: Artificial Sequence
<220> FEATURE:
<223> OTHER INFORMATION: Synthetic sequence hzG2.43D VH T68S, I69L,
      R71V, V109L

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser

<210> SEQ ID NO 87
<211> LENGTH: 114
<212> TYPE: PRT
<213> ORGANISM: Artificial Sequence
<220> FEATURE:
<223> OTHER INFORMATION: Synthetic sequence hzG2.44D VH T68S, I69L,
      R71V, A93T, R94S, V109L

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 88
<211> LENGTH: 114
<212> TYPE: PRT
<213> ORGANISM: Artificial Sequence
<220> FEATURE:
<223> OTHER INFORMATION: Synthetic sequence hzG2.45D VH A93T, R94S,
      V109L

<400> SEQUENCE: 88

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser

<210> SEQ ID NO 89
<211> LENGTH: 113
<212> TYPE: PRT
<213> ORGANISM: Artificial Sequence
<220> FEATURE:
<223> OTHER INFORMATION: Synthetic sequence hzK2E VH

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
            100                 105                 110

Ser

<210> SEQ ID NO 90
<211> LENGTH: 113
<212> TYPE: PRT
<213> ORGANISM: Artificial Sequence
<220> FEATURE:
<223> OTHER INFORMATION: Synthetic sequence hzK2.1E VH R66K, V67T

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Glu Tyr Asn Gln Lys Phe
    50                  55                  60

Lys Asp Lys Thr Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
            85                  90                  95
Ala Arg Lys Phe Asp Tyr Trp Gly Gln Gly Thr Thr Val Thr Val Ser
                100                 105                 110

Ser

<210> SEQ ID NO 91
<211> LENGTH: 113
<212> TYPE: PRT
<213> ORGANISM: Artificial Sequence
<220> FEATURE:
<223> OTHER INFORMATION: Synthetic sequence hzK2.2E VH R66K, V67T, M69L,
      R71A

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Ser Pro Ser Ser Gly Tyr Thr Glu Tyr Asn Gln Lys Phe
    50                  55                  60

Lys Asp Lys Thr Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
                100                 105                 110

Ser

<210> SEQ ID NO 92
<211> LENGTH: 113
<212> TYPE: PRT
<213> ORGANISM: Artificial Sequence
<220> FEATURE:
<223> OTHER INFORMATION: Synthetic sequence hzK2.3E VH R66K, V67T, M69L,
      R71A, T73K

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Ser Pro Ser Ser Gly Tyr Thr Glu Tyr Asn Gln Lys Phe
    50                  55                  60

Lys Asp Lys Thr Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
                100                 105                 110

Ser

<210> SEQ ID NO 93
<211> LENGTH: 113
<212> TYPE: PRT
```

<213> ORGANISM: Artificial Sequence
<220> FEATURE:
<223> OTHER INFORMATION: Synthetic sequence hzK2.4E VH M69L, R71A

<400> SEQUENCE: 93

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Tyr Asn Gln Lys Phe
    50                  55                  60

Lys Asp Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
            100                 105                 110

Ser
```

<210> SEQ ID NO 94
<211> LENGTH: 121
<212> TYPE: PRT
<213> ORGANISM: Artificial Sequence
<220> FEATURE:
<223> OTHER INFORMATION: Synthetic sequence hzL4L VH

<400> SEQUENCE: 94

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Arg Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120
```

<210> SEQ ID NO 95
<211> LENGTH: 121
<212> TYPE: PRT
<213> ORGANISM: Artificial Sequence
<220> FEATURE:
<223> OTHER INFORMATION: Synthetic sequence hzL4.1L VH S30T, V67I, T68S,
      S70T, V71R

<400> SEQUENCE: 95

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30
```

Tyr Ala Trp Asn Trp Ile Arg Gln His Pro Gly Lys Gly Leu Glu Trp
            35                  40                  45

Ile Gly Tyr Ile Ser Tyr Ser Gly Ser Thr Arg Tyr Asn Pro Ser Leu
     50                  55                  60

Lys Ser Arg Ile Ser Ile Thr Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Arg Tyr Arg Tyr Asp Glu Gly Tyr Gly Met Asp Tyr Trp Gly
             100                 105                 110

Gln Gly Thr Thr Val Thr Val Ser Ser
         115                 120

<210> SEQ ID NO 96
<211> LENGTH: 121
<212> TYPE: PRT
<213> ORGANISM: Artificial Sequence
<220> FEATURE:
<223> OTHER INFORMATION: Synthetic sequence hzL4.2L VH G27Y, S30T, V67I,
    T68S, S70T, V71R

<400> SEQUENCE: 96

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
             20                  25                  30

Tyr Ala Trp Asn Trp Ile Arg Gln His Pro Gly Lys Gly Leu Glu Trp
            35                  40                  45

Ile Gly Tyr Ile Ser Tyr Ser Gly Ser Thr Arg Tyr Asn Pro Ser Leu
     50                  55                  60

Lys Ser Arg Ile Ser Ile Thr Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Arg Tyr Arg Tyr Asp Glu Gly Tyr Gly Met Asp Tyr Trp Gly
             100                 105                 110

Gln Gly Thr Thr Val Thr Val Ser Ser
         115                 120

<210> SEQ ID NO 97
<211> LENGTH: 121
<212> TYPE: PRT
<213> ORGANISM: Artificial Sequence
<220> FEATURE:
<223> OTHER INFORMATION: Synthetic sequence hzL4.3L VH G27Y, S30T

<400> SEQUENCE: 97

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
             20                  25                  30

Tyr Ala Trp Asn Trp Ile Arg Gln His Pro Gly Lys Gly Leu Glu Trp
            35                  40                  45

Ile Gly Tyr Ile Ser Tyr Ser Gly Ser Thr Arg Tyr Asn Pro Ser Leu
     50                  55                  60

Lys Ser Arg Val Thr Ile Ser Val Asp Thr Ser Lys Asn Gln Phe Ser
 65                  70                  75                  80

-continued

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120

<210> SEQ ID NO 98
<211> LENGTH: 121
<212> TYPE: PRT
<213> ORGANISM: Artificial Sequence
<220> FEATURE:
<223> OTHER INFORMATION: Synthetic sequence hzL4.4L VH G27Y, V67I, T68S,
      S70T, V71R

<400> SEQUENCE: 98

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Arg Tyr Asn Pro Ser Leu
    50                  55                  60

Lys Ser Arg Ile Ser Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120

<210> SEQ ID NO 99
<211> LENGTH: 121
<212> TYPE: PRT
<213> ORGANISM: Artificial Sequence
<220> FEATURE:
<223> OTHER INFORMATION: Synthetic sequence hzL4.5L VH G27Y, S30T, S70T,
      V71R

<400> SEQUENCE: 99

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Arg Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120

<210> SEQ ID NO 100
<211> LENGTH: 121
<212> TYPE: PRT
<213> ORGANISM: Artificial Sequence
<220> FEATURE:
<223> OTHER INFORMATION: Synthetic sequence hzL4.6L VH G27Y, S70T, V71R

<400> SEQUENCE: 100

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Arg Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120
```

<210> SEQ ID NO 101
<211> LENGTH: 121
<212> TYPE: PRT
<213> ORGANISM: Artificial Sequence
<220> FEATURE:
<223> OTHER INFORMATION: Synthetic sequence hzL4.7L VH G27Y, S30T, V67I,
    T68S

<400> SEQUENCE: 101

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Arg Tyr Asn Pro Ser Leu
    50                  55                  60

Lys Ser Arg Ile Ser Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Thr Val Thr Val Ser Ser
        115                 120
```

<210> SEQ ID NO 102
<211> LENGTH: 121
<212> TYPE: PRT
<213> ORGANISM: Artificial Sequence
<220> FEATURE:
<223> OTHER INFORMATION: Synthetic sequence hzL4.8L VH G27Y, V67I, T68S

<400> SEQUENCE: 102

-continued

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Tyr Ser Gly Ser Thr Tyr Asn Pro Ser Leu
50                  55                  60

Lys Ser Arg Ile Ser Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Arg Tyr Asp Glu Gly Tyr Gly Met Asp Tyr Trp Gly
                100                 105                 110

Gln Gly Thr Thr Val Thr Val Ser Ser
            115                 120

<210> SEQ ID NO 103
<211> LENGTH: 123
<212> TYPE: PRT
<213> ORGANISM: Artificial Sequence
<220> FEATURE:
<223> OTHER INFORMATION: Synthetic sequence hzH8K VH

<400> SEQUENCE: 103

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
                100                 105                 110

Trp Gly Gln Gly Thr Thr Val Thr Val Ser Ser
            115                 120

<210> SEQ ID NO 104
<211> LENGTH: 123
<212> TYPE: PRT
<213> ORGANISM: Artificial Sequence
<220> FEATURE:
<223> OTHER INFORMATION: Synthetic sequence hzH8.1K VH S30T

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
50                  55                  60

-continued

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
            115                 120

<210> SEQ ID NO 105
<211> LENGTH: 123
<212> TYPE: PRT
<213> ORGANISM: Artificial Sequence
<220> FEATURE:
<223> OTHER INFORMATION: Synthetic sequence hzH8.2K VH G27F, S30T

<400> SEQUENCE: 105

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Ser Asp
            20                  25                  30

Tyr Ala Trp Asn Trp Ile Arg Gln His Pro Gly Lys Gly Leu Glu Trp
            35                  40                  45

Ile Gly Tyr Arg Ser Tyr Arg Gly Ser Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
            115                 120

<210> SEQ ID NO 106
<211> LENGTH: 123
<212> TYPE: PRT
<213> ORGANISM: Artificial Sequence
<220> FEATURE:
<223> OTHER INFORMATION: Synthetic sequence hzH8.3K VH V67I, T68S, S70T,
      V71R

<400> SEQUENCE: 106

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Tyr Ala Trp Asn Trp Ile Arg Gln His Pro Gly Lys Gly Leu Glu Trp
            35                  40                  45

Ile Gly Tyr Arg Ser Tyr Arg Gly Ser Thr Ser Tyr Asn Pro Ser Leu
    50                  55                  60

Lys Ser Arg Ile Ser Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

```
Trp Gly Gln Gly Thr Thr Val Thr Val Ser Ser
        115                 120
```

<210> SEQ ID NO 107
<211> LENGTH: 123
<212> TYPE: PRT
<213> ORGANISM: Artificial Sequence
<220> FEATURE:
<223> OTHER INFORMATION: Synthetic sequence hzH8.4K VH S30T, V67I, T68S,
      S70T, V71R

<400> SEQUENCE: 107

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
    50                  55                  60

Lys Ser Arg Ile Ser Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
        115                 120
```

<210> SEQ ID NO 108
<211> LENGTH: 123
<212> TYPE: PRT
<213> ORGANISM: Artificial Sequence
<220> FEATURE:
<223> OTHER INFORMATION: Synthetic sequence hzH8.5K VH G27F, S30T, V67I,
      T68S, S70T, V71R

<400> SEQUENCE: 108

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
    50                  55                  60

Lys Ser Arg Ile Ser Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
        115                 120
```

<210> SEQ ID NO 109
<211> LENGTH: 123
<212> TYPE: PRT
<213> ORGANISM: Artificial Sequence
<220> FEATURE:

<223> OTHER INFORMATION: Synthetic sequence hzH8.6K VH S30T, V67I, T68S

<400> SEQUENCE: 109

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
    50                  55                  60

Lys Ser Arg Ile Ser Ile Ser Val Asp Thr Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
        115                 120

<210> SEQ ID NO 110
<211> LENGTH: 123
<212> TYPE: PRT
<213> ORGANISM: Artificial Sequence
<220> FEATURE:
<223> OTHER INFORMATION: Synthetic sequence hzH8.7K VH S30T, S70T, V71R

<400> SEQUENCE: 110

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Arg Ser Tyr Arg Gly Ser Thr Ser Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
        115                 120

<210> SEQ ID NO 111
<211> LENGTH: 123
<212> TYPE: PRT
<213> ORGANISM: Artificial Sequence
<220> FEATURE:
<223> OTHER INFORMATION: Synthetic sequence hzH8.8K VH V67I, T68S

<400> SEQUENCE: 111

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Tyr Ala Trp Asn Trp Ile Arg Gln His Pro Gly Lys Gly Leu Glu Trp

```
                35                  40                  45

Ile Gly Tyr Arg Ser Tyr Arg Gly Ser Thr Ser Tyr Asn Pro Ser Leu
         50                  55                  60

Lys Ser Arg Ile Ser Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
            115                 120

<210> SEQ ID NO 112
<211> LENGTH: 123
<212> TYPE: PRT
<213> ORGANISM: Artificial Sequence
<220> FEATURE:
<223> OTHER INFORMATION: Synthetic sequence hzH8.9K VH S70T, V71R

<400> SEQUENCE: 112

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Asp
                 20                  25                  30

Tyr Ala Trp Asn Trp Ile Arg Gln His Pro Gly Lys Gly Leu Glu Trp
             35                  40                  45

Ile Gly Tyr Arg Ser Tyr Arg Gly Ser Thr Ser Tyr Asn Pro Ser Leu
         50                  55                  60

Lys Ser Arg Val Thr Ile Thr Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Arg Gly Tyr Tyr Gly Ser Ser Ser His Trp Tyr Phe Asp Val
            100                 105                 110

Trp Gly Gln Gly Thr Thr Val Thr Val Ser Ser
            115                 120

<210> SEQ ID NO 113
<211> LENGTH: 115
<212> TYPE: PRT
<213> ORGANISM: Artificial Sequence
<220> FEATURE:
<223> OTHER INFORMATION: Synthetic sequence hzJ4F VH

<400> SEQUENCE: 113

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Ile Asn Trp Val Arg Gln Ala Pro Gly Gln Gly Leu Glu Trp Met
             35                  40                  45

Gly Arg Ile Val Pro Gly Ser Gly Ser Thr Tyr Tyr Asn Glu Met Phe
         50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

Ala Arg Lys Pro Asn Phe Asp Val Trp Gly Gln Gly Thr Thr Val Thr
            100                 105                 110

Val Ser Ser
      115

<210> SEQ ID NO 114
<211> LENGTH: 115
<212> TYPE: PRT
<213> ORGANISM: Artificial Sequence
<220> FEATURE:
<223> OTHER INFORMATION: Synthetic sequence hzJ4.1F VH V37I

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
      115

<210> SEQ ID NO 115
<211> LENGTH: 115
<212> TYPE: PRT
<213> ORGANISM: Artificial Sequence
<220> FEATURE:
<223> OTHER INFORMATION: Synthetic sequence hzJ4.2F VH V37I, R38K, M48I

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Lys Gln Ala Pro Gly Gln Gly Leu Glu Trp Ile
        35                  40                  45

Gly Arg Ile Val Pro Gly Ser Gly Ser Thr Tyr Tyr Asn Glu Met Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
      115

<210> SEQ ID NO 116
<211> LENGTH: 115
<212> TYPE: PRT
<213> ORGANISM: Artificial Sequence

```
<220> FEATURE:
<223> OTHER INFORMATION: Synthetic sequence hzJ4.3F VH V37I, R66K, V67A

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Lys Ala Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115

<210> SEQ ID NO 117
<211> LENGTH: 115
<212> TYPE: PRT
<213> ORGANISM: Artificial Sequence
<220> FEATURE:
<223> OTHER INFORMATION: Synthetic sequence hzJ4.4F VH V37I, R38K, M48I,
      R66K, V67A

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Lys Gln Ala Pro Gly Gln Gly Leu Glu Trp Ile
        35                  40                  45

Gly Arg Ile Val Pro Gly Ser Gly Ser Thr Tyr Tyr Asn Glu Met Phe
    50                  55                  60

Lys Asp Lys Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115

<210> SEQ ID NO 118
<211> LENGTH: 115
<212> TYPE: PRT
<213> ORGANISM: Artificial Sequence
<220> FEATURE:
<223> OTHER INFORMATION: Synthetic sequence hzJ4.5F VH R66K, V67A

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Ile Asn Trp Val Arg Gln Ala Pro Gly Gln Gly Leu Glu Trp Met
            35                  40                  45

Gly Arg Ile Val Pro Gly Ser Gly Ser Thr Tyr Tyr Asn Glu Met Phe
        50                  55                  60

Lys Asp Lys Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
                100                 105                 110

Val Ser Ser
        115

<210> SEQ ID NO 119
<211> LENGTH: 115
<212> TYPE: PRT
<213> ORGANISM: Artificial Sequence
<220> FEATURE:
<223> OTHER INFORMATION: Synthetic sequence hzJ4.6F VH R66K, V67A, V78A

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
            35                  40                  45

Gly Arg Ile Val Pro Gly Ser Gly Ser Thr Tyr Tyr Asn Glu Met Phe
        50                  55                  60

Lys Asp Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
                100                 105                 110

Val Ser Ser
        115

<210> SEQ ID NO 120
<211> LENGTH: 115
<212> TYPE: PRT
<213> ORGANISM: Artificial Sequence
<220> FEATURE:
<223> OTHER INFORMATION: Synthetic sequence hzJ4.7F VH R66K, V67A, V78A,
      M80I, E81Q

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
            35                  40                  45

Gly Arg Ile Val Pro Gly Ser Gly Ser Thr Tyr Tyr Asn Glu Met Phe
        50                  55                  60

Lys Asp Lys Ala Thr Met Thr Arg Asp Thr Ser Thr Ser Thr Ala Tyr
65                  70                  75                  80
```

```
Ile Gln Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115

<210> SEQ ID NO 121
<211> LENGTH: 115
<212> TYPE: PRT
<213> ORGANISM: Artificial Sequence
<220> FEATURE:
<223> OTHER INFORMATION: Synthetic sequence hzJ4.8F VH R66K, V67A, M69L,
      R71V

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Lys Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115

<210> SEQ ID NO 122
<211> LENGTH: 115
<212> TYPE: PRT
<213> ORGANISM: Artificial Sequence
<220> FEATURE:
<223> OTHER INFORMATION: Synthetic sequence hzJ4.9F VH M69L, R71V

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115
```

<210> SEQ ID NO 123
<211> LENGTH: 115
<212> TYPE: PRT
<213> ORGANISM: Artificial Sequence
<220> FEATURE:
<223> OTHER INFORMATION: Synthetic sequence hzJ4.10F VH R71V

<400> SEQUENCE: 123

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115
```

<210> SEQ ID NO 124
<211> LENGTH: 115
<212> TYPE: PRT
<213> ORGANISM: Artificial Sequence
<220> FEATURE:
<223> OTHER INFORMATION: Synthetic sequence hzJ4.11F VH V78A

<400> SEQUENCE: 124

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Arg Ile Val Pro Gly Ser Gly Ser Thr Tyr Tyr Asn Glu Met Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Pro Asn Phe Asp Val Trp Gly Gln Gly Thr Thr Val Thr
            100                 105                 110

Val Ser Ser
        115
```

<210> SEQ ID NO 125
<211> LENGTH: 115
<212> TYPE: PRT
<213> ORGANISM: Artificial Sequence
<220> FEATURE:
<223> OTHER INFORMATION: Synthetic sequence hzJ4.12F VH V78A, M80I, E81Q

<400> SEQUENCE: 125

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
            35                  40                  45

Gly Arg Ile Val Pro Gly Ser Gly Ser Thr Tyr Tyr Asn Glu Met Phe
 50                  55                  60

Lys Asp Arg Val Thr Met Thr Arg Asp Thr Ser Thr Ser Thr Ala Tyr
 65                  70                  75                  80

Ile Gln Leu Ser Ser Leu Arg Ser Glu Asp Thr Ala Val Tyr Tyr Cys
                 85                  90                  95

Ala Arg Lys Pro Asn Phe Asp Val Trp Gly Gln Gly Thr Thr Val Thr
            100                 105                 110

Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Synthetic sequence G2D VL

<400> SEQUENCE: 126

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Val Ile Asn Ser Tyr
            20                  25                  30

Leu Ser Trp Phe Gln Gln Lys Pro Gly Lys Ser Pro Glu Thr Leu Ile
            35                  40                  45

Tyr Arg Ala Asn Thr Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Leu Gly Ile Tyr Tyr Cys Leu Gln Tyr Ala Glu Phe Pro Tyr
                 85                  90                  95

Thr Phe Gly Gly Gly Thr Lys Leu Glu Ile Lys
            100                 105

<210> SEQ ID NO 127
<211> LENGTH: 107
<212> TYPE: PRT
<213> ORGANISM: Artificial Sequence
<220> FEATURE:
<223> OTHER INFORMATION: Synthetic sequence K2E VL

<400> SEQUENCE: 127

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
 50                  55                  60

Ser Gly Ser Gly Gln Asp Phe Ser Leu Thr Ile Ser Ser Leu Glu Tyr
 65                  70                  75                  80

Glu Asp Met Gly Ile Tyr Tyr Cys Leu Gln Tyr Asp Glu Phe Pro Phe
```

```
                    85                  90                  95

Thr Phe Gly Ser Gly Thr Lys Leu Glu Ile Lys
                100                 105

<210> SEQ ID NO 128
<211> LENGTH: 108
<212> TYPE: PRT
<213> ORGANISM: Artificial Sequence
<220> FEATURE:
<223> OTHER INFORMATION: Synthetic sequence L4L VL

<400> SEQUENCE: 128

Asp Ile Gln Met Thr Gln Ser Pro Ala Ser Leu Ser Val Phe Val Gly
1               5                   10                  15

Glu Ile Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Thr Gly
    50                  55                  60

Ser Gly Ser Gly Thr Gln Phe Ser Leu Lys Ile Asn Ser Leu Gln Ser
65                  70                  75                  80

Glu Asp Phe Gly Asn Tyr Tyr Cys Gln His Phe Trp Gly Thr Pro Pro
                85                  90                  95

Trp Thr Phe Gly Gly Gly Thr Lys Leu Glu Ile Lys
                100                 105

<210> SEQ ID NO 129
<211> LENGTH: 107
<212> TYPE: PRT
<213> ORGANISM: Artificial Sequence
<220> FEATURE:
<223> OTHER INFORMATION: Synthetic sequence H8K VL

<400> SEQUENCE: 129

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ser Gly Thr Lys Leu Glu Leu Lys
                100                 105

<210> SEQ ID NO 130
<211> LENGTH: 107
<212> TYPE: PRT
<213> ORGANISM: Artificial Sequence
<220> FEATURE:
<223> OTHER INFORMATION: Synthetic sequence J4F VL

<400> SEQUENCE: 130

Asp Ile Val Met Thr Gln Ser Gln Lys Phe Met Ser Thr Ser Val Gly
1               5                   10                  15
```

```
Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Val Ile
        35                  40                  45

Tyr Ser Ala Ser Tyr Arg Phe Ser Gly Val Pro Asp Arg Leu Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105
```

<210> SEQ ID NO 131
<211> LENGTH: 107
<212> TYPE: PRT
<213> ORGANISM: Artificial Sequence
<220> FEATURE:
<223> OTHER INFORMATION: Synthetic sequence hzG2D VLa

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
            100                 105
```

<210> SEQ ID NO 132
<211> LENGTH: 107
<212> TYPE: PRT
<213> ORGANISM: Artificial Sequence
<220> FEATURE:
<223> OTHER INFORMATION: Synthetic sequence hzG2.1D VLa D56S

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
```

<210> SEQ ID NO 133
<211> LENGTH: 107
<212> TYPE: PRT
<213> ORGANISM: Artificial Sequence
<220> FEATURE:
<223> OTHER INFORMATION: Synthetic sequence hzG2.2D VLa D56E

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: Synthetic sequence hzK2E VL

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 135
<211> LENGTH: 107
<212> TYPE: PRT
<213> ORGANISM: Artificial Sequence
<220> FEATURE:
<223> OTHER INFORMATION: Synthetic sequence hzK2.1E VL S46T

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

```
Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 136
<211> LENGTH: 107
<212> TYPE: PRT
<213> ORGANISM: Artificial Sequence
<220> FEATURE:
<223> OTHER INFORMATION: Synthetic sequence hzK2.2E VL D56E

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 137
<211> LENGTH: 107
<212> TYPE: PRT
<213> ORGANISM: Artificial Sequence
<220> FEATURE:
<223> OTHER INFORMATION: Synthetic sequence hzK2.3E VL S46T D56E

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105
```

-continued

```
<210> SEQ ID NO 138
<211> LENGTH: 108
<212> TYPE: PRT
<213> ORGANISM: Artificial Sequence
<220> FEATURE:
<223> OTHER INFORMATION: Synthetic sequence hzL4L VL

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Trp Thr Phe Gly Gly Gly Thr Lys Val Glu Ile Lys
            100                 105

<210> SEQ ID NO 139
<211> LENGTH: 108
<212> TYPE: PRT
<213> ORGANISM: Artificial Sequence
<220> FEATURE:
<223> OTHER INFORMATION: Synthetic sequence hzL4.1L VL D56S

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Trp Thr Phe Gly Gly Gly Thr Lys Val Glu Ile Lys
            100                 105

<210> SEQ ID NO 140
<211> LENGTH: 108
<212> TYPE: PRT
<213> ORGANISM: Artificial Sequence
<220> FEATURE:
<223> OTHER INFORMATION: Synthetic sequence hzL4.2L VL D56E

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45
```

Tyr Ala Ala Thr Asn Leu Ala Glu Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Trp Thr Phe Gly Gly Gly Thr Lys Val Glu Ile Lys
            100                 105

<210> SEQ ID NO 141
<211> LENGTH: 108
<212> TYPE: PRT
<213> ORGANISM: Artificial Sequence
<220> FEATURE:
<223> OTHER INFORMATION: Synthetic sequence hzL4.3L VL G57A

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Trp Thr Phe Gly Gly Gly Thr Lys Val Glu Ile Lys
            100                 105

<210> SEQ ID NO 142
<211> LENGTH: 107
<212> TYPE: PRT
<213> ORGANISM: Artificial Sequence
<220> FEATURE:
<223> OTHER INFORMATION: Synthetic sequence hzH8K VL

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gly Gly Thr Lys Val Glu Ile Lys
            100                 105

<210> SEQ ID NO 143
<211> LENGTH: 107
<212> TYPE: PRT

```
<213> ORGANISM: Artificial Sequence
<220> FEATURE:
<223> OTHER INFORMATION: Synthetic sequence hzJ4F VL

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 144
<211> LENGTH: 107
<212> TYPE: PRT
<213> ORGANISM: Artificial Sequence
<220> FEATURE:
<223> OTHER INFORMATION: Synthetic sequence hzJ4.1F VL Q3V

<400> SEQUENCE: 144

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 145
<211> LENGTH: 107
<212> TYPE: PRT
<213> ORGANISM: Artificial Sequence
<220> FEATURE:
<223> OTHER INFORMATION: Synthetic sequence hzJ4.2F VL Q3V L46A

<400> SEQUENCE: 145

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Phe Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 146
<211> LENGTH: 107
<212> TYPE: PRT
<213> ORGANISM: Artificial Sequence
<220> FEATURE:
<223> OTHER INFORMATION: Synthetic sequence hzJ4.3F VL L46A

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Leu Ile
            35                  40                  45

Tyr Ser Ala Ser Tyr Arg Phe Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 147
<211> LENGTH: 107
<212> TYPE: PRT
<213> ORGANISM: Artificial Sequence
<220> FEATURE:
<223> OTHER INFORMATION: Synthetic sequence hzJ4.4F VL L46A, L47V

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Val Ile
            35                  40                  45

Tyr Ser Ala Ser Tyr Arg Phe Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 148
<211> LENGTH: 107
<212> TYPE: PRT
<213> ORGANISM: Artificial Sequence
<220> FEATURE:
<223> OTHER INFORMATION: Synthetic sequence hzJ4.5F VL L46A, L47V, F62L
```

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Val Ile
        35                  40                  45

Tyr Ser Ala Ser Tyr Arg Phe Ser Gly Val Pro Ser Arg Leu Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 149
<211> LENGTH: 107
<212> TYPE: PRT
<213> ORGANISM: Artificial Sequence
<220> FEATURE:
<223> OTHER INFORMATION: Synthetic sequence hzJ4.6F VL L46A, L47V, S60D,
      F62L, S63T

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Val Ile
        35                  40                  45

Tyr Ser Ala Ser Tyr Arg Phe Ser Gly Val Pro Asp Arg Leu Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 150
<211> LENGTH: 444
<212> TYPE: PRT
<213> ORGANISM: Artificial Sequence
<220> FEATURE:
<223> OTHER INFORMATION: Synthetic sequence chG2D Heavy Chain

<400> SEQUENCE: 150

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Lys Ser Ser Ser Thr Ala Tyr

```
            65                  70                  75                  80
Met Glu Phe His Ser Leu Thr Ser Glu Asp Ser Ala Val Tyr Tyr Cys
                    85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                    165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 151
<211> LENGTH: 443
<212> TYPE: PRT
<213> ORGANISM: Artificial Sequence
<220> FEATURE:
<223> OTHER INFORMATION: Synthetic sequence chK2E Heavy Chain
```

<400> SEQUENCE: 151

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Ser Pro Ser Ser Gly Tyr Thr Glu Tyr Asn Gln Lys Phe
        50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Lys Phe Asp Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
              420                 425                 430

Thr Gln Lys Ser Leu Ser Leu Ser Pro Gly Lys
        435                 440

<210> SEQ ID NO 152
<211> LENGTH: 451
<212> TYPE: PRT
<213> ORGANISM: Artificial Sequence
<220> FEATURE:
<223> OTHER INFORMATION: Synthetic sequence chL4L Heavy Chain

<400> SEQUENCE: 152

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Tyr Arg Tyr Asp Glu Gly Tyr Gly Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
                435                 440                 445

Pro Gly Lys
    450

<210> SEQ ID NO 153
<211> LENGTH: 453
<212> TYPE: PRT
<213> ORGANISM: Artificial Sequence
<220> FEATURE:
<223> OTHER INFORMATION: Synthetic sequence chH8K Heavy Chain

<400> SEQUENCE: 153

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
            20                  25                  30

Tyr Ala Trp Asn Trp Ile Arg Gln Phe Pro Gly Asn Gln Leu Glu Trp
        35                  40                  45

Met Gly Tyr Arg Ser Tyr Arg Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Gly Tyr Tyr Gly Ser Ser His Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 154
<211> LENGTH: 445
<212> TYPE: PRT
<213> ORGANISM: Artificial Sequence
<220> FEATURE:
<223> OTHER INFORMATION: Synthetic sequence chJ4F Heavy Chain

<400> SEQUENCE: 154

Gln Val Gln Leu Gln Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly Arg Ile Val Pro Gly Ser Gly Ser Thr Tyr Tyr Asn Glu Met Phe
    50                  55                  60

Lys Asp Lys Ala Thr Leu Thr Val Asp Thr Ser Ser Ser Thr Ala Tyr
65                  70                  75                  80

Ile Gln Leu Ser Ser Leu Ser Ser Glu Asp Ser Ala Val Tyr Phe Cys
                85                  90                  95

Ala Arg Lys Pro Asn Phe Asp Val Trp Gly Ala Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 155
<211> LENGTH: 444
<212> TYPE: PRT
<213> ORGANISM: Artificial Sequence
<220> FEATURE:
<223> OTHER INFORMATION: Synthetic sequence hzG2D Heavy Chain V109L

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 156
<211> LENGTH: 444
<212> TYPE: PRT
<213> ORGANISM: Artificial Sequence
<220> FEATURE:

<223> OTHER INFORMATION: Synthetic sequence hzG2.1D Heavy Chain T28S, V109L

<400> SEQUENCE: 156

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Thr | Gly | Tyr |
| | | | 20 | | | | | 25 | | | | | 30 | | |
| Tyr | Met | His | Trp | Val | Arg | Gln | Ala | Pro | Gly | Gln | Arg | Leu | Glu | Trp | Met |
| | | 35 | | | | | 40 | | | | | 45 | | | |
| Gly | Arg | Ile | Asn | Pro | Asn | Asn | Gly | Ala | Thr | Asn | Tyr | Asn | Gln | Asn | Phe |
| 50 | | | | | 55 | | | | | 60 | | | | | |
| Lys | Asp | Arg | Val | Thr | Ile | Thr | Arg | Asp | Thr | Ser | Ala | Ser | Thr | Ala | Tyr |
| 65 | | | | 70 | | | | | 75 | | | | | 80 | |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Val | Asn | Phe | Tyr | Tyr | Trp | Gly | Gln | Gly | Thr | Thr | Leu | Thr | Val |
| | | | 100 | | | | | 105 | | | | | 110 | | |
| Ser | Ser | Ala | Ser | Thr | Lys | Gly | Pro | Ser | Val | Phe | Pro | Leu | Ala | Pro | Ser |
| | | | 115 | | | | | 120 | | | | | 125 | | |
| Ser | Lys | Ser | Thr | Ser | Gly | Gly | Thr | Ala | Ala | Leu | Gly | Cys | Leu | Val | Lys |
| | 130 | | | | | 135 | | | | | 140 | | | | |
| Asp | Tyr | Phe | Pro | Glu | Pro | Val | Thr | Val | Ser | Trp | Asn | Ser | Gly | Ala | Leu |
| 145 | | | | | 150 | | | | | 155 | | | | | 160 |
| Thr | Ser | Gly | Val | His | Thr | Phe | Pro | Ala | Val | Leu | Gln | Ser | Ser | Gly | Leu |
| | | | | 165 | | | | | 170 | | | | | 175 | |
| Tyr | Ser | Leu | Ser | Ser | Val | Val | Thr | Val | Pro | Ser | Ser | Ser | Leu | Gly | Thr |
| | | | 180 | | | | | 185 | | | | | 190 | | |
| Gln | Thr | Tyr | Ile | Cys | Asn | Val | Asn | His | Lys | Pro | Ser | Asn | Thr | Lys | Val |
| | | | 195 | | | | | 200 | | | | | 205 | | |
| Asp | Lys | Lys | Val | Glu | Pro | Lys | Ser | Cys | Asp | Lys | Thr | His | Thr | Cys | Pro |
| | 210 | | | | | 215 | | | | | 220 | | | | |
| Pro | Cys | Pro | Ala | Pro | Glu | Leu | Leu | Gly | Gly | Pro | Ser | Val | Phe | Leu | Phe |
| 225 | | | | | 230 | | | | | 235 | | | | | 240 |
| Pro | Pro | Lys | Pro | Lys | Asp | Thr | Leu | Met | Ile | Ser | Arg | Thr | Pro | Glu | Val |
| | | | | 245 | | | | | 250 | | | | | 255 | |
| Thr | Cys | Val | Val | Val | Asp | Val | Ser | His | Glu | Asp | Pro | Glu | Val | Lys | Phe |
| | | | 260 | | | | | 265 | | | | | 270 | | |
| Asn | Trp | Tyr | Val | Asp | Gly | Val | Glu | Val | His | Asn | Ala | Lys | Thr | Lys | Pro |
| | | | | 275 | | | | | 280 | | | | | 285 | |
| Arg | Glu | Glu | Gln | Tyr | Asn | Ser | Thr | Tyr | Arg | Val | Val | Ser | Val | Leu | Thr |
| | 290 | | | | | 295 | | | | | 300 | | | | |
| Val | Leu | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | Asn | Lys | Ala | Leu | Pro | Ala | Pro | Ile | Glu | Lys | Thr | Ile | Ser | Lys | Ala |
| | | | | 325 | | | | | 330 | | | | | 335 | |
| Lys | Gly | Gln | Pro | Arg | Glu | Pro | Gln | Val | Tyr | Thr | Leu | Pro | Pro | Ser | Arg |
| | | | 340 | | | | | 345 | | | | | 350 | | |
| Glu | Glu | Met | Thr | Lys | Asn | Gln | Val | Ser | Leu | Thr | Cys | Leu | Val | Lys | Gly |
| | | | | 355 | | | | | 360 | | | | | 365 | |
| Phe | Tyr | Pro | Ser | Asp | Ile | Ala | Val | Glu | Trp | Glu | Ser | Asn | Gly | Gln | Pro |
| | | 370 | | | | | 375 | | | | | 380 | | | |
| Glu | Asn | Asn | Tyr | Lys | Thr | Thr | Pro | Pro | Val | Leu | Asp | Ser | Asp | Gly | Ser |
| 385 | | | | | 390 | | | | | 395 | | | | | 400 |

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 157
<211> LENGTH: 444
<212> TYPE: PRT
<213> ORGANISM: Artificial Sequence
<220> FEATURE:
<223> OTHER INFORMATION: Synthetic sequence hzG2.2D Heavy Chain T28S,
      R66K, V67A, V109L

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val

```
            305                 310                 315                 320
Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
                435                 440
```

<210> SEQ ID NO 158
<211> LENGTH: 444
<212> TYPE: PRT
<213> ORGANISM: Artificial Sequence
<220> FEATURE:
<223> OTHER INFORMATION: Synthetic sequence hzG2.3D Heavy Chain T28S,
      R66K, V67A, A93T, R94S, V109L

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
    210                 215                 220
```

```
Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 159
<211> LENGTH: 444
<212> TYPE: PRT
<213> ORGANISM: Artificial Sequence
<220> FEATURE:
<223> OTHER INFORMATION: Synthetic sequence hzG2.4D Heavy Chain T28S,
      R66K, V67A, T68S, I69L, R71V, V109L

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140
```

```
Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 160
<211> LENGTH: 444
<212> TYPE: PRT
<213> ORGANISM: Artificial Sequence
<220> FEATURE:
<223> OTHER INFORMATION: Synthetic sequence hzG2.5D Heavy Chain T28S,
      R66K, V67A, T68S, I69L, R71V, A93T, R94S, V109L

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
```

```
            50                  55                  60
Lys Asp Lys Ala Ser Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
                130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
                275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 161
<211> LENGTH: 444
<212> TYPE: PRT
<213> ORGANISM: Artificial Sequence
```

<220> FEATURE:
<223> OTHER INFORMATION: Synthetic sequence hzG2.6D Heavy Chain T28S, T68S, I69L, R71V, V109L

<400> SEQUENCE: 161

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
```

```
                385                 390                 395                 400
Phe Phe Leu Tyr Ser Lys Leu Thr Val Asp Lys Ser Arg Trp Gln Gln
                    405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 162
<211> LENGTH: 444
<212> TYPE: PRT
<213> ORGANISM: Artificial Sequence
<220> FEATURE:
<223> OTHER INFORMATION: Synthetic sequence hzG2.7D Heavy Chain T28S,
      T68S, I69L, R71V, A93T, R94S, V109L

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300
```

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 163
<211> LENGTH: 444
<212> TYPE: PRT
<213> ORGANISM: Artificial Sequence
<220> FEATURE:
<223> OTHER INFORMATION: Synthetic sequence hzG2.8D Heavy Chain T28S,
      A93T, R94S, V109L

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
            210                 215                 220

```
Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 164
<211> LENGTH: 444
<212> TYPE: PRT
<213> ORGANISM: Artificial Sequence
<220> FEATURE:
<223> OTHER INFORMATION: Synthetic sequence hzG2.9D Heavy Chain T28S,
      N54Q

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
```

```
            130                 135                 140
Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 165
<211> LENGTH: 444
<212> TYPE: PRT
<213> ORGANISM: Artificial Sequence
<220> FEATURE:
<223> OTHER INFORMATION: Synthetic sequence hzG2.10D Heavy Chain T28S,
      N54Q, R66K, V67A

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45
```

Gly Arg Ile Asn Pro Asn Gln Gly Ala Thr Asn Tyr Asn Gln Asn Phe
            50                  55                  60

Lys Asp Lys Ala Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 166
<211> LENGTH: 444
<212> TYPE: PRT

-continued

<213> ORGANISM: Artificial Sequence
<220> FEATURE:
<223> OTHER INFORMATION: Synthetic sequence hzG2.11D Heavy Chain T28S,
     N54Q, R66K, V67A, A93T, R94S

<400> SEQUENCE: 166

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

```
Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 167
<211> LENGTH: 444
<212> TYPE: PRT
<213> ORGANISM: Artificial Sequence
<220> FEATURE:
<223> OTHER INFORMATION: Synthetic sequence hzG2.12D Heavy Chain T28S,
      N54Q, R66K, V67A, T68S, I69L, R71V

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300
```

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 168
<211> LENGTH: 444
<212> TYPE: PRT
<213> ORGANISM: Artificial Sequence
<220> FEATURE:
<223> OTHER INFORMATION: Synthetic sequence hzG2.13D Heavy Chain T28S,
      N54Q, R66K, V67A, T68S, I69L, R71V, A93T, R94S

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
        50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro

-continued

```
                210                 215                 220
Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440
```

<210> SEQ ID NO 169
<211> LENGTH: 444
<212> TYPE: PRT
<213> ORGANISM: Artificial Sequence
<220> FEATURE:
<223> OTHER INFORMATION: Synthetic sequence hzG2.14D Heavy Chain T28S, N54Q, T68S, I69L, R71V

<400> SEQUENCE: 169

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
        50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125
```

```
Ser Lys Ser Thr Ser Gly Gly Thr Ala Ala Leu Gly Cys Leu Val Lys
    130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440

<210> SEQ ID NO 170
<211> LENGTH: 444
<212> TYPE: PRT
<213> ORGANISM: Artificial Sequence
<220> FEATURE:
<223> OTHER INFORMATION: Synthetic sequence hzG2.15D Heavy Chain T28S,
      N54Q, T68S, I69L, R71V, A93T, R94S

<400> SEQUENCE: 170

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Gly Tyr
            20                  25                  30
Tyr Met His Trp Val Arg Gln Ala Pro Gly Gln Arg Leu Glu Trp Met
        35                  40                  45
```

```
Gly Arg Ile Asn Pro Asn Gln Gly Ala Thr Asn Tyr Asn Gln Asn Phe
 50                  55                  60

Lys Asp Arg Val Ser Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 171
<211> LENGTH: 444
```

<212> TYPE: PRT
<213> ORGANISM: Artificial Sequence
<220> FEATURE:
<223> OTHER INFORMATION: Synthetic sequence hzG2.16D Heavy Chain T28S,
      N54Q, A93T, R94S

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

-continued

Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 172
<211> LENGTH: 444
<212> TYPE: PRT
<213> ORGANISM: Artificial Sequence
<220> FEATURE:
<223> OTHER INFORMATION: Synthetic sequence hzG2.17D Heavy Chain T28S,
      G55A

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
        180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr

```
        290                 295                 300
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 173
<211> LENGTH: 444
<212> TYPE: PRT
<213> ORGANISM: Artificial Sequence
<220> FEATURE:
<223> OTHER INFORMATION: Synthetic sequence hzG2.18D Heavy Chain T28S,
      G55A, R66K, V67A

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Ala Ala Thr Asn Tyr Asn Gln Asn Phe
        50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205
```

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 174
<211> LENGTH: 444
<212> TYPE: PRT
<213> ORGANISM: Artificial Sequence
<220> FEATURE:
<223> OTHER INFORMATION: Synthetic sequence hzG2.19D Heavy Chain T28S,
      G55A, R66K, V67A, A93T, R94S

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 175
<211> LENGTH: 444
<212> TYPE: PRT
<213> ORGANISM: Artificial Sequence
<220> FEATURE:
<223> OTHER INFORMATION: Synthetic sequence hzG2.20D Heavy Chain T28S,
      G55A, R66K, V67A, T68S, I69L, R71V

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Arg Leu Glu Trp Met

```
            35                  40                  45
Gly Arg Ile Asn Pro Asn Asn Ala Ala Thr Asn Tyr Asn Gln Asn Phe
 50                  55                  60

Lys Asp Lys Ala Ser Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 176
```

```
<211> LENGTH: 444
<212> TYPE: PRT
<213> ORGANISM: Artificial Sequence
<220> FEATURE:
<223> OTHER INFORMATION: Synthetic sequence hzG2.21D Heavy Chain T28S,
      G55A, R66K, V67A, T68S, I69L, R71V, A93T, R94S

<400> SEQUENCE: 176
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Thr | Gly | Tyr |
| | | | 20 | | | | | 25 | | | | | 30 | | |
| Tyr | Met | His | Trp | Val | Arg | Gln | Ala | Pro | Gly | Gln | Arg | Leu | Glu | Trp | Met |
| | | 35 | | | | | 40 | | | | | 45 | | | |
| Gly | Arg | Ile | Asn | Pro | Asn | Asn | Ala | Ala | Thr | Asn | Tyr | Asn | Gln | Asn | Phe |
| 50 | | | | | 55 | | | | | 60 | | | | | |
| Lys | Asp | Lys | Ala | Ser | Leu | Thr | Val | Asp | Thr | Ser | Ala | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Thr | Ser | Val | Asn | Phe | Tyr | Tyr | Trp | Gly | Gln | Gly | Thr | Thr | Leu | Thr | Val |
| | | | 100 | | | | | 105 | | | | | 110 | | |
| Ser | Ser | Ala | Ser | Thr | Lys | Gly | Pro | Ser | Val | Phe | Pro | Leu | Ala | Pro | Ser |
| | | 115 | | | | | 120 | | | | | 125 | | | |
| Ser | Lys | Ser | Thr | Ser | Gly | Gly | Thr | Ala | Ala | Leu | Gly | Cys | Leu | Val | Lys |
| | 130 | | | | | 135 | | | | | 140 | | | | |
| Asp | Tyr | Phe | Pro | Glu | Pro | Val | Thr | Val | Ser | Trp | Asn | Ser | Gly | Ala | Leu |
| 145 | | | | | 150 | | | | | 155 | | | | | 160 |
| Thr | Ser | Gly | Val | His | Thr | Phe | Pro | Ala | Val | Leu | Gln | Ser | Ser | Gly | Leu |
| | | | | 165 | | | | | 170 | | | | | 175 | |
| Tyr | Ser | Leu | Ser | Ser | Val | Val | Thr | Val | Pro | Ser | Ser | Ser | Leu | Gly | Thr |
| | | | 180 | | | | | 185 | | | | | 190 | | |
| Gln | Thr | Tyr | Ile | Cys | Asn | Val | Asn | His | Lys | Pro | Ser | Asn | Thr | Lys | Val |
| | | 195 | | | | | 200 | | | | | 205 | | | |
| Asp | Lys | Lys | Val | Glu | Pro | Lys | Ser | Cys | Asp | Lys | Thr | His | Thr | Cys | Pro |
| 210 | | | | | 215 | | | | | 220 | | | | | |
| Pro | Cys | Pro | Ala | Pro | Glu | Leu | Leu | Gly | Gly | Pro | Ser | Val | Phe | Leu | Phe |
| 225 | | | | | 230 | | | | | 235 | | | | | 240 |
| Pro | Pro | Lys | Pro | Lys | Asp | Thr | Leu | Met | Ile | Ser | Arg | Thr | Pro | Glu | Val |
| | | | | 245 | | | | | 250 | | | | | 255 | |
| Thr | Cys | Val | Val | Val | Asp | Val | Ser | His | Glu | Asp | Pro | Glu | Val | Lys | Phe |
| | | | 260 | | | | | 265 | | | | | 270 | | |
| Asn | Trp | Tyr | Val | Asp | Gly | Val | Glu | Val | His | Asn | Ala | Lys | Thr | Lys | Pro |
| | | 275 | | | | | 280 | | | | | 285 | | | |
| Arg | Glu | Glu | Gln | Tyr | Asn | Ser | Thr | Tyr | Arg | Val | Val | Ser | Val | Leu | Thr |
| 290 | | | | | 295 | | | | | 300 | | | | | |
| Val | Leu | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | Asn | Lys | Ala | Leu | Pro | Ala | Pro | Ile | Glu | Lys | Thr | Ile | Ser | Lys | Ala |
| | | | | 325 | | | | | 330 | | | | | 335 | |
| Lys | Gly | Gln | Pro | Arg | Glu | Pro | Gln | Val | Tyr | Thr | Leu | Pro | Pro | Ser | Arg |
| | | | 340 | | | | | 345 | | | | | 350 | | |
| Glu | Glu | Met | Thr | Lys | Asn | Gln | Val | Ser | Leu | Thr | Cys | Leu | Val | Lys | Gly |
| | | 355 | | | | | 360 | | | | | 365 | | | |
| Phe | Tyr | Pro | Ser | Asp | Ile | Ala | Val | Glu | Trp | Glu | Ser | Asn | Gly | Gln | Pro |

```
                    370                 375                 380
Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 177
<211> LENGTH: 444
<212> TYPE: PRT
<213> ORGANISM: Artificial Sequence
<220> FEATURE:
<223> OTHER INFORMATION: Synthetic sequence hzG2.22D Heavy Chain T28S,
      G55A, T68S, I69L, R71V

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285
```

```
Arg Glu Glu Gln Tyr Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
                435                 440
```

<210> SEQ ID NO 178
<211> LENGTH: 444
<212> TYPE: PRT
<213> ORGANISM: Artificial Sequence
<220> FEATURE:
<223> OTHER INFORMATION: Synthetic sequence hzG2.23D Heavy Chain T28S,
    G55A, T68S, I69L, R71V, A93T, R94S

<400> SEQUENCE: 178

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Gly Tyr
                20                  25                  30
Tyr Met His Trp Val Arg Gln Ala Pro Gly Gln Arg Leu Glu Trp Met
            35                  40                  45
Gly Arg Ile Asn Pro Asn Asn Ala Ala Thr Asn Tyr Asn Gln Asn Phe
50                  55                  60
Lys Asp Arg Val Ser Leu Thr Val Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Ser Val Asn Phe Tyr Tyr Trp Gly Gln Gly Thr Thr Leu Thr Val
                100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
            130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
                180                 185                 190
Gln Thr Tyr Ile Cys Asn Val Asn His Lys Pro Ser Asn Thr Lys Val
            195                 200                 205
```

```
Asp Lys Lys Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 179
<211> LENGTH: 444
<212> TYPE: PRT
<213> ORGANISM: Artificial Sequence
<220> FEATURE:
<223> OTHER INFORMATION: Synthetic sequence hzG2.24D Heavy Chain T28S,
      G55A, A93T, R94S

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
```

```
            115                 120                 125
Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 180
<211> LENGTH: 444
<212> TYPE: PRT
<213> ORGANISM: Artificial Sequence
<220> FEATURE:
<223> OTHER INFORMATION: Synthetic sequence hzG2.25D Heavy Chain N54Q,
      R66K, V67A

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

```
Tyr Met His Trp Val Arg Gln Ala Pro Gly Gln Arg Leu Glu Trp Met
         35                  40                  45
Gly Arg Ile Asn Pro Asn Gln Gly Ala Thr Asn Tyr Asn Gln Asn Phe
 50                  55                  60
Lys Asp Lys Ala Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Val Asn Phe Tyr Tyr Trp Gly Gln Gly Thr Thr Leu Thr Val
                100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
            130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
            195                 200                 205
Asp Lys Lys Val Glu Pro Lys Ser Cys Asp Lys Thr His Thr Cys Pro
            210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
            435                 440
```

<210> SEQ ID NO 181
<211> LENGTH: 444
<212> TYPE: PRT
<213> ORGANISM: Artificial Sequence
<220> FEATURE:
<223> OTHER INFORMATION: Synthetic sequence hzG2.26D Heavy Chain N54Q, R66K, V67A, A93T, R94S

<400> SEQUENCE: 181

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 182
<211> LENGTH: 444
<212> TYPE: PRT
<213> ORGANISM: Artificial Sequence
<220> FEATURE:
<223> OTHER INFORMATION: Synthetic sequence hzG2.27D Heavy Chain N54Q,
      R66K, V67A, T68S, I69L, R71V

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 183
<211> LENGTH: 444
<212> TYPE: PRT
<213> ORGANISM: Artificial Sequence
<220> FEATURE:
<223> OTHER INFORMATION: Synthetic sequence hzG2.28D Heavy Chain N54Q,
    R66K, V67A, T68S, I69L, R71V, A93T, R94S

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Gln Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val

```
            195                 200                 205
Asp Lys Lys Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 184
<211> LENGTH: 444
<212> TYPE: PRT
<213> ORGANISM: Artificial Sequence
<220> FEATURE:
<223> OTHER INFORMATION: Synthetic sequence hzG2.29D Heavy Chain N54Q,
      T68S, I69L, R71V

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110
```

```
Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 185
<211> LENGTH: 444
<212> TYPE: PRT
<213> ORGANISM: Artificial Sequence
<220> FEATURE:
<223> OTHER INFORMATION: Synthetic sequence hzG2.30D Heavy Chain N54Q,
      T68S, I69L, R71V, A93T, R94S

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

```
Tyr Met His Trp Val Arg Gln Ala Pro Gly Gln Arg Leu Glu Trp Met
     35                  40                  45
Gly Arg Ile Asn Pro Asn Gln Gly Ala Thr Asn Tyr Asn Gln Asn Phe
     50                  55                  60
Lys Asp Arg Val Ser Leu Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Thr Ser Val Asn Phe Tyr Tyr Trp Gly Gln Gly Thr Thr Leu Thr Val
                100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
        130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440
```

<210> SEQ ID NO 186
<211> LENGTH: 444
<212> TYPE: PRT
<213> ORGANISM: Artificial Sequence
<220> FEATURE:
<223> OTHER INFORMATION: Synthetic sequence hzG2.31D Heavy Chain N54Q, A93T, R94S

<400> SEQUENCE: 186

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Gln Gly Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440
```

<210> SEQ ID NO 187
<211> LENGTH: 444
<212> TYPE: PRT
<213> ORGANISM: Artificial Sequence
<220> FEATURE:
<223> OTHER INFORMATION: Synthetic sequence hzG2.32D Heavy Chain G55A,
      R66K, V67A

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Ala Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
```

```
                275                 280                 285
Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440
```

<210> SEQ ID NO 188
<211> LENGTH: 444
<212> TYPE: PRT
<213> ORGANISM: Artificial Sequence
<220> FEATURE:
<223> OTHER INFORMATION: Synthetic sequence hzG2.33D Heavy Chain G55A,
      R66K, V67A, A93T, R94S

<400> SEQUENCE: 188

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
                35                  40                  45

Gly Arg Ile Asn Pro Asn Asn Ala Ala Thr Asn Tyr Asn Gln Asn Phe
                50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Leu Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
                130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190
```

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
        260                 265                 270

Asn Trp Tyr Val Asp Gly Val Glu Val His Asn Ala Lys Thr Lys Pro
    275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 189
<211> LENGTH: 444
<212> TYPE: PRT
<213> ORGANISM: Artificial Sequence
<220> FEATURE:
<223> OTHER INFORMATION: Synthetic sequence hzG2.34D Heavy Chain G55A,
      R66K, V67A, T68S, I69L, R71V

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Phe Tyr Tyr Trp Gly Gln Gly Thr Thr Leu Thr Val
            100                 105                 110

```
Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 190
<211> LENGTH: 444
<212> TYPE: PRT
<213> ORGANISM: Artificial Sequence
<220> FEATURE:
<223> OTHER INFORMATION: Synthetic sequence hzG2.35D Heavy Chain G55A,
      R66K, V67A, T68S, I69L, R71V, A93T, R94S

<400> SEQUENCE: 190

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
                    20                  25                  30
Tyr Met His Trp Val Arg Gln Ala Pro Gly Gln Arg Leu Glu Trp Met
             35                  40                  45
Gly Arg Ile Asn Pro Asn Asn Ala Ala Thr Asn Tyr Asn Gln Asn Phe
 50                  55                  60
Lys Asp Lys Ala Ser Leu Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
             85                  90                  95
Thr Ser Val Asn Phe Tyr Tyr Trp Gly Gln Gly Thr Thr Leu Thr Val
            100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
            130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
            165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
            195                 200                 205
Asp Lys Lys Val Glu Pro Lys Ser Cys Asp Lys Thr His Thr Cys Pro
            210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
            325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
            405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
            435                 440
```

<210> SEQ ID NO 191
<211> LENGTH: 444
<212> TYPE: PRT
<213> ORGANISM: Artificial Sequence
<220> FEATURE:
<223> OTHER INFORMATION: Synthetic sequence hzG2.36D Heavy Chain G55A,
      T68S, I69L, R71V

<400> SEQUENCE: 191

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Ala Ala Thr Asn Tyr Asn Gln Asn Phe
    50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Phe Tyr Tyr Trp Gly Gln Gly Thr Thr Leu Thr Val
        100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
        180                 185                 190

Gln Thr Tyr Ile Cys Asn Val Asn His Lys Pro Ser Asn Thr Lys Val
    195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
        260                 265                 270

Asn Trp Tyr Val Asp Gly Val Glu Val His Asn Ala Lys Thr Lys Pro
    275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
```

```
                355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
            435                 440

<210> SEQ ID NO 192
<211> LENGTH: 444
<212> TYPE: PRT
<213> ORGANISM: Artificial Sequence
<220> FEATURE:
<223> OTHER INFORMATION: Synthetic sequence hzG2.37D Heavy Chain G55A,
      T68S, I69L, R71V, A93T, R94S

<400> SEQUENCE: 192

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Arg Leu Glu Trp Met
        35                  40                  45
Gly Arg Ile Asn Pro Asn Asn Ala Ala Thr Asn Tyr Asn Gln Asn Phe
    50                  55                  60
Lys Asp Arg Val Ser Leu Thr Val Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Ser Val Asn Phe Tyr Tyr Trp Gly Gln Gly Thr Thr Leu Thr Val
            100                 105                 110
Ser Ser Ala Ser Thr Lys Gly Pro Ser Val Phe Pro Leu Ala Pro Ser
        115                 120                 125
Ser Lys Ser Thr Ser Gly Gly Thr Ala Ala Leu Gly Cys Leu Val Lys
    130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
```

```
Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 193
<211> LENGTH: 444
<212> TYPE: PRT
<213> ORGANISM: Artificial Sequence
<220> FEATURE:
<223> OTHER INFORMATION: Synthetic sequence hzG2.38D Heavy Chain G55A,
      A93T, R94S

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Ala Ala Thr Asn Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190
```

```
Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
    435                 440

<210> SEQ ID NO 194
<211> LENGTH: 444
<212> TYPE: PRT
<213> ORGANISM: Artificial Sequence
<220> FEATURE:
<223> OTHER INFORMATION: Synthetic sequence hzG2.39D Heavy Chain R66K,
      V67A, V109L

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
```

100                 105                 110
Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 195
<211> LENGTH: 444
<212> TYPE: PRT
<213> ORGANISM: Artificial Sequence
<220> FEATURE:
<223> OTHER INFORMATION: Synthetic sequence hzG2.40D Heavy Chain R66K,
    V67A, A93T, R94S, V109L

<400> SEQUENCE: 195

Gln Val Gln Leu Val Gln Ser Gly Ala Glu Val Lys Lys Pro Gly Ala
1               5                   10                  15

```
                                    -continued

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
50                  55                  60

Lys Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
370                 375                 380

Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
```

435                 440

<210> SEQ ID NO 196
<211> LENGTH: 444
<212> TYPE: PRT
<213> ORGANISM: Artificial Sequence
<220> FEATURE:
<223> OTHER INFORMATION: Synthetic sequence hzG2.41D Heavy Chain R66K,
      V67A, T68S, I69L, R71V, V109L

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 197
<211> LENGTH: 444
<212> TYPE: PRT
<213> ORGANISM: Artificial Sequence
<220> FEATURE:
<223> OTHER INFORMATION: Synthetic sequence hzG2.42D Heavy Chain R66K,
      V67A, T68S, I69L, R71V, A93T, R94S, V109L

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270
```

```
Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440

<210> SEQ ID NO 198
<211> LENGTH: 444
<212> TYPE: PRT
<213> ORGANISM: Artificial Sequence
<220> FEATURE:
<223> OTHER INFORMATION: Synthetic sequence hzG2.43D Heavy Chain T68S,
      I69L, R71V, V109L

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
        50                  55                  60

Lys Asp Arg Val Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Phe Tyr Tyr Trp Gly Gln Gly Thr Leu Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
```

-continued

```
                180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
        245                 250                 255
Thr Cys Val Val Val Asp Val Ser His Glu Asp Pro Glu Val Lys Phe
        260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
        290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
        325                 330                 335
Lys Gly Gln Pro Arg Glu Pro Gln Val Tyr Thr Leu Pro Pro Ser Arg
        340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
        370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
        405                 410                 415
Gly Asn Val Phe Ser Cys Ser Val Met His Glu Ala Leu His Asn His
        420                 425                 430
Tyr Thr Gln Lys Ser Leu Ser Leu Ser Pro Gly Lys
        435                 440

<210> SEQ ID NO 199
<211> LENGTH: 444
<212> TYPE: PRT
<213> ORGANISM: Artificial Sequence
<220> FEATURE:
<223> OTHER INFORMATION: Synthetic sequence hzG2.44D Heavy Chain T68S,
      I69L, R71V, A93T, R94S, V109L

<400> SEQUENCE: 199

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Arg Leu Glu Trp Met
        35                  40                  45
Gly Arg Ile Asn Pro Asn Asn Gly Ala Thr Asn Tyr Asn Gln Asn Phe
    50                  55                  60
Lys Asp Arg Val Ser Leu Thr Val Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
```

```
Thr Ser Val Asn Phe Tyr Tyr Trp Gly Gln Gly Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 200
<211> LENGTH: 444
<212> TYPE: PRT
<213> ORGANISM: Artificial Sequence
<220> FEATURE:
<223> OTHER INFORMATION: Synthetic sequence hzG2.45D Heavy Chain A93T,
      R94S, V109L

<400> SEQUENCE: 200

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

-continued

Tyr Thr Gln Lys Ser Leu Ser Leu Ser Pro Gly Lys
            435                 440

<210> SEQ ID NO 201
<211> LENGTH: 443
<212> TYPE: PRT
<213> ORGANISM: Artificial Sequence
<220> FEATURE:
<223> OTHER INFORMATION: Synthetic sequence hzK2E Heavy Chain

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

```
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440
```

<210> SEQ ID NO 202
<211> LENGTH: 443
<212> TYPE: PRT
<213> ORGANISM: Artificial Sequence
<220> FEATURE:
<223> OTHER INFORMATION: Synthetic sequence hzK2.1E Heavy Chain R66K, V67T

<400> SEQUENCE: 202

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Thr Met His Trp Val Arg Gln Ala Pro Gly Gln Gly Leu Glu Trp Met
        35                  40                  45
Gly Tyr Ile Ser Pro Ser Ser Gly Tyr Thr Glu Tyr Asn Gln Lys Phe
    50                  55                  60
Lys Asp Lys Thr Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Lys Phe Asp Tyr Trp Gly Gln Gly Thr Thr Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
    130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Lys Val Glu Pro Lys Ser Cys Asp Lys Thr His Thr Cys Pro Pro
    210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
```

```
Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 203
<211> LENGTH: 443
<212> TYPE: PRT
<213> ORGANISM: Artificial Sequence
<220> FEATURE:
<223> OTHER INFORMATION: Synthetic sequence hzK2.2E Heavy Chain R66K,
      V67T, M69L, R71A

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Glu Tyr Asn Gln Lys Phe
    50                  55                  60

Lys Asp Lys Thr Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
```

```
                180             185                 190
Thr Tyr Ile Cys Asn Val Asn His Lys Pro Ser Asn Thr Lys Val Asp
            195                 200                 205
Lys Lys Val Glu Pro Lys Ser Cys Asp Lys Thr His Thr Cys Pro Pro
            210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
            275                 280                 285
Glu Glu Gln Tyr Asn Ser Thr Tyr Arg Val Val Ser Val Leu Thr Val
            290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440

<210> SEQ ID NO 204
<211> LENGTH: 443
<212> TYPE: PRT
<213> ORGANISM: Artificial Sequence
<220> FEATURE:
<223> OTHER INFORMATION: Synthetic sequence hzK2.3E Heavy Chain R66K,
      V67T, M69L, R71A, T73K

<400> SEQUENCE: 204

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Thr Met His Trp Val Arg Gln Ala Pro Gly Gln Gly Leu Glu Trp Met
        35                  40                  45
Gly Tyr Ile Ser Pro Ser Ser Gly Tyr Thr Glu Tyr Asn Gln Lys Phe
    50                  55                  60
Lys Asp Lys Thr Thr Leu Thr Ala Asp Lys Ser Thr Ser Thr Val Tyr
65                  70                  75                  80
Met Glu Leu Ser Ser Leu Arg Ser Glu Asp Thr Ala Val Tyr Tyr Cys
                85                  90                  95
```

-continued

Ala Arg Lys Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 205
<211> LENGTH: 443
<212> TYPE: PRT
<213> ORGANISM: Artificial Sequence
<220> FEATURE:
<223> OTHER INFORMATION: Synthetic sequence hzK2.4E Heavy Chain M69L,
      R71A

<400> SEQUENCE: 205

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Ser Pro Ser Ser Gly Tyr Thr Glu Tyr Asn Gln Lys Phe
50                  55                  60

Lys Asp Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 206
<211> LENGTH: 214
<212> TYPE: PRT
<213> ORGANISM: Artificial Sequence
<220> FEATURE:
<223> OTHER INFORMATION: Synthetic sequence chG2D Light Chain

<400> SEQUENCE: 206

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Val Ile Asn Ser Tyr
            20                  25                  30

Leu Ser Trp Phe Gln Gln Lys Pro Gly Lys Ser Pro Glu Thr Leu Ile
        35                  40                  45

Tyr Arg Ala Asn Thr Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Leu Gly Ile Tyr Tyr Cys Leu Gln Tyr Ala Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 207
<211> LENGTH: 214
<212> TYPE: PRT
<213> ORGANISM: Artificial Sequence
<220> FEATURE:
<223> OTHER INFORMATION: Synthetic sequence chK2E Light Chain

<400> SEQUENCE: 207

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Ser Leu Thr Ile Ser Ser Leu Glu Tyr
65                  70                  75                  80

```
Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 208
<211> LENGTH: 215
<212> TYPE: PRT
<213> ORGANISM: Artificial Sequence
<220> FEATURE:
<223> OTHER INFORMATION: Synthetic sequence chL4L Light Chain

<400> SEQUENCE: 208

Asp Ile Gln Met Thr Gln Ser Pro Ala Ser Leu Ser Val Phe Val Gly
1               5                   10                  15

Glu Ile Val Thr Ile Thr Cys Arg Ala Ser Glu Asn Ile Tyr Ser Asn
                20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Thr Gly
    50                  55                  60

Ser Gly Ser Gly Thr Gln Phe Ser Leu Lys Ile Asn Ser Leu Gln Ser
65                  70                  75                  80

Glu Asp Phe Gly Asn Tyr Tyr Cys Gln His Phe Trp Gly Thr Pro Pro
                85                  90                  95

Trp Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215
```

<210> SEQ ID NO 209
<211> LENGTH: 214
<212> TYPE: PRT
<213> ORGANISM: Artificial Sequence
<220> FEATURE:
<223> OTHER INFORMATION: Synthetic sequence chH8K Light Chain

<400> SEQUENCE: 209

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ser Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 210
<211> LENGTH: 214
<212> TYPE: PRT
<213> ORGANISM: Artificial Sequence
<220> FEATURE:
<223> OTHER INFORMATION: Synthetic sequence chJ4F Light Chain

<400> SEQUENCE: 210

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Val Ile
        35                  40                  45

Tyr Ser Ala Ser Tyr Arg Phe Ser Gly Val Pro Asp Arg Leu Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ser Tyr Pro Leu

```
                85                  90                  95
Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 211
<211> LENGTH: 214
<212> TYPE: PRT
<213> ORGANISM: Artificial Sequence
<220> FEATURE:
<223> OTHER INFORMATION: Synthetic sequence hzG2D Light Chain

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 212
<211> LENGTH: 214
<212> TYPE: PRT
<213> ORGANISM: Artificial Sequence
<220> FEATURE:
<223> OTHER INFORMATION: Synthetic sequence hzG2.1D Light Chain D56S

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 213
<211> LENGTH: 214
<212> TYPE: PRT
<213> ORGANISM: Artificial Sequence
<220> FEATURE:
<223> OTHER INFORMATION: Synthetic sequence hzG2.2D Light Chain D56E

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95
```

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 214
<211> LENGTH: 214
<212> TYPE: PRT
<213> ORGANISM: Artificial Sequence
<220> FEATURE:
<223> OTHER INFORMATION: Synthetic sequence hzK2E Light Chain

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
            85                  90                  95

Thr Phe Gly Gln Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 215
<211> LENGTH: 214

```
<212> TYPE: PRT
<213> ORGANISM: Artificial Sequence
<220> FEATURE:
<223> OTHER INFORMATION: Synthetic sequence hzK2.1E Light Chain S46T

<400> SEQUENCE: 215
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Phe Gln Gln Lys Pro Gly Lys Ala Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 216
<211> LENGTH: 214
<212> TYPE: PRT
<213> ORGANISM: Artificial Sequence
<220> FEATURE:
<223> OTHER INFORMATION: Synthetic sequence hzK2.2E Light Chain D56E

<400> SEQUENCE: 216
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Phe Gln Gln Lys Pro Gly Lys Ala Pro Lys Ser Leu Ile
            35                  40                  45

Tyr Arg Ala Asn Arg Leu Val Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 217
<211> LENGTH: 214
<212> TYPE: PRT
<213> ORGANISM: Artificial Sequence
<220> FEATURE:
<223> OTHER INFORMATION: Synthetic sequence hzK2.3E Light Chain S46T
      D56E

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 218
<211> LENGTH: 5
<212> TYPE: PRT
```

-continued

```
<213> ORGANISM: Artificial Sequence
<220> FEATURE:
<223> OTHER INFORMATION: Synthetic sequence ASGR1 mAb-C VH CDR1

<400> SEQUENCE: 218

Ser Tyr Ala Met Ser
1               5

<210> SEQ ID NO 219
<211> LENGTH: 17
<212> TYPE: PRT
<213> ORGANISM: Artificial Sequence
<220> FEATURE:
<223> OTHER INFORMATION: Synthetic sequence ASGR1 mAb-C VH CDR2

<400> SEQUENCE: 219

Ala Ile Ser Gly Ser Gly Gly Ser Thr Tyr Tyr Ala Asp Ser Val Lys
1               5                   10                  15

Gly

<210> SEQ ID NO 220
<211> LENGTH: 11
<212> TYPE: PRT
<213> ORGANISM: Artificial Sequence
<220> FEATURE:
<223> OTHER INFORMATION: Synthetic sequence ASGR1 mAb-C VH CDR3

<400> SEQUENCE: 220

Asp Phe Ser Ser Arg Arg Trp Tyr Leu Glu Tyr
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Synthetic sequence ASGR1 mAb-C VL CDR1

<400> SEQUENCE: 221

Gln Gly Asp Ser Leu Arg Ser Tyr Tyr Ala Ser
1               5                   10

<210> SEQ ID NO 222
<211> LENGTH: 7
<212> TYPE: PRT
<213> ORGANISM: Artificial Sequence
<220> FEATURE:
<223> OTHER INFORMATION: Synthetic sequence ASGR1 mAb-C VL CDR2

<400> SEQUENCE: 222

Gly Lys Asn Asn Arg Pro Ser
1               5

<210> SEQ ID NO 223
<211> LENGTH: 12
<212> TYPE: PRT
<213> ORGANISM: Artificial Sequence
<220> FEATURE:
<223> OTHER INFORMATION: Synthetic sequence ASGR1 mAb-C VL CDR3

<400> SEQUENCE: 223

Asn Ser Leu Glu Arg Ile Gly Tyr Leu Ser Tyr Val
1               5                   10

<210> SEQ ID NO 224
<211> LENGTH: 120
```

<212> TYPE: PRT
<213> ORGANISM: Artificial Sequence
<220> FEATURE:
<223> OTHER INFORMATION: Synthetic sequence ASGR1 mAb-C VH

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Arg Arg Trp Tyr Leu Glu Tyr Trp Gly Gln
            100                 105                 110

Gly Thr Leu Val Thr Val Ser Ser
        115                 120

<210> SEQ ID NO 225
<211> LENGTH: 109
<212> TYPE: PRT
<213> ORGANISM: Artificial Sequence
<220> FEATURE:
<223> OTHER INFORMATION: Synthetic sequence ASGR1 mAb-C VL

<400> SEQUENCE: 225

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu
            100                 105

<210> SEQ ID NO 226
<211> LENGTH: 120
<212> TYPE: PRT
<213> ORGANISM: Artificial Sequence
<220> FEATURE:
<223> OTHER INFORMATION: Synthetic sequence mzASGR1 mAb-C VH

<400> SEQUENCE: 226

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val

```
                35                  40                  45
Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Lys Asp Phe Ser Ser Arg Arg Trp Tyr Leu Glu Tyr Trp Gly Gln
             100                 105                 110

Gly Thr Thr Leu Thr Val Ser Ser
             115                 120

<210> SEQ ID NO 227
<211> LENGTH: 109
<212> TYPE: PRT
<213> ORGANISM: Artificial Sequence
<220> FEATURE:
<223> OTHER INFORMATION: Synthetic sequence mzASGR1 mAb-C VL

<400> SEQUENCE: 227

Gln Ala Val Leu Thr Gln Glu Pro Ala Leu Ser Val Ser Leu Gly Gln
 1               5                  10                  15

Thr Val Thr Leu Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Val Pro Ala Arg Phe Ser Gly Ser
         50                  55                  60

Leu Ile Gly Asp Lys Ala Ala Leu Thr Ile Thr Gly Ala Gln Thr Glu
 65                  70                  75                  80

Asp Glu Ala Ile Tyr Tyr Cys Asn Ser Leu Glu Arg Ile Gly Tyr Leu
                 85                  90                  95

Ser Tyr Val Phe Gly Gly Gly Thr Lys Val Thr Val Leu
             100                 105

<210> SEQ ID NO 228
<211> LENGTH: 450
<212> TYPE: PRT
<213> ORGANISM: Artificial Sequence
<220> FEATURE:
<223> OTHER INFORMATION: Synthetic sequence mzASGR1 mAb-C Heavy Chain
      (VH-IgG2a)

<400> SEQUENCE: 228

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Ala Met Ser Trp Val Arg Gln Thr Pro Glu Lys Arg Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Lys Asp Phe Ser Ser Arg Arg Trp Tyr Leu Glu Tyr Trp Gly Gln
             100                 105                 110
```

```
Gly Thr Thr Leu Thr Val Ser Ser Ala Lys Thr Thr Ala Pro Ser Val
            115                 120                 125

Tyr Pro Leu Ala Pro Val Cys Gly Asp Thr Thr Gly Ser Ser Val Thr
            130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
            195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
            290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
    450

<210> SEQ ID NO 229
<211> LENGTH: 216
<212> TYPE: PRT
<213> ORGANISM: Artificial Sequence
<220> FEATURE:
<223> OTHER INFORMATION: Synthetic sequence mzASGR1 mAb-C Light Chain
      (VL-kappa)

<400> SEQUENCE: 229

Gln Ala Val Leu Thr Gln Glu Pro Ala Leu Ser Val Ser Leu Gly Gln
```

```
            1               5                  10                 15
         Thr Val Thr Leu Thr Cys Gln Gly Asp Ser Leu Arg Ser Tyr Tyr Ala
                         20                  25                 30

Ser Trp Tyr Gln Gln Lys Pro Gly Gln Ala Pro Val Leu Val Ile Tyr
                         35                  40                 45

Gly Lys Asn Asn Arg Pro Ser Gly Val Pro Ala Arg Phe Ser Gly Ser
                     50                  55                  60

Leu Ile Gly Asp Lys Ala Ala Leu Thr Ile Thr Gly Ala Gln Thr Glu
         65                  70                  75                  80

Asp Glu Ala Ile Tyr Tyr Cys Asn Ser Leu Glu Arg Ile Gly Tyr Leu
                             85                  90                  95

Ser Tyr Val Phe Gly Gly Gly Thr Lys Val Thr Val Leu Arg Ala Asp
                         100                 105                110

Ala Ala Pro Thr Val Ser Ile Phe Pro Pro Ser Ser Glu Gln Leu Thr
                         115                 120                 125

Ser Gly Gly Ala Ser Val Val Cys Phe Leu Asn Asn Phe Tyr Pro Lys
                     130                 135                 140

Asp Ile Asn Val Lys Trp Lys Ile Asp Gly Ser Glu Arg Gln Asn Gly
         145                 150                 155                 160

Val Leu Asn Ser Trp Thr Asp Gln Asp Ser Lys Asp Ser Thr Tyr Ser
                             165                 170                 175

Met Ser Ser Thr Leu Thr Leu Thr Lys Asp Glu Tyr Glu Arg His Asn
                         180                 185                 190

Ser Tyr Thr Cys Glu Ala Thr His Lys Thr Ser Thr Ser Pro Ile Val
                         195                 200                 205

Lys Ser Phe Asn Arg Asn Glu Cys
                     210                 215

<210> SEQ ID NO 230
<211> LENGTH: 330
<212> TYPE: PRT
<213> ORGANISM: Artificial Sequence
<220> FEATURE:
<223> OTHER INFORMATION: Synthetic sequence Human IgG1 Heavy Chain
      Constant Region

<400> SEQUENCE: 230

Ala Ser Thr Lys Gly Pro Ser Val Phe Pro Leu Ala Pro Ser Ser Lys
         1               5                   10                  15

Ser Thr Ser Gly Gly Thr Ala Ala Leu Gly Cys Leu Val Lys Asp Tyr
                         20                  25                  30

Phe Pro Glu Pro Val Thr Val Ser Trp Asn Ser Gly Ala Leu Thr Ser
                         35                  40                  45

Gly Val His Thr Phe Pro Ala Val Leu Gln Ser Ser Gly Leu Tyr Ser
                     50                  55                  60

Leu Ser Ser Val Val Thr Val Pro Ser Ser Ser Leu Gly Thr Gln Thr
         65                  70                  75                  80

Tyr Ile Cys Asn Val Asn His Lys Pro Ser Asn Thr Lys Val Asp Lys
                             85                  90                  95

Lys Val Glu Pro Lys Ser Cys Asp Lys Thr His Thr Cys Pro Pro Cys
                         100                 105                 110

Pro Ala Pro Glu Leu Leu Gly Gly Pro Ser Val Phe Leu Phe Pro Pro
                     115                 120                 125

Lys Pro Lys Asp Thr Leu Met Ile Ser Arg Thr Pro Glu Val Thr Cys
                     130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 231
<211> LENGTH: 330
<212> TYPE: PRT
<213> ORGANISM: Artificial Sequence
<220> FEATURE:
<223> OTHER INFORMATION: Synthetic sequence Human IgG1null Heavy Chain
      Constant Region

<400> SEQUENCE: 231

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Ala Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 232
<211> LENGTH: 107
<212> TYPE: PRT
<213> ORGANISM: Artificial Sequence
<220> FEATURE:
<223> OTHER INFORMATION: Synthetic sequence Human Kappa Light Chain
      Constant Region

<400> SEQUENCE: 232

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 233
<211> LENGTH: 330
<212> TYPE: PRT
<213> ORGANISM: Artificial Sequence
<220> FEATURE:
<223> OTHER INFORMATION: Synthetic sequence Mouse IgG2a Heavy Chain
      Constant Region

<400> SEQUENCE: 233

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30
```

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
            130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
            210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 234
<211> LENGTH: 107
<212> TYPE: PRT
<213> ORGANISM: Artificial Sequence
<220> FEATURE:
<223> OTHER INFORMATION: Synthetic sequence Mouse Kappa Light Chain
      Constant Region

<400> SEQUENCE: 234

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser

```
                50              55              60
Thr Tyr Ser Met Ser Ser Thr Leu Thr Leu Thr Lys Asp Glu Tyr Glu
 65                      70                  75                  80

Arg His Asn Ser Tyr Thr Cys Glu Ala Thr His Lys Thr Ser Thr Ser
                     85                  90                  95

Pro Ile Val Lys Ser Phe Asn Arg Asn Glu Cys
            100                 105

<210> SEQ ID NO 235
<211> LENGTH: 331
<212> TYPE: PRT
<213> ORGANISM: Artificial Sequence
<220> FEATURE:
<223> OTHER INFORMATION: Synthetic sequence Rat IgG2b Heavy Chain
      Constant Region

<400> SEQUENCE: 235

Ala Gln Thr Thr Ala Pro Ser Val Tyr Pro Leu Ala Pro Gly Cys Gly
  1               5                  10                  15

Asp Thr Thr Ser Ser Thr Val Thr Leu Gly Cys Leu Val Lys Gly Tyr
                 20                  25                  30

Phe Pro Glu Pro Val Thr Val Thr Trp Asn Ser Gly Ala Leu Ser Ser
             35                  40                  45

Asp Val His Thr Phe Pro Ala Val Leu Gln Ser Gly Leu Tyr Thr Leu
         50                  55                  60

Thr Ser Ser Val Thr Ser Ser Thr Trp Pro Ser Gln Thr Val Thr Cys
 65                  70                  75                  80

Asn Val Ala His Pro Ala Ser Ser Thr Lys Val Asp Lys Lys Val Glu
                 85                  90                  95

Arg Arg Asn Gly Gly Ile Gly His Lys Cys Pro Thr Cys Pro Thr Cys
            100                 105                 110

His Lys Cys Pro Val Pro Glu Leu Leu Gly Gly Pro Ser Val Phe Ile
        115                 120                 125

Phe Pro Pro Lys Pro Lys Asp Ile Leu Leu Ile Ser Gln Asn Ala Lys
130                 135                 140

Val Thr Cys Val Val Val Asp Val Ser Glu Glu Glu Pro Asp Val Gln
145                 150                 155                 160

Phe Ser Trp Phe Val Asn Asn Val Glu Val His Thr Ala Gln Thr Gln
                165                 170                 175

Pro Arg Glu Glu Gln Tyr Asn Ser Thr Phe Arg Val Val Ser Ala Leu
            180                 185                 190

Pro Ile Gln His Gln Asp Trp Met Ser Gly Lys Glu Phe Lys Cys Lys
        195                 200                 205

Val Asn Asn Lys Ala Leu Pro Ser Pro Ile Glu Lys Thr Ile Ser Lys
210                 215                 220

Pro Lys Gly Leu Val Arg Lys Pro Gln Val Tyr Val Met Gly Pro Pro
225                 230                 235                 240

Thr Glu Gln Leu Thr Glu Gln Thr Val Ser Leu Thr Cys Leu Thr Ser
                245                 250                 255

Gly Phe Leu Pro Asn Asp Ile Gly Val Glu Trp Thr Ser Asn Gly His
            260                 265                 270

Ile Glu Lys Asn Tyr Lys Asn Thr Glu Pro Val Met Asp Ser Asp Gly
        275                 280                 285

Ser Phe Phe Met Tyr Ser Lys Leu Asn Val Glu Arg Ser Arg Trp Asp
290                 295                 300
```

```
Ser Arg Ala Pro Phe Val Cys Ser Val Val His Glu Gly Leu His Asn
305                 310                 315                 320

His His Val Glu Lys Ser Ile Ser Arg Pro Pro
                325                 330
```

<210> SEQ ID NO 236
<211> LENGTH: 107
<212> TYPE: PRT
<213> ORGANISM: Artificial Sequence
<220> FEATURE:
<223> OTHER INFORMATION: Synthetic sequence Rat kappa Light Chain
      Constant Region

<400> SEQUENCE: 236

```
Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 237
<211> LENGTH: 5
<212> TYPE: PRT
<213> ORGANISM: Artificial Sequence
<220> FEATURE:
<223> OTHER INFORMATION: Synthetic sequence LPXTG recognition motif
<220> FEATURE:
<221> NAME/KEY: VARIANT
<222> LOCATION: (1)..(5)
<223> OTHER INFORMATION: Xaa = Any Amino Acid

<400> SEQUENCE: 237

```
Leu Pro Xaa Thr Gly
1               5
```

<210> SEQ ID NO 238
<211> LENGTH: 114
<212> TYPE: PRT
<213> ORGANISM: Artificial Sequence
<220> FEATURE:
<223> OTHER INFORMATION: Synthetic sequence hzG2.46D VH R66K, V67A,
      T68S, I69L, R71V

<400> SEQUENCE: 238

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Val Asn Phe Tyr Tyr Trp Gly Gln Gly Thr Thr Val Thr Val
                100                 105                 110

Ser Ser

<210> SEQ ID NO 239
<211> LENGTH: 114
<212> TYPE: PRT
<213> ORGANISM: Artificial Sequence
<220> FEATURE:
<223> OTHER INFORMATION: Synthetic sequence hzG2.47D VH R66K, V67A,
      T68S, I69L, R71V, A93T, R94S

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Thr Ser Val Asn Phe Tyr Tyr Trp Gly Gln Gly Thr Thr Val Thr Val
                100                 105                 110

Ser Ser

<210> SEQ ID NO 240
<211> LENGTH: 114
<212> TYPE: PRT
<213> ORGANISM: Artificial Sequence
<220> FEATURE:
<223> OTHER INFORMATION: Synthetic sequence hzG2.48D VH G55A, R66K,
      V67A, T68S, I69L, R71V, A93T, R94S

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Ala Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Thr Ser Val Asn Phe Tyr Tyr Trp Gly Gln Gly Thr Thr Val Thr Val
                100                 105                 110

Ser Ser
```

-continued

```
<210> SEQ ID NO 241
<211> LENGTH: 114
<212> TYPE: PRT
<213> ORGANISM: Artificial Sequence
<220> FEATURE:
<223> OTHER INFORMATION: Synthetic sequence hzG2.49D VH R38K, R66K,
      V67A, T68S, I69L, R71V, A93T, R94S

<400> SEQUENCE: 241
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Lys Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Val Asn Phe Tyr Tyr Trp Gly Gln Gly Thr Thr Val Thr Val
            100                 105                 110

Ser Ser

```
<210> SEQ ID NO 242
<211> LENGTH: 114
<212> TYPE: PRT
<213> ORGANISM: Artificial Sequence
<220> FEATURE:
<223> OTHER INFORMATION: Synthetic sequence hzG2.50D VH R66K, V67A,
      T68S, I69L, R71V, L82F, S82aH, A93T, R94S

<400> SEQUENCE: 242
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Arg Ile Asn Pro Asn Asn Gly Ala Thr Asn Tyr Asn Gln Asn Phe
    50                  55                  60

Lys Asp Lys Ala Ser Leu Thr Val Asp Thr Ser Ala Ser Thr Ala Tyr
65                  70                  75                  80

Met Glu Phe His Ser Leu Arg Ser Glu Asp Thr Ala Val Tyr Tyr Cys
                85                  90                  95

Thr Ser Val Asn Phe Tyr Tyr Trp Gly Gln Gly Thr Thr Val Thr Val
            100                 105                 110

Ser Ser

```
<210> SEQ ID NO 243
<211> LENGTH: 114
<212> TYPE: PRT
<213> ORGANISM: Artificial Sequence
<220> FEATURE:
<223> OTHER INFORMATION: Synthetic sequence hzG2.51D VH R66K, V67A,
      T68S, I69L, R71V, R84T, A93T, R94S

<400> SEQUENCE: 243
```

Gln Val Gln Leu Val Gln Ser Gly Ala Glu Val Lys Lys Pro Gly Ala

```
                1               5                   10                  15
Ser Val Lys Val Ser Cys Lys Ala Ser Gly Tyr Thr Phe Thr Gly Tyr
                20                  25                  30

Tyr Met His Trp Val Arg Gln Ala Pro Gly Gln Arg Leu Glu Trp Met
            35                  40                  45

Gly Arg Ile Asn Pro Asn Asn Gly Ala Thr Asn Tyr Asn Gln Asn Phe
        50                  55                  60

Lys Asp Lys Ala Ser Leu Thr Val Asp Thr Ser Ala Ser Thr Ala Tyr
65                  70                  75                  80

Met Glu Leu Ser Ser Leu Thr Ser Glu Asp Thr Ala Val Tyr Tyr Cys
                85                  90                  95

Thr Ser Val Asn Phe Tyr Tyr Trp Gly Gln Gly Thr Thr Val Thr Val
                100                 105                 110

Ser Ser

<210> SEQ ID NO 244
<211> LENGTH: 107
<212> TYPE: PRT
<213> ORGANISM: Artificial Sequence
<220> FEATURE:
<223> OTHER INFORMATION: Synthetic sequence hzG2.3D VLa K45E, S46T

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
                20                  25                  30

Leu Ser Trp Phe Gln Gln Lys Pro Gly Lys Ala Pro Glu Thr Leu Ile
            35                  40                  45

Tyr Arg Ala Asn Thr Leu Val Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
                100                 105

<210> SEQ ID NO 245
<211> LENGTH: 107
<212> TYPE: PRT
<213> ORGANISM: Artificial Sequence
<220> FEATURE:
<223> OTHER INFORMATION: Synthetic sequence hzG2.4D VLa Q79E, P80Y

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
                20                  25                  30

Leu Ser Trp Phe Gln Gln Lys Pro Gly Lys Ala Pro Lys Ser Leu Ile
            35                  40                  45

Tyr Arg Ala Asn Thr Leu Val Asp Gly Val Pro Ser Arg Phe Ser Gly
        50                  55                  60

Ser Gly Ser Gly Thr Asp Phe Thr Leu Thr Ile Ser Ser Leu Glu Tyr
65                  70                  75                  80

Glu Asp Phe Ala Thr Tyr Tyr Cys Leu Gln Tyr Ala Glu Phe Pro Tyr
```

```
                85                  90                  95
Thr Phe Gly Gly Gly Thr Lys Val Glu Ile Lys
            100                 105

<210> SEQ ID NO 246
<211> LENGTH: 107
<212> TYPE: PRT
<213> ORGANISM: Artificial Sequence
<220> FEATURE:
<223> OTHER INFORMATION: Synthetic sequence hzG2.5D VLa F71Y, T72S

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Thr Leu Val Asp Gly Val Pro Ser Arg Phe Ser Gly
    50                  55                  60

Ser Gly Ser Gly Thr Asp Tyr Ser Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
            100                 105

<210> SEQ ID NO 247
<211> LENGTH: 107
<212> TYPE: PRT
<213> ORGANISM: Artificial Sequence
<220> FEATURE:
<223> OTHER INFORMATION: Synthetic sequence hzG2D VLb

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Thr Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                85                  90                  95

Thr Phe Gly Gly Gly Thr Lys Val Glu Ile Lys
            100                 105

<210> SEQ ID NO 248
<211> LENGTH: 107
<212> TYPE: PRT
<213> ORGANISM: Artificial Sequence
<220> FEATURE:
<223> OTHER INFORMATION: Synthetic sequence hzG2.6D VLb D56S

<400> SEQUENCE: 248

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Val Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Thr Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Glu Phe Pro Tyr
                    85                  90                  95

Thr Phe Gly Gly Gly Thr Lys Val Glu Ile Lys
            100                 105
```

```
<210> SEQ ID NO 249
<211> LENGTH: 107
<212> TYPE: PRT
<213> ORGANISM: Artificial Sequence
<220> FEATURE:
<223> OTHER INFORMATION: Synthetic sequence hzG2D VLc

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Val Ile Asn Ser Tyr
            20                  25                  30

Leu Ser Trp Tyr Gln Gln Lys Pro Gly Lys Val Pro Lys Leu Leu Ile
        35                  40                  45

Tyr Arg Ala Asn Thr Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Ala Glu Phe Pro Tyr
                    85                  90                  95

Thr Phe Gly Gly Gly Thr Lys Val Glu Ile Lys
            100                 105
```

```
<210> SEQ ID NO 250
<211> LENGTH: 4
<212> TYPE: PRT
<213> ORGANISM: Artificial Sequence
<220> FEATURE:
<223> OTHER INFORMATION: Synthetic sequence cleavable peptide linker

<400> SEQUENCE: 250

Gly Phe Leu Gly
1
```

```
<210> SEQ ID NO 251
<211> LENGTH: 4
<212> TYPE: PRT
<213> ORGANISM: Artificial Sequence
<220> FEATURE:
<223> OTHER INFORMATION: Synthetic sequence cleavable peptide linker

<400> SEQUENCE: 251

Ala Leu Ala Leu
1
```

```
<210> SEQ ID NO 252
<211> LENGTH: 7
```

```
<212> TYPE: PRT
<213> ORGANISM: Artificial Sequence
<220> FEATURE:
<223> OTHER INFORMATION: hzG2D Anti-ASGR1 - VH CDR1

<400> SEQUENCE: 252

Gly Tyr Ser Phe Thr Gly Tyr
1               5

<210> SEQ ID NO 253
<211> LENGTH: 10
<212> TYPE: PRT
<213> ORGANISM: Artificial Sequence
<220> FEATURE:
<223> OTHER INFORMATION: hzG2D Anti-ASGR1 - VH CDR1

<400> SEQUENCE: 253

Gly Tyr Ser Phe Thr Gly Tyr Tyr Met His
1               5                   10

<210> SEQ ID NO 254
<211> LENGTH: 6
<212> TYPE: PRT
<213> ORGANISM: Artificial Sequence
<220> FEATURE:
<223> OTHER INFORMATION: hzG2D Anti-ASGR1 - VH CDR1

<400> SEQUENCE: 254

Thr Gly Tyr Tyr Met His
1               5

<210> SEQ ID NO 255
<211> LENGTH: 8
<212> TYPE: PRT
<213> ORGANISM: Artificial Sequence
<220> FEATURE:
<223> OTHER INFORMATION: hzG2D Anti-ASGR1 - VH CDR1

<400> SEQUENCE: 255

Gly Tyr Ser Phe Thr Gly Tyr Tyr
1               5

<210> SEQ ID NO 256
<211> LENGTH: 6
<212> TYPE: PRT
<213> ORGANISM: Artificial Sequence
<220> FEATURE:
<223> OTHER INFORMATION: hzG2D Anti-ASGR1 - VH CDR2

<400> SEQUENCE: 256

Asn Pro Asn Asn Ala Ala
1               5

<210> SEQ ID NO 257
<211> LENGTH: 10
<212> TYPE: PRT
<213> ORGANISM: Artificial Sequence
<220> FEATURE:
<223> OTHER INFORMATION: hzG2D Anti-ASGR1 - VH CDR2

<400> SEQUENCE: 257

Arg Ile Asn Pro Asn Asn Ala Ala Thr Asn
1               5                   10

<210> SEQ ID NO 258
<211> LENGTH: 13
<212> TYPE: PRT
```

```
<213> ORGANISM: Artificial Sequence
<220> FEATURE:
<223> OTHER INFORMATION: hzG2D Anti-ASGR1 - VH CDR2

<400> SEQUENCE: 258

Trp Met Gly Arg Ile Asn Pro Asn Asn Ala Ala Thr Asn
1               5                   10

<210> SEQ ID NO 259
<211> LENGTH: 8
<212> TYPE: PRT
<213> ORGANISM: Artificial Sequence
<220> FEATURE:
<223> OTHER INFORMATION: hzG2D Anti-ASGR1 - VH CDR2

<400> SEQUENCE: 259

Ile Asn Pro Asn Asn Ala Ala Thr
1               5

<210> SEQ ID NO 260
<211> LENGTH: 6
<212> TYPE: PRT
<213> ORGANISM: Artificial Sequence
<220> FEATURE:
<223> OTHER INFORMATION: hzG2D Anti-ASGR1 - VH CDR3

<400> SEQUENCE: 260

Thr Ser Val Asn Phe Tyr
1               5

<210> SEQ ID NO 261
<211> LENGTH: 7
<212> TYPE: PRT
<213> ORGANISM: Artificial Sequence
<220> FEATURE:
<223> OTHER INFORMATION: hzG2D Anti-ASGR1 - VH CDR3

<400> SEQUENCE: 261

Thr Ser Val Asn Phe Tyr Tyr
1               5

<210> SEQ ID NO 262
<211> LENGTH: 7
<212> TYPE: PRT
<213> ORGANISM: Artificial Sequence
<220> FEATURE:
<223> OTHER INFORMATION: hzG2D Anti-ASGR1 - VL CDR1

<400> SEQUENCE: 262

Asn Ser Tyr Leu Ser Trp Phe
1               5

<210> SEQ ID NO 263
<211> LENGTH: 6
<212> TYPE: PRT
<213> ORGANISM: Artificial Sequence
<220> FEATURE:
<223> OTHER INFORMATION: hzG2D Anti-ASGR1 - VL CDR1

<400> SEQUENCE: 263

Gln Val Ile Asn Ser Tyr
1               5

<210> SEQ ID NO 264
<211> LENGTH: 10
<212> TYPE: PRT
<213> ORGANISM: Artificial Sequence
```

```
<220> FEATURE:
<223> OTHER INFORMATION: hzG2D Anti-ASGR1 - VL CDR2

<400> SEQUENCE: 264

Ser Leu Ile Tyr Arg Ala Asn Thr Leu Val
1               5                   10

<210> SEQ ID NO 265
<211> LENGTH: 8
<212> TYPE: PRT
<213> ORGANISM: Artificial Sequence
<220> FEATURE:
<223> OTHER INFORMATION: hzG2D Anti-ASGR1 - VL CDR3

<400> SEQUENCE: 265

Leu Gln Tyr Ala Glu Phe Pro Tyr
1               5

<210> SEQ ID NO 266
<211> LENGTH: 7
<212> TYPE: PRT
<213> ORGANISM: Artificial Sequence
<220> FEATURE:
<223> OTHER INFORMATION: hzK2E Anti-ASGR1 - VH CDR1

<400> SEQUENCE: 266

Gly Tyr Thr Phe Thr Ser Tyr
1               5

<210> SEQ ID NO 267
<211> LENGTH: 10
<212> TYPE: PRT
<213> ORGANISM: Artificial Sequence
<220> FEATURE:
<223> OTHER INFORMATION: hzK2E Anti-ASGR1 - VH CDR1

<400> SEQUENCE: 267

Gly Tyr Thr Phe Thr Ser Tyr Thr Met His
1               5                   10

<210> SEQ ID NO 268
<211> LENGTH: 6
<212> TYPE: PRT
<213> ORGANISM: Artificial Sequence
<220> FEATURE:
<223> OTHER INFORMATION: hzK2E Anti-ASGR1 - VH CDR1

<400> SEQUENCE: 268

Thr Ser Tyr Thr Met His
1               5

<210> SEQ ID NO 269
<211> LENGTH: 8
<212> TYPE: PRT
<213> ORGANISM: Artificial Sequence
<220> FEATURE:
<223> OTHER INFORMATION: hzK2E Anti-ASGR1 - VH CDR1

<400> SEQUENCE: 269

Gly Tyr Thr Phe Thr Ser Tyr Thr
1               5

<210> SEQ ID NO 270
<211> LENGTH: 6
<212> TYPE: PRT
<213> ORGANISM: Artificial Sequence
<220> FEATURE:
```

<223> OTHER INFORMATION: hzK2E Anti-ASGR1 - VH CDR2

<400> SEQUENCE: 270

Ser Pro Ser Ser Gly Tyr
1               5

<210> SEQ ID NO 271
<211> LENGTH: 10
<212> TYPE: PRT
<213> ORGANISM: Artificial Sequence
<220> FEATURE:
<223> OTHER INFORMATION: hzK2E Anti-ASGR1 - VH CDR2

<400> SEQUENCE: 271

Tyr Ile Ser Pro Ser Ser Gly Tyr Thr Glu
1               5                  10

<210> SEQ ID NO 272
<211> LENGTH: 13
<212> TYPE: PRT
<213> ORGANISM: Artificial Sequence
<220> FEATURE:
<223> OTHER INFORMATION: hzK2E Anti-ASGR1 - VH CDR2

<400> SEQUENCE: 272

Trp Met Gly Tyr Ile Ser Pro Ser Ser Gly Tyr Thr Glu
1               5                  10

<210> SEQ ID NO 273
<211> LENGTH: 8
<212> TYPE: PRT
<213> ORGANISM: Artificial Sequence
<220> FEATURE:
<223> OTHER INFORMATION: hzK2E Anti-ASGR1 - VH CDR2

<400> SEQUENCE: 273

Ile Ser Pro Ser Ser Gly Tyr Thr
1               5

<210> SEQ ID NO 274
<211> LENGTH: 5
<212> TYPE: PRT
<213> ORGANISM: Artificial Sequence
<220> FEATURE:
<223> OTHER INFORMATION: hzK2E Anti-ASGR1 - VH CDR3

<400> SEQUENCE: 274

Ala Arg Lys Phe Asp
1               5

<210> SEQ ID NO 275
<211> LENGTH: 6
<212> TYPE: PRT
<213> ORGANISM: Artificial Sequence
<220> FEATURE:
<223> OTHER INFORMATION: hzK2E Anti-ASGR1 - VH CDR3

<400> SEQUENCE: 275

Ala Arg Lys Phe Asp Tyr
1               5

<210> SEQ ID NO 276
<211> LENGTH: 6
<212> TYPE: PRT
<213> ORGANISM: Artificial Sequence
<220> FEATURE:
<223> OTHER INFORMATION: hzK2E Anti-ASGR1 - VL CDR1

```
<400> SEQUENCE: 276

Gln Asp Ile Asn Ser Tyr
1               5

<210> SEQ ID NO 277
<211> LENGTH: 10
<212> TYPE: PRT
<213> ORGANISM: Artificial Sequence
<220> FEATURE:
<223> OTHER INFORMATION: hzK2E Anti-ASGR1 - VL CDR2

<400> SEQUENCE: 277

Ser Leu Ile Tyr Arg Ala Asn Arg Leu Val
1               5                   10

<210> SEQ ID NO 278
<211> LENGTH: 13
<212> TYPE: PRT
<213> ORGANISM: Artificial Sequence
<220> FEATURE:
<223> OTHER INFORMATION: hzK2E Anti-ASGR1 - VL CDR3

<400> SEQUENCE: 278

Phe Gly Gln Gly Thr Lys Leu Glu Ile Lys Arg Thr Val
1               5                   10

<210> SEQ ID NO 279
<211> LENGTH: 8
<212> TYPE: PRT
<213> ORGANISM: Artificial Sequence
<220> FEATURE:
<223> OTHER INFORMATION: hzK2E Anti-ASGR1 - VL CDR3

<400> SEQUENCE: 279

Leu Gln Tyr Asp Glu Phe Pro Phe
1               5

<210> SEQ ID NO 280
<211> LENGTH: 8
<212> TYPE: PRT
<213> ORGANISM: Artificial Sequence
<220> FEATURE:
<223> OTHER INFORMATION: hzL4L Anti-ASGR1 - VH CDR1

<400> SEQUENCE: 280

Gly Gly Ser Ile Ser Ser Asp Tyr
1               5

<210> SEQ ID NO 281
<211> LENGTH: 11
<212> TYPE: PRT
<213> ORGANISM: Artificial Sequence
<220> FEATURE:
<223> OTHER INFORMATION: hzL4L Anti-ASGR1 - VH CDR1

<400> SEQUENCE: 281

Gly Gly Ser Ile Ser Ser Asp Tyr Ala Trp Asn
1               5                   10

<210> SEQ ID NO 282
<211> LENGTH: 7
<212> TYPE: PRT
<213> ORGANISM: Artificial Sequence
<220> FEATURE:
<223> OTHER INFORMATION: hzL4L Anti-ASGR1 - VH CDR1
```

<400> SEQUENCE: 282

Ser Ser Asp Tyr Ala Trp Asn
1               5

<210> SEQ ID NO 283
<211> LENGTH: 9
<212> TYPE: PRT
<213> ORGANISM: Artificial Sequence
<220> FEATURE:
<223> OTHER INFORMATION: hzL4L Anti-ASGR1 - VH CDR1

<400> SEQUENCE: 283

Gly Gly Ser Ile Ser Ser Asp Tyr Ala
1               5

<210> SEQ ID NO 284
<211> LENGTH: 5
<212> TYPE: PRT
<213> ORGANISM: Artificial Sequence
<220> FEATURE:
<223> OTHER INFORMATION: hzL4L Anti-ASGR1 - VH CDR2

<400> SEQUENCE: 284

Ser Tyr Ser Gly Ser
1               5

<210> SEQ ID NO 285
<211> LENGTH: 9
<212> TYPE: PRT
<213> ORGANISM: Artificial Sequence
<220> FEATURE:
<223> OTHER INFORMATION: hzL4L Anti-ASGR1 - VH CDR2

<400> SEQUENCE: 285

Tyr Ile Ser Tyr Ser Gly Ser Thr Arg
1               5

<210> SEQ ID NO 286
<211> LENGTH: 12
<212> TYPE: PRT
<213> ORGANISM: Artificial Sequence
<220> FEATURE:
<223> OTHER INFORMATION: hzL4L Anti-ASGR1 - VH CDR2

<400> SEQUENCE: 286

Trp Ile Gly Tyr Ile Ser Tyr Ser Gly Ser Thr Arg
1               5                   10

<210> SEQ ID NO 287
<211> LENGTH: 7
<212> TYPE: PRT
<213> ORGANISM: Artificial Sequence
<220> FEATURE:
<223> OTHER INFORMATION: hzL4L Anti-ASGR1 - VH CDR2

<400> SEQUENCE: 287

Ile Ser Tyr Ser Gly Ser Thr
1               5

<210> SEQ ID NO 288
<211> LENGTH: 13
<212> TYPE: PRT
<213> ORGANISM: Artificial Sequence
<220> FEATURE:
<223> OTHER INFORMATION: hzL4L Anti-ASGR1 - VH CDR3

<400> SEQUENCE: 288

```
Ala Arg Arg Tyr Arg Tyr Asp Glu Gly Tyr Gly Met Asp
1               5                   10
```

<210> SEQ ID NO 289
<211> LENGTH: 14
<212> TYPE: PRT
<213> ORGANISM: Artificial Sequence
<220> FEATURE:
<223> OTHER INFORMATION: hzL4L Anti-ASGR1 - VH CDR3

<400> SEQUENCE: 289

```
Ala Arg Arg Tyr Arg Tyr Asp Glu Gly Tyr Gly Met Asp Tyr
1               5                   10
```

<210> SEQ ID NO 290
<211> LENGTH: 7
<212> TYPE: PRT
<213> ORGANISM: Artificial Sequence
<220> FEATURE:
<223> OTHER INFORMATION: hzL4L Anti-ASGR1 - VL CDR1

<400> SEQUENCE: 290

```
Tyr Ser Asn Leu Ala Trp Tyr
1               5
```

<210> SEQ ID NO 291
<211> LENGTH: 6
<212> TYPE: PRT
<213> ORGANISM: Artificial Sequence
<220> FEATURE:
<223> OTHER INFORMATION: hzL4L Anti-ASGR1 - VL CDR1

<400> SEQUENCE: 291

```
Glu Asn Ile Tyr Ser Asn
1               5
```

<210> SEQ ID NO 292
<211> LENGTH: 10
<212> TYPE: PRT
<213> ORGANISM: Artificial Sequence
<220> FEATURE:
<223> OTHER INFORMATION: hzL4L Anti-ASGR1 - VL CDR2

<400> SEQUENCE: 292

```
Leu Leu Ile Tyr Ala Ala Thr Asn Leu Ala
1               5                   10
```

<210> SEQ ID NO 293
<211> LENGTH: 9
<212> TYPE: PRT
<213> ORGANISM: Artificial Sequence
<220> FEATURE:
<223> OTHER INFORMATION: hzL4L Anti-ASGR1 - VL CDR3

<400> SEQUENCE: 293

```
Gln His Phe Trp Gly Thr Pro Pro Trp
1               5
```

<210> SEQ ID NO 294
<211> LENGTH: 10
<212> TYPE: PRT
<213> ORGANISM: Artificial Sequence
<220> FEATURE:
<223> OTHER INFORMATION: hzJ4F Anti-ASGR1 - VH CDR1

<400> SEQUENCE: 294

Gly Tyr Thr Phe Thr Ser Tyr Trp Ile Asn
1               5                   10

<210> SEQ ID NO 295
<211> LENGTH: 6
<212> TYPE: PRT
<213> ORGANISM: Artificial Sequence
<220> FEATURE:
<223> OTHER INFORMATION: hzJ4F Anti-ASGR1 - VH CDR1

<400> SEQUENCE: 295

Thr Ser Tyr Trp Ile Asn
1               5

<210> SEQ ID NO 296
<211> LENGTH: 8
<212> TYPE: PRT
<213> ORGANISM: Artificial Sequence
<220> FEATURE:
<223> OTHER INFORMATION: hzJ4F Anti-ASGR1 - VH CDR1

<400> SEQUENCE: 296

Gly Tyr Thr Phe Thr Ser Tyr Trp
1               5

<210> SEQ ID NO 297
<211> LENGTH: 6
<212> TYPE: PRT
<213> ORGANISM: Artificial Sequence
<220> FEATURE:
<223> OTHER INFORMATION: hzJ4F Anti-ASGR1 - VH CDR2

<400> SEQUENCE: 297

Val Pro Gly Ser Gly Ser
1               5

<210> SEQ ID NO 298
<211> LENGTH: 10
<212> TYPE: PRT
<213> ORGANISM: Artificial Sequence
<220> FEATURE:
<223> OTHER INFORMATION: hzJ4F Anti-ASGR1 - VH CDR2

<400> SEQUENCE: 298

Arg Ile Val Pro Gly Ser Gly Ser Thr Tyr
1               5                   10

<210> SEQ ID NO 299
<211> LENGTH: 13
<212> TYPE: PRT
<213> ORGANISM: Artificial Sequence
<220> FEATURE:
<223> OTHER INFORMATION: hzJ4F Anti-ASGR1 - VH CDR2

<400> SEQUENCE: 299

Trp Met Gly Arg Ile Val Pro Gly Ser Gly Ser Thr Tyr
1               5                   10

<210> SEQ ID NO 300
<211> LENGTH: 8
<212> TYPE: PRT
<213> ORGANISM: Artificial Sequence
<220> FEATURE:
<223> OTHER INFORMATION: hzJ4F Anti-ASGR1 - VH CDR2

<400> SEQUENCE: 300

Ile Val Pro Gly Ser Gly Ser Thr

```
<210> SEQ ID NO 301
<211> LENGTH: 7
<212> TYPE: PRT
<213> ORGANISM: Artificial Sequence
<220> FEATURE:
<223> OTHER INFORMATION: hzJ4F Anti-ASGR1 - VH CDR3

<400> SEQUENCE: 301

Ala Arg Lys Pro Asn Phe Asp
1               5

<210> SEQ ID NO 302
<211> LENGTH: 8
<212> TYPE: PRT
<213> ORGANISM: Artificial Sequence
<220> FEATURE:
<223> OTHER INFORMATION: hzJ4F Anti-ASGR1 - VH CDR3

<400> SEQUENCE: 302

Ala Arg Lys Pro Asn Phe Asp Val
1               5

<210> SEQ ID NO 303
<211> LENGTH: 7
<212> TYPE: PRT
<213> ORGANISM: Artificial Sequence
<220> FEATURE:
<223> OTHER INFORMATION: hzJ4F Anti-ASGR1 - VL CDR1

<400> SEQUENCE: 303

Gly Thr Asn Val Ala Trp Tyr
1               5

<210> SEQ ID NO 304
<211> LENGTH: 6
<212> TYPE: PRT
<213> ORGANISM: Artificial Sequence
<220> FEATURE:
<223> OTHER INFORMATION: hzJ4F Anti-ASGR1 - VL CDR1

<400> SEQUENCE: 304

Gln Asn Val Gly Thr Asn
1               5

<210> SEQ ID NO 305
<211> LENGTH: 10
<212> TYPE: PRT
<213> ORGANISM: Artificial Sequence
<220> FEATURE:
<223> OTHER INFORMATION: hzJ4F Anti-ASGR1 - VL CDR2

<400> SEQUENCE: 305

Ala Val Ile Tyr Ser Ala Ser Tyr Arg Phe
1               5                   10

<210> SEQ ID NO 306
<211> LENGTH: 8
<212> TYPE: PRT
<213> ORGANISM: Artificial Sequence
<220> FEATURE:
<223> OTHER INFORMATION: hzJ4F Anti-ASGR1 - VL CDR3

<400> SEQUENCE: 306

Gln Gln Tyr Asn Ser Tyr Pro Leu
1               5
```

<210> SEQ ID NO 307
<211> LENGTH: 5
<212> TYPE: PRT
<213> ORGANISM: Artificial Sequence
<220> FEATURE:
<223> OTHER INFORMATION: hzH8K Anti-ASGR1 - VH - CDR2

<400> SEQUENCE: 307

Ser Tyr Arg Gly Ser
1               5

<210> SEQ ID NO 308
<211> LENGTH: 9
<212> TYPE: PRT
<213> ORGANISM: Artificial Sequence
<220> FEATURE:
<223> OTHER INFORMATION: hzH8K Anti-ASGR1 - VH - CDR2

<400> SEQUENCE: 308

Tyr Arg Ser Tyr Arg Gly Ser Thr Ser
1               5

<210> SEQ ID NO 309
<211> LENGTH: 12
<212> TYPE: PRT
<213> ORGANISM: Artificial Sequence
<220> FEATURE:
<223> OTHER INFORMATION: hzH8K Anti-ASGR1 - VH - CDR2

<400> SEQUENCE: 309

Trp Ile Gly Tyr Arg Ser Tyr Arg Gly Ser Thr Ser
1               5                   10

<210> SEQ ID NO 310
<211> LENGTH: 7
<212> TYPE: PRT
<213> ORGANISM: Artificial Sequence
<220> FEATURE:
<223> OTHER INFORMATION: hzH8K Anti-ASGR1 - VH - CDR2

<400> SEQUENCE: 310

Arg Ser Tyr Arg Gly Ser Thr
1               5

<210> SEQ ID NO 311
<211> LENGTH: 15
<212> TYPE: PRT
<213> ORGANISM: Artificial Sequence
<220> FEATURE:
<223> OTHER INFORMATION: hzH8K Anti-ASGR1 - VH - CDR3

<400> SEQUENCE: 311

Ala Arg Arg Gly Tyr Tyr Gly Ser Ser Ser His Trp Tyr Phe Asp
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: hzH8K Anti-ASGR1 - VH - CDR3

<400> SEQUENCE: 312

Ala Arg Arg Gly Tyr Tyr Gly Ser Ser Ser His Trp Tyr Phe Asp Val
1               5                   10                  15

```
<210> SEQ ID NO 313
<211> LENGTH: 7
<212> TYPE: PRT
<213> ORGANISM: Artificial Sequence
<220> FEATURE:
<223> OTHER INFORMATION: hzH8K Anti-ASGR1 - VL - CDR1

<400> SEQUENCE: 313

Tyr Ser Tyr Leu Ala Trp Tyr
1               5

<210> SEQ ID NO 314
<211> LENGTH: 6
<212> TYPE: PRT
<213> ORGANISM: Artificial Sequence
<220> FEATURE:
<223> OTHER INFORMATION: hzH8K Anti-ASGR1 - VL - CDR1

<400> SEQUENCE: 314

Glu Asn Ile Tyr Ser Tyr
1               5

<210> SEQ ID NO 315
<211> LENGTH: 10
<212> TYPE: PRT
<213> ORGANISM: Artificial Sequence
<220> FEATURE:
<223> OTHER INFORMATION: hzH8K Anti-ASGR1 - VL - CDR2

<400> SEQUENCE: 315

Leu Leu Ile Tyr Asn Ala Lys Thr Leu Ala
1               5                   10

<210> SEQ ID NO 316
<211> LENGTH: 8
<212> TYPE: PRT
<213> ORGANISM: Artificial Sequence
<220> FEATURE:
<223> OTHER INFORMATION: hzH8K Anti-ASGR1 - VL - CDR3

<400> SEQUENCE: 316

Gln His His Tyr Gly Thr Pro Leu
1               5
```